United States Patent
Sluch et al.

(10) Patent No.: US 12,344,655 B2
(45) Date of Patent: *Jul. 1, 2025

(54) GENE-EDITED NATURAL KILLER CELLS

(71) Applicant: CRISPR Therapeutics AG, Zug (CH)

(72) Inventors: Valentin Sluch, South Boston, MA (US); Alireza Rezania, South Boston, MA (US); Jason Sagert, South Boston, MA (US); Danielle Swain, South Boston, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 224 days.

This patent is subject to a terminal disclaimer.

(21) Appl. No.: 18/068,056

(22) Filed: Dec. 19, 2022

(65) Prior Publication Data
US 2023/0227532 A1 Jul. 20, 2023

Related U.S. Application Data

(63) Continuation of application No. 17/538,699, filed on Nov. 30, 2021, now Pat. No. 11,591,381.

(60) Provisional application No. 63/250,048, filed on Sep. 29, 2021, provisional application No. 63/214,134, filed on Jun. 23, 2021, provisional application No. 63/119,512, filed on Nov. 30, 2020.

(51) Int. Cl.
| | |
|---|---|
| *C12N 15/85* | (2006.01) |
| *A61K 40/15* | (2025.01) |
| *A61K 40/31* | (2025.01) |
| *A61K 40/42* | (2025.01) |
| *C07K 14/54* | (2006.01) |
| *C07K 14/715* | (2006.01) |
| *C07K 14/725* | (2006.01) |
| *C07K 14/74* | (2006.01) |
| *C07K 14/81* | (2006.01) |
| *C07K 16/28* | (2006.01) |
| *C12N 5/0735* | (2010.01) |
| *C12N 5/074* | (2010.01) |
| *C12N 5/0783* | (2010.01) |
| *C12N 5/10* | (2006.01) |
| *C12N 15/66* | (2006.01) |
| *C12N 15/90* | (2006.01) |

(52) U.S. Cl.
CPC ........ *C07K 14/70539* (2013.01); *A61K 40/15* (2025.01); *A61K 40/31* (2025.01); *A61K 40/4215* (2025.01); *C07K 14/5443* (2013.01); *C07K 14/7051* (2013.01); *C07K 14/7155* (2013.01); *C07K 14/8121* (2013.01); *C07K 16/2878* (2013.01); *C12N 5/0606* (2013.01); *C12N 5/0646* (2013.01); *C12N 5/0696* (2013.01); *C12N 5/10* (2013.01); *C12N 15/66* (2013.01); *C12N 15/85* (2013.01); *C12N 15/907* (2013.01); *A61K 2239/31* (2023.05); *A61K 2239/38* (2023.05); *A61K 2239/48* (2023.05); *C07K 2319/00* (2013.01); *C12N 2310/20* (2017.05); *C12N 2506/11* (2013.01); *C12N 2510/00* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton |
| 7,387,776 B2 | 6/2008 | Keler et al. |
| 8,652,845 B2 | 2/2014 | Niwa et al. |
| 9,121,011 B2 | 9/2015 | Osafune et al. |
| 9,260,696 B2 | 2/2016 | Kaufman et al. |
| 9,629,877 B2 | 4/2017 | Cooper et al. |
| 9,765,330 B1 | 9/2017 | Niazi et al. |
| 9,834,754 B2 | 12/2017 | Keller et al. |
| 9,890,357 B2 | 2/2018 | Osafune et al. |
| 9,931,377 B2 | 4/2018 | Pavlakis et al. |
| 9,938,499 B2 | 4/2018 | Slukvin et al. |
| 10,150,805 B2 | 12/2018 | Wong et al. |
| 10,166,255 B2 | 1/2019 | Moriarity et al. |

(Continued)

FOREIGN PATENT DOCUMENTS

| | | |
|---|---|---|
| CN | 111235105 | 6/2020 |
| EP | 2699593 | 8/2017 |

(Continued)

OTHER PUBLICATIONS

Gornalusse et al. Nat Biotechnology 2017:35(8):765-777 (Year: 2017).*

(Continued)

*Primary Examiner* — Marcia S Noble
(74) *Attorney, Agent, or Firm* — Dickinson Wright PLLC

(57) ABSTRACT

The present invention relates to, inter alia, an engineered cell (e.g., iPSC, IPS-derived NK, or NK cell) comprising a disrupted B2M gene and an inserted polynucleotide encoding one or more of SERPINB9, a fusion of IL15 and IL15Rα, and/or HLA-E. The engineered cell can further comprise a disrupted CIITA gene and an inserted polynucleotide encoding a CAR, wherein the CAR can be an anti-BCMA CAR or an anti-CD30 CAR. The engineered cell may further comprise a disrupted ADAM17 gene, a disrupted FAS gene, a disrupted CISH gene, and/or a disrupted REGNASE-1 gene. Methods for producing the engineered cells are also provided, and therapeutic uses of the engineered cells are also described. Guide RNA sequences targeting described target sequences are also described.

19 Claims, 66 Drawing Sheets

Specification includes a Sequence Listing.

(56) References Cited

U.S. PATENT DOCUMENTS

| | | |
|---|---|---|
| 10,196,652 B2 | 2/2019 | Conway et al. |
| 10,287,606 B2 | 5/2019 | Valamehr et al. |
| 10,370,452 B2 | 8/2019 | Themeli et al. |
| 10,428,305 B2 | 10/2019 | Campana et al. |
| 10,500,229 B2 | 12/2019 | Lee et al. |
| 10,501,543 B2 | 12/2019 | Bernett et al. |
| 10,626,372 B1 | 4/2020 | Valamehr et al. |
| 10,738,279 B2 | 8/2020 | Lee |
| 10,815,301 B2 | 10/2020 | Kochenderfer |
| 10,894,944 B2 | 1/2021 | Elefanty et al. |
| 10,905,743 B2 | 2/2021 | Qu et al. |
| 10,927,346 B2 | 2/2021 | Valamehr et al. |
| 10,968,426 B2 | 4/2021 | Meissner et al. |
| 11,059,876 B2 | 7/2021 | Yeung et al. |
| 11,072,781 B2 | 7/2021 | Valamehr et al. |
| 11,136,547 B2 | 10/2021 | Eto et al. |
| 11,459,372 B2 | 10/2022 | Sluch et al. |
| 11,473,060 B2 | 10/2022 | Kyrychenko et al. |
| 11,591,381 B2 | 2/2023 | Sluch et al. |
| 2009/0238791 A1 | 9/2009 | Jacques et al. |
| 2013/0287751 A1 | 10/2013 | Kaufman et al. |
| 2014/0068797 A1 | 3/2014 | Doudna et al. |
| 2016/0002595 A1 | 1/2016 | Keller et al. |
| 2016/0097035 A1 | 4/2016 | Yonemitsu et al. |
| 2016/0120906 A1 | 5/2016 | Galetto et al. |
| 2017/0112109 A1 | 4/2017 | Park et al. |
| 2017/0175128 A1 | 6/2017 | Welstead et al. |
| 2018/0008637 A1 | 1/2018 | Murphy et al. |
| 2018/0021378 A1 | 1/2018 | Kang et al. |
| 2018/0044636 A1 | 2/2018 | Spanholtz et al. |
| 2018/0072992 A1 | 3/2018 | Valamehr et al. |
| 2018/0142034 A1 | 5/2018 | Chang |
| 2018/0298101 A1 | 10/2018 | Huntington et al. |
| 2018/0305664 A1 | 10/2018 | Vodyanyk et al. |
| 2018/0346877 A1 | 12/2018 | Zhang et al. |
| 2019/0048060 A1 | 2/2019 | Conway et al. |
| 2019/0054122 A1 | 2/2019 | Moriarty et al. |
| 2019/0060363 A1 | 2/2019 | Moriarty et al. |
| 2019/0060364 A1 | 2/2019 | Moriarty et al. |
| 2019/0062735 A1 | 2/2019 | Welstead et al. |
| 2019/0125795 A1 | 5/2019 | Rosen et al. |
| 2019/0134095 A1 | 5/2019 | Stassinopoulos et al. |
| 2019/0136261 A1 | 5/2019 | Conway et al. |
| 2019/0144828 A1 | 5/2019 | Ng et al. |
| 2019/0153389 A1 | 5/2019 | Fischkoff et al. |
| 2019/0271005 A1 | 9/2019 | Valamehr et al. |
| 2019/0309259 A1 | 10/2019 | Meissner et al. |
| 2019/0330592 A1 | 10/2019 | Hariri et al. |
| 2019/0345491 A1 | 11/2019 | Zhao et al. |
| 2019/0365812 A1 | 12/2019 | Sutlu et al. |
| 2019/0365876 A1 | 12/2019 | Russell et al. |
| 2019/0376036 A1 | 12/2019 | Dipierro |
| 2019/0376045 A1 | 12/2019 | Schrepfer et al. |
| 2019/0381154 A1 | 12/2019 | Russell et al. |
| 2020/0024342 A9 | 1/2020 | Ma et al. |
| 2020/0069734 A1 | 3/2020 | Valamehr et al. |
| 2020/0078402 A1 | 3/2020 | Ostertag et al. |
| 2020/0080059 A1 | 3/2020 | Thomson et al. |
| 2020/0080114 A1 | 3/2020 | Rezania et al. |
| 2020/0085872 A1 | 3/2020 | Rezvani et al. |
| 2020/0095543 A1 | 3/2020 | Bhattacharya et al. |
| 2020/0095544 A1 | 3/2020 | Boehm et al. |
| 2020/0095604 A1 | 3/2020 | Valamehr et al. |
| 2020/0123501 A1 | 4/2020 | Vodyanyk et al. |
| 2020/0131475 A1 | 4/2020 | Kimbrel et al. |
| 2020/0157503 A1 | 5/2020 | Lanza et al. |
| 2020/0163992 A1 | 5/2020 | Metelitsa et al. |
| 2020/0181573 A1 | 6/2020 | Rosen et al. |
| 2020/0208111 A1 | 7/2020 | Moriarty et al. |
| 2020/0224163 A1 | 7/2020 | Busser et al. |
| 2020/0255494 A1 | 8/2020 | Pule et al. |
| 2020/0263133 A1 | 8/2020 | Van Dijk et al. |
| 2020/0281977 A1 | 9/2020 | Mantovani et al. |
| 2020/0289564 A1 | 9/2020 | Patakas et al. |
| 2020/0299661 A1 | 9/2020 | Gori et al. |
| 2020/0306310 A1 | 10/2020 | Moriarty et al. |
| 2020/0309776 A1 | 10/2020 | Hantash |
| 2020/0332255 A1 | 10/2020 | Lee et al. |
| 2020/0354673 A1 | 11/2020 | Schrepfer et al. |
| 2020/0407458 A1 | 12/2020 | Chmielewski et al. |
| 2020/0407686 A1 | 12/2020 | Campana et al. |
| 2020/0407713 A1 | 12/2020 | Lim et al. |
| 2020/0407728 A1 | 12/2020 | Zhao et al. |
| 2021/0015859 A1 | 1/2021 | Valamehr et al. |
| 2021/0017494 A1 | 1/2021 | Vodyanyk et al. |
| 2021/0024884 A1 | 1/2021 | Chaplin et al. |
| 2021/0024897 A1 | 1/2021 | Matsuo et al. |
| 2021/0032664 A1 | 2/2021 | Bartsevich et al. |
| 2021/0040449 A1 | 2/2021 | Gschweng et al. |
| 2021/0062151 A1 | 3/2021 | Valamehr et al. |
| 2021/0087537 A1 | 3/2021 | Valamehr et al. |
| 2021/0106622 A1 | 4/2021 | Metelitsa et al. |
| 2021/0106655 A1 | 4/2021 | Qu et al. |
| 2021/0123022 A1 | 4/2021 | Yang et al. |
| 2021/0130785 A1 | 5/2021 | Akashi et al. |
| 2021/0145883 A1 | 5/2021 | Kaufman et al. |
| 2021/0161971 A1 | 6/2021 | Nagy et al. |
| 2021/0163622 A1 | 6/2021 | Valamehr et al. |
| 2021/0163895 A1 | 6/2021 | Valamehr et al. |
| 2021/0180017 A1 | 6/2021 | Valamehr et al. |
| 2021/0187025 A1 | 6/2021 | Dipierro et al. |
| 2021/0198342 A1 | 7/2021 | Boissel et al. |
| 2021/0207100 A1 | 7/2021 | Mostoslavsky et al. |
| 2021/0220403 A1 | 7/2021 | Metelitsa et al. |
| 2021/0222126 A1 | 7/2021 | Valamehr et al. |
| 2021/0230243 A1 | 7/2021 | Desjarlais et al. |
| 2021/0230548 A1 | 7/2021 | Daher et al. |
| 2021/0254005 A1 | 8/2021 | Kang et al. |
| 2021/0260117 A1 | 8/2021 | Moriarty et al. |
| 2021/0268087 A1 | 9/2021 | Odunsi et al. |
| 2021/0284965 A1 | 9/2021 | Germeroth |
| 2021/0292715 A1 | 9/2021 | Schrepfer et al. |
| 2021/0308183 A1 | 10/2021 | Schrepfer et al. |
| 2021/0395684 A1 | 12/2021 | Feng et al. |
| 2022/0169700 A1 | 6/2022 | Kyrychenko et al. |

FOREIGN PATENT DOCUMENTS

| | | | |
|---|---|---|---|
| EP | 3692794 | 8/2020 | |
| EP | 3693384 | 8/2020 | |
| EP | 3699268 | 8/2020 | |
| EP | 3071223 | 1/2021 | |
| EP | 3380117 | 1/2021 | |
| EP | 3783098 | 2/2021 | |
| EP | 3789485 | 3/2021 | |
| EP | 3805371 | 4/2021 | |
| EP | 3875578 | 9/2021 | |
| EP | 3712268 | 3/2022 | |
| KR | 102292843 B1 | 8/2021 | |
| WO | WO2001083692 | 11/2001 | |
| WO | WO2010099539 | 9/2010 | |
| WO | WO2013090648 | 6/2013 | |
| WO | WO2016183041 | 11/2016 | |
| WO | WO2016209021 | 12/2016 | |
| WO | WO2017078807 | 5/2017 | |
| WO | WO2017079673 | 5/2017 | |
| WO | WO2017100861 | 6/2017 | |
| WO | WO2017152015 | 9/2017 | |
| WO | WO2017193177 | 11/2017 | |
| WO | WO2017222593 | 12/2017 | |
| WO | WO2018227286 | 12/2018 | |
| WO | WO2019013626 | 1/2019 | |
| WO | WO2019032334 | 2/2019 | |
| WO | WO2019068099 | 4/2019 | |
| WO | WO2019112899 | 6/2019 | |
| WO | WO2019118516 | 6/2019 | |
| WO | WO-2019126748 A1 * | 6/2019 | ............. A61K 35/17 |
| WO | WO2019143292 | 7/2019 | |
| WO | WO2019209991 | 10/2019 | |
| WO | WO2019213517 | 11/2019 | |
| WO | WO2019213610 | 11/2019 | |
| WO | WO2019217956 | 11/2019 | |
| WO | WO2019226708 | 11/2019 | |
| WO | WO2019229109 | 12/2019 | |

(56) References Cited

FOREIGN PATENT DOCUMENTS

| | | |
|---|---|---|
| WO | WO2020007593 | 1/2020 |
| WO | WO2020012033 | 1/2020 |
| WO | WO2020018620 | 1/2020 |
| WO | WO2020086889 | 4/2020 |
| WO | WO2020096646 | 5/2020 |
| WO | WO2020097164 | 5/2020 |
| WO | WO2020097346 | 5/2020 |
| WO | WO2020112669 | 6/2020 |
| WO | WO2020112870 | 6/2020 |
| WO | WO2020113029 | 6/2020 |
| WO | WO2020113182 | 6/2020 |
| WO | WO2020117526 | 6/2020 |
| WO | WO2020118447 | 6/2020 |
| WO | WO2020150534 | 7/2020 |
| WO | WO2020154412 | 7/2020 |
| WO | WO2020168300 | 8/2020 |
| WO | WO2020168317 | 8/2020 |
| WO | WO2020172555 | 8/2020 |
| WO | WO2020198128 | 10/2020 |
| WO | WO2020209759 | 10/2020 |
| WO | WO2020210398 | 10/2020 |
| WO | WO2020228039 | 11/2020 |
| WO | WO2020245747 | 12/2020 |
| WO | WO2020247392 | 12/2020 |
| WO | WO2020252303 | 12/2020 |
| WO | WO2020260563 | 12/2020 |
| WO | WO2021011936 | 1/2021 |
| WO | WO2021015615 | 1/2021 |
| WO | WO2021016606 | 1/2021 |
| WO | WO2021016609 | 1/2021 |
| WO | WO2021022223 | 2/2021 |
| WO | WO2021027795 | 2/2021 |
| WO | WO2021032851 | 2/2021 |
| WO | WO2021032855 | 2/2021 |
| WO | WO2021041316 | 3/2021 |
| WO | WO-2021041316 A1 * | 3/2021 ............ A61K 35/17 |
| WO | WO2021051042 | 3/2021 |
| WO | WO2021051088 | 3/2021 |
| WO | WO2021055985 | 3/2021 |
| WO | WO2021062227 | 4/2021 |
| WO | WO2021062281 | 4/2021 |
| WO | WO2021071962 | 4/2021 |
| WO | WO2021072302 | 4/2021 |
| WO | WO2021077117 | 4/2021 |
| WO | WO2021085462 | 5/2021 |
| WO | WO2021092252 | 5/2021 |
| WO | WO2021092581 | 5/2021 |
| WO | WO2021097346 | 5/2021 |
| WO | WO2021097521 | 5/2021 |
| WO | WO2021102324 | 5/2021 |
| WO | WO2021113577 | 6/2021 |
| WO | WO2021127594 | 6/2021 |
| WO | WO 2021133861 | 7/2021 |
| WO | WO2021146719 | 7/2021 |
| WO | WO2021173458 | 9/2021 |
| WO | WO2021174004 | 9/2021 |
| WO | WO2021222928 | 11/2021 |
| WO | WO2022113056 | 6/2022 |
| WO | WO2022144632 | 7/2022 |
| WO | WO2022145832 | 7/2022 |
| WO | WO2022269393 | 12/2022 |

OTHER PUBLICATIONS

Ellis, Gavin I., Neil C. Sheppard, and James L. Riley. "Genetic engineering of T cells for immunotherapy." Nature Reviews Genetics 22.7 (2021): 427-447.
Non-Final Office Action dated Jun. 24, 2024 in U.S. Appl. No. 17/898,540.
Notice of allowance dated Nov. 1, 2024 in U.S. Appl. No. 17/898,540.
Ueda, Tatsuki, et al. "Non-clinical efficacy, safety and stable clinical cell processing of induced pluripotent stem cell-derived anti-glypican-3 chimeric antigen receptor-expressing natural killer/innate lymphoid cells." Cancer science 111.5 (2020): 1478-1490.
Wagner, Dimitrios L., et al. "Immunogenicity of CAR T cells in cancer therapy." Nature reviews Clinical oncology 18.6 (2021): 379-393.
Abel, Alex M., et al. "Natural killer cells: development, maturation, and clinical utilization." Frontiers in immunology 9 (2018): 1869.
Armbruster D.A., et al., "Limit of Blank, Limit of Detection and Limit of Quantitation," The Clinical Biochemist Reviews, Aug. 2008, vol. 29, No. 1, pp. S49-S52.
Belfort M., et al., "Homing Endonucleases: From Genetic Anomalies to Programmable Genomic Clippers," Methods in Molecular Biology, May 19, 2015, vol. 1123, pp. 1-27.
Bhardwaj, G., et al. "Sonic hedgehog induces the proliferation of primitive human hematopoietic cells via BMP regulation." Nature immunology 2.2 (2001): 172-180.
Bhatia et al., "Bone Morphogenetic Proteins Regulate the Developmental Program of Human Hematopoietic Stem Cells", Journal of Experimental Medicine, Apr. 5, 1999, pp. 1139-1147, vol. 189, No. 7.
BLAKE p. R., et al., "The Ontogeny of Fairness in Seven Societies." Nature, 2015, vol. 528, pp. 258-261.
Boch, Jens, et al. "Breaking the code of DNA binding specificity of TAL-type III effectors." Science 326.5959 (2009): 1509-1512.
Boissel S., et al., "Assembly and Characterization of MegaTALs for Hyperspecific Genome Engineering Applications," Chromosomal Mutagenesis, Methods in Molecular Biology, Second Edition, Chapter 9, 2015, vol. 1239, p. 171-196.
Boissel S., et al., "MegaTALs: A Rare-Cleaving Nuclease Architecture for Therapeutic Genome Engineering," Nucleic Acids Research, Feb. 2014, vol. 42(4), pp. 2591-2601.
Braasch D.A., et al., "Novel Antisense and Peptide Nucleic Acid Strategies for Controlling Gene Expression," Biochemistry, Apr. 9, 2002, vol. 41(14), pp. 4503-4510.
Cao et al., "Differentiation and Functional Comparison of Monocytes and Macrophages from hiPSCs with Peripheral Blood Derivatives", Stem Cell Reports, Jun. 11, 2019, pp. 1282-1297, vol. 12.
Ceccaldi et al., "Homologous recombination-deficient tumors are hyper-dependent on Polθ-mediated repair", Nature, Feb. 2015, pp. 258-262, vol. 518.
Cermak T., et al., "Efficient Design and Assembly of Custom TALEN and Other TAL Effector-Based Constructs for DNA Targeting," Nucleic Acids Research, Jul. 2011, e82, vol. 39(12), pp. 1-11.
Cermak T., et al., "Efficient Design and Assembly of Custom TALENs Using the Golden Gate Platform," Methods in Molecular Biology, 2015, vol. 1239, pp. 133-159.
Chadwick et al., "Cytokines and BMP-4 promote hematopoietic differentiation of human embryonic stem cells", Blood, Aug. 1, 2003, pp. 906-915, vol. 102, No. 3.
Chang et al., "A Chimeric Receptor with NKG2D Specificity Enhances Natural Killer Cell Activation and Killing of Tumor Cells", Cancer Research, Mar. 15, 2013, pp. 1777-1786, vol. 73, No. 6.
Chen et al., "Small molecule-mediated disruption of Wnt-dependent signaling in tissue regeneration and cancer", Nat Chem Biol., Feb. 2009, pp. 100-107, vol. 5, No. 2.
Chen, Chih-Wei, et al. "Pharmacological inhibition of porcupine induces regression of experimental skin fibrosis by targeting Wnt signalling." Annals of the rheumatic diseases 76.4 (2017): 773-778.
Cho et al., "DNA repair: Familiar ends with alternative endings", Nature, Feb. 2015, pp. 174-176, vol. 518.
Cichocki et al., "iPSC-derived NK cells maintain high cytotoxicity and enhance in vivo tumor control in concert with T cells and anti-PD-1 therapy", Sci Transl Med., Nov. 2020, 30 pgs., vol. 12.
Cichocki, Frank et al. "The Past, Present, and Future of NK Cells in Hematopoietic Cell Transplantation and Adoptive Transfer." Current topics in microbiology and immunology vol. 395 (2016): 225-43.
Cox et al., "Therapeutic Genome Editing: Prospects and Challenges", Nature Medicine, Feb. 2015, pp. 121-131, vol. 21, No. 2.
Cunningham, Thomas D., Xinguo Jiang, and David J. Shapiro. "Expression of high levels of human proteinase inhibitor 9 blocks both perforin/granzyme and Fas/Fas ligand-mediated cytotoxicity." Cellular immunology 245.1 (2007): 32-41.

(56) References Cited

OTHER PUBLICATIONS

Davidson et al., "Turning Mesoderm into Blood: The Formation of Hematopoietic Stem Cells during Embryogenesis", Current Topics in Developmental Biology, 2000, pp. 45-60, vol. 50.
Delconte, Rebecca B., et al. "CIS is a potent checkpoint in NK cell-mediated tumor immunity." Nature immunology 17.7 (2016): 816-824.
Deltcheva, Elitza, et al. "CRISPR RNA maturation by trans-encoded small RNA and host factor RNase III." Nature 471.7340 (2011): 602-607.
Deng, Youcai, et al. "Transcription factor Foxo1 is a negative regulator of natural killer cell maturation and function." Immunity 42.3 (2015): 457-470.
Dodge et al., "Diverse Chemical Scaffolds Support Direct Inhibition of the Membrane-Bound O-Acyltransferase Porcupine", Journal of Biological Chemistry, Jun. 29, 2012, pp. 23246-23254, vol. 287, No. 27.
Dreier B., et al., "Development of Zinc Finger Domains for Recognition of the 5'-CNN-3' Family DNASequences and Their Use in the Construction of Artificial Transcription Factors," The Journal of Biological Chemistry, Oct. 21, 2005, vol. 280(42), pp. 35588-35597.
Dreier B., et al., "Insights into the Molecular Recognition of the 5'-GNN-3' Family of DNA Sequences by Zinc Finger Domains," Journal of Molecular Biology, 2000, vol. 303, pp. 489-502.
Dreier, Birgit, et al. "Development of zinc finger domains for recognition of the 5'-ANN-3' family of DNA sequences and their use in the construction of artificial transcription factors." Journal of Biological Chemistry 276.31 (2001): 29466-29478.
Drexler et al., "FL T3: Receptor and Ligand", Growth Factors, Jun. 2004, pp. 71-73, vol. 22, No. 2.
Duraiswamy et al., "Discovery and Optimization of a Porcupine Inhibitor", Journal of Medicinal Chemistry, 2015, 11 pgs., vol. 58.
Dutton K., et al., "A Morpholino Phenocopy of the Colourless Mutant," Genesis, Jul. 2001, vol. 30, No. 3, pp. 188-189.
Enblad et al., "CART-Cell Therapy: The Role of Physical Barriers and Immunosuppression in Lymphoma", Human Gene Therapy, 2015, pp. 498-505, vol. 26, No. 8.
Enblad, Gunilla, et al. "CAR T-cell therapy: the role of physical barriers and immunosuppression in lymphoma." Human gene therapy 26.8 (2015): 498-505.
Ensembl ,Gene: B2M ENSG00000166710, Available at: https://grch37.ensembl.org/Homo_sapiens/Gene/Summary?g=ENSG00000166710;r=15:45003675-45011075 last accessed on Nov. 10, 2023 in 2 Pages.
Fonfara., et al., "Phylogeny of Cas9 Determines Functional Exchange-ability of Dual-RNA and Cas9 Among Orthologous Type II CRISPR-Cas Systems," Nucleic Acids Research, 2014, vol. 42(4), pp. 2577-2590.
Gebeyehu G., et al., "Novel Biotinylated Nucleotide—Analogs for Labeling and Colorimetric Detection of DNA," Nucleic Acids Research, 1987, vol. 15(11), pp. 4513-4534.
Gornalusse et al., "HLA-E-expressing pluripotent stem cells escape allogeneic responses and lysis by NK cells", Nature Biotechnology, 2017, pp. 765-773, vol. 35.
Guilinger et al., "Fusion of Catalytically Inactive Cas9 to Fokl Nuclease Improves the Specificity of Genome Modification", Nature Biotechnology, Jun. 2014, vol. 32(6), pp. 577-582.
Guo et al., "Immunobiology of the IL-15/IL-15Ra complex as an antitumor and antiviral agent", Cytokine and Growth Factor Reviews, 2017, pp. 10-21, vol. 38.
Guo et al., "Structure-based rational design of a novel chimeric PD1-NKG2D receptor for natural killer cells", Molecular Immunology, 2019, pp. 108-113, vol. 114.
Haddad N.E., et al., "The Novel Role of SERPINB9 in Cytotoxic Protection of Human Mesenchymal Stem Cells," The Journal of Immunology, 2011, pp. 2252-2260.
Hafez M., et al., "Homing Endonucleases: DNA Scissors on a Mission," Genome, 2012, vol. 55, pp. 553-569.

Hagn, Magdalena, Vivien R. Sutton, and Joseph A. Trapani. "A colorimetric assay that specifically measures Granzyme B proteolytic activity: hydrolysis of Boc-Ala-Ala-Asp-S-Bzl." JoVE (Journal of Visualized Experiments) 93 (2014): e52419.
Han et al., "Generation of hypoimmunogenic human pluripotent stem cells", PNAS, May 2019, pp. 10441-10446, vol. 116, No. 21.
Harding et al., "Induction of long-term allogeneic cell acceptance and formation of immune privileged tissue in 32 mmunocompetent hosts", Jul. 30, 2019, pp. 1-34; XP055718117, DOI: 10.1101/716571. Retrieved from the Internet: URL:https://www.biorxiv.org/contenl/10.1101/716571v1 .full.pdf (retrieved Jul. 27, 2020).
Heasman J., "Morpholino Oligos: Making Sense of Antisense?," Developmental Biology, 2002, vol. 243, pp. 209-214.
Huber et al., "Cooperative Effects of Growth Factors Involved in the Induction of Hematopoietic Mesoderm", Blood, Dec. 1, 1998, pp. 4128-4137, vol. 92, No. 11.
Hurton et al., "Tethered IL-15 augments antitumor activity and promotes a stem-cell memory subset in tumorspecific T cells", PNAS, Nov. 14, 2016, pp. E7788-E7797, vol. 113, No. 48.
Imai, Chihaya, Shotaro Iwamoto, and Dario Campana. "Genetic modification of primary natural killer cells overcomes inhibitory signals and induces specific killing of leukemic cells." Blood 106.1 (2005): 376-383.
International preliminary report on patentability relating to International Application No. PCT/IB2021/061148, dated May 30, 2023.
International preliminary report on patentability relating to International Application No. PCT/IB2021/061150, dated Jul. 4, 2023.
International Search Report and Written Opinion dated Oct. 6, 2022 in PCT Application No. PCT/IB2022/055149.
International Search Report and Written Opinion relating to International Application No. PCT/IB2021/061148, dated Feb. 22, 2022; 17 pgs.
International Search Report and Written Opinion relating to International Application No. PCT/IB2021/061150, dated Mar. 7, 2022; 17 pgs.
International Search Report and Written Opinion relating to International Application No. PCT/IB2023/055613, dated Sep. 22, 2023; 15 pgs.
Jackson, Steven A., et al. "Differentiating embryonic stem cells pass through 'temporal windows' that mark responsiveness to exogenous and paracrine mesendoderm inducing signals." Plos one 5.5 (2010): e10706.
Jiang et al., "Inactivating mutations of RNF43 confer Wnt dependency in pancreatic ductal adenocarcinoma", PNAS, Jul. 2013, pp. 12649-12654, vol. 110, No. 31.
Jiang L., et al., "Direct Tumor Killing and Immunotherapy Through Anti-SerpinB9 Therapy," Cell, 2020, vol. 183, pp. 1219-1233.
Jinek, Martin, et al. "A programmable dual-RNA-guided DNA endonuclease in adaptive bacterial immunity." science 337.6096 (2012): 816-821.
Kakarla et al., "CART cells for solid tumors: armed and ready to go?", Cancer Journal, 2014, pp. 151-155, vol. 20.
Kent et al., "Mechanism of Microhomology-Mediated End-Joining Promoted by Human DNA Polymerase θ", Nature Structural and Molecular Biology, Mar. 2015, pp. 230-237, vol. 22.
Kiselyov et al., "Structural Basis for a Direct Interaction between FGFR1 and NCAM and Evidence for a Regulatory Role of ATP", Structure, Jun. 2003, pp. 691-701, vol. 11.
Kitajima, Kenji, et al. "GSK3β inhibition activates the CDX/HOX pathway and promotes hemogenic endothelial progenitor differentiation from human pluripotent stem cells." Experimental hematology 44.1 (2016): 68-74.
Kleinstiver B.P., et al., "The I-Tevl Nuclease and Linker Domains Contribute to the Specificity of Monomeric TALENs," Genes, Genomes, Genetics, 2014, vol. 4(6), pp. 1155-1165.
Kornberg A., "DNA Replication," Freeman & Company, W. H., San Francisco, 1980, pp. 75-77.
Lacerra G., et al., "Restoration of Hemoglobin A Synthesis in Erythroid Cells from Peripheral Blood of Thalassemic 13 Patients," Proceedings of the National Academy of Sciences of the United States of America, Aug. 15, 2000, vol. 97(17), pp. 9591-9596.

(56) References Cited

OTHER PUBLICATIONS

Lanza, Robert, David W. Russell, and Andras Nagy. "Engineering universal cells that evade immune detection." Nature Reviews Immunology 19.12 (2019): 723-733.
Li, et al., "Modularly Assembled Designer TAL Effector Nucleases for Targeted Gene Knockout and Gene Replacement in Eukaryotes," Nucleic Acids Research, 2011, vol. 39(14), pp. 6315-6325.
Lin, Xinhua, et al. "Synthetic peptide F2A4-K-NS mimics fibroblast growth factor-2 in vitro and is angiogenic in vivo." International journal of molecular medicine 17.5 (2006): 833-839.
Liu et al., "Targeting Wnt-driven cancer through the inhibition of Porcupine by LGK974", PNAS, Dec. 2013, pp. 20224-20229, vol. 110, No. 50.
Liu et al., Validated Zinc Finger Protein Designs for All 16 GNN DNA Triplet Targets, The Journal of Biological Chemistry, 2002, vol. 277(6), pp. 3850-3856.
Ludwig et al., "Derivation of human embryonic stem cells in defined conditions", Nature Biotechnology, Feb. 2006, pp. 185-187, vol. 24, No. 2.
Lupo, Kyle B., et al. "Differentiation of natural killer cells from induced pluripotent stem cells under defined, serum-and feeder-free conditions." Cytotherapy 23.10 (2021): 939-952.
Madan et al., "Wnt addiction of genetically defined cancers reversed by PORCN inhibition", Oncogene, 2016, pp. 2197-2207, vol. 35.
Mak, Amanda Nga-Sze, et al. "The crystal structure of TAL effector PthXo1 bound to its DNA target." Science 335.6069 (2012): 716-719.
Mangan M. S. J., et al., "The Role of Serpins in Vertebrate Immunity," Tissue Antigens, 2008, vol. 72, pp. 1-10.
Marshall, Caroline J., Christine Kinnon, and Adrian J. Thrasher. "Polarized expression of bone morphogenetic protein-4 in the human aorta-gonad-mesonephros region." Blood, The Journal of the American Society of Hematology 96.4 (2000): 1591-1593.
Mateos-Gomez et al., "Mammalian Polymerase 8 Promotes Alternative-NHEJ and Suppresses Recombination", Nature, Feb. 2015, pp. 254-257, vol. 518.
Matsubara et al., "Induction of human pluripotent stem cell-derived natural killer cells for immunotherapy under chemically defined conditions", Biochemical and Biophysical Research Communications, 2019, pp. 1-8, vol. 515.
Maude et al., "CD19-targeted chimeric antigen receptor T-cell therapy for acute lymphoblastic leukemia", Blood, Jun. 2015, pp. 4017-4023, vol. 125, No. 26.
Mishra et al., "Anti-ADAM17 monoclonal antibody MEDI3622 increases IFNy production by human NK cells in the presence of antibody-bound tumor cells", Cancer Immunol Immunother., Sep. 2018, pp. 1407-1416, vol. 67.
Moscou M.J., et al., "A Simple Cipher Governs DNA Recognition by TAL Effectors," Science, Dec. 11, 2009, vol. 326, pp. 1501.
Nasevicius A., et al., "Effective Targeted Gene Knockdown in Zebrafish," Nature Genetics, Oct. 2000, vol. 26, pp. 216-220.
NCBI Gene ID : 3122, HLA-DRA major histocompatibility complex, class II, DR alpha [ *Homo sapiens* (human) ], National Library of Medicine 2023, avaialbe at https://www.ncbi.nlm.nih.gov/gene/3122, last accessed on Nov. 10, 2023 in 9 Pages.
NCBI Gene ID: 1154, CISH cytokine inducible SH2 containing proteiCISH cytokine inducible SH2 containing protein [ *Homo sapiens* (human) ], National Library of Medicine 2023, availabe at: https://www.ncbi.nlm.nih.gov/gene/1154, last accessed on Nov. 14, 2023 in 7 Pages.
NCBI Gene ID: 135,ADORA2A adenosine A2a receptor [ *Homo sapiens* (human) ], National Library of Medicine 2023, availabe at: https://www.ncbi.nlm.nih.gov/gene/135, last accessed on Nov. 14, 2023 in 9 Pages.
NCBI Gene ID: 136, ADORA2B adenosine A2b receptor [ *Homo sapiens* (human) ], National Library of Medicine 2023, availabe at: https://www.ncbi.nim.nih.gov/gene/136, last accessed on Nov. 14, 2023 in 8 Pages.
NCBI Gene ID: 1493, CTLA4 cytotoxic T-lymphocyte associated protein 4 [ *Homo sapiens* (human) ], National Library of Medicine 2023, availale at: https://www.ncbi.nlm.nih.gov/gene/1493 last accessed on Nov. 10, 2023 in 8 Pages.
NCBI Gene ID: 201633, TIGIT T cell immunoreceptor with Ig and ITIM domains [ *Homo sapiens* (human) ], National Library of Medicine 2023, availabe at: https://www.ncbi.nlm.nih.gov/gene/201633, last accessed on Nov. 14, 2023 in 6 Pages.
NCBI Gene ID: 2209, CD274 CD274 molecule [ *Homo sapiens* (human) ], National Library of Medicine 2023, availabe at: https://www.ncbi.nlm.nih.gov/gene/2209, last accessed on Nov. 14, 2023 in 8 Pages.
NCBI Gene ID: 2214, FCGR3A Fc gamma receptor IIIa [ *Homo sapiens* (human) ], National Library f Medicine 2023, availabe at: https://www.ncbi.nlm.nih.gov/gene/2214, last accessed on Nov. 14, 2023 in 9 Pages.
NCBI Gene ID: 2313, FLI1 Fli-1 proto-oncogene, ETS transcription factor [ *Homo sapiens* (human) ], National Library of Medicine 2023, available at: https://www.ncbi.nlm.nih.gov/gene/2313 Last accessed on Nov. 10, 2023 in 8 Pages.
NCBI Gene ID: 29126, CD274 CD274 molecule [ *Homo sapiens* (human) ], National Library of Medicine 2023, availabe at: https://www.ncbi.nlm.nih.gov/gene/29126, last accessed on Nov. 14, 2023 in 6 Pages.
NCBI Gene ID: 3105, HLA-A major histocompatibility complex, class I, A [ *Homo sapiens* (human) ], National Library of Medicine 2023, available at: https://www.ncbi.nlm.nih.gov/gene/?term=3105 Last accessed on Nov. 10, 2023 in 10 Pages.
NCBI Gene ID: 3106, HLA-B major histocompatibility complex, class I, B [ *Homo sapiens* (human) ], National Library of Medicine 2023, available at: https://www.ncbi.nlm.nih.gov/gene/?term=3106%5Buid%5D Last accessed on Nov. 10, 2023 in 9 Pages.
NCBI Gene ID: 3107, HLA-C major histocompatibility complex, class I, C [ *Homo sapiens* (human) ], National Library of Medicine 2023, available at: https://www.ncbi.nlm.nih.gov/gene/?term=3107 Last accessed on Nov. 10, 2023 in 9 Pages.
NCBI Gene ID: 3108, HLA-DMA major histocompatibility complex, class II, DM alpha [ *Homo sapiens* (human) ], National Library of Medicine 2023, available at: https://www.ncbi.nlm.nih.gov/gene/3108, last accessed on Nov. 10, 2023 in 7 Pages.
NCBI Gene ID: 3109, HLA-DMB major histocompatibility complex, class II, DM beta [ *Homo sapiens* (human)], National Library of Medicine 2023, available at: https://www.ncbi.nlm.nih.gov/gtr/genes/3109/, last accessed on Nov. 10, 2023 in 8 Pages.
NCBI Gene ID: 3111, HLA-DOA major histocompatibility complex, class II, DO alpha [ *Homo sapiens* (human) ], National Library of Medicine 2023, available at: https://www.ncbi.nlm.nih.gov/gene/3111, last accessed on Nov. 10, 2023 in 6 Pages.
NCBI Gene ID: 3112, HLA-DOB major histocompatibility complex, class II, DO beta [ *Homo sapiens* (human) ], National Library of Medicine 2023, avaialbe at: https://www.ncbi.nlm.nih.gov/gene/?term=3112, last accessed on Nov. 10, 2023 in 7 Pages.
NCBI Gene ID: 3117, HLA-DQA1 major histocompatibility complex, class II, DQ alpha 1 [ *Homo sapiens* (human) ], National Library of Medicine 2023, avaialbe at: https://www.ncbi.nlm.nih.gov/gene/3117, last access on Nov. 10, 2023 in 9 Pages.
NCBI Gene ID: 3119, HLA-DQB1 major histocompatibility complex, class II, DQ beta 1 [ *Homo sapiens* (human) ], National Library of Medicine 2023, avaiable at: https://www.ncbi.nlm.nih.gov/gene/?term=3119, last accessed on Nov. 10, 2023 in 9 Pages.
NCBI Gene ID: 3123, HLA-DRB1 major histocompatibility complex, class II, DR beta 1 [ *Homo sapiens* (human) ], National Library of Medicine 2023, available at: https://www.ncbi.nlm.nih.gov/gene/3123, last accessed on Nov. 10, 2023 in 10 Pages.
NCBI Gene ID: 3133, HLA-E major histocompatibility complex, class I, E [ *Homo sapiens* (human) ], National Library of Medicine 2023, available at: https://www.ncbi.nlm.nih.gov/gene/?term=3133, last accessed on Nov. 10, 2023 in 9 Pages.
NCBI Gene ID: 3135, HLA-G major histocompatibility complex, class I, G [ *Homo sapiens* (human) ], National Library of Medicine 2023, avaialbe at:https://www.ncbi.nlm.nih.gov/gene/3135, last accessed on Nov. 10, 2023 in 11 Pages.

(56) References Cited

OTHER PUBLICATIONS

NCBI Gene ID: 355, FAS Fas cell surface death receptor [ *Homo sapiens* (human) ], National Library of Medicine 2023, availabe at: https://www.ncbi.nlm.nih.gov/gene/355, last accessed on Nov. 14, 2023 in 10 Pages.
NCBI Gene ID: 3821, KLRC1 killer cell lectin like receptor C1 [ *Homo sapiens* (human) ], National Library of Medicine 2023, availabe at: https://www.ncbi.nlm.nih.gov/gene/3821, last accessed on Nov. 14, 2023 in 6 Pages.
NCBI Gene ID: 4261, CIITA class II major histocompatibility complex transactivator [ *Homo sapiens* (human) ], National Library of Medicine 2023, avaiable at: https://www.ncbi.nlm.nih.gov/gene/4261, last accessed on Nov. 10, 2023 in 14 Pages.
NCBI Gene ID: 5133, PDCD1 programmed cell death 1 [ *Homo sapiens* (human) ], National Library of Medicine 2023, availabe at: https://www.ncbi.nlm.nih.gov/gene/5133, last accessed on Nov. 14, 2023 in 6 Pages.
NCBI Gene ID: 5272, SERPINB9 serpin family B member 9 [ *Homo sapiens* (human) ], National Library of Medicine 2023, availabe at: https://www.ncbi.nlm.nih.gov/gene/5272, last accessed on Nov. 14, 2023 in 6 Pages.
NCBI Gene ID: 567, B2M beta-2-microglobulin [ *Homo sapiens* (human) ], National Library of Medicine 2023, available at: https://www.ncbi.nlm.nih.gov/gene/567, last accessed on Nov. 10, 2023 in 8 Pages.
NCBI Gene ID: 6868, ADAM17 Adam metallopeptidase domain 17 [ HomoADAM17 ADAM metallopeptidase domain 17 [ *Homo sapiens* (human) ], National Library of Medicine 2023, availabe at: https://www.ncbi.nlm.nih.gov/gene/6868, last accessed on Nov. 14, 2023 in 9 Pages.
NCBI Gene ID: 6935, ZEB1 zinc finger E-box binding homeobox 1 [ *Homo sapiens* (human) ], National Library of Medicine 2023, availabe at: https://www.ncbi.nlm.nih.gov/gene/6935, last accessed on Nov. 14, 2023 in 17 Pages.
NCBI Gene ID: 7046, TGFBR1 transforming growth factor beta receptoTGFBR1 transforming growth factor beta receptor 1 [ *Homo sapiens* (human) ], National Library of Medicine 2023, availabe at: https://www.ncbi.nlm.nih.gov/gene/7046, last accessed on Nov. 14, 2023 in 11 Pages.
NCBI Gene ID: 7048, TGFBR2 transforming growth factor beta receptor 2 [ *Homo sapiens* (human) ], National Library of Medicine 2023, availabe at: https://www.ncbi.nlm.nih.gov/gene/7048, last accessed on Nov. 14, 2023 in 6 Pages.
NCBI Gene ID: 80149, ZC3H12A zinc finger CCCH-type containing 12A [ *Homo sapiens* (human) ], National Library of Medicine 2023, availabe at: https://www.ncbi.nlm.nih.gov/gene/80149, last accessed on Nov. 14, 2023 in 7 Pages.
NCBI Gene ID: 84166, NLRC5 NLR family CARD domain containing 5 [ *Homo sapiens* (human) ], National Library of Medicine 2023, avaiable at: https://www.ncbi.nlm.nih.gov/gene/84166, last accessed on Nov. 10, 2023 in 15 Pages.
NCBI Gene ID: 952, CD38 CD38 molecule [ *Homo sapiens* (human) ], National Library of Medicine 2023, availabe at: https://www.ncbi.nlm.nih.gov/gene/952, last accessed on Nov. 14, 2023 in 7 Pages.
NCBI Gene ID: 961, CD47 CD47 molecule [ *Homo sapiens* (human) ], National Library of Medicine 2023, available at: https://www.ncbi.nlm.nih.gov/gene/961, last accessed on Nov. 10, 2023 in 8 Pages.
NCBI Gene ID:3113, HLA-DPA1 major histocompatibility complex, class II, DP alpha 1 [ *Homo sapiens* (human) ], National Library of Medicine 2023, availabe at: https://www.ncbi.nlm.nih.gov/gene/?term=3113, last accessed on Nov. 10, 2023 in HLA-DPAin 8 Pages.
NCBI Gene ID:3115, HLA-DPB1 major histocompatibility complex, class II, DP beta 1 [ *Homo sapiens* (human) ], National Library of Medicine 2023, available at: https://www.ncbi.nlm.nih.gov/gene/3115, last accessed on Nov. 10, 2023 in 8 Pages.
Ng et al., "A protocol describing the use of a recombinant protein-based, animal product-free medium (APEL) for human embryonic stem cell differentiation as spin embryoid bodies", Nature Protocols, 2008, pp. 768-776, vol. 3, No. 5.
Non-Final Office Action dated Dec. 12, 2022 in U.S. Appl. No. 17/830,278.
Non-Final Office Action dated Feb. 7, 2022 in U.S. Appl. No. 17/538,719.
Non-Final Office Action dated Mar. 10, 2023 in U.S. Appl. No. 17/830,278.
Non-Final Office Action dated Nov. 4, 2022 in U.S. Appl. No. 17/830,273.
Notice of Allowance dated Aug. 10, 2022 in U.S. Appl. No. 17/538,566.
Notice of Allowance dated Jun. 9, 2022 in U.S. Appl. No. 17/538,719.
Notice of Allowance dated Mar. 7, 2022 in U.S. Appl. No. 17/538,566.
Notice of Allowance dated May 20, 2022 in U.S. Appl. No. 17/538,719.
Notice of Allowance dated May 4, 2022 in U.S. Appl. No. 17/538,566.
Notice of Allowance dated Sep. 30, 2022 in U.S. Appl. No. 17/538,699, 6 Pages.
Non-Final Office Action dated Jun. 13, 2022 for U.S. Appl. No. 17/538,699, 10 Pages.
Office Action dated Mar. 21, 2022 for U.S. Appl. No. 17/538,699, 10 Pages.
Peer D., et al., "Special Delivery: Targeted Therapy with Small RNAs," Gene Therapy, 2011, vol. 18, pp. 1127-1133.
Poulsen et al., "A Pharmacophore Model for Wnl/Porcupine Inhibitors and its Use for Drug Design", Journal of Chemical Information and Modeling, 2015, pp. 1-49, vol. 55.
Proffitt et al., "Pharmacological Inhibition of the Wnt Acyltransferase PORCN Prevents Growth of WNT-Driven Mammary Cancer", Cancer Research, Jan. 2013, pp. 502-507, vol. 73.
Ratajczak et al., "Effect of basic (FGF-2) and acidic (FGF-1) fibroblast growth factors on early haemopoietic cell Development", British Journal of Haematology, 1996, pp. 772-782, vol. 93.
Rautela, Jai, et al. "Therapeutic blockade of activin-A improves NK cell function and antitumor immunity." Science Signaling 12.596 (2019): eaat7527.
Sadelain M., et al., "Safe Harbours for the Integration of New DNA in the Human Genome," Nature Reviews Cancer, Jan. 2012, vol. 12, pp. 51-58.
Sapranauskas R., et al., "The *Streptococcus thermophilus* Crispr/Cas System Provides Immunity in *Escherichia coli*," Nucleic Acids Research, Nov. 2011, vol. 39(21 ), pp. 9275-9282.
Savoldo et al., "CD28 costimulation improves expansion and persistence of chimeric antigen receptor-modified T cells in lymphoma patients", The Journal of Clinical Investigation, May 2011, pp. 1822-1826, vol. 121, No. 5.
Segal D.J., et al., "Toward Controlling Gene Expression at Will: Selection and Design of Zinc Finger Domains Recognizing Each of the 5'-GNN-3' DNA Target Sequences," Proceedings of the National Academy of Sciences of the United States of America, Mar. 1999, vol. 96, pp. 2758-2763.
Steentoft C., et al., "Precision Genome Editing: A Small Revolution for Glycobiology," Glycobiology, Aug. 2014, vol. 24(8), pp. 663-680.
Stegen et al., "The Pharmacology of Second-Generation Chimeric Antigen Receptors," Nature Reviews Drug Discovery, Jul. 2015, vol. 14, pp. 499-509.
Tsai S.Q., et al., "Dimeric CRISPR RNA-Guided Fokl Nucleases for Highly Specific Genome Editing," Nature Biotechnology, Jun. 2014, vol. 32(6), pp. 569-576.
Uenishi G., et al., "Tenascin C Promotes Hematoendothelial Development and T Lymphoid Commitment from Human Pluripotent Stem Cells in Chemically Defined Conditions," Stem Cell Reports, 2014, vol. 3, No. 6, pp. 1073-1084.
Van Der Stegen et al., "The pharmacology of second-generation chimeric antigen receptors", Nature Reviews, Drug Discovery, Jul. 2015, pp. 499-509, vol. 14.
Wang et al., "The Development of Highly Potent Inhibitors for Porcupine", J Med Chem., Mar. 2013, pp. 2700-2704, vol. 56.
Wang S., et al., "Rapid and Efficient Assembly of Transcription Activator-Like Effector Genes by USER Cloning," Journal of Genetics and Genomics, 2014, vol. 41, pp. 339-347.

(56) References Cited

OTHER PUBLICATIONS

Wang, Jing, et al. "Cyclohexene nucleic acids (CeNA): serum stable oligonucleotides that activate RNase H and increase duplex stability with complementary RNA." Journal of the American Chemical Society 122.36 (2000): 8595-8602.

Weber E., et al., "A Modular Cloning System for Standardized Assembly of Multigene Constructs," PLoS One, 2011, vol. 6(2), e16765, pp. 1-11.

Wolfs, Jason M., et al. "MegaTevs: single-chain dual nucleases for efficient gene disruption." Nucleic acids research 42.13 (2014): 8816-8829.

Wu, Jianming, Hemant K. Mishra, and Bruce Walcheck. "Role of ADAM17 as a regulatory checkpoint of CD16A in NK cells and as a potential target for cancer immunotherapy." Journal of leukocyte biology 105.6 (2019): 1297-1303.

Xie et al., "CAR-NK cells: A promising cellular immunotherapy for cancer", EBioMedicine, 2020, 102975, pp. 1-10, vol. 59.

Yuan, Shaohui, et al. "Effect of growth factors (BMP-4/7 & bFGF) on proliferation & osteogenic differentiation of bone marrow stromal cells." The Indian Journal of Medical Research 138.1 (2013): 104.

Zhao et al., "Strategies for Genetically Engineering Hypoimmunogenic Universal Pluripotent Stem Cells", iScience, Jun. 2020, 101162, pp. 1-9, vol. 23.

Zhu et al., "An Improved Method to Produce Clinical-Scale Natural Killer Cells from Human Pluripotent Stem Cells", Methods in Molecular Biology, 2019, pp. 107-119, vol. 2048.

Zhu, Huang, et al. "Metabolic reprograming via deletion of CISH in human iPSC-derived NK cells promotes in vivo persistence and enhances anti-tumor activity." Cell Stem Cell 27.2 (2020): 224-237.

\* cited by examiner

GENE-EDITED NATURAL KILLER CELLS

CROSS-REFERENCE TO RELATED APPLICATIONS

This application is a continuation application of U.S. application Ser. No. 17/538,699, filed Nov. 30, 2021, which claims the benefit of U.S. Provisional Application No. 63/119,512, filed Nov. 30, 2020, U.S. Provisional Application No. 63/214,134, filed Jun. 23, 2021, and U.S. Provisional Application No. 63/250,048, filed Sep. 29, 2021, the disclosure of each is hereby incorporated by reference in its entirety.

INCORPORATION BY REFERENCE OF SEQUENCE LISTING

The present application is being filed along with a Sequence Listing in electronic format. The Sequence Listing is provided as a file entitled 80EM-341744-US4_Sequence_Listing, created Dec. 18, 2022, which is 298 kilobytes in size. The information in the electronic format of the Sequence Listing is incorporated herein by reference in its entirety.

FIELD OF THE INVENTION

The invention relates to the field of gene-edited iPSC and Natural Killer (NK) cells.

BACKGROUND

There is a need for adoptive cell therapy that does not rely on the use of cells obtained from patients or donors and does not induce allogeneic rejection. Natural Killer (NK) cells are potent anti-tumor effectors, making them attractive candidates for cancer immunotherapy. However, the use of NK cells, in particular NK cells expressing a chimeric antigen receptor (CAR), for adoptive cell therapy remains to be challenging. For example, there is a need to improve the efficacy, persistence, cytotoxic activity, immune evasion and tumor targeting of therapeutic NK cells. There is also a need for a uniform pool of therapeutic NK cells that can be manufactured in a consistent manner for use in any patients in need thereof.

SUMMARY OF THE INVENTION

In some aspects, the present disclosure provides engineered cells that have been edited using, for example, CRISPR/Cas9 gene editing technology, to prevent alloimmune responses, be immune evasive, have increased survival and persistence, increased activation, and/or specific cell targeting.

In some aspects, the present disclosure provides engineered cells comprising (a) a disrupted beta-2-microglobulin (B2M) gene, and (b) an insertion of a first polynucleotide and a second polynucleotide in the disrupted B2M gene, the first polynucleotide encoding a SERPINB9 protein and the second polynucleotide encoding a fusion protein of interleukin 15 (IL15) and interleukin 15 receptor subunit alpha (IL15Rα), wherein the cells express the SERPINB9 protein and the fusion protein of IL15 and IL15Rα, and the cells have disrupted expression of B2M. In some embodiments, the engineered cells comprise a disrupted Class II major histocompatibility complex transactivator (CIITA) gene, wherein the cells have disrupted expression of CIITA. In still other embodiments, the engineered cells further comprise an insertion of a third polynucleotide encoding a chimeric antigen receptor (CAR), wherein the cells express the CAR. In additional embodiments, the engineered cells further comprise an insertion of a fourth polynucleotide encoding a human leukocyte antigen E (HLA-E) trimer, and the cells further express the HLA-E trimer. In other embodiments, the engineered cells further comprise a disrupted cytokine-inducible SH2-containing protein (CISH) gene, wherein the cells have disrupted expression of CISH. In still other embodiments, the engineered cells further comprise a disrupted Fas cell surface death receptor (FAS) gene, wherein the cells have disrupted expression of FAS.

In further aspects, the present disclosure provides an in vitro method for generating an engineered cell, the method comprising delivering to a cell: (a) a first RNA-guided nuclease and a first guide RNA (gRNA) targeting a target site in a B2M gene locus; (b) a first vector comprising a nucleic acid, the nucleic acid comprising: (i) nucleotide sequence encoding a SERPINB9 protein and a nucleotide sequence encoding a fusion protein of IL15 and IL15Rα; (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii); wherein the B2M gene locus is cleaved at the target site and the nucleotide sequences encoding the SERPINB9 protein and the fusion protein of IL15 and IL15Rα are inserted into the B2M gene locus, thereby disrupting the B2M gene. In some embodiments, the method further comprising delivering to the cell: (c) a second RNA-guided nuclease and a second gRNA targeting a target site in a CIITA gene locus; and (d) a second vector comprising a nucleic acid, the nucleic acid comprising: (i) a nucleotide sequence encoding a chimeric antigen receptor (CAR); (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii); and wherein the CIITA gene locus is cleaved at the target site and the nucleotide sequence encoding the CAR is inserted into the CIITA gene locus, thereby disrupting the CIITA gene. In some embodiments, the nucleotide sequence of (d)(i) further comprises a nucleotide sequence encoding an HLA-E trimer. In some embodiments, the method further comprises delivering to the cell a third RNA-guided nuclease and a third gRNA targeting a target site in a CISH gene locus; wherein the CISH gene locus is cleaved at the target site and at least one insertion-deletion mutation is introduced into the CISH gene, thereby disrupting the CISH gene. In some embodiments, the method further comprises delivering to the cell a fourth RNA-guided nuclease and a fourth gRNA targeting a target site in a FAS gene locus, wherein the FAS gene locus is cleaved at the target site and at least one insertion-deletion mutation is introduced into the FAS gene, thereby disrupting the FAS gene.

In further aspects, the present disclosure provides a plurality of any of the engineered cells described herein. The present disclosure also provides compositions comprising any of the engineered cells disclosed herein or cells derived from or obtained from any of the engineered cells disclosed herein, wherein any of the composition is used as a medicament. In some embodiments, any of the compositions disclosed herein is for use in treating cancer.

In some aspects, the present disclosure provides a method for treating of a subject in need thereof, the method comprising: (a) obtaining or having obtained the plurality of engineered cells described herein following differentiation into lineage-restricted progenitor cells or fully differentiated somatic cells; and (b) administering the lineage-restricted progenitor cells or fully differentiated somatic cells to the subject.

Other aspects and iterations of the present disclosure are detailed below.

BRIEF DESCRIPTION OF THE DRAWINGS

FIG. 10 provides an image of an agarose gel demonstrating B2M indels. Clones with a band at 573 bp demonstrate a WT, unedited or heterozygous genotype. Clones with no band demonstrate a clone with successful knock-in.

BCMA+") bulk cells were cultured at different E:T ratios with K562 or RPMI cells for 24 hours.

Figure 22:
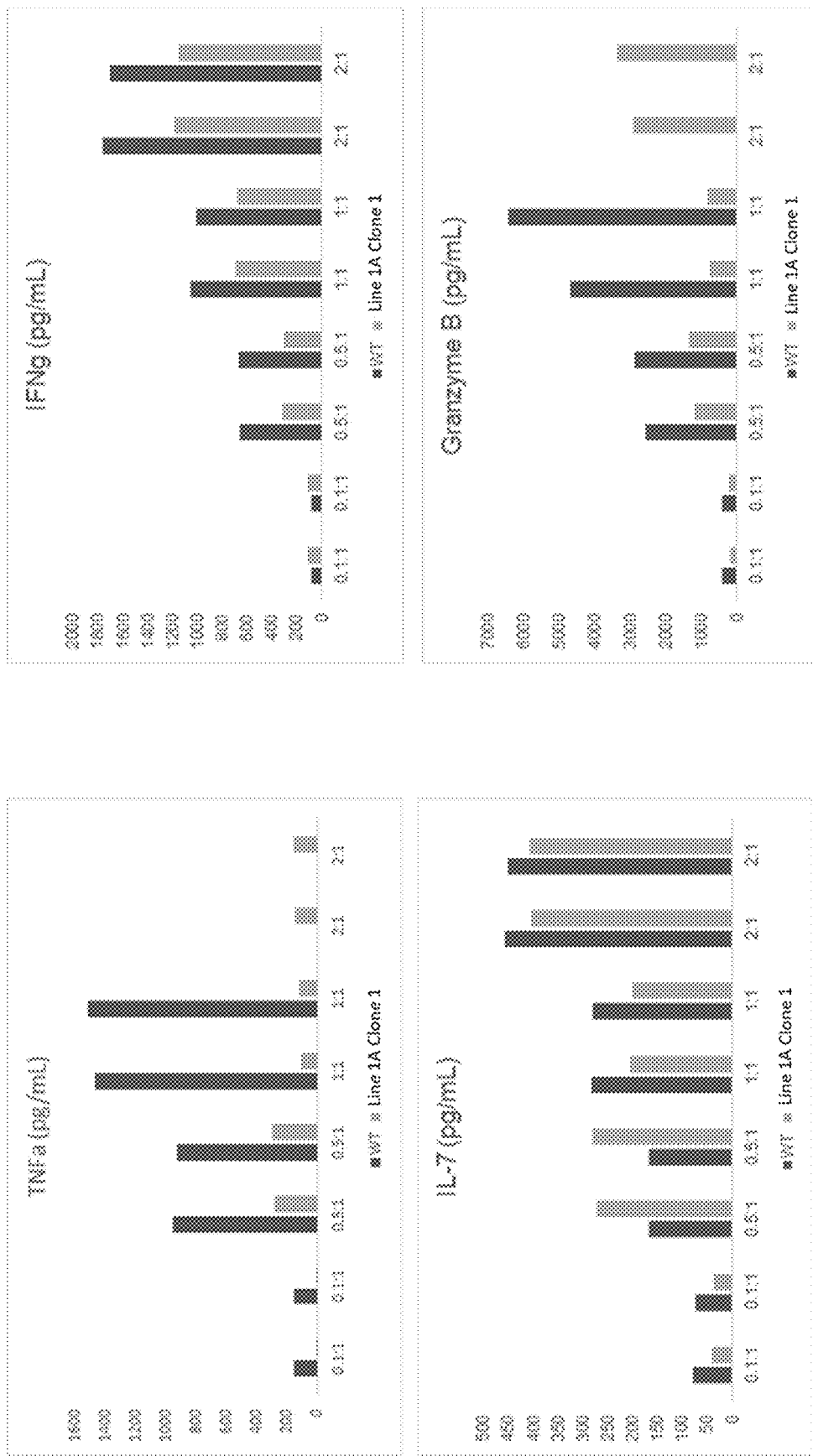

FIG. 22 provides graphs measuring TNFa, IFNg, IL-7, and Granzyme B levels in WT and Line 1A clone 1 cells co-cultured at different E:T ratios with RPMI cells.

Figure 23:
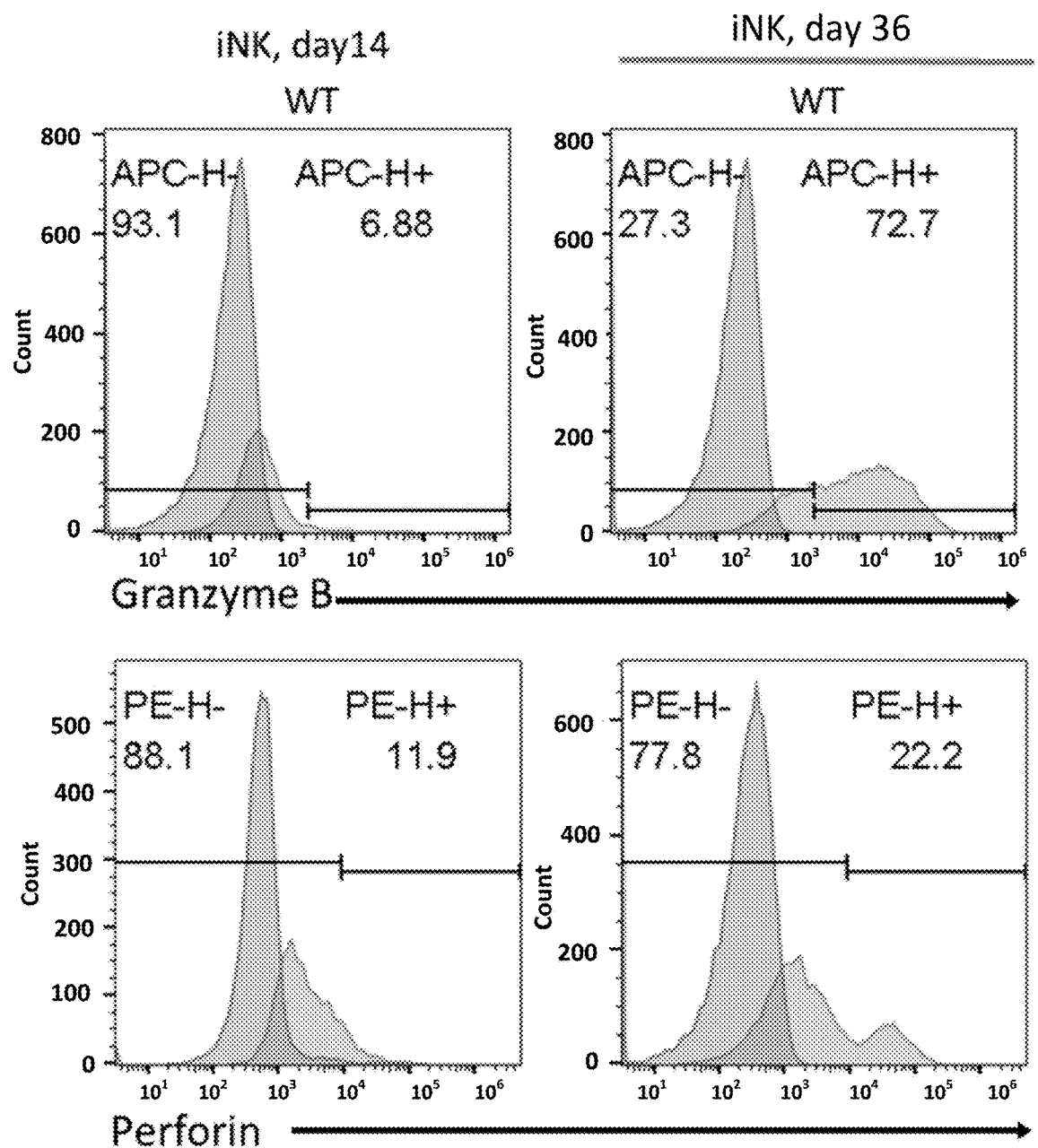
Figure 23:
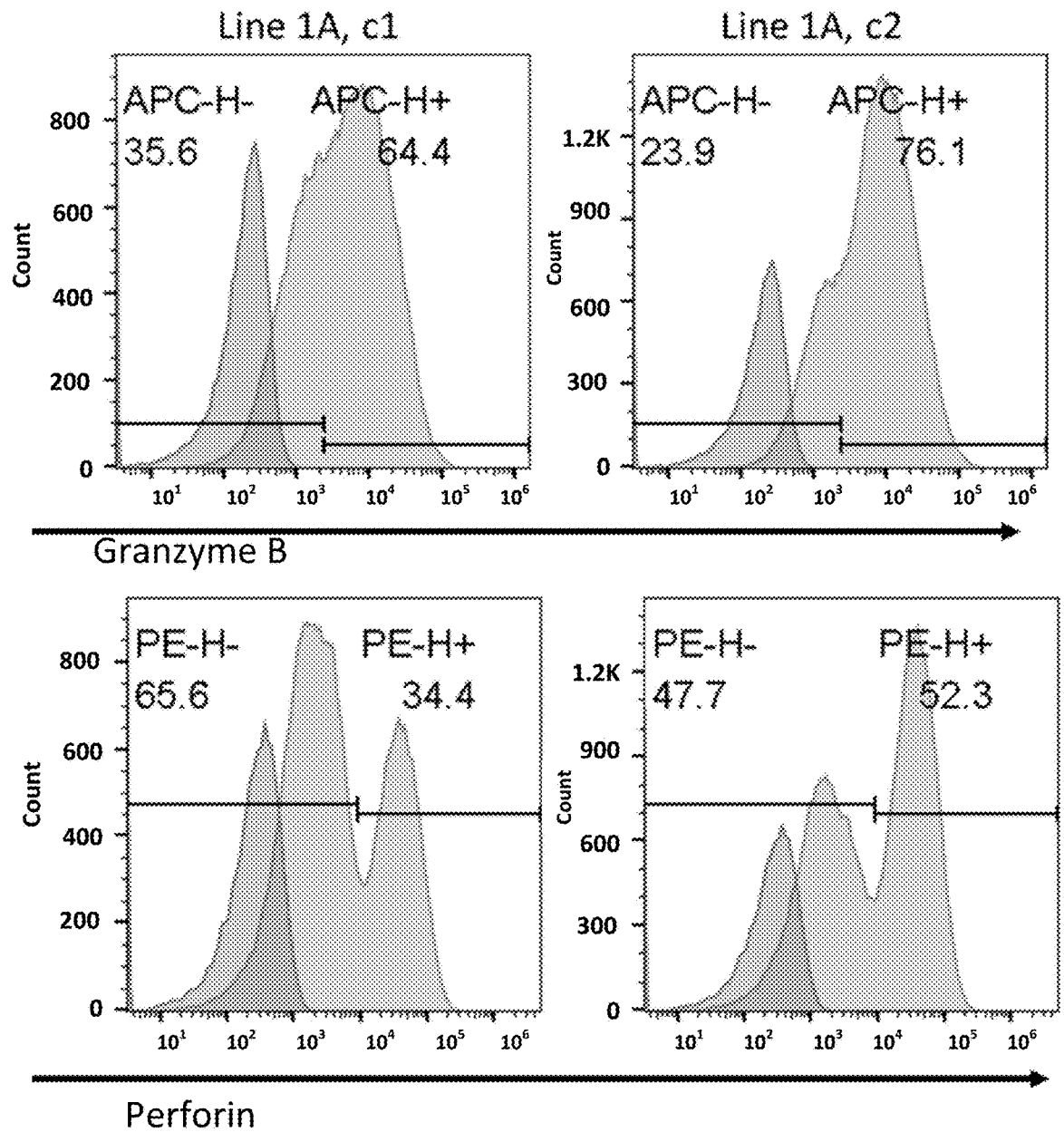

FIG. 23 provides flow cytometry graphs measuring Granzyme B and Perforin expressing cells at Day 14 (WT) and Day 36 (WT and Line 1A clones 1 and 2) of differentiation.

Figure 24:
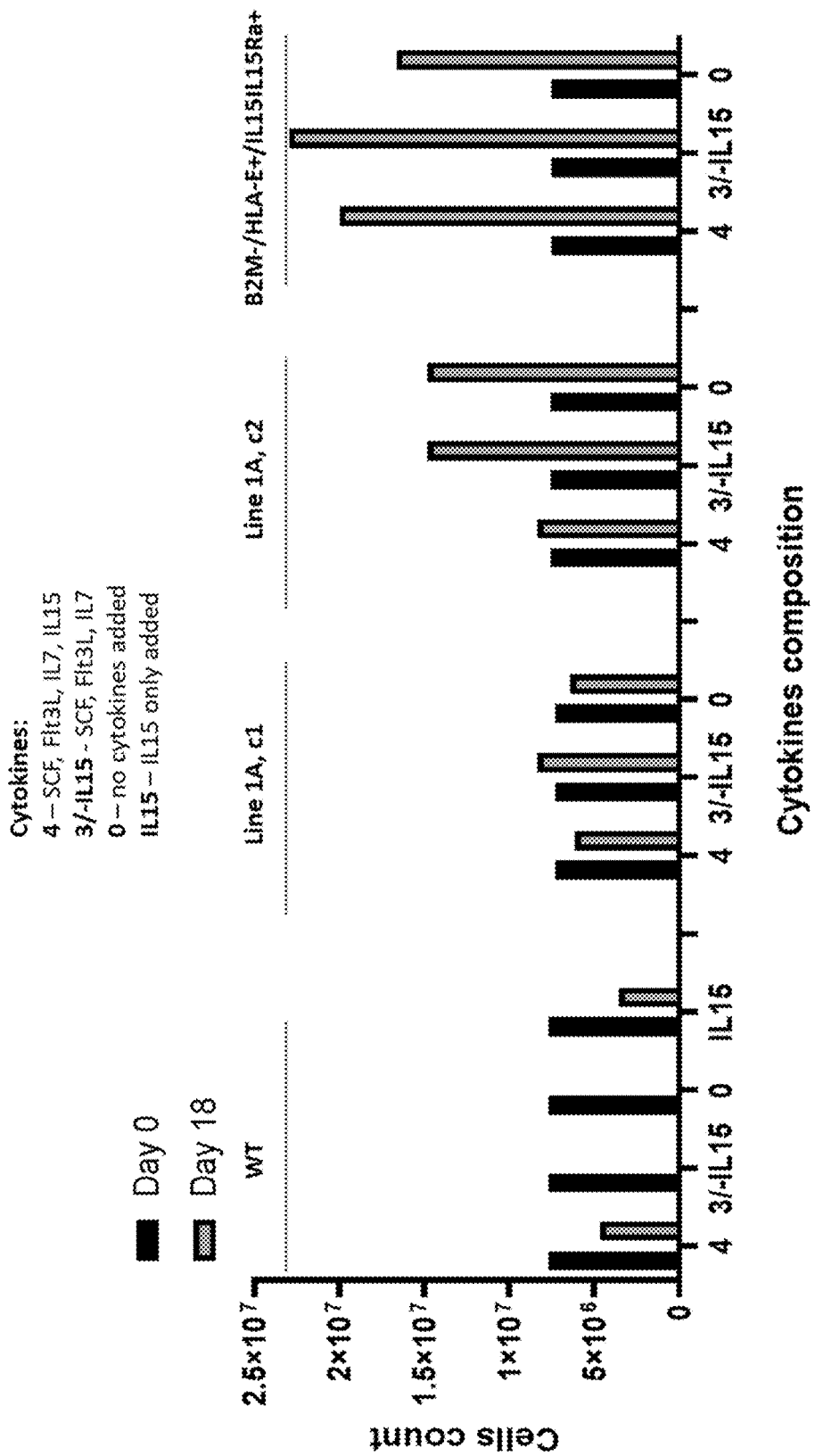

FIG. 24 provides graphs demonstrating cell count in wild-type (WT), Line 1A clone 1 ("Line 1A, c1"), Line 1A clone 2 ("Line 1A, c2"), and Clone 3 ("B2M−/HLA-E+/IL15/IL15Rα+"; IL15/IR15α-P2A-HLA-E trimer knock-in, B2M Null hPSC) derived iNK cells when administered exogenous IL15 or not administered exogenous IL 15. Cells were administered SCF, Flt3L, IL7, and IL15 ("4"), SCF, Flt3L, and IL7 ("3/−IL15−"), no cytokines ("0"); or only IL15 ("IL15") on day 0 and day 9.

Figure 25A:
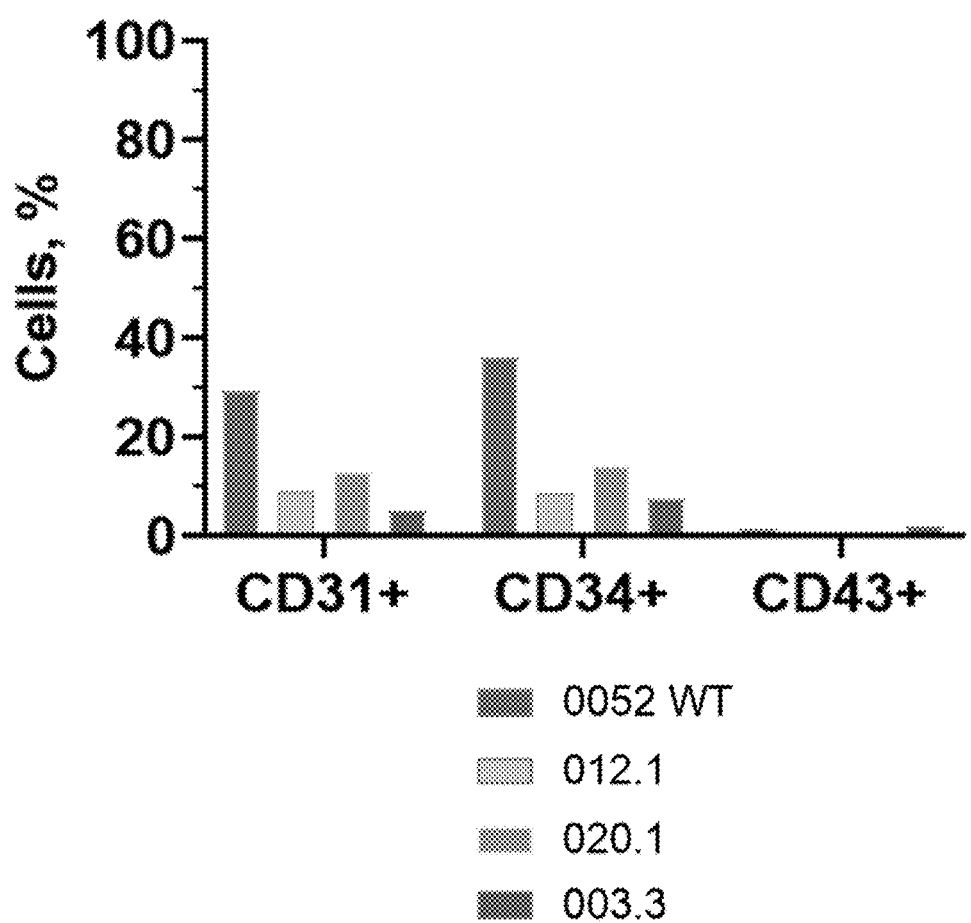
Figure 25B:
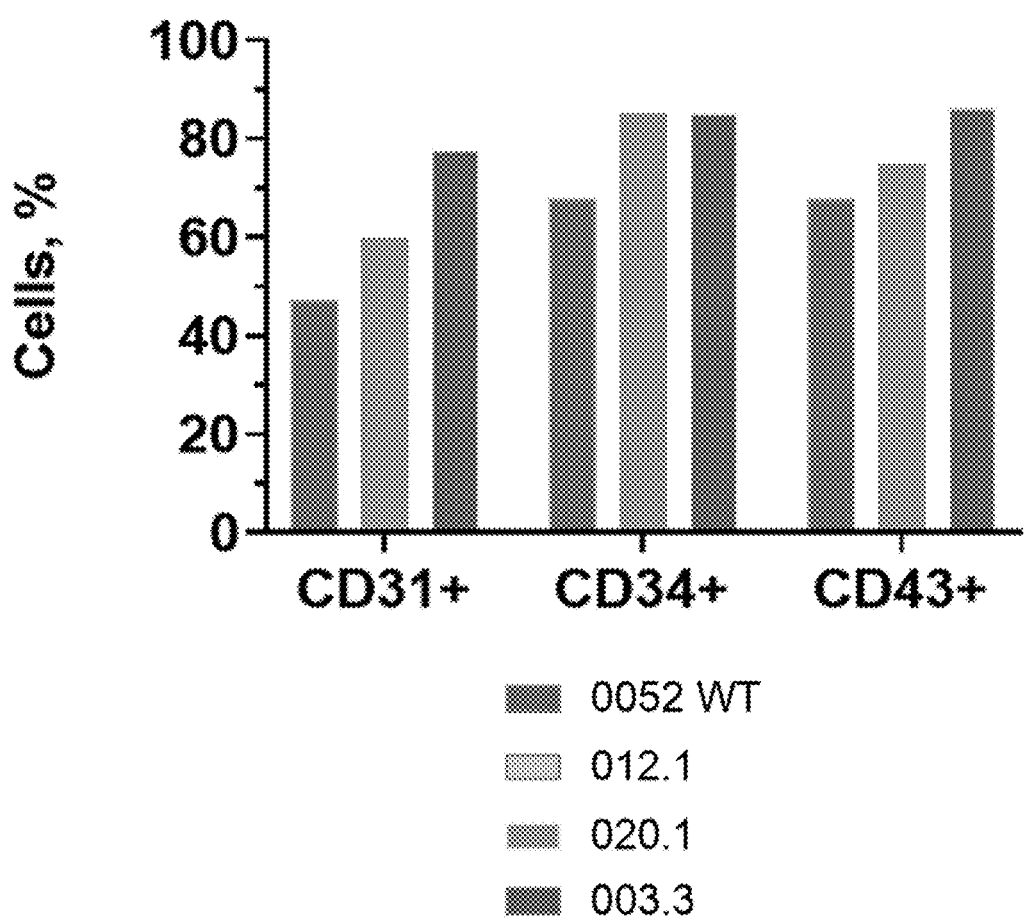

FIGS. 25A and 25B show CD31/CD34/CD45 expression profiles in aggregates after 10 days (FIG. 25A) or 14 days (FIG. 25B) of differentiation. Cell were differentiated from WT cells, IL15/IR15α-P2A-HLA-E trimer KI, BCMA CAR KI, CIITA Null, B2M Null, ADAM17 Null cells ("012.1") cells, IL15/IR15α-P2A-HLA-E trimer KI, BCMA CAR KI, CIITA Null, B2M Null, ADAM17 Null, FAS Null, CISH Null, REGNASE-1 Null cells ("020.1") cells, and IL15/IR15α-P2A-HLA-E KI, B2M null ("003.3") cells.

Figure 26:
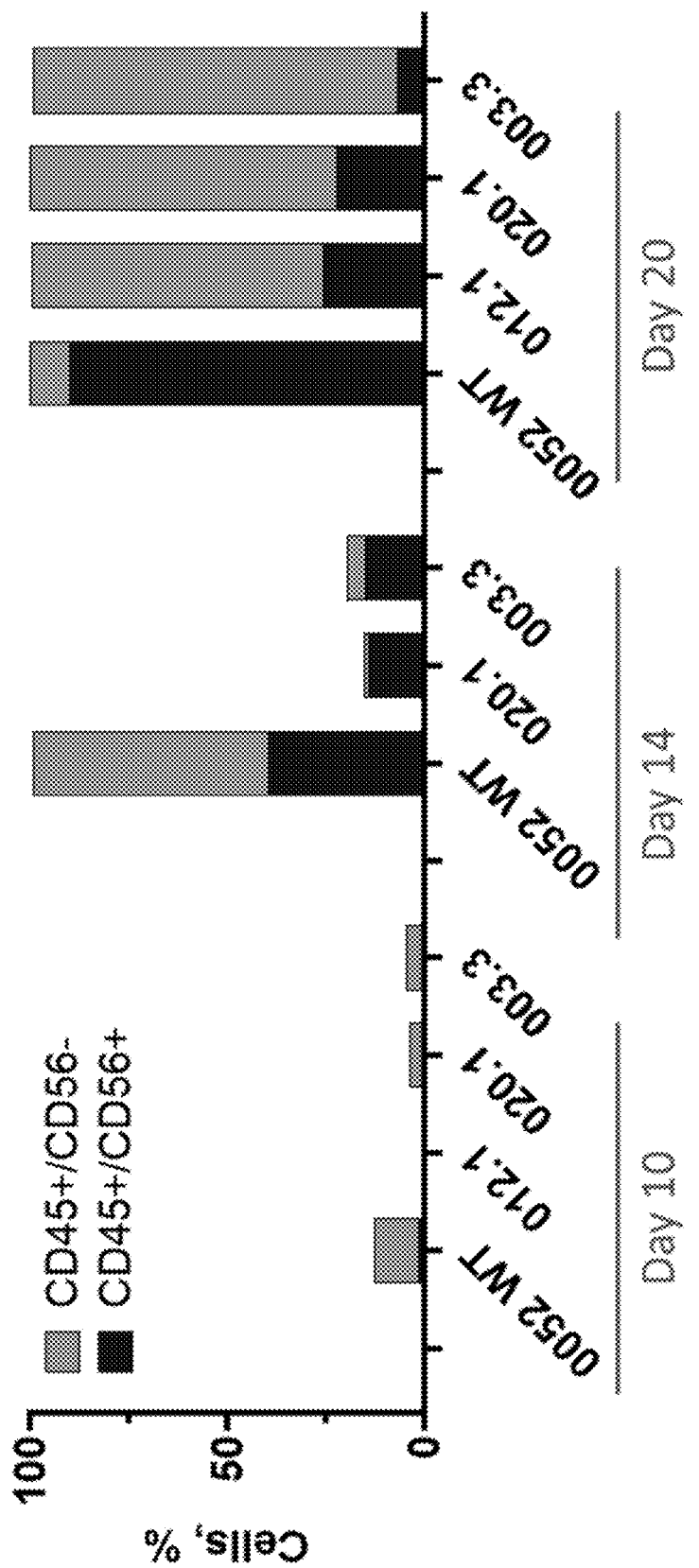

FIG. 26 present CD45/CD56 expression profiles in aggregates after 10 days, 14 days, or 20 days of differentiation. Cell were differentiated from WT cells, IL15/IR15α-P2A-HLA-E trimer KI, BCMA CAR KI, CIITA Null, B2M Null, ADAM17 Null cells ("012.1") cells, IL15/IR15α-P2A-HLA-E trimer KI, BCMA CAR KI, CIITA Null, B2M Null, ADAM17 Null, FAS Null, CISH Null, REGNASE-1 Null cells ("020.1") cells, and IL15/IR15α-P2A-HLA-E KI, B2M null ("003.3") cells.

Figure 27A:
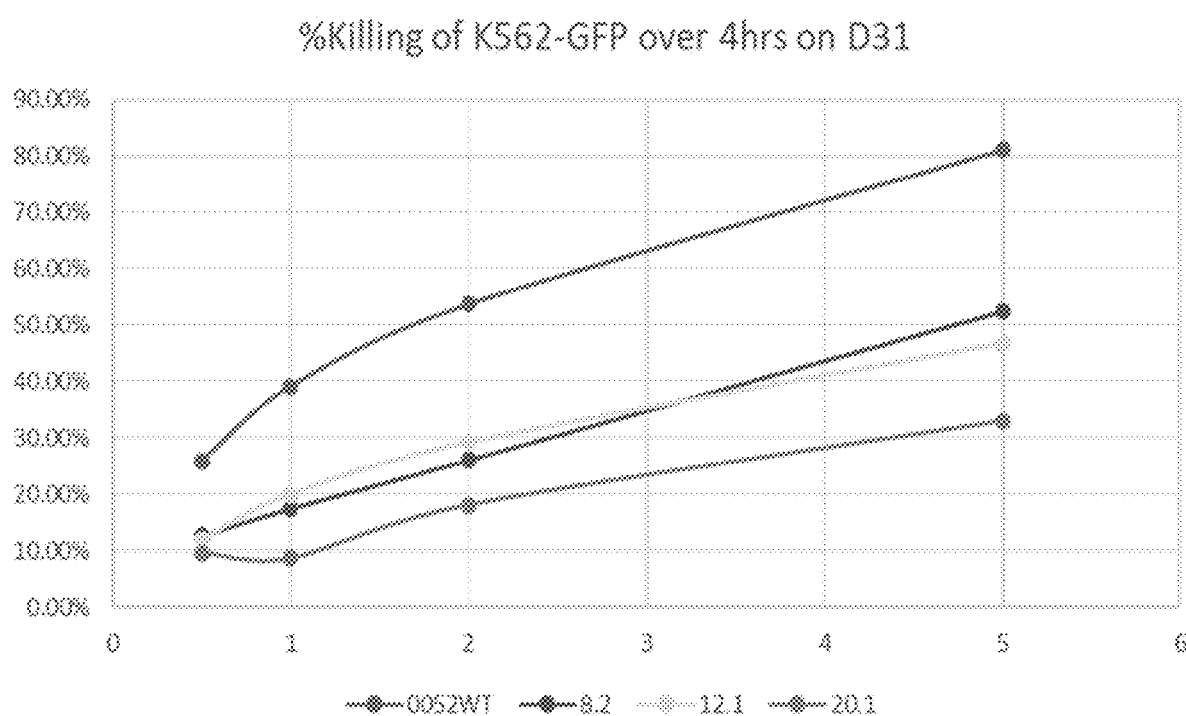
Figure 27B:
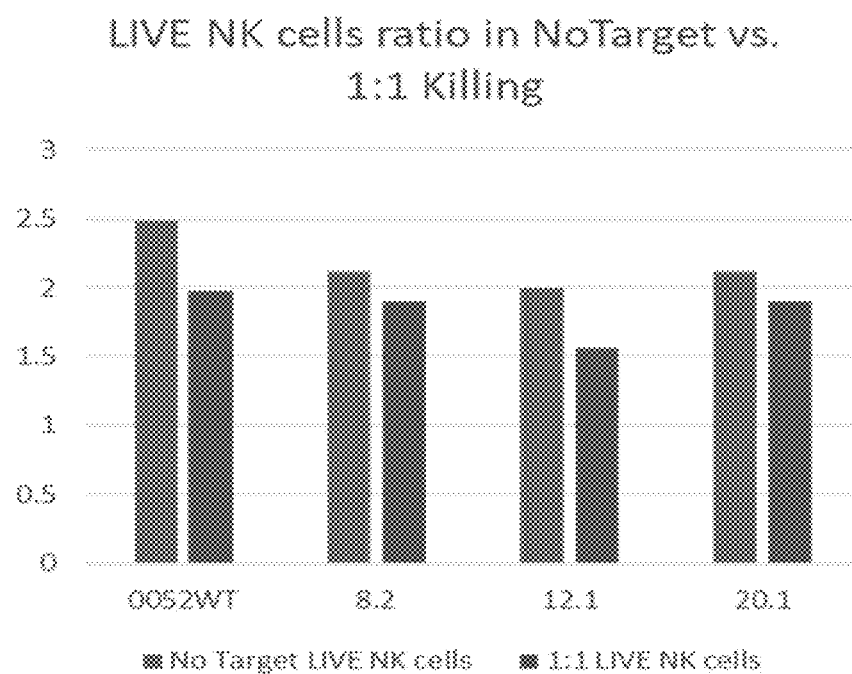

FIG. 27A shows the percent of killing of K562-GFP cells over 4 hours on Day 31 and FIG. 27B presents live NK cell ratios in NoTarget vs. 1:1 Killing in cells differentiated from WT cells, IL15/IR15α fusion-P2A-HLA-E KI into B2M and BCMA CAR into CIITA ("8.2") cells, IL15/IR15α fusion-P2A-HLA-E KI into B2M, BCMA CAR into CIITA, and ADAM17 KO ("12.1") cells, and IL15/IR15α fusion-P2A-HLA-E KI into B2M, BCMA CAR into CIITA, ADAM17 KO, FAS KO, CISH KO, and REGNASE-1 KO ("20.1") cells.

Figure 28A:
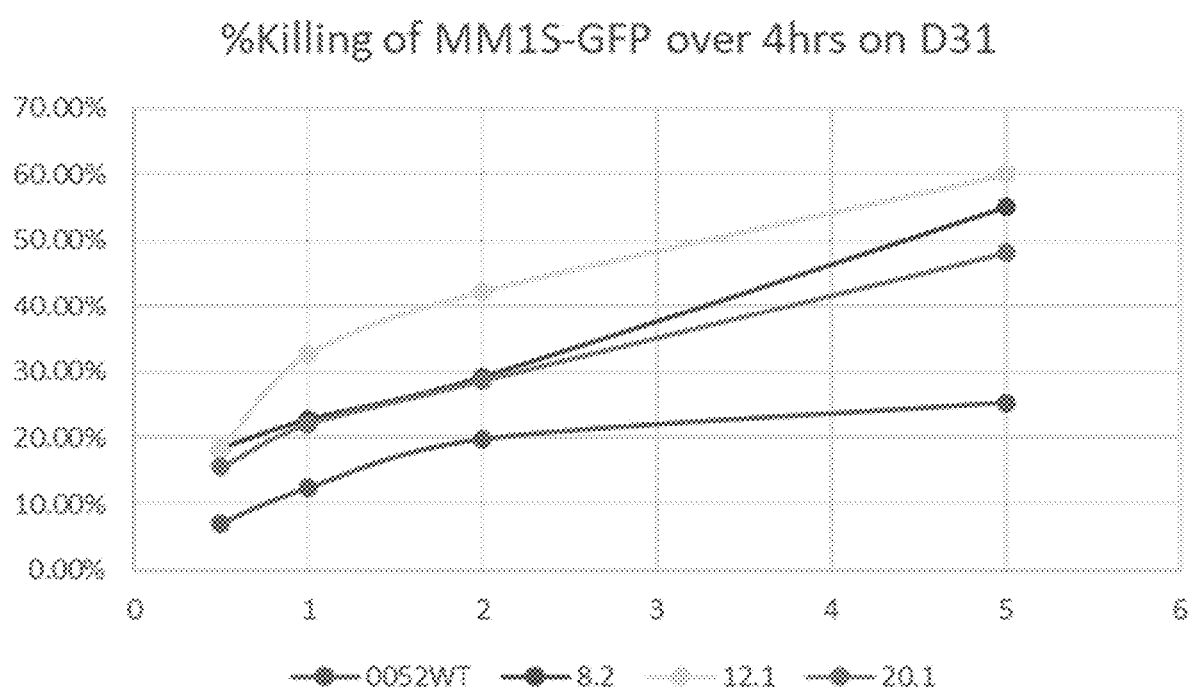
Figure 28B:
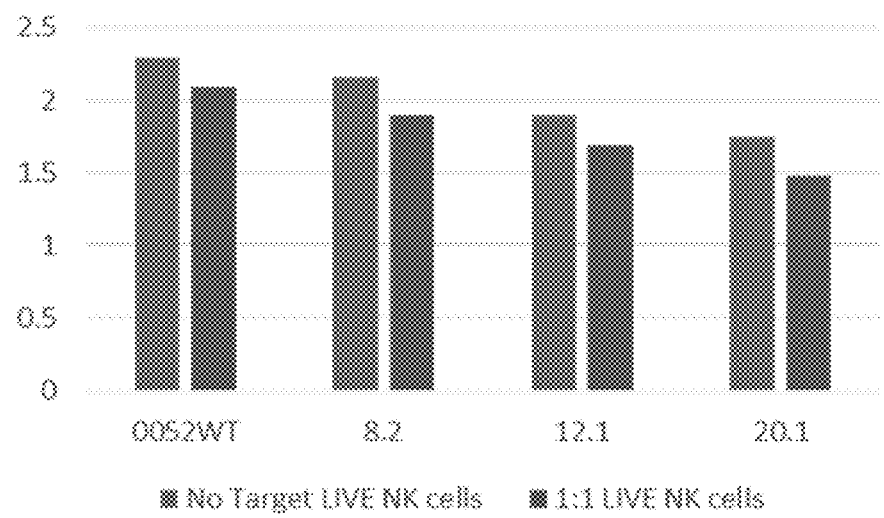

FIG. 28A shows the percent of killing of MM1S-GFP cells over 4 hours on Day 31 and FIG. 28B presents live NK cell ratios in NoTarget vs. 1:1 Killing in cells differentiated from WT cells, IL15/IR15α fusion-P2A-HLA-E KI into B2M and BCMA CAR into CIITA ("8.2") cells, IL15/IR15α fusion-P2A-HLA-E KI into B2M, BCMA CAR into CIITA, and ADAM17 KO ("12.1") cells, and IL15/IR15α fusion-P2A-HLA-E KI into B2M, BCMA CAR into CIITA, ADAM17 KO, FAS KO, CISH KO, and REGNASE-1 KO ("20.1") cells.

Figure 29A:
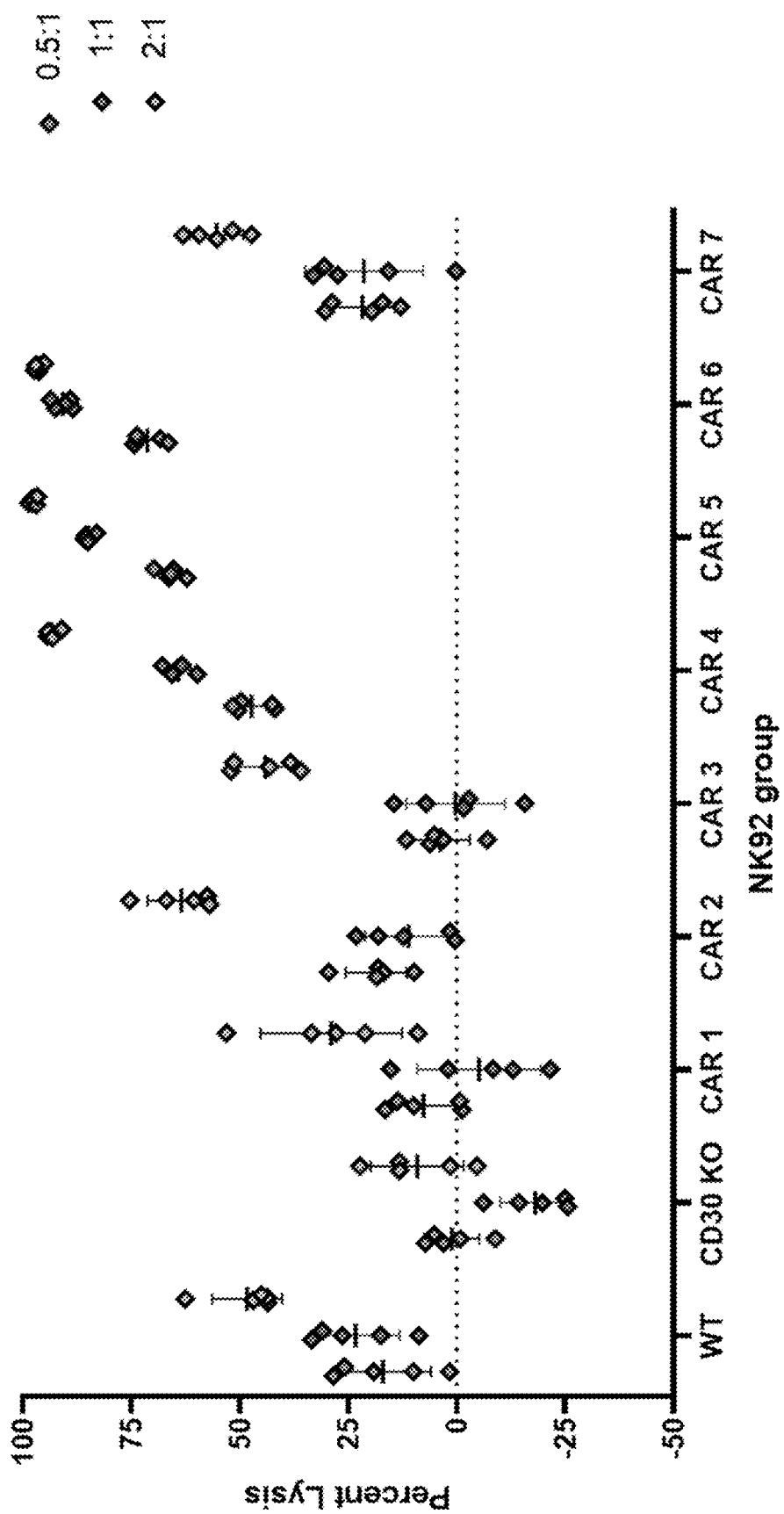
Figure 29B:
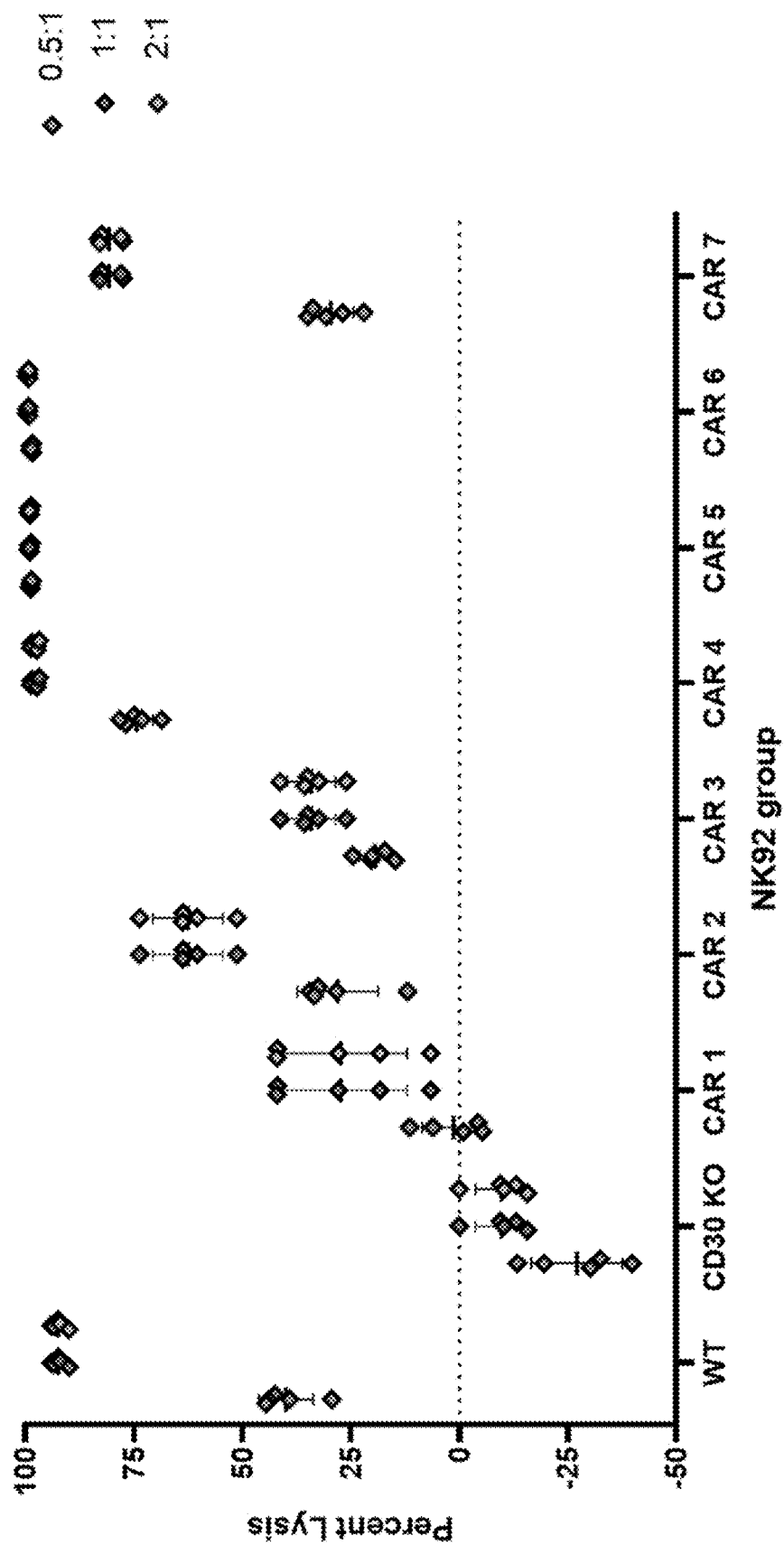

FIG. 29A shows killing of L428 cells after 4 hours and FIG. 29B shows killing of L428 cells after 24 hours by the indicated NK92 cells.

Figure 30A:
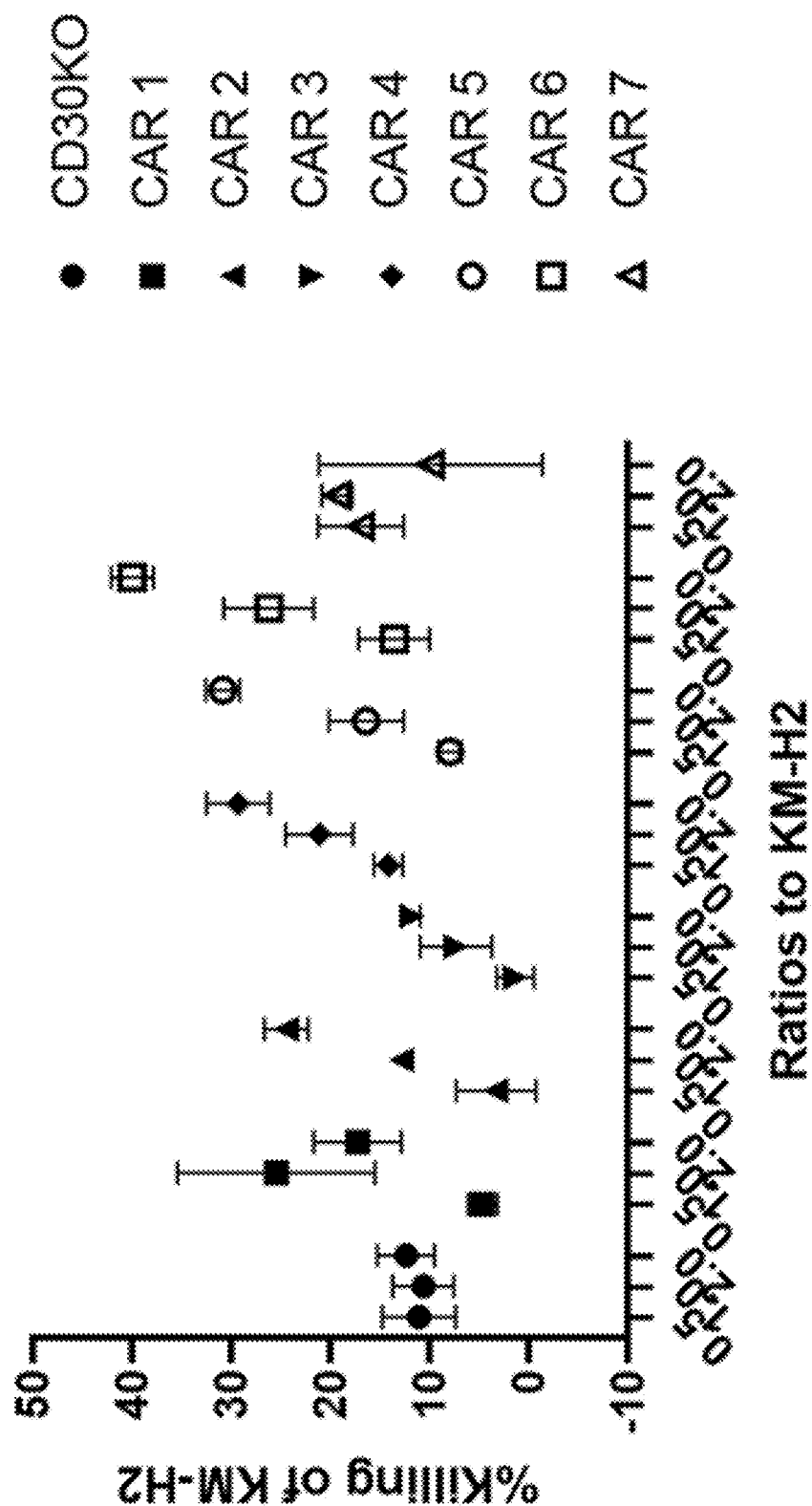
Figure 30B:
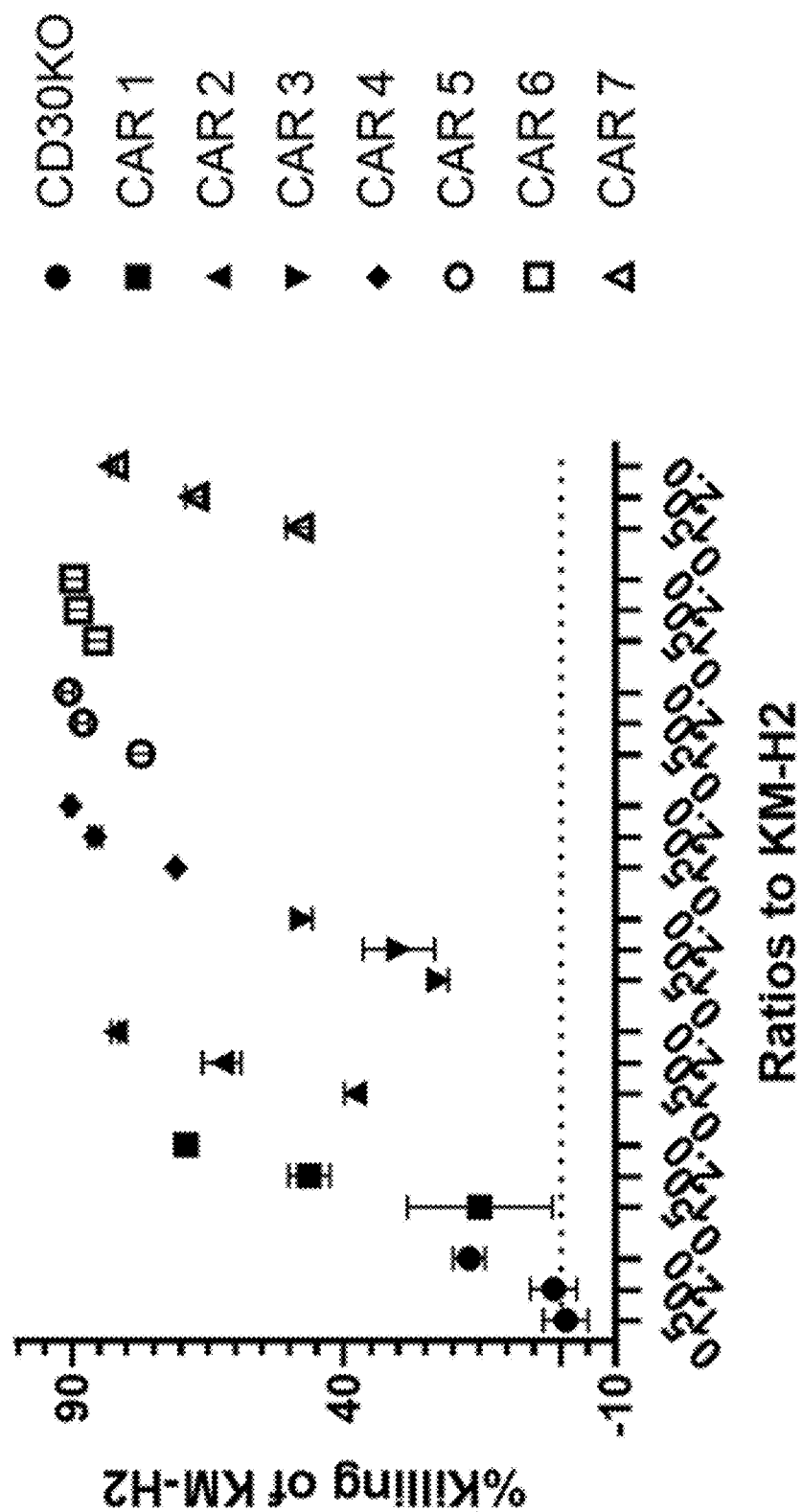

FIG. 30A shows killing of KM-H2 cells after 4 hours and FIG. 30B shows killing of KM-H2 cells after 24 hours by the indicated NK92 cells.

Figure 31:
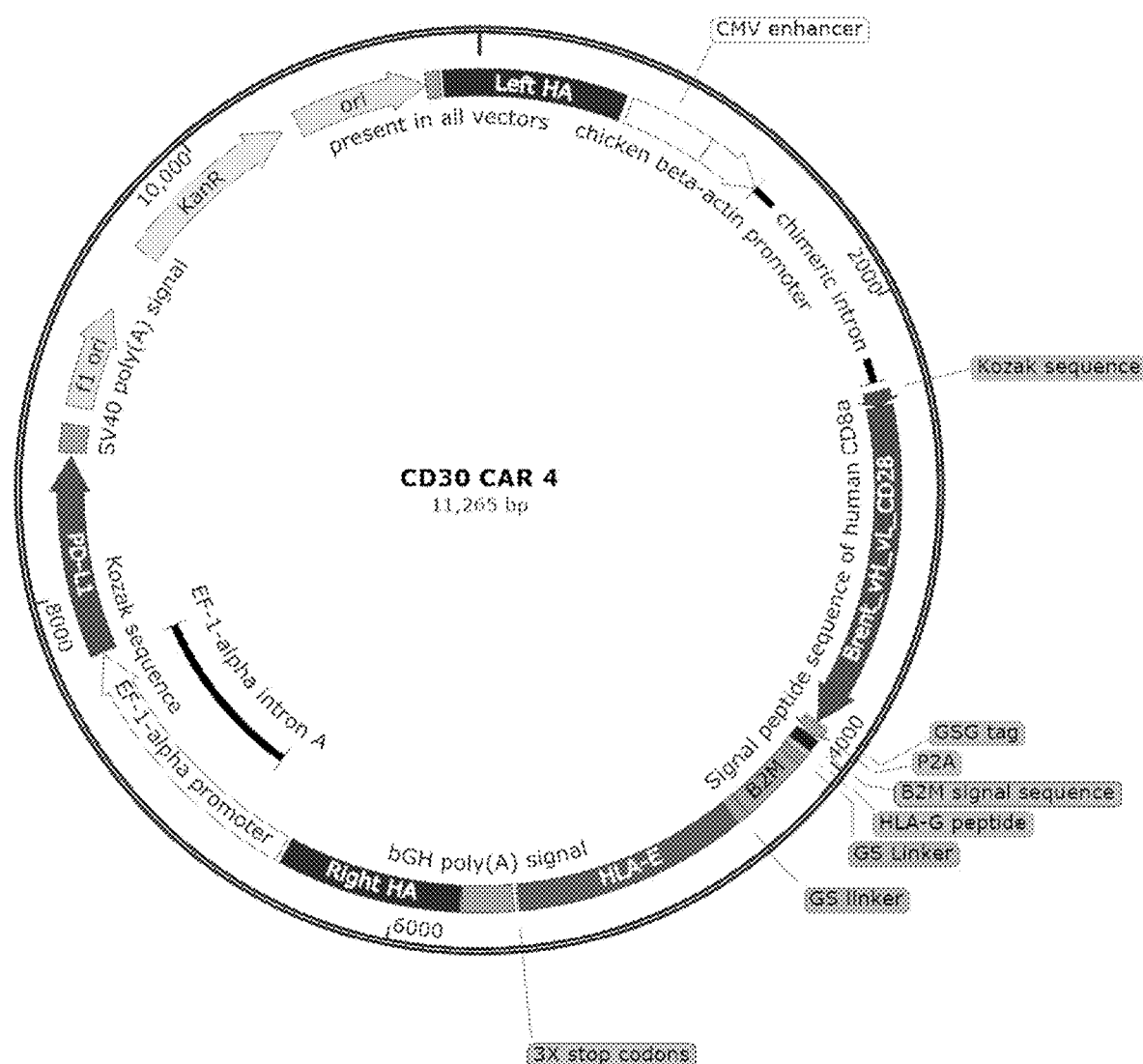

FIG. 31 presents the plasmid map of CD30 CAR 4-P2A-HLA-E trimer knock-in and CIITA knock-out.

Figure 32:
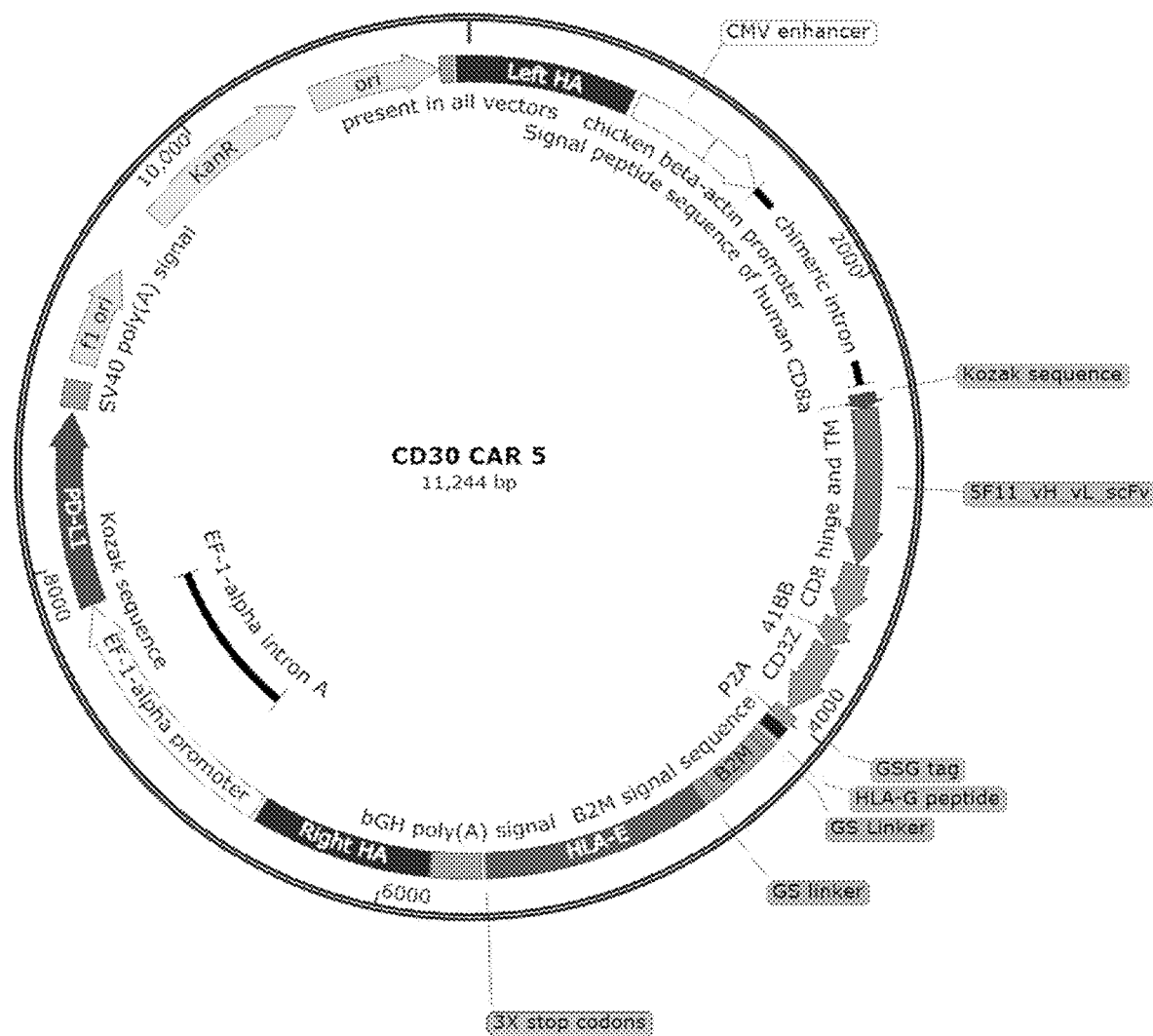

FIG. 32 presents the plasmid map of CD30 CAR 5-P2A-HLA-E trimer knock-in and CIITA knock-out.

Figure 33:
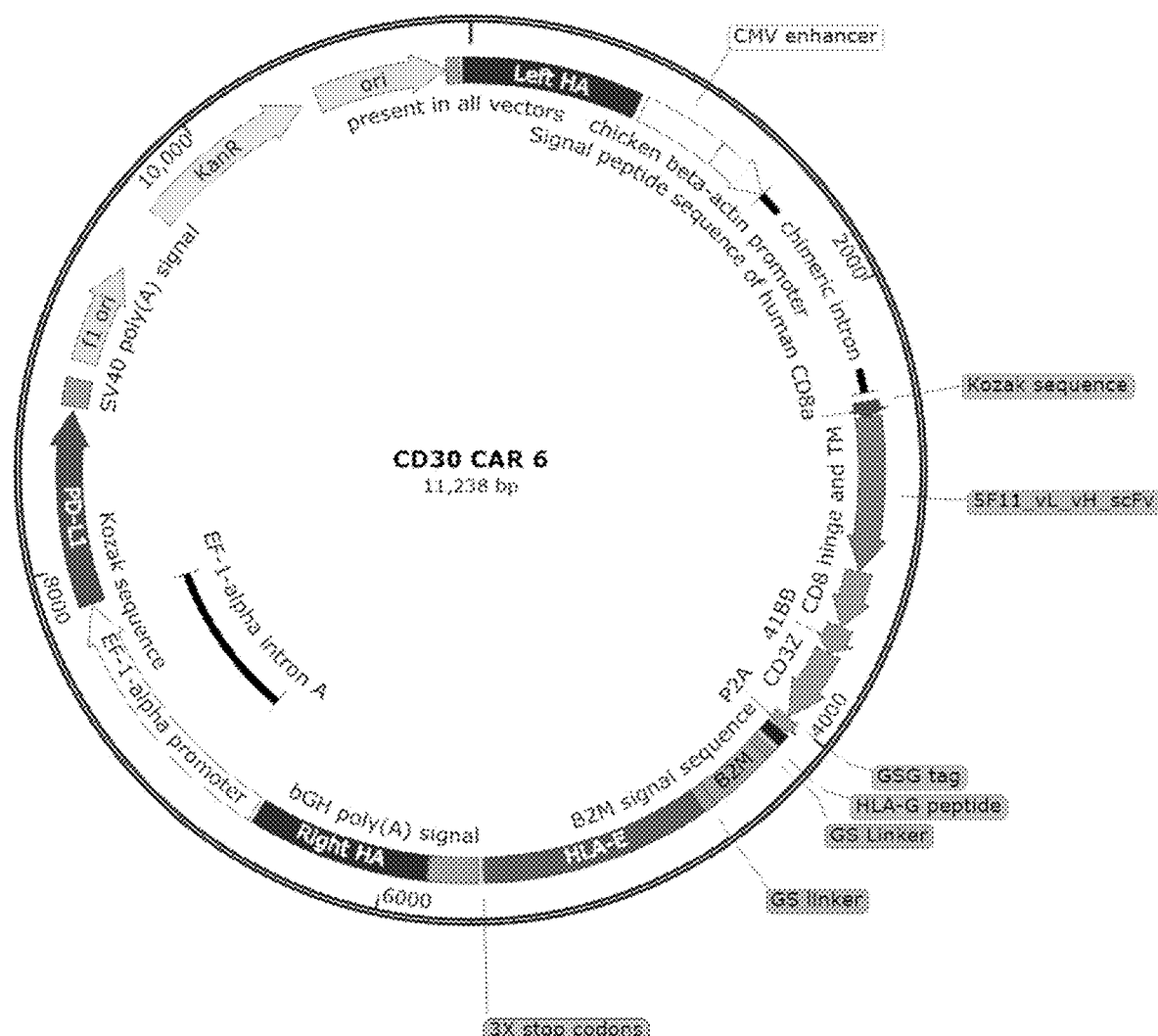

FIG. 33 presents the plasmid map of CD30 CAR 6-P2A-HLA-E trimer knock-in and CIITA knock-out.

Figure 34:
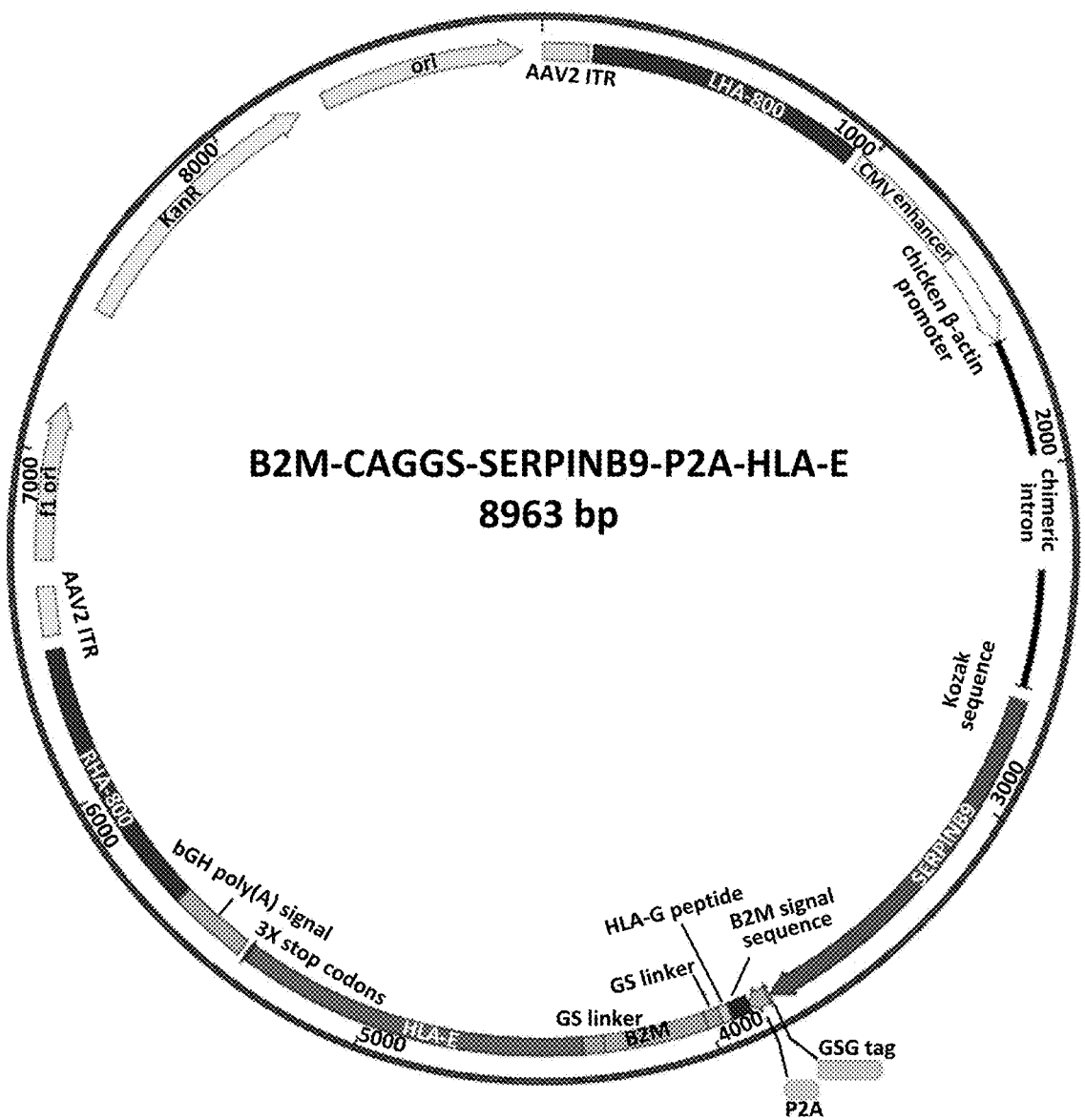

FIG. 34 presents a map of the B2M-CAGGS-SERPINB9-P2A-HLA-E donor plasmid.

Figure 35:
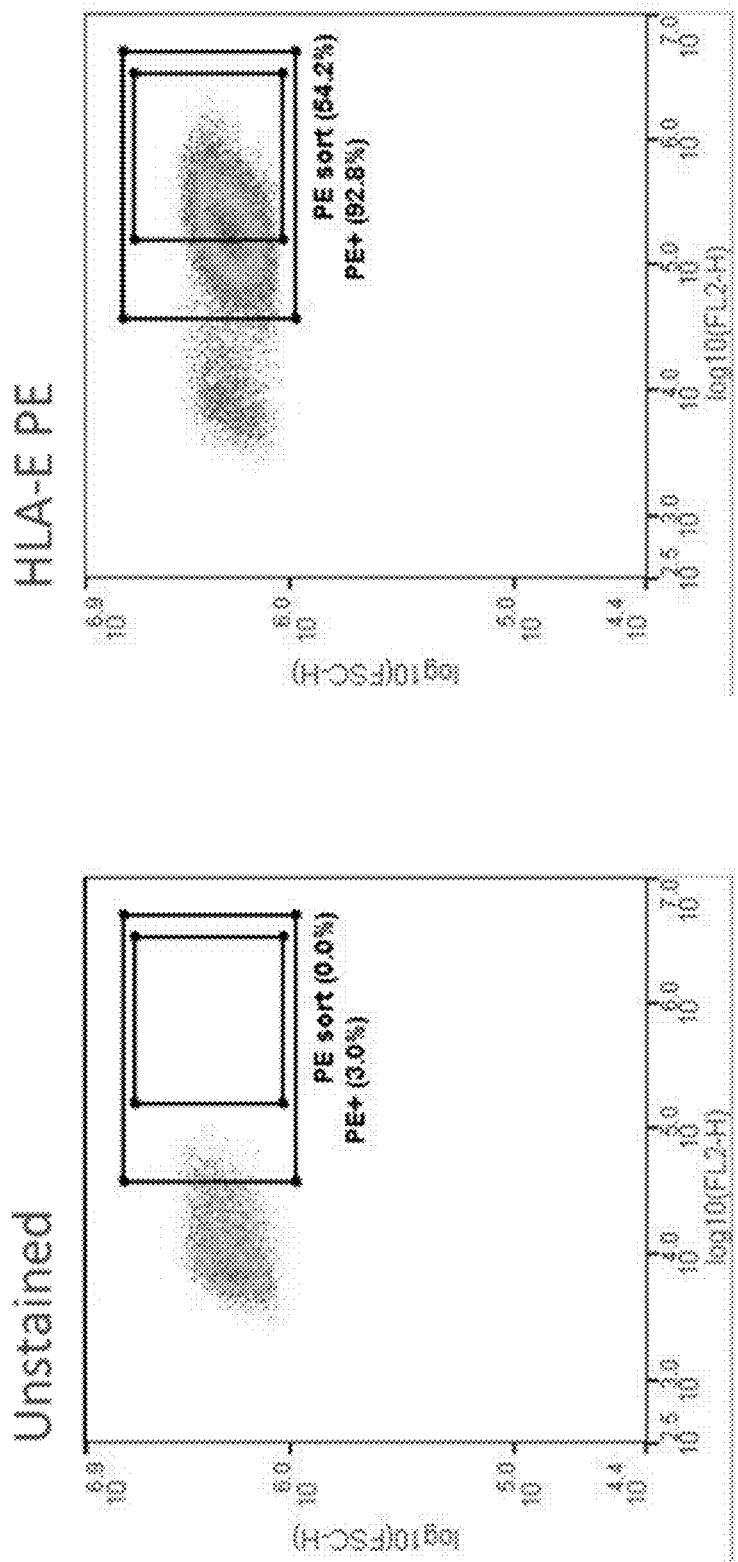

FIG. 35 shows FACS plots generated during the single cell sorting of the B2M-SERPINB9-P2A-HLA-E bulk population previously enriched by MACS.

Figure 36:
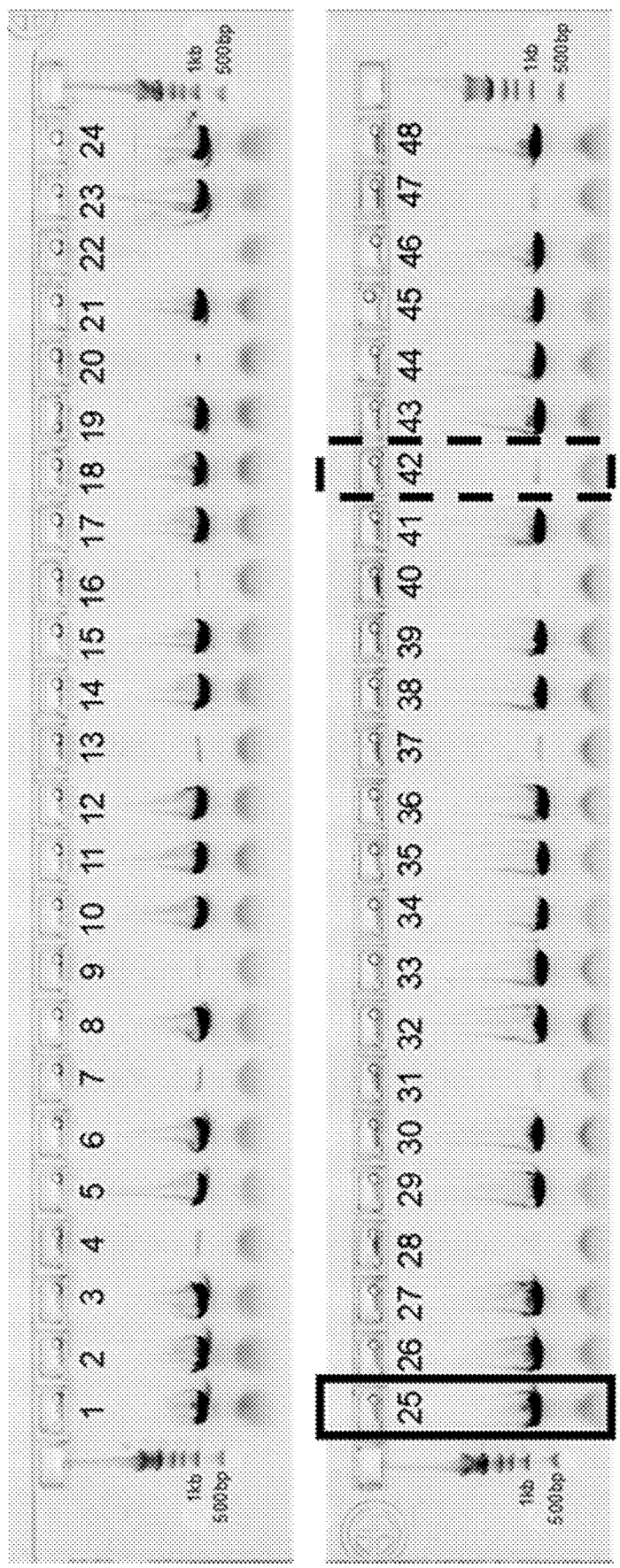

FIG. 36 presents PCR analysis of SERPINB9/HLA-E KI at the B2M gene locus. The gel shows PCR amplification of B2M region of the genome with the 3' primer stationed outside the knock-in (KI) site (not present in the plasmid donor) and the 5' primer stationed inside the KI-only region. Presence of a 1.1 kilo base (kb) band indicates successful integration of the KI construct into the B2M gene locus, the absence of a band indicates a WT genotype.

Figure 37:
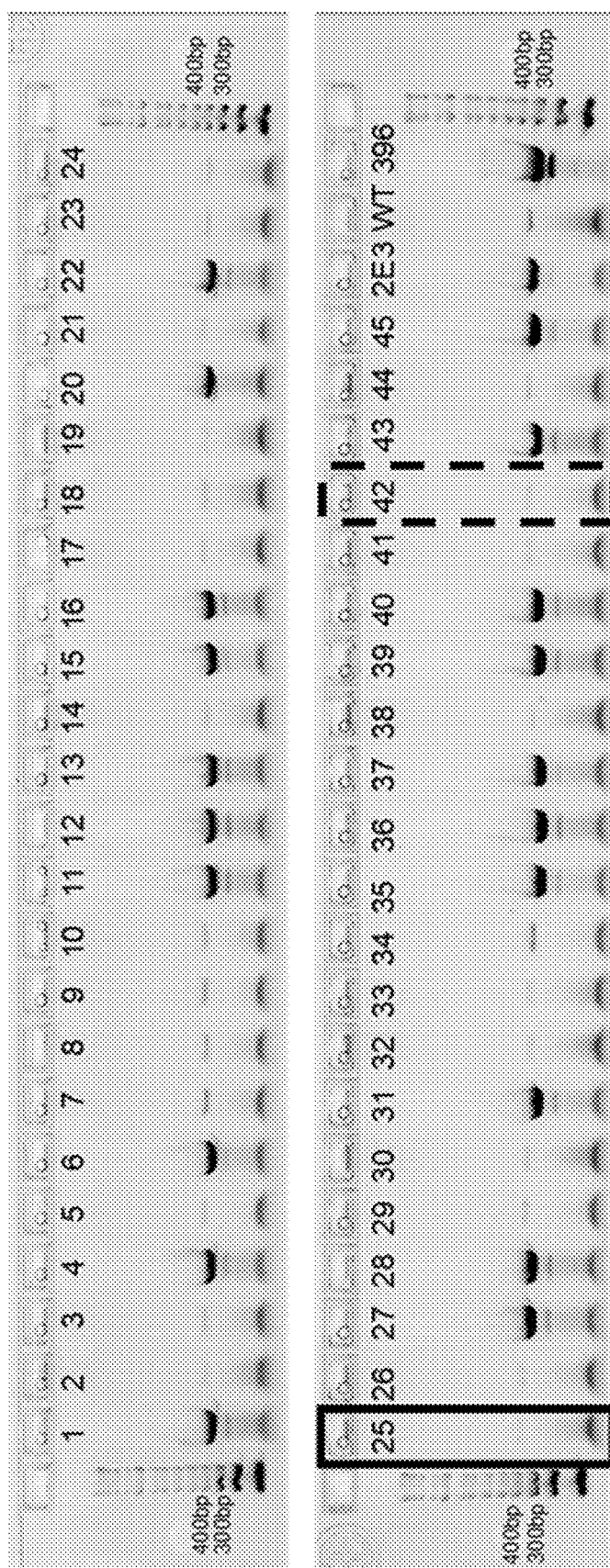

FIG. 37 shows PCR 1 analysis of random plasmid insertions during knock-in of SERPINB9/HLA-E in the B2M gene locus. PCR was performed with 5' and 3' primers that bind outside of the homology arms within the KI plasmid. Presence of a 340 base pair (bp) band indicates that there is random integration of the plasmid backbone within the genome, clones without bands do not have random plasmid insertion.

Figure 38:
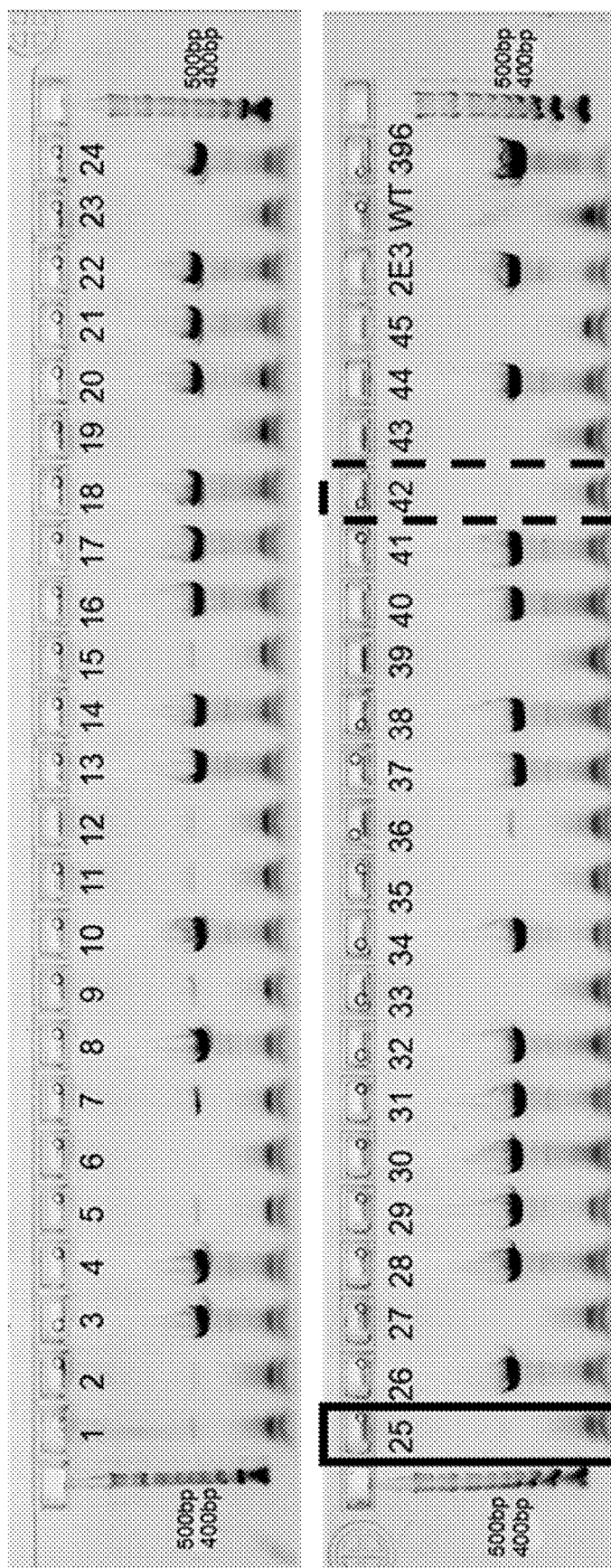

FIG. 38 shows PCR 2 analysis of random plasmid insertions during knock-in of SERPINB9/HLA-E in the B2M gene locus. PCR was performed with 5' and 3' primers that bind outside of the homology arms within the KI plasmid. Presence of a 476 bp band indicates that there is random integration of the plasmid backbone within the genome, clones without bands do not have random plasmid insertion.

Figure 39:
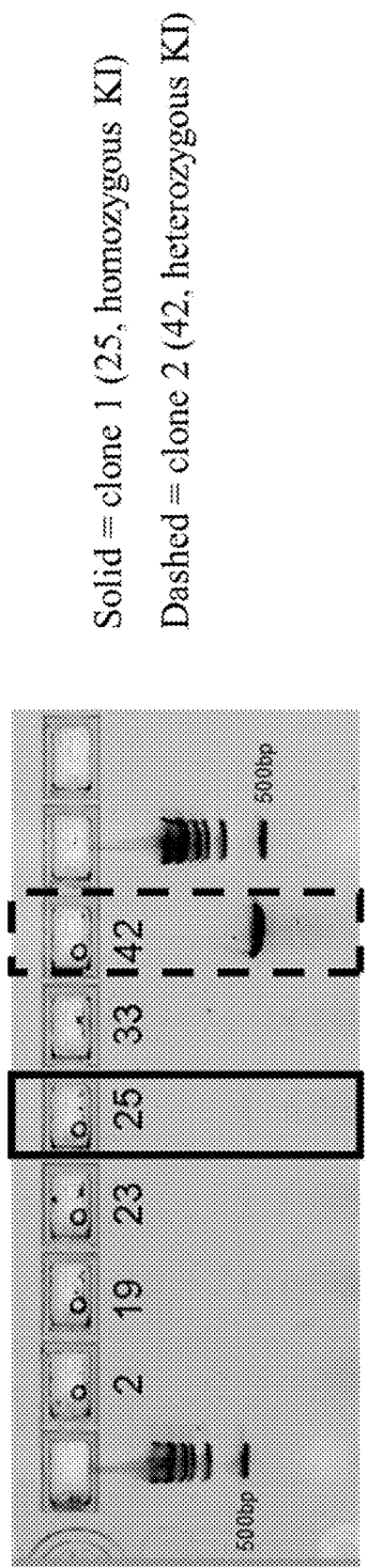

FIG. 39 shows zygosity at the B2M gene locus following knock-in of SERPINB9/HLA-E. Gel shows PCR products after amplification using primers spanning the gRNA cut site. Presence of a 573 bp band indicates a wild-type (WT) genotype which will be found in clones that are unedited or are heterozygous for the KI construct, a clone with a homozygous KI would not produce a band in this PCR because the KI size would be too large for the elongation time of this reaction.

Figure 40:
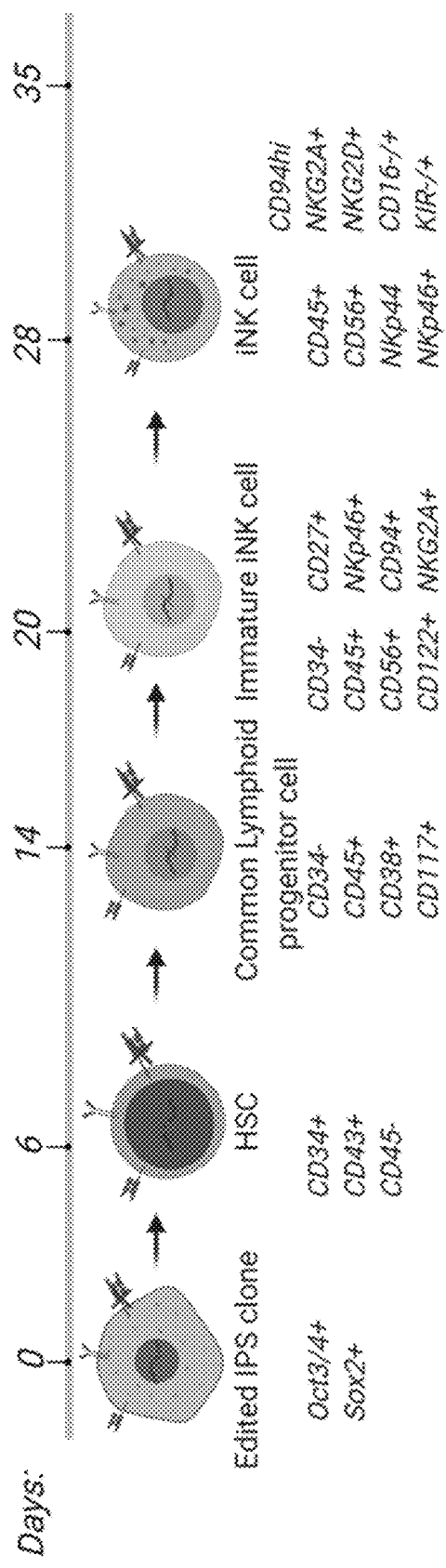

FIG. 40 presents a time course of NK cell differentiation.

Figure 41:
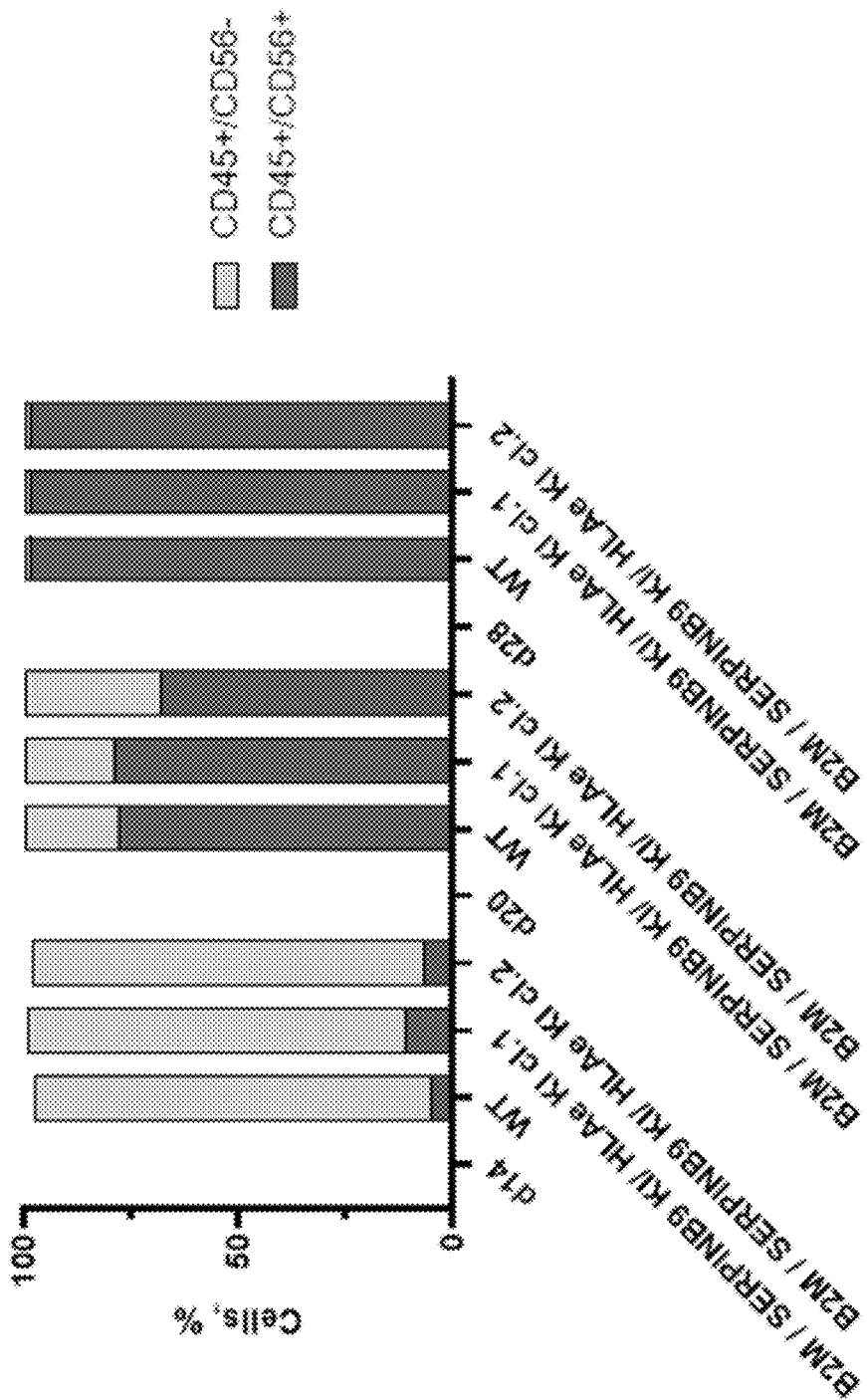

FIG. 41 shows the development of CD45+/CD56+ iNK over the differentiation time course, derived from WT or SERPINB9 KI/HLA-E KI/B2M KO clonal iPSCs.

Figure 42A:
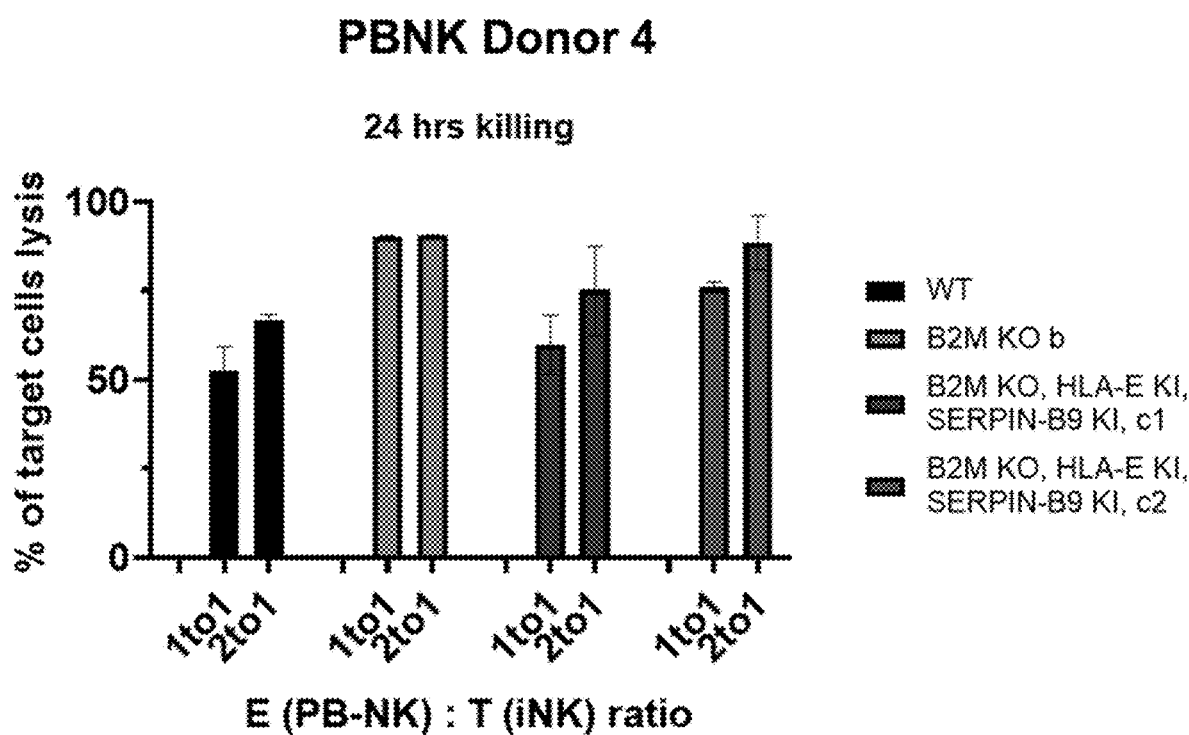

FIG. 42A presents a plot of the percentage of target (iNK) cells killed by peripheral blood NK (PB-NK) cells from PBNK donor 4. Various iNK cells were incubated with PB-NK cells at various E:T ratios for 24 hours.

Figure 42B:
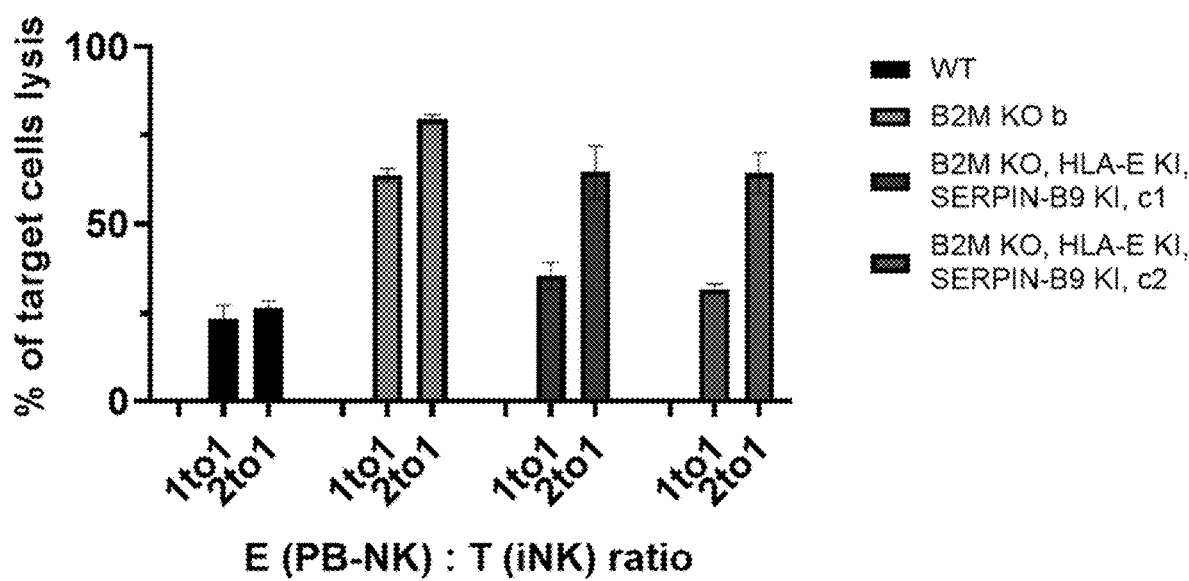

FIG. 42B shows a plot of the percentage of target iNK cells killed by PB-NK cells from PBNK donor 6. Various iNK cells were incubated with PB-NK cells at various E:T ratios for 24 hours.

Figure 42C:
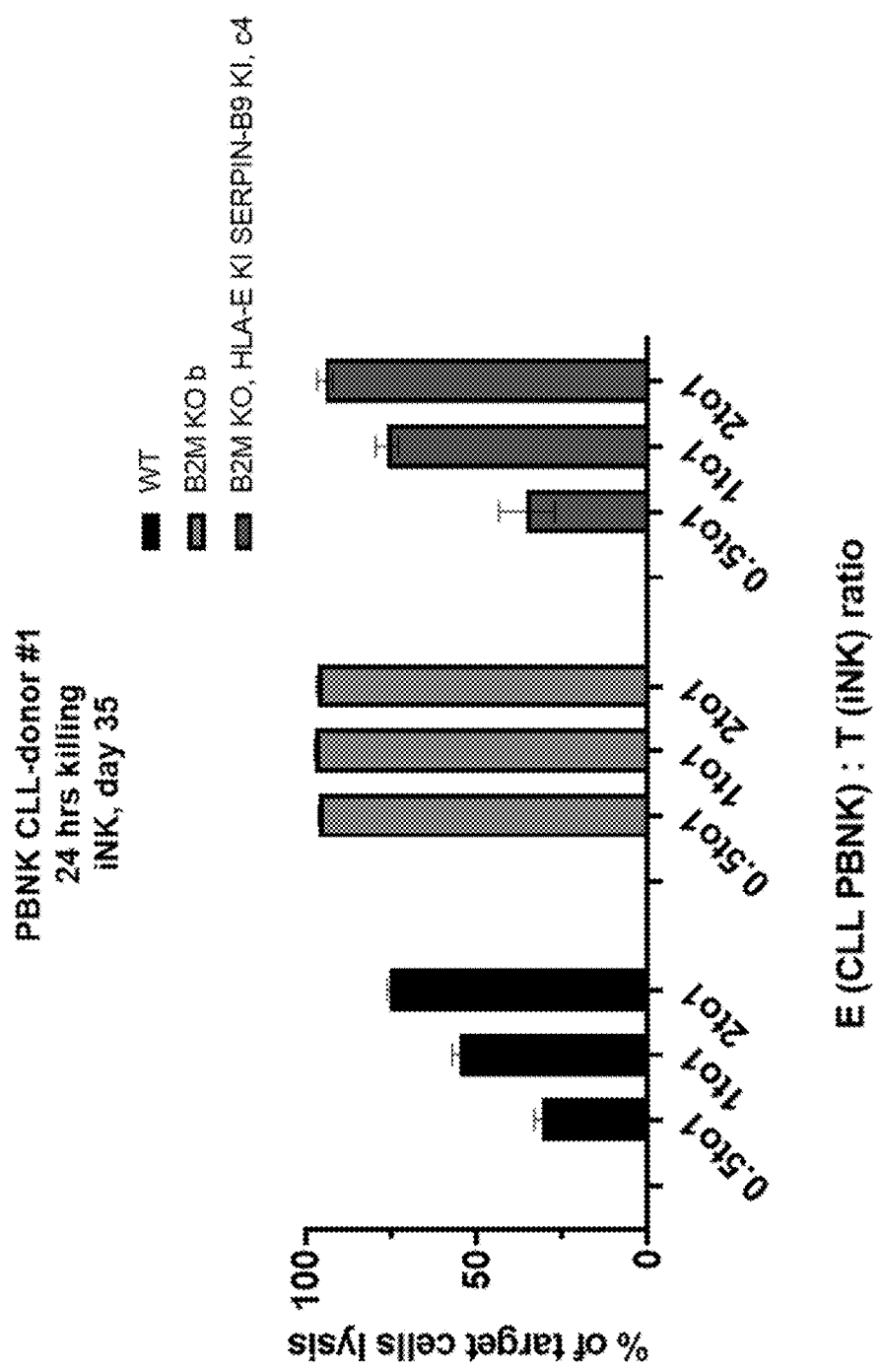

FIG. 42C shows a plot of the percentage of target iNK cells killed by PB-NK cells from PBNK-CLL donor 1. Various iNK cells were incubated with PB-NK cells at various E:T ratios for 24 hours.

Figure 42D:
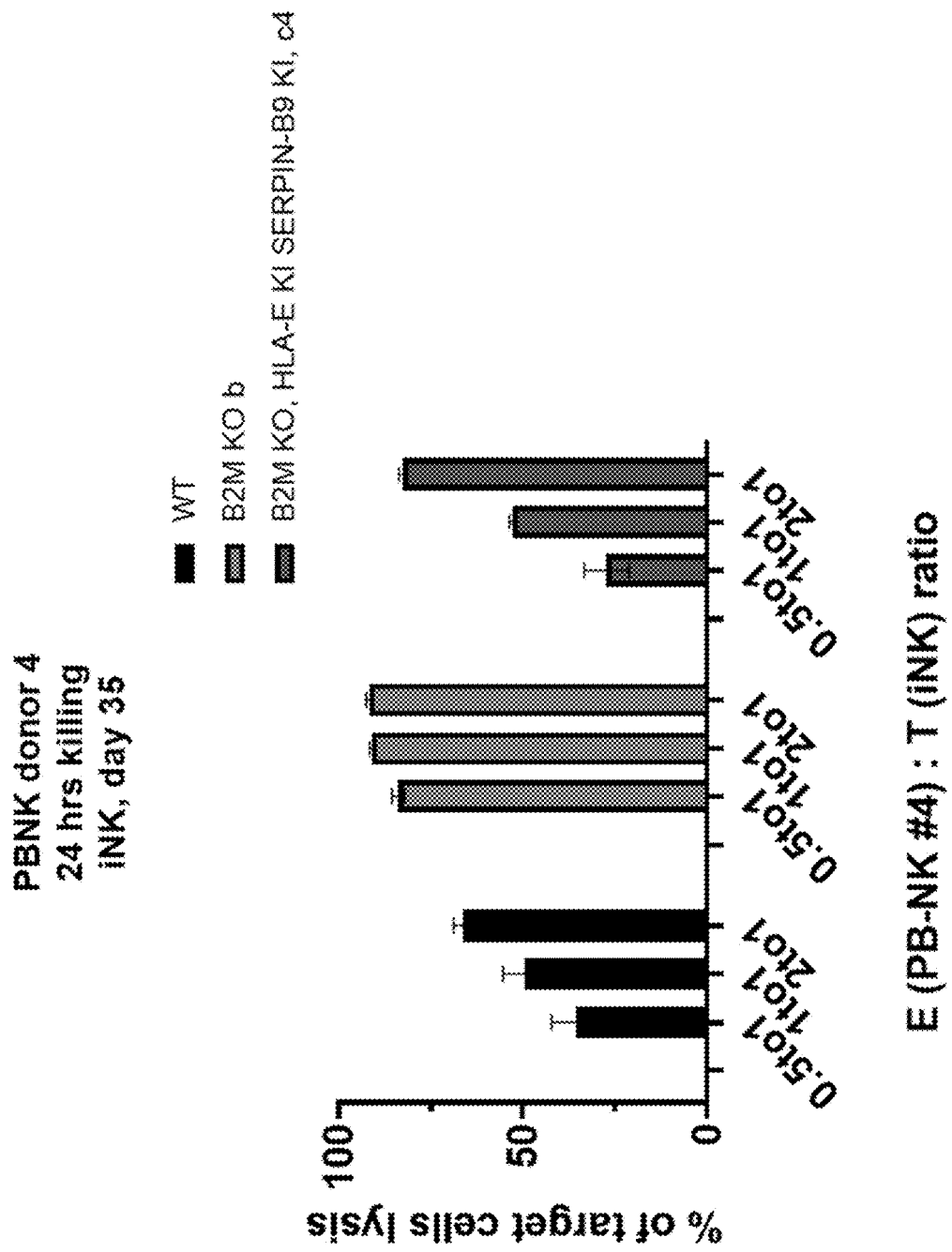

FIG. 42D shows a plot of the percentage of target iNK cells killed by PB-NK cells from PBNK donor 4. Various iNK cells were incubated with PB-NK cells at various E:T ratios for 24 hours.

Figure 42E:
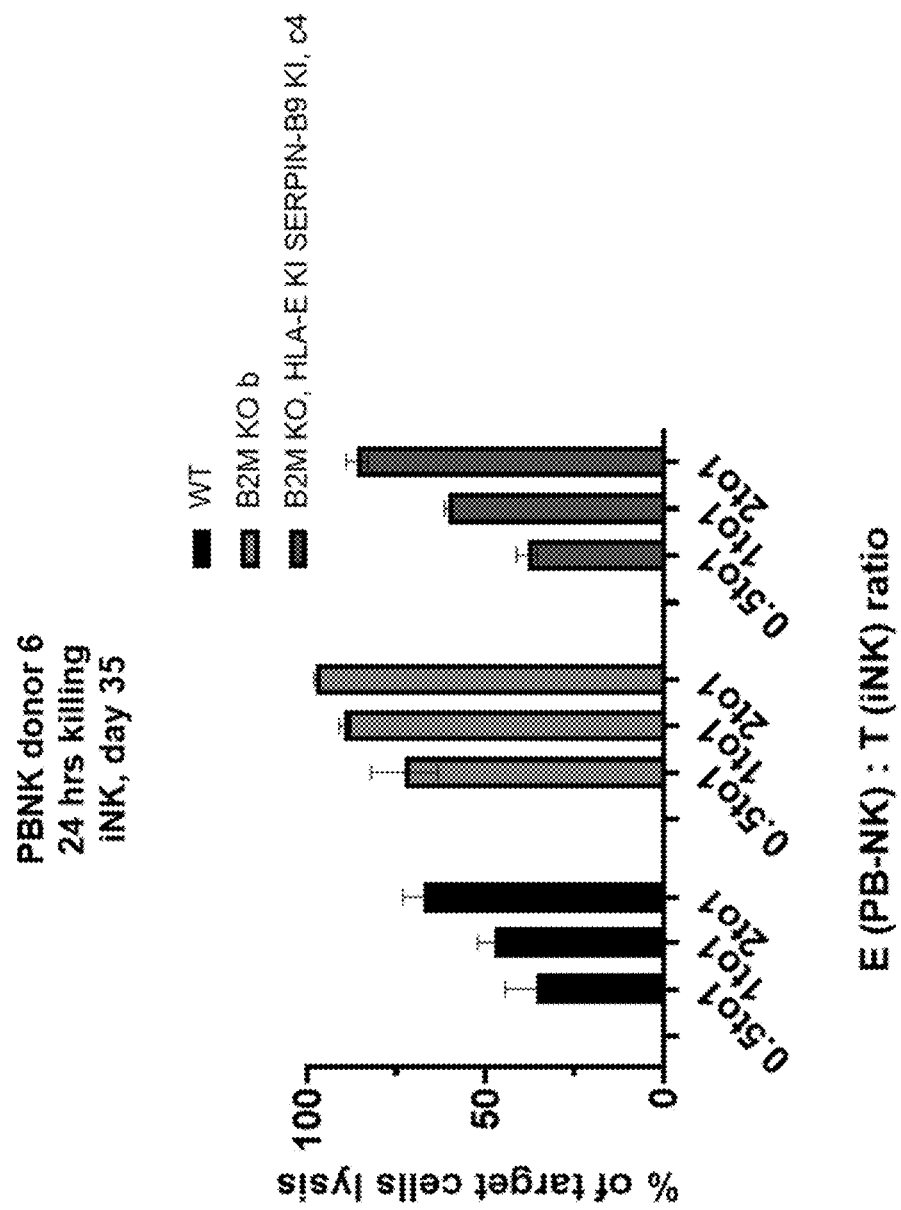

FIG. 42E shows a plot of the percentage of target iNK cells killed by PB-NK cells from PBNK donor 6. Various iNK cells were incubated with PB-NK cells at various E:T ratios for 24 hours.

Figure 43:
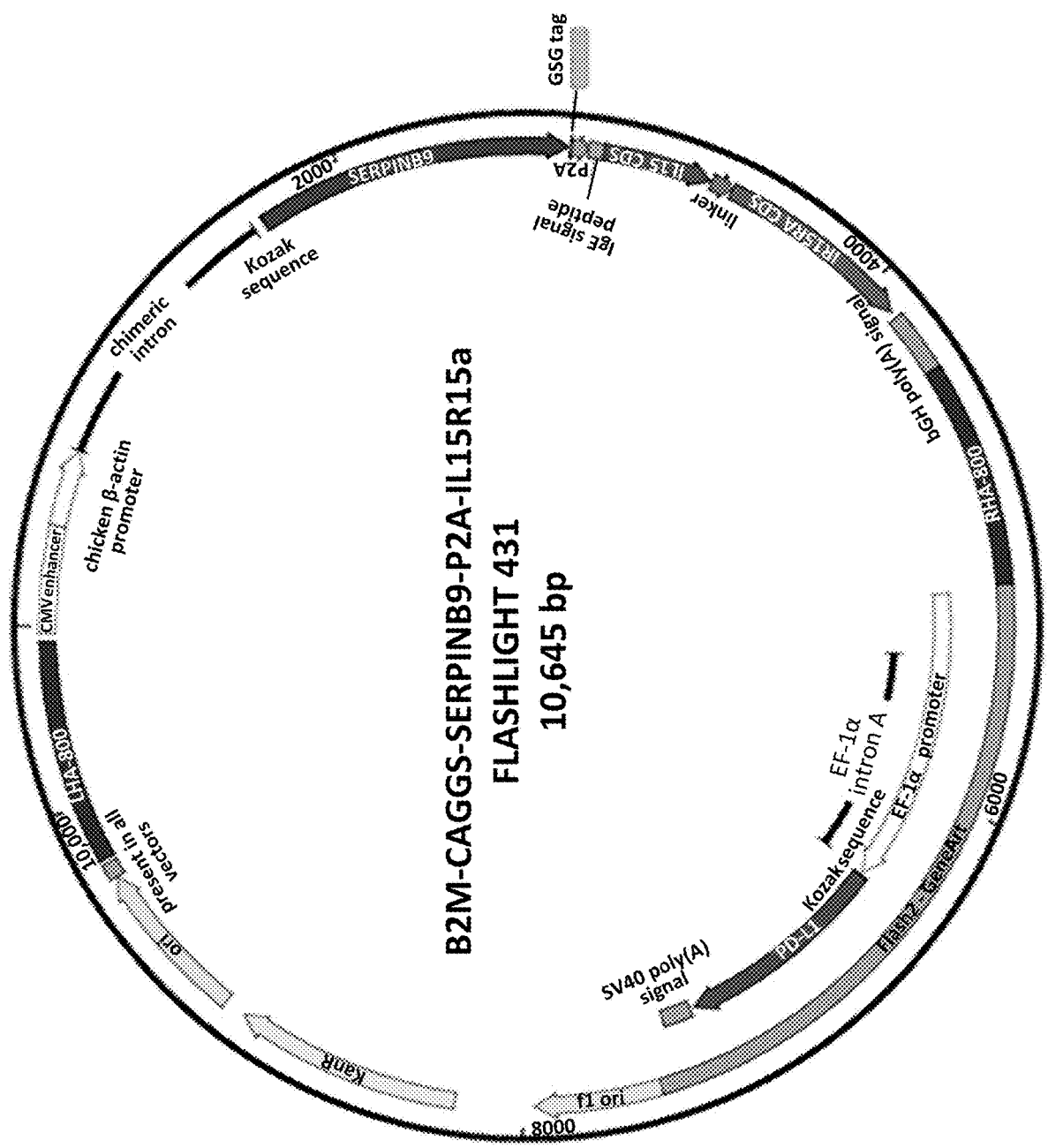

FIG. 43 presents a map the B2M-CAGGS-SERPINB9-P2A-IL15/IL15Rα fusion donor plasmid.

Figure 44:
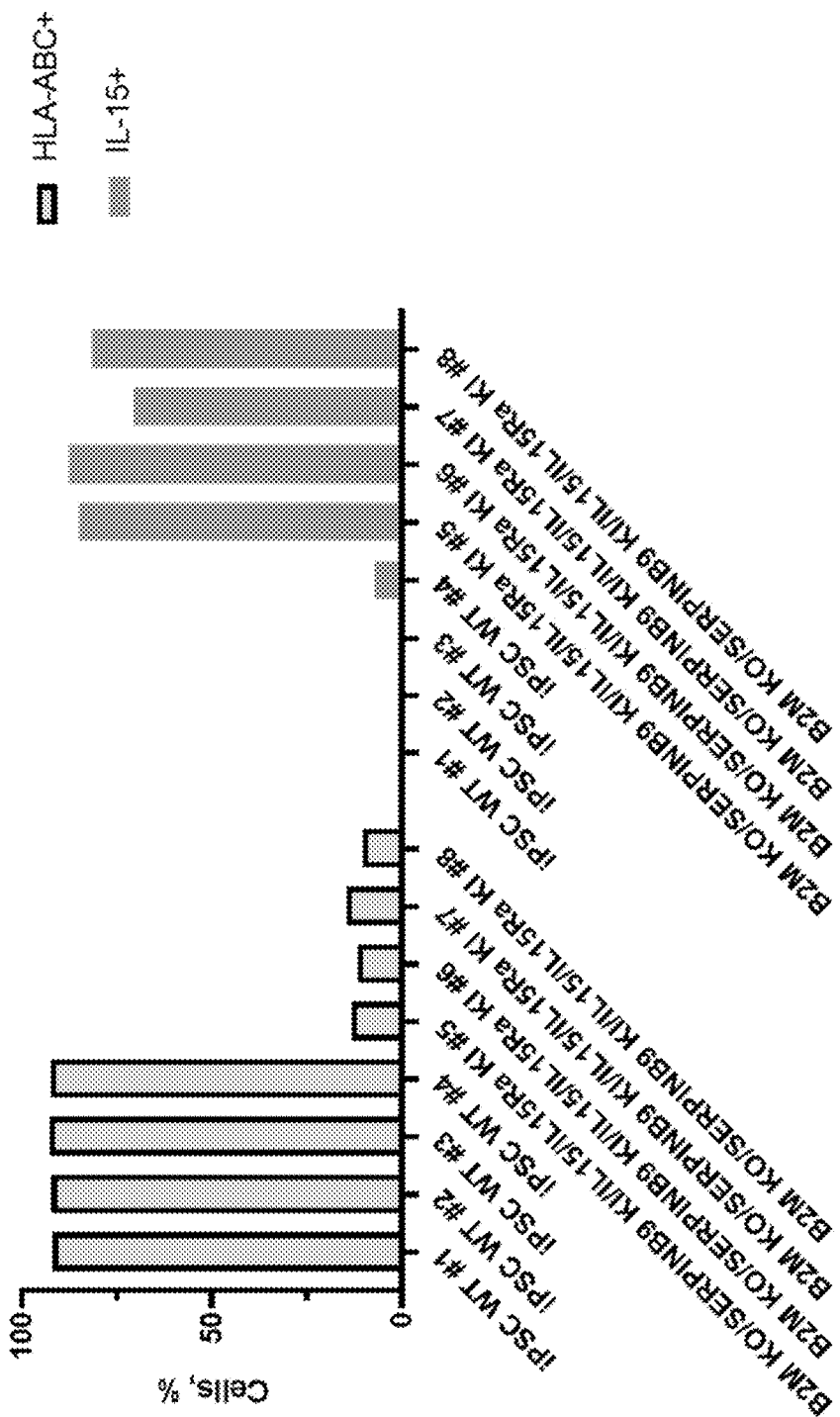

FIG. 44 shows percentage of cells in a bulk population that had HLA-ABC+ expression or IL15 surface expression. Cells were analyzed by flow cytometry.

Figure 45A:
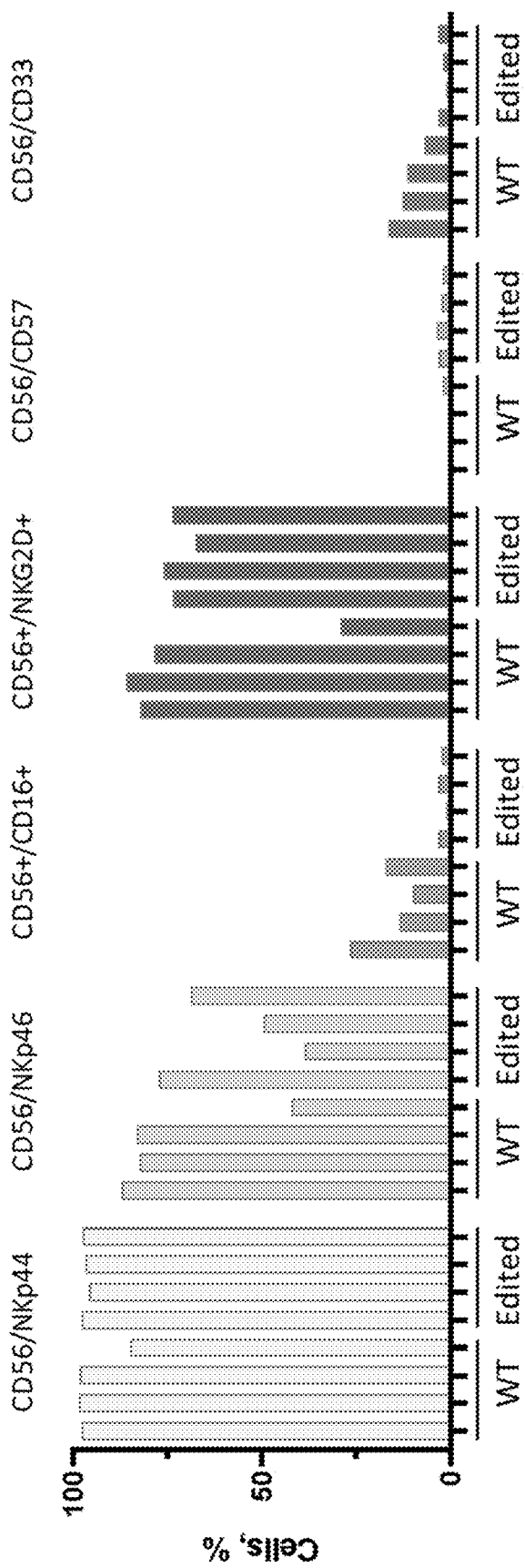
Figure 45B:
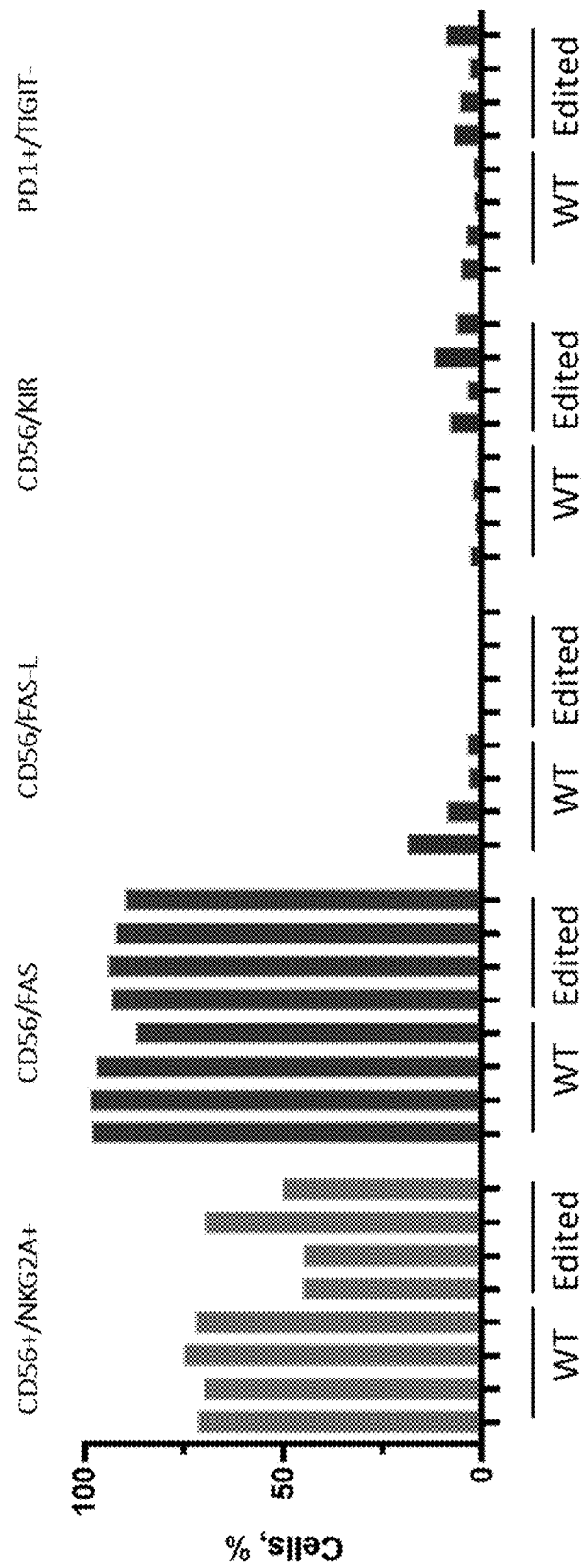

FIGS. 45A and 45B provide graphs demonstrating expression of differentiation markers in iPSC WT derived iNK cells and base edited iPSC derived iNK cells (B2M KO, SERPINB9 KI, IL15/IL15Rα KI). Cells were analyzed by flow cytometry for CD56+/NKp44+, CD56+/NKp46+, CD56+/CD16+, CD56+ NKG2D+, CD56+/CD57+, and CD56+/CD33+ (FIG. 45A) and CD56+/NKG2A+, CD56+/FAS+, CD56+/FAS-L+, CD56+/KIR+, and PD1+/TIGIT− (FIG. 45B).

Figure 46:
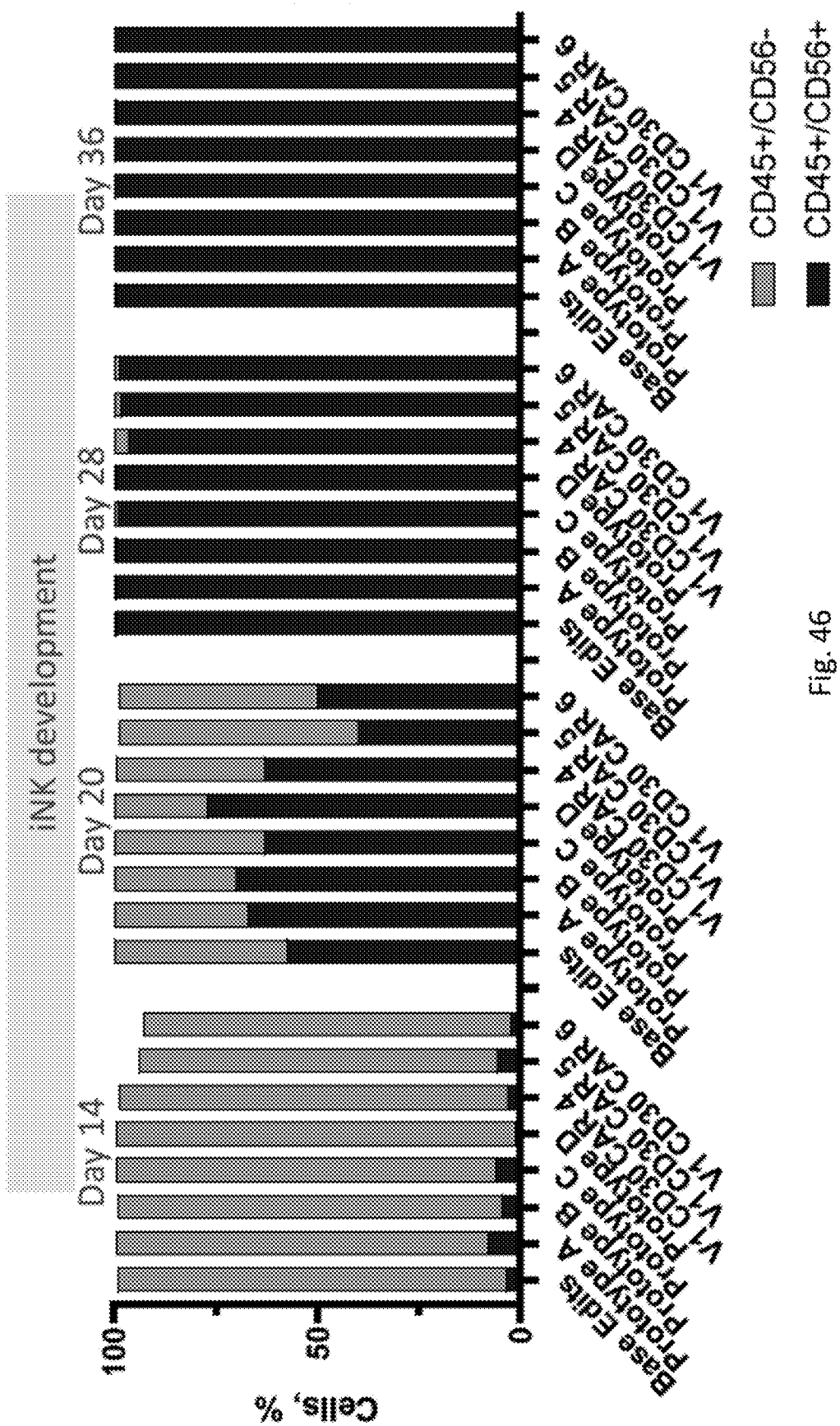

FIG. 46 presents the percentage of cells expressing of CD45 and/or CD56 at days 14, 20, 28, and 36 during differentiation of iNK cells from iPSCs with base edits (B2M KO, SERPINB9 KI, IL15/IL15Rα KI), prototype (B2M KO, SERPINB9 KI, IL15/IL15Rα KI, CISH KO. FAS KO), and prototype+CD30 CAR (4, 5, or 6) KI and HLA-E KI.

Figure 47A:
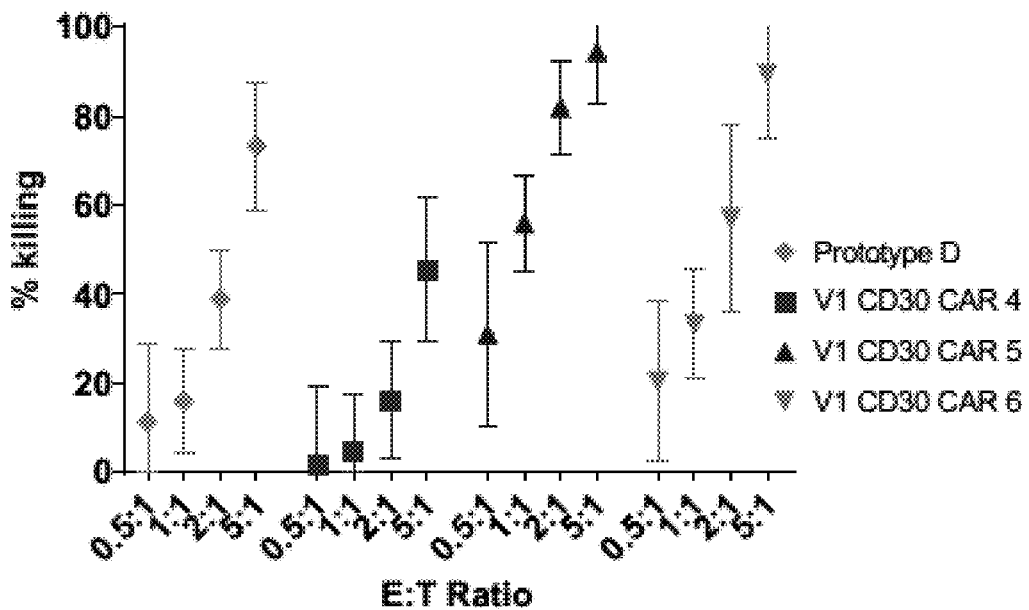
Figure 47B:
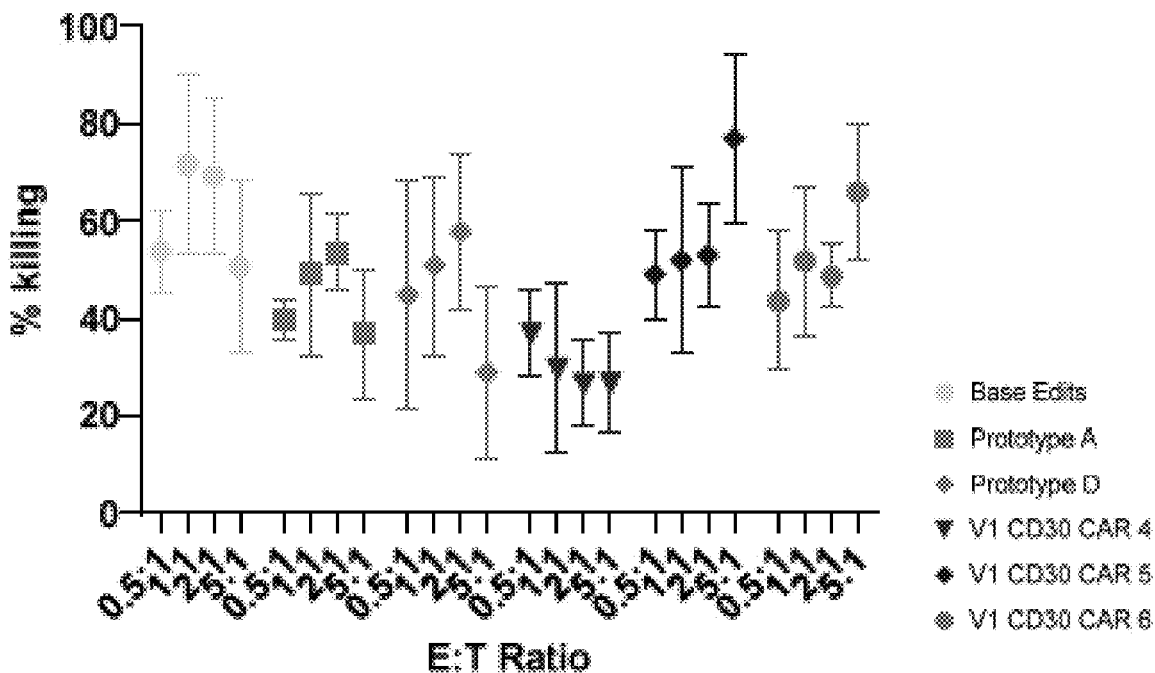
Figure 47C:
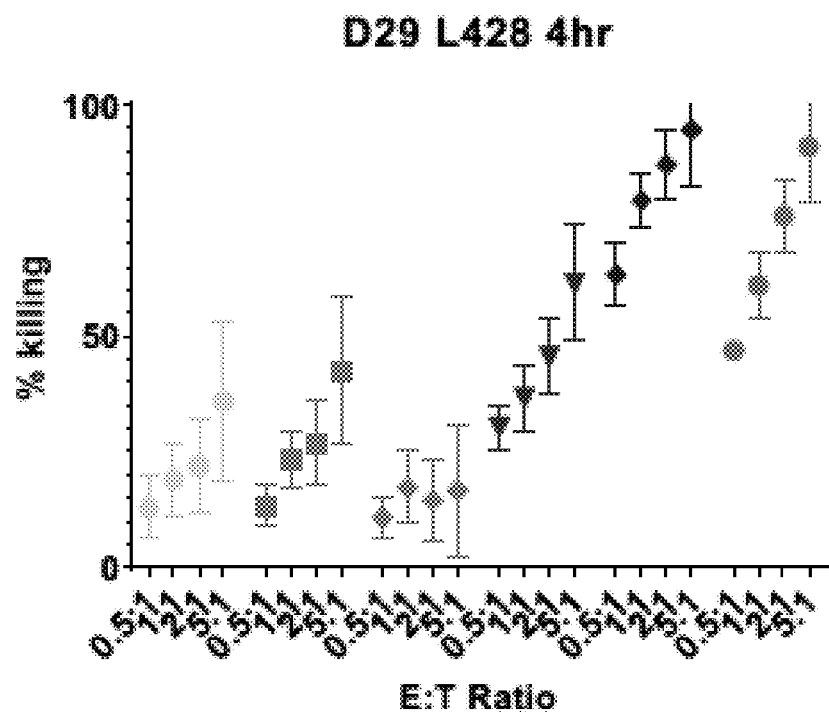
Figure 47D:
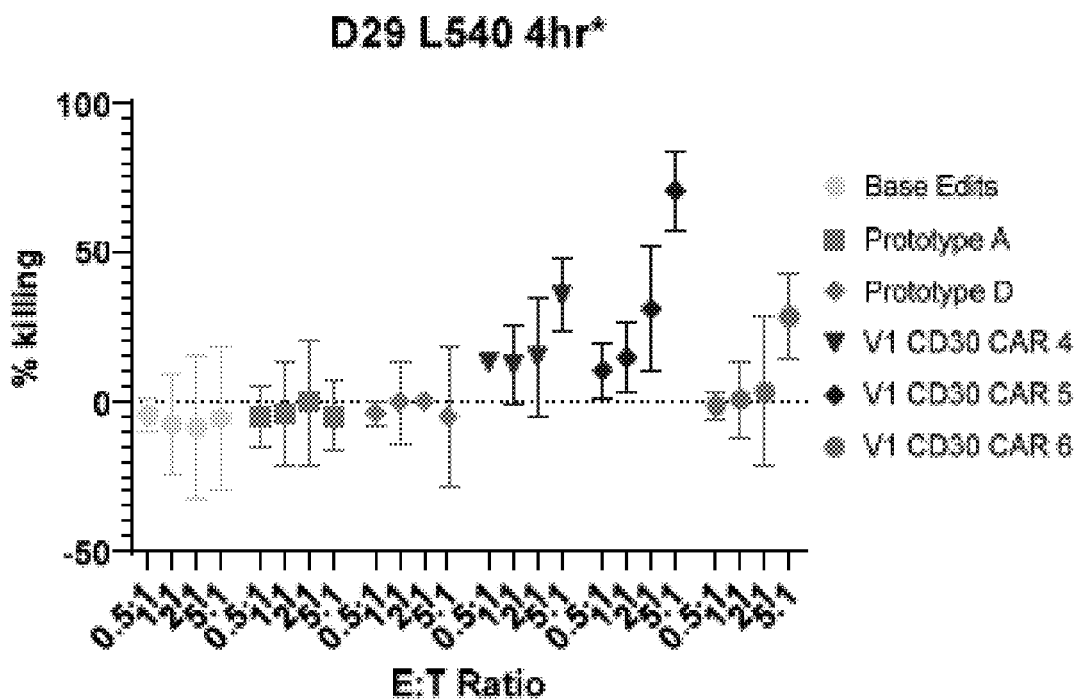

FIG. 47A-D present percent of killing by day 29 iNK cells differentiated from cells with base edits (B2M KO, SERPINB9 KI, IL15/IL15Rα KI), prototype (B2M KO, SERPINB9 KI, IL15/IL15Rα KI, CISH KO. FAS KO), and prototype+CD30 CAR (4, 5, or 6) KI and HLA-E KI of K562 cancer cells (FIG. 47A), KMH2 cancer cells (FIG. 47B), L428 cancer cells (FIG. 47C), or L540 cancer cells (FIG. 47D).

Figure 48:
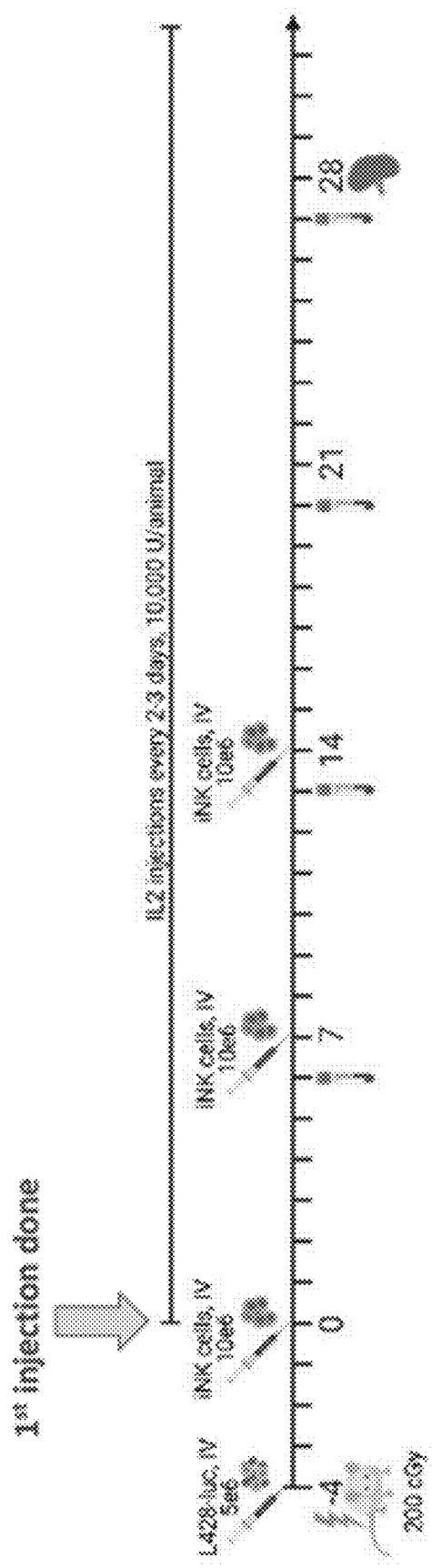

FIG. 48 present a schematic for an in vivo protocol to test the cytotoxicity of iNK cells comprising B2M KO, SERPINB9 KI, IL15/IL15Rα KI, CISH KO. FAS KO, CD30 CAR KI, HLA-E KI, and CIITA KO.

DETAILED DESCRIPTION OF THE INVENTION

The present disclosure provides compositions of engineered stem cells (e.g., iPSCs), and lineage-restricted progenitor cells or fully differentiated somatic cells derived therefrom (e.g., hematopoietic cells such as NK cells, in particular, human NK cells).

In certain embodiments, the engineered cells described herein evade immune response and/or survive following engraftment into a subject at higher success rates than an unmodified cell. In some embodiments, the engineered cells are hypoimmunogenic. In some embodiments, the engineered cells have improved persistency, (ii) improved immune evasiveness, (iii) improved cytotoxic activity, (iv) improved ADCC activity, and/or (v) improved anti-tumor activity as compared to a unmodified or wild-type cell, e.g., a wild-type iPSC or a wild-type NK cell.

In some embodiments, the engineered cells lack a functional major histocompatibility complex (MHC). In some embodiments, the engineered cells described herein are gene-edited to disrupt one or more of the genes of an MHC-I or NHC-II complex.

In some embodiments, the engineered cells have a disrupted B2M gene and have a reduced expression of B2M (e.g., express less than 30%, less than 25%, less than 20%, less than 10%, less than 5% of the level of an unmodified cell) or eliminated expression of B2M (e.g., do not express a detectable level of level of B2M).

In some embodiments, the engineered cells have a disrupted CIITA gene and have a reduced expression of CIITA (e.g., express less than 30%, less than 25%, less than 20%, less than 10%, less than 5% of the level of an unmodified cell) or eliminated expression of CIITA (e.g., do not express a detectable level of CIITA).

In some embodiments, the engineered cells have a disrupted ADAM17 gene and have a reduced expression of ADAM17 (e.g., express less than 30%, less than 25%, less than 20%, less than 10%, less than 5% of the level of an unmodified cell) or eliminated expression of ADAM17 (e.g., do not express a detectable level of ADAM17).

In some embodiments, the engineered cells have a disrupted FAS gene and have a reduced expression of FAS (e.g., express less than 30%, less than 25%, less than 20%, less than 10%, less than 5% of the level of an unmodified cell) or eliminated expression of FAS (e.g., do not express a detectable level of FAS).

In some embodiments, the engineered cells have a disrupted CISH gene and have a reduced expression of CISH (e.g., express less than 30%, less than 25%, less than 20%, less than 10%, less than 5% of the level of an unmodified cell) or eliminated expression of CISH (e.g., do not express a detectable level of CISH).

In some embodiments, the engineered cells have a disrupted REGNASE-1 gene and have a reduced expression of REGNASE-1 (e.g., express less than 30%, less than 25%, less than 20%, less than 10%, less than 5% of the level of an unmodified cell) or eliminated expression of REGNASE-1 (e.g., do not express a detectable level of REGNASE-1).

In some embodiments, the genome of the engineered cells has a disrupted B2M gene and one or more inserted polynucleotide(s) encoding one or all of: SERPINB9, IL15, IL15Rα, and HLA-E. In certain embodiments, the one or more inserted polynucleotide encodes a fusion protein of IL15 and IL15Rα ("IL15/IL15Rα") and an HLA-E trimer comprising a B2M signal peptide fused to an HLA-G presentation peptide fused to the B2M membrane protein fused to the HLA-E protein without a signal peptide. In certain embodiments, the one or more inserted polynucleotide encodes SERPINB9 and a fusion protein of IL15 and IL15Rα. The inserted polynucleotide(s) can be inserted in the disrupted B2M gene locus (e.g., in exon 1 of the B2M gene locus).

In some embodiments, the genome of the engineered cells has a disrupted CIITA gene and one or more inserted polynucleotide(s) encoding one or more CARs (e.g., a BCMA CAR or a CD30 CAR). The inserted polynucleotide(s) can be inserted in the disrupted CIITA gene locus (e.g., in exon 2 of the CIITA gene locus).

In some embodiments, the genome of the engineered cells has a disrupted CIITA gene and one or more inserted polynucleotide(s) encoding CAR and/or HLA-E trimer. In some embodiments, the one or more inserted polynucleotide(s) encodes a CAR (e.g., a CD30 CAR) and HLA-E trimer. The inserted polynucleotide(s) can be inserted in the disrupted CIITA gene locus (e.g., in exon 2 of the CIITA gene locus).

In some embodiments, the genome of the engineered cells has one or more disrupted genes encoding a component of a MHC-I or MHC-II complex, a disrupted ADAM17, and one or more inserted polynucleotide(s) encoding one or more CARs (e.g., a BCMA CAR or a CD30 CAR).

In some embodiments, the genome of the engineered cells has one, two, three, four or all of the following gene edits: (i) a disrupted B2M gene; (ii) one or more inserted polynucleotide(s) encoding one or all of: SERPINB9, IL15/IL15Rα, and HLA-E (e.g., a polynucleotide encoding a fusion protein of IL15 and IL15Rα and an HLA-E trimer comprising a B2M signal peptide fused to an HLA-G presentation peptide fused to the B2M membrane protein fused to the HLA-E protein without a signal peptide, or a polynucleotide encoding SERPINB9 and fusion protein of IL15 and IL15Rα); (iii) a disrupted CIITA gene; (iv) one or more inserted polynucleotide(s) encoding one or more CARs (e.g., a BCMA CAR or a CD30 CAR); and (v) a disrupted ADAM17 gene. In some embodiments, the engineered cell further comprises a disrupted FAS, CISH, and/or REGNASE-1 gene.

In some embodiments, the genome of the engineered cells comprises (a) a disrupted B2M gene; (b) an insertion of a first polynucleotide and a second polynucleotide in the disrupted B2M gene, the first polynucleotide encoding a SERPINB9 protein and the second polynucleotide encoding a fusion of IL15 and IL15Rα; (c) a disrupted CIITA gene; (d) an insertion of a third polynucleotide and a fourth polynucleotide in the disrupted CIITA gene, the third polynucleotide encoding a CAR and the fourth polynucleotide encoding an HLA-E trimer; (e) a disrupted CISH gene; and (f) a disrupted FAS gene.

In some embodiments, the engineered cells described herein are stem cells. In some embodiments, the engineered cells described herein are iPSCs. In some embodiments, the engineered cells described herein are mesodermal cells. In some embodiments, the engineered cells described herein are hemogenic endothelium (HE) cells (e.g., definitive hemogenic endothelium cells). In some embodiments, the engineered cells described herein are hematopoietic stem or progenitor cells (HSPCs) (e.g., definitive hematopoietic stem or progenitor cells). In some embodiments, the engineered cells described herein are common lymphoid progenitor (CLP) cells. In some embodiments, the engineered cells described herein are NK progenitor cells. In some embodiments, the engineered cells described herein are immature NK cells. In some embodiments, the engineered cells described herein are NK cells. In some embodiments, the engineered cells described herein are fully differentiated hematopoietic cells (e.g., NK cells). In some embodiments, stem cells (e.g., iPSCs) are gene-edited as described herein and then differentiated into one, two, three, four, five, six or more of the following cell types: mesodermal cells, HE cells, HSPCs, CLP cells, NK progenitor cells, immature NK cells and NK cells. In some embodiments, the differentiated cells maintain all edits made in the cells from which they were derived (e.g., NK cells maintain all edits of gene-edited stem cells (e.g., iPSC cells) from which they were derived. In some embodiments, the engineered cells described herein are CD34$^+$ cells. In some embodiments, the engineered cells described herein are multipotent progenitors (MPP). In some embodiments, the engineered cells described herein are common lymphoid progenitor cells. In some embodiments, the engineered cells described herein are T cell progenitors.

In some embodiments, a hematopoietic cell such as an NK cell (derived from an engineered stem cell) comprises the gene-edits described herein.

Definitions

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "induced pluripotent stem cells" or, iPSCs, means that the stem cells are produced from differentiated adult, neonatal or fetal cells that have been induced or changed, i.e., reprogrammed into cells capable of differentiating into tissues of all three germ or dermal layers: mesoderm, endoderm, and ectoderm. The iPSCs produced do not refer to cells as they are found in nature.

The term "hematopoietic stem and progenitor cells," "hematopoietic stem cells," "hematopoietic progenitor cells," or "hematopoietic precursor cells" refers to cells which are committed to a hematopoietic lineage but are capable of further hematopoietic differentiation and include, multipotent hematopoietic stem cells (hematoblasts), myeloid progenitors, megakaryocyte progenitors, erythrocyte progenitors, and lymphoid progenitors. Hematopoietic stem and progenitor cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T cells, B cells, NK cells). The term "definitive hematopoietic stem cell" as used herein, refers to CD34$^+$ hematopoietic cells capable of giving rise to both mature myeloid and lymphoid cell types including T cells, NK cells and B cells. Hematopoietic cells also include various subsets of primitive hematopoietic cells that give rise to primitive erythrocytes, megakarocytes and macrophages.

As used herein, the term "NK cell" or "Natural Killer cell" refer to a subset of peripheral blood lymphocytes defined by the expression of CD56 or CD16 and the absence of the T cell receptor (CD3). As used herein, the terms "adaptive NK cell" and "memory NK cell" are interchangeable and refer to a subset of NK cells that are phenotypically CD3$^-$ and CD56$^+$, expressing at least one of NKG2C and CD57, and optionally, CD16, but lack expression of one or more of the following: PLZF, SYK, FceRy, and EAT-2. In some embodiments, isolated subpopulations of CD56$^+$ NK cells comprise expression of CD16, NKG2C, CD57, NKG2D, NCR ligands, NKp30, NKp40, NKp46, activating and inhibitory KIRs, NKG2A and/or DNAM-1.

As used herein, the terms "disruption," "genetic modification" or "gene-edit" generally refer to a genetic modification wherein a site or region of genomic DNA is altered, e.g., by a deletion or insertion, by any molecular biology method, e.g., methods described herein, e.g., by delivering to a site of genomic DNA an endonuclease and at least one gRNA. Exemplary genetic modifications include insertions, deletions, duplications, inversions, and translocations, and combinations thereof. In some embodiments, a genetic modification is a deletion. In some embodiments, a genetic modification is an insertion. In other embodiments, a genetic modification is an insertion-deletion mutation (or indel), such that the reading frame of the target gene is shifted leading to an altered gene product or no gene product. As used herein, the term "engineered cell" refers to a cell with any disruption, genetic modification, or gene-edit.

As used herein, the term "deletion" which may be used interchangeably with the terms "genetic deletion", "knockout", or "KO", generally refers to a genetic modification wherein a site or region of genomic DNA is removed by any molecular biology method, e.g., methods described herein, e.g., by delivering to a site of genomic DNA an endonuclease and at least one gRNA. Any number of nucleotides can be deleted. In some embodiments, a deletion involves the removal of at least one, at least two, at least three, at least four, at least five, at least ten, at least fifteen, at least twenty, or at least 25 nucleotides. In some embodiments, a deletion involves the removal of 10-50, 25-75, 50-100, 50-200, or more than 100 nucleotides. In some embodiments, a deletion involves the removal of part of a target gene, e.g., all or part of a promoter and/or coding sequence of a B2M gene, a CIITA gene, a ADAM17 gene, a FAS gene, a CISH gene, and/or a REGNASE-1 gene. In some embodiments, a deletion involves the removal of an entire target gene, e.g., a B2M gene, a CIITA gene, a ADAM17 gene, a FAS gene, a CISH gene, and/or a REGNASE-1 gene. In some embodiments, a deletion involves the removal of a transcriptional regulator, e.g., a promoter region, of a target gene. In some embodiments, a deletion involves the removal of all or part of a coding region such that the product normally expressed by the coding region is no longer expressed, is expressed as a truncated form, or expressed at a reduced level. In some embodiments, a deletion leads to a decrease in expression of a gene relative to an unmodified cell. In some embodiments, the decrease in expression can be a reduced level of expression (e.g., express less than 30%, less than 25%, less than 20%, less than 10%, less than 5% of the level of an unmodified cell). In some embodiments, the decrease in expression can be eliminated expression (e.g., no expression or do not express a detectable level of RNA and/or protein). Expression can be measured using any standard RNA-based, protein-based, and/or antibody-based detection method (e.g., RT-PCR, ELISA, flow cytometry, immunocytochemistry, and the like). Detectable levels are defined as being higher that the limit of detection (LOD), which is the lowest concentration that can be measured (detected) with statistical significance by means of a given detection method.

As used herein, the term "endonuclease" generally refers to an enzyme that cleaves phosphodiester bonds within a polynucleotide. In some embodiments, an endonuclease specifically cleaves phosphodiester bonds within a DNA polynucleotide. In some embodiments, an endonuclease is a zinc finger nuclease (ZFN), transcription activator like effector nuclease (TALEN), homing endonuclease (HE), meganuclease, MegaTAL, or a CRISPR-associated endonuclease. In some embodiments, an endonuclease is a RNA-guided endonuclease. In certain aspects, the RNA-guided endonuclease is a CRISPR nuclease, e.g., a Type II CRISPR Cas9 endonuclease or a Type V CRISPR Cpf1 endonuclease. In some embodiments, an endonuclease is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a homolog thereof, a recombination of the naturally occurring molecule thereof, a codon-optimized version thereof, or a modified version thereof, or combinations thereof. In some embodiments, an endonuclease may introduce one or more single-stranded breaks (SSBs) and/or one or more double-stranded breaks (DSBs).

As used herein, the term "guide RNA" or "gRNA" generally refers to short ribonucleic acid that can interact with, e.g., bind to, to an endonuclease and bind, or hybridize to a target genomic site or region. In some embodiments, a gRNA is a single-molecule guide RNA (sgRNA). In some embodiments, a gRNA may comprise a spacer extension region. In some embodiments, a gRNA may comprise a tracrRNA extension region. In some embodiments, a gRNA is single-stranded. In some embodiments, a gRNA comprises naturally occurring nucleotides. In some embodiments, a gRNA is a chemically modified gRNA. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, a gRNA may be pre-complexed with a DNA endonuclease.

As used herein, the term "insertion" which may be used interchangeably with the terms "genetic insertion" or "knock-in", generally refers to a genetic modification wherein a polynucleotide is introduced or added into a site or region of genomic DNA by any molecular biological method, e.g., methods described herein, e.g., by delivering to a site of genomic DNA an endonuclease and at least one gRNA. In some embodiments, an insertion may occur within or near a site of genomic DNA that has been the site of a prior genetic modification, e.g., a deletion or insertion-deletion mutation. In some embodiments, an insertion occurs at a site of genomic DNA that partially overlaps, completely overlaps, or is contained within a site of a prior genetic modification, e.g., a deletion or insertion-deletion mutation. In some embodiments, an insertion involves the introduction of a polynucleotide that encodes a protein of interest. In some embodiments, an insertion involves the introduction of a polynucleotide that encodes a tolerogenic factor (e.g., HLA-E), a CAR, a fusion protein of IL15 and ILRα, and/or SERPINB9. In some embodiments, an insertion involves the introduction of an exogenous promoter, e.g., a constitutive promoter, e.g., a CAG promoter. In some embodiments, an insertion involves the introduction of a polynucleotide that encodes a noncoding gene. In general, a polynucleotide to be inserted is flanked by sequences (e.g., homology arms) having substantial sequence homology with genomic DNA at or near the site of insertion.

As used herein, the terms "Major histocompatibility complex class I" or "MHC-I" generally refer to a class of biomolecules that are found on the cell surface of all nucleated cells in vertebrates, including mammals, e.g., humans; and function to display peptides of non-self or foreign antigens, e.g., proteins, from within the cell (i.e. cytosolic) to cytotoxic T cells, e.g., $CD8^+$ T cells, in order to stimulate an immune response. In some embodiments, a MHC-I biomolecule is a MHC-I gene or a MHC-I protein. Complexation of MHC-I proteins with beta-2 microglobulin (β2M) protein is required for the cell surface expression of all MHC-I proteins. In some embodiments, decreasing the expression of a MHC-I human leukocyte antigen (HLA) relative to an unmodified cell involves a decrease (or reduction) in the expression of a MHC-I gene. In some embodiments, decreasing the expression of a MHC-I human leukocyte antigen (HLA) relative to an unmodified cell involves a decrease (or reduction) in the cell surface expression of a MHC-I protein. In some embodiments, a MHC-I biomolecule is HLA-A (NCBI Gene ID No: 3105), HLA-B (NCBI Gene ID No: 3106), HLA-C(NCBI Gene ID No: 3107), or B2M (NCBI Gene ID No: 567).

As used herein, the term "Major histocompatibility complex class II" or "MHC-II" generally refer to a class of biomolecules that are typically found on the cell surface of antigen-presenting cells in vertebrates, including mammals, e.g., humans; and function to display peptides of non-self or foreign antigens, e.g., proteins, from outside of the cell (extracellular) to cytotoxic T cells, e.g., $CD8^+$ T cells, in order to stimulate an immune response. In some embodiments, an antigen-presenting cell is a dendritic cell, macrophage, or a B cell. In some embodiments, a MHC-II biomolecule is a MHC-II gene or a MHC-II protein. In some embodiments, decreasing the expression of a MHC-II human leukocyte antigen (HLA) relative to an unmodified cell involves a decrease (or reduction) in the expression of a MHC-II gene. In some embodiments, decreasing the expression of a MHC-II human leukocyte antigen (HLA) relative to an unmodified cell involves a decrease (or reduction) in the cell surface expression of a MHC-II protein. In some embodiments, a MHC-II biomolecule is HLA-DPA (NCBI Gene ID No: 3113), HLA-DPB (NCBI Gene ID No: 3115), HLA-DMA (NCBI Gene ID No: 3108), HLA-DMB (NCBI Gene ID No: 3109), HLA-DOA (NCBI Gene ID No: 3111), HLA-DOB (NCBI Gene ID No: 3112), HLA-DQA (NCBI Gene ID No: 3117), HLA-DQB (NCBI Gene ID No: 3119), HLA-DRA (NCBI Gene ID No: 3122), or HLA-DRB (NCBI Gene ID No: 3123).

As used herein, the term "polynucleotide", which may be used interchangeably with the term "nucleic acid" generally refers to a biomolecule that comprises two or more nucleotides. In some embodiments, a polynucleotide comprises at least two, at least five at least ten, at least twenty, at least 30, at least 40, at least 50, at least 100, at least 200, at least 250, at least 500, or any number of nucleotides. A polynucleotide may be a DNA or RNA molecule or a hybrid DNA/RNA molecule. A polynucleotide may be single-stranded or double-stranded. In some embodiments, a polynucleotide is a site or region of genomic DNA. In some embodiments, a polynucleotide is an endogenous gene that is comprised within the genome of an unmodified cell or gene-edited iPSC. In some embodiments, a polynucleotide is an exogenous polynucleotide that is not integrated into genomic DNA. In some embodiments, a polynucleotide is an exogenous polynucleotide that is integrated into genomic DNA. In some embodiments, a polynucleotide is a plasmid or an adeno-associated viral vector. In some embodiments, a polynucleotide is a circular or linear molecule.

As used herein, the term "subject" refers to a mammal. In some embodiments, a subject is non-human primate or rodent. In some embodiments, a subject is a human. In some embodiments, a subject has, is suspected of having, or is at risk for, a disease or disorder. In some embodiments, a subject has one or more symptoms of a disease or disorder.

As used herein, the term "transcriptional regulator of MHC-I or MHC-II" generally refers to a biomolecule that modulates, e.g., increases or decreases, the expression of an MHC-I and/or MHC-II human leukocyte antigen. In some embodiments, a biomolecule is a polynucleotide, e.g., a gene, or a protein. In some embodiments, a transcriptional regulator of MHC-I or MHC-II will increase or decrease the cell surface expression of at least one MHC-I or MHC-II protein. In some embodiments, a transcriptional regulator of MHC-I or MHC-II will increase or decrease the expression of at least one MHC-I or MHC-II gene. In some embodiments, the transcriptional regulator is CIITA (NCBI Gene ID No: 4261) or NLRC5 (NCBI Gene ID No: 84166). In some embodiments, deletion or reduction of expression of CIITA or NLRC5 decreases expression of at least one MHC-I or MHC-II gene.

As used herein, the term "engineered cell" generally refers to a genetically modified cell that is less susceptible to allogeneic rejection during a cellular transplant and/or demonstrates increased survival after transplantation, relative to an unmodified cell. In some embodiments, a genetically modified cell as described herein is an engineered cell. In some embodiments, the engineered cell has increased immune evasion and/or cell survival compared to an unmodified cell. In some embodiments, the engineered cell has increased cell survival compared to an unmodified cell. In some embodiments, the engineered cell has improved persistency, (ii) improved immune evasiveness, (iii) improved cytotoxic activity, (iv) improved ADCC activity, and/or (v) improved anti-tumor activity compared to an unmodified cell. In some embodiments, an engineered cell may be a stem cell. In some embodiments, an engineered cell may be an embryonic stem cell (ESC), an adult stem cell (ASC), an induced pluripotent stem cell (iPSC), or a hematopoietic stem or progenitor cell (HSPC). In some embodiments, an engineered cell may be a differentiated cell. In some embodiments, an engineered cell may be a somatic cell (e.g., immune system cells). In some embodiments, an engineered cell is administered to a subject. In some embodiments, an engineered cell is administered to a subject who has, is suspected of having, or is at risk for a disease. In some embodiments, the engineered cell is capable of being differentiated into lineage-restricted progenitor cells or fully differentiated somatic cells. In some embodiments, the lineage-restricted progenitor cells are pancreatic endoderm progenitors, pancreatic endocrine progenitors, mesenchymal progenitor cells, muscle progenitor cells, blast cells, or neural progenitor cells. In some embodiments, the fully differentiated somatic cells are endocrine secretory cells such as pancreatic beta cells, epithelial cells, endodermal cells, macrophages, hepatocytes, adipocytes, kidney cells, blood cells, or immune system cells.

As used herein, the term "unmodified cell" refers to a cell that has not been subjected to a genetic modification involving a polynucleotide or gene that encodes any of the genes described herein. In some embodiments, an unmodified cell may be a stem cell. In some embodiments, an unmodified cell may be an embryonic stem cell (ESC), an adult stem cell (ASC), an induced pluripotent stem cell (iPSC), or a hematopoietic stem or progenitor cell (HSPC). In some embodiments, an unmodified cell may be a differentiated cell. In some embodiments, an unmodified cell may be selected from somatic cells (e.g., immune system cells, e.g., a T cell, e.g., a $CD8^+$ T cell). If a gene-edited iPSC or NK cell is compared "relative to an unmodified cell", the iPSC or NK cell and the unmodified cell are the same cell type or share a common parent cell line, e.g., a gene-edited NK cell is compared relative to an unmodified NK cell.

As used herein, the term "within or near a gene" refers to a site or region of genomic DNA that is an intronic or exonic component of a said gene or is located proximal to a said gene. In some embodiments, a site of genomic DNA is within a gene if it comprises at least a portion of an intron or exon of said gene. In some embodiments, a site of genomic DNA located near a gene may be at the 5' or 3' end of said gene (e.g., the 5' or 3' end of the coding region of said gene). In some embodiments, a site of genomic DNA located near a gene may be a promoter region or repressor region that modulates the expression of said gene. In some embodiments, a site of genomic DNA located near a gene may be on the same chromosome as said gene. In some embodiments, a site or region of genomic DNA is near a gene if it is within 50 Kb, 40 Kb, 30 Kb, 20 Kb, 10 Kb, 5 Kb, 1 Kb, or closer to the 5' or 3' end of said gene (e.g., the 5' or 3' end of the coding region of said gene).

As used herein, the term "tolerogenic factor" generally refers to a protein (e.g., expressed by a polynucleotide as described herein) that, when increased or decreased in a cell, enables the cell, e.g., an engineered cell, to inhibit or evade immune rejection after transplantation or engraftment into a host subject at higher rates relative to an unmodified cell. In some embodiments, a tolerogenic factor is a human tolerogenic factor. In some embodiments, the genetic modification of at least one tolerogenic factor (e.g., the insertion or deletion of at least one tolerogenic factor) enables a cell, e.g., an engineered cell. to inhibit or evade immune rejection with rates at least 1.05, at least 1.1, at least 1.25, at least 1.5, at least 2, at least 3, at least 4, at least 5, at least 10, at least 20, or at least 50 times higher than an unmodified cell following engraftment. In some embodiments, a tolerogenic factor is HLA-E (NCBI Gene ID No: 3133), HLA-G (NCBI Gene ID No: 3135), CTLA-4 (NCBI Gene ID No: 1493), CD47 (NCBI Gene ID No: 961), or PD-L1 (NCBI Gene ID No: 29126). In some embodiments, a tolerogenic factor is inserted into a cell, e.g., an engineered cell. In some embodiments, a tolerogenic factor is deleted from a cell, e.g., an engineered cell. In some embodiments, an insertion of a polynucleotide that encodes HLA-E, HLA-G, CTLA-4, CD47, and/or PD-L1 enables a cell, e.g., an engineered cell, to inhibit or evade immune rejection after transplantation or engraftment into a host subject.

As used herein, the term "comprising" or "comprises" is inclusive or open-ended and does not exclude additional, unrecited elements, ingredients, or method steps; the phrase "consisting of" or "consists of" is closed and excludes any element, step, or ingredient not specified; and the phrase "consisting essentially of" or "consists essentially" means that specific further components can be present, namely those not materially affecting the essential characteristics of the compound, composition, or method. When used in the context of a sequence, the phrase "consisting essentially of" or "consists essentially" means that the sequence can comprise substitutions and/or additional sequences that do not change the essential function or properties of the sequence.

Gene Editing

Described herein are strategies to enable genetically modified cells to evade immune response and/or increase their survival, or viability following engraftment into a subject. In some embodiments, these strategies enable gene-edited cells to evade immune response and/or survive at higher success rates than an unmodified cell.

In certain embodiments, any cells described herein are gene-edited using any of the gene-editing methods described herein (e.g., using CRISPR/Cas gene editing to insert or delete one or more nucleotides). In some embodiments, a disrupted gene is a gene that does not encode functional protein. In some embodiments, a cell that comprises a disrupted gene does not express (e.g., at the cell surface) a detectable level (e.g. by antibody, e.g., by flow cytometry) of the protein encoded by the gene. A cell that does not express a detectable level of the protein may be referred to as a knockout cell.

In some embodiments, the cells described herein are gene-edited to disrupt one or more of the genes encoding an MHC-I or MHC-II human leukocyte antigen, a component of a MHC-I or MHC-II complex, or a transcriptional regulator of a MHC-I or MHC-II complex. In some embodiments, the cells described herein are gene-edited to disrupt one or more of the genes encoding an MHC-I or MHC-II human leukocyte antigen. In some embodiments, the cells described herein are gene-edited to disrupt one or more of the genes encoding one or more components of an MHC-I or MHC-II complex. In some embodiments, the cells described herein are gene-edited to disrupt one or more of the genes encoding one or more transcriptional regulator of an MHC-I or MHC-II complex.

In some embodiments, the cells described herein are gene-edited to disrupt one or more genes including but not limited to: B2M, CIITA, ADAM17, CISH, REGNASE1, FAS, TIGIT, PD-1, NKG2A, CD70 and/or ALK4, type I activin receptor (e.g., conditionally). In some embodiments, the cells described herein are gene-edited to disrupt B2M, CIITA, CISH, FAS, and/or ADAM17. In some embodiments, the cells described herein are gene-edited to disrupt B2M. In some embodiments, the cells described herein are gene-edited to disrupt CIITA. In some embodiments, the cells described herein are gene-edited to disrupt ADAM17. In some embodiments, the cells described herein are gene-edited to disrupt CISH. In some embodiments, the cells described herein are gene-edited to disrupt REGNASE1. In some embodiments, the cells described herein are gene-edited to disrupt FAS. In some embodiments, the cells described herein are gene-edited to disrupt TIGIT. In some embodiments, the cells described herein are gene-edited to disrupt PD-1. In some embodiments, the cells described herein are gene-edited to disrupt NKG2A. In some embodiments, the cells described herein are gene-edited to disrupt CD70. In some embodiments, the cells described herein are gene-edited to disrupt ALK4, type I activin receptor (e.g., conditionally).

In some embodiments, the cells described herein are gene-edited to insert a polynucleotide encoding, without limitation, one or more of the following: a tolerogenic factor, IL15, IL15Rα, IL15/IL15Rα, HLA-E, a CAR, and SERPINB9. In some embodiments, the cells described herein are gene-edited to insert a polynucleotide encoding IL15. In some embodiments, the cells described herein are gene-edited to insert a polynucleotide encoding IL15Rα. In some embodiments, the cells described herein are gene-edited to insert a polynucleotide encoding a fusion protein of IL15 and IL15Rα. In some embodiments, the cells described herein are gene-edited to insert a polynucleotide encoding a tolerogenic factor, such as HLA-E (e.g., wherein the HLA-E is a trimer comprising a B2M signal peptide fused to an HLA-G presentation peptide fused to the B2M membrane protein fused to the HLA-E protein without a signal peptide). In some embodiments, the cells described herein are gene-edited to insert a polynucleotide encoding a CAR. In some embodiments, the cells described herein are gene-edited to insert a polynucleotide encoding an IL15/IL15Rα-P2A-HLA-E trimer construct. In some embodiments, the cells described herein are gene-edited to insert a polynucleotide encoding a SERPINB9-P2A-HLA-E trimer construct. In some embodiments, the cells described herein are gene-edited to insert a polynucleotide encoding a SERPINB9-P2A-IL15/IL15Rα construct. In some embodiments the cells described herein are gene-edited to insert a polynucleotide encoding a CAR-P2A-HLA-E trimer construct.

In some embodiments, the cells described herein are gene-edited to insert a polynucleotide encoding CD16 (e.g., a high affinity non-cleavable CD16). In some embodiments, the cells described herein are not gene-edited to insert a polynucleotide encoding CD16. In some embodiments, the cells described herein are not gene-edited to insert a polynucleotide encoding a high affinity non-cleavable CD16. In some embodiments, the cells described herein are gene-edited to insert a polynucleotide encoding, without limitation, one or more of the following: IL15, IL15Rα, IL15/IL15Rα, HLA-E and CD16 (e.g., a high affinity non-cleavable CD16), wherein the cell has a disrupted expression of B2M (e.g., the cell is gene-edited to disrupt B2M leading to, e.g., elimination of B2M expression). In some embodiments, the polynucleotide encoding IL15/IL15Rα, and HLA-E (e.g., HLA-E trimer comprising a B2M signal peptide fused to an HLA-G presentation peptide fused to the B2M membrane protein fused to the HLA-E protein without a signal peptide), or the polynucleotide encoding IL15/IL15Rα-P2A-HLA-E trimer is inserted in the B2M gene locus (e.g., in exon 1 of the B2M gene locus).

In some embodiments, the cells described herein are gene-edited to insert any of the polynucleotides described herein wherein the cell has a disrupted expression of CIITA (e.g., the cell is gene-edited to disrupt CIITA leading to, e.g., elimination of CIITA expression). In some embodiments, the cells described herein are gene-edited to insert any of the polynucleotides described herein in the disrupted CIITA gene locus (e.g., in exon 2 of the CIITA gene locus).

In some embodiments, the cells described herein are gene-edited to insert a polynucleotide encoding one or more chimeric antigen receptors (CARs). In some embodiments, and without limitation, the CAR is a BCMA (i.e., B cell maturation antigen) CAR, CD30 CAR, CD19 CAR, CD33 CAR, NKG2D (i.e., natural killer group 2D receptor) CAR (or a CAR or receptor comprising an NKG2D ectodomain), CD70 CAR, NKp30 (i.e., natural killer protein 30) CAR, CD73 CAR, GPR87 (i.e., G protein-coupled receptor 87) CAR, or SLC7A11 (i.e., solute carrier family 7 member 11, which is also called xCT) CAR. In some embodiments, the CAR is a BCMA CAR. In some embodiments, the polynucleotide encoding a CAR comprises or has the sequence of SEQ ID NO: 70. In some embodiments, the CAR is a CD33 CAR. In some embodiments, the CAR is a CD19 CAR. In some embodiments, the CAR is a CD33 CAR. In some embodiments, the CAR is a NKG2D CAR (or a CAR or receptor comprising an NKG2D ectodomain). In some embodiments, the CAR is a CD70 CAR. In some embodiments, the CAR is a NKp30 CAR. In some embodiments, the CAR is a CD73 CAR. In some embodiments, the CAR is a GPR87 CAR. In some embodiments, the CAR is a SLC7A11 (xCT) CAR.

In some embodiments, the cells described herein are gene-edited to insert a polynucleotide encoding a CAR, wherein the cell has a disrupted expression of CIITA (e.g., the cell is gene-edited to disrupt CIITA leading to, e.g., elimination of CIITA expression). In some embodiments, the polynucleotide encoding a CAR is inserted in the disrupted CIITA gene. In some embodiments, the polynucleotide encoding a CAR is inserted in exon 2 of the CIITA gene locus. In some embodiments, the cells described herein are gene-edited to insert a polynucleotide encoding a CAR-P2A-HLA-E trimer construct, wherein the cell has a disrupted expression of CIITA (e.g., the cell is gene-edited to disrupt CIITA leading to, e.g., elimination of CIITA expression). In some embodiments, the polynucleotide encoding a CAR-P2A-HLA-E trimer construct is inserted in the disrupted CIITA gene. In some embodiments, the polynucleotide encoding a CAR-P2A-HLA-E trimer construct is inserted in exon 2 of the CIITA gene locus.

In some embodiments, the cells described herein are gene-edited to insert a polynucleotide encoding a CAR, wherein the cell has a disrupted expression of B2M (e.g., the cell is gene-edited to disrupt B2M leading to, e.g., elimination of B2M expression). In some embodiments, the CAR is inserted in the disrupted B2M gene locus (e.g., in exon 1 of the B2M gene locus).

In some embodiments, the cells described herein are edited to disrupt (i) one or more of the genes encoding an MHC-I or MHC-II human leukocyte antigen, a component of a MHC-I or MHC-II complex, or a transcriptional regulator of a MHC-I or MHC-II complex, and (ii) ADAM17. In some embodiments, such cells are further gene-edited to insert a polynucleotide encoding one or more chimeric antigen receptors (CARs), such as any CARs described herein (e.g., a BCMA CAR). In some embodiments, such cells are hypoimmunogenic. In some embodiments, such cells are further gene-edited to disrupt one or more genes described herein, e.g., CIITA. In some embodiments, such cells are further gene-edited to insert any polynucleotide described herein, e.g., a polynucleotide encoding IL15, IL15Rα, IL15/IL15Rα, HLA-E (e.g., HLA-E trimer comprising a B2M signal peptide fused to an HLA-G presentation peptide fused to the B2M membrane protein fused to the HLA-E protein without a signal peptide), or a polynucleotide encoding IL15/IL15Rα-P2A-HLA-E trimer.

In some embodiments, the present disclosure provides a method of generating genome-engineered stem cells (e.g., iPSCs), wherein the stem cells comprise at least one targeted genomic modification at one or more selected sites in genome, the method comprising genetically engineering a cell type as described herein by introducing into said cells one or more constructs to allow targeted modification at a selected site; introducing into said cells one or more double strand breaks at the selected sites using one or more endonuclease capable of selected site recognition; and culturing the edited cells to allow endogenous DNA repair to generate targeted insertions or deletions at the selected sites; thereby obtaining genome-modified stem cells. In some embodiments, the cell that is engineered (i.e., the starting cell) is a stem cell (e.g., an embryonic stem cell (ESC), an adult stem cell (ASC), an induced pluripotent stem cell (iPSC), or a hematopoietic stem or progenitor cell (HSPC)). The stem cells (e.g., iPSCs) generated or obtainable by this method will comprise at least one functional targeted genomic modification, and wherein the genome-modified cells, are then capable of being differentiated into progenitor cells or fully-differentiated cells (e.g., natural killer (NK) cells). In some embodiments, the differentiated cells (e.g., NK cells) maintain all of the gene-edits of the cells from which they were derived.

In some embodiments, a ribonucleoprotein particle (RNP) containing an RNA-guided nuclease (e.g., a Cas nuclease, such as a Cas9 nuclease) and a gRNA targeting the gene to be disrupted are delivered to any cell described herein (e.g., iPSC). A RNP is an RNA-guided nuclease (e.g., Cas9) pre-complexed/complexed with a gRNA. In other embodiments, the RNA-guided nuclease and gRNA are delivered separately to cells. In some embodiments, at least 50% of the engineered cells of a population of cells does not express a detectable level of the protein encoded by the disrupted gene. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population do not express a detectable level of the disrupted gene product.

In some embodiments, at least 50% of the engineered cells of a population of cells expresses a detectable level of the protein encoded by the inserted polynucleotide. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population express a detectable level of the protein encoded by the inserted polynucleotide.

MHC I and MHC II Edits

Major histocompatibility complex I and II (MHC I and MHC II respectively) are cell surface proteins which perform an essential role in the adaptive immune system. The genes that encode the major histocompatibility complex (MHC) are located on human Chr. 6p21. The resultant proteins coded by the MHC genes are a series of surface proteins that are essential in donor compatibility during cellular transplantation. MHC genes are divided into MHC class I (MHC-I) and MHC class II (MHC-II). MHC-I genes (HLA-A, HLA-B, and HLA-C) are expressed in almost all tissue cell types, presenting "non-self" antigen-processed peptides to CD8+ T cells, thereby promoting their activation to cytolytic CD8+ T cells. Transplanted or engrafted cells expressing "non-self" MHC-I molecules will cause a robust cellular immune response directed at these cells and ultimately resulting in their demise by activated cytolytic CD8+ T cells. MHC-I proteins are intimately associated with beta-2-microglobulin (B2M) in the endoplasmic reticulum, which is essential for forming functional MHC-I molecules on the cell surface. In addition, there are three non-classical MHC-II molecules (HLA-E, HLA-F, and HLA-G), which have immune regulatory functions. MHC-II biomolecule include HLA-DP, HLA-DM, HLA-DOA, HLA-DOB, HLA-DQ, and HLA-DR. Due to their primary function in the immune response, MHC-I and MHC-II biomolecules contribute to immune rejection following cellular engraftment of non-host cells, e.g., cellular engraftment for purposes of regenerative medicine.

In some embodiments, a cell comprises a genomic modification of one or more MHC-I or MHC-II genes. In some embodiments, a cell comprises a genomic modification of one or more polynucleotide sequences that regulates the expression of MHC-I and/or MHC-II. In some embodiments, a genetic modification of the disclosure is performed using any gene editing method including but not limited to those methods described herein.

In some embodiments, any of the cells described herein have MHC I and/or MHC II genetic modifications. In some embodiments, MHC I is disrupted. In some embodiments, MHC II is disrupted. In some embodiments, both MHC I and MHC II are disrupted. In some embodiments, an MHC I encoding gene is inserted. In some embodiments, an MHC II encoding gene is inserted. In some embodiments, any genetically modified cell described herein comprises the introduction of at least one genetic modification within or near at least one gene that decreases the expression of one or more MHC-I and MHC-II human leukocyte antigens relative to an unmodified cell; at least one genetic modification that increases the expression of at least one polynucleotide that encodes a tolerogenic factor relative to an unmodified cell. In some embodiments, genetically modified cells comprise the introduction of at least one genetic modification within or near at least one gene that decreases the expression of one or more MHC-I and MHC-II human leukocyte antigens relative to an unmodified cell; at least one genetic modification that increases the expression of at least one polynucleotide that encodes a tolerogenic factor relative to an unmodified cell. In other embodiments, genetically modified cells comprise at least one deletion or insertion-deletion mutation within or near at least one gene that alters the expression of one or more MHC-I and MHC-II human leukocyte antigens relative to an unmodified cell; and at least one insertion of a polynucleotide that encodes at least one tolerogenic factor at a site that partially overlaps, completely overlaps, or is contained within, the site of a deletion of a gene that alters the expression of one or more MHC-I and MHC-II HLAs.

In some embodiments, decreasing the expression of one or more MHC-I and MHC-II human leukocyte antigens relative to an unmodified cell is accomplished by targeting, e.g., for genetic deletion and/or insertion of at least one base pair, in a MHC-I and/or MHC-II gene directly. In some embodiments, decreasing the expression of one or more MHC-I and MHC-II human leukocyte antigens relative to an unmodified cell is accomplished by targeting, e.g., for genetic deletion, a CIITA gene. In some embodiments, decreasing the expression of one or more MHC-I and MHC-II human leukocyte antigens relative to an unmodified cell is accomplished by targeting, e.g., for genetic deletion, at least one transcriptional regulator of MHC-I or MHC-II. In some embodiments, a transcriptional regulator of MHC-I or MHC-II is a NLRC5, or CIITA gene. In some embodiments, a transcriptional regulator of MHC-I or MHC-II is a RFX5, RFXAP, RFXANK, NFY-A, NFY-B, NFY-C, IRF-1, and/or TAP1 gene.

In some embodiments, the genome of a cell has been modified to delete the entirety or a portion of an HLA-A, HLA-B, and/or HLA-C gene. In some embodiments, the genome of a cell has been modified to delete the entirety or a portion of a promoter region of an HLA-A, HLA-B, and/or HLA-C gene. In some embodiments, the genome of a cell has been modified to delete the entirety or a portion of a gene that encodes a transcriptional regulator of MHC-I or MHC-II. In some embodiments, the genome of a cell has been modified to delete the entirety or a portion of a promoter region of a gene that encodes a transcriptional regulator of MHC-I or MHC-II.

MHC-I cell surface molecules are composed of MHC-encoded heavy chains (HLA-A, HLA-B, or HLA-C) and the invariant subunit beta-2-microglobulin (B2M). Thus, a reduction in the concentration of B2M within a cell allows for an effective method of reducing the cell surface expression of MHC-I cell surface molecules. In some embodiments, tolerogenic factors can be inserted or reinserted into genetically modified cells to create immune-privileged iPSC or NK cells. In some embodiments, the iPSC or NK cells disclosed herein have been further modified to express one or more tolerogenic factors. Exemplary tolerogenic factors include, without limitation, one or more of HLA-C, HLA-E, HLA-F, HLA-G, PD-L1, CTLA-4-Ig, CD47, CI-inhibitor, and TL-35. In some embodiments, the genetic modification, e.g., insertion, of at least one polynucleotide encoding at least one tolerogenic factor enables a gene-edited iPSC or NK cell to inhibit or evade immune rejection with rates at least 1.05, at least 1.1, at least 1.25, at least 1.5, at least 2, at least 3, at least 4, at least 5, at least 10, at least 20, or at least 50 times higher than an unmodified cell following engraftment. In some embodiments, an insertion of a polynucleotide that encodes HLA-E, HLA-G, CTLA-4, CD47, and/or PD-L1 enables a iPSC or NK cell to inhibit or evade immune rejection after transplantation or engraftment into a host subject.

The polynucleotide encoding the tolerogenic factor generally comprises left and right homology arms that flank the sequence encoding the tolerogenic factor. The homology arms have substantial sequence homology to genomic DNA at or near the targeted insertion site. For example, the left homology arm can be a nucleotide sequence homologous with a region located to the left or upstream of the target site or cut site and the right homology arm can be a nucleotide sequence homologous with a region located to the right or downstream of the target site or cut site. The proximal end of each homology arm can be homologous to genomic DNA sequence abutting the cut site. Alternatively, the proximal end of each homology arm can be homologous to genomic DNA sequence located up to about 10, 20, 30, 40, 50, 60, or 70 nucleobases away from the cut site. As such, the polynucleotide encoding the tolerogenic factor can be inserted into the targeted gene locus within about 10, 20, 30, 40, 50, 60, or 70 base pairs of the cut site, and additional genomic DNA bordering the cut site (and having no homology to a homolog arm) can be deleted. The homology arms can range in length from about 50 nucleotides to several of thousands of nucleotides. In some embodiments, the homology arms can range in length from about 500 nucleotides to about 1000 nucleotides. In some embodiments, the homology arms are 600 bp, 700 bp, 800 bp, or 900 bp. In some embodiments, the homology arms are 800 bp. In some embodiments, the substantial sequence homology between the homology arms and the genomic DNA is at least about 80%, at least about 85%, at least about 90%, at least about 95%, or at least about 99%. In some embodiments, the homology arms have 100% sequence identity with genomic DNA flanking the target site.

In some embodiments, the at least one polynucleotide encoding at least one tolerogenic factor is operably linked to an exogenous promoter. In some embodiments, the exogenous promoter can be a constitutive, inducible, temporal-, tissue-, or cell type-specific promoter. In some embodiments, the exogenous promoter is a CAGGS, CMV, EFla, PGK, CAG, or UBC promoter.

In some embodiments, the at least one polynucleotide encoding at least one tolerogenic factor is inserted into a safe harbor locus, e.g., the AAVS 1 locus. In some embodiments, a safe harbor locus for inserting any gene described herein is selected from, but not limited to AAVS1 (PPP1 R12C), ALB, Angptl3, ApoC3, ASGR2, CCR5, FIX (F9), G6PC, Gys2, HGD, Lp(a), Pcsk9, Serpina1, TF, and TTR.

In some embodiments, the at least one polynucleotide encoding at least one tolerogenic factor is inserted into a site or region of genomic DNA that partially overlaps, completely overlaps, or is contained within (i.e., is within or near) a MHC-I gene, MHC-II gene, or a transcriptional regulator of MHC-I or MHC-II.

In some embodiments, the genome of a cell has been modified to decrease the expression of the NLR family, CARD domain containing 5 (NLRC5). NLRC5 is a critical regulator of MHC-I-mediated immune responses and, similar to CIITA, NLRC5 is highly inducible by IFN-7 and can translocate into the nucleus. NLRC5 activates the promoters of MHC-I genes and induces the transcription of MHC-I as well as related genes involved in MHC-I antigen presentation.

In some embodiments, cells having no MHC-II expression and moderate expression of MHC-I are genetically modified to have no surface expression of MHC-I or MHC-II. In another embodiment, cells with no surface expression of MHC-I/II are further edited to have expression of programmed death ligand-1 (PD-L1), e.g., insertion of a polynucleotide encoding PD-L1. In yet another embodiment, cells with no surface expression of MHC-I/II are further edited to have expression of PD-L1, e.g., insertion of a polynucleotide encoding PD-L1.

In some embodiments, the cells further comprise increased or decreased expression, e.g., by a genetic modification, of one or more additional genes that are not necessarily implicated in either immune evasion or cell survival post-engraftment. In some embodiments, the cells further comprise increased expression of one or more safety switch proteins relative to an unmodified cell. In some embodiments, the cells comprise increased expression of one or more additional genes that encode a safety switch protein. In some embodiments, a safety switch is also a suicide gene. In some embodiments, a safety switch is herpes simplex virus-1 thymidine kinase (HSV-tk) or inducible caspase-9. In some embodiments, a polynucleotide that encodes at least one safety switch is inserted into a genome, e.g., into a safe harbor locus. In some other embodiments, the one or more additional genes that are genetically modified encode one or more of safety switch proteins; targeting modalities; receptors; signaling molecules; transcription factors; pharmaceutically active proteins or peptides; drug target candidates; and proteins promoting engraftment, trafficking, homing, viability, self-renewal, persistence, and/or survival thereof integrated with the construct.

B2M Gene Edits

In some embodiments, the genome of any cell described herein is modified to disrupt beta-2-microglobulin (B2M or β2M) gene (NCBI Gene ID: 567). B2M is a non-polymorphic gene that encodes a common protein subunit required for surface expression of all polymorphic MHC class I heavy chains. HLA-I proteins are intimately associated with B2M in the endoplasmic reticulum, which is essential for forming functional, cell-surface expressed HLA-I molecules. Disrupting its expression by gene editing will prevent host versus therapeutic cell responses leading to increased therapeutic cell persistence. In some embodiments, expression of the endogenous B2M gene is eliminated to prevent a host-versus-graft response. In some embodiments, the disrupted B2M can prevent allo-immune response due to MHC-I.

In some embodiments, any of the gene-editing methods described herein are used to disrupt the B2M gene. In some embodiments, any engineered cell described herein comprises a disrupted B2M gene. In some embodiments, an iPSC described herein comprises a disrupted B2M gene. In some embodiments, an NK cell described herein comprises a disrupted B2M gene.

In some embodiments, a ribonucleoprotein particle (RNP) containing an RNA-guided nuclease (e.g., a Cas nuclease, such as a Cas9 nuclease) and a gRNA targeting the B2M gene (or any other gene of interest) are delivered to any cell described herein (e.g., iPSC). A ribonucleoprotein particle (RNP) is an RNA-guided nuclease (e.g., Cas9) pre-complexed/complexed with a gRNA. In other embodiments, the RNA-guided nuclease and gRNA are delivered separately to cells. In some embodiments, the gRNA targets a site in the B2M gene. Non-limiting examples of modified and unmodified B2M gRNA sequences that may be used as provided herein to create a genomic disruption in the B2M gene include sequences corresponding to a sequence of SEQ ID NOs: 34, 78 and 79. In some embodiments, a gRNA is used to target the B2M site for gene-editing. Other gRNA sequences may be designed using the B2M gene sequence located on Chromosome 15 (GRCh38 coordinates: Chromosome 15: 44,711,477-44,718,877; Ensembl: ENSG00000166710). In some embodiments, any B2M RNP described herein is used in combination with a donor plasmid containing B2M homology arms for insertion of any polynucleotide described herein.

In some embodiments, the gRNA comprises a polynucleotide sequence corresponding to a sequence of any one of SEQ ID NO: 34, SEQ ID NO: 78, and SEQ ID NO: 79. In some embodiments, a gRNA/CRISPR nuclease complex targets and cleaves a target site in the B2M gene locus. In some embodiments, the B2M gRNA targets a sequence comprising SEQ ID NOS: 34, 78, or 79. Repair of a double-stranded break by NHEJ can result in a deletion of at least on nucleotide and/or an insertion of at least one nucleotide, thereby disrupting or eliminating expression of B2M. In some embodiments, the B2M gene locus is targeted by at least two CRISPR systems each comprising a different gRNA, such that cleavage at two sites in the B2M gene locus leads to a deletion of the sequence between the two cuts, thereby eliminating expression of B2M.

In some embodiments, the homology arms are used with B2M guides (e.g., gRNA comprising the nucleotide sequence of SEQ ID NO: 34). In some embodiments, the homology arms are designed to be used with any B2M guide that would eliminate the start site of the B2M gene. In some embodiments, the B2M homology arms comprise or consist essentially of a polynucleotides of the sequence of SEQ ID NOs: 36 and 54, or polynucleotides having at least 85%, 90%, 95%, or 99% sequence identity with that of SEQ ID NOs: 36 or 54. In some embodiments, the left B2M homology arm can comprise or consist essentially of SEQ ID NO: 36, or a polynucleotide sequence having at least 85%, 90%, 95%, or 99% sequence identity with that of SEQ ID NO: 36. In some embodiments, the right B2M homology arm can comprise or consist essentially of SEQ ID NO: 54, or a polynucleotide sequence having at least 85%, 90%, 95%, or 99% sequence identity with that of SEQ ID NO:54.

In some embodiments, gRNAs targeting the B2M genomic region create Indels in the B2M gene disrupting expression of the mRNA or protein.

In some embodiments, at least 50% of the engineered cells of a population of cells does not express a detectable level of B2M surface protein. For example, at least 55%, at least 60%, at least 70%, at least 75%, at least 80%, at least 85%, at least 90%, or at least 95% of the engineered cells of a population may not express a detectable level of B2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population does not express a detectable level of B2M surface protein.

In some embodiments, less than 50% of the engineered cells of a population of cells express a detectable level of B2M surface protein. In some embodiments, less than 30% of the engineered cells of a population of cells express a detectable level of B2M surface protein. For example, less than 50%, less than 30%, less than 25%, less than 20%, less than 15%, less than 10%, or less than 5% of the engineered cells of a population of cells express a detectable level of B2M surface protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of B2M surface protein.

CIITA Gene Edits

In some embodiments, the genome of any cell described herein is modified to disrupt Class II major histocompatibility complex transactivator (CIITA) gene (NCBI Gene ID: 4261). CIITA is a member of the LR or nucleotide binding domain (NBD) leucine-rich repeat (LRR) family of proteins and regulates the transcription of MHC-II by associating with the MHC enhanceosome. The expression of CIITA is induced in B cells and dendritic cells as a function of developmental stage and is inducible by IFN-γ in most cell types. In some embodiments, the disrupted CIITA gene locus can prevent allo-immune response due to MHC-II.

In some embodiments, any of the gene-editing methods described herein are used to disrupt the CIITA gene. In some embodiments, any engineered cell described herein comprises a disrupted CIITA gene. In some embodiments, an iPSC described herein comprises a disrupted CIITA gene. In some embodiments, an NK cell described herein comprises a disrupted CIITA gene.

In some embodiments, a ribonucleoprotein particle (RNP) containing an RNA-guided nuclease (e.g., a Cas nuclease, such as a Cas9 nuclease) and a gRNA targeting the CIITA gene (or any other gene of interest) are delivered to any cell described herein (e.g., iPSC). A ribonucleoprotein particle (RNP) is a RNA-guided nuclease (e.g., Cas9) pre-complexed/complexed with a gRNA. In other embodiments, the RNA-guided nuclease and gRNA are delivered separately to cells. Non-limiting examples of modified and unmodified CIITA gRNA sequences that may be used as provided herein to create a genomic disruption in the CIITA gene are listed in Table 15 (e.g., corresponding sequences of SEQ ID NOS: 13-17). In some embodiments, the gRNA targets a site within the CIITA gene. In some embodiments, the CIITA gRNA targets a sequence comprising SEQ ID NOS: 13-17. In some embodiments, the gRNA comprises a polynucleotide sequence corresponding to a sequence of SEQ ID NO: 13. In some embodiments, any CIITA RNP described herein is used in combination with a donor plasmid containing CIITA homology arms for insertion of any polynucleotide described herein.

In some embodiments, gRNAs targeting the CIITA genomic region create Indels in the CIITA gene disrupting expression of the mRNA or protein. In some embodiments, a gRNA/CRISPR nuclease complex targets and cleaves a target site in the CIITA gene locus. Repair of a double-stranded break by NHEJ can result in a deletion of at least on nucleotide and/or an insertion of at least one nucleotide, thereby disrupting or eliminating expression of CIITA. In some embodiments, the CIITA gene locus is targeted by at least two CRISPR systems each comprising a different gRNA, such that cleavage at two sites in the CIITA gene locus leads to a deletion of the sequence between the two cuts, thereby eliminating expression of CIITA.

In some embodiments, the homology arms are used with CIITA guides (e.g., gRNAs comprising a nucleotide sequence corresponding to a sequence of any one of SEQ ID NOs: 13-17). In some embodiments, the homology arms are designed to be used with any CIITA guide that would eliminate the start site of the CIITA gene. In some embodiments, the CIITA homology arms comprise or consist essentially of polynucleotides of SEQ ID NOs: 22 and 32, or polynucleotide sequences having at least 85%, 90%, 95%, or 99% sequence identity with that of SEQ ID NOs: 22 or 32. In some embodiments, the left CIITA homology arm can comprise or consist essentially of SEQ ID NO: 22, or a polynucleotide sequence having at least 85%, 90%, 95%, or 99% sequence identity with that of SEQ ID NO: 22. In some embodiments, the right CIITA homology arm can comprise or consist essentially of SEQ ID NO: 32, or a polynucleotide sequence having at least 85%, 90%, 95%, or 99% sequence identity with that of SEQ ID NO: 32.

In some embodiments, at least 50% of the engineered cells of a population of cells does not express a detectable level of CIITA protein. For example, at least 55%, at least 60%, at least 70%, at least 75%, at least 80%, at least 85%, at least 90%, or at least 95% of the engineered cells of a population may not express a detectable level of CIITA surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population does not express a detectable level of CIITA protein.

In some embodiments, less than 50% of the engineered cells of a population of cells express a detectable level of CIITA protein. In some embodiments, less than 30% of the engineered cells of a population of cells express a detectable level of CIITA protein. For example, less than 50%, less than 30%, less than 25%, less than 20%, less than 15%, less than 10%, or less than 5% of the engineered cells of a population of cells express a detectable level of CIITA protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of CIITA protein.

In some embodiments, any polynucleotide described herein is inserted into the CIITA gene locus such that 86 base pairs (bp) of the CIITA exon 2 are removed after homology directed repair.

HLA-E Gene Edits

In some embodiments, the genome of any cell described herein comprises an insertion of a polynucleotide encoding human leukocyte antigen E (HLA-E; also called major histocompatibility complex, class I, E). HLA-E is encoded by HLA-E gene (gene (NCBI Gene ID: 3133). HLA-E is a heterodimer class I molecule. HLA-E primarily functions as a ligand for the NK cell inhibitory receptor KLRD1-KLRC1. HLA-E enables NK cells to monitor other MHC class I molecule expression and to tolerate self-expression. In some embodiments, the insertion of the HLA-E can protect the iNK from PB-NK "missing self" response. In some embodiments, expression of HLA-E is increased in cells. In some embodiments, an iPSC comprises an inserted polynucleotide encoding in HLA-E (or HLA-E knock-in). In some embodiments, an NK cell comprises an inserted polynucleotide encoding in HLA-E (or HLA-E knock-in). In some embodiments, the HLA-E is an HLA-E trimer.

Non-limiting examples of modified and unmodified HLA-E cDNA sequences that may be used as provided herein to create a genomic knock-in of the HLA-E gene include SEQ ID NO: 51 (i.e., HLA-E CDS) and SEQ ID NO: 75 (e.g., HLA-E trimer, consisting of SEQ ID NOS: 46-51). In some embodiments, the HLA-E trimer polynucleotide has at least 90%, 91%, 92%, 93%, 94%, 95%, 96%, 97%, 98%, or 99% identity to SEQ ID NO: 75. In some embodiments, the HLA trimer has the amino acid sequence of SEQ ID NO: 142.

In some embodiments, at least 50% of the engineered cells of a population of cells express a detectable level of HLA-E surface protein. For example, at least 55%, at least 60%, at least 70%, at least 75%, at least 80%, at least 85%, at least 90%, or at least 95% of the engineered cells of a population express a detectable level of HLA-E surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population express a detectable level of HLA-E surface protein.

In some embodiments, less than 50% of the engineered cells of a population of cells do not express a detectable level of HLA-E surface protein. In some embodiments, less than 30% of the engineered cells of a population of cells do not express a detectable level of HLA-E surface protein. For example, less than 50%, less than 30%, less than 25%, less than 20%, less than 15%, less than 10%, or less than 5% of the engineered cells of a population of cells do not express a detectable level of HLA-E surface protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells do not express a detectable level of HLA-E surface protein.

In some embodiments, any of the HLA-E polynucleotides described herein are inserted into any safe-harbor locus described herein. In some embodiments, any of the HLA-E polynucleotides described herein are inserted into any B2M gene locus described herein. In some embodiments, any of the HLA-E polynucleotides described herein are inserted into any CIITA gene locus described herein. In some embodiments, the HLA-E polynucleotide is an HLA-E trimer composed of a B2M signal peptide fused to an HLA-G presentation peptide fused to the B2M membrane protein fused to the HLA-E protein without its signal peptide. In some embodiments, the HLA-E trimer comprises or consists essentially of SEQ ID NO: 75. In some embodiments, the HLA-E polynucleotide has at least 90%, 91%, 92%, 93%, 94%, 95%, 96%, 97%, 98%, or 99% identity to SEQ ID NO: 75. In some embodiments, the trimer design is that described in Gornalusse et al. (2017) Nat. Biotechnol. 35(8): 765-772, which is incorporated herein in its entirety.

IL15 and IL15Rα Gene Edits

In some embodiments, the genome of any cell described herein comprises an insertion of polynucleotide encoding interleukin-15 (IL15), IL15Rα, and/or a fusion protein of IL15 and IL15Rα ("IL15/IL15Rα"). IL15 is a cytokine that functions in regulating NK cell proliferation and activation, and is encoded by IL15 gene (MCBI Gene ID: 3600). IL15Rα (also called IR15α) is the receptor that binds IL15, and is encoded by IL15Rα gene (MCBI Gene ID: 16169). In some embodiments, the insertion of the polynucleotide encoding IL15, IL15Rα, and/or fusion protein of IL15 and IL15Rα can lead to increased iNK persistence of the engineered cell.

In some embodiments, a cell has insertion of a polynucleotide encoding IL15, and the polynucleotide comprises or consists of SEQ ID NO: 41. In some embodiments, a cell has insertion of a polynucleotide encoding IL15Rα, and the polynucleotide comprises or consists of SEQ ID NO: 43. In some embodiments, a cell has insertion of a polynucleotide encoding a fusion protein of IL15 and IL15Rα ("IL15/IL15Rα"). In some embodiments, the fusion sequence is as described in Hurton et al. (2016) Proc Natl Acad Sci USA; 113(48):E7788-E7797. doi: 10.1073/pnas.1610544113, which is incorporated herein in its entirety. In some embodiments, the polynucleotide encoding IL15/IL15Rα comprises or consists of SEQ ID NO: 76 (which consists of SEQ ID NOS: 40-44). In some embodiments, the IL15 IL15Rα polynucleotide has at least 90%, 91%, 92%, 93%, 94%, 95%, 96%, 97%, 98%, or 99% identity to SEQ ID NO: 76. In some embodiments, the IL15/IL15Rα fusion has the amino acid sequence of SEQ ID NO: 143.

In some embodiments, IL15 and IL15Rα are co-expressed. In some embodiments, a self-cleaving peptide is used to co-express IL15 and IL15Rα. In some embodiments, the self-cleaving peptide is selected from, but not limited to, P2A (derived from porcine teschovirus-1 2A), E2A (derived from equine rhinitis A virus), F2A (derived from foot-and-mouth disease virus 18), and T2A (derived thosea asigna virus 2A). In some embodiments, the self-cleaving peptide is derived from P2A. In some embodiments, a cell has insertion of a polynucleotide encoding IL15, P2A, IL15Rα (IL15-P2A-IL15Rα). In some embodiments, an iPSC comprises a knock-in of the IL15-P2A-IL15Rα polynucleotide. In some embodiments, an NK cell comprises a knock-in of the IL15-P2A-IL15Rα polynucleotide.

In some embodiments, at least 50% of the engineered cells of a population of cells express a detectable level of any IL15, IL15Rα, and/or IL15/IL15Rα described herein. For example, at least 55%, at least 60%, at least 70%, at least 75%, at least 80%, at least 85%, at least 90%, or at least 95% of the engineered cells of a population express a detectable level of IL15, IL15Rα, and/or IL15/IL15Rα. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population expresses a detectable level of IL15, IL15Rα, and/or IL15/IL15Rα.

In some embodiments, less than 50% of the engineered cells of a population of cells do not express a detectable level of IL15, IL15Rα, and/or IL15/IL15Rα. In some embodiments, less than 30% of the engineered cells of a population of cells do not express a detectable level of IL15, IL15Rα, and/or IL15/IL15Rα. For example, less than 50%, less than 30%, less than 25%, less than 20%, less than 15%, less than 10%, or less than 5% of the engineered cells of a population of cells do not express a detectable level of IL15, IL15Rα, and/or IL15/IL15Rα. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells do not express a detectable level of IL15, IL15Rα, and/or IL15/IL15Rα.

In some embodiments, any of the IL15, IL15Rα, and/or IL15/IL15Rα polynucleotides described herein are inserted into any safe-harbor locus described herein. In some embodiments, any of the IL15, IL15Rα, and/or IL15/IL15Rα polynucleotides described herein are inserted into any B2M gene locus described herein.

SERPINB9 Gene Edits

In some embodiments, the genome of any cell described herein comprises an insertion of a polynucleotide encoding SERPINB9. SERPINB9, which is encoded by SERPINB9 gene (NCBI Gene ID: 5272), is a member of a large family of apoptosis inhibitors that mainly function by targeting intermediate proteases (e.g., covalently bind a protease in 1:1 complex, thereby inhibiting the protease). As such, expression of SERPINB9 may increase survival of the engineered cells. For example, iNK cells engineered to express SERPINB9 can survive NK cell attack by inhibiting activity of the released granzymes. In some embodiments, expression of SERPINB9 is increased in cells. In some embodiments, an iPSC comprises an insertion of a polynucleotide encoding SERPINB9 (or a SERPINB9 knock-in). In some embodiments, an NK cell comprises an insertion of a polynucleotide encoding SERPINB9 (or a SERPINB9 knock-in).

An example of a SERPINB9 cDNA sequence that may be used as provided herein to create a genomic knock-in of the SERPINB9 gene is SEQ ID NO: 129. In some embodiments, the SERPINB9 polynucleotide has at least 90%, 91%, 92%, 93%, 94%, 95%, 96%, 97%, 98%, or 99% identity to SEQ ID NO: 129. In some embodiments, the SERPINB9 protein has the amino acid sequence of SEQ ID NO: 144.

In some embodiments, at least 50% of the engineered cells of a population of cells express a detectable level of SERPINB9 protein. For example, at least 55%, at least 60%, at least 70%, at least 75%, at least 80%, at least 85%, at least 90%, or at least 95% of the engineered cells of a population express a detectable level of SERPINB9 protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population express a detectable level of SERPINB9 protein.

In some embodiments, less than 50% of the engineered cells of a population of cells do not express a detectable level of SERPINB9. In some embodiments, less than 30% of the engineered cells of a population of cells do not express a detectable level of SERPINB9. For example, less than 50%, less than 30%, less than 25%, less than 20%, less than 15%, less than 10%, or less than 5% of the engineered cells of a population of cells do not express a detectable level of SERPINB9. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells do not express a detectable level of SERPINB9.

In some embodiments, any of the SERPINB9 polynucleotides described herein are inserted into any safe-harbor locus described herein. In some embodiments, any of the SERPINB9 polynucleotides described herein are inserted into any B2M gene locus described herein.

ADAM17 Gene Edits

In some embodiments, the genome of any cell described herein is modified to disrupt a disintegrin and metalloprotease domain 17 (ADAM17) gene (NCBI Gene ID: 6868). ADAM17 cleaves TNF-α precursor. ADAM17 is responsible for proteolytic cleavage of several surface proteins. In some embodiments, the disrupted ADAM17 can increase ADCC killing by preventing CD16 cleavage.

In some embodiments, any of the gene-editing methods described herein are used to disrupt the ADAM17 gene. In some embodiments, an iPSC comprises a disrupted ADAM17 gene. In some embodiments, an NK cell comprises a disrupted ADAM17 gene.

In some embodiments, a ribonucleoprotein particle (RNP) containing an RNA-guided nuclease (e.g., a Cas nuclease, such as a Cas9 nuclease) and a gRNA targeting the ADAM17 gene (or any other gene of interest) are delivered to any cell described herein (e.g., iPSC). A ribonucleoprotein particle (RNP) is RNA-guided nuclease (e.g., Cas9) pre-complexed/complexed with a gRNA. In other embodiments, the RNA-guided nuclease and gRNA are delivered separately to cells.

Non-limiting examples of modified and unmodified ADAM17 gRNA sequences that may be used as provided herein to create a genomic disruption in the ADAM17 gene include sequences corresponding to sequences of SEQ ID NOS: 1-10. In some embodiments, the ADAM17 gRNA targets a sequence comprising any one of SEQ ID NOS: 1-10.

In some embodiments, gRNAs targeting the ADAM17 genomic region create Indels in the ADAM17 gene disrupting expression of the mRNA or protein.

In some embodiments, at least 50% of the engineered cells of a population of cells does not express a detectable level of ADAM17 protein. For example, at least 55%, at least 60%, at least 70%, at least 75%, at least 80%, at least 85%, at least 90%, or at least 95% of the engineered cells of a population may not express a detectable level of ADAM17 surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population does not express a detectable level of ADAM17 protein.

In some embodiments, less than 50% of the engineered cells of a population of cells express a detectable level of ADAM17 protein. In some embodiments, less than 30% of the engineered cells of a population of cells express a detectable level of ADAM17 protein. For example, less than 50%, less than 30%, less than 25%, less than 20%, less than 15%, less than 10%, or less than 5% of the engineered cells of a population of cells express a detectable level of ADAM17 protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of ADAM17 protein.

CISH Gene Edits

In some embodiments, the genome of any cell described herein is modified to disrupt a cytokine inducible SH2 containing protein (CISH, also called CIS) gene (NCBI Gene ID: 1154). CISH is a transcriptional co-activator that controls expression of HLA class II genes. In some embodiments, the disrupted CISH can increase iNK sensitivity to cytokines, improve iNK persistence, and/or increase tumor killing. In some embodiments, an iPSC comprises a disrupted CISH gene. In some embodiments, an NK cell comprises a disrupted CISH gene.

In some embodiments, gRNAs targeting the CISH genomic region create Indels in the CISH gene disrupting expression of the mRNA or protein. In some embodiments, the gRNA targets a site within the CISH gene. In some embodiments, the CISH gRNA targets a sequence comprising SEQ ID NOS: 81-92. In some embodiments, a gRNA targeting the CISH gene comprises a spacer sequence corresponding to a sequence comprising any one of SEQ ID NOS: 81-92.

In some embodiments, at least 50% of the engineered cells of a population of cells does not express a detectable level of CISH protein. For example, at least 55%, at least 60%, at least 70%, at least 75%, at least 80%, at least 85%, at least 90%, or at least 95% of the engineered cells of a population may not express a detectable level of CISH surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population does not express a detectable level of CISH protein.

In some embodiments, less than 50% of the engineered cells of a population of cells express a detectable level of CISH protein. In some embodiments, less than 30% of the engineered cells of a population of cells express a detectable level of CISH protein. For example, less than 50%, less than 30%, less than 25%, less than 20%, less than 15%, less than 10%, or less than 5% of the engineered cells of a population of cells express a detectable level of CISH surface protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of CISH protein.

REGNASE-1 Gene Edits

In some embodiments, the genome of any cell described herein is modified to disrupt a REGNASE-1 gene encoding zinc finger CCCH-type containing 12A (NCBI Gene ID: 80149). REGNASE-1 is an endoribonuclease involved in mRNA decay. In some embodiments, the disrupted REGNASE-1 can increase iNK persistence and/or increase tumor killing. In some embodiments, an iPSC comprises a disrupted REGNASE-1 gene. In some embodiments, an NK cell comprises a disrupted REGNASE-1 gene.

In some embodiments, gRNAs targeting the REGNASE-1 genomic region create Indels in the REGNASE-1 gene disrupting expression of the mRNA or protein. In some embodiments, the gRNA targets a site within the REGNASE-1 gene. In some embodiments, the REGNASE-1 gRNA targets a sequence comprising SEQ ID NOS: 93-101. In some embodiments, a gRNA targeting the REGNASE-1 gene comprises a spacer sequence corresponding to a sequence comprising any one of SEQ ID NOS: 93-101.

In some embodiments, at least 50% of the engineered cells of a population of cells does not express a detectable level of REGNASE-1 protein. For example, at least 55%, at least 60%, at least 70%, at least 75%, at least 80%, at least 85%, at least 90%, or at least 95% of the engineered cells of a population may not express a detectable level of REGNASE-1 protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population does not express a detectable level of REGNASE-1 protein.

In some embodiments, less than 50% of the engineered cells of a population of cells express a detectable level of REGNASE-1 protein. In some embodiments, less than 30% of the engineered cells of a population of cells express a detectable level of REGNASE-1 protein. For example, less than 50%, less than 30%, less than 25%, less than 20%, less than 15%, less than 10%, or less than 5% of the engineered cells of a population of cells express a detectable level of REGNASE-1 protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of REGNASE-1 protein.

FAS Gene Edits

In some embodiments, the genome of any cell described herein is modified to disrupt a Fas cell surface death receptor (FAS) gene (NCBI Gene ID: 355). FAS is a member of the TNF-receptor superfamily and contributes to the regulation of programmed cell death. In some embodiments, the disrupted FAS can reduce activation-induced cell death (AICD), resist apoptosis, and/or increase tumor killing. In some embodiments, an iPSC comprises a disrupted FAS gene. In some embodiments, an NK cell comprises a disrupted FAS gene.

In some embodiments, gRNAs targeting the FAS genomic region create Indels in the FAS gene disrupting expression of the mRNA or protein. In some embodiments, the gRNA targets a site within the FAS gene. In some embodiments, the FAS gRNA targets a sequence comprising SEQ ID NOS: 35, 37, 38, 39, 53, 55, or 80. In some embodiments, a gRNA targeting the FAS gene comprises a spacer sequence corresponding to a sequence comprising any one of SEQ ID NOS: 35, 37, 38, 39, 53, 55, or 80.

In some embodiments, at least 50% of the engineered cells of a population of cells does not express a detectable level of FAS protein. For example, at least 55%, at least 60%, at least 70%, at least 75%, at least 80%, at least 85%, at least 90%, or at least 95% of the engineered cells of a population may not express a detectable level of FAS surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered cells of a population does not express a detectable level of FAS protein.

In some embodiments, less than 50% of the engineered cells of a population of cells express a detectable level of FAS protein. In some embodiments, less than 30% of the engineered cells of a population of cells express a detectable level of FAS protein. For example, less than 50%, less than 30%, less than 25%, less than 20%, less than 15%, less than 10%, or less than 5% of the engineered cells of a population of cells express a detectable level of FAS protein. In some embodiments, 40%-30%, 40%-20%, 40%-10%, 40%-5%, 30%-20%, 30%-10%, 30%-5%, 20%-10%, 20%-5%, or 10%-5% of the engineered cells of a population of cells express a detectable level of FAS protein.

Edits to Knock-In Chimeric Antigen Receptors

A chimeric antigen receptor (CAR) refers to an artificial immune cell receptor that is engineered to recognize and bind to an antigen expressed by tumor cells. CARs or nucleotides encoding a CAR can be inserted into any cells described herein. CARs are chimeras of a signaling domain of the T-cell receptor (TCR) complex and an antigen-recognizing domain (e.g., a single chain fragment (scFv) of an antibody or other antibody fragment) (Enblad et al., Human Gene Therapy. 2015; 26(8):498-505). CARs have the ability to redirect cell specificity and reactivity toward a selected target in a non-MHC-restricted manner. The non-MHC-restricted antigen recognition gives cells expressing CARs the ability to recognize an antigen independent of antigen processing, thus bypassing a major mechanism of tumor escape. CARs are often referenced to by the antigen they bind. For example, a "CD30 CAR", "CD19 CAR", a "CD70 CAR", a "CD33 CAR" and a "BCMA CAR" are CARs comprising antigen binding domains that specifically bind to CD30, CD19, CD70, CD33 or BCMA, respectively. Accordingly, such terms are interchangeable with anti-CD30 CAR, anti-CD19 CAR, anti-CD70 CAR, anti-CD33 CAR and anti-BCMA CAR. It will be understood by those of ordinary skill in the art that a CAR that specifically binds an antigen can be referred to with either terminology.

In some embodiments, any iPSC described herein expresses a CAR. In some embodiments, any NK cell described herein expresses a CAR. In some embodiments, any HSPC described herein expresses a CAR.

There are four generations of CARs, each of which contains different components. First generation CARs join an antibody-derived scFv to the CD3zeta (ζ or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TCR CD3ζ chain. Third-generation costimulatory domains may include, e.g., a combination of CD3ζ, CD27, CD28, 4-1BB, ICOS, or OX40. Fourth-generation CARs include immune stimulatory cytokines to improve cell persistence and expansion. Cytokines for fourth-generation CARS include individually or in combination any of IL-7, IL-12, IL-15, IL-18, or IL-23. CARs, in some embodiments, contain an ectodomain, commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., Blood. 2015; 125(26):4017-4023; Kakarla and Gottschalk, Cancer J. 2014; 20(2):151-155).

CARs typically differ in their functional properties. The CD3ζ signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-1BB CARs, but preclinical in vivo studies suggest that 4-1BB CARs may produce superior proliferation and/or persistence. Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency.

In some embodiments, a chimeric antigen receptor is a first-generation CAR. In other embodiments, a chimeric antigen receptor is a second-generation CAR. In yet other embodiments, a chimeric antigen receptor is a third-generation CAR. In some embodiments, a chimeric antigen receptor is a fourth-generation CAR.

A CAR, in some embodiments, comprises an extracellular (ecto) domain comprising an antigen binding domain (e.g., an antibody, such as an scFv), a transmembrane domain, and a cytoplasmic (endo) domain.

Ectodomain of CARs

The ectodomain is the region of the CAR that is exposed to the extracellular fluid and, in some embodiments, includes an antigen binding domain, and optionally a signal peptide, a spacer domain, and/or a hinge domain. In some embodiments, the antigen binding domain is a single-chain variable fragment (scFv) that includes the VL and VH of immunoglobulins connected with a short linker peptide. The linker, in some embodiments, includes hydrophilic residues with stretches of glycine and serine for flexibility as well as stretches of glutamate and lysine for added solubility. A single-chain variable fragment (scFv) is not actually a fragment of an antibody, but instead is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. In some embodiments, the scFv of the present disclosure is humanized. In other embodiments, the scFv is fully human. In yet other embodiments, the scFv is a chimera (e.g., of mouse and human sequence).

In some embodiments, the scFv is an anti-BCMA scFv (binds specifically to BCMA or B-cell maturation antigen). In some embodiments, the anti-BCA scFv comprises or consists of the nucleotide sequence of SEQ ID NO: 71. In some embodiments, the anti-BCA scFv polynucleotide has at least 90%, 91%, 92%, 93%, 94%, 95%, 96%, 97%, 98%, or 99% identity to SEQ ID NO: 71. In some embodiments, the anti-BCMA CAR comprises the amino acid sequence of SEQ ID NO: 74.

In some embodiments, the scFv is an anti-CD30 scFv (binds specifically to CD30, also called TNF receptor superfamily member 8 or TNFRSF8). In some embodiments, anti-CD30 scFv may comprise variable domains from mouse monoclonal AC10 (e.g., Brentuximab). In other embodiments, anti-CD30 scFv may comprise variable domains from human 5F11 antibody (U.S. Pat. No. 7,387,776). In some embodiments the scFV of a CD30 CAR may comprise the nucleotide sequence of SEQ ID NO: 106, SEQ ID NO: 111, or SEQ ID NO: 115. In some embodiments, the anti-CD30 CAR coding sequence comprises SEQ ID NO: 108, SEQ ID NO: 112, or SEQ ID NO: 116. In some embodiments, the anti-CD30 CAR coding sequence polynucleotide has at least 90%, 91%, 92%, 93%, 94%, 95%, 96%, 97%, 98%, or 99% identity to SEQ ID NO: 108, SEQ ID NO: 112, or SEQ ID NO: 116. Non-limiting examples of a CD30 CAR that may be used as provided herein may include the amino acid sequence of SEQ ID NO: 109, SEQ ID NO: 113, or SEQ ID NO: 117.

In some embodiments, the scFv is an anti-CD19 scFv (binds specifically to CD19).

In some embodiments, the scFv is an anti-CD70 scFv (binds specifically to CD70).

In some embodiments, the scFv is an anti-CD33 scFv (binds specifically to CD33).

Other scFv proteins may be used.

The signal peptide can enhance the antigen specificity of CAR binding. Signal peptides can be derived from antibodies, such as, but not limited to, CD8, as well as epitope tags such as, but not limited to, GST or FLAG. Examples of signal peptides include MLLLVTSLLLCELPHPAFLLIP (SEQ ID NO: 68) and MALPVTALLLPLALLLHAARP (SEQ ID NO: 69). Other signal peptides may be used.

In some embodiments, a spacer domain or hinge domain is located between an extracellular domain (comprising the antigen binding domain) and a transmembrane domain of a CAR, or between a cytoplasmic domain and a transmembrane domain of the CAR. A spacer domain is any oligopeptide or polypeptide that functions to link the transmembrane domain to the extracellular domain and/or the cytoplasmic domain in the polypeptide chain. A hinge domain is any oligopeptide or polypeptide that functions to provide flexibility to the CAR, or domains thereof, or to prevent steric hindrance of the CAR, or domains thereof. In some embodiments, a spacer domain or a hinge domain may comprise up to 300 amino acids (e.g., 10 to 100 amino acids, or 5 to 20 amino acids). In some embodiments, one or more spacer domain(s) may be included in other regions of a CAR. In some embodiments, the hinge domain is a CD8 hinge domain. Other hinge domains may be used.

Transmembrane Domain of CARs

The transmembrane domain is a hydrophobic alpha helix that spans the membrane. The transmembrane domain provides stability of the CAR. In some embodiments, the transmembrane domain of a CAR as provided herein is a CD8 transmembrane domain. In other embodiments, the transmembrane domain is a CD28 transmembrane domain. In yet other embodiments, the transmembrane domain is a chimera of a CD8 and CD28 transmembrane domain. Other transmembrane domains may be used as provided herein. In some embodiments, the CD8a transmembrane domain is the nucleotide of SEQ ID NO: 28. In some embodiments, the transmembrane domain is a CD8a transmembrane domain: FVPVFLPAKPTTTPAPRPPTPAPTIASQPLSLRPEACR-PAAGGAVHTRGLDFACDIYIWAPLA GTCGVLLLSLVITLYCNHRNR (SEQ ID NO: 72). In some embodiments, the transmembrane domain is a CD8a transmembrane domain comprising the amino acid sequence: IYIWAPLAGTCGVLLLSLVITLY (SEQ ID NO: 73). In some embodiments, the transmembrane domain is a CD8 transmembrane domain comprising the amino acid sequence SAAAFVPVFLPAKPTTTPAPRPPTPAPTIA-SQPLSLRPEACRPAAGGAVHTRGLDFACDIYIW APLAGTCGVLLLSLVITLYCNHRNR (SEQ ID NO: 122). Other transmembrane domains may be used.

In some embodiments, the transmembrane domain is selected from transmembrane domains of: NKG2D, FcYRIIIa, NKp44, NKp30, NKp46, actKIR, NKG2C, CD8a, and IL15Rb. In some embodiments, the transmembrane domain is an NKG2D transmembrane domain.

Endodomain of CARs

The endodomain is the functional end of the receptor. Following antigen recognition, receptors cluster and a signal is transmitted to the cell. The most commonly used endodomain component is CD3-zeta, which contains three (3) immunoreceptor tyrosine-based activation motif (ITAM)s. This transmits an activation signal to the T cell after the antigen is bound. In many cases, CD3-zeta may not provide a fully competent activation signal and, thus, a co-stimulatory signaling is used. For example, CD28 and/or 4-1BB may be used with CD3-zeta (CD3ζ) to transmit a proliferative/survival signal. Thus, in some embodiments, the co-stimulatory molecule of a CAR as provided herein is a CD28 co-stimulatory molecule. In other embodiments, the co-stimulatory molecule is a 4-1BB co-stimulatory molecule. In some embodiments, a CAR includes CD3-zeta and CD28. In other embodiments, a CAR includes CD3-zeta and 4-1BB. In still other embodiments, a CAR includes CD3ζ, CD28, and 4-1BB. Table A provides examples of signaling domains derived from CD28, 4-1BB, and CD3-zeta that may be used herein.

TABLE A

| Name | Sequence | SEQ ID NO: |
|------|----------|------------|
| CD28 | SKRSRLLHSDYMNMTPRRPGPTRKHYQPYAPPRDFAAYRS | 123 |
| 4-1BB | KRGRKKLLYIFKQPFMRPVQTTQEEDGCSCRFPEEEEGGCEL | 124 |
| CD3-zeta | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 125 |

In some embodiments, any of the CARs described herein have one, two or more intracellular signaling domains from, e.g., CD137/41 BB, DNAM-1, NKrdO, 2B4, NTBA, CRACC, CD2, CD27, one or more integrins (e.g., ITGB1, ITGB2, or ITGB3), IL-15R, IL-18R, IL-12R, IL-21 R, or IRE1a (e.g., any combination of signaling domains from two or more of these molecules).

Natural Killer cells express a number of transmembrane adapters providing them with signal enhancement. In some embodiments, the intracellular signaling domain of any CAR described herein comprises a transmembrane adapter. In some embodiments, the transmembrane adapter is a transmembrane adaptor from one or more of: FeceR1 y, CD3ζ, DAP 12, and DAP 10.

In some embodiments, any CARs described herein have one of more co-stimulatory domains. In some embodiments, a 2B4 co-stimulatory domain is used. In some embodiments, a CD3ζ intracellular signaling domain is used. In some embodiments, a DAP10 or DAP12 co-stimulatory domains are used with a CD3ζ intracellular signaling domain. In some embodiments, a DAP10 co-stimulatory signaling domain is used with an NKG2D transmembrane domain. In some embodiments, the transmembrane domain is from NKG2D, and the endodomain is from DAP10 and CD3ζ (e.g., as described in Chang Y H et al. *Caner Res.* 2013. 73(6):1777-86). In some embodiments, the CAR comprises an NKG2D transmembrane domain fused to 4-1BB and DAP10 signaling and/or co-stimulatory domains (e.g., as described in Guo C. et al. *Mol Immunol.* 2019. 114:108-113). In some embodiments, the CAR comprises a co-stimulatory domain from 2B4. In some embodiments, the CAR comprises a CD8 transmembrane domain and 4-1BB-CD3ζ signaling domains (e.g., as in a construct as described by Imai C, et al. *Blood.* 2005, 106(1). 376-383).

In some embodiments, the CAR has a CD8 transmembrane domain, a 4-1BB intracellular domain, and a CD3ζ signaling domain. In some embodiments, the CAR has a CD28 transmembrane domain, a CD28 intracellular domain, and a CD3ζ signaling domain. In some embodiments, the CAR has a DAP12 transmembrane and intracellular domains. In some embodiments, the CAR has a 2B4 transmembrane and intracellular domains and a CD3ζ signaling domain. In some embodiments, the CAR has a CD8 transmembrane domain, a 2B4 intracellular domain, and a CD3ζ signaling domain. In some embodiments, the CAR has a CD28 transmembrane and intracellular domains, a 4-1BB intracellular domain, and a CD3ζ signaling domain. In some embodiments, the CAR has a CD16 transmembrane domain, a 2134 intracellular domain, and a CD3ζ signaling domain. In some embodiments, the CAR has a NKp44 transmembrane domain, a DAP10 intracellular domain, and a CD3ζ signaling domain. In some embodiments, the CAR has a NKp46 transmembrane domain, a2B4 intracellular domain, and a CD3r signaling domain. In some embodiments, the CAR has a NKG2D transmembrane domain, a 4-1BB intracellular domain, and a CD3ζ signaling domain. In some embodiments, the CAR has a NKG2D transmembrane domain, a 4-1BB intracellular domain, and a CD3ζ signaling domain. In some embodiments, the CAR has an NKG2D transmembrane domain, a DAP12 intracellular domain, a 2B4 intracellular domain, and a CD3ζ signaling domain. In some embodiments, the CAR has an NKG2D transmembrane domain, a DAP10 intracellular domain, a 2B4 intracellular domain, and a CD3ζ signaling domain. In some embodiments, the CAR has an NKG2D transmembrane domain, a 4-1BB intracellular domain, a 2B4 intracellular domain, and a CD3ζ signaling domain. In some embodiments, the CAR has an NKG2D transmembrane domain and a CD3' signaling domain.

Multi-Gene Editing

In some embodiments, the engineered cells of the present disclosure include more than one gene edit, for example, in more than one gene. In some embodiments, two, three, four, five, six or more genes are edited. In some embodiments, the gene-edit is an insertion (KI). In some embodiments, the gene-edit is a disruption (KO). In some embodiments, the combination of two or more gene edits described herein is a combination of insertions (KI) and disruptions (KO). In some embodiments, the gene-edits are any combination of one, two, three, four, five, six or more of the gene-edits selected from: B2M KO, IL15 KI, IL15Rα KI, IL15/IL15Rα KI, HLA-E KI, SERPINB9 KI, CIITA KO, ADAM17 KO, BCMA CAR KI, CD30 CAR KI, CISH KO, REGNASE-1 KO, FAS KO, TIGIT KO, PD-1 KO, NKG2A KO, CD70 KO, ALK4 type I activin receptor KO (e.g., a conditional KO), CD16 KI, CD70 CAR KI, CD19 CAR KI, CD33 CAR KI, NKGD2 CAR KI, a CAR or receptor comprising NKG2D ectodomain KI, NKp30 CAR KI, CD73 CAR KI, GPR87 CAR KI, and SLC7A11(xCT) CAR KI. In some embodiments, the editing of two or more genes is simultaneous, such as in the same method step. For example, an engineered cell may comprise a disrupted CIITA gene, a disrupted B2M gene, or a combination thereof. In some embodiments, any iPSC cell described herein has a disrupted CIITA gene and a disrupted B2M gene. In some embodiments, any engineered NK cell described herein comprises a disrupted CIITA gene and a disrupted B2M gene.

In some embodiments, any of the inserted polynucleotides described herein are linked to a promoter. In some embodiments, any of the inserted polynucleotides described herein are linked to an exogenous promoter. In some embodiments, the promoter is selected from but not limited to CAG promoter (also known as CBA promoter or CAGGS promoter), CMV promoter (derived from cytomegalovirus), EF-1 alpha promoter (derived from alpha subunit of EF-1 gene), PGK promoter (derived from phosphoglycerate kinase gene), UBC promoter (derived from ubiquitin C gene), or other constitutive, inducible, temporal-, tissue-, or cell type-specific promoter.

In some embodiments, the genome-engineered cells comprise introduced or increased expression in at least one of HLA-E, IL15/IL15Rα, a CAR, and SERPINB9. In some embodiments, any genome-engineered cell is HLA class I and/or class II deficient. In some embodiments, the genome-engineered cells comprise integrated or non-integrated exogenous polynucleotide encoding one or more of HLA-E, IL15/IL15Rα, a CAR, and SERPINB9 proteins. In some embodiments, said introduced expression is an increased expression from either non-expressed or lowly expressed genes comprised in said cells. In some embodiments, the non-integrated exogenous polynucleotides are introduced using Sendai virus, AAV, episomal, or plasmid. In some embodiments, the cells are B2M null, with introduced expression of HLA-E. In some embodiments, the cells are HLA-A, HLA-B, and HLA-C null, with introduced expression of HLA-E. In some embodiments, the cells are B2M null, with introduced expression of one or more of HLA-E, IL15/IL15Rα, and SERPINB9. Methods of generating any of the genetically modified cells described herein are contemplated to be performed using but not limited to, any of the gene editing methods described herein.

In some embodiments, a polynucleotide encoding HLA-E is inserted at a site within or near a B2M gene locus in any cell described herein. In some embodiments, a polynucleotide encoding HLA-E is inserted at a site within or near a B2M gene locus concurrent with or following a deletion of all or part of a B2M gene or promoter. In some embodiments, the polynucleotide encoding HLA-E is operably linked to an exogenous promoter. In some embodiments, the polynucleotide encoding HLA-E is operably linked to the CAGGS promoter. In some embodiments, any cell described herein is gene edited to express a polynucleotide encoding HLA-E operably linked to the CAGGS promoter.

In some embodiments, a polynucleotide encoding IL15/IL15Rα fusion protein is inserted at a site within or near a B2M gene locus in any cell described herein. In some embodiments, a polynucleotide encoding IL15/IL15Rα fusion protein is inserted at a site within or near a B2M gene locus concurrent with or following a deletion of all or part of a B2M gene or promoter. In some embodiments, the polynucleotide encoding IL15/IL15Rα fusion protein is operably linked to an exogenous promoter. In some embodiments, the polynucleotide encoding IL15/IL15Rα fusion protein is operably linked to the CAGGS promoter. In some embodiments, any cell described herein is gene edited to express a polynucleotide encoding IL15/IL15Rα fusion protein operably linked to the CAGGS promoter.

In some embodiments, a polynucleotide encoding SERPINB9 is inserted at a site within or near a B2M gene locus in any cell described herein. In some embodiments, a polynucleotide encoding SERPINB9 is inserted at a site within or near a B2M gene locus concurrent with or following a deletion of all or part of a B2M gene or promoter. In some embodiments, the polynucleotide encoding SERPINB9 is operably linked to an exogenous promoter. In some embodiments, the polynucleotide encoding SERPINB9 is operably linked to the CAGGS promoter. In some embodiments, any cell described herein is gene edited to express a polynucleotide encoding SERPINB9 operably linked to the CAGGS promoter.

In some embodiments, the edited cells described herein express at least one chimeric antigen receptor (CAR). In some embodiments, the CAR is inserted at a specific gene locus. In some embodiments, the CAR is inserted at a specific locus to simultaneously disrupt expression of a target gene.

In some embodiments, a polynucleotide encoding any CAR described herein is inserted within or near a CIITA gene locus. In some embodiments, a polynucleotide encoding any CAR described herein is inserted within or near a CIITA gene locus concurrent with or following a deletion of CIITA. In some embodiments, a polynucleotide encoding a BCMA-CAR is inserted within the CIITA gene locus. In some embodiments, the polynucleotide of SEQ ID NO: 66 encoding a BCMA-CAR is inserted at a site within or near a CIITA gene locus. In some embodiments, a polynucleotide encoding BCMA-CAR is inserted at a site within or near a CIITA gene locus concurrent with or following a deletion of a CIITA gene or promoter. In some embodiments, the BCMA CAR is inserted into the CIITA gene locus wherein 86 base pairs (bp) of CIITA exon 2 are removed after homology directed repair. In some embodiments, the BCMA CAR is inserted in the CIITA gene locus using into a donor plasmid. In some embodiments, a BCMA CAR donor plasmid is electroporated into any cell described herein along with the ribonucleoprotein (RNP) complex made of up of any CIITA targeting gRNA and Cas9 protein. In some embodiments, the BCMA-CAR inserted into the CIITA gene locus is driven by any promoter described herein. In some embodiments, the BCMA-CAR inserted into the CIITA gene locus is driven by the CAG promoter. In some embodiments, any cell described herein is gene-edited to express a BCMA-CAR within the CIITA gene locus. In some embodiments, an iPSC is gene-edited to express a BCMA-CAR within the CIITA gene locus.

In some embodiments, the BCMA-CAR donor plasmid (SEQ ID NO: 66) is electroporated into any cell described herein along with the ribonucleoprotein (RNP) complex made of up of any CIITA targeting gRNA (corresponding to a sequence of any one of SEQ ID NOs: 13-17) and Cas9 protein to yield a CIITA null, BCMA-CAR expressing cell. In some embodiments, the BCMA CAR donor plasmid (SEQ ID NO: 66) is electroporated into any iPSC described herein along with the ribonucleoprotein (RNP) complex made of up of CIITA targeting gRNA (SEQ ID NO: 13) and Cas9 protein to yield a CIITA null, BCMA-CAR KI expressing cell.

In some embodiments, a polynucleotide encoding a CD30-CAR is inserted within the CIITA gene locus. In some embodiments, the polynucleotide of SEQ ID NO: 108, 112, or 116 encoding a CD30 CAR is inserted at a site within or near a CIITA gene locus. In some embodiments, the polynucleotide of SEQ ID NO: 119, 120, or 121 encoding a CD30 CAR-P2A-HLA-E trimer is inserted at a site within or near a CIITA gene locus. In some embodiments, a polynucleotide encoding CD30 CAR or CD30 CAR-P2A-HLA-E trimer is inserted at a site within or near a CIITA gene locus concurrent with or following a deletion of a CIITA gene or promoter. In some embodiments, the CD30 CAR or CD30 CAR-P2A-HLA-E trimer is inserted into the CIITA gene locus wherein 86 base pairs (bp) of CIITA exon 2 are removed after homology directed repair. In some embodiments, the CD30 CAR or CD30 CAR-P2A-HLA-E trimer is inserted into in the CIITA gene locus using a donor plasmid. In some embodiments, a CD30 CAR or CD30 CAR-P2A-HLA-E trimer donor plasmid is electroporated into any cell described herein along with the ribonucleoprotein (RNP) complex made of up of any CIITA targeting gRNA and Cas9 protein. In some embodiments, the CD30 CAR or CD30 CAR-P2A-HLA-E trimer inserted into the CIITA gene locus is driven by any promoter described herein. In some embodiments, the CD30 CAR or CD30 CAR-P2A-HLA-E trimer inserted into the CIITA gene locus is driven by the CAG promoter. In some embodiments, any cell described herein is gene-edited to express a CD30 CAR or CD30 CAR-P2A-HLA-E trimer within the CIITA gene locus. In some embodiments, an iPSC is gene-edited to express a CD30 CAR or CD30 CAR-P2A-HLA-E trimer within the CIITA gene locus.

In some embodiments, the CD30 CAR-P2A-HLA-E trimer donor plasmid (SEQ ID NO: 110, 114, or 118) is electroporated into any cell described herein along with the ribonucleoprotein (RNP) complex made of up of any CIITA targeting gRNA (corresponding to a sequence of any one of SEQ ID NOs: 13-17) and Cas9 protein to yield a CIITA null, CD30 CAR, HLA-E expressing cell. In some embodiments, the CD30 CAR-P2A-HLA-E trimer donor plasmid (SEQ ID NO: 110, 114, or 118) is electroporated into any iPSC described herein along with the ribonucleoprotein (RNP) complex made of up of CIITA targeting gRNA (SEQ ID NO: 13) and Cas9 protein to yield a CIITA null, CD30 CAR, HLA-E expressing cell.

In some embodiments, a cell described herein has an insertion of a polynucleotide encoding any one or more of IL15/IL15Rα, P2A, HLA-E trimer, and SERPINB9. In some embodiments, any cell described herein has an insertion of a polynucleotide encoding any one or more of IL15/IL15Rα, P2A, HLA-E trimer, and SERPINB9 into the B2M gene locus. In some embodiments, any cell described herein has insertion of a polynucleotide encoding IL15/IL15Rα fusion protein. In some embodiments, the IL15/IL15Rα fusion protein is designed as previously described in Hurton et al. (2016) Proc Natl Acad Sci USA; 113(48): E7788-E7797. doi: 10.1073/pnas.1610544113, or which is incorporated herein in its entirety.

In some embodiments, a cell described herein has insertion of a polynucleotide encoding an IL15/IL15Rα-P2A-HLA-E trimer. In some embodiments, a cell described herein has insertion of a polynucleotide encoding an IL15/IL15Rα-P2A-HLA-E trimer encoded by SEQ ID NO: 77. In some embodiments, a cell has insertion of a polynucleotide encoding IL15/IL15Rα-P2A-HLA-E trimer into the B2M gene locus. In some embodiments, the IL15/IL15Rα-P2A-HLA-E trimer coding sequence is driven by any promoter described herein. In some embodiments, the IL15/IL15Rα-P2A-HLA-E trimer coding sequence is driven by a CAGGS promoter. In some embodiments, a donor plasmid comprising IL15/IL15Rα-P2A-HLA-E trimer sequence driven by a CAGGS promoter comprises the nucleotide sequence of SEQ ID NO: 67. In some embodiments, any cell described herein is gene-edited to express an IL15/IL15Rα-P2A-HLA-E trimer. In some embodiments, an iPSC is gene-edited to express an IL15/IL15Rα-P2A-HLA-E trimer. In some embodiments, a NK cell is gene-edited to express an IL15/IL15Rα-P2A-HLA-E trimer.

In some embodiments, the IL15/IR15α-P2A-HLA-E trimer donor plasmid (SEQ ID NO: 67) is electroporated into any cell described herein along with the ribonucleoprotein (RNP) complex made of up of B2M targeting gRNA (corresponding to a sequence of SEQ ID NOs:34, 78, or 79) and Cas9 protein to yield a B2M null, IL15/IL15Rα-P2A-HLA-E trimer expressing cell. In some embodiments, the IL15/IR15α-P2A-HLA-E trimer donor plasmid (SEQ ID NO: 67) is electroporated into any iPSC described herein along with the ribonucleoprotein (RNP) complex made of up of B2M targeting gRNA (SEQ ID NO: 34) and Cas9 protein to yield a B2M null, IL15/IR15α-P2A-HLA-E trimer expressing cell.

In some embodiments, a cell described herein has insertion of a polynucleotide encoding SERPINB9-P2A-HLA-E trimer. In some embodiments, a cell described herein has insertion of a polynucleotide encoding a SERPINB9-P2A-HLA-E trimer, wherein the polynucleotide comprises the sequence of SEQ ID NO: 131. In some embodiments, a cell has insertion of a polynucleotide encoding SERPINB9-P2A-HLA-E trimer into the B2M gene locus. In some embodiments, the SERPINB9-P2A-HLA-E trimer sequence is driven by any promoter described herein. In some embodiments, the SERPINB9-P2A-HLA-E trimer sequence is driven by a CAGGS promoter. In some embodiments, a plasmid comprising the polynucleotide encoding SERPINB9-P2A-HLA-E trimer driven by a CAGGS promoter comprises SEQ ID NO: 130. In some embodiments, any cell described herein is gene-edited to express a SERPINB9-P2A-HLA-E trimer. In some embodiments, an iPSC is gene-edited to express a SERPINB9-P2A-HLA-E trimer. In some embodiments, a NK cell is gene-edited to express a SERPINB9-P2A-HLA-E trimer.

In some embodiments, the SERPINB9-P2A-HLA-E trimer donor plasmid (SEQ ID NO: 130) is electroporated into any cell described herein along with the ribonucleoprotein (RNP) complex made of up of B2M targeting gRNA (corresponding to a sequence of SEQ ID NOs:34, 78, or 79) and Cas9 protein to yield a B2M null, SERPINB9-P2A-HLA-E trimer expressing cell. In some embodiments, the SERPINB9-P2A-HLA-E trimer donor plasmid (SEQ ID NO: 130 is electroporated into any iPSC described herein along with the ribonucleoprotein (RNP) complex made of up of B2M targeting gRNA (SEQ ID NO: 34) and Cas9 protein to yield a B2M null, SERPINB9-P2A-HLA-E trimer expressing cell.

In some embodiments, a cell described herein has insertion of a polynucleotide encoding SERPINB9-P2A-IL15/IL15Rα. In some embodiments, a cell described herein has insertion of a polynucleotide encoding SERPINB9-P2A-IL15/IL15Rα, wherein the coding sequence comprises SEQ ID NO: 137. In some embodiments, a cell has insertion of a polynucleotide encoding SERPINB9-P2A-IL15/IL15Rα into the B2M gene locus. In some embodiments, the SERPINB9-P2A-IL15/IL15Rα sequence is driven by any promoter described herein. In some embodiments, the SERPINB9-P2A-IL15/IL15Rα sequence is driven by a CAGGS promoter. In some embodiments, a plasmid comprising the polynucleotide encoding SERPINB9-P2A-IL15/IL15Rα driven by a CAGGS promoter comprises SEQ ID NO: 148. In some embodiments, any cell described herein is gene-edited to express SERPINB9-P2A-IL15/IL15Rα. In some embodiments, an iPSC is gene-edited to express SERPINB9-P2A-IL15/IL15Rα. In some embodiments, a NK cell is gene-edited to express SERPINB9-P2A-IL15/IL15Rα.

In some embodiments, the SERPINB9-P2A-IL15/IL15Rα donor plasmid (SEQ ID NO: 148) is electroporated into any cell described herein along with the ribonucleoprotein (RNP) complex made of up of B2M targeting gRNA (corresponding to a sequence of SEQ ID NOs:34, 78, or 79) and Cas9 protein to yield a B2M null, SERPINB9-P2A-IL15/IL15Rα expressing cell. In some embodiments, the SERPINB9-P2A-IL15/IL15Rα donor plasmid (SEQ ID NO: 148 is electroporated into any iPSC described herein along with the ribonucleoprotein (RNP) complex made of up of B2M targeting gRNA (SEQ ID NO: 34) and Cas9 protein to yield a B2M null, SERPINB9-P2A-IL15/IL15Rα expressing cell.

In some embodiments, any B2M null, IL15/IR15α-P2A-HLA-E trimer KI cell described herein is electroporated with BCMA-CAR donor plasmid (SEQ ID NO: 66) along with the ribonucleoprotein (RNP) complex made of up of CIITA targeting gRNA (corresponding to a sequence of any one of SEQ ID NOs: 13-17) and Cas9 protein to yield a B2M null, IL15/IL15Rα-P2A-HLA-E trimer KI, BCMA-CAR KI, CIITA null expressing cell. In some embodiments, any B2M null, IL15/IR15α-P2A-HLA-E trimer KI iPSC described herein is electroporated with BCMA-CAR donor plasmid (SEQ ID NO: 66) along with the ribonucleoprotein (RNP) complex made of up of CIITA targeting gRNA (corresponding to a sequence of any one of SEQ ID NOs: 13-17) and Cas9 protein to yield a B2M null, IL15/IL15Rα-P2A-HLA-E trimer expressing, CIITA null BCMA-CAR expressing iPSC. The engineered iPSC may then be differentiated into an NK cell.

In some embodiments, any CIITA null, BCMA-CAR KI cell described herein is electroporated with IL15/IR15α-P2A-HLA-E trimer donor plasmid (SEQ ID NO: 67) along with the ribonucleoprotein (RNP) complex made of up of B2M targeting gRNA (corresponding to a sequence of SEQ ID NO: 34) and Cas9 protein to yield a B2M null, IL15/IL15Rα-P2A-HLA-E trimer KI, BCMA-CAR KI, CIITA null expressing cell. In some embodiments, any CIITA null, BCMA-CAR KI iPSC described herein is electroporated with IL15/IR15α-P2A-HLA-E trimer donor plasmid (SEQ ID NO: 67) along with the ribonucleoprotein (RNP) complex made of up of B2M targeting gRNA (corresponding to a sequence of SEQ ID NO: 34) and Cas9 protein to yield a B2M null, IL15/IL15Rα-P2A-HLA-E trimer expressing, CIITA null, BCMA-CAR expressing iPSC. The engineered iPSC may then be differentiated into an NK cell.

In some embodiments, any B2M null, SERPINB9-P2A-IL15/IR15α KI cell described herein is electroporated with a CAR-P2A-HLA-E donor plasmid (SEQ ID NOS: 110, 114, 118) along with the ribonucleoprotein (RNP) complex made of up of CIITA targeting gRNA (corresponding to a sequence of any one of SEQ ID NOs: 13-17) and Cas9 protein to yield a B2M null, SERPINB9-P2A-IL15/IR15α expressing, CIITA null, CD30 CAR-P2A-HLA-E trimer expressing cell.

In some embodiments, any CIITA null, CAR-P2A-HLA-E trimer KI cell described herein is electroporated with a SERPINB9-P2A-IL15/IR15α donor plasmid (SEQ ID NO: 148) along with the ribonucleoprotein (RNP) complex made of up of B2M targeting gRNA (corresponding to a sequence of SEQ ID NO: 34) and Cas9 protein to yield a B2M null, CAR-P2A-HLA-E trimer expressing, CIITA null, SERPINB9-P2A-IL15/IR15α expressing cell.

In some embodiments, any B2M null, SERPINB9-P2A-IL15/IR15α expressing, CIITA null, CAR-P2A-HLA-E trimer expressing cell further comprises FAS KO and CISH KO.

In some embodiments, any cell described herein has disruption of the ADAM17 gene.

In some embodiments, any B2M null, IL15/IR15α-P2A-HLA-E trimer KI, BCMA-CAR KI, CIITA null cell described herein is gene-edited to disrupt ADAM17. In some embodiments, a B2M null, IL15/IR15α-P2A-HLA-E trimer KI, BCMA-CAR KI, CIITA null iPSC is gene-edited to disrupt ADAM17. In some embodiments ADAM17 is knocked-out using an RNP with a gRNA corresponding to a sequence consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In some embodiments, ADAM17 is knocked-out using an RNP with the gRNA corresponding to a sequence of SEQ ID NO: 1. In some embodiments, an iPSC described herein is a B2M null, IL15/IR15α-P2A-HLA-E trimer KI, BCMA-CAR KI, CIITA null, ADAM17 null. In some embodiments, a NK cell described herein is B2M null, IL15/IR15α-P2A-HLA-E trimer KI, BCMA-CAR KI, CIITA null, ADAM17 null. In some embodiments, the cell further comprises FAS KO, CISH KO, and/or REGNASE-1 KO.

In some embodiments, a B2M null, IL15/IR15α-P2A-HLA-E trimer KI, BCMA-CAR KI, CIITA null iPSC is gene-edited to disrupt ADAM17 and then differentiated into an NK cell. In some embodiments, a B2M null, IL15/IR15α-P2A-HLA-E trimer KI, BCMA-CAR KI, CIITA null iPSC is gene-edited to disrupt ADAM17, FAS, CISH, REGNASE-1 and then differentiated into an NK cell.

Genome Editing Methods

Genome editing generally refers to the process of modifying the nucleotide sequence of a genome, preferably in a precise or pre-determined manner. In some embodiments, genome editing methods as described herein, e.g., the CRISPR-endonuclease system, are used to genetically modify a cell as described herein, e.g., to create a gene-edited iPSC cell. In some embodiments, genome editing methods as described herein, e.g., the CRISPR-endonuclease system, are used to genetically modify a cell as described herein, e.g., to introduce at least one genetic modification within or near at least one gene that increases the expression of one or more MIC-I and/or MHC-II human leukocyte antigens or other components of the MHC-I or MHC-II complex relative to an unmodified cell; to introduce at least one genetic modification that increases the expression of at least one polynucleotide that encodes a tolerogenic factor relative to an unmodified cell; and/or introduce at least one genetic modification that increases or decreases the expression of at least one gene that encodes a targeting factor that improves immunogenicity.

Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and non-homologous end joining (NHEJ), as described in Cox et al., "Therapeutic genome editing: prospects and challenges,", Nature Medicine, 2015, 21(2), 121-31. These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor sequence can be an exogenous polynucleotide, such as a plasmid, a single-strand oligonucleotide, a double-stranded oligonucleotide, a duplex oligonucleotide or a virus, that has regions (e.g., left and right homology arms) of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ," in which the genetic outcome is similar to NHEJ in that small deletions and insertions can occur at the cleavage site. MMEJ can make use of homologous sequences of a few base pairs flanking the DNA break site to drive a more favored DNA end joining repair outcome, and recent reports have further elucidated the molecular mechanism of this process; see, e.g., Cho and Greenberg, Nature, 2015, 518, 174-76; Kent et al., Nature Structural and Molecular Biology, 2015, 22(3):230-7; Mateos-Gomez et al., Nature, 2015, 518, 254-57; Ceccaldi et al., Nature, 2015, 528, 258-62. In some instances, it may be possible to predict likely repair outcomes based on analysis of potential microhomologies at the site of the DNA break.

Each of these genome editing mechanisms can be used to create desired genetic modifications. A step in the genome editing process can be to create one or two DNA breaks, the latter as double-strand breaks or as two single-stranded breaks, in the target locus as near the site of intended mutation. This can be achieved via the use of endonucleases, as described and illustrated herein.

In general, the genome editing methods described herein can be in vitro or ex vivo methods. In some embodiments, the genome editing methods disclosed herein are not methods for treatment of the human or animal body by therapy and/or are not processes for modifying the germ line genetic identity of human beings.

CRISPR Endonuclease System

The CRISPR-endonuclease system is a naturally occurring defense mechanism in prokaryotes that has been repurposed as an RNA-guided DNA-targeting platform used for gene editing. CRISPR systems include Types I, II, III, IV, V, and VI systems. In some aspects, the CRISPR system is a Type II CRISPR/Cas9 system. In other aspects, the CRISPR system is a Type V CRISPR/Cprf system. CRISPR systems rely on a DNA endonuclease, e.g., Cas9, and two noncoding RNAs—crisprRNA (crRNA) and trans-activating RNA (tracrRNA)—to target the cleavage of DNA.

The crRNA drives sequence recognition and specificity of the CRISPR-endonuclease complex through Watson-Crick base pairing, typically with a ~20 nucleotide (nt) sequence in the target DNA. Changing the sequence of the 5' 20 nt in the crRNA allows targeting of the CRISPR-endonuclease complex to specific loci. The CRISPR-endonuclease complex only binds DNA sequences that contain a sequence match to the first 20 nt of the single-guide RNA (sgRNA) if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the endonuclease to form the catalytically active CRISPR-endonuclease complex, which can then cleave the target DNA.

Once the CRISPR-endonuclease complex is bound to DNA at a target site, two independent nuclease domains within the endonuclease each cleave one of the DNA strands three bases upstream of the PAM site, leaving a double-strand break (DSB) where both strands of the DNA terminate in a base pair (a blunt end).

In some embodiments, the endonuclease is a Cas9 (CRISPR associated protein 9). In some embodiments, the Cas9 endonuclease is from *Streptococcus pyogenes*, although other Cas9 homologs may be used, e.g., *S. aureus* Cas9, *N. meningitidis* Cas9, *S. thermophilus* CRISPR 1 Cas9, *S. thermophilus* CRISPR 3 Cas9, or *T. denticola* Cas9.

In some embodiments, the CRISPR endonuclease is Cpf1, e.g., *L. bacterium* ND2006 Cpf1 or *Acidaminococcus* sp. BV3L6 Cpf1. In some embodiments, the endonuclease is Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease. In some embodiments, wild-type variants may be used. In some embodiments, modified versions (e.g., a homolog thereof, a recombination of the naturally occurring molecule thereof, codon-optimized thereof, or modified versions thereof) of the preceding endonucleases may be used.

The CRISPR nuclease can be linked to at least one nuclear localization signal (NLS). The at least one NLS can be located at or within 50 amino acids of the amino-terminus of the CRISPR nuclease and/or at least one NLS can be located at or within 50 amino acids of the carboxy-terminus of the CRISPR nuclease.

Exemplary CRISPR/Cas polypeptides include the Cas9 polypeptides as published in Fonfara et al., "Phylogeny of Cas9 determines functional exchangeability of dual-RNA and Cas9 among orthologous type II CRISPR-Cas systems," Nucleic Acids Research, 2014, 42: 2577-2590. The CRISPR/Cas gene naming system has undergone extensive rewriting since the Cas genes were discovered. Fonfara et al. also provides PAM sequences for the Cas9 polypeptides from various species.

Zinc Finger Nucleases

Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., Proc Natl Acad Sci, 1999 96(6):2758-63; Dreier B et al., J Mol Biol., 2000, 303(4):489-502; Liu Q et al., J Biol Chem., 2002, 277(6):3850-6; Dreier et al., J Biol Chem., 2005, 280(42):35588-97; and Dreier et al., J Biol Chem. 2001, 276(31):29466-78.

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs are comprised of tandem arrays of 33-35 amino acid repeats, with each repeat recognizing a single base pair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefitted from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9 or CRISPR/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, Science, 2009 326(5959):1509-12; Mak et al., Science, 2012, 335(6069):716-9; and Moscou et al., Science, 2009, 326(5959):1501. The use of TALENs based on the "Golden Gate" platform, or cloning scheme, has been described by multiple groups; see, e.g., Cermak et al., Nucleic Acids Res., 2011, 39(12):e82; Li et al., Nucleic Acids Res., 2011, 39(14):6315-25; Weber et al., PLoS One, 2011, 6(2):e16765; Wang et al., J Genet Genomics, 2014, 41(6):339-47; and Cermak T et al., Methods Mol Biol., 2015 1239:133-59.

Homing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including GIY-YIG, His-Cis box, H-N-H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., Glycobiology, 2014, 24(8):663-80; Belfort and Bonocora, Methods Mol Biol., 2014, 1123:1-26; and Hafez and Hausner, Genome, 2012, 55(8):553-69.

MegaTAL Tev-mTALEN MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., Nucleic Acids Res., 2014, 42: 2591-2601; Kleinstiver et al., G3, 2014, 4:1155-65; and Boissel and Scharenberg, Methods Mol. Biol., 2015, 1239: 171-96.

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., Nucleic Acids Res., 2014, 42, 8816-29. It is anticipated that other combinations of existing nuclease-based approaches will evolve and be useful in achieving the targeted genome modifications described herein.

dCas9-FokI or dCpf1-Fok1 and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., Nature Biotech, 2014, 32: 569-76; and Guilinger et al., Nature Biotech., 2014, 32: 577-82. Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

Base Editing

In some embodiments, a gene is edited in a cell using base editing. Base Editing is a technique enabling the conversion of one nucleotide into another without double-stranded breaks in the DNA. Base editing allows for conversion of a C to T, G to A, or vice versa. An example editor for cytosine includes rAPOBEC1 which is fused to a catalytically inactive form of Cas9. The Cas9 helps to bind a site of interest and the rAPOBEC1 cytidine deaminase induces the point mutation. Conversion of adenine requires a mutant transfer RNA adenosine deaminase (TadA), a Cas9 nickase, and a sgRNA, as described herein. The construct is able to introduce the site-specific mutation without introducing a strand break. In some embodiments, Base Editing is used to introduce one or more mutations in a cell described herein.

RNA-Guided Endonucleases

The RNA-guided endonuclease systems as used herein can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary endonuclease, e.g., Cas9 from *S. pyogenes*, US2014/0068797 Sequence ID No. 8 or Sapranauskas et al., Nucleic Acids Res, 39(21): 9275-9282 (2011). The endonuclease can comprise at least 70, 75, 80, 85, 90, 95, 97, 99, or 100% identity to a wild-type endonuclease (e.g., Cas9 from *S. pyogenes*, supra) over 10 contiguous amino acids. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids. The endonuclease can comprise at least: 70, 75, 80, 85, 90, 95, 97, 99, or 100% identity to a wild-type endonuclease (e.g., Cas9 from *S. pyogenes*, supra) over 10 contiguous amino acids in a HNH nuclease domain of the endonuclease. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids in a HNH nuclease domain of the endonuclease. The endonuclease can comprise at least: 70, 75, 80, 85, 90, 95, 97, 99, or 100% identity to a wild-type endonuclease (e.g., Cas9 from *S. pyogenes*, supra) over 10 contiguous amino acids in a RuvC nuclease domain of the endonuclease. The endonuclease can comprise at most: 70, 75, 80, 85, 90, 95, 97, 99, or 100% identity to a wild-type endonuclease (e.g., Cas9 from *S. pyogenes*, supra) over 10 contiguous amino acids in a RuvC nuclease domain of the endonuclease.

The endonuclease can comprise a modified form of a wild-type exemplary endonuclease. The modified form of the wild-type exemplary endonuclease can comprise a mutation that reduces the nucleic acid-cleaving activity of the endonuclease. The modified form of the wild-type exemplary endonuclease can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary endonuclease (e.g., Cas9 from *S. pyogenes*, supra). The modified form of the endonuclease can have no substantial nucleic acid-cleaving activity. When an endonuclease is a modified form that has no substantial nucleic acid-cleaving activity, it is referred to herein as "enzymatically inactive."

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagine, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

Guide RNAs

The present disclosure provides a guide RNAs (gRNAs) that can direct the activities of an associated endonuclease to a specific target site within a polynucleotide. A guide RNA can comprise at least a spacer sequence that hybridizes to a target nucleic acid sequence of interest, and a CRISPR repeat sequence. In CRISPR Type II systems, the gRNA also comprises a second RNA called the tracrRNA sequence. In the CRISPR Type II guide RNA (gRNA), the CRISPR repeat sequence and tracrRNA sequence hybridize to each other to form a duplex. In CRISPR Type V systems, the gRNA comprises a crRNA that forms a duplex. In some embodiments, a gRNA can bind an endonuclease, such that the gRNA and endonuclease form a complex. The gRNA can provide target specificity to the complex by virtue of its association with the endonuclease. The genome-targeting nucleic acid thus can direct the activity of the endonuclease.

Exemplary guide RNAs include a spacer sequences that comprises 15-200 nucleotides wherein the gRNA targets a genome location based on the GRCh38 human genome assembly. As is understood by the person of ordinary skill in the art, each gRNA can be designed to include a spacer sequence complementary to its genomic target site or region. See Jinek et al., Science, 2012, 337, 816-821 and Deltcheva et al., Nature, 2011, 471, 602-607.

The gRNA can be a double-molecule guide RNA. The gRNA can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

In some embodiments, a sgRNA comprises a 20 nucleotide spacer sequence at the 5' end of the sgRNA sequence. In some embodiments, a sgRNA comprises a less than a 20 nucleotide spacer sequence at the 5' end of the sgRNA sequence. In some embodiments, a sgRNA comprises a more than 20 nucleotide spacer sequence at the 5' end of the sgRNA sequence. In some embodiments, a sgRNA comprises a variable length spacer sequence with 17-30 nucleotides at the 5' end of the sgRNA sequence. In some embodiments, a sgRNA comprises a spacer extension sequence with a length of more than 1, 5, 10, 15, 20, 25, 30, 35, 40, 45, 50, 60, 70, 80, 90, 100, 120, 140, 160, 180, or 200 nucleotides. In some embodiments, a sgRNA comprises a spacer extension sequence with a length of less than 3, 5, 10, 15, 20, 25, 30, 35, 40, 45, 50, 60, 70, 80, 90, or 100 nucleotides.

In some embodiments, a sgRNA comprises a spacer extension sequence that comprises another moiety (e.g., a stability control sequence, an endoribonuclease binding sequence, or a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

In some embodiments, a sgRNA comprises a spacer sequence that hybridizes to a sequence in a target polynucleotide. The spacer of a gRNA can interact with a target polynucleotide in a sequence-specific manner via hybridization (i.e., base pairing). The nucleotide sequence of the spacer can vary depending on the sequence of the target nucleic acid of interest.

In a CRISPR-endonuclease system, a spacer sequence can be designed to hybridize to a target polynucleotide that is located 5' of a PAM of the endonuclease used in the system. The spacer may perfectly match the target sequence or may have mismatches. Each endonuclease, e.g., Cas9 nuclease, has a particular PAM sequence that it recognizes in a target DNA. For example, *S. pyogenes* Cas9 recognizes a PAM that comprises the sequence 5'-NRG-3', where R comprises either A or G, where N is any nucleotide and N is immediately 3' of the target nucleic acid sequence targeted by the spacer sequence.

A target polynucleotide sequence can comprise 20 nucleotides. The target polynucleotide can comprise less than 20 nucleotides. The target polynucleotide can comprise more than 20 nucleotides. The target polynucleotide can comprise at least: 5, 10, 15, 16, 17, 18, 19, 20, 21, 22, 23, 24, 25, 30 or more nucleotides. The target polynucleotide can comprise at most: 5, 10, 15, 16, 17, 18, 19, 20, 21, 22, 23, 24, 25, 30 or more nucleotides. The target polynucleotide sequence can comprise 20 bases immediately 5' of the first nucleotide of the PAM.

A spacer sequence that hybridizes to a target polynucleotide can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides. In some examples, the spacer can comprise 18 nucleotides. In some examples, the spacer can comprise 22 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

A tracrRNA sequence can comprise nucleotides that hybridize to a minimum CRISPR repeat sequence in a cell. A minimum tracrRNA sequence and a minimum CRISPR repeat sequence may form a duplex, i.e. a base-paired double-stranded structure. Together, the minimum tracrRNA sequence and the minimum CRISPR repeat can bind to an RNA-guided endonuclease. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild-type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

In some embodiments, a tracrRNA may be a 3' tracrRNA. In some embodiments, a 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

In some embodiments, a gRNA may comprise a tracrRNA extension sequence. A tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, or 200 nucleotides. The tracrRNA extension sequence can have a length from about 20 to about 5000 or more nucleotides. The tracrRNA extension sequence can have a length of less than 5, 10, 15, 20, 25, 30, 35, 40, 45, 50, 60, 70, 80, 90, or 100 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt.

In some embodiments, a sgRNA may comprise a linker sequence with a length from about 3 nucleotides to about 100 nucleotides. In Jinek et al., supra, for example, a simple 4 nucleotide "tetraloop" (-GAAA-) was used (Jinek et al., Science, 2012, 337(6096):816-821). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used (Jinek et al., Science, 2012, 337(6096):816-821), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

In some embodiments, a sgRNA does not comprise a uracil, e.g., at the 3' end of the sgRNA sequence. In some embodiments, a sgRNA does comprise one or more uracils, e.g., at the 3' end of the sgRNA sequence. In some embodiments, a sgRNA comprises 1, 2, 3, 4, 5, 6, 7, 8, 9, or 10 uracils (U) at the 3' end of the sgRNA sequence.

A sgRNA may be chemically modified. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, chemical modifications enhance stability, reduce the likelihood or degree of innate immune response, and/or enhance other attributes, as described in the art.

In some embodiments, a modified gRNA may comprise a modified backbones, for example, phosphorothioates, phosphotriesters, morpholinos, methyl phosphonates, short chain alkyl or cycloalkyl intersugar linkages or short chain heteroatomic or heterocyclic intersugar linkages.

Morpholino-based compounds are described in Braasch and David Corey, Biochemistry, 2002, 41(14): 4503-4510; Genesis, 2001, Volume 30, Issue 3; Heasman, Dev. Biol., 2002, 243: 209-214; Nasevicius et al., Nat. Genet., 2000, 26:216-220; Lacerra et al., Proc. Natl. Acad. Sci., 2000, 97: 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122: 8595-8602.

In some embodiments, a modified gRNA may comprise one or more substituted sugar moieties, e.g., one of the following at the 2' position: OH, SH, $SCH_3$, F, OCN, $OCH_3$, $OCH_3 O(CH_2)_n CH_3$, $O(CH_2)_n NH_2$, or $O(CH_2)_n CH_3$, where n is from 1 to about 10; C1 to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; 2'-O-(2-methoxyethyl); 2'-methoxy (2'-O—$CH_3$); 2'-propoxy (2'-$OCH_2CH_2CH_3$); and 2'-fluoro (2'-F). Similar modifications may also be made at other positions on the gRNA, particularly the 3' position of the sugar on the 3' terminal nucleotide and the 5' position of 5' terminal nucleotide. In some examples, both a sugar and an internucleoside linkage, i.e., the backbone, of the nucleotide units can be replaced with novel groups.

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp 75-77, 1980; Gebeyehu et al., Nucl. Acids Res. 1997, 15:4513. A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Complexes of a Genome-Targeting Nucleic Acid and an Endonuclease

A gRNA interacts with an endonuclease (e.g., a RNA-guided nuclease such as Cas9), thereby forming a complex. The gRNA guides the endonuclease to a target polynucleotide.

The endonuclease and gRNA can each be administered separately to a cell or a subject. In some embodiments, the endonuclease can be pre-complexed with one or more guide RNAs, or one or more crRNA together with a tracrRNA. The pre-complexed material can then be administered to a cell or a subject. Such pre-complexed material is known as a ribonucleoprotein particle (RNP). The endonuclease in the RNP can be, for example, a Cas9 endonuclease or a Cpf1 endonuclease. The endonuclease can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The weight ratio of genome-targeting nucleic acid to endonuclease in the RNP can be 1:1. For example, the weight ratio of sgRNA to Cas9 endonuclease in the RNP can be 1:1.

Cells

Provided herein are any of the cells described herein having any of the gene-edits described herein. In some embodiments, a cell (and corresponding unmodified cell) is a mammalian cell. In some embodiments, a cell (and corresponding unmodified cell) is a human cell. In some embodiments, a cell (and corresponding unmodified cell) is a stem cell. In some embodiments, a cell (and corresponding unmodified cell) is a pluripotent stem cell (PSC). In some embodiments, a cell (and corresponding unmodified cell) is an embryonic stem cell (ESC), an adult stem cell (ASC), an induced pluripotent stem cell (iPSC), or a hematopoietic stem or progenitor cell (HSPC). In some embodiments, a cell is an iPSC. In some embodiments, a cell may be a differentiated cell. In some embodiments, a cell is a somatic cell, e.g., an immune system cell or a contractile cell, e.g., a skeletal muscle cell.

In some embodiments, the stem cells described herein (e.g., iPSCs) are gene-edited as described herein and then differentiated into a cell type of interest. In some embodiments, the differentiated cell retains the gene-edits of the cell from which it is derived.

The cells described herein may be differentiated into relevant cell types. In general, differentiation comprises maintaining the cells of interest for a period time and under conditions sufficient for the cells to differentiate into the differentiated cells of interest. For example, the engineered stem cells disclosed herein may be differentiated into mesenchymal progenitor cells (MPCs), hypoimmunogenic cardiomyocytes, muscle progenitor cells, blast cells, endothelial cells (ECs), macrophages, natural killer cells, hepatocytes, beta cells (e.g., pancreatic beta cells), pancreatic endoderm progenitors, pancreatic endocrine progenitors, or neural progenitor cells (NPCs). In some embodiments, any of the stem cells described herein are differentiated after gene-editing. In some embodiments, a cell is differentiated into a natural killer (NK) cell.

Stem cells are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell that itself is derived from a multipotent cell, and so on. While each of these multipotent cells may be considered stem cells, the range of cell types that each can give rise to may vary considerably. Some differentiated cells also have the capacity to give rise to cells of greater developmental potential. Such capacity may be natural or may be induced artificially upon treatment with various factors. In many biological instances, stem cells can also be "multipotent" because they can produce progeny of more than one distinct cell type, but this is not required for "stem-ness."

A "differentiated cell" is a cell that has progressed further down the developmental pathway than the cell to which it is being compared. Thus, stem cells can differentiate into lineage-restricted precursor cells (such as a hematopoietic stem and progenitor cell (HSPC)), which in turn can differentiate into other types of precursor cells further down the pathway (such as a common lymphoid progenitor cell), and then to an end-stage differentiated cell, such as a natural killer cell, which plays a characteristic role in a certain tissue type, and may or may not retain the capacity to proliferate further.

In some embodiments, any of the gene-edited cells described herein have one of more of the following characteristics; increased persistency, immune evasiveness, lack of an alloimmune T cell response, increased cytotoxic activity, improved antibody-dependent cellular cytotoxicity (ADCC), or increased anti-tumor activity. In some embodiments, any of the gene-edited cells described herein have one of more of the following characteristics relative to an un-edited (wild-type) cell described herein; increased persistency, immune evasiveness, lack of an alloimmune T cell response, increased cytotoxic activity, improved antibody-dependent cellular cytotoxicity (ADCC), or increased anti-tumor activity. In some embodiments, any of the gene-edited cells described herein are capable of cell expansion in the absence of exogenous IL15.

Embryonic Stem Cells

The cells described herein may be embryonic stem cells (ESCs). ESCs are derived from blastocytes of mammalian embryos and are able differentiate into any cell type and propagate rapidly. ESCs are also believed to have a normal karyotype, maintaining high telomerase activity, and exhibiting remarkable long-term proliferative potential, making these cells excellent candidates for use as gene-edited stem cells. In some embodiments, ESCs with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Adult Stem Cells

The cells described herein may be adult stem cells (ASCs). ASCs are undifferentiated cells that may be found in mammals, e.g., humans. ASCs are defined by their ability to self-renew, e.g., be passaged through several rounds of cell replication while maintaining their undifferentiated state, and ability to differentiate into several distinct cell types, e.g., glial cells. Adult stem cells are a broad class of stem cells that may encompass hematopoietic stem cells, mammary stem cells, intestinal stem cells, mesenchymal stem cells, endothelial stem cells, neural stem cells, olfactory adult stem cells, neural crest stem cells, and testicular cells. In some embodiments, ASCs with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Induced Pluripotent Stem Cells

The cells described herein may be induced pluripotent stem cells (iPSCs). An iPSC may be generated directly from an adult human cell by introducing genes that encode critical transcription factors involved in pluripotency, e.g., Oct4, Sox2, cMyc, and Klf4. An iPSC may be derived from the same subject to which subsequent progenitor cells are to be administered. That is, a somatic cell can be obtained from a subject, reprogrammed to an induced pluripotent stem cell, and then re-differentiated into a progenitor cell to be administered to the subject (e.g., autologous cells). However, in the case of autologous cells, a risk of immune response and poor viability post-engraftment remain. In some embodiments, iPSC are generated from adult somatic cells using genetic reprogramming methods known in the art. In some embodiments, the iPSCs are derived from a commercial source. In some embodiments, the cells described herein are iPSCs or a derivative cell. In some embodiments, iPSC with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Mesoderm

The cells described herein may be mesodermal cells. This cell type is one of the three germinal layers in embryonic development. The mesoderm eventually differentiates into, but is not limited to muscle, connective tissue, bone, red blood cells, white blood cells, and microglia. In some embodiments, the gene-edited cells described herein are mesodermal cells. In some embodiments, mesodermal cells are derived from any of the stem cells described herein. In some embodiments, mesodermal cells are derived from iPSC. In some embodiments, the mesodermal cells have any of the gene-edits described herein. In some embodiments, the mesodermal cells are differentiated into NK cells. In some embodiments, mesodermal cells with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Hemogenic Endothelium

The cells described herein may be hemogenic endothelium (HE) cells. This cell type is an intermediate precursor of hematopoietic progenitors. In some embodiments, the cells described herein are hemogenic endothelium cells. In some embodiments, the gene-edited cells described herein are hemogenic endothelium cells. In some embodiments, hemogenic endothelium cells are derived from any of the stem cells described herein. In some embodiments, hemogenic endothelium cells are derived from iPSC. In some embodiments, the hemogenic endothelial cells have any of the gene-edits described herein. In some embodiments, the hemogenic endothelial cells are differentiated into NK cells. In some embodiments, HE cells with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Human Hematopoietic Stem and Progenitor Cells

The cells described herein may be human hematopoietic stem and progenitor cells (hHSPCs). This stem cell lineage gives rise to all blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells). Blood cells are produced by the proliferation and differentiation of a very small population of pluripotent hematopoietic stem cells (HSCs) that also have the ability to replenish themselves by self-renewal. During differentiation, the progeny of HSCs progress through various intermediate maturational stages, generating multi-potential and lineage-committed progenitor cells prior to reaching maturity. Bone marrow (BM) is the major site of hematopoiesis in humans and, under normal conditions, only small numbers of hematopoietic stem and progenitor cells (HSPCs) can be found in the peripheral blood (PB). Treatment with cytokines, some myelosuppressive drugs used in cancer treatment, and compounds that disrupt the interaction between hematopoietic and BM stromal cells can rapidly mobilize large numbers of stem and progenitors into the circulation. In some embodiments, HSPCs are derived from any of the stem cells described herein. In some embodiments, HSPCs are derived from iPSCs. In some embodiments, the HSPCs have any of the gene-edits described herein. In some embodiments, the HSPCs cells are differentiated into NK cells. In some embodiments, HSPCs with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Common Lymphoid Progenitor

The cells described herein may be common lymphoid progenitor (CLP) cells. CLPs are descendants of HSPCs. These cells differentiate into the lymphoid lineage of blood cells. Further differentiation yields B-cell progenitor cells, Natural Killer cells, and Thymocytes. In some embodiments, the cells described herein are common lymphoid progenitors. In some embodiments, the gene-edited cells described herein are common lymphoid progenitors. In some embodiments, CLP cells are derived from iPSCs. In some embodiments, the CLP cells have any of the gene-edits described herein. In some embodiments, the CLP cells are differentiated into NK cells. In some embodiments, CLP cells with one, two, three, four, five, six or all of the following edits: B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null, are differentiated into NK cells.

Differentiation of Cells into Other Cell Types

Another step of the methods of the present disclosure may comprise differentiating cells into differentiated cells. The differentiating step may be performed according to any method known in the art. For example, human iPSCs are differentiated into natural killer cells using methods known in the art. In some embodiments, the differentiating step may be performed according to Zhu and Kaufman, bioRxiv 2019; dx.doi.org/10.1101/614792. A differentiated cell may be any somatic cell of a mammal, e.g., a human. In some embodiments, a somatic cell may be an endocrine secretory epithelial cell (e.g., thyroid hormone secreting cells, adrenal cortical cells), an exocrine secretory epithelial cell (e.g., salivary gland mucous cell, prostate gland cell), a hormone-secreting cell (e.g., anterior pituitary cell, pancreatic islet cell), a keratinizing epithelial cell (e.g., epidermal keratinocyte), a wet stratified barrier epithelial cell, a sensory transducer cell (e.g., a photoreceptor), an autonomic neuron cells, a sense organ and peripheral neuron supporting cell (e.g., Schwann cell), a central nervous system neuron, a glial cell (e.g., astrocyte, oligodendrocyte), a lens cell, an adipocyte, a kidney cell, a barrier function cell (e.g., a duct cell), an extracellular matrix cell, a contractile cell (e.g., skeletal muscle cell, heart muscle cell, smooth muscle cell), a blood cell (e.g., erythrocyte), an immune system cell (e.g., megakaryocyte, microglial cell, neutrophil, mast cell, a T cell, a B cell, a Natural Killer cell), a germ cell (e.g., spermatid), a nurse cell, or an interstitial cell. In some embodiments, any of the stem cells described herein are differentiated into NK cells. In some embodiments, any of the derivative cell types described herein are differentiated into NK cells.

Provided herein, in some embodiments, are methods for generating Natural Killer (NK) cells from stem cells. The method includes: (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, WNT C-59 and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; (g) culturing the cell population in a seventh medium comprising IL-7, FLT3L, IL-15 and SCF for a time sufficient to generate NK cells. In some embodiments, the method includes (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; (g) culturing the cell population in a seventh medium comprising IL-7, FLT3L, IL-15 and SCF and (h) culturing the cell population in an eighth medium comprising IL-7, FLT3L, IL-15, SCF and nicotinamide for a time sufficient to generate NK cells. In some embodiments, the method includes (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; (g) culturing the cell population in a seventh medium comprising IL-7, FLT3L, IL-15 and SCF and (h) culturing the cell population in an eighth medium comprising IL-7, FLT3L, IL-15, and SCF for a time sufficient to generate NK cells. In some embodiments, the second medium further includes a ROCK inhibitor. In some embodiments, the ROCK inhibitor is thiazovivin. In some embodiments, the ROCK inhibitor is Y27652. In some embodiments, the WNT pathway activator is CHIR-99021. In some embodiments, the activin/nodal inhibitor is SB-431542.

In some embodiments, steps (a)-(g) occurs between 20-35 days. In some embodiments, step (a) includes culturing for 12-48 hours. In some embodiments, step (b) includes culturing for up to 24 hours. In some embodiments, step (c) includes culturing for 1-3 days. In some embodiments, step (d) includes culturing for 1-3 days. In some embodiments, step (e) includes culturing for 1-3 days. In some embodiments, step (f) includes culturing for up to 7 days. In some embodiments, step (g) includes culturing for at least 6 days and up to 21-28 days total. In some embodiments, step (a) includes culturing for 16-20 hours; step (b) includes culturing for 6-10 hours; step (c) includes culturing for 2 days; step (d) includes culturing for 2 days; step (e) includes culturing for 2 days; step (f) includes culturing for 4 days; and/or step (g) includes culturing for 14-28 days.

In some embodiments, steps (a)-(h) occurs between 19 and 36 days. In some embodiments, steps (a)-(h) occurs between 19 and 33 days. In some embodiments, steps (a)-(h) occurs between 24 and 36 days. In some embodiments, step (a) includes culturing for 12-48 hours. In some embodiments, step (b) includes culturing for up to 24 hours. In some embodiments, step (c) includes culturing for 1-3 days. In some embodiments, step (d) includes culturing for 1-3 days. In some embodiments, step (e) includes culturing for 1-3 days. In some embodiments, step (f) includes culturing for up to 7 days. In some embodiments, step (g) includes culturing for up to 6 days. In some embodiments, step (h) includes culturing for at least 6 days and up to 10-16 days total. In some embodiments, step (a) includes culturing for 16-20 hours; step (b) includes culturing for 6-10 hours; step (c) includes culturing for 2 days; step (d) includes culturing for 2 days; step (e) includes culturing for 2 days; step (f)

includes culturing for 4 days; step (g) includes culturing for 6 days and/or step (h) includes culturing for 10-16 days.

In some embodiments, the method is carried out under suspension agitation. In some embodiments, the suspension agitation includes rotation. In some embodiments, the first media includes StemFlex or StemBrew medium. In some embodiments, the second, third, fourth and fifth media include APEL medium. In some embodiments, the sixth and seventh media can include DMEM/F12 medium. In some aspects, the sixth and seventh media comprise DMEM (high glucose)/F12 medium. In some embodiments, the sixth and seventh media include human serum (e.g., at the concentration of 10-20%), zinc sulfate (e.g., at a concentration of about 20-40 μM), ethanolamine (e.g., at a concentration of about 10-100 μM), β-mercaptoethanol (e.g., at a concentration of about 0.1-5 μM), glucose (e.g., at a total concentration of 2-40 mM), or any combination thereof. In some embodiments, the sixth and seventh media include human serum (e.g., at the concentration of 15%), zinc sulfate (e.g., at a concentration of about 36 or 37 μM), ethanolamine (e.g., at a concentration of about 50 μM), β-mercaptoethanol (e.g., at a concentration of about 1 μM), glucose (e.g., at a total concentration of 27 mM), or any combination thereof. In some embodiments, the sixth and seventh media include human serum (e.g., at a concentration of about 10-40%), zinc sulfate (e.g., at a concentration of about 20-40 μM), ethanolamine (e.g., at a concentration of about 10-100 μM), glucose (e.g., at a total concentration of about 2-40 mM), or any combination thereof. In some embodiments, the sixth and seventh media include human serum (e.g., at a concentration of about 20%), zinc sulfate (e.g., at a concentration of about 37 μM), ethanolamine (e.g., at a concentration of about 50 μM), glucose (e.g., at a total concentration of about 20 mM), or any combination thereof. In some embodiments, the eighth media includes human serum (e.g., at a concentration of about 2-15%), zinc sulfate (e.g., at a concentration of about 20-40 μM), ethanolamine (e.g., at a concentration of about 10-100 μM), glucose (e.g., at a total concentration of about 2-40 mM), or any combination thereof. In some embodiments, the eighth media can include DMEM/F12 medium. In some aspects, the eighth media comprises DMEM (high glucose)/F12 medium. In some embodiments, the eighth media includes human serum (e.g., at a concentration of about 10%), zinc sulfate (e.g., at a concentration of about 37 μM), ethanolamine (e.g., at a concentration of about 50 μM), glucose (e.g., at a total concentration of about 20 mM), or any combination thereof. In any of the sixth, seventh, and eighth media provided herein, the total glucose concentration comprises glucose from all sources including glucose present in the base media and any added glucose. In each of the sixth, seventh, and eighth media provided herein, additional glucose may be added to a glucose containing base media (e.g., DMEM, F12 or DMEM (high glucose)/F12 medium) to reach the "total" glucose concentration. In some embodiments, about 10.25 mM of glucose is added to the base media of the sixth or seventh media to reach the total glucose concentration of about 27 mM. In some embodiments, about 4.66 mM of glucose is added to the base media of the sixth or seventh media to reach the total glucose concentration of about 20 mM. In some embodiments, about 2.33 mM of glucose is added to the base media of the eighth media to reach the total glucose concentration of about 20 mM. In some embodiments, the first medium includes 10 μM of the ROCK inhibitor. In some embodiments, the second medium includes 30 ng/mL BMP-4. In some embodiments, the second medium includes 30 ng/mL BMP-4 and 10 μM of a ROCK inhibitor. In some embodiments, the third medium includes 30 ng/mL BMP-4, 100 ng/mL FGF2, 6 μM CHIR-99021, and 2.5-5 ng/mL Activin A. In some embodiments, the third medium includes 30 ng/mL BMP-4, 100 ng/mL FGF2, 7 μM CHIR-99021, and 2.5-5 ng/mL Activin A.

In some embodiments, half of the third medium is added to the stem cell aggregates. In some embodiments, the fourth and fifth media include 20 ng/mL FGF, 20 ng/mL VEGF, 20 ng/mL TPO, 100 ng/mL SCF, 40 ng/mL IL-3, and 10-20 ng/mL FLT3L. In some embodiments, the fourth medium further includes 2 μM WNT C-59 and 5 μM SB-431542. In some embodiments, the fourth medium further includes 5 μM SB-431542. In some embodiments, the fourth medium does not include WNT C-59. In some embodiments, the sixth and seventh media includes 20 ng/mL IL-7, 10-20 ng/mL FLT3L, 10-20 ng/mL IL-15, and 20 ng/mL SCF. In some embodiments, the sixth medium includes 5 ng/mL IL-3. In some embodiments, the eighth media includes IL-7, FLT3L, IL-15, SCF and nicotinamide. In various embodiments, the eighth medium includes 10-20 ng/mL IL-7, 5-20 ng/mL FLT3L, 10-30 ng/mL IL-15, 20-40 ng/mL SCF, and 1-15 mM nicotinamide. In various embodiments, the eighth medium includes 10 ng/mL IL-7, 7.5 ng/mL FLT3L, 15 ng/mL IL-15, 20 ng/mL SCF and 6.5 mM nicotinamide. In some embodiments, the eighth media includes IL-7, FLT3L, IL-15, and SCF. In various embodiments, the eighth medium includes 10-20 ng/mL IL-7, 5-20 ng/mL FLT3L, 10-30 ng/mL IL-15, and 20-40 ng/mL SCF. In various embodiments, the eighth medium includes 10 ng/mL IL-7, 7.5 ng/mL FLT3L, 15 ng/mL IL-15, and 20 ng/mL SCF. In some embodiments, the eighth medium does not comprise nicotinamide.

In some embodiments, the HSPCs of step (d) express CD34. In some embodiments, the NK cells express CD56. In some embodiments, the NK cells express at least one activating receptor. In some embodiments, the at least one activating receptor is selected from the group of NKp44, NKp46, CD16, KIR2DL4, and any combination thereof. In some embodiments, the NK cells express at least one inhibitory receptor. In some embodiments, the at least one inhibitory receptor is selected from the group of CD94, NKG2A, KIR3DL2, and any combination thereof.

In some embodiments, the NK cells include at least one function associated with endogenous NK cells. In some embodiments, the at least one function includes the ability to induce cell lysis and cell death of a target cell. In some embodiments, the at least one function includes degranulation. In some embodiments, the degranulation includes release of perforin and granzyme B. In some embodiments, the degranulation includes expression of CD107a on the cell surface of an NK cell.

In some embodiments, the population of stem cells is a population of engineered cells, such as the engineered cells generated or obtained by the methods disclosed herein. In some embodiments, the population of engineered cells is differentiated by the methods of generating Natural Killer (NK) cells from stem cells disclosed herein.

In some embodiments, a plurality of Natural Killer (NK) cells is generated or obtained by the method of generating Natural Killer (NK) cells from stem cells disclosed herein. Also disclosed herein is a plurality of NK cells is for use in treating a subject in need thereof. In some embodiments, the subject is a human who has, is suspected of having, or is at risk for a cancer. Also disclosed herein is a method comprising administering to a subject the plurality of NK cells.

Natural Killer Cells

Natural killer (NK) cells are a subpopulation of lymphocytes which play a critical role in the innate immune system. NK cells have cytotoxicity against a variety of cells including but not limited to tumor cells and virus-infected cells. In some embodiments, the stem cells described herein are differentiated to Natural Killer cells. In some embodiments, iPSCs are differentiated into NK cells. In some embodiments, the engineered NK cells (such as cells derived from gene-edited iPSCs by differentiation, i.e., iNK cells) have enhanced anti-tumor activity as compared to un-edited or wild-type NK cells. In some embodiments, anti-tumor activity of the engineered NK cells is increased by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, or at least 90% relative to control (e.g., un-edited or wild-type) NK cells.

In some embodiments, the engineered NK cells exhibit increased cellular lysis capability relative to control cells. In some embodiments, the engineered NK cells of the present disclosure exhibit at least 10% increase in cellular lysis capability (kill at least 10% more target cells), or at least 20% increase in cellular lysis capability (kill at least 20% more target cells), relative to control (e.g., un-edited or wild-type) cells. For example, the engineered NK cells of the present disclosure may exhibit an at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, or at least 90% increase in cellular lysis capability, relative to control (e.g., un-edited or wild-type) cells. In some embodiments, the engineered NK cells of the present disclosure exhibit a 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% increase in cellular lysis capability, relative to control (e.g., un-edited or wild-type) cells. In some embodiments, the target cells are T cells. In some embodiments, the target cells are cancer cells. In some embodiments, the target cells are leukemia cells. In some embodiments, this increase in cellular lysis capability is observed at E:T (effector:target cell) ratio of at or about 0.1:1. In some embodiments, this increase in cellular lysis capability is observed at E:T (effector:target cell) ratio of at or about 0.5:1. In some embodiments, this increase in cellular lysis capability is observed at E:T (effector:target cell) ratio of at or about 1:1. In some embodiments, this increase in cellular lysis capability is observed at E:T (effector:target cell) ratio of at or about 0.1:1, when the target cell is K562 and when the cells are co-cultured for, e.g., 24 hours. In some embodiments, this increase in cellular lysis capability is observed at E:T (effector:target cell) ratio of at or about 0.5:1, when the target cell is K562 and when the cells are co-cultured for, e.g., 24 hours. In some embodiments, this increase in cellular lysis capability is observed at E:T (effector:target cell) ratio of at or about 1:1, when the target cell is K562 and when the cells are co-cultured for, e.g., 24 hours. In some embodiments, this increase in cellular lysis capability is observed at E:T (effector:target cell) ratio of at or about 0.1:1, when the target cell is RPMI and when the cells are co-cultured for, e.g., 24 hours. In some embodiments, this increase in cellular lysis capability is observed at E:T (effector:target cell) ratio of at or about 0.5:1, when the target cell is RPMI and when the cells are co-cultured for, e.g., 24 hours. In some embodiments, this increase in cellular lysis capability is observed at E:T (effector:target cell) ratio of at or about 1:1, when the target cell is RPMI and when the cells are co-cultured for, e.g., 24 hours.

In some embodiments, the engineered NK cells express at least one, two, three, four, five, six, seven, eight or all of the following markers: CD45, CD56, CD94, NKG2A, CD16, NKp44, NKp46, KIR2DL4, and KIR3DL2, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells expresses at least one, two, three, four, five or all of the following markers: CD56, NKp44, NKp46, CD94, NKG2A and KIR2DL4, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells have at least 25%, at least 30%, at least 40%, at least 50%, at least 60%, at least 70%, at least 80%, at least 90%, at least 95% or at least 99% of the cell population expressing one, two, three, four, five, six, seven, eight or all of the following markers: CD45, CD56, CD94, NKG2A, CD16, NKp44, NKp46, KIR2DL4, and KIR3DL2. In some embodiments, the engineered NK cells have at least 25%, at least 30%, at least 40%, at least 50%, at least 60%, at least 70%, at least 80%, at least 90%, at least 95% or at least 99% of the cell population expressing one, two, three, four, five or all of the following markers: CD56, NKp44, NKp46, CD94, NKG2A and KIR2DL4.

In some embodiments, the engineered NK cells express at least one, two, three or all of the following markers: CD38, CD96, DNAM-1, and ICAM-1, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells express at least one, two, three or all of the following markers: CD38, CD96, DNAM-1, and ICAM-1, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells have at least 25%, at least 30%, at least 40%, at least 50%, at least 60%, at least 70%, at least 80%, at least 90%, at least 95% or at least 99% of the cell population expressing one, two, three or all of the following markers: CD38, CD96, DNAM-1, and ICAM-1. In some embodiments, the engineered NK cells have at least 25%, at least 30%, at least 40%, at least 50%, at least 60%, at least 70%, at least 80%, at least 90%, at least 95% or at least 99% of the cell population expressing one, two, three or all of the following markers: CD38, CD96, DNAM-1, and ICAM-1.

In some embodiments, the engineered NK cells express at least one, two, three or all of the following markers: NKG2D, TIM3, CD16, and CD25, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells express at least one, two, three or all of the following markers: NKG2D, TIM3, CD16, and CD25, and optionally wherein the markers are expressed at least at 25%, 30%, 40%, 50%, 75%, 80%, 90%, 95% or 100% level or more relative to their expression in un-edited or wild-type NK cells. In some embodiments, the engineered NK cells have at least 10%, at least 15%, at least 20%, at least 25%, at least 30%, at least 40%, at least 50%, at least 60%, at least 70%, at least 80%, at least 90%, at least 95% or at least 99% of the cell population expressing one, two, three or all of the following markers: NKG2D, TIM3, CD16, and CD25. In some embodiments, the engineered NK cells have at least 10%, at least 15%, at least 20%, at least 25%, at least 30%, at least 40%, at least 50%, at least 60%, at least 70%, at least 80%, at least 90%, at least 95% or at least 99% of the cell population expressing one, two, three or all of the following markers: NKG2D, TIM3, CD16, and CD25.

In some embodiments, the engineered NK cells of the present disclosure exhibit an increased cytokine secretion relative to control (e.g., un-edited or wild-type) cells. In some embodiments, the engineered NK cells of the present disclosure exhibit about the same cytokine secretion level relative to control (e.g., un-edited or wild-type) cells. In some embodiments, the engineered NK cells of the present disclosure exhibit a reduced (e.g., reduced by less than 10%, less than 20%, less than 30%, less than 40%, or less than 50%) cytokine secretion level relative to control (e.g., un-edited or wild-type) cells. In some embodiments, the engineered NK cells of the present disclosure exhibit a reduced (e.g., reduced by more than 20%, more than 30%, more than 40%, more than 50%, or more than 75%) cytokine secretion level relative to control (e.g., un-edited or wild-type) cells. In some embodiments, the engineered NK cells of the present disclosure exhibit an increased (e.g., increased by at least 5%, at least 10%, at least 20%, at least 30%, at least 40%, at least 50%, or at least 75%) cytokine secretion level relative to control (e.g., un-edited or wild-type) cells. The cytokine(s) being measured can be, without limitation any one or more of: TNFα, IFNγ and IL-7. In some embodiments, the level of cytokines (e.g., TNFα, IFNγ and IL-7) secreted by the engineered NK cells is about the same as the level in control (e.g., un-edited or wild-type) cells, when cells are co-cultured with target cells at the E:T ratio of or about 0.1:1. In some embodiments, the level of cytokines (e.g., TNFα, IFNγ and IL-7) secreted by the engineered NK cells is reduced (by, e.g., at least 10%, 20%, 30%, 40%, 50%, 60% or 70%, and/or no more than 50%, 60%, 70%, 80%, or 90%) relative to the level in control (e.g., un-edited or wild-type) cells, when cells are co-cultured with target cells at the E:T ratio of or about 0.1:1. In some embodiments, the level of cytokines (e.g., TNFα, IFNγ and IL-7) secreted by the engineered NK cells is increased (by, e.g., at least 5%, 10%, 20%, 30%, 40%, 50%, 60% or 70%) relative to the level in control (e.g., un-edited or wild-type) cells, when cells are co-cultured with target cells at the E:T ratio of or about 0.1:1.

In some embodiments, the engineered NK cells of the present disclosure exhibit an increased expression or release of Granzyme B or perforin relative to control (e.g., un-edited or wild-type) cells. In some embodiments, the engineered NK cells of the present disclosure exhibit about the same expression or release level of Granzyme B or perforin relative to control (e.g., un-edited or wild-type) cells. In some embodiments, the engineered NK cells of the present disclosure exhibit a reduced (e.g., reduced by less than 10%, less than 20%, less than 30%, less than 40%, or less than 50%) Granzyme B or perforin expression or release level relative to control (e.g., un-edited or wild-type) cells. In some embodiments, the engineered NK cells of the present disclosure exhibit a reduced (e.g., reduced by more than 20%, more than 30%, more than 40%, more than 50%, or more than 75%) Granzyme B or perforin expression or release level relative to control (e.g., un-edited or wild-type) cells. In some embodiments, the engineered NK cells of the present disclosure exhibit an increased (e.g., increased by at least 5%, at least 10%, at least 20%, at least 30%, at least 40%, at least 50%, or at least 75%) Granzyme B or perforin expression or release level relative to control (e.g., un-edited or wild-type) cells. In some embodiments, the level of Granzyme B or perforin secreted by the engineered NK cells is about the same as the level in control (e.g., un-edited or wild-type) cells, when cells are co-cultured with target cells at the E:T ratio of or about 0.1:1. In some embodiments, the level of Granzyme B or perforin secreted by the engineered NK cells is reduced (by, e.g., at least 10%, 20%, 30%, 40%, 50%, 60% or 70%, and/or no more than 50%, 60%, 70%, 80%, or 90%) relative to the level in control (e.g., un-edited or wild-type) cells, when cells are co-cultured with target cells at the E:T ratio of or about 0.1:1. In some embodiments, the level of Granzyme B or perforin secreted by the engineered NK cells is increased (by, e.g., at least 5%, 10%, 20%, 30%, 40%, 50%, 60% or 70%) relative to the level in control (e.g., un-edited or wild-type) cells, when cells are co-cultured with target cells at the E:T ratio of or about 0.1:1.

In some embodiments, the engineered NK cells of the present disclosure exhibit an increased (e.g., increased by at least 5%, at least 10%, at least 20%, at least 30%, at least 40%, at least 50%, or at least 75%) expression level of CD107a relative to control (e.g., un-edited or wild-type) cells. In some embodiments, the engineered NK cells of the present disclosure exhibit about the same expression level of CD107a relative to control (e.g., un-edited or wild-type) cells. In some embodiments, engineered NK cells of the present disclosure exhibit a reduced (e.g., reduced by less than 10%, less than 20%, less than 30%, less than 40%, or less than 50%) CD107a expression level relative to control (e.g., un-edited or wild-type) cells. In some embodiments, the engineered NK cells of the present disclosure exhibit a reduced (e.g., reduced by more than 20%, more than 30%, more than 40%, more than 50%, or more than 75%) CD107a expression level relative to control (e.g., un-edited or wild-type) cells.

In some embodiments, the engineered NK cells have higher proliferative capacity as compared to un-edited or wild-type NK cells. In some embodiments, the engineered NK cells have approximately the same proliferative capacity compared to un-edited or wild-type NK cells.

In some embodiments, the engineered NK cells do not exhibit exhaustion or exhibit a low level of exhaustion (e.g., a level of exhaustion markers associated with a functional NK cell). In some embodiments, exhaustion is detected by detecting a reduced expression of IFNγ, granzyme B, perforin, CD107a, and/or TNFα in cells. In some embodiments, exhaustion is detected by detecting increased expression (e.g., on the surface of the cell) of an exhaustion marker, e.g., PD-1, LAG-3, TIGIT and/or TIM-3. In some embodiments, the engineered NK cells have normal or higher than normal expression of perforin, granzyme B, CD107a, IFNγ and/or TNFα (relative to un-edited or wild-type cells). In some embodiments, the engineered NK cells have lower than normal or no expression of PD-1, LAG-3, TIGIT and/or TIM-3 (relative to un-edited or wild-type cells). In some embodiments, engineered NK cells of the present disclosure exhibit reduced exhaustion, relative to control (e.g., un-edited cells or wild-type) NK cells.

In some embodiments, the engineered NK cells of the present disclosure exhibit about the same cellular viability as control (e.g., un-edited or wild-type) cells. In some embodiments, the engineered NK cells of the present disclosure exhibit increased cellular viability relative to control (e.g., un-edited or wild-type) cells. In some embodiments, the engineered NK cells of the present disclosure exhibit at least 10% or at least 20% increase in cellular viability, relative to control cells. For example, the engineered NK cells of the present disclosure may exhibit at least 25%, at least 30%, at least 35%, at least 40%, at least 45%, at least 50%, at least 55%, at least 60%, at least 65%, at least 70%, at least 75%, at least 80%, or at least 90% increase in cellular viability, relative to control cells. In some embodiments, the engineered NK cells of the present disclosure exhibit a 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60% increase in cellular viability, relative to control cells. Methods of measuring cell viability are known to those of skill in the art and described herein.

In some embodiments, the engineered NK cells have higher expression of one or more cell cycle genes, one or more cell division genes, and/or one or more DNA replication genes, as compared to un-edited or wild-type NK cells. In some embodiments, the engineered NK cells have approximately the same expression of one or more cell cycle genes, one or more cell division genes, and/or one or more DNA replication genes, as compared to un-edited or wild-type NK cells.

In some embodiments, gene-edited iPSC cells are differentiated into NK cell having any of the characteristics described herein. In some embodiments, iPSC cells are gene-edited with one or more of the following, B2M null, CIITA null, ADAM17 null, HLA-E knock-in, IL15/IL15Rα knock-in, BCMA CAR knock-in, CD30 CAR knock-in, SERPINB9 knock-in, FAS null, CISH null, and REGNASE-1 null CAR, then differentiated into NK cells. In some embodiments, iPSC cells are edited with B2M null, IL15/IL15Rα KI, and HLA-E KI, then differentiated into NK cells. In some embodiments, iPSC cells are edited with B2M null, SERPINB9 KI, and HLA-E KI, then differentiated into NK cells. In some embodiments, iPSC cells are edited with B2M null, SERPINB9 KI, IL15/IL15Rα KI, then differentiated into NK cells. In some embodiments, B2M null, CIITA null, ADAM17 null, HLA-E knock-in, IL 15/IL15Rα knock-in, CAR KI gene-edited iPSC cells are differentiated into NK cells. The CAR can be, without limitation, a BCMA CAR or a CD30 CAR. In some embodiments, B2M null, CIITA null, CISH null, FAS null, SERPINB9 knock-in, IL15/IL15Rα knock-in, CD30 CAR knock-in, HLA-E knock-in gene-edited iPSC cells are differentiated into NK cells.

In some embodiments, the engineered NK cells having any of the characteristics described herein have the following gene edits: B2M null, IL15/IL15Rα KI, and HLA-E KI (e.g., IL15/IL15Rα-P2A-HLA-E trimer KI, B2M KO). In some embodiments, the engineered NK cells having any of the characteristics described herein have the following gene edits: B2M null, CIITA null, ADAM17 null, HLA-E knock-in, IL15/IL15Rα knock-in, CAR KI. In some embodiments, the CAR is BCMA. In some embodiments, the engineered NK cells express a CAR specific for BCMA and the target cell (e.g., cancer cell) expresses BCMA. In some embodiments, the CAR is CD30. In some embodiments, the engineered NK cells express a CAR specific for CD30 and the target cell (e.g., cancer cell) expresses CD30.

In some embodiments, the engineered NK cells having any of the characteristics described herein have the following gene edits: B2M null, CIITA null, CISH null, FAS null, SERPINB9 knock-in, IL15/IL15Rα knock-in, CD30 CAR knock-in, HLA-E knock-in (e.g., SERPINB9-P2A-IL15/IL15Rα KI, CD30 CAR-P2A-HLA-E trimer KI, B2M KO, CIITA KO, CISH KO, FAS KO).

In some embodiments, any of the engineered NK cells described herein have one of more of the following characteristics relative to an un-edited (wild-type) NK cell described herein: increased persistency, increased immune evasiveness, lack of an alloimmune T cell response, increased cytotoxic activity, improved antibody-dependent cellular cytotoxicity (ADCC), or increased anti-tumor activity.

In some embodiments, the population of engineered cells of the present disclosure is engineered (e.g., by use of CRISPR-Cas9 gene-editing) to induce a site-specific disruption in a target gene sequence that eliminates the expression of an allogeneic antigen. In some embodiments, an allogeneic antigen is a major histocompatibility antigen. In some embodiments, a major histocompatibility antigen is a MHC I complex. In some embodiments, the target gene sequence is found in the B2M gene that encodes a protein component of the MHC I complex.

In some embodiments, persistence of the engineered cells is assessed by analyzing their presence and quantity in one or more tissue samples that are collected from a subject following administration of the engineered cells to the subject. In some embodiments, persistence is defined as the longest duration of time from administration to a time wherein a detectable level of the engineered cells is present in a given tissue type (e.g., peripheral blood). In some embodiments, persistence is defined as the continued absence of disease (e.g., complete response or partial response). Determination of the absence of disease and response to treatment are known to those of skill in the art and described herein.

Methods of appropriate tissue collection, preparation, and storage are known to one skilled in the art. In some embodiments, persistence of cells is assessed in one or more tissue samples from a group comprised of peripheral blood, cerebrospinal fluid, tumor, skin, bone, bone marrow, breast, kidney, liver, lung, lymph node, spleen, gastrointestinal tract, tonsils, thymus and prostate. In some embodiments, a quantity of cells is measured in a single type of tissue sample (e.g., peripheral blood). In some embodiments, a quantity of cells is measured in multiple tissue types (e.g., peripheral blood in addition to bone marrow and cerebrospinal fluid). By measuring quantity of cells in multiple tissue types, the distribution of cells throughout different tissues of the body can be determined. In some embodiments, a quantity of cells is measured in one or more tissue samples at a single time point following administration. In some embodiments, a quantity of cells is measured in one or more tissue samples at multiple time points following administration.

A detectable level of the engineered cells in a given tissue can be measured by known methodologies. Methods for assessing the presence or quantity of cells in a tissue of interest are known to those of skill in the art. Such methods include, but are not limited to, reverse transcription polymerase chain reaction (RT-PCR), competitive RT-PCR, real-time RT-PCR, RNase protection assay (RPA), quantitative immunofluorescence (QIF), flow cytometry, northern blotting, nucleic acid microarray using DNA, western blotting, enzyme-linked immunosorbent assay (ELISA), radioimmunoassay (RIA), tissue immunostaining, immunoprecipitation assay, complement fixation assay, fluorescence-activated cell sorting (FACS), mass spectrometry, magnetic bead-antibody immunoprecipitation, or protein chip.

As used herein, in some embodiments, persistence is the longest period from the time of administration to a time wherein a detectable level of the engineered cells is measured. In some embodiments, a detectable level of cells is defined in terms of the limit of detection of a method of analysis. The limit of detection can be defined as the lowest quantity of a component or substance that can be reliably and reproducibly measured by an analytical procedure when compared to a tissue sample expected to have no quantity of the component or substance of interest. A non-limiting exemplary method to determine a reproducible limit of detection is to measure the analytical signal for replicates of a zero calibrator relative to a blank sample (Armbruster, D. et al. (2008) Clin Biochem Rev. 29:S49-S52). A blank sample is known to be devoid of an analyte of interest. A zero calibrator is the highest dilution of a test sample of known concentration or quantity that gives analytical signal above that measured for the blank sample. By quantifying the analytical signal for at least 5, 6, 7, 8, 9, 10, 11, 12, 13, 14, 15, 16, 17, 18, 19, 20, 21, 22, 23, 24, 25, 26, 27, 28, 29, or 30 replicates of a zero calibrator, one can determine an average and standard deviation (SD) for the limit of detection of an analytical method of interest. Selection of a method with a suitable limit of detection for quantifying donor T cells in a given tissue can be ascertained by one skilled in the art. In some embodiments, a detectable level of cells is any quantity of cells in a tissue sample that gives an analytical signal above the limit of detection for a method of analysis. In some embodiments, a detectable level of cells is any quantity of cells in a tissue sample that gives an analytical signal that is at least 2 SDs, 3 SDs, 4 SDs, 5 SDs, 6 SDs, 7 SDs, 8 SDs, 9 SDs, or 10 SDs, above the limit of detection for the method of analysis.

It is known that CAR-expressing donor cells can undergo expansion following administration to a recipient. Expansion is a response to antigen recognition and signal activation (Savoldo, B. et al. (2011) J Clin Invest. 121:1822; van der Stegen, S. et al. (2015) Nat Rev Drug Discov. 14:499-509). In some embodiments, following expansion, CAR-expressing engineered cells undergo a contraction period, wherein a portion of the cell population that are short-lived effector cells are eliminated and what remains is a portion of the cell population that are long-lived memory cells. In some embodiments, persistence is a measure of the longevity of the engineered cell population following expansion and contraction. The duration of the expansion, contraction and persistence phases are evaluated using a pharmacokinetic profile. In some embodiments, a pharmacokinetic (PK) profile is a description of the cells measured in a given tissue over time and is readily ascertained by one skilled in the art by measuring the cells in a given tissue (e.g., peripheral blood) at multiple time points. In some embodiments, a measure of a PK profile provides a method of evaluating or monitoring the effectiveness of the engineered cell therapy in a subject (e.g., having cancer). In some embodiments, a measure of a PK profile provides a method of evaluating the persistence of the engineered cells in a subject. In some embodiments, a PK profile provides a method of evaluating the expansion of the engineered cells in a subject. In some embodiments, a measure of persistence of engineered cells in a subject is used to evaluate the effectiveness of engineered cell therapy in a subject. In some embodiments, a measure of expansion of engineered cells in a subject is used to evaluate the effectiveness of engineered cell therapy in a subject.

In some embodiments, a PK profile is prepared by measuring a quantity of engineered cells in a sample of a given tissue type (e.g., peripheral blood) collected from a recipient and repeating the assessment at different time points. In some embodiments, a baseline tissue sample is collected from a recipient no more than 1 day, 2 days, 3 days, 4 days, 5 days, 6 days, 7 days, 8 days, 9 days, 10 days, 12 days, 13 days, 14 days, or 15 days prior to administration. In some embodiments, tissue collection from a recipient is performed within 0.25-2 hours, within 1-3 hours, within 2-6 hours, within 3-11 hours, within 4-20 hours, within 5-48 hours of the time of administration of engineered cells. In some embodiments, tissue collection from a recipient is performed on a daily basis starting on day 1, day 2, day 3, or day 4 and continuing through at least day 5, day 6, day 7, day 8, day 9, day 10, day 11, day 12, day 13, day 14, day 15, day 16, day 17, day 18, day 19, or day 20. In some embodiments, tissue collection from a recipient is performed at least 1 time, 2 times, 3 times, 4 times, 5 times, or 6 times per week for up to 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, or 16 weeks following administration of cells. In some embodiments, tissue collection from a recipient is performed at least 1 time, 2 times, 3 times, 4 times, 5 times, or 6 times per month for up to 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, or 24 months following administration of cells. In some embodiments, tissue collection from a recipient is performed at least 1 time, 2 times, 3 times, 4 times, 5 times, or 6 times per year for up to 1 year, 2 years, 3 years, 4 years, 5 years, 6 year, 7 years, 8 years, 9 years, or 10 years following administration of cells.

In some embodiments, engineered cell persistence is defined as the duration of time from administration wherein a quantity of engineered cells is present that is at least 0.005-0.05%, 0.01-0.1%, 0.05-0.5%, 0.1-1%, 0.5%-5%, 1-10%, 5%-10%, or 10%-15% (e.g., at least 1%, 5%, 10%, or 15%) of the peak quantity of engineered cells. In some embodiments, a persistence of cells is determined by comparing the quantity of cells measured in a given tissue type (e.g., peripheral blood) to the peak quantity of cells that is measured in the same tissue type. In some embodiments, a persistence of cells is determined by comparing the quantity of cells measured in a given subject (e.g., peripheral blood) to the peak quantity of cells that is measured in the same subject. In some embodiments, a persistence of cells is determined by comparing the quantity of cells measured in a given subject (e.g., peripheral blood) to the peak quantity of cells that is measured in a different subject (i.e., a subject with partial response, a subject with complete response).

In some embodiments, a persistence of engineered cells is present in one or more tissue types (e.g. peripheral blood) following administration wherein engineered cells are administered on day 1. In some embodiments, a persistence of engineered cells is present in one or more tissue types (e.g. peripheral blood) up to 1 day, 2 days, 3 days, 4, days, 5 days, 6 days, 7 days, 8 days, 9 days, 10 days, 11 days, 12 days, 13 days, 14 days, 15 days, 16 days, 17 days, 18 days, 19 days, 21 days, 21 days, 22 days, 23 days, 24 days, 25 days, 26 days, 27 days, 28 days, 29 days, 30 days, 31 days, 32 days, 33 days, 34 days, or 35 days following administration wherein engineered cells are administered on day 1. In some embodiments, a persistence of engineered cells is present in one or more tissue types (e.g. peripheral blood) up to 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 21 months, 22 months, 23 months, or 24 months following administration of engineered cells). In some embodiments, a persistence of engineered cells is measured in one or more tissue types (e.g. peripheral blood) up to 1 year, 2 years, 3 years, 4 years, 5 years, 6 years, 7 years, 8 years, 9 years, and 10 years following administration of engineered cells. In some embodiments, a persistence of engineered cells that is at least 10-25 days, at least 25-50 days, at least 50-100 days, at least 100-364 days, at least one year, at least two years, at least three years, at least four years or at least five years from administration wherein engineered cells are administered on day 1 is indicative of a response in a recipient (e.g. complete response or partial response).

Isolation and Purification of Cells
Purification

In some embodiments, the population of gene-edited cells (e.g., iPSC, iNK, or NK cells) described herein are activated and/or expanded before or after genome editing. In some embodiments, iPSC cells are differentiated after gene-editing. In some embodiments, cells are activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to genome editing.

In some embodiments, the disclosure provides a method for substantially isolating cells that express a detectable level of a surface protein (e.g., B2M) from a population of cells comprising any of the engineered NK cells disclosed herein (e.g., IL15/IL15Rα KI, HLA-E KI, B2M null, CIITA null, CAR KI, ADAM17 null cells or SERPINB9 KI, IL15/IL15Rα KI, HLA-E KI, CAR KI, B2M null, CIITA null, FAS null, CISH null cells).

In some embodiments, the disclosure provides a method for isolating a population of cells comprising any of the engineered CAR NK cells disclosed herein (e.g., comprising CAR KI and B2M KO, CIITA KO, ADAM17 KO, FAS KO, CISH KO. REGNASE-1 KO, IL15/IL15Rα KI, HLA-E KI, and/or SERPINB9 KI) comprising: providing the population of cells wherein the engineered CAR NK cells comprise a disrupted CIITA gene, a disrupted B2M gene, a disrupted ADAM17 gene, a disrupted FAS gene, a disrupted CISH gene, and/or a disrupted REGNASE-1 gene; and isolating the population of cells expressing a CAR (e.g. such that >99% of the population comprises the CAR expressing cells).

In some embodiments, the disclosure provides a population of cells comprising engineered NK cells described herein (e.g., B2M KO, CIITA KO, ADAM17 KO, FAS KO, CISH KO. REGNASE-1 KO, IL15/IL15Rα KI, HLA-E KI, CAR KI, and/or SERPINB9 KI) wherein less than 0.5% of the cells in the population express a detectable level of ADAM17, B2M, CIITA, FAS, and/or CISH. In some embodiments, the disclosure provides a population of cells comprising engineered NK cells described herein, wherein less than 0.1%, less than 0.2%, less than 0.3%, less than 0.4%, less than 0.5%, less than 1%, less than 2%, less than 3%, less than 4%, less than 5% or less than 10% of the cells in the population express a detectable level of ADAM17, B2M, CIITA. FAS, CISH, and/or REGNASE-1.

Removal of a subset of cells from a population can be performed using conventional cell purification methods. Non-limiting examples of cell sorting methods include fluorescence-activated cell sorting, immunomagnetic separation, chromatography, and microfluidic cell sorting. In some embodiments, CAR-expressing cells are removed from a population of cells comprising engineered NK cells by immunomagnetic separation. In some embodiments, HLA-E-expressing cells are removed from a population of cells comprising engineered NK cells by immunomagnetic separation.

In some embodiments, genome edited cells are sorted into single cells. In some embodiments, single cell isolates of gene-edited cells are grown into single cell clonal populations. In some embodiments, multiple single-cell clones are generated. In some embodiments, an edited clone is expanded to generate a master cell bank (MCB).

Formulations and Administrations
Formulation and Delivery for Gene Editing

Guide RNAs, polynucleotides, e.g., polynucleotides that encode any protein described herein or polynucleotides that encode an endonuclease, and endonucleases as described herein may be formulated and delivered to cells in any manner known in the art.

Guide RNAs and/or polynucleotides may be formulated with pharmaceutically acceptable excipients such as carriers, solvents, stabilizers, adjuvants, diluents, etc., depending upon the particular mode of administration and dosage form. Guide RNAs and/or polynucleotides compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 2011, 18: 1127-1133 (which focuses on non-viral delivery vehicles for siRNA that are also useful for delivery of other polynucleotides).

For polynucleotides of the disclosure, the formulation may be selected from any of those taught, for example, in International Application WO 2013090648.

Polynucleotides, such as guide RNA, sgRNA, and mRNA encoding an endonuclease, may be delivered to a cell or a subject by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle may range in size from 1-1000 nm, 1-500 nm, 1-250 nm, 25-200 nm, 25-100 nm, 35-75 nm, or 25-60 nm.

LNPs may be made from cationic, anionic, or neutral lipids. Neutral lipids, such as the fusogenic phospholipid DOPE or the membrane component cholesterol, may be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs may also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce an LNP. In addition, the polynucleotide(s) can be combined with lipid(s) in a wide range of molar ratios to produce an LNP.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes described herein. Production of pseudotyped rAAV is disclosed in, for example, international patent application publication number WO 01/83692.

Formulation and Administration of Cells

Genetically modified cells, as described herein may be formulated and administered to a subject by any manner known in the art.

The terms "administering," "introducing", "implanting", "engrafting" and "transplanting" are used interchangeably in the context of the placement of cells, e.g., progenitor cells, into a subject, by a method or route that results in at least partial localization of the introduced cells at a desired site. The cells e.g., progenitor cells, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the lifetime of the subject, i.e., long-term engraftment.

In some embodiments, a genetically modified cell as described herein is viable after administration to a subject for a period that is longer than that of an unmodified cell.

In some embodiments, a composition comprising cells as described herein are administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

In some embodiments, a composition comprising cells may be administered to a subject, e.g., a human subject, who has, is suspected of having, or is at risk for a disease. In some embodiments, a composition may be administered to a subject who does not have, is not suspected of having or is not at risk for a disease. In some embodiments, a subject is a healthy human. In some embodiments, a subject e.g., a human subject, who has, is suspected of having, or is at risk for a genetically inheritable disease. In some embodiments, the subject is suffering or is at risk of developing symptoms indicative of a disease.

Treatment Methods

Provided herein, in some embodiments, are methods for treating cancer (e.g., leukemias, e.g., acute myeloid leukemia) using any engineered cells described herein (or any population of cells described herein). Non-limiting examples of cancers that may be treated as provided herein include multiple myeloma, Hodgkin's lymphoma, lung cancer, leukemia, B-cell acute lymphoblastic leukemia (B-ALL), B-cell non-Hodgkin's lymphoma (B-NL), chronic lymphocytic leukemia (C-CLL), acute myeloid leukemia (AML), T cell lymphoma, T cell leukemia, clear cell renal cell carcinoma (ccRCC), thyroid cancer, nasopharyngeal cancer, non-small cell lung cancer (NSCLC), pancreatic cancer, melanoma, ovarian cancer, colon cancer, glioblastoma, and cervical cancer.

In some embodiments, leukemias that may be treated as provided herein include chronic lymphocytic leukemia (CLL), non-Hodgkin lymphomas (e.g., diffuse large B-cell lymphoma (DLBCL), high grade B-cell lymphoma, transformed follicular lymphoma (FL), grade 3B FL, and Richter's transformation of CLL, and acute lymphoblastic leukemia (ALL). In some embodiments, provided herein is a method of treating cancer in a subject (e.g., human) in need thereof, comprising administering any engineered cell described herein to the subject (e.g., wherein the subject has or has been diagnosed with cancer). In some embodiments, provided herein is a method of treating a non-Hodgkin lymphoma (e.g., diffuse large B-cell lymphoma (DLBCL), high grade B-cell lymphoma, transformed follicular lymphoma (FL), grade 3B FL, and Richter's transformation of CLL in a subject (e.g., human) in need thereof, comprising administering any engineered cell described herein to the subject (e.g., wherein the subject has or has been diagnosed with a non-Hodgkin lymphoma, or is at risk of a non-Hodgkin lymphoma). In some embodiments, the subject (e.g., a human) has (e.g., has been diagnosed with) a relapsed and/or refractory non-Hodgkin lymphoma. In some embodiments, the subject (e.g., a human) has (e.g., has been diagnosed with) a non-relapsed or early stage non-Hodgkin lymphoma. In some embodiments, provided herein is a method of treating chronic lymphocytic leukemia (CLL) or acute lymphoblastic leukemia (ALL) in a subject (e.g., human) in need thereof, comprising administering any engineered cell described herein to the subject (e.g., wherein the subject has or has been diagnosed with CLL or ALL). In some embodiments, the subject (e.g., a human) has (e.g., has been diagnosed with) a relapsed and/or refractory CLL or ALL. In some embodiments, the subject (e.g., a human) has (e.g., has been diagnosed with) a non-relapsed or early stage CLL or ALL. The engineered cell can be administered at any dose described herein, in particular, in a therapeutically effective amount. In some embodiments, a human being treated is an adult, e.g., a human over 18 years of age. In some embodiments, a human being treated is under 18 years of age. In some embodiments, the method is not a method for treatment of the human or animal body by therapy.

In some embodiments, the methods comprise delivering the engineered cells (e.g., anti-BCMA CAR NK cells) of the present disclosure to a subject having a cancer (e.g., leukemia), wherein cancer cells express BCMA. In some embodiments, the methods comprise delivering the engineered cells (e.g., anti-CD30 CAR NK cells) of the present disclosure to a subject having a cancer (e.g., leukemia), wherein cancer cells express CD30. In some embodiments where the disease being treated is a non-Hodgkin lymphoma, the cells used express a CD30 CAR (e.g., anti-CD30 CAR NK cells).

The step of administering may include the placement (e.g., transplantation) of cells, e.g., engineered NK cells, into a subject, by a method or route that results in at least partial localization of the introduced cells at a desired site, such as tumor, such that a desired effect(s) is produced. Engineered cells can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life-time of the subject, i.e., long-term engraftment. For example, in some embodiments, an effective amount of engineered NK cell is administered via a systemic route of administration, such as an intraperitoneal or intravenous route.

A subject may be any subject for whom diagnosis, treatment, or therapy is desired. In some embodiments, the subject is a mammal. In some embodiments, the subject is a human.

In some embodiments, an engineered NK cell population being administered according to the methods described herein comprises gene edited hematopoietic cells (e.g., NK cells) differentiated from gene-edited stem cells (e.g., iPSC cells).

In some embodiments, an engineered cell population (e.g. NK cells) being administered according to the methods described herein does not induce toxicity in the subject, e.g., the engineered NK cells do not induce toxicity in non-cancer cells. In some embodiments, an engineered cell population (e.g., NK cells) being administered does not trigger complement mediated lysis, or does not stimulate antibody-dependent cell mediated cytotoxicity (ADCC).

In some embodiments, the subject being treated has no chronic immune suppression.

An effective amount refers to the amount of a population of engineered cells (e.g., NK cells) needed to prevent or alleviate at least one or more signs or symptoms of a medical condition (e.g., cancer), and relates to a sufficient amount of a composition to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

In some embodiments, a subject is administered a population of cells comprising any of the engineered cells disclosed herein at a dose in the range of about $1 \times 10^7$ to $1 \times 10^9$ engineered cells. In some embodiments, a subject is administered a population of cells comprising any of the engineered cells disclosed herein at a dose in the range of about $1 \times 10^7$ to $3 \times 10^8$ engineered cells. In some embodiments, a subject is administered a population of cells comprising any of the engineered cells disclosed herein at a dose in the range of about $3 \times 10^7$ to $3 \times 10^8$ engineered cells.

In some embodiments, the cells are NK cells. In some embodiments, the cells are derived from iPSCs. In some embodiments, the cells are expanded in culture prior to administration to a subject in need thereof.

Modes of administration include but are not limited to injection and infusion. In some embodiments, injection includes, without limitation, intravenous, intrathecal, intraperitoneal, intraspinal, intracerebrospinal, and intrasternal infusion. In some embodiments, the route is intravenous. In some embodiments, cells described herein are administered as a bolus or by continuous infusion (e.g., intravenous infusion) over a period of time. In some embodiments, cells described herein are administered in several doses over a period of time (e.g., several infusions over a period of time). The cells described herein can be administered in a single dose or in 2, 3, 4, 5, 6 or more doses (or infusions). In some embodiments, the subject being treated is dosed (e.g., with an infusion) about every 1, 2, 3, 4, 5, 6, 7 or 8 weeks. In some embodiments, the subject being treated is dosed (e.g., with an infusion) every 2-4 weeks (e.g., every 2 weeks, 3 weeks or 4 weeks).

In some embodiments, engineered cells (e.g., NK cells) are administered systemically, which refers to the administration of a population of cells other than directly into a target site, tissue, or organ, such that it enters, instead, the subject's circulatory system and, thus, is subject to metabolism and other like processes.

The efficacy of a treatment comprising a composition for the treatment of a medical condition can be determined by the skilled clinician. A treatment is considered "effective treatment," if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

In some embodiments, the disclosure provides methods for treating a non-Hodgkin lymphoma (NHL) in a human patient by administering an intravenous dose of about $1\times10^7$-$3\times10^8$ engineered NK cells expressing a detectable level of CAR described herein (e.g., anti-BCMA CAR or anti-CD30 CAR). In some embodiments, the disclosure provides methods for treating a non-Hodgkin lymphoma (NHL) in a human patient by administering an intravenous dose of about $3\times10^7$ engineered NK cells expressing a detectable level of CAR described herein (e.g., anti-BCMA CAR or anti-CD30 CAR). In some embodiments, the disclosure provides methods for treating a non-Hodgkin lymphoma (NHL) in a human patient by administering an intravenous dose of about $1\times10^8$ engineered NK cells expressing a detectable level of CAR described herein (e.g., anti-BCMA CAR or anti-CD30 CAR). In some embodiments, the disclosure provides methods for treating a non-Hodgkin lymphoma (NHL) in a human patient by administering an intravenous dose of about $3\times10^8$ engineered NK cells expressing a detectable level of CAR described herein (e.g., anti-BCMA CAR or anti-CD30 CAR).

In some embodiments, the disclosure provides methods for treating a non-Hodgkin lymphoma (NHL) in a human patient by intravenously administering NK cells at a dose of about $1\times10^7$-$3\times10^8$ engineered NK cells expressing a detectable level of anti-BCMA CAR or anti-CD30 CAR. In some embodiments, the disclosure provides methods for treating a non-Hodgkin lymphoma (NHL) in a human patient by intravenously administering NK cells at a dose of about $3\times10^7$ engineered NK cells expressing a detectable level of anti-BCMA CAR or anti-CD30 CAR. In some embodiments, the disclosure provides methods for treating a non-Hodgkin lymphoma (NHL) in a human patient by intravenously administering NK cells at a dose of about $1\times10^8$ engineered NK cells expressing a detectable level of anti-BCMA CAR or anti-CD30 CAR. In some embodiments, the disclosure provides methods for treating a non-Hodgkin lymphoma (NHL) in a human patient by intravenously administering NK cells at a dose of about $3\times10^8$ engineered NK cells expressing a detectable level of anti-BCMA CAR or anti-CD30 CAR.

Lymphodepletion Conditioning Therapy

In some embodiments, any engineered cells described herein (or any population of cells described herein) are administered to a subject (e.g., a human patient having a cancer, e.g., a non-Hodgkin lymphoma) after a subject has received a lymphodepleting regimen.

In some embodiments, the lymphodepleting regimen comprises administering at least one chemotherapeutic agent. In some embodiments, at least one chemotherapeutic agent is cyclophosphamide. In some embodiments, the lymphodepleting regimen comprises administering at least two chemotherapeutic agents. In some embodiments, at least two chemotherapeutic agents are cyclophosphamide and fludarabine.

In some embodiments, the first dose (e.g., infusion) of the engineered cells described herein is administered to a subject after lymphodepletion.

Specific Compositions and Methods of the Disclosure

Accordingly, the present disclosure relates, in particular, to the following non-limiting compositions and methods.

In a first composition, Composition 1, the present disclosure provides a composition comprising a engineered cell comprising: (a) a disrupted beta-2-microglobulin (B2M) gene, and (b) a first polynucleotide and a second polynucleotide inserted in the disrupted B2M gene, wherein i. the first polynucleotide encodes human leukocyte antigen E or HLA class I histocompatibility antigen, alpha chain E (HLA-E) and ii. the second polynucleotide encodes a fusion protein of Interleukin-15 (IL15) and Interleukin-15 receptor subunit alpha (IL15Rα), wherein the cell expresses HLA-E and the fusion protein of IL15 and IL15Rα and the cell has a disrupted expression of B2M.

In another composition, Composition 2, the present disclosure provides a composition, as provided in Composition 1, wherein disrupted expression of B2M comprises reduced or eliminated expression of B2M.

In another composition, Composition 3, the present disclosure provides a composition, as provided in Compositions 1 or 2, wherein the HLA-E is an HLA-E trimer comprising a B2M signal peptide fused to an HLA-G presentation peptide fused to the B2M membrane protein fused to the HLA-E protein without a signal peptide.

In another composition, Composition 4, the present disclosure provides a composition, as provided in Composition 3, wherein the first polynucleotide and second polynucleotide are inserted as a polynucleotide encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and the HLA-E trimer.

In another composition, Composition 5, the present disclosure provides a composition, as provided in Composition 4, wherein the polynucleotide encoding the IL15/IL15Rα-P2A-HLA-E trimer is inserted in exon 1 of the B2M gene locus.

In another composition, Composition 6, the present disclosure provides a composition, as provided in Compositions 1-5, further comprising a disrupted Class II Major Histocompatibility Complex Transactivator (CIITA) gene, wherein the cell has a disrupted expression of CIITA.

In another composition, Composition 7, the present disclosure provides a composition, as provided in Composition 6, wherein the disrupted expression of CIITA comprises reduced or eliminated expression of CIITA.

In another composition, Composition 8, the present disclosure provides a composition, as provided in Compositions 1-7, further comprising an insertion of a polynucleotide encoding a chimeric antigen receptor (CAR).

In another composition, Composition 9, the present disclosure provides a composition, as provided in Composition 8, wherein the CAR is inserted in the disrupted CIITA gene.

In another composition, Composition 10, the present disclosure provides a composition, as provided in Compositions 8 or 9, wherein the CAR is inserted in exon 2 of the CIITA gene locus.

In another composition, Composition 11, the present disclosure provides a composition, as provided in Compositions 1-10, further comprising a disrupted ADAM metallopeptidase domain 17 (ADAM17) gene, wherein the cell has a disrupted expression of ADAM17.

In another composition, Composition 12, the present disclosure provides a composition, as provided in Composition 11, wherein the disrupted expression of ADAM17 comprises reduced or eliminated expression of ADAM17.

In another composition, Composition 13, the present disclosure provides a composition comprising an engineered cell comprising: (a) a disrupted B2M gene, (b) a first polynucleotide and a second polynucleotide inserted in the disrupted B2M gene, wherein i. the first polynucleotide encodes HLA-E, and ii. the second polynucleotide encodes a fusion protein of IL15 and IL15Rα, (c) a disrupted CIITA gene, (d) an insertion of a polynucleotide encoding a CAR, optionally wherein the CAR is inserted in the disrupted CIITA gene, and (e) a disrupted ADAM17 gene, wherein the cell expresses HLA-E, the fusion protein of IL15 and IL15Rα, and the CAR, and the cell has a disrupted expression of B2M, CIITA, and ADAM17.

In another composition, Composition 14, the present disclosure provides a composition, as provided in Composition 13, wherein the disrupted expression of B2M, CIITA, and/or ADAM17 comprises reduced or eliminated expression of B2M, CIITA, and/or ADAM17.

In another composition, Composition 15, the present disclosure provides a composition, as provided in Compositions 13 or 14, wherein the HLA-E is an HLA-E trimer comprising a B2M signal peptide fused to an HLA-G presentation peptide fused to the B2M membrane protein fused to the HLA-E protein without a signal peptide.

In another composition, Composition 16, the present disclosure provides a composition, as provided in Composition 15, wherein the first polynucleotide and second polynucleotide are inserted as a polynucleotide encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and the HLA-E trimer.

In another composition, Composition 17, the present disclosure provides a composition, as provided in Composition 16, wherein the polynucleotide encoding the IL15/IL15Rα-P2A-HLA-E trimer construct is inserted in exon 1 of the B2M gene locus.

In another composition, Composition 18, the present disclosure provides a composition, as provided in Compositions 13-17, wherein the CAR is inserted in exon 2 of the CIITA gene locus.

In another composition, Composition 19, the present disclosure provides a composition comprising an engineered cell comprising: (a) a disrupted ADAM17 gene, (b) a disrupted gene encoding an MHC-I or MHC-II human leukocyte antigen, or a component of, or a transcriptional regulator of, a MHC-I or MHC-II complex, and (c) an insertion of a polynucleotide encoding a CAR, wherein the cell expresses the CAR, has a disrupted expression of ADAM17, has a disrupted expression of the MHC-I or MHC-II human leukocyte antigen, or the component of, or the transcriptional regulator of, a MHC-I or MHC-II complex, and is hypoimmunogenic.

In another composition, Composition 20, the present disclosure provides a composition, as provided in Composition 19, wherein the disrupted expression of ADAM17 and/or the MHC-I or MHC-II human leukocyte antigen, or the component of, or the transcriptional regulator of, a MHC-I or MHC-II complex, comprises reduced or eliminated expression of the MHC-I or MHC-II human leukocyte antigen or the component of, or the transcriptional regulator of, a MHC-I or MHC-II complex.

In another composition, Composition 21, the present disclosure provides a composition, as provided in Compositions 19 or 20, wherein the disrupted gene encoding the MHC-I or MHC-II human leukocyte antigen or the component of, or the transcriptional regulator of, a MHC-I or MHC-II complex is a disrupted B2M gene.

In another composition, Composition 22, the present disclosure provides a composition, as provided in Composition 21, further comprising (d) an insertion of a first polynucleotide that encodes HLA-E, and (e) an insertion of a second polynucleotide that encodes a fusion protein of IL15 and IL15Rα, wherein the first polynucleotide and the second polynucleotide are inserted in the disrupted B2M gene, and wherein the cell expresses HLA-E and the fusion protein of IL15 and IL15Rα.

In another composition, Composition 23, the present disclosure provides a composition, as provided in Composition 22, wherein the HLA-E is an HLA-E trimer comprising a B2M signal peptide fused to an HLA-G presentation peptide fused to the B2M membrane protein fused to the HLA-E protein without a signal peptide.

In another composition, Composition 24, the present disclosure provides a composition, as provided in Composition 23, wherein the first polynucleotide and second polynucleotide are inserted as a polynucleotide encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and the HLA-E trimer.

In another composition, Composition 25, the present disclosure provides a composition, as provided in Composition 24, wherein the polynucleotide encoding the IL15/IL15Rα-P2A-HLA-E trimer is inserted in exon 1 of the B2M gene locus.

In another composition, Composition 26, the present disclosure provides a composition, as provided in Compositions 19-25, wherein the disrupted gene encoding the MHC-I or MHC-II human leukocyte antigen or the component of, or the transcriptional regulator of, a MHC-I or MHC-II complex is a disrupted CIITA gene.

In another composition, Composition 27, the present disclosure provides a composition, as provided in Compositions 19-26, wherein the CAR is inserted in the CIITA gene.

In another composition, Composition 28, the present disclosure provides a composition, as provided in Composition 27, wherein the CAR is inserted in exon 2 of the CIITA gene locus.

In another composition, Composition 29, the present disclosure provides a composition comprising an engineered cell comprising a disrupted CIITA gene and an insertion of a polynucleotide encoding a CAR in the disrupted CIITA gene, wherein the cell expresses the CAR and the cell has a disrupted expression of CIITA.

In another composition, Composition 30, the present disclosure provides a composition, as provided in Composition 29, wherein the disrupted expression of CIITA comprises reduced or eliminated expression of CIITA.

In another composition, Composition 31, the present disclosure provides a composition, as provided in Compositions 29 or 30, wherein the CAR is inserted in exon 2 of the CIITA gene locus.

In another composition, Composition 32, the present disclosure provides a composition, as provided in Compositions 29-31, further comprising a disrupted B2M gene, a first polynucleotide and a second polynucleotide inserted in the disrupted B2M gene, and optionally a disrupted ADAM17 gene, wherein the first polynucleotide encodes HLA-E and the second polynucleotide encodes a fusion protein of IL15 and IL15Rα, and wherein the cell expresses HLA-E and the fusion protein of IL15 and IL15Rα and the cell has a disrupted expression of B2M and/or ADAM17.

In another composition, Composition 33, the present disclosure provides a composition, as provided in Composition 32, wherein the disrupted expression of B2M and/or ADAM17 comprises reduced or eliminated expression of ADAM17.

In another composition, Composition 34, the present disclosure provides a composition, as provided in Composition 32 or 33, wherein the HLA-E is an HLA-E trimer comprising a B2M signal peptide fused to an HLA-G presentation peptide fused to the B2M membrane protein fused to the HLA-E protein without a signal peptide.

In another composition, Composition 35, the present disclosure provides a composition, as provided in Composition 34, wherein the first polynucleotide and second polynucleotide are inserted as a polynucleotide encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and the HLA-E trimer.

In another composition, Composition 36, the present disclosure provides a composition, as provided in Composition 35, wherein the polynucleotide encoding the IL15/IL15Rα-P2A-HLA-E trimer is inserted in exon 1 of the B2M gene locus.

In another composition, Composition 37, the present disclosure provides a composition, as provided in Compositions 8-36, wherein the CAR comprises an ectodomain that binds anti-B cell maturation antigen.

In another composition, Composition 38, the present disclosure provides a composition, as provided in Composition 37, wherein the CAR comprises a polynucleotide sequence of SEQ ID NO: 70.

In another composition, Composition 39, the present disclosure provides a composition, as provided in Compositions 4-12, 16-18, 24-28, and 35-38, wherein the IL15/IL15Rα-P2A-HLA-E trimer construct comprises a polynucleotide sequence of SEQ ID NO: 77.

In another composition, Composition 40, the present disclosure provides a composition, as provided in Compositions 1-39, wherein the engineered cell does not comprise an insertion of a polynucleotide encoding CD16; optionally, wherein the genome of the cell does not comprise an insertion of a polynucleotide encoding a high affinity non-cleavable CD16 variant.

In another composition, Composition 41, the present disclosure provides a composition, as provided in Compositions 1-40, wherein the engineered cell is a stem cell.

In another composition, Composition 42, the present disclosure provides a composition, as provided in Composition 41, wherein the stem cell is an induced pluripotent stem cell (iPSC), a hematopoietic stem cell, an embryonic stem cell, or an adult stem cell.

In another composition, Composition 43, the present disclosure provides a composition, as provided in Compositions 1-40, wherein the engineered cell is a genome-edited iPSC.

In another composition, Composition 44, the present disclosure provides a composition, as provided in Compositions 1-40, wherein the engineered cell is a natural killer (NK) cell obtained from a genome-edited iPSC.

In another composition, Composition 45, the present disclosure provides a composition, as provided in Compositions 1-40, wherein the engineered cell is a differentiated cell or a somatic cell.

In another composition, Composition 46, the present disclosure provides a composition, as provided in Compositions 1-40, wherein the engineered cell is capable of being differentiated into lineage-restricted progenitor cells or fully differentiated somatic cells.

In another composition, Composition 47, the present disclosure provides a composition, as provided in Compositions 1-40, wherein the engineered cell is a natural killer (NK) cell.

In another composition, Composition 48, the present disclosure provides a composition, as provided in Composition 47, wherein the NK cell has been differentiated from a genome-edited iPSC, wherein the NK cell comprises the genome edits of the genome-edited iPSC, wherein the NK cell has not been genome-edited after the differentiation.

In another composition, Composition 49, the present disclosure provides a composition, as provided in Compositions 1-48, wherein the engineered cell expresses at least one, two, three, four or five of the following markers: CD56, NKp44, NKp46, CD94, NKG2A and KIR2DL4, and optionally wherein the markers are expressed at least at 25%, 30%, 40%, 50%, or 75% level relative to their expression in wild-type NK cells.

In another composition, Composition 50, the present disclosure provides a composition, as provided in Compositions 1-49, wherein the engineered cell has at least one of the following characteristics, or any combination thereof: (i) an alloimmune T cell reaction of less than 10% relative to an unmodified cell, and (ii) cytotoxic activity resulting in killing more than 50% of target cells when the engineered cells are mixed with the target cells at the ratio of 1:1; (iii) at least 50% increase in cellular viability relative to an unmodified cell.

In another composition, Composition 51, the present disclosure provides a composition, as provided in Compositions 1-49, wherein the engineered cell has at least one of the following characteristics, or any combination thereof: (i) improved persistency, (ii) improved immune evasiveness, (iii) improved cytotoxic activity, (iv) improved ADCC activity, and (v) improved anti-tumor activity; wherein the characteristics are improved relative to a wild-type cell, optionally, relative to a wild-type iPSC or a wild-type NK cell.

In another composition, Composition 52, the present disclosure provides a composition, as provided in Compositions 1-51, wherein the engineered cell is capable of cell expansion in the absence of exogenous IL15 in cell culture media.

In another composition, Composition 53, the present disclosure provides a composition comprising a plurality of engineered cells according to any one of Compositions 1 to 52.

In another composition, Composition 54, the present disclosure provides a composition, comprising a population of lineage-restricted progenitor cells or fully differentiated somatic cells derived from the plurality of engineered cells of Composition 53.

In another composition, Composition 55, the present disclosure provides a composition comprising the population of cells of Composition 54, wherein the lineage-restricted progenitor cells are hematopoietic progenitor cells, mesodermal cells, definitive hemogenic endothelium, definitive hematopoietic stem or progenitor cells, CD34$^+$ cells, multipotent progenitors (MPP), common lymphoid progenitor cells, T cell progenitors, NK cell progenitors, pancreatic endoderm progenitors, pancreatic endocrine progenitors, mesenchymal progenitor cells, muscle progenitor cells, blast cells, or neural progenitor cells, and the fully differentiated somatic cells are hematopoietic cells, pancreatic beta cells, epithelial cells, endodermal cells, macrophages, hepatocytes, adipocytes, kidney cells, blood cells, cardiomyocytes, or immune system cells.

In another composition, Composition 56, the present disclosure provides a composition, comprising the population of cells of Composition 55, wherein the hematopoietic cells are NK cells, T cells, B cells, or NKT cells.

In another composition, Composition 57, the present disclosure provides a composition comprising the population of cells of Composition 56, wherein the hematopoietic cells are human NK cells.

In another composition, Composition 58, the present disclosure provides a composition comprising the population of cells of any one of Compositions 54-57, wherein at least 25% or at least 50% of engineered cells of the population express the CAR, HLA-E, and/or the fusion protein of IL15 and IL15Rα.

In another composition, Composition 59, the present disclosure provides a composition comprising the population of cells of any one of Compositions 54-58, wherein at least 50% of engineered cells of the population do not express a detectable level of B2M protein, CIITA protein, and/or ADAM17 protein.

In another composition, Composition 60, the present disclosure provides a composition comprising the population of cells of any one of Compositions 57-59, wherein engineered human NK cells of the population, when co-cultured in vitro with a population of cancer cells, induce cell lysis of at least 70%, at least 80%, or at least 90% of the population of cancer cells.

In another composition, Composition 61, the present disclosure provides a composition comprising the population of cells of any one of Compositions 57-60, wherein engineered human NK cells of the population, when co-cultured in vitro with a population of cancer cells, secrete IFNγ.

In another composition, Composition 62, the present disclosure provides a composition comprising the population of cells of Compositions 60 or 61, wherein the ratio of engineered human NK cells to cancer cells is 0.1:1 to 2:1.

In another composition, Composition 63, the present disclosure provides a composition comprising the plurality of engineered cells of Composition 53 or the population of cells of Compositions 54-62.

In another composition, Composition 64, the present disclosure provides a composition, as provided in Composition 63 for use in treating a subject in need thereof.

In another composition, Composition 65, the present disclosure provides a composition, as provided in Composition 63 for use in treating cancer in a subject in need thereof.

In another composition, Composition 66, the present disclosure provides a composition, as provided in Composition 65, wherein the subject has multiple myeloma. Hodgkin's lymphoma, lung cancer, leukemia, B-cell acute lymphoblastic leukemia (B-ALL), B-cell non-Hodgkin's lymphoma (B-NL), Chronic lymphocytic leukemia (C-CLL), T cell lymphoma, T cell leukemia, clear cell renal cell carcinoma (ccRCC), thyroid cancer, nasopharyngeal cancer, non-small cell lung (NSCLC), pancreatic cancer, melanoma, ovarian cancer, glioblastoma, or cervical cancer.

In another composition, Composition 67, the present disclosure provides a composition, as provided in any one of Composition 64-66, wherein the subject is human.

In a first method, Method 1, the present disclosure provides a method of obtaining cells for administration to a subject in need thereof, the method comprising: (a) obtaining or having obtained the plurality of engineered cells of Composition 53, and (b) maintaining the plurality of engineered cells for a time and under conditions sufficient for the cells to differentiate into lineage-restricted progenitor cells or fully differentiated somatic cells.

In another method, Method 2, the present disclosure provides a method for treating of a subject in need thereof, the method comprising: (a) obtaining or having obtained the plurality of engineered cells of Composition 53 following differentiation into lineage-restricted progenitor cells or fully differentiated somatic cells; and (b) administering the lineage-restricted progenitor cells or fully differentiated somatic cells to the subject.

In another method, Method 3, the present disclosure provides a method as provided in Methods 1 or 2, wherein the lineage-restricted progenitor cells are hematopoietic progenitor cells, mesodermal cells, definitive hemogenic endothelium, definitive hematopoietic stem or progenitor cells, CD34$^+$ cells, multipotent progenitors (MPP), common lymphoid progenitor cells, T cell progenitors, NK cell progenitors, pancreatic endoderm progenitors, pancreatic endocrine progenitors, mesenchymal progenitor cells, muscle progenitor cells, blast cells, or neural progenitor cells, and the fully differentiated somatic cells are hematopoietic cells, pancreatic beta cells, epithelial cells, endodermal cells, macrophages, hepatocytes, adipocytes, kidney cells, blood cells, cardiomyocytes, or immune system cells.

In another method, Method 4, the present disclosure provides a method as provided in any one of Methods 1-3, wherein the subject has, is suspected of having, or is at risk for a cancer.

In another method, Method 5, the present disclosure provides a method as provided in any one of Methods 1-4, wherein the subject is human.

In another method, Method 6, the present disclosure provides an in vitro method for generating an engineered cell, the method comprising delivering to a cell: (a) a first ribonucleoprotein (RNP) complex comprising an RNA-guided nuclease and a guide RNA (gRNA) targeting a target site in a beta-2 microglobulin (B2M) gene locus; (b) a first vector comprising a nucleic acid, the nucleic acid comprising: (i) a nucleotide sequence encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and a HLA-E trimer; (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii), wherein the B2M gene locus is cleaved at the target site and the nucleic acid comprising the nucleotide sequence encoding the IL15/IL15Rα-P2A-HLA-E trimer construct is inserted into the B2M gene locus, thereby disrupting the B2M gene.

In another method, Method 7, the present disclosure provides an in vitro method of Method 6, further comprising delivering to the cell: (c) a second RNP complex comprising an RNA-guided nuclease and a gRNA targeting a target site in a CIITA gene locus, (d) a second vector comprising a nucleic acid, the nucleic acid comprising: (i) a nucleotide sequence encoding a CAR; (ii) a nucleotide sequence having sequence homology with a genomic region located left of the target site in the CIITA gene locus, and (iii) a nucleotide sequence having sequence homology with a genomic region located right of the target site in the CIITA gene locus, wherein (i) is flanked by (ii) and (iii), and (e) a third RNP complex comprising an RNA-guided nuclease and a gRNA targeting a target site in a ADAM17 gene locus, wherein the CIITA gene locus is cleaved at the target site and the nucleic acid comprising the nucleotide sequence encoding the CAR is inserted into the CIITA gene locus, thereby disrupting the CIITA gene, and wherein the ADAM17 gene locus is cleaved at the target site and the ADAM17 gene is disrupted.

In another method, Method 8, the present disclosure provides an in vitro method for generating an engineered cell, the method comprising delivering to a cell: (a) a first ribonucleoprotein (RNP) complex comprising an RNA-guided nuclease and a guide RNA (gRNA) targeting a target site in a beta-2 microglobulin (B2M) gene locus, (b) a first vector comprising a nucleic acid, the nucleic acid comprising: (i) a nucleotide sequence encoding a IL15/IL15Rα-P2A-HLA-E trimer construct, wherein the IL15/IL15Rα-P2A-HLA-E trimer construct comprises a fusion protein of IL15 and IL15Rα, a P2A peptide sequence, and a HLA-E trimer; (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii), (c) a second RNP complex comprising an RNA-guided nuclease and a gRNA targeting a target site in a CIITA gene locus, (d) a second vector comprising a nucleic acid, the nucleic acid comprising: (i) a nucleotide sequence encoding a CAR; (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii); and (e) a third RNP complex comprising an RNA-guided nuclease and a gRNA targeting a target site in a ADAM17 gene locus, wherein the B2M gene locus is cleaved at the target site and the nucleic acid comprising the nucleotide sequence encoding the IL15/IL15Rα-P2A-HLA-E trimer construct is inserted into the B2M gene locus, thereby disrupting the B2M gene, wherein the CIITA gene locus is cleaved at the target site and the nucleic acid comprising the nucleotide sequence encoding the CAR is inserted into the CIITA gene locus, thereby disrupting the CIITA gene, and wherein the ADAM17 gene locus is cleaved at the target site and the ADAM17 gene is disrupted.

In another method, Method 9, the present disclosure provides in vitro method of any one of Methods 6-8, wherein the engineered cell has reduced or eliminated expression of B2M.

In another method, Method 10, the present disclosure provides in vitro method of any one of Methods 7-9, wherein the engineered cell has reduced or eliminated expression of CIITA.

In another method, Method 11, the present disclosure provides in vitro method of any one of Methods 7-10, wherein the engineered cell has reduced or eliminated expression of ADAM17.

In another method, Method 12, the present disclosure provides in vitro method of any one of Methods 6-11, wherein the gRNA of the first RNP complex comprises a spacer sequence corresponding to a sequence consisting of: SEQ ID NO:34, SEQ ID NO:78, or SEQ ID NO:79.

In another method, Method 13, the present disclosure provides in vitro method of any one of Methods 7-12, wherein the gRNA of the second RNP complex comprises a spacer sequence corresponding to a sequence consisting of SEQ ID NO: 13, SEQ ID NO: 14, SEQ ID NO: 15, SEQ ID NO: 16, or SEQ ID NO: 17 and the gRNA of the third RNP complex comprises a spacer sequence corresponding to a sequence consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In another method, Method 14, the present disclosure provides in vitro method of any one of Methods 6-13, wherein the gRNA of the first RNP complex comprises a spacer sequence corresponding to a sequence consisting of SEQ ID NO: 34.

In another method, Method 15, the present disclosure provides in vitro method of any one of Methods 7-14, wherein the gRNA of the second RNP complex comprises a spacer sequence corresponding to a sequence consisting of SEQ ID NO: 13, SEQ ID NO: 14, SEQ ID NO: 15, SEQ ID NO: 16, or SEQ ID NO: 17, and the gRNA of the third RNP complex comprises a spacer sequence corresponding to a sequence consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In another method, Method 16, the present disclosure provides in vitro method of any one of Methods 6-15, wherein the first vector is a plasmid vector.

In another method, Method 17, the present disclosure provides in vitro method of any one of Methods 7-16, wherein the second vector is a plasmid vector.

In another method, Method 18, the present disclosure provides in vitro method of any one of Methods 6-17, wherein the nucleotide sequence encoding the HLA-E trimer sequence consists essentially of SEQ ID NO: 75.

In another method, Method 19, the present disclosure provides in vitro method of any one of Methods 6-18, wherein the nucleotide sequence encoding the IL15/IL15Rα sequence consists essentially of SEQ ID NO: 76.

In another method, Method 20, the present disclosure provides in vitro method of any one of Methods 6-19, wherein the nucleotide sequence encoding the IL15/IL15Rα-P2A-HLA-E trimer construct consists essentially of SEQ ID NO: 77.

In another method, Method 21, the present disclosure provides in vitro method of any one of Methods 6-20, wherein the nucleotide sequence encoding the IL15/IL15Rα-P2A-HLA-E trimer construct is operably linked to an exogenous promoter.

In another method, Method 22, the present disclosure provides in vitro method of any one of Methods 7-21, wherein the nucleotide sequence encoding the CAR is operably linked to an exogenous promoter.

In another method, Method 23, the present disclosure provides in vitro method of any one of Methods 21 or 22, wherein the exogenous promoter is a CMV, EF1α, PGK, CAG, or UBC promoter.

In another method, Method 24, the present disclosure provides in vitro method of any one of Methods 6-23, wherein of the first RNP complex comprises a molar ratio of RNA-guided nuclease to gRNA of 1:3.

In another method, Method 25, the present disclosure provides in vitro method of any one of Methods 7-24, wherein each of the second RNP complex and third RNP complex comprises a molar ratio of RNA-guided nuclease to gRNA of 1:3.

In another method, Method 26, the present disclosure provides in vitro method of any one of Methods 7-25, wherein the RNA-guided nuclease of the first RNP complex is a Cas9 nuclease.

In another method, Method 27, the present disclosure provides in vitro method of any one of Methods 7-26, wherein each of the RNA-guided nuclease of the second RNP complex and the third RNP complex is a Cas9 nuclease.

In another method, Method 28, the present disclosure provides in vitro method of Methods 26 or 27, wherein the Cas9 nuclease is linked to at least one nuclear localization signal.

In another method, Method 29, the present disclosure provides in vitro method of any one of Methods 6-28, wherein the cell is a stem cell.

In another method, Method 30, the present disclosure provides in vitro method of Method 29, wherein the stem cell is an embryonic stem cell, an adult stem cell, an induced pluripotent stem cell, or a hematopoietic stem cell.

In another method, Method 31, the present disclosure provides in vitro method of any one of Methods 29 or 30, wherein the stem cell is a human stem cell.

In another method, Method 32, the present disclosure provides in vitro method of any one of Methods 6-31, wherein the nucleotide sequence of (b)(ii) consists essentially of SEQ ID NO: 36, and the nucleotide sequence of (b)(iii) consists essentially of SEQ ID NO: 54.

In another method, Method 33, the present disclosure provides in vitro method of any one of Methods 6-32, wherein the nucleotide sequence of (d)(ii) consists essentially of SEQ ID NO: 22, and the nucleotide sequence of (d)(iii) consists essentially of SEQ ID NO: 32.

In another method, Method 34, the present disclosure provides in vitro method for generating an engineered cell, the method comprising delivering to a cell: (a) a first RNP complex comprising an RNA-guided nuclease and a gRNA targeting a target site in a CIITA gene locus, (b) a first vector comprising a nucleic acid, the nucleic acid comprising: (i) a nucleotide sequence encoding a CAR; (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii); and wherein the CIITA gene locus is cleaved at the target site and the nucleic acid comprising the nucleotide sequence encoding the CAR is inserted into the CIITA gene locus, thereby disrupting the CIITA gene.

In another method, Method 35, the present disclosure provides in vitro method for generating an engineered cell, the method comprising delivering to a cell: (a) a first ribonucleoprotein (RNP) complex comprising an RNA-guided nuclease and a guide RNA (gRNA) targeting a target site in a ADAM17 gene locus, (b) a second RNP complex comprising an RNA-guided nuclease and a gRNA targeting a target site in a MIC-I or MHC-II human leukocyte antigen, or a component of, or a transcriptional regulator of, a MIC-I or MHC-II complex gene locus, (c) a first vector comprising a nucleic acid, the nucleic acid comprising: (i) a nucleotide sequence encoding a CAR; (ii) a nucleotide sequence having sequence homology with a genomic region located left of the target site in the MIC-I or MHC-II human leukocyte antigen or the component of, or the transcriptional regulator of, a MIC-I or MHC-II complex gene locus; and (iii) a nucleotide sequence having sequence homology with a genomic region located right of the target site in the MIC-I or MHC-II human leukocyte antigen, or the component of, or the transcriptional regulator of, a MIC-I or MHC-II complex gene locus, wherein (i) is flanked by (ii) and (iii), wherein the ADAM17 gene locus is cleaved at the target site and the ADAM17 gene is disrupted, and wherein the MHC-I or MHC-II human leukocyte antigen or a component or a transcriptional regulator of a MHC-I or MHC-II complex gene locus is cleaved at the target site and the nucleic acid comprising the nucleotide sequence encoding the CAR is inserted into the MHC-I or MHC-II human leukocyte antigen or the component of, or the transcriptional regulator of, a MIC-I or MHC-II complex gene locus, thereby disrupting the MIC-I or MHC-II human leukocyte antigen or the component of, or the transcriptional regulator of, a MIC-I or MHC-II complex gene.

In another composition, Composition 68, the present disclosure provides a plurality of engineered cells generated or obtainable by the method of any one of Methods 6-35.

In another composition, Composition 69, the present disclosure provides a plurality of engineered cells of Composition 68 maintained for a time and under conditions sufficient for the cells to undergo differentiation.

In another composition, Composition 70, the present disclosure provides a plurality of engineered cells of Compositions 69 or 70 for use in treating a subject in need thereof.

In another composition, Composition 71, the present disclosure provides a plurality of cells for use of Composition 70, wherein the subject is a human who has, is suspected of having, or is at risk for a cancer.

In another method, Method 36, the present disclosure provides a method comprising administering to a subject the plurality of engineered cells of Compositions 68 or 69.

In another method, Method 37, the present disclosure provides a method for treating of a subject in need thereof, the method comprising: (a) obtaining or having obtained the plurality of engineered cells of Composition 68 following differentiation into lineage-restricted progenitor cells or fully differentiated somatic cells, and (b) administering the lineage-restricted progenitor cells or fully differentiated somatic cells to the subject.

In another method, Method 38, the present disclosure provides a method of obtaining cells for administration to a subject in need thereof, the method comprising: (a) obtaining or having obtained the engineered cells of Composition 68, and (b) maintaining the engineered cells for a time and under conditions sufficient for the cells to differentiate into lineage-restricted progenitor cells or fully differentiated somatic cells.

In another method, Method 39, the present disclosure provides a method of Method 37 or 38, wherein the lineage-restricted progenitor cells are hematopoietic progenitor cells, mesodermal cells, definitive hemogenic endothelium, definitive hematopoietic stem or progenitor cells, CD34+ cells, multipotent progenitors (MPP), common lymphoid progenitor cells, T cell progenitors, NK cell progenitors, pancreatic endoderm progenitors, pancreatic endocrine progenitors, mesenchymal progenitor cells, muscle progenitor cells, blast cells, or neural progenitor cells.

In another method, Method 40, the present disclosure provides the method of Methods 37 or 38, wherein the fully differentiated somatic cells are hematopoietic cells, pancreatic beta cells, epithelial cells, endodermal cells, macrophages, hepatocytes, adipocytes, kidney cells, blood cells, cardiomyocytes, or immune system cells.

In another method, Method 41, the present disclosure provides the method of any one of Methods 36-40, wherein the subject is a human who has, is suspected of having, or is at risk for cancer.

In another method, Method 42, the present disclosure provides the method of Methods 41, wherein the subject has multiple myeloma. Hodgkin's lymphoma, lung cancer, leukemia, B-cell acute lymphoblastic leukemia (B-ALL), B-cell non-Hodgkin's lymphoma (B-NL), Chronic lymphocytic leukemia (C-CLL), T cell lymphoma, T cell leukemia, clear cell renal cell carcinoma (ccRCC), thyroid cancer, nasopharyngeal cancer, non-small cell lung (NSCLC), pancreatic cancer, melanoma, ovarian cancer, glioblastoma, or cervical cancer.

In another composition, Composition 72, the present disclosure provides a guide RNA comprising a spacer sequence corresponding to a sequence consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In another composition, Composition 73, the present disclosure provides a guide RNA comprising a spacer sequence corresponding to a sequence consisting of SEQ ID NO: 1.

In another method, Method 43, the present disclosure provides a method for generating Natural Killer (NK) cells from stem cells, the method comprising: (a) culturing a population of stem cells in a first medium comprising a ROCK inhibitor under conditions sufficient to form aggregates, (b) culturing the aggregates in a second medium comprising BMP-4, (c) culturing the aggregates in a third medium comprising BMP-4, FGF2, a WNT pathway activator, and Activin A, (d) culturing the aggregates in a fourth medium comprising FGF2, VEGF, TPO, SCF, IL-3, FLT3L, WNT C-59 and an activin/nodal inhibitor to form a cell population comprising hematopoietic stem and progenitor cells (HSPCs), (e) culturing the cell population in a fifth medium comprising FGF2, VEGF, TPO, SCF, IL-3 and FLT3L, (f) culturing the cell population in a sixth medium comprising IL-3, IL-7, FLT3L, IL-15 and SCF, (g) culturing the cell population in a seventh medium comprising IL-7, FLT3L, IL-15 and SCF; and, optionally (h) culturing the cell population in an eighth medium comprising TL-7, FLT3L, IL-15, SCF and nicotinamide for a time sufficient to generate NK cells.

In another method, Method 44, the present disclosure provides the method of Method 43, wherein the second medium further comprises a ROCK inhibitor.

In another method, Method 45, the present disclosure provides the method of Method 43 or Method 44, wherein the ROCK inhibitor is thiazovivin or Y27632.

In another method, Method 46, the present disclosure provides the method of any one of Methods 43-45, wherein the WNT pathway activator is CHIR-99021.

In another method, Method 47, the present disclosure provides the method of any one of Methods 43-46, wherein the activin/nodal inhibitor is SB-431542.

In another method, Method 48, the present disclosure provides the method of any one of Methods 43-47, wherein steps (a)-(g) occurs between 20-35 days or steps (a)-(h) occurs between 24-36 days.

In another method, Method 49, the present disclosure provides the method of any one of Methods 43-48, wherein (a) comprises culturing for 12-48 hours.

In another method, Method 50, the present disclosure provides the method of any one of Methods 43-49, wherein (b) comprises culturing for up to 24 hours.

In another method, Method 51, the present disclosure provides the method of any one of Methods 43-50, wherein (c) comprises culturing for 1-3 days.

In another method, Method 52, the present disclosure provides the method of any one of Methods 43-51, wherein (d) comprises culturing for 1-3 days.

In another method, Method 53, the present disclosure provides the method of any one of Methods 43-52, wherein (e) comprises culturing for 1-3 days.

In another method, Method 54, the present disclosure provides the method of any one of Methods 43-53, wherein (f) comprises culturing for up to 7 days.

In another method, Method 55, the present disclosure provides the method of any one of Methods 43-54, wherein (g) comprises culturing for at least 6 days and up to 21-28 days total; or wherein (g) comprises culturing for up to 6 days and (h) comprises culturing for at least 6 days and up to 10-16 days total.

In another method, Method 56, the present disclosure provides the method of any one of Methods 43-56, wherein: (a) comprises culturing for 16-20 hours, (b) comprises culturing for 6-10 hours, (c) comprises culturing for 2 days, (d) comprises culturing for 2 days, (e) comprises culturing for 2 days, (f) comprises culturing for 4 days, (g) comprises culturing for 14-28 days or (a) comprises culturing for 16-20 hours, (b) comprises culturing for 6-10 hours, (c) comprises culturing for 2 days, (d) comprises culturing for 2 days, (e) comprises culturing for 2 days, (f) comprises culturing for 4 days, (g) comprises culturing for 6 days, and (h) comprises culturing for 10-16 days.

In another method, Method 57, the present disclosure provides the method of any one of Methods 43-56, wherein the method is carried out under suspension agitation.

In another method, Method 58, the present disclosure provides the method of any one of Methods 57, wherein suspension agitation comprises rotation.

In another method, Method 59, the present disclosure provides the method of any one of Methods 43-58, wherein the first media comprises StemFlex or StemBrew medium.

In another method, Method 60, the present disclosure provides the method of any one of Methods 43-59, wherein the second, third, fourth and fifth media comprise APEL medium.

In another method, Method 61, the present disclosure provides the method of any one of Methods 43-60, wherein the sixth and seventh media comprising DMEM/F12 medium.

In another method, Method 62, the present disclosure provides the method of any one of Methods 43-61, wherein the sixth and seventh media comprise (a) human serum, zinc sulfate, ethanolamine, β-mercaptoethanol, glucose, or any combination thereof or (b) human serum, zinc sulfate, ethanolamine, glucose, or any combination thereof, and/or the eighth medium comprises human serum, zinc sulfate, ethanolamine, glucose, or any combination thereof In another method, Method 63, the present disclosure provides the method of any one of Method 62, wherein the concentration of human serum is 10-20%, 10%, 15% or 20%.

In another method, Method 64, the present disclosure provides the method of any one of Methods 43-63, wherein the first medium comprises 10 µM of the ROCK inhibitor.

In another method, Method 65, the present disclosure provides the method of any one of Methods 43-64, wherein the second medium comprises 30 ng/mL BMP-4 and, optionally, 10 µM of a ROCK inhibitor.

In another method, Method 66, the present disclosure provides the method of any one of Methods 43-65, wherein the third medium comprises 30 ng/mL BMP-4, 100 ng/mL FGF2, 6 µM or 7 µM CHIR-99021, and 2.5-5 ng/mL Activin A.

In another method, Method 67, the present disclosure provides the method of any one of Method 66, wherein half of the third medium is added to the stem cell aggregates.

In another method, Method 68, the present disclosure provides the method of any one of Methods 43-66, wherein the fourth and fifth media comprise 20 ng/mL FGF, 20 ng/mL VEGF, 20 ng/mL TPO, 100 ng/mL SCF, 40 ng/mL IL-3, and 10-20 ng/mL FLT3L.

In another method, Method 69, the present disclosure provides the method of any one of Methods 43-68, wherein the fourth medium further comprises 5 µM SB-431542 and, optionally, 2 µM WNT C-59.

In another method, Method 70, the present disclosure provides the method of any one of Methods 43-69, wherein the sixth and seventh media comprises 20 ng/mL IL-7, 10-20 ng/mL FLT3L, 10-20 ng/mL IL-15, and 20 ng/mL SCF.

In another method, Method 71, the present disclosure provides the method of any one of Methods 43-70, wherein the sixth medium comprises 5 ng/mL IL-3.

In another method, Method 72, the present disclosure provides the method of any one of Methods 43-71, wherein the HSPCs of (d) express CD34.

In another method, Method 73, the present disclosure provides the method of any one of Methods 43-72, wherein the NK cells express CD56.

In another method, Method 74, the present disclosure provides the method of any one of Methods 43-73, wherein the NK cells express at least one activating receptor.

In another method, Method 75, the present disclosure provides the method of any one of Method 74, wherein the at least one activating receptor is selected from the group of NKp44, NKp46, CD16, KIR2DL4, and any combination thereof.

In another method, Method 76, the present disclosure provides the method of any one of Methods 43-75, wherein the NK cells express at least one inhibitory receptor.

In another method, Method 77, the present disclosure provides the method of any one of Method 76, wherein the at least one inhibitory receptor is selected from the group of CD94, NKG2A, KIR3DL2, and any combination thereof.

In another method, Method 78, the present disclosure provides the method of any one of Methods 43-77, wherein the NK cells comprise at least one function associated with endogenous NK cells.

In another method, Method 79, the present disclosure provides the method of any one of Method 78, wherein the at least one function comprises the ability to induce cell lysis and cell death of a target cell.

In another method, Method 80, the present disclosure provides the method of any one of Methods 78 or 79, wherein the at least one function comprises degranulation.

In another method, Method 81, the present disclosure provides the method of any one of Method 80, wherein degranulation comprises release of perforin and granzyme B.

In another method, Method 82, the present disclosure provides the method of any one of Methods 80 or 81, wherein degranulation comprises expression of CD107a on the cell surface of an NK cell.

In another method, Method 83, the present disclosure provides the method of any one of Methods 43-82, wherein the population of stem cells is a population of engineered cells.

In another composition, Composition 74, the present disclosure provides a population of engineered cells generated or obtainable by the method of any one of Methods 6-35.

In another composition, Composition 75, the present disclosure provides a population of engineered cells is differentiated by the method of any one of Methods 43-82.

In another composition, Composition 76, the present disclosure provides the method of any one of Methods 43-82, wherein the population of stem cells is a population of engineered cells of Composition 75.

In another composition, Composition 77, the present disclosure provides a plurality of Natural Killer (NK) cells generated or obtainable by the method of any one of Methods 43-83.

In another composition, Composition 78, the present disclosure provides the plurality of engineered cells of Composition 77 for use in treating a subject in need thereof.

In another composition, Composition 79, the present disclosure provides the plurality of cells for use of Composition 78, wherein the subject is a human who has, is suspected of having, or is at risk for a cancer.

In another composition, Composition 80, the present disclosure provides a method comprising administering to a subject the plurality of NK cells of Composition 77.

In another composition, Composition 81, the present disclosure provides an engineered cell comprising: (a) a disrupted B2M gene, and (b) a first polynucleotide and a second polynucleotide inserted in the disrupted B2M gene, wherein (i) the first polynucleotide encodes SERPINB9 and (ii) the second polynucleotide encodes a fusion protein of Interleukin-15 (IL15) and Interleukin-15 receptor subunit alpha (IL15Rα), wherein the cell expresses SERPINB9 and the fusion protein of IL15 and IL15Rα and the cell has a disrupted expression of B2M.

In another composition, Composition 82, the present disclosure provides the engineered cell of Composition 81, wherein the disrupted expression of B2M comprises reduced or eliminated expression of B2M.

In another composition, Composition 83, the present disclosure provides the engineered cell of Compositions 81 or 82, wherein the first polynucleotide and second polynucleotide are inserted as a polynucleotide encoding a SERPINB9-P2A-IL15/IL15Rα construct, wherein the polynucleotide encoding the SERPINB9 is linked to the polynucleotide encoding the IL15/IL15Rα fusion by a 2A peptide coding sequence.

In another composition, Composition 84, the present disclosure provides the engineered cell of Composition 83, wherein the polynucleotide encoding the SERPINB9-P2A-IL15/IL15Rα is inserted in exon 1 of the B2M gene locus.

In another composition, Composition 85, the present disclosure provides the engineered cell of any one of Compositions 81-84, further comprising a disrupted CIITA gene, wherein the cell has a disrupted expression of CIITA.

In another composition, Composition 86, the present disclosure provides the engineered cell of Composition 85, wherein the disrupted expression of CIITA comprises reduced or eliminated expression of CIITA.

In another composition, Composition 87, the present disclosure provides 170. The engineered cell of any one of Compositions 81-86, further comprising an insertion of a polynucleotide encoding a chimeric antigen receptor (CAR), wherein the cell expresses the CAR.

In another composition, Composition 88, the present disclosure provides the engineered cell of Composition 87, wherein the CAR is inserted in the disrupted CIITA gene.

In another composition, Composition 89, the present disclosure provides the engineered cell of Compositions 87 or 88, wherein the CAR is inserted in exon 2 of the CIITA gene locus.

In another composition, Composition 90, the present disclosure provides the engineered cell of any one of Compositions 87-89, wherein the polynucleotide encoding the CAR is linked to a polynucleotide encoding HLA-E by a 2A peptide coding sequence (CAR-P2A-HLA-E), and wherein the cell expresses the CAR and HLA-E.

In another composition, Composition 91, the present disclosure provides the engineered cell of any one of Compositions 81-90, further comprising a disrupted CISH gene, wherein the cell has a disrupted expression of CISH.

In another composition, Composition 92, the present disclosure provides the engineered cell of Composition 91, wherein the disrupted expression of CISH comprises reduced or eliminated expression of CISH.

In another composition, Composition 93, the present disclosure provides the engineered cell of any one of Compositions 81-92, further comprising a disrupted FAS gene, wherein the cell has a disrupted expression of FAS.

In another composition, Composition 94, the present disclosure provides the engineered cell of Composition 93, wherein the disrupted expression of FAS comprises reduced or eliminated expression of FAS.

In another composition, Composition 95, the present disclosure provides an engineered cell comprising: (a) a disrupted B2M gene, and (b) an insertion of a first polynucleotide and a second polynucleotide, optionally wherein the first polynucleotide and the second polynucleotide are inserted in the disrupted B2M gene, wherein (i) the first polynucleotide encodes SERPINB9 and (ii) the second polynucleotide encodes a fusion protein of Interleukin-15 (IL15) and Interleukin-15 receptor subunit alpha (IL15Rα), (c) a disrupted CIITA gene, (d) an insertion of a third polynucleotide encoding a CAR and a fourth polynucleotide encoding HLA-E, optionally wherein the CAR and HLA-E are inserted in the disrupted CIITA gene, (e) a disrupted CISH gene, and (f) a disrupted FAS gene, wherein the cell expresses SERPINB9, the fusion protein of IL15 and IL15Rα, HLA-E, and the CAR, and the cell has a disrupted expression of B2M, CIITA, CISH, and FAS.

In another composition, Composition 96, the present disclosure provides the engineered cell of Composition 95, wherein the disrupted expression of B2M, CIITA, CISH, and FAS comprises reduced or eliminated expression of B2M, CIITA, CISH, and FAS.

In another composition, Composition 97, the present disclosure provides the engineered cell of Compositions 95 or 96, wherein the first polynucleotide and second polynucleotide are inserted as a polynucleotide encoding a SERPINB9-P2A-IL15/IL15Rα construct, wherein the polynucleotide encoding the SERPINB9 is linked to the polynucleotide encoding the IL15/IL15Rα fusion by a 2A peptide coding sequence.

In another composition, Composition 98, the present disclosure provides the engineered cell of Composition 97, wherein the polynucleotide encoding the SERPINB9-P2A-IL15/IL15Rα construct is inserted in exon 1 of the B2M gene locus.

In another composition, Composition 99, the present disclosure provides the engineered cell of any one of Compositions 83-94, 97, and 98, wherein the polynucleotide encoding the SERPINB9-P2A-IL15/IL15Rα construct comprises a polynucleotide sequence of SEQ ID NO: 137.

In another composition, Composition 100, the present disclosure provides the engineered cell of any one of Compositions 83-94 and 97-99, wherein SERPINB9-P2A-IL15/IL15Rα is operably linked to an exogenous promoter.

In another composition, Composition 101, the present disclosure provides the engineered cell of Composition 100, wherein the exogenous promoter is a CAG, CMV, EF1a, PGK, or UBC promoter.

In another composition, Composition 102, the present disclosure provides the engineered cell of Compositions 100 or 101, wherein the exogenous promoter is CAG and CAG-SERPINB9-P2A-IL15/IL15Rα consists essentially of SEQ ID NO: 138.

In another composition, Composition 103, the present disclosure provides the engineered cell of any one of Compositions 95-102, wherein the third polynucleotide and fourth polynucleotide are inserted as a polynucleotide encoding a CAR-P2A-HLA-E construct, wherein the polynucleotide encoding the CAR is linked to the polynucleotide encoding the HLA-E by a 2A peptide coding sequence In another composition, Composition 104, the present disclosure provides the engineered cell of Composition 103 wherein the CAR-P2A-HLA-E construct is inserted in exon 2 of the CIITA gene locus.

In another composition, Composition 105, the present disclosure provides the engineered cell of any one of Composition 90-104, wherein the HLA-E is an HLA-E trimer comprising a B2M signal peptide fused to an HLA-G presentation peptide fused to the B2M membrane protein fused to the HLA-E protein without a signal peptide.

In another composition, Composition 106, the present disclosure provides the engineered cell of any one of Compositions 87-105 wherein the CAR is a CD30 CAR, a BCMA CAR, a GPC3 CAR, a CD19 CAR, a CD33 CAR, a NKG2D CAR, a CD70 CAR, an NKp30 CAR, a CD73 CAR, a GPR87 CAR, a L1V1A CAR, a A33 CAR, a EGFR CAR, a CD20 CAR, or a SLC7A11 CAR.

In another composition, Composition 107, the present disclosure provides the engineered cell of any one of Compositions 87-106, wherein the CAR comprises an ectodomain that binds to CD30.

In another composition, Composition 108, the present disclosure provides the engineered cell of Composition 107, wherein the ectodomain that binds CD30 comprises a polynucleotide sequence of SEQ ID NO: 106, SEQ ID NO: 111, or SEQ ID NO: 115.

In another composition, Composition 109, the present disclosure provides the engineered cell of Compositions 107 or 108, wherein the polynucleotide encoding CAR-P2A-HLA-E comprises a polynucleotide sequence of SEQ ID NO: 119, SEQ ID NO: 120, or SEQ ID NO: 121.

In another composition, Composition 110, the present disclosure provides the engineered cell of any one of Compositions 90-94 and 103-109, wherein CAR-P2A-HLA-E is operably linked to an exogenous promoter.

In another composition, Composition 111, the present disclosure provides the engineered cell of Compositions 110, wherein the exogenous promoter is a CAG, CMV, EF1α, PGK, or UBC promoter.

In another composition, Composition 112, the present disclosure provides the engineered cell of Compositions 110 or 111, wherein the exogenous promoter is CAG and CAG-CAR-P2A-HLA-E consists essentially of SEQ ID NO: 139, SEQ ID NO: 140, or SEQ ID NO: 141.

In another composition, Composition 113, the present disclosure provides the engineered cell of any one of Compositions 81-112, wherein the engineered cell is a stem cell.

In another composition, Composition 114, the present disclosure provides the engineered cell of Compositions 113, wherein the stem cell is an induced pluripotent stem cell (iPSC), a hematopoietic stem cell, an embryonic stem cell, or an adult stem cell.

In another composition, Composition 115, the present disclosure provides the engineered cell of any one of Compositions 81-114, wherein the engineered cell is a genome-edited iPSC.

In another composition, Composition 116, the present disclosure provides the engineered cell of any one of Compositions 81-112, wherein the engineered cell is a natural killer (NK) cell obtained from a genome-edited iPSC.

In another composition, Composition 117, the present disclosure provides the engineered cell of any one of Compositions 81-112, wherein the engineered cell is a differentiated cell or a somatic cell.

In another composition, Composition 118, the present disclosure provides the engineered cell of any one of Compositions 81-112, wherein the engineered cell is capable of being differentiated into lineage-restricted progenitor cells or fully differentiated somatic cells.

In another composition, Composition 119, the present disclosure provides the engineered cell of any one of Compositions 81-118, wherein the engineered cell is a natural killer (NK) cell.

In another composition, Composition 120, the present disclosure provides the engineered cell of Composition 119, wherein the NK cell has been differentiated from a genome-edited iPSC, wherein the NK cell comprises the genome edits of the genome-edited iPSC, wherein the NK cell has not been genome-edited after the differentiation.

In another composition, Composition 121, the present disclosure provides the engineered cell of any one of Compositions 81-120, wherein the engineered cell expresses at least one, two, three, four or five of the following markers: CD56, NKp44, NKp46, CD94, NKG2A and KIR2DL4, and optionally wherein the markers are expressed at least at 25%, 30%, 40%, 50%, or 75% level relative to their expression in wild-type NK cells.

In another composition, Composition 122, the present disclosure provides the engineered cell of any one of Compositions 81-121, wherein the engineered cell has at least one of the following characteristics, or any combination thereof: (i) an alloimmune T cell reaction of less than 10% relative to an unmodified cell, and (ii) cytotoxic activity resulting in killing more than 50% of target cells when the engineered cells are mixed with the target cells at the ratio of 1:1; (iii) at least 50% increase in cellular viability relative to an unmodified cell.

In another composition, Composition 123, the present disclosure provides the engineered cell of any one of Composition 81-122, wherein the engineered cell has at least one of the following characteristics, or any combination thereof: (i) improved persistency, (ii) improved immune evasiveness, (iii) improved cytotoxic activity, (iv) improved ADCC activity, and (v) improved anti-tumor activity; wherein the characteristics are improved relative to a wild-type cell, optionally, relative to a wild-type iPSC or a wild-type NK cell.

In another composition, Composition 124, the present disclosure provides the engineered cell of any one of Compositions 81-123, wherein the engineered cell is capable of cell expansion in the absence of exogenous IL15 in cell culture media.

In another composition, Composition 125, the present disclosure provides a plurality of engineered cells according to any one of Compositions 81 to 124.

In another composition, Composition 126, the present disclosure provides a population of lineage-restricted progenitor cells or fully differentiated somatic cells derived from the plurality of engineered cells of Composition 125.

In another composition, Composition 127, the present disclosure provides the population of cells of Composition 126, wherein the lineage-restricted progenitor cells are hematopoietic progenitor cells, mesodermal cells, definitive hemogenic endothelium, definitive hematopoietic stem or progenitor cells, CD34$^+$ cells, multipotent progenitors (MPP), common lymphoid progenitor cells, T cell progenitors, NK cell progenitors, pancreatic endoderm progenitors, pancreatic endocrine progenitors, mesenchymal progenitor cells, muscle progenitor cells, blast cells, or neural progenitor cells, and the fully differentiated somatic cells are hematopoietic cells, pancreatic beta cells, epithelial cells, endodermal cells, macrophages, hepatocytes, adipocytes, kidney cells, blood cells, cardiomyocytes, or immune system cells.

In another composition, Composition 128, the present disclosure provides the population of cells of Composition 127, wherein the hematopoietic cells are NK cells, T cells, B cells, or NKT cells.

In another composition, Composition 129, the present disclosure provides the population of cells of Composition 128, wherein the hematopoietic cells are human NK cells.

In another composition, Composition 130, the present disclosure provides the population of cells of any one of Compositions 126-129, wherein at least 25% or at least 50% of engineered cells of the population express the CAR, HLA-E, and/or the fusion protein of IL15 and IL15Rα.

In another composition, Composition 131, the present disclosure provides the population of cells of any one of Compositions 126-130, wherein at least 50% of engineered cells of the population do not express a detectable level of B2M protein, CIITA protein, and/or ADAM17 protein.

In another composition, Composition 132, the present disclosure provides the population of cells of any one of Composition 129-131, wherein engineered human NK cells of the population, when co-cultured in vitro with a population of cancer cells, induce cell lysis of at least 70%, at least 80%, or at least 90% of the population of cancer cells.

In another composition, Composition 133, the present disclosure provides the population of cells of any one of Compositions 129-132, wherein engineered human NK cells of the population, when co-cultured in vitro with a population of cancer cells, secrete IFNγ.

In another composition, Composition 134, the present disclosure provides the population of cells of Compositions 132 or 133, wherein the ratio of engineered human NK cells to cancer cells is 0.1:1 to 2:1.

In another composition, Composition 135, the present disclosure provides a composition comprising the plurality of engineered cells of Composition 125 or the population of cells of any one of Composition 126-134.

In another composition, Composition 136, the present disclosure provides the composition of Composition 135 for use in treating a subject in need thereof.

In another composition, Composition 137, the present disclosure provides the composition of Composition 135 for use in treating cancer in a subject in need thereof.

In another composition, Composition 138, the present disclosure provides the composition or Composition 137, wherein the subject has multiple myeloma. Hodgkin's lymphoma, lung cancer, leukemia, B-cell acute lymphoblastic leukemia (B-ALL), B-cell non-Hodgkin's lymphoma (B-NL), Chronic lymphocytic leukemia (C-CLL), T cell lymphoma, T cell leukemia, clear cell renal cell carcinoma (ccRCC), thyroid cancer, nasopharyngeal cancer, non-small cell lung (NSCLC), pancreatic cancer, melanoma, ovarian cancer, glioblastoma, or cervical cancer.

In another composition, Composition 139, the present disclosure provides the composition of any one of Compositions 136-138, wherein the subject is human.

In another method, Method 84, the present disclosure provides a method of obtaining cells for administration to a subject in need thereof, the method comprising: (a) obtaining or having obtained the plurality of engineered cells of Composition 125, and (b) maintaining the plurality of engineered cells for a time and under conditions sufficient for the cells to differentiate into lineage-restricted progenitor cells or fully differentiated somatic cells.

In another method, Method 85, the present disclosure provides a method for treating of a subject in need thereof, the method comprising: (a) obtaining or having obtained the plurality of engineered cells of Composition 125 following differentiation into lineage-restricted progenitor cells or fully differentiated somatic cells; and (b) administering the lineage-restricted progenitor cells or fully differentiated somatic cells to the subject.

In another method, Method 86, the present disclosure provides the method of Methods 84 or 85, wherein the lineage-restricted progenitor cells are hematopoietic progenitor cells, mesodermal cells, definitive hemogenic endothelium, definitive hematopoietic stem or progenitor cells, CD34+ cells, multipotent progenitors (MPP), common lymphoid progenitor cells, T cell progenitors, NK cell progenitors, pancreatic endoderm progenitors, pancreatic endocrine progenitors, mesenchymal progenitor cells, muscle progenitor cells, blast cells, or neural progenitor cells, and the fully differentiated somatic cells are hematopoietic cells, pancreatic beta cells, epithelial cells, endodermal cells, macrophages, hepatocytes, adipocytes, kidney cells, blood cells, cardiomyocytes, or immune system cells.

In another method, Method 87, the present disclosure provides the method the method of any one of Methods 84-86, wherein the subject has, is suspected of having, or is at risk for a cancer.

In another method, Method 88, the present disclosure provides the method the method of any one of Methods 84-87, wherein the subject is human.

In another method, Method 89, the present disclosure provides an in vitro method for generating an engineered cell, the method comprising delivering to a cell: (a) a first RNP complex comprising an RNA-guided nuclease and a gRNA targeting a target site in a B2M gene locus; and (b) a first vector comprising a nucleic acid, the nucleic acid comprising: (i) nucleotide sequence encoding a SERPINB9 and a nucleotide sequence encoding an IL15/IL15Rα fusion; (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii); wherein the B2M gene locus is cleaved at the target site and the nucleotide sequences encoding the SERPINB9 and the IL15/IL15Rα fusion are inserted into the B2M gene locus, thereby disrupting the B2M gene.

In another method, Method 90, the present disclosure provides the method 229 the in vitro method of Method 89, wherein the gRNA of the first RNP complex comprises a spacer sequence corresponding to a sequence consisting of: SEQ ID NO: 34, SEQ ID NO: 78, or SEQ ID NO: 79, optionally a spacer sequence corresponding to a sequence consisting of SEQ ID NO: 34.

In another method, Method 91, the present disclosure provides the in vitro method of 89 or 90, wherein the engineered cell has reduced or eliminated expression of B2M.

In another method, Method 92, the present disclosure provides the method the in vitro method of any one of Methods 89 to 91, wherein the nucleotide sequence of (b)(i) comprises the nucleotide sequence encoding the SERPINB9 linked to a nucleotide sequence encoding a P2A peptide sequence linked to the nucleotide sequence encoding the IL15/IL15Rα fusion (SERPINB9-P2A-IL15/IL15Rα).

In another method, Method 93, the present disclosure provides the in vitro method of Method 92, wherein SERPINB9-P2A-IL15/IL15Rα consists essentially of SEQ ID NO: 137.

In another method, Method 94, the present disclosure provides the in vitro method of Methods 92 or 93, wherein SERPINB9-P2A-IL15/IL15Rα is operably linked to an exogenous promoter.

In another method, Method 95, the present disclosure provides the in vitro method of Method 94, wherein the exogenous promoter is CAG (CAG-SERPINB9-P2A-IL15/IL15Rα), and CAG-SERPINB9-P2A-IL15/IL15Rα consists essentially of SEQ ID NO: 138.

In another method, Method 96, the present disclosure provides the in vitro method of any one of Methods 89 to 94, wherein the nucleotide sequence of (b)(ii) consists essentially of SEQ ID NO: 36, and the nucleotide sequence of (b)(iii) consists essentially of SEQ ID NO: 54.

In another method, Method 97, the present disclosure provides the in vitro method of any one of Methods 89 to 96, wherein the first vector consists essentially of SEQ ID NO: 148.

In another method, Method 98, the present disclosure provides the in vitro method of any one of Methods 89 to 97, further comprising delivering to the cell: (c) a second RNP complex comprising an RNA-guided nuclease and a gRNA targeting a target site in a CIITA gene locus, (d) a second vector comprising a nucleic acid, the nucleic acid comprising: (i) a nucleotide sequence encoding a CAR and a nucleotide sequence encoding a HLA-E trimer; (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii), and wherein the CIITA gene locus is cleaved at the target site and the nucleotide sequences encoding the CAR and the HLA-E trimer are inserted into the CIITA gene locus, thereby disrupting the CIITA gene.

In another method, Method 99, the present disclosure provides the in vitro method of Method 98, wherein the gRNA of the second RNP complex comprises a spacer sequence corresponding to a sequence consisting of any one of SEQ ID NOS: 13-17, optionally a spacer sequence corresponding to a sequence consisting of SEQ ID NO: 13.

In another method, Method 100, the present disclosure provides the in vitro method of Methods 98 or 99, wherein the engineered cell has reduced or eliminated expression of CIITA.

In another method, Method 101, the present disclosure provides the in vitro method of any one of Methods 98 to 100, wherein the nucleotide sequence of (d)(i) comprises the nucleotide sequence encoding the CAR linked to a nucleotide sequence encoding a P2A peptide sequence linked to the nucleotide sequence encoding the HLA-E trimer.

In another method, Method 102, the present disclosure provides the in vitro method of any one of Methods 98 to 101, wherein the nucleotide sequence of (d)(ii) consists essentially of SEQ ID NO: 22, and the nucleotide sequence of (d)(iii) consists essentially of SEQ ID NO: 32.

In another method, Method 103, the present disclosure provides the in vitro method of any one of Methods 89 to 102, further comprising delivering to the cell a third RNP complex comprising an RNA-guided nuclease and a gRNA targeting a target site in a CISH gene locus.

In another method, Method 104, the present disclosure provides the in vitro method of Method 103, wherein the gRNA of the third RNP complex comprises a spacer sequence corresponding to a sequence consisting of SEQ ID NOS: 81-92, optionally a spacer sequence corresponding to a sequence consisting of SEQ ID NO: 82.

In another method, Method 105, the present disclosure provides the in vitro method of Methods 103 or 104, wherein the engineered cell has reduced or eliminated expression of CISH.

In another method, Method 106, the present disclosure provides the in vitro method of any one of Methods 89 to 105, further comprising delivering to the cell a fourth RNP complex comprising an RNA-guided nuclease and a gRNA targeting a target site in a FAS gene locus.

In another method, Method 107, the present disclosure provides the in vitro method of Method 106, wherein the gRNA of the fourth RNP complex comprises a spacer sequence corresponding to a sequence consisting of any one of SEQ ID NOS: 35, 37, 38, 39, 53, 55, and 80, optionally a spacer sequence corresponding to a sequence consisting of SEQ ID NO: 37.

In another method, Method 108, the present disclosure provides the in vitro method of Methods 106 or 107, wherein the engineered cell has reduced or eliminated expression of FAS.

In another method, Method 109, the present disclosure provides an in vitro method for generating an engineered cell, the method comprising delivering to a cell: (a) a first RNP complex comprising an RNA-guided nuclease and a gRNA targeting a target site in a B2M gene locus, (b) a first vector comprising a nucleic acid, the nucleic acid comprising: (i) nucleotide sequence encoding a SERPINB9 and a nucleotide sequence encoding an IL15/IL15Rα fusion; (ii) a nucleotide sequence having sequence homology with a genomic region located left of the target site in the B2M gene locus; and (iii) a nucleotide sequence having sequence homology with a genomic region located right of the target site in the B2M gene locus, wherein (i) is flanked by (ii) and (iii), (c) a second RNP complex comprising an RNA-guided nuclease and a gRNA targeting a target site in a CIITA gene locus; and (d) a second vector comprising a nucleic acid, the nucleic acid comprising: (i) a nucleotide sequence encoding a CAR and a nucleotide sequence encoding a HLA-E trimer; (ii) a nucleotide sequence having sequence homology with a genomic region located left of the target site in the CIITA gene locus; and (iii) a nucleotide sequence having sequence homology with a genomic region located right of the target site in the CIITA gene locus, wherein (i) is flanked by (ii) and (iii), (e) a third RNP complex comprising an RNA-guided nuclease and a gRNA targeting a target site in a CISH gene locus, and (f) a fourth RNP complex comprising an RNA-guided nuclease and a gRNA targeting a target site in a FAS gene locus, wherein the B2M gene locus is cleaved at the target site and the nucleotide sequences encoding the SERPINB9 and the IL15/IL15Rα fusion are inserted into the B2M gene locus, thereby disrupting the B2M gene, wherein the CIITA gene locus is cleaved at the target site and the nucleotide sequences encoding the CAR and the HLA-E trimer are inserted into the CIITA gene locus, thereby disrupting the CIITA gene, wherein the CISH gene locus is cleaved at the target site, thereby disrupting the CISH gene and wherein the FAS gene locus is cleaved at the target sire, thereby disrupting the FAS gene.

In another method, Method 110, the present disclosure provides the in vitro method of Method 109, wherein the gRNA of the first RNP complex comprises a spacer sequence corresponding to a sequence consisting of: SEQ ID NO: 34, SEQ ID NO: 78, or SEQ ID NO: 79, optionally a spacer sequence corresponding to a sequence consisting of SEQ ID NO: 34.

In another method, Method 111, the present disclosure provides the in vitro method of Methods 109 or 110, wherein the engineered cell has reduced or eliminated expression of B2M.

In another method, Method 112, the present disclosure provides the in vitro method of any one of Methods 109-111, wherein the nucleotide sequence of (b)(i) comprises the nucleotide sequence encoding the SERPINB9 linked to a nucleotide sequence encoding a P2A peptide sequence linked to the nucleotide sequence encoding the IL15/IL15Rα fusion (SERPINB9-P2A-IL15/IL15Rα).

In another method, Method 113, the present disclosure provides the method the in vitro method of Method 112, wherein SERPINB9-P2A-IL15/IL15Rα consists essentially of SEQ ID NO: 137.

In another method, Method 114, the present disclosure provides the in vitro method of Methods 112 or 113, wherein SERPINB9-P2A-IL15/IL15Rα is operably linked to an exogenous promoter.

In another method, Method 115, the present disclosure provides the in vitro method of Method 114, wherein the exogenous promoter is CAG (CAG-SERPINB9-P2A-IL15/IL15Rα), and CAG-SERPINB9-P2A-IL15/IL15Rα consists essentially of SEQ ID NO: 138.

In another method, Method 116, the present disclosure provides the in vitro method of any one of Methods 109 to 115, wherein the nucleotide sequence of (b)(ii) consists essentially of SEQ ID NO: 36, and the nucleotide sequence of (b)(iii) consists essentially of SEQ ID NO: 54.

In another method, Method 117, the present disclosure provides the in vitro method of any one of Methods 109 to 116, wherein the first vector consists essentially of SEQ ID NO: 148.

In another method, Method 118, the present disclosure provides the in vitro method of any one of Methods 109 to 117, wherein the gRNA of the second RNP complex comprises a spacer sequence corresponding to a sequence consisting of any one of SEQ ID NOS: 13-17, optionally a spacer sequence corresponding to a sequence consisting of SEQ ID NO: 13.

In another method, Method 119, the present disclosure provides the in vitro method of Method 118, wherein the engineered cell has reduced or eliminated expression of CIITA.

In another method, Method 120, the present disclosure provides the in vitro method of any one of Methods 109 to 119, wherein the nucleotide sequence of (d)(i) comprises the nucleotide sequence encoding the CAR linked to a nucleotide sequence encoding a P2A peptide sequence linked to the nucleotide sequence encoding the HLA-E trimer.

In another method, Method 121, the present disclosure provides the in vitro method of any one of Methods 109 to 120, wherein the nucleotide sequence of (d)(ii) consists essentially of SEQ ID NO: 22, and the nucleotide sequence of (d)(iii) consists essentially of SEQ ID NO: 32.

In another method, Method 122, the present disclosure provides the in vitro method of any one of Methods 98-121, wherein the HLA-E is an HLA-E trimer comprising a B2M signal peptide fused to an HLA-G presentation peptide fused to the B2M membrane protein fused to the HLA-E protein without a signal peptide.

In another method, Method 123, the present disclosure provides the in vitro method of any one of Methods 98-122, wherein the CAR is a CD30 CAR, a BCMA CAR, a GPC3 CAR, a CD19 CAR, a CD33 CAR, a NKG2D CAR, a CD70 CAR, an NKp30 CAR, a CD73 CAR, a GPR87 CAR, a L1V1A CAR, a A33 CAR, a EGFR CAR, a CD20 CAR, or a SLC7A11 CAR.

In another method, Method 124, the present disclosure provides the in vitro method of any one of Methods 98-123, wherein the CAR comprises an ectodomain that binds to CD30.

In another method, Method 125, the present disclosure provides the in vitro method of Method 124, wherein the ectodomain that binds CD30 comprises a polynucleotide sequence of SEQ ID NO: 106, SEQ ID NO: 111, or SEQ ID NO: 115.

In another method, Method 126, the present disclosure provides the in vitro method of Methods 124 or 125, wherein the polynucleotide encoding CAR-P2A-HLA-E comprises a polynucleotide sequence of SEQ ID NO: 119, SEQ ID NO: 120, or SEQ ID NO: 121.

In another method, Method 127, the present disclosure provides the in vitro method of any one of Methods 101-108 and 120-126, wherein CAR-P2A-HLA-E is operably linked to an exogenous promoter.

In another method, Method 128, the present disclosure provides the in vitro method of Method 127, wherein the exogenous promoter is a CAG, CMV, EF1α, PGK, or UBC promoter.

In another method, Method 129, the present disclosure provides the in vitro method of any one of Methods 109-128, wherein the gRNA of the third RNP complex comprises a spacer sequence corresponding to a sequence consisting of any one of SEQ ID NOS: 81-92, optionally a spacer sequence corresponding to a sequence consisting of SEQ ID NO: 82.

In another method, Method 130, the present disclosure provides the in vitro method of Method 129, wherein the engineered cell has reduced or eliminated expression of CISH.

In another method, Method 131, the present disclosure provides the in vitro method of any one of Methods 109-130, wherein the gRNA of the fourth RNP complex comprises a spacer sequence corresponding to a sequence consisting of any one of SEQ ID NOS: 35, 37, 38, 39, 53, 55, and 80, optionally a spacer sequence corresponding to a sequence consisting of SEQ ID NO: 37.

In another method, Method 132, the present disclosure provides the in vitro method of Method 131, wherein the engineered cell has reduced or eliminated expression of FAS.

In another method, Method 133, the present disclosure provides the in vitro method of any one of Methods 98-132, wherein the first vector is a plasmid vector, wherein the first vector consists essentially of SEQ ID NO: 148.

In another method, Method 134, the present disclosure provides the in vitro method of any one of Methods 98-133, wherein the second vector is a plasmid vector, wherein the second vector consists essentially of SEQ ID NO: 110, SEQ ID NO: 114, or SEQ ID NO: 118.

In another method, Method 135, the present disclosure provides the in vitro method of any one of Methods 89 to 135, wherein the RNA-guided nuclease is a Cas9 nuclease.

In another method, Method 136, the present disclosure provides the in vitro method of Method 135, wherein the Cas9 nuclease is linked to at least one nuclear localization signal.

In another method, Method 137, the present disclosure provides the in vitro method of any one of Methods 89 to 136, wherein the cell is a stem cell.

In another method, Method 138, the present disclosure provides the in vitro method of Method 137, wherein the stem cell is an embryonic stem cell, an adult stem cell, an induced pluripotent stem cell, or a hematopoietic stem cell.

In another method, Method 139, the present disclosure provides the in vitro method of Methods 137 or 138, wherein the stem cell is a human stem cell.

In another composition, Composition 140, the present disclosure provides a plurality of engineered cells generated or obtainable by the method of any one of Methods 89 to 139.

In another composition, Composition 141, the present disclosure provides the plurality of engineered cells of Composition 140 maintained for a time and under conditions sufficient for the cells to undergo differentiation.

In another composition, Composition 142, the present disclosure provides the plurality of engineered cells of Compositions 140 or 141 for use in treating a subject in need thereof.

In another composition, Composition 143, the present disclosure provides the plurality of cells for use of Composition 142, wherein the subject is a human who has, is suspected of having, or is at risk for a cancer.

In another method, Method 140, the present disclosure provides a method comprising administering to a subject the plurality of engineered cells of Compositions 140 or 141.

In another method, Method 141, the present disclosure provides a method for treating of a subject in need thereof, the method comprising: (a) obtaining or having obtained the plurality of engineered cells of Composition 140 following differentiation into lineage-restricted progenitor cells or fully differentiated somatic cells, and (b) administering the lineage-restricted progenitor cells or fully differentiated somatic cells to the subject.

In another method, Method 142, the present disclosure provides a method of obtaining cells for administration to a subject in need thereof, the method comprising: (a) obtaining or having obtained the engineered cells of Composition 140, and (b) maintaining the engineered cells for a time and under conditions sufficient for the cells to differentiate into lineage-restricted progenitor cells or fully differentiated somatic cells.

In another method, Method 143, the present disclosure provides the method of Methods 141 or 142, wherein the lineage-restricted progenitor cells are hematopoietic progenitor cells, mesodermal cells, definitive hemogenic endothelium, definitive hematopoietic stem or progenitor cells, $CD34^+$ cells, multipotent progenitors (MPP), common lymphoid progenitor cells, T cell progenitors, NK cell progenitors, definitive endoderm, hepatoblasts, pancreatic endoderm progenitors, pancreatic endocrine progenitors, mesenchymal progenitor cells, muscle progenitor cells, blast cells, or neural progenitor cells, and the fully differentiated somatic cells are hematopoietic cells, hepatocytes, pancreatic beta cells, epithelial cells, endodermal cells, macrophages, hepatocytes, adipocytes, kidney cells, blood cells, cardiomyocytes, or immune system cells.

In another method, Method 144, the present disclosure provides the method of any one of Methods 139 to 143, wherein the subject is a human who has, is suspected of having, or is at risk for a cancer.

In another method, Method 145, the present disclosure provides the method of Method 143, wherein the subject has multiple myeloma. Hodgkin's lymphoma, lung cancer, leukemia, B-cell acute lymphoblastic leukemia (B-ALL), B-cell non-Hodgkin's lymphoma (B-NL), Chronic lymphocytic leukemia (C-CLL), T cell lymphoma, T cell leukemia, clear cell renal cell carcinoma (ccRCC), thyroid cancer, nasopharyngeal cancer, non-small cell lung (NSCLC), pancreatic cancer, liver cancer, melanoma, ovarian cancer, glioblastoma, or cervical cancer.

In another composition, Composition 144, the present disclosure provides a gRNA comprising a spacer sequence corresponding to a sequence consisting of any one of SEQ ID NOS: 35, 37, 38, 39, 53, 55, and 80.

In another composition, Composition 145, the present disclosure provides a gRNA comprising a spacer sequence corresponding to a sequence consisting of any one of SEQ ID NOS: 81-92.

In another composition, Composition 146, the present disclosure provides a gRNA comprising a spacer sequence corresponding to a sequence consisting of any one of SEQ ID NOS: 93-101.

EXAMPLES

Example 1: Cell Maintenance and Expansion

Maintenance of hiPSCs. Cells of human induced pluripotent stem cell (hiPSC) line were maintained in STEMFLEX™ Complete media (Life Technologies, A3349401) with single cell passaging using ACCUTASE® (Stemcell Technologies 07920 or equivalent) on BIOLAMININ 521 LN (LN521), BIOLAMININ 511 LN (LN511), or Recombinant Laminin iMatrix-511 E8 (AMSBIO, AMS.892 011). For passaging, 1% REVITACELL™ Supplement (100×) was added.

Single cell cloning of hPSCs. For single cell cloning, hiPSCs were fed with STEMFLEX™ Complete media (Life Technologies, A3349401) with 1% REVITACELL™ Supplement (100×) (ThermoFisher Cat #A2644501). Following dissociation with ACCUTASE®, the cells were sorted as a single cell per well of a pre-coated plate. The 96 well plates were pre-coated with a 1:10 or a 1:20 dilution of BIOLAMININ 521 LN (LN521) in DPBS, calcium, magnesium (Life Technologies, 14040133) for 2 hours at 37° C. The WOLF FACS-sorter (Nanocellect) was used to sort single cells into the wells. The plates were pre-filled with 100-200 µL of STEMFLEX™ Complete with REVITACELL™ Supplement (100×) and 4 µL/mL of Recombinant Laminin iMatrix-511 E8 (AMSBIO, AMS.892 011). Three days post cell seeding, the cells were fed with fresh STEMFLEX™ and continued to be fed every other day with 100-200 µL of media. After 10 days of growth, the cells were fed daily with STEMFLEX™ until day 12-16. At this time, the plates were dissociated with ACCUTASE® and the collected cell suspensions were split 1:2 with half going into a new 96 well plate for maintenance and half going into a DNA extraction solution QuickExtract™ DNA Extraction Solution (Lucigen). Following DNA extraction, PCR was performed to assess presence or absence of desired gene edits at the targeted DNA locus. Sanger sequencing was used to verify desired knock-out (KO) edits.

Expansion of single cell derived hiPSCs clones. Successfully targeted clones were passaged from 96-well plates to 24-well plates using STEMFLEX™ and BIOLAMININ 521 or Recombinant Laminin iMatrix-511 E8 and 1% REVITACELL™ Supplement (100×). Following expansion in 24-well plates, the cells were passaged onto 6-well plates and then T25 and larger flask formats.

Example 2: Differentiating Stem Cells into Natural Killer Cells—Protocol 1

Protocol 1 was utilized to differentiate stem cells, such as wild-type and/or edited induced pluripotent stem (iPS) cells, into hematopoietic stem and progenitor cells (HSPCs) and then into natural killer (NK) cells. Prior to differentiation, frozen iPS cells were thawed and re-suspended in NK-MED-001 medium (Table 1). Flasks pre-coated with laminin-521 were used for cell culturing. Medium was changed daily using NK-MED-002 (Table 2) medium until cells were used for differentiation.

NK Cell Differentiation. iPS Cells were Differentiated Using the Following Steps:

Day −1 (afternoon), iPSC aggregation: NK-MED-002 (Table 2) medium was aspirated from flasks containing iPSC and the cells were washed with DPBS (no calcium, no magnesium) (Thermo Fisher Scientific, 14190250). DPBS was aspirated and 2 mL ACCUTASE® (Innovative Cell Technologies, AT-104) was added per T25 flask (or 80 µL of ACCUTASE® per 1 cm$^2$). Cells were incubated at 37° C. for 3-5 min or until all the colonies detached. Accutase digested cells were diluted with NK-MED-002 medium to a ratio of at least 3:1 (NK-MED-002:ACCUTASE®). Cells were gently resuspended and transferred to a conical tube. Enough NK-MED-002 medium was added to cells to dilute the ACCUTASE® to a ratio of 4:1 (NK-MED-002:ACCUTASE®). Cells were pelleted and re-suspended in 10 ml of NK-MED-003 medium (Table 3). Cells were counted and the cell concentration was diluted to $1\times10^6$/mL. $6\times10^6$ cells were transferred to another tube and resuspended in a total of 6 mL of NK-MED-003 medium. The cells were transferred to 1 well of ultra-low adhesion 6-well plate (Corning, 3471) and the plate was placed on a platform shaker and rotated at 98 RPM for 18+/−2 hours (overnight).

2. At day 0, morning, at 18+/−2 hours after iPSC aggregation: The plate was rotated in a circular motion to move aggregates towards center of the well and aggregates were collected in a conical tube. Alternatively, all the aggregate solution mix was collected. Aggregates were allowed to settle for 15+/−5 minutes. Cells were resuspended in NK-MED-004 medium (Table 4). The cell number in aggregates was counted. The seeding density was adjusted as needed to resuspend $3\times10^5$ cells in aggregates in 2 mL NK-MED-004 medium and plated in one well of a 6-well low adhesion plate. Alternatively, for scale up, an appropriate number of cells was resuspended and transferred to a PBS spinner vessel (PBS Biotech). Seeding density tested for PBS seeding vessel was approximately $1\text{-}1.2\times10^5$ cells per mL per final media volume (day 0+8 hrs). The plate was placed on a platform shaker and rotated at 98 RPM for 8 hours or the PBS spinner vessel were placed on a PBS base (PBS-MINI MagDrive Base Unit; PBS Biotech), in $CO_2$ incubator with a rotation speed of RPM 38 to 39.

3. At day 0, afternoon, at 8 hours after NK-MED-004 medium addition: 2 mL per well of NK-MED-005 medium (Table 5) was added or scaled up for PBS spinner vessels. The plate was returned to platform shaker or PBS spinner vessel to its base in the $CO_2$ incubator and left undisturbed until day 2. NK-MED-005 medium components were 2× of their final concentration, therefore it was added to cells in NK-MED-004 at a 1:1 volume ratio.

4. At day 2: NK-MED-005 medium was replaced with NK-MED-006 medium (Table 6).

5. At day 4: NK-MED-006 medium was replaced with NK-MED-007 medium (Table 7).

6. At day 6: Starting at day 6, medium with all aggregates and single cells was transferred into an appropriate volume centrifuge conical tube. Cells were centrifuged and resuspended in NK-MED-008 medium (Table 8) and placed back into original wells and onto platform shaker, or into original vessels and onto base, and returned for continued culture.

7. At day 10: Half media change was made with NK-MED-008 medium.

8. At day 14: Full media change was made with NK-MED-009 medium (Table 9).

9. From day 17 onwards: Starting at day 17 (and at day 20, and every 2 to 3 days from day 20 onwards), single cell density was estimated from cell culture. If cell density exceeded $3\times10^6$, cells were diluted to $1\text{-}2\times10^6$ either by topping up cultures with fresh NK-MED-009 medium or by a complete medium change if medium color has completely turned yellow. Representative culture samples were harvested at day 6, day 10, day 14, day 17, day 20, and day 28 for FACS and TruSeq analysis to monitor differentiation of the cells.

In the tables below, the volumes are approximate to get the desired concentration.

TABLE 1

Medium composition for NK-MED-001

| Component | Working Conc. | Volume | Stock Conc. |
|---|---|---|---|
| STEMFLEX ™ Basal (Thermo Fisher, A3349401) | 90% | 900 mL | 100% |
| STEMFLEX ™ Supplement (Thermo Fisher, A3349401) | 1 X | 100 mL | 10 X |
| Thiazovivin (Biological Industry, 1226056-71-8) | 2 µM | 200 µL | 10 mM |

TABLE 2

Medium composition for NK-MED-002

| Component | Working Conc. | Volume | Stock Conc. |
|---|---|---|---|
| STEMFLEX ™ Basal (Thermo Fisher, A3349401) | 90% | 900 mL | 100% |
| STEMFLEX ™ Supplement (Thermo Fisher, A3349401) | 1 X | 100 mL | 10 X |

TABLE 3

Medium composition for NK-MED-003

| Component | Working Conc. | Volume | Stock Conc. |
|---|---|---|---|
| STEMFLEX ™ Basal (Thermo Fisher, A3349401) | 90% | 899 mL | 100% |
| STEMFLEX ™ Supplement (Thermo Fisher, A3349401) | 1 X | 100 mL | 10 X |
| Thiazovivin (Biological Industry, 1226056-71-8) | 10 µM | 1000 µL | 10 mM |

TABLE 4

Medium composition for NK-MED-004

| Component | Working Conc. | Volume | Stock Conc. |
|---|---|---|---|
| STEMdiff APEL 2 Medium (STEMCELL Technologies, 05275) | 100% | 999 mL | 100% |
| rh BMP-4 (Peprotech, 120-05ET) | 30 ng/mL | 300 µL | 100 µg/mL |
| Thiazovivin (Biological Industry, 1226056-71-8) | 10 µM | 1000 µL | 10 mM |

TABLE 5

Medium composition for NK-MED-005

| Component | Working Conc. | Volume | Stock Conc. |
|---|---|---|---|
| STEMdiff APEL 2 Medium (STEMCELL Technologies, 05275) | 100% | 998 mL | 100% |
| rh BMP-4 (Peprotech, 120-05ET) | 30 ng/mL | 300 μL | 100 μg/mL |
| rh FGF2 (Peprotech, 100-18C-1MG) | 100 ng/mL | 1000 μL | 100 μg/mL |
| CHIR 99021 (Selleckchem, S1263) | 6 μM | 600 μL | 10 mM |
| Activin-A (R&D Systems, 338-AC-01M/CF | 5 ng/mL | 100 μL | 50 μg/mL |

TABLE 6

Medium composition for NK-MED-006

| Component | Working Conc. | Volume | Stock Conc. |
|---|---|---|---|
| STEMdiff APEL 2 Medium (STEMCELL Technologies, 05275) | 100% | 997 mL | 100% |
| rh FGF2 (Peprotech, 100-18C-1MG) | 20 ng/mL | 200 μL | 100 μg/mL |
| rh VEGF165 (Peprotech, 100-20-1MG) | 20 ng/mL | 200 μL | 100 μg/mL |
| rh TPO (Peprotech, 300-18) | 20 ng/mL | 200 μL | 100 μg/mL |
| rh SCF (Peprotech, 300-07) | 100 ng/mL | 1000 μL | 100 μg/mL |
| rh IL-3 (Peprotech, 200-03-100UG) | 40 ng/mL | 400 μL | 100 μg/mL |
| rh Flt3L (Peprotech, 300-19) | 20 ng/mL | 200 μL | 100 μg/mL |
| WNT C-59 (Selleckchem, S7037) | 2 μM | 200 μL | 10 mM |
| SB431542 (Selleckchem, S1067) | 5 μM | 500 μL | 10 mM |

TABLE 7

Medium composition for NK-MED-007

| Component | Working Conc. | Volume | Stock Conc. |
|---|---|---|---|
| STEMdiff APEL 2 Medium (STEMCELL Technologies, 05275) | 100% | 998 mL | 100% |
| rh FGF2 (Peprotech, 100-18C-1MG | 20 ng/mL | 200 μL | 100 μg/mL |
| rh VEGF165 (Peprotech, 100-20-1MG) | 20 ng/mL | 200 μL | 100 μg/mL |
| rh TPO (Peprotech, 300-18) | 20 ng/mL | 200 μL | 100 μg/mL |
| rh SCF (Peprotech, 300-07) | 100 ng/mL | 1000 μL | 100 μg/mL |
| rh IL-3 (Peprotech, 200-03-100UG) | 40 ng/mL | 400 μL | 100 μg/mL |
| rh Flt3L (Peprotech, 300-19) | 20 ng/mL | 200 μL | 100 μg/mL |

TABLE 8

Medium composition for NK-MED-008

| Component | Working Conc. | Volume | Stock Conc. |
|---|---|---|---|
| DMEM (high glucose, GlutaMAX) (Thermo Fisher, 10566016) | 55.47% | 555 mL | 100% |
| F-12 with GlutaMAX (Thermo Fisher, 31765035) | 27.74% | 277 mL | 100% |
| GlutaMAX (Thermo Fisher, 35050079) | 1 X | 10 mL | 100 X |
| Glucose* | 10.25 mM | 4.1 mL | 2500 mM |
| Human AB serum (Valley Biomedical Inc, HP1022) | 15% | 150 mL | 100% |
| Zinc sulfate (Millipore Sigma, Z0251) | 37 μM | 978 μL | 37 mM |
| Ethanolamine (Millipore Sigma, E0135) | 50 μM | 3 μL | 16.6 M |
| Ascorbic acid (Fisher Scientific, NC0762606) | 20 μg/mL | 2000 μL | 10 mg/mL |
| Sodium selenite (Millipore Sigma, S9133-1MG) | 5 ng/mL | 50 μL | 100 μg/mL |
| β-mercaptoethanol (Thermo Fisher, 21985-023) | 1 μM | 18 μL | 55 mM |
| rh IL-3 (Peprotech, 200-03-100UG) | 5 ng/mL | 50 μL | 100 μg/mL |
| rh IL-7 (Peprotech, 200-07) | 20 ng/mL | 200 μL | 100 μg/mL |
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | 100 μg/mL |

*Total glucose concentration in medium is 27 mM (accounting for glucose in DMEM medium, F12 supplement and added glucose provided here).

TABLE 9

Medium composition for NK-MED-009

| Component | Working Conc. | Volume | Stock Conc. |
|---|---|---|---|
| DMEM (high glucose, GlutaMAX) (Thermo Fisher, 10566016) | 55.47% | 555 mL | 100% |
| F-12 with GlutaMAX (Thermo Fisher, 31765035) | 27.74% | 277 mL | 100% |
| GlutaMAX (Thermo Fisher, 35050079) | 1 X | 10 mL | 100 X |
| Glucose* | 10.25 mM | 4.1 mL | 2500 mM |
| Human AB serum (Valley Biomedical Inc, HP1022) | 15% | 150 mL | 100% |
| Zinc sulfate (Millipore Sigma, Z0251) | 37 µM | 978 µL | 37 mM |
| Ethanolamine (Millipore Sigma, E0135) | 50 µM | 3 µL | 16.6 M |
| Ascorbic acid (Fisher Scientific, NC0762606) | 20 µg/mL | 2000 µL | 10 mg/mL |
| Sodium selenite (Millipore Sigma, S9133-1MG) | 5 ng/mL | 50 µL | 100 µg/mL |
| β-mercaptoethanol (Thermo Fisher, 21985-023) | 1 µM | 18 µL | 55 mM |
| rh IL-7 (Peprotech, 200-07) | 20 ng/mL | 200 µL | 100 µg/mL |
| rh Flt3L (Peprotech, 300-19) | 15 ng/mL | 150 µL | 100 µg/mL |
| rh IL-15 (Peprotech, 200-15) | 15 ng/mL | 150 µL | 100 µg/mL |
| rh SCF (Peprotech, 300-07) | 20 ng/mL | 200 µL | 100 µg/mL |

*Total glucose concentration in medium is 27 mM (accounting for glucose in DMEM medium, F12 supplement and added glucose provided here).

Example 3: Differentiating Stem Cells into Natural Killer Cells—Protocol 1.5

Protocol 1.5 was utilized to differentiate stem cells, such as wild-type and/or edited iPS cells, into hematopoietic stem and progenitor cells (HSPCs) and then into natural killer (NK) cells. iPS cells were cultured in STEMFLEX™ (SF) (Thermo Fisher, A3349401) media prior to beginning differentiation. iPS cells were differentiated using the following steps. Media used throughout is shown in Tables 10-11:

Day −1 (afternoon): STEMFLEX™ media (SF) was aspirated and cells were washed with DPBS (no calcium, no magnesium) (Thermo Fisher Scientific, 14190250). DPBS was aspirated and 2 mL pre-warmed ACCUTASE® (Innovative Cell Technologies, AT-104) was added per flask (scale up if needed: 80 µL of ACCUTASE® per 1 cm²). Cells were incubated at 37° C. for 3-5 minutes or until all the colonies detached. Accutase digested cells were diluted with SF for a ratio of 3:1 (SF:ACCUTASE®). Cells were gently pipetted 2-3 times with a serological pipet until cells detached. Cells were transferred to a conical tube and the plate was rinsed with SF, the rinse was added to the same tube. Enough SF was added to cells to dilute the ACCUTASE® to a ratio of 4:1 (SF:ACCUTASE®). Cells were spun for 5 minutes at 300 g. Supernatant was aspirated and cells were re-suspended in SF. Cells were counted. The cell concentration was adjusted to 1×10⁶/mL by transferring 6×10⁶ cells to another tube, resuspended in total 6 mL of NK-MED-003 medium. Cells were transferred to 1 well of ultra-low adhesion 6-well plate (Corning, 3471). The plate was placed on a horizontal orbital shaker.

2. Day 0 (morning): 16 hours later: Start differentiation: The plate was rotated in a circular motion to move aggregates towards center of the well, and aggregates were collected and transferred to a conical tube. The aggregates were allowed to settle. Aggregates were resuspended in NK-MED-004 medium (2 mL per aggregated well). Cell number in aggregates was counted. The cells in aggregates density was adjusted by resuspending 3×10⁵ cells in aggregates in 2 mL APEL-B media and plated in 1 well of a 6-well low adhesion plate. The plate was placed on a horizontal orbital shaker and rotated for 8 hours.

3. Day 0 (afternoon, following 8 hours of pre-incubation): 2 mL per well of NK-MED-005 medium was added per well. The plate was returned to the orbital shaker and left untouched until day 2.

4. Day 2: NK-MED-006 was replaced with A-FVTSIF-SW media.

5. Day 4: NK-MED-007 media was replaced with A-FVTSIF media.

6. Day 6: Using this method, single cells (HSPCs) started emerging at day 5-6. Media with all embryoid bodies (EBs) and single cells were transferred into an appropriate volume centrifuge conical tube and centrifuged. For 6-well plates: EBs from each well were resuspended in 3 mL of DF-NK+ IL3 media (Table 10) and transferred into their original wells. The plate was returned to the orbital shaker.

7. Day 10: 6-well plates: 3 mL of DF-NK+IL3 media was added to each well on top of the original media and then returned to orbital shaker.

8. Day 14: Full media change. Transfer cells to DF-NK media (Table 11), no IL3 was added from this point. Media with all EBs and single cells was transferred into a centrifuge conical tube and centrifuged. Supernatant was removed. 6-well plates: EBs from each well were resuspended in 3 mL of DF-NK media and transferred into their original wells.

9. Days 14-28: Every 3-4 days media was topped off with 3 mL of fresh DF-NK media, then 3-4 days later spent media was replaced with 3 mL of fresh DF-NK media by collecting the cells in a conical tube and centrifuging. Representative culture samples were harvested at days 6, 10, 14, 21, 28 and 35 for FACS and TruSeq analysis to monitor differentiation of the cells.

TABLE 10

DF-NK + IL3 Media

| Component | Working Conc. | Volume | Stock Conc. | Vendor | Item# |
|---|---|---|---|---|---|
| DMEM (high glucose, GlutaMAX) | Ratio 2 to F12 | 558 | 100% | Thermo Fisher Scientific | 10566016 |
| F-12 with GlutaMAX | Ratio 1 to DMEM | 279 | 100% | Thermo Fisher Scientific | 31765035 |
| GlutaMAX | 1X | 10 mL | 100X | | |
| Human AB serum | 15% | 150 mL | 100% | Valley Biomedical Inc | HP1022 |
| Ascorbic acid | 20 µg/mL | 2000 µL | 10 mg/mL | MilliporeSigma | |
| Sodium selenite | 5 ng/mL | 50 µL | 100 µg/mL | MilliporeSigma | |
| rh IL-3 | 5 ng/mL | 50 µL | 100 µg/mL | PeproTech | 200-03 |
| rh IL-7 | 20 ng/mL | 200 µL | 100 µg/mL | PeproTech | 200-07 |
| rh Flt3L | 15 ng/mL | 150 µL | 100 µg/mL | PeproTech | 300-19 |
| rh IL-15 | 15 ng/mL | 150 µL | 100 µg/mL | PeproTech | 200-15 |
| rh SCF | 20 ng/mL | 200 µL | 100 µg/mL | PeproTech | 300-07 |

TABLE 11

DF-NK Media

| Component | Working Conc. | Volume | Stock Conc. | Vendor | Item# |
|---|---|---|---|---|---|
| DMEM (high glucose, GlutaMAX) | Ratio 2 to F12 | 558 | 100% | Thermo Fisher Scientific | 10566016 |
| F-12 with GlutaMAX | Ratio 1 to DMEM | 279 | 100% | Thermo Fisher Scientific | 31765035 |
| GlutaMAX | 1X | 10 mL | 100X | | |
| Human AB serum | 15% | 150 mL | 100% | Valley Biomedical Inc | HP1022 |
| Ascorbic acid | 20 µg/mL | 2000 µL | 10 mg/mL | MilliporeSigma | |
| Sodium selenite | 5 ng/mL | 50 µL | 100 µg/mL | MilliporeSigma | |
| rh IL-3 | | | | | |
| rh IL-7 | 20 ng/mL | 200 µL | 100 µg/mL | PeproTech | 200-07 |
| rh Flt3L | 15 ng/mL | 150 µL | 100 µg/mL | PeproTech | 300-19 |
| rh IL-15 | 15 ng/mL | 150 µL | 100 µg/mL | PeproTech | 200-15 |
| rh SCF | 20 ng/mL | 200 µL | 100 µg/mL | PeproTech | 300-07 |

Example 4: Generation of ADAM17-Null Human Pluripotent Stem Cells (hPSCs)

Guide RNA (gRNA) Selection for ADAM17 in hPSCs.

Ten ADAM17 targeting gRNAs were designed for targeting exon 1 of the ADAM17 coding sequence. These gRNAs had predicted low off-target scores based on sequence homology prediction using gRNA design software. The target sequences of the gRNAs with the corresponding PAMs are presented in Table 12. In some embodiments, the gRNA comprises RNA sequence corresponding to the target DNA sequence.

TABLE 12

ADAM17 gRNA Target Sequences

| Name | Target Sequence (5'-3') | SEQ ID NO: | PAM |
|---|---|---|---|
| ADAM17 Ex1_T2 | GGTCGCGGCGCCAGCACGAA | 1 | AGG |
| ADAM17 Ex1_T4 | CCGAAGCCCGGGTCATCCGG | 2 | AGG |
| ADAM17 Ex1_T9 | CCGCGACCTCCGGATGACCC | 3 | GGG |
| ADAM17 Ex1_T10 | CGTGCTGGCGCCGCGACCTC | 4 | CGG |
| ADAM17 Ex1_T11 | CGAAAGGAACCACGCTGGTC | 5 | AGG |
| ADAM17 Ex1_T12 | CAGCGTGGTTCCTTTCGTGC | 6 | TGG |
| ADAM17 Ex1_T19 | GCCGCGACCTCCGGATGACC | 7 | CGG |
| ADAM17 Ex1_T24 | GAACCACGCTGGTCAGGAAT | 8 | AGG |
| ADAM17 Ex1_T25 | CAGCACGAAAGGAACCACGC | 9 | TGG |
| ADAM17 Ex1_T28 | GTAGCGGGCCGGGAACATG | 10 | AGG |

To assess their cutting efficiency in hPSCs, iPS cells were electroporated using the Neon Electroporator (Neon Transfection Kit ThermoFisher Cat #MPK5000) with a ribonucleoprotein (RNP) mixture of Cas9 protein (Biomay) and guide RNA (IDT) (See Table 12 for gRNA sequences) at a molar ratio of 5:1 (gRNA:Cas9) with absolute values of 125 pmol Cas9 and 625 pmol gRNA. To form the RNP complex, gRNA and Cas9 were combined in one vessel with R-buffer (Neon Transfection Kit) to a total volume of 25 μL and incubated for 15 min at RT. Cells were dissociated using ACCUTASE®, then resuspended in STEMFLEX™ media (Gibco, cat #11320033), counted using an NC-200 (ChemoMetec) and centrifuged. A total of 1×10⁶ cells were resuspended with the RNP complex and R-buffer was added to a total volume of 125 μL. This mixture was then electroporated with 1 pulse for 20 ms at 1500 V and 1 pulse for 100 ms at 500 V. Following electroporation, the cells were pipetted out into an Eppendorf tube filled with STEMFLEX™ media with REVITACELL™ Supplement (100×). This cell suspension was then plated into tissue culture dishes pre-coated with BIOLAMININ 521 CTG at 1:20 dilution. Cells were cultured in a normoxia incubator (37° C., 8% $CO_2$) for 48 hours. After 48 hours, genomic DNA was harvested from the cells using QuickExtract (Lucigen, Middleton, WI; Cat #QE09050).

PCR for the target ADAM17 sequence was performed and the resulting amplified DNA was assessed for cutting efficiency by TIDE analysis. PCR for relevant regions was performed using Platinum Taq Supermix (Invitrogen, cat #125320176 and Cat #11495017). The sequences of the PCR primers are presented in Table 13; and the cycling conditions are provided in Table 14.

TABLE 13

ADAM17 TIDE/Indel Primers

| Name | Type | Sequence (5'-3') | SEQ ID NO: |
|---|---|---|---|
| ADAM17 F2 | forward | AGAATCTTCCCAGTAGGCGG | 11 |
| ADAM17 R2 | reverse | CTCAGGCGCTCAGTCACTAC | 12 |

TABLE 14

ADAM17 PCR/Indel PCR Cycling Parameters

| Step | Temperature | Time | Cycles |
|---|---|---|---|
| Denaturation | 94° C. | 2 min | 1 |
| Denaturation | 94° C. | 15 sec | 34 |
| Annealing | 57° C. | 30 sec | |
| Extension | 68° C. | 45 sec | |
| Elongation | 68° C. | 5 min | 1 |
| Hold | 4° C. | hold | |

Figure 1:
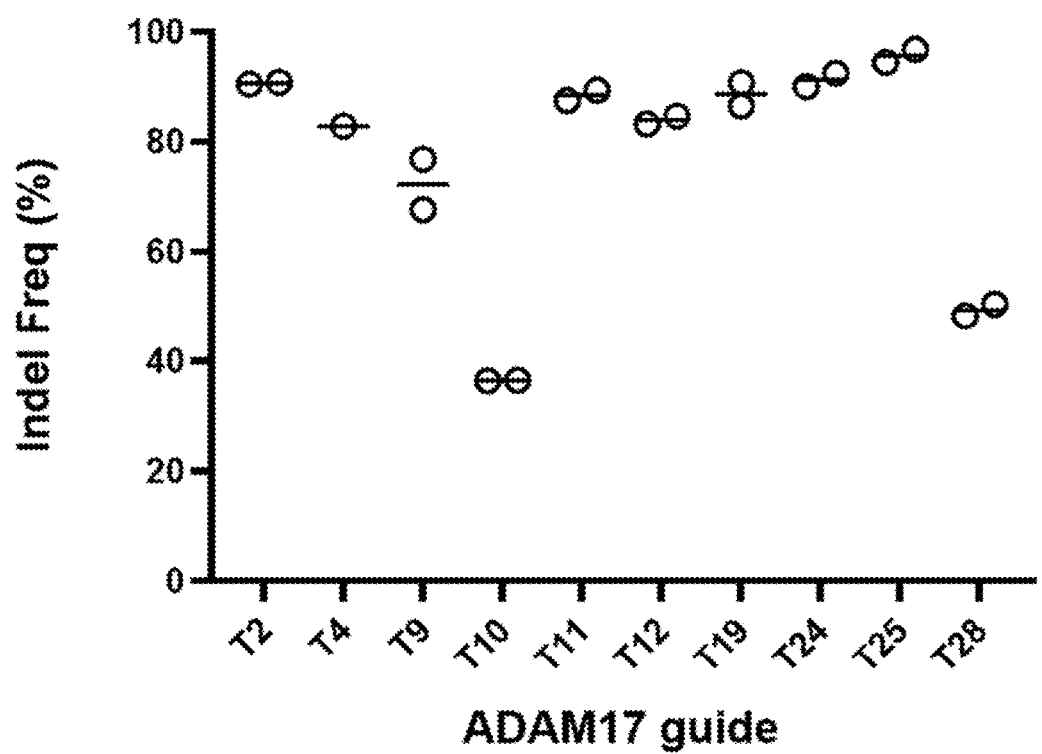
FIG. 1 provides a graph showing the cutting efficiency of 10 ADAM17 guides. Inducible pluripotent stem cells (iPSC) were electroporated with ADAM17 gRNA and sequenced to measured indel frequency.

The resulting amplicons were submitted for PCR cleanup and Sanger sequencing. Sanger sequencing results were input into Tsunami software along with the guide sequence. Indel percentages and identities were calculated by the software. Particular gRNAs were then selected based on their indel frequency in hPSCs. FIG. 1 shows the cutting efficiency of 10 ADAM17 guides. ADAM17 Ex1_T2 was chosen for further clone generation due to its high on-target activity.

ADAM17 KO hPSC Clone Generation and Characterization.

Using ADAM17 T2 gRNA, iPSCs were electroporated and single-cell sorted 3 days post electroporation using the WOLF FACS-sorter (Nanocellect) into BIOLAMININ 521 CTG coated 96-well plates with STEMFLEX™ and REVITACELL™ Supplement (100×). Plated single cells were grown in a normoxia incubator (37° C., 8% $CO_2$) with every other day media changes until colonies were large enough to be re-seeded as single cells. When confluent, samples were split for maintenance and genomic DNA extraction.

The ADAM17 KO state of clones was confirmed via PCR and Sanger sequencing, as described above. The resulting DNA sequences of the target ADAM17 region were aligned in Snapgene software to determine indel identity and homo- or heterozygosity. Karyotypic status of clones was evaluated through Cell Line Genetics service (Madison, WI) and normal karyotype was reported.

Example 5: Generation and Selection of CIITA gRNA

Guide RNA (gRNA) Selection for CIITA in hPSCs.

5 CIITA targeting gRNAs were designed for targeting exons 2 and 3 of the CIITA coding sequence. These gRNAs had predicted low off-target scores based on sequence homology prediction using gRNA design software. The target sequences of the gRNAs are presented in Table 15. In some embodiments, the gRNA comprises RNA sequence corresponding to the target DNA sequence.

TABLE 15

CIITA gRNA Target Sequences

| Name | Target Sequence (5'-3') | SEQ ID NO: | PAM |
|---|---|---|---|
| CIITA Ex3_T6 | GGTCCATCTGGTCATAGAAG | 13 | TGG |
| CIITA Ex3_T16 | GCTCCAGGTAGCCACCTTCT | 14 | AGG |
| CIITA Ex3_T20 | TAGGGGCCCCAACTCCATGG | 15 | TGG |
| CIITA Ex4_T1 | GGCTTATGCCAATATCGGTG | 16 | AGG |
| CIITA Ex4_T25 | AGGTGATGAAGAGACCAGGG | 17 | AGG |

To assess their cutting efficiency in hPSCs, human embryonic stem cells were electroporated using the Neon Electroporator (Neon Transfection Kit ThermoFisher Cat #MPK5000) with a ribonucleoprotein (RNP) mixture of Cas9 protein (Biomay) and guide RNA (Agilent) (See Table 15 for gRNA sequences) at a molar ratio of 5:1 (gRNA: Cas9) with absolute values of 125 pmol Cas9 and 625 pmol gRNA. To form the RNP complex, gRNA and Cas9 were combined in one vessel with R-buffer (Neon Transfection Kit) to a total volume of 25 μL and incubated for 15 min at RT. Cells were dissociated using ACCUTASE®, then resuspended in STEMFLEX™ media (Gibco, cat #11320033), counted using an NC-200 (ChemoMetec) and centrifuged. A total of 1×10⁶ cells were resuspended with the RNP complex and R-buffer was added to a total volume of 125 μL. This mixture was then electroporated with 3 pulses for 30 ms at 1100 V. Following electroporation, the cells were pipetted out into an Eppendorf tube filled with STEMFLEX™ media with RevitaCell™. This cell suspension was then plated into tissue culture dishes pre-coated with BIOLAMININ 521 CTG at 1:20 dilution. Cells were cultured in a normoxia incubator (37° C., 8% $CO_2$) for 48 hours. After 48 hours, genomic DNA was harvested from the cells using QuickExtract (Lucigen, Middleton, WI; Cat #QE09050).

PCR for the target CIITA sequence was performed and the resulting amplified DNA was assessed for cutting efficiency by TIDE analysis. PCR for relevant regions was performed using Platinum Taq Supermix (Invitrogen, cat #125320176 and Cat #11495017). The sequences of the PCR primers are presented in Table 16; and the cycling conditions provided in Table 17.

TABLE 16

CIITA TIDE/Indel Primers

| Name | Type | Sequence (5'-3') | SEQ ID NO: |
|---|---|---|---|
| CIITA F5 | forward | TCCTGACTCTCTGGTGTGAGAT | 18 |
| CIITA R5 | reverse | CAGAGAGCGTCCCACAGAC | 19 |

TABLE 17

CIITA PCR/Indel PCR Cycling Parameters

| Step | Temperature | Time | Cycles |
|---|---|---|---|
| Denaturation | 94° C. | 2 min | 1 |
| Denaturation | 94° C. | 15 sec | 34 |
| Annealing | 57° C. | 30 sec | |
| Extension | 68° C. | 45 sec | |
| Elongation | 68° C. | 5 min | 1 |
| Hold | 4° C. | hold | |

Figure 2:
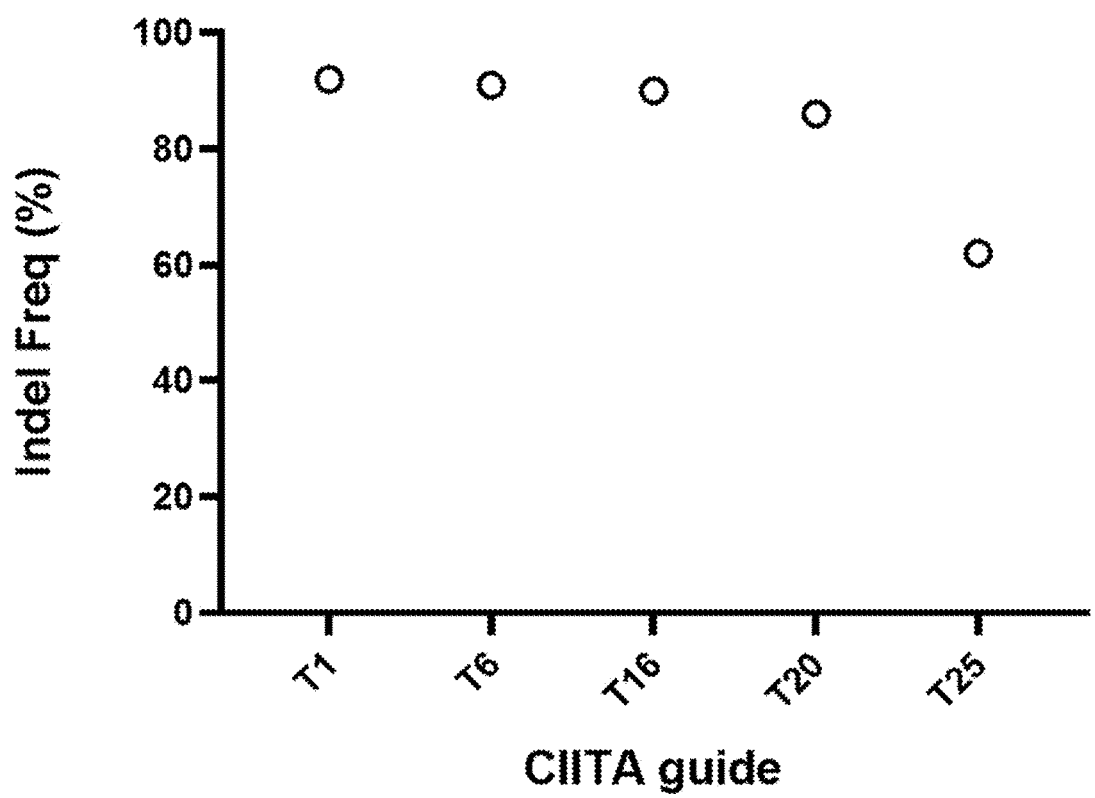
FIG. 2 provides a graph showing the cutting efficiency of 5 CIITA guides. Human embryonic stem cells were electroporated with CIITA gRNA and sequenced to measured indel frequency.

The resulting amplicons were submitted for PCR cleanup and Sanger sequencing. Sanger sequencing results were input into Tsunami software along with the guide sequence. Indel percentages and identities were calculated by the software. Particular gRNAs were then selected based on their indel frequency in hPSCs. FIG. 2 shows the cutting efficiency of 5 CIITA guides.

Off-targets of the selected gRNAs were assessed in the stem cell-derived DNA using hybrid capture analysis of the sequence similarity predicted sites. CIITA Ex3_T6 and CIITA Ex4_T1 guides did not show detectable off-target effects. CIITA T6 gRNA was chosen for further clone generation due to its high on-target activity and undetectable off-target activity.

Figure 3:
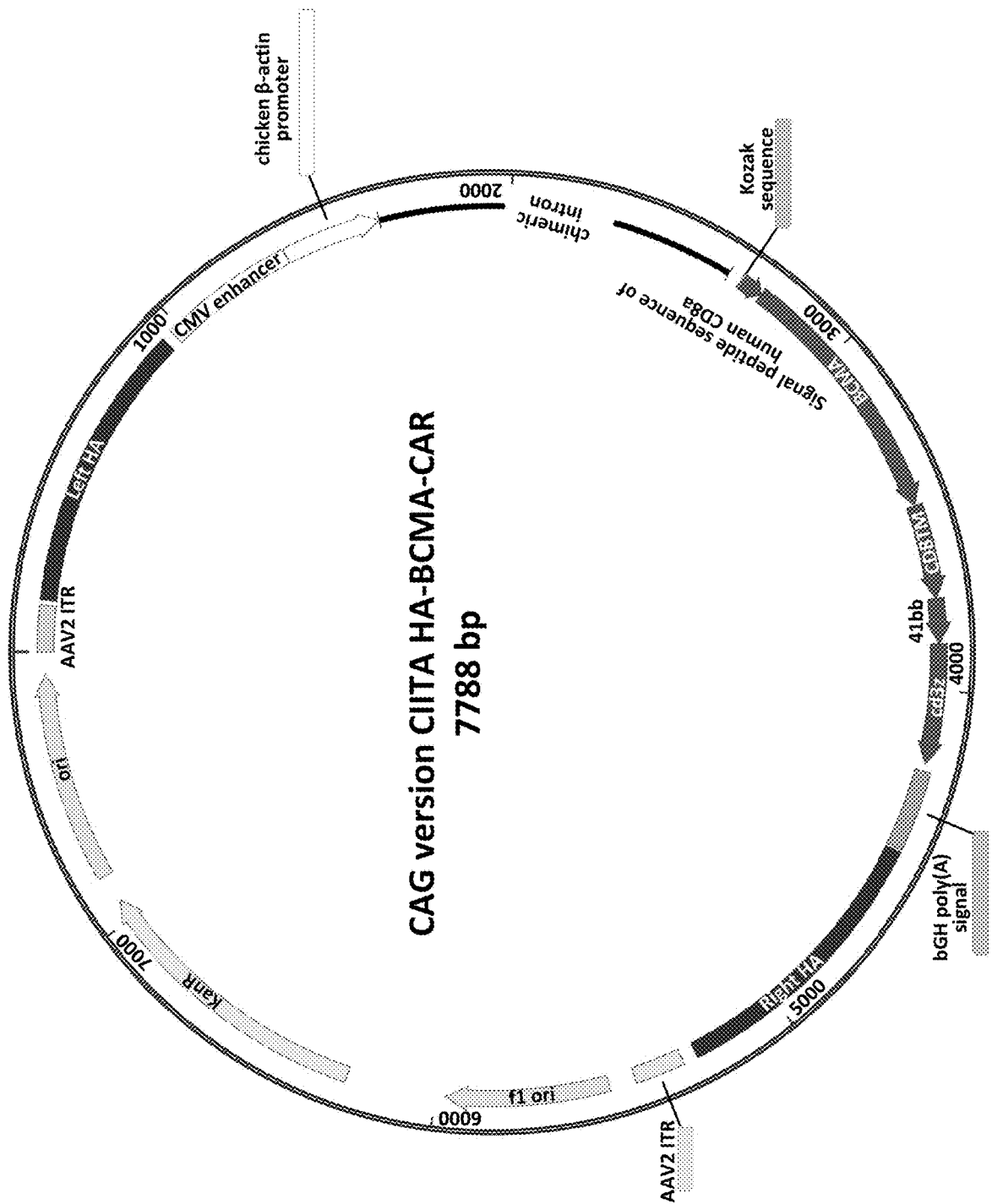
FIG. 3 provides the plasmid map of BCMA CAR knock-in, and CIITA knock-out.

Example 6: Generation of CAR Knock-In, CIITA Null Human Pluripotent Stem Cells (hPSCs) Design of CIITA KO, CAR KI Strategy Plasmid design to insert a CAR sequence, such as a BCMA CAR sequence, into the CIITA gene locus was made such that 86 base pairs (bp) of the CIITA exon 2 (GCCAC-CATGGAGTTGGGGCCCCTAGAAGGTGGCTACCTG-GAGCTTCTTAACA GCGATGCTGACCCCCTGTGCCTCTACCACTTCTA (SEQ ID NO: 20)) would be removed after undergoing homology directed repair (HDR). The removal of this portion of CIITA would result in a frame shift of the CIITA coding sequence (CDS) nullifying the expression of functional CIITA protein. Successful HDR would also result in the insertion of the CAR sequence into the genome. The donor plasmid contained a CAGGS promoter driven cDNA of a CAR sequence flanked by 800 base pair homology arms with identical sequence to the CIITA gene locus around exon 2. FIG. 3 presents a schematic of an example BCMA CAR encoding plasmid (SEQ ID NO: 66) and Table 18 identifies the elements and locations therein.

TABLE 18

Elements of BCMA CAR Donor Plasmid

| Element | Location (size in bp) | SEQ ID NO: |
|---|---|---|
| Left ITR | 1-130 (130) | 21 |
| LHA-CIITA | 145-944 (800) | 22 |
| CMV enhancer | 973-1352 (380) | 23 |
| chicken β-actin promoter | 1355-1630 (276) | 24 |
| chimeric intron | 1631-2639 (1009) | 25 |
| CD8a signal peptide | 2684-2746 (63) | 26 |
| BCMA targeting fragment | 2747-3481 (735) | 27 |
| CD8TM | 3482-3745 (264) | 28 |
| 41BB co-stim domain | 3746-3871 (126) | 29 |
| CD3Z domain | 3872-4207 (336) | 30 |
| bGH poly(A) signal | 4229-4453 (225) | 31 |
| RHA-CIITA | 4460-5259 (800) | 32 |
| Right ITR | 5301-5441 (141) | 33 |

The CIITA-T6 gRNA (Table 19) was used to facilitate insertion of the BCMA CAR transgene at the targeted CIITA gene locus. The target sequence of CIITA-T6 is not present in the donor plasmid and thus the donor plasmid itself would not be targeted by this gRNA. CIITA-T6 induced CRISPR cutting in the human genome at exon 2 of CIITA would lead to a frameshift and loss of CIITA protein. The BCMA CAR donor plasmid was introduced along with the ribonucleoprotein (RNP) complex made up of the CIITA targeting gRNA and Cas9 protein. Per 1 million of human embryonic stem cells, 4 μg of plasmid DNA was delivered along with the RNP via electroporation. Electroporation was carried out in hiPSC cells using the Neon Electroporator (Neon Transfection Kit ThermoFisher Cat #MPK5000) with the RNP mixture of Cas9 protein (Biomay) and guide RNA (Synthego) at a molar ratio of 5:1 (gRNA:Cas9) with absolute values of 125 pmol Cas9 and 625 pmol gRNA per 1 million cells. To form the RNP complex, gRNA and Cas9 were combined in one vessel with R-buffer (Neon Transfection Kit) to a total volume of 25-50 μL and incubated for 15 min at room temperature (RT). Cells were dissociated using ACCUTASE®, then resuspended in STEMFLEX™ media, counted using an NC-200 (ChemoMetec) and centrifuged. A total of 2×10⁶ cells were resuspended with the RNP complex and R-buffer was added to a total volume of 115 μL. This mixture was then electroporated with 1 pulse for 20 ms at 1500 V followed by 1 pulse for 100 ms at 500 V. Following electroporation, the cells were pipetted out into a well of a 6 well plate filled with STEMFLEX™ media with REVITACELL™ Supplement (100×) and laminin 511. The plates were pre-coated with BIOLAMININ 521 CTG at 1:10 dilution. Cells were cultured in a normoxia incubator (37° C., 8% CO₂).

Seven to ten days post electroporation, the cells were enriched for BCMA CAR expressing cells using an antibody against BCMA CAR (15C04-APC or 15C04-PE) via magnetic assisted cell sorting (MACS) using anti-mouse IgG Dynabeads (ThermoFisher, CELLection™ Pan Mouse IgG Kit, 11531D). These enriched cells represent a bulk KI population of BCMA-CAR positive cells.

TABLE 19 gRNA Target Sequences

| Name | Target Sequence (5'-3') | SEQ ID NO: | PAM |
|---|---|---|---|
| CIITA Ex3_T6 gRNA | GGTCCATCTGGTCATAGAAG | 13 | TGG |
| B2M-2 gRNA (Exon 1_T2) | GGCCGAGATGTCTCGCTCCG | 34 | TGG |
| ADAM17 Ex1_T2 gRNA | GGTCGCGGCGCCAGCACGAA | 1 | AGG |

Example 7. Generation of IL15/IR15α-P2A-HLA-E Trimer Knock-In, BCMA CAR Knock-In, CIITA Null, B2M Null Human Pluripotent Stem Cells (hPSCs)

Design of B2M KO, IL15/IR15α-P2A-HLA-E Trimer KI Strategy.

Figure 4:
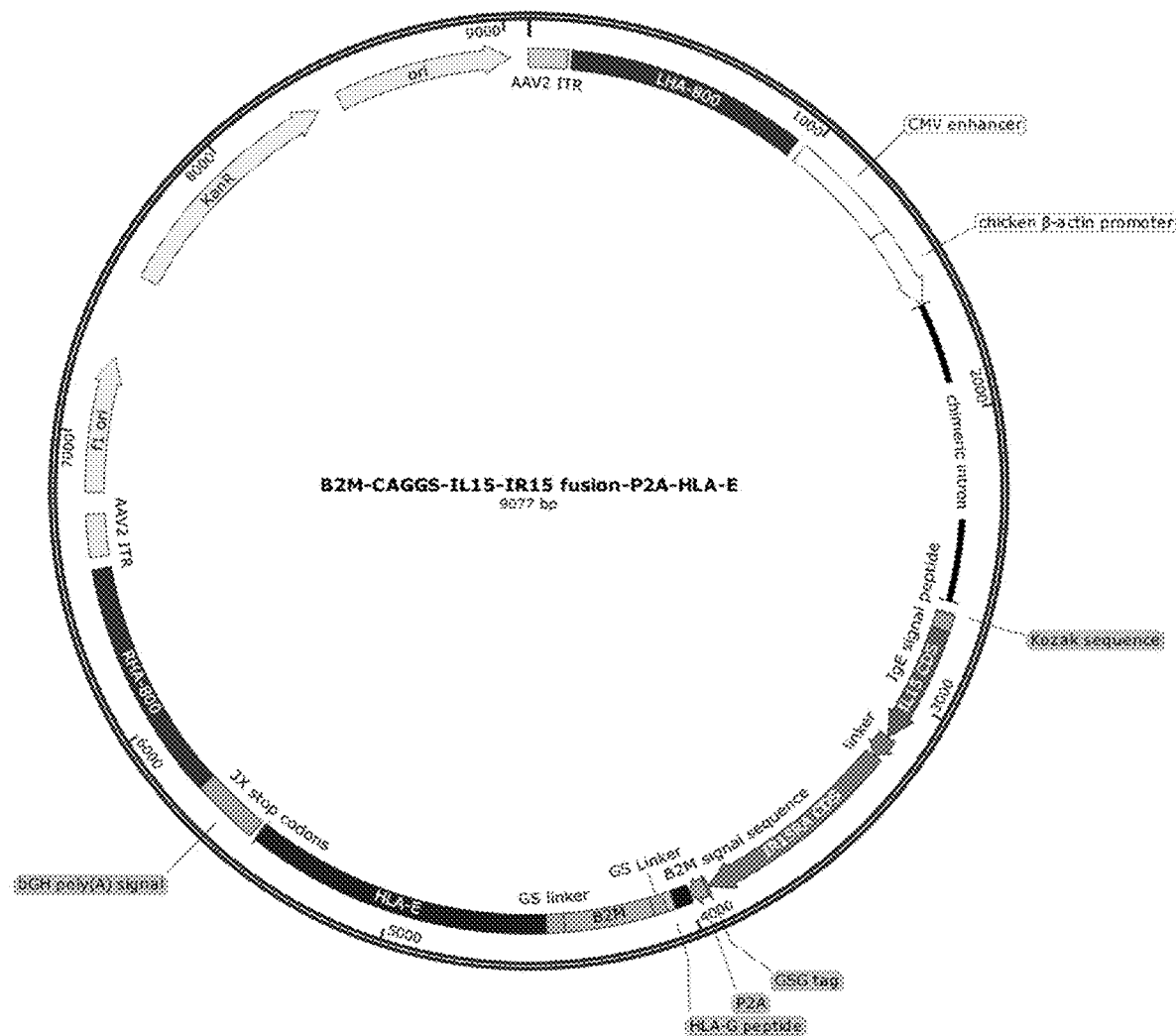
FIG. 4 provides the plasmid map of B2M-CAGGS-IL15-IR15 fusion-P2A-HLA-E. The IL15/IR15α-P2A-HLA-E trimer was inserted near exon 1 of the B2M gene locus to generate a B2M knock-out (KO)/IL15/IR15α-P2A-HLA-E knock-in (KI) plasmid.

Plasmid design to insert IL15/IR15α-P2A-HLA-E trimer into the B2M gene locus was made such that the starting codon of B2M was removed after undergoing homology directed repair (HDR) to insert IL15/IR15α-P2A-HLA-E trimer, nullifying any chance of partial B2M expression. FIG. 4 presents a schematic of the plasmid SEQ ID NO: 67 and Table 20 identifies the elements and locations therein. The donor plasmid contained a CAGGS promoter driven cDNA of IL15/IR15α-P2A-HLA-E trimer flanked by 800 base pair homology arms with identical sequence to the B2M gene locus around exon 1.

The IL15/IR15α fusion sequence was designed as previously published (Hurton et al. (2016) Proc Natl Acad Sci USA; 113(48):E7788-E7797. doi: 10.1073/pnas.1610544113.) The IL15/IR15α fusion coding sequence (including linkers) is SEQ ID NO: 76 (i.e., SEQ ID NOs: 40, 41, 42, 43, and 44).

The HLA-E trimer cDNA was composed of a B2M signal peptide fused to an HLA-G presentation peptide fused to the B2M membrane protein fused to the HLA-E protein without its signal peptide. The HLA-E trimer coding sequence (including linkers) is SEQ ID NO: 75 (i.e., SEQ ID NOs: 46, 47, 48, 49, 50, and 51). This trimer design has been previously published (Gornalusse et al. (2017) Nat. Biotechnol. 35(8): 765-772).

The P2A peptide sequence (derived from porcine teschovirus-1 2A) connecting IL15/IR15α fusion and the HLA-E trimer allows for the separate expression of both proteins from a single mRNA.

TABLE 20

Elements of IL15/IR15α-P2A-HLA-E Trimer Donor Plasmid

| Element | Location (size in bp) | SEQ ID NO: |
|---|---|---|
| Left ITR | 1-130 (130) | 21 |
| LHA-B2M | 145-944 (800) | 36 |
| CMV enhancer | 973-1352 (380) | 23 |
| chicken β-actin promoter | 1355-1630 (276) | 24 |
| chimeric intron | 1631-2639 (1009) | 25 |
| IgE signal peptide | 2684-2737 (54) | 40 |
| IL15 CDS | 2738-3136 (399) | 41 |
| linker | 3137-3214 (78) | 42 |
| IL15Rα CDS | 3215-3925 (711) | 43 |
| GSG tag | 3926-3934 (9) | 44 |
| P2A | 3935-3991 (57) | 45 |
| B2M signal sequence | 3992-4051 (60) | 46 |
| HLA-G peptide | 4052-4078 (27) | 47 |
| GS linker | 4079-4123 (45) | 48 |
| B2M | 4124-4420 (297) | 49 |
| GS linker | 4421-4480 (60) | 50 |
| HLA-E | 4481-5491 (1011) | 51 |
| 3X Stop codons | 5492-5500 (9) | 52 |
| bGH poly(A) signal | 5518-5742 (225) | 31 |
| RHA-B2M | 5749-6548 (800) | 54 |
| Right ITR | 6590-6730 (141) | 33 |

To insert the IL15/IR15α-P2A-HLA-E trimer sequence into hiPSCs, BCMA CAR-enriched hiPSCs were produced, as described in Example 6. This population was first electroporated with donor plasmid only (without CRISPR editing reagents) one day prior to a second electroporation. In the first electroporation, the Neon Electroporator was used to deliver 1 g of donor plasmid DNA per 1 million of hiPSCs. The cells were dissociated using ACCUTASE®, then resuspended in STEMFLEX™ media, counted using an NC-200 (ChemoMetec) and centrifuged. A total of 24×10⁶ cells were resuspended with R-buffer and donor plasmid DNA to a total volume of ~600 µL. This mixture was then electroporated with 1 pulse for 20 ms at 1500 V followed by 1 pulse for 100 ms at 500 V. A total of 6 electroporations were performed and the cells were pipetted out into a 6 well plate filled with STEMFLEX™ media with REVITACELL™ Supplement (100×) and laminin 511. Cells were cultured in a normoxia incubator (37° C., 8% $CO_2$).

The following day, these cells were dissociated from the plate and electroporated again using additional reagents. The B2M-2 gRNA (Table 19) was used to facilitate the insertion of the IL15/IR15α-P2A-HLA-E trimer transgene at the targeted B2M gene locus. The IL15/IR15α-P2A-HLA-E trimer donor plasmid was introduced along with the ribonucleoprotein (RNP) complex made up of the B2M targeting gRNA and Cas9 protein. Per 1 million of hiPSC cells, 2 µg of plasmid DNA was delivered along with the RNP via electroporation. Electroporation was carried out in hiPSC cells using the Neon Electroporator with the RNP mixture of Cas9 protein (Biomay) and guide RNA (Biospring) at a molar ratio of 5:1 (gRNA:Cas9) with absolute values of 62.5 pmol Cas9 and 312.5 pmol gRNA per 1 million cells. To form the RNP complex, gRNA and Cas9 were combined in one vessel with R-buffer (Neon Transfection Kit) to a total volume of 25-50 µL and incubated for 15 min at room temperature (RT). Cells were dissociated using ACCUTASE®, then resuspended in STEMFLEX™ media, counted using an NC-200 (ChemoMetec) and centrifuged. A total of 7×10⁶ cells were resuspended with the RNP complex and R-buffer was added to a total volume of ~300 µL. This mixture was then electroporated with 1 pulse for 20 ms at 1500 V followed by 1 pulse for 100 ms at 500 V. A total of 3 electroporations were performed. Following electroporation, the cells were pipetted out into 2 wells of a 6 well plate filled with STEMFLEX™ media with REVITACELL™ Supplement (100×) and laminin 511. Cells were cultured in a normoxia incubator (37° C., 8% $CO_2$).

Seven to ten days post electroporation, the cells were enriched for HLA-E trimer expressing cells using an antibody against HLA-E (see Table 21) via magnetic assisted cell sorting (MACS) using anti-mouse IgG Dynabeads (ThermoFisher, CELLection™ Pan Mouse IgG Kit, 11531D). These enriched cells represent a bulk KI population of IL15/IR15α-P2A-HLA-E trimer positive cells.

TABLE 21

Antibodies for Flow Cytometry

| Antigen | Clone | Fluorophore | Manufacturer | Catalog # |
|---|---|---|---|---|
| BCMA CAR | 15C04 | PE or APC | CRISPRtx | Custom |
| IL15 | 34559 | PE | ThermoFisher | MA5-23561 |
| B2M | 2M2 | PE | Biolegend | 316305 |
| HLA-ABC | W6/32 | Alexa 488 | Biolegend | 311415 |
| mIgG1 kappa | N/A | PE | BD Bioscience | 555749 |
| PD-L1 | B7-H1 | Alexa-488 | ThermoFisher | 53-5983-42 |
| HLA-E | 3D12 | PE | ThermoFisher | 12-9953-42 |
| HLA-E | 3D12 | APC | ThermoFisher | 17-9953-42 |

Example 8: Generation and Characterization of IL15/IR15α-P2A-HLA-E Trimer Knock-In, B2M Null Human Pluripotent Stem Cells (hPSCs)

The IL15/IR15α-P2A-HLA-E trimer sequence, as described in Example 7, was inserted into a hiPSC line. B2M-2 gRNA (Table 19) was used to facilitate the insertion of the IL15/IR15α-P2A-HLA-E trimer transgene at the targeted B2M gene locus. The IL15/IR15α-P2A-HLA-E trimer donor plasmid was introduced along with the ribonucleoprotein (RNP) complex made up of the B2M targeting gRNA and Cas9 protein. Per 1 million of hiPSC cells, 2 μg of plasmid DNA was delivered along with the RNP via electroporation. Electroporation was carried out in hiPSC cells using the Neon Electroporator with the RNP mixture of Cas9 protein (Biomay) and guide RNA (Biospring) at a molar ratio of 10:1 (gRNA:Cas9) with absolute values of 62.5 pmol Cas9 and 625 pmol gRNA per 1 million cells. To form the RNP complex, gRNA and Cas9 were combined in one vessel with R-buffer (Neon Transfection Kit) to a total volume of 25-50 μL and incubated for 15 min at room temperature (RT). Cells were dissociated using ACCUTASE®, then resuspended in STEMFLEX™ media, counted using an NC-200 (ChemoMetec) and centrifuged. A total of $2 \times 10^6$ cells were resuspended with the RNP complex and R-buffer was added to a total volume of ~115 μL. This mixture was then electroporated with 1 pulse for 20 ms at 1500 V followed by 1 pulse for 100 ms at 500 V. One electroporation was performed. Following electroporation, the cells were pipetted out into a well of a 6 well plate filled with STEMFLEX™ media with REVITACELL™ Supplement (100×) and laminin 511. The plates were pre-coated with BIOLAMININ 521 CTG at 1:10 dilution. Cells were cultured in a normoxia incubator (37° C., 8% CO₂).

Figure 5A:
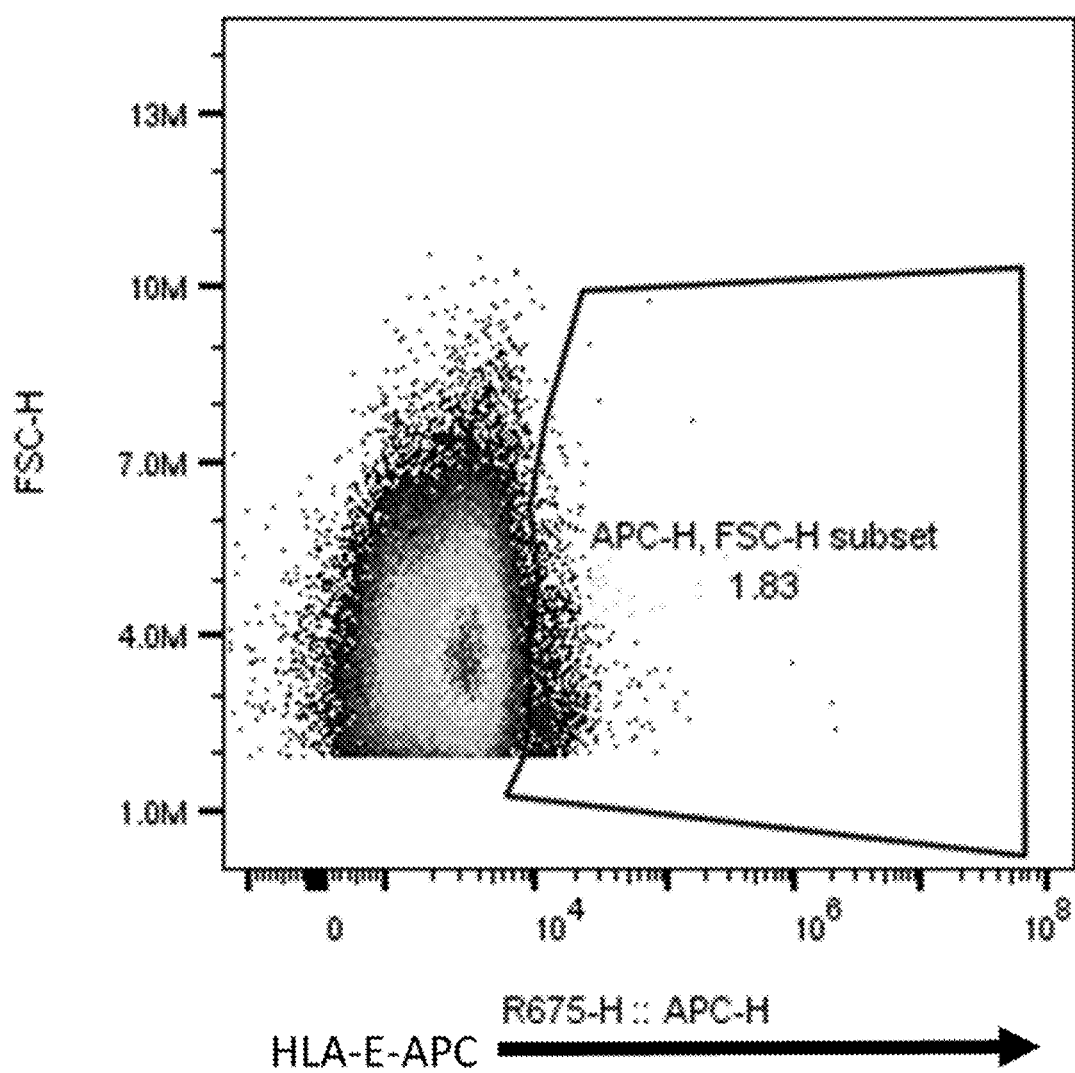
FIGS. 5A and 5B provide graphs of the flow cytometry analysis of HLA-E in IL15/IR15α-P2A-HLA-E trimer knock-in, B2M Null Human Pluripotent Stem Cells (hPSCs). Wild-type inducible pluripotent stem cells (iPSC) (FIG. 5A) and HLA-E edited iPSC (FIG. 5B) were analyzed using anti-HLA-E APC.
Figure 5B:
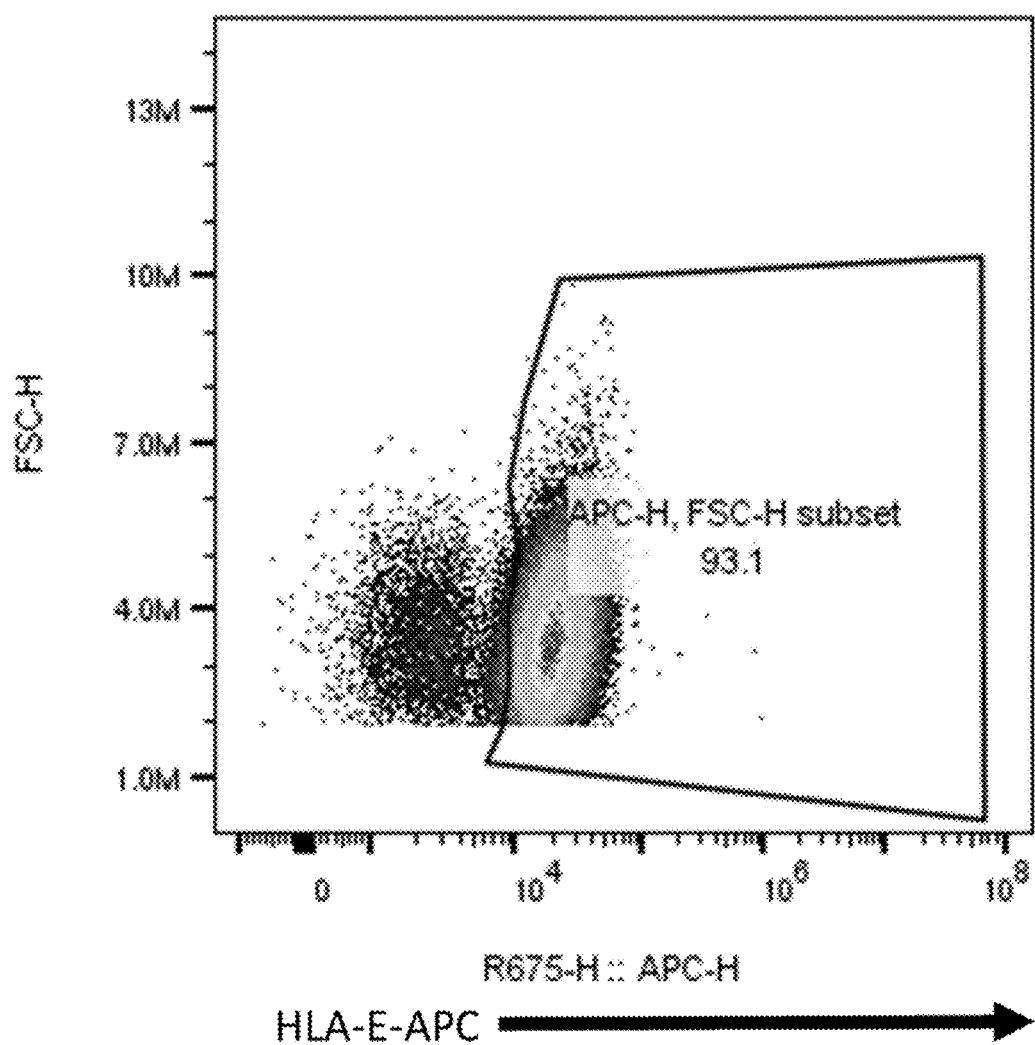

Seven to ten days post electroporation, the cells were enriched for HLA-E trimer expressing cells using an antibody against HLA-E (see Table 21) via magnetic assisted cell sorting (MACS) using anti-mouse IgG Dynabeads (ThermoFisher, CELLection™ Pan Mouse IgG Kit, 11531D). These enriched cells represent a bulk KI population of IL15/IR15α-P2A-HLA-E trimer positive cells. This population was assessed for HLA-E expression by flow cytometry, showing >90% HLA-E expression (FIG. 5B). WT iPSC cells were a negative control (FIG. 5A).

Figure 6:
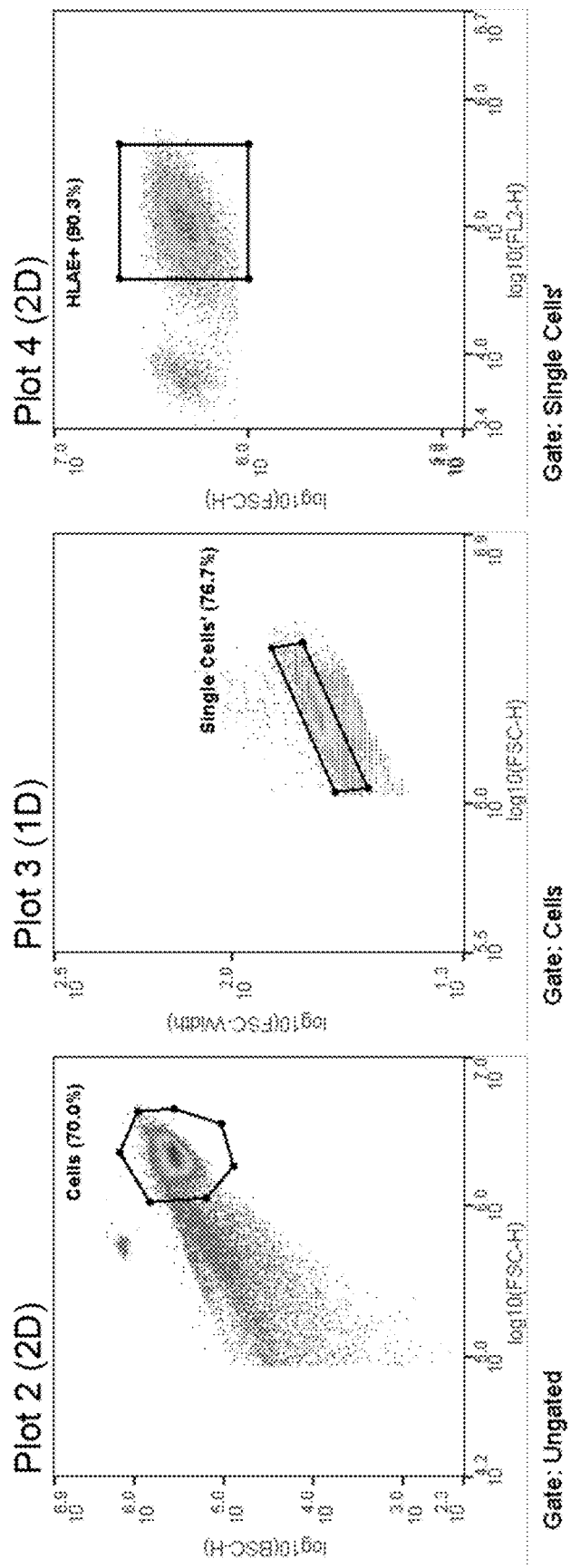
FIG. 6 demonstrates gating strategy for single-cell sorting of IL15/IR15α-P2A-HLA-E trimer knock-in, B2M Null hPSCs using an anti-HLA-E-PE antibody. FACS was used to sort single cells into 96-well plates.

Following MACS-enrichment, the cells were single-cell sorted as described in Example 1. The anti-HLA-E-PE antibody (see Table 21) was used for FACS-sorting into 96-well plates (FIG. 6). For FACS-sorting, unedited cells served as a negative control. After sorting, the cells were expanded as described in Example 1 and when confluent, samples were split for maintenance and genomic DNA extraction.

Figure 7A:
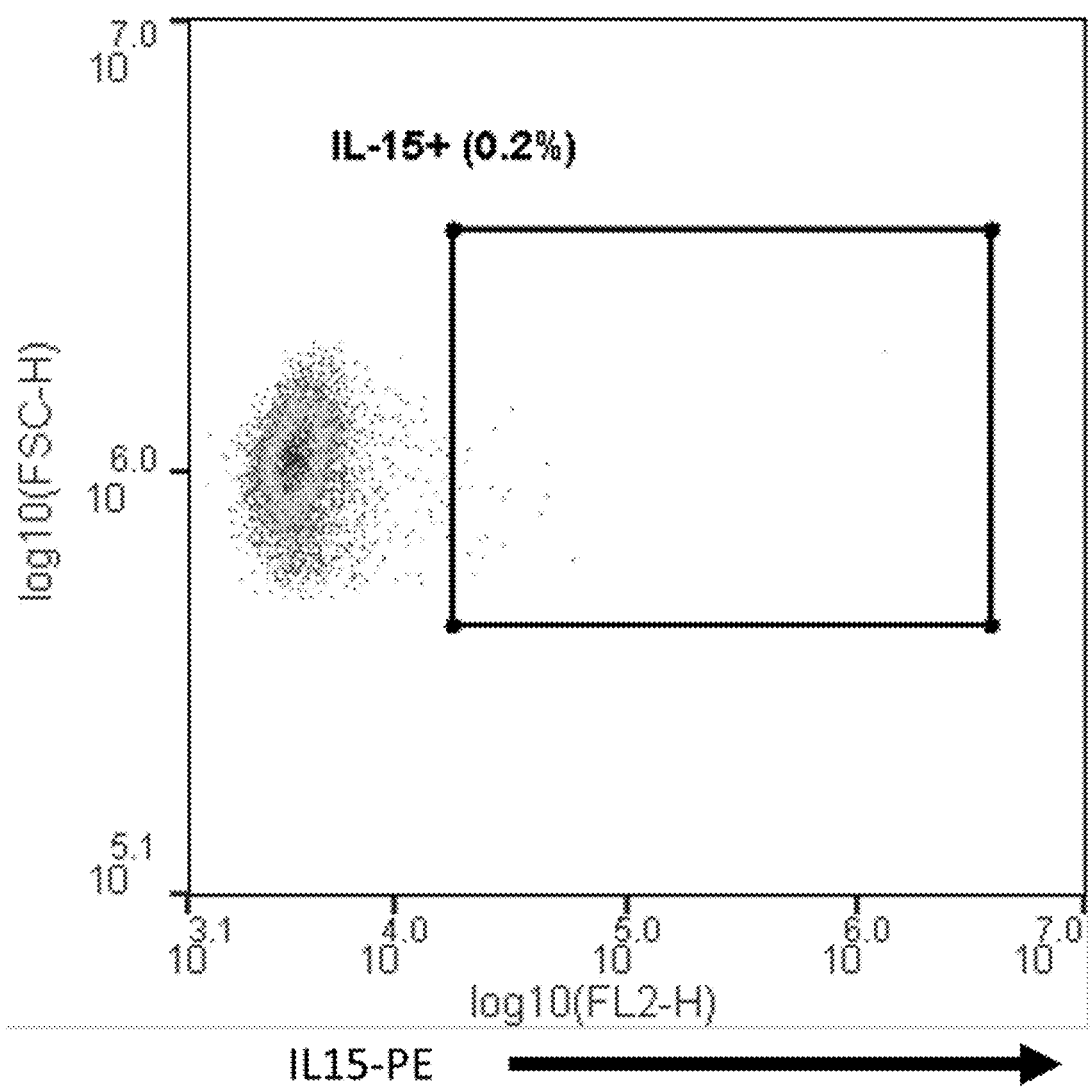
FIGS. 7A and 7B provide graphs of the flow cytometry analysis of IL-15 in single-cell "Clone 3" (IL15/IR15α-P2A-HLA-E trimer knock-in, B2M Null hPSCs). Wild-type inducible pluripotent stem cells (iPSC) (FIG. 7A) and Clone 3 IL-15 edited iPSC (FIG. 7B) were analyzed using anti-IL-15 PE.
Figure 7B:
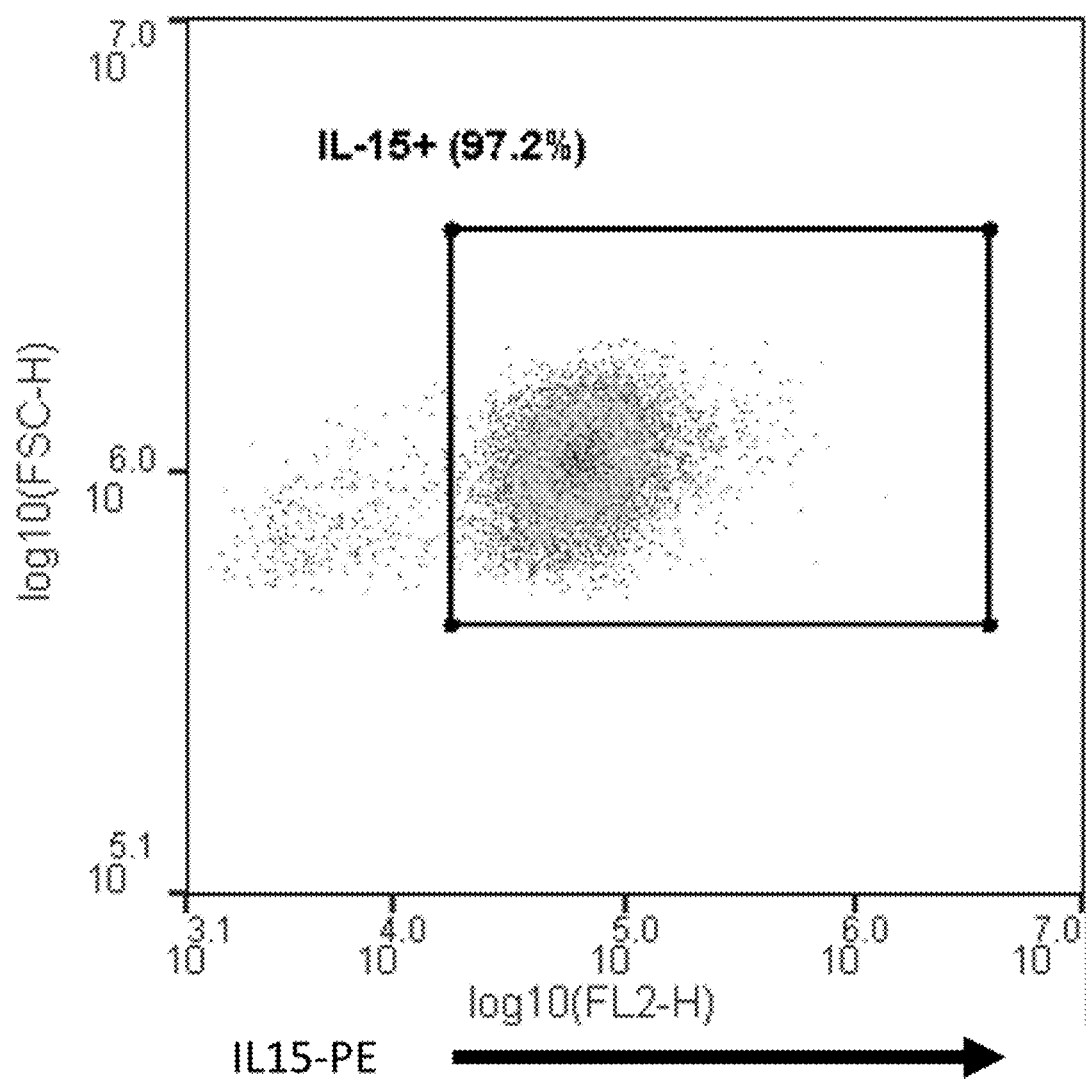

The single cell derived clones demonstrated IL15-PE expression post expansion confirming fidelity of the edit. The IL-15-PE expression in a clone named "Clone 3" (FIG. 7B) and WT iPSC control (FIG. 7A) was determined.

Figure 8:
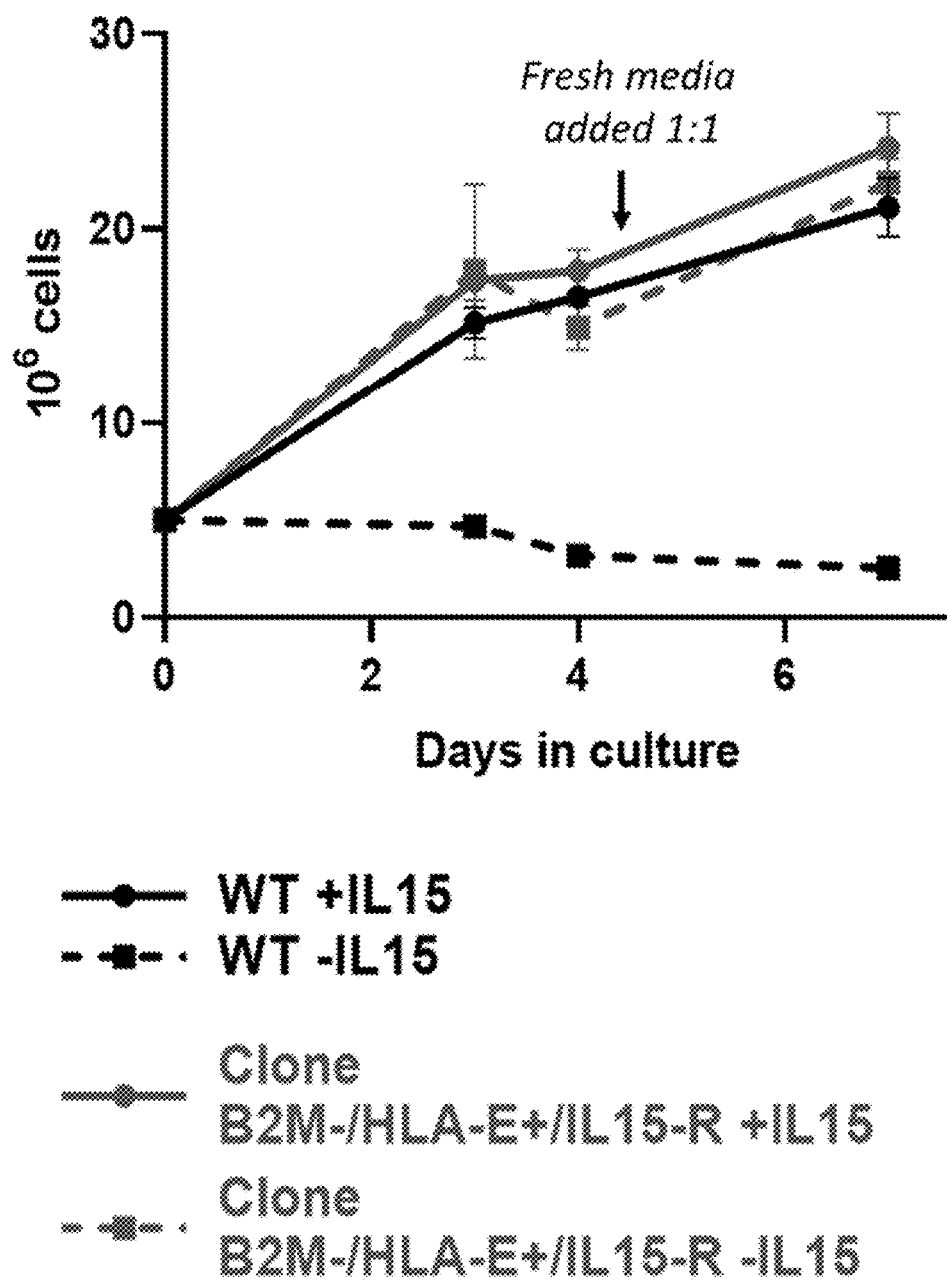
FIG. 8 provides a line graph demonstrating cell growth in wild-type (WT) and Clone 3 (IL15/IR15α-P2A-HLA-E trimer knock-in, B2M Null hPSC) derived iNK cells when administered exogenous IL15 or not administered exogenous IL 15. Cells were administered 20 ng/mL of IL-15 in addition to SCF (20 ng/mL), Flt3L (15 ng/mL), IL-7 (20 ng/mL) on day 0 and day 4.

Clone 3, an hiPSC gene edited clone containing the edits IL15/IR15α-P2A-HLA-E trimer knock-in, B2M Null, was differentiated to iNK cells using Protocol 2, as described in Example 3, using PBS spinner vessels. Day 20 iNK cells differentiated from WT or Clone 3 (IL15/IR15α-P2A-HLA-E trimer knock-in, B2M Null hPSC) were plated at $5 \times 10^6$ cells/well and grown with or without exogenous IL15 (20 ng/mL). In addition, all cells were administered SCF (20 ng/mL), Flt3L (15 ng/mL), IL-7 (20 ng/mL) on day 0 and day 4. Clone 3 (IL15/IR15α-P2A-HLA-E trimer knock-in, B2M Null hPSC) derived iNK expanded similarly in the presence or absence of exogenous IL15 in the culture media. FIG. 8 shows that the clone 3 cells persisted and expanded in the absence of exogenous IL15 while the WT iNK cell number declined in the absence of exogenous IL15.

The cytotoxicity of the day 36 Clone 3 derived iNK cells towards K562 cells was determined using a 24-hour killing assay. K562-GFP cells (50,000 cells per vial) were incubated with iNK effector cell lines at different ratios as indicated for 24 hours. After incubation, the cells were spun, and resuspended in 175 μl media containing SyTox Blue at a 1:1000 concentration. 25 μL of countbright beads per well were added. The plate was read using the Flow cytometer 100 μL volume per well was collected for analysis. GFP-positive, SyTox Blue-negative target cells (live cancer cells) and countbright beads were selected and measured absolute events count. Total live cells were calculated as follows:

[Total Cells=((No of live cells)/(Bead count for that sample))/(Bead count per 50 μL/2).

Figure 9:
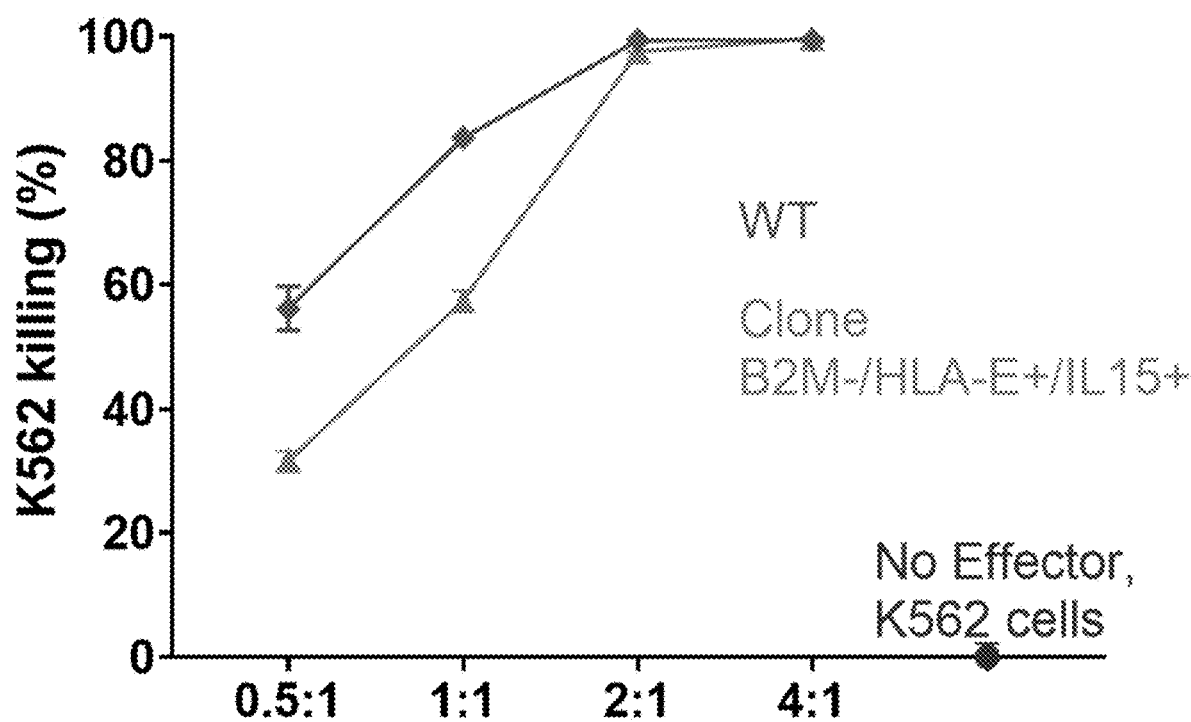
FIG. 9 provides a graph demonstrating K562 cell killing by WT and Clone 3 (IL15/IR15α-P2A-HLA-E trimer knock-in, B2M Null hPSC) derived iNK cells. Effector and K562 cells were plated at different effector:target (E:T) ratios for 24-hours. A no effector, K562 only cell, negative control was used.

The % of cell lysis was calculated using following formula:

% Cell lysis=(1−((Total Number of target Cells in Test Sample)/(Total Number of Target Cells in Control Sample))×100. The WT and edited lines displayed effective cytotoxicity against K562 (FIG. 9).

Example 9: Generation of IL15/IR15α-P2A-HLA-E Trimer Knock-In, BCMA CAR Knock-In, CIITA Null, B2M Null, ADAM17 Null Human Pluripotent Stem Cells (hPSCs)

Design of ADAM17 KO.

The ADAM17-T2 gRNA (Table 19) was used to knock-out the ADAM17 protein by causing a frameshift mutation in the ADAM17 gene exon 1. BCMA CAR and IL15/IR15α-P2A-HLA-E trimer enriched hiPSCs were generated as described in Examples 6 and 7. Electroporation was carried out in these enriched hiPSC cells using the Neon Electroporator with the RNP mixture of Cas9 protein (Biomay) and guide RNA (IDT) at a molar ratio of 5:1 (gRNA:Cas9) with absolute values of 125 pmol Cas9 and 625 pmol gRNA per 1 million cells. To form the RNP complex, gRNA and Cas9 were combined in one vessel with R-buffer (Neon Transfection Kit) to a total volume of 25-50 μL and incubated for 15 min at room temperature (RT). This mixture was then combined with the cells to a total volume of ~115 μL using R-buffer. This mixture was then electroporated with 1 pulse for 20 ms at 1500 V followed by 1 pulse for 100 ms at 500 V. Following electroporation, the cells were pipetted out into a 6 well plate filled with STEMFLEX™ media with REVITACELL™ Supplement (100×) and laminin 511. Cells were cultured in a normoxia incubator (37° C., 8% $CO_2$).

Three to five days post electroporation, the cells were single-cell sorted as described in Example 1. The anti-BCMA CAR antibody (see Table 21) was used for FACS-sorting into 96-well plates. For FACS-sorting, unedited cells served as a negative control. After sorting, the cells were expanded as described in Example 1 and when confluent, samples were split for maintenance and genomic DNA extraction.

PCR for the genotyping of the edited clones (IL15/IR15α-P2A-HLA-E trimer knock-in, BCMA CAR knock-in, CIITA Null, B2M Null, ADAM17 Null Human Pluripotent Stem Cells (hPSCs)) was performed and the resulting amplified DNA was assessed for cutting efficiency by TIDE analysis.

For determining indels in the target B2M sequence, PCR for relevant regions was performed using Platinum Taq Supermix (Invitrogen, cat #125320176 and Cat #11495017). The sequences of the PCR primers are presented in Table 22; and the cycling conditions provided in Table 23.

TABLE 22

B2M Indel Primers

| Name | Type | Sequence (5'-3') | SEQ ID NO: |
|---|---|---|---|
| B2MF2 | Forward | CAGACAGCAAACTCACCCAG | 56 |
| B2MR2 | Reverse | AAACTTTGTCCCGACCCTCC | 57 |

TABLE 23

B2M Indel PCR Cycling Parameters

| Step | Temperature | Time | Cycles |
|---|---|---|---|
| Denaturation | 94° C. | 2 min | 1 |
| Denaturation | 94° C. | 15 sec | 30 |
| Annealing | 56° C. | 30 sec | |
| Extension | 68° C. | 45 sec | |
| Elongation | 68° C. | 5 min | 1 |
| Hold | 4° C. | hold | |

Figure 10:
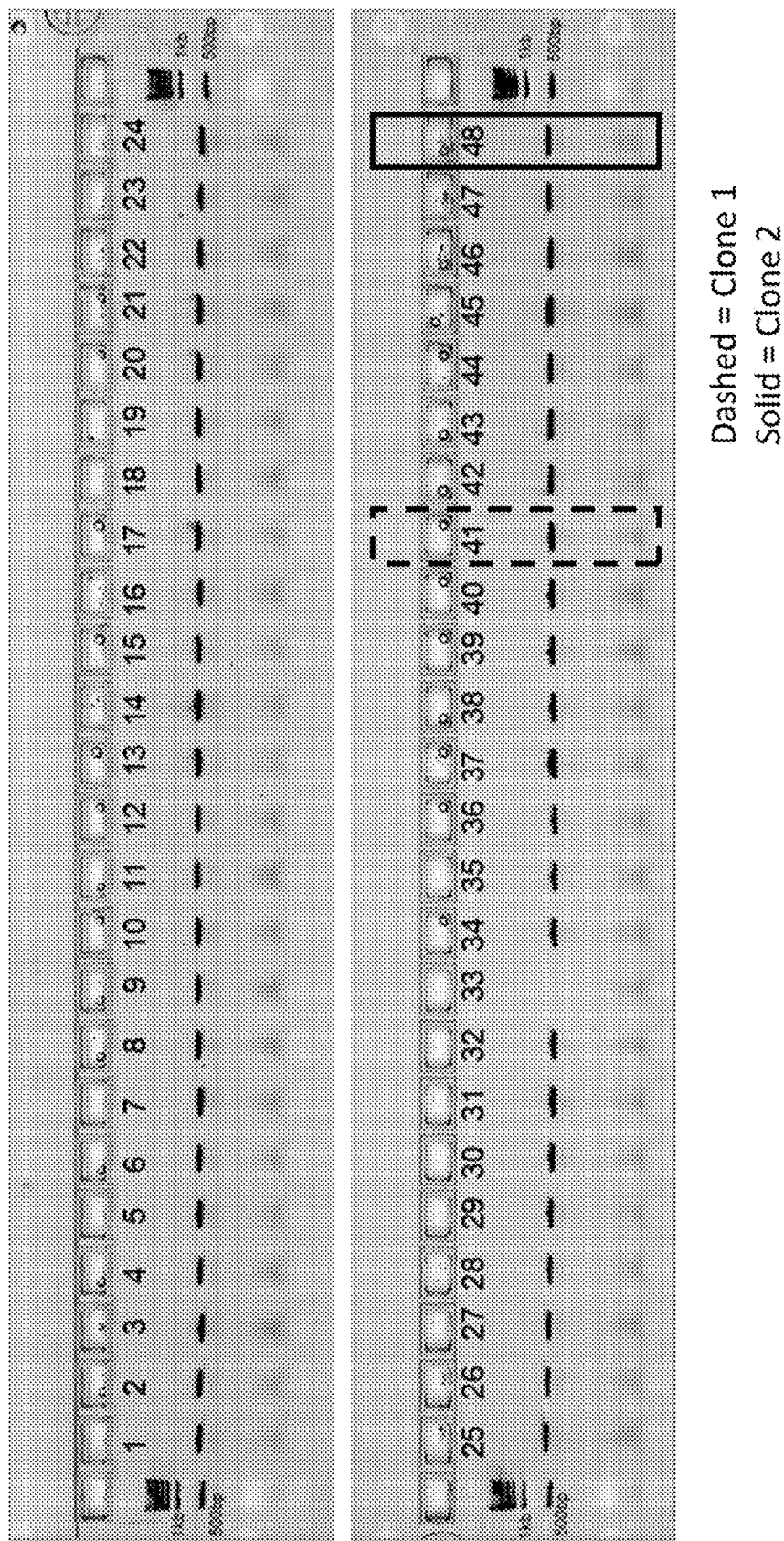

N07301 FIG. 10 shows the B2M indel results for various edited clones. The presence of a 573 bp band indicated a WT genotype which would be found in clones that are unedited or are heterozygous for the KI construct, as homozygous clones will not have a band. For determining B2M zygosity, PCR for relevant regions was performed using Platinum Taq Supermix (Invitrogen, cat #125320176 and Cat #11495017). The sequence of the PCR primers are presented in Table 24; and the cycling conditions provided in Table 25.

TABLE 24

B2M Zygosity Primers

| Name | Type | Sequence (5'-3') | SEQ ID NO: |
|---|---|---|---|
| B2M-geno-F1 | forward | AAAAGATCTGTGGACTCCACCACCACGAAATGGCGGCACCTTATTTATGGTC | 58 |
| B2M-geno-R1 | reverse | GCTCTGGAGAATCTCACGCAGAAGGCAGGCGTTTTTCTTAAAAAAAAATGCACGAATTA | 59 |

TABLE 25

B2M Zygosity PCR Cycling Parameters

| Step | Temperature | Time | Cycles |
|---|---|---|---|
| Denaturation | 94° C. | 2 min | 1 |
| Denaturation | 98° C. | 10 sec | 30 |
| Annealing | 65° C. | 30 sec | |
| Extension | 68° C. | 6 min 30 sec | |
| Elongation | 68° C. | 5 min | 1 |
| Hold | 4° C. | hold | |

Figure 11:
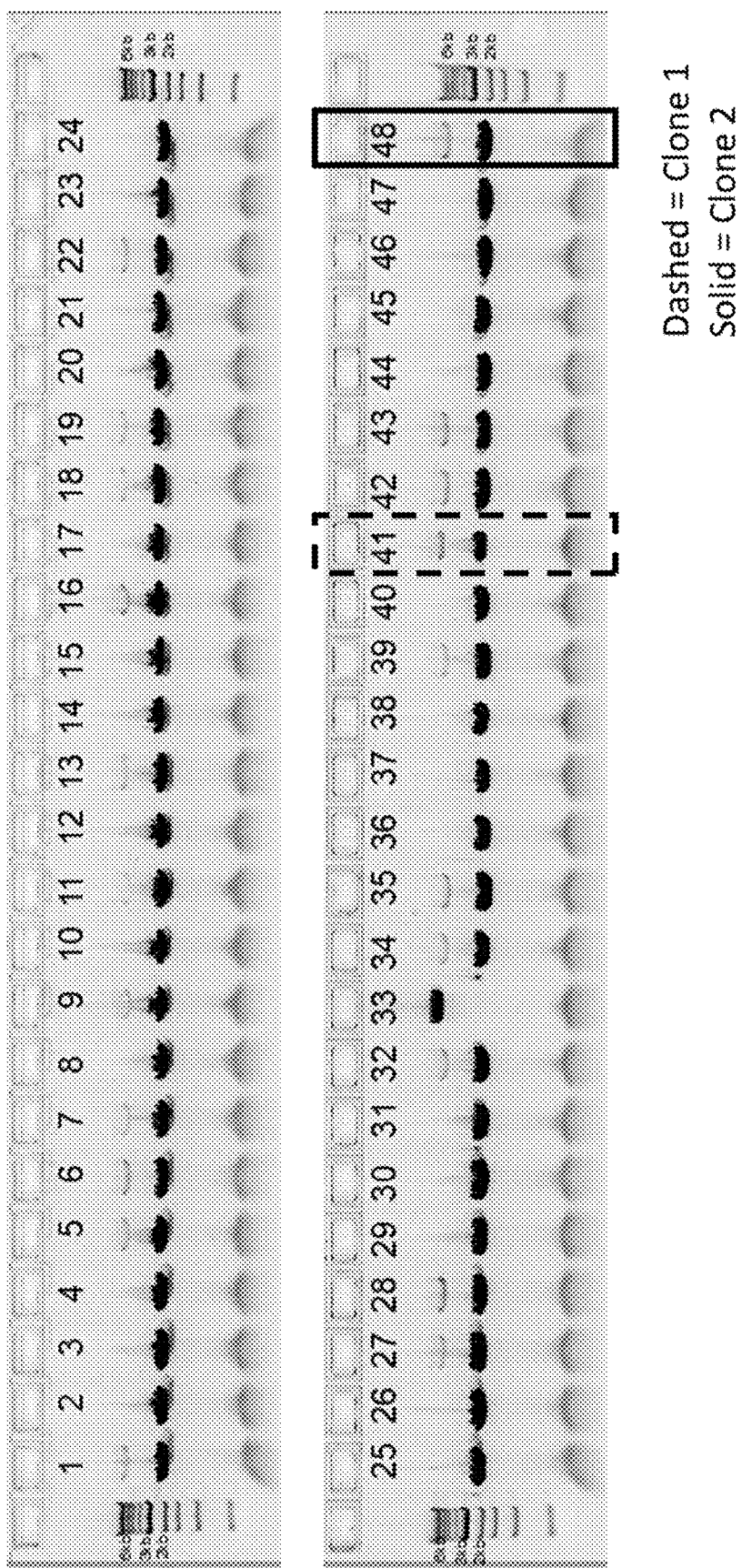
FIG. 11 provides an image of an agarose gel demonstrating B2M zygosity results. A 2.5 kb band indicates a WT unedited clone. Clones with a 6.6 kb band indicate successful integration of the IL15/IR15α-P2A-HLA-E trimer.

FIG. 11 shows the B2M zygosity results for various edited clones. The presence of a ~2.5 kb band indicated a WT genotype while the presence of a 6.6 kb band indicated successful integration of the KI construct into the B2M gene locus. Unedited clones would only have the WT band, clone heterozygous for the KI would have both bands, and homozygous clones would only have the KI band. The resulting amplicons were submitted for PCR cleanup and Sanger sequencing. Sanger sequencing results were input into Tsunami software along with the guide sequence. The resulting DNA sequences of the target B2M region were aligned in Snapgene software to determine indel identity and homo- or heterozygosity. For determining IL15/IR15α-P2A-HLA-E trimer knock-in genotyping in the target B2M sequence, PCR for relevant regions was performed using Platinum Taq Supermix (Invitrogen, cat #125320176 and Cat #11495017). The sequence of the PCR primers are presented in Table 26; and the cycling conditions provided in Table 27.

TABLE 26

B2M KI Primers

| Name | Type | Sequence (5'-3') | SEQ ID NO: |
|---|---|---|---|
| Poly-A-F | forward | AGGATTGGGAAGACAATAGCAGGCATGCTGGGGATGCGGTGG | 60 |
| B2M-geno-R1 | reverse | GCTCTGGAGAATCTCACGCAGAAGGCAGGCGTTTTTCTTAAAAAAAAATGCACGAATTA | 61 |

TABLE 27

B2M KI PCR Cycling Parameters

| Step | Temperature | Time | Cycles |
|---|---|---|---|
| Denaturation | 98° C. | 30 sec | 1 |
| Denaturation | 98° C. | 10 sec | 30 |
| Annealing | 65° C. | 30 sec | |
| Extension | 72° C. | 1 min 30 sec | |
| Elongation | 72° C. | 5 min | 1 |
| Hold | 4° C. | hold | |

Figure 12:
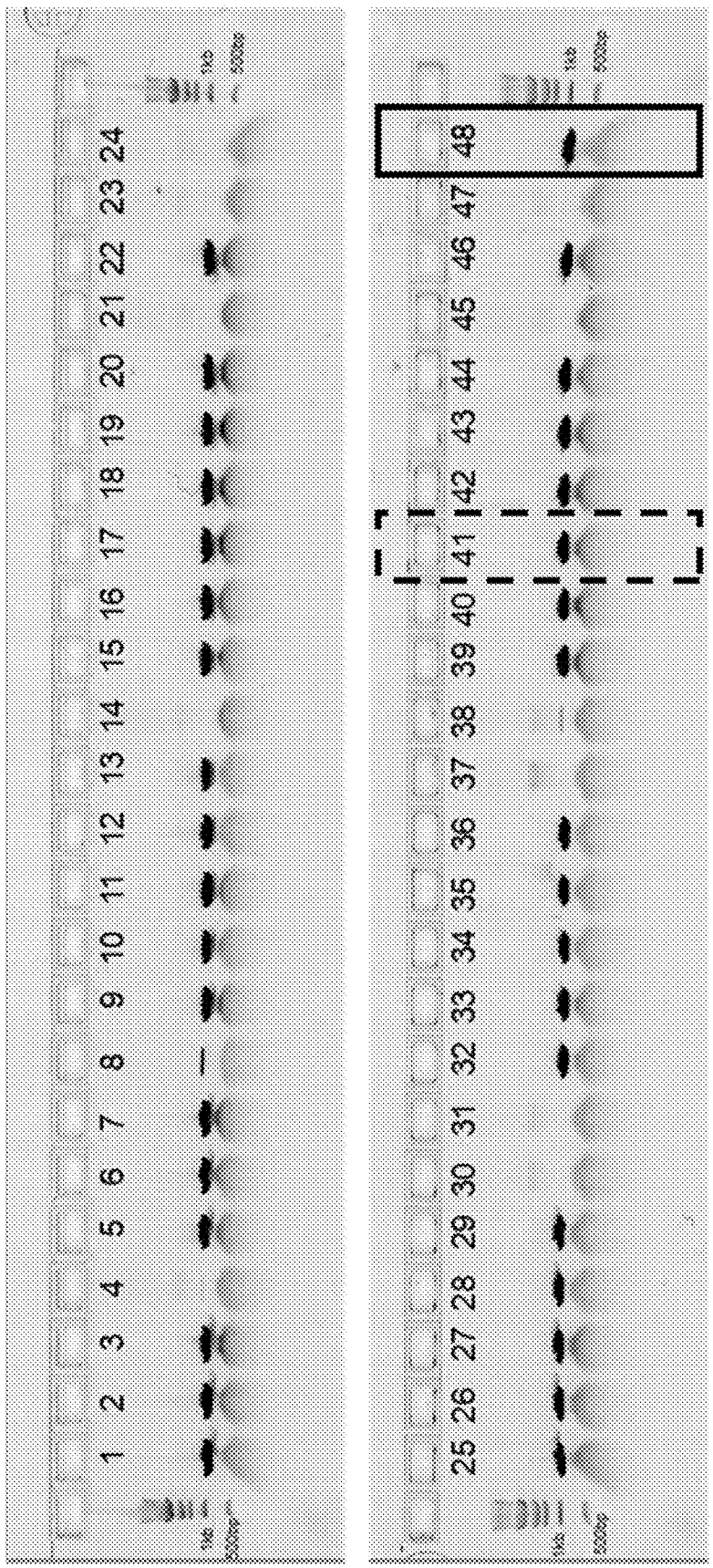
FIG. 12 provides an image of an agarose gel demonstrating B2M knock-in genotyping results. No band indicates a WT unedited clone. A 1.1 kb band indicates successful integration of the IL15/IR15α-P2A-HLA-E trimer.
Figure 13:
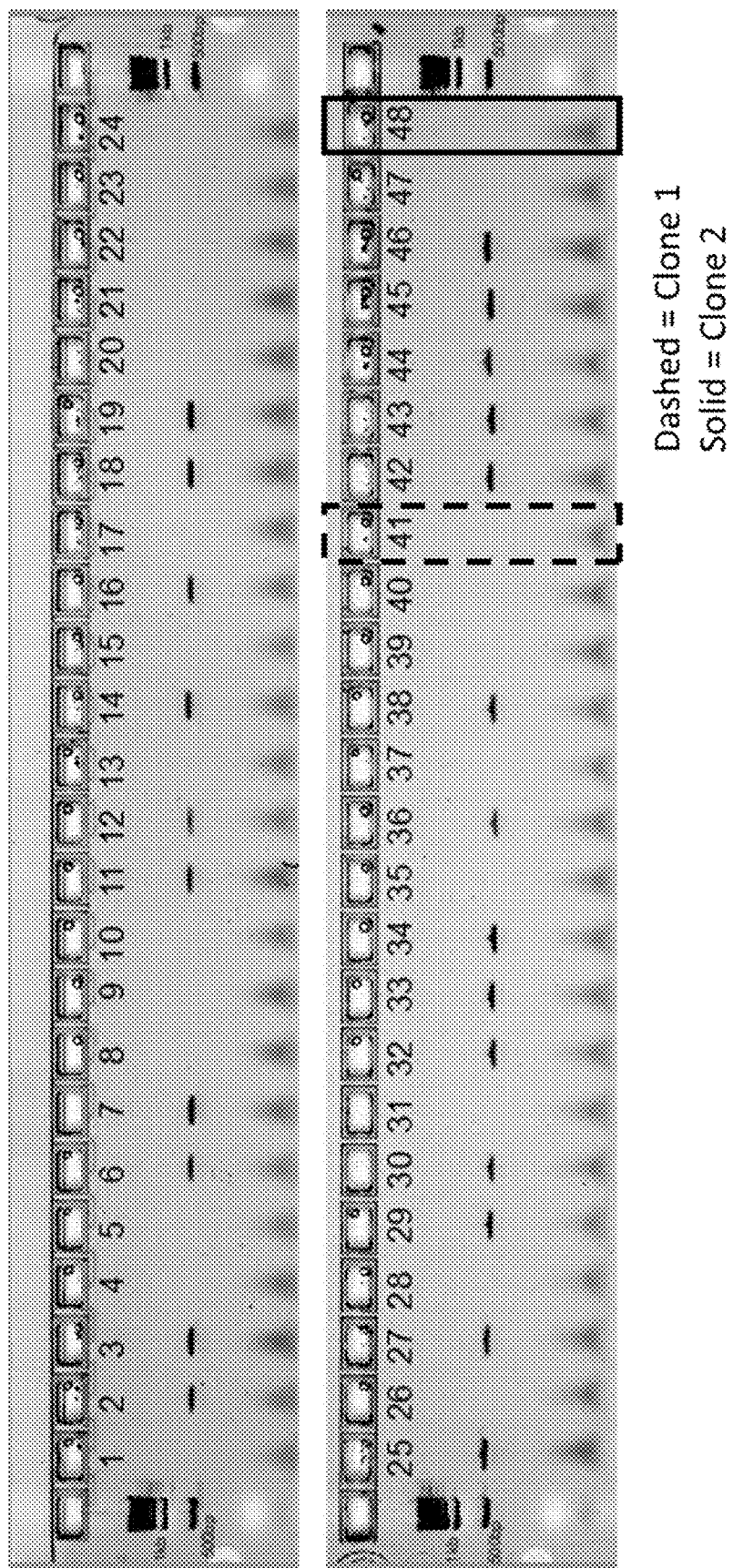
FIG. 13 provides an image of an agarose gel demonstrating CIITA genotyping results. A 557 bp indicates a WT unedited clone. Edited constructs do not have a band.

FIG. 12 shows the B2M KI genotyping results for various edited clones. The presence of a 1.1 kb band indicated successful integration of the KI construct into the B2M gene locus, while the absence of a band indicated a WT genotype. For determining indels in the target CIITA sequence, PCR for relevant regions was performed using Platinum Taq Supermix (Invitrogen, cat #125320176 and Cat #11495017). The sequence of the PCR primers are presented in Table 16; and the cycling conditions provided in Table 17. FIG. 13 shows the CIITA indel results for various edited clones. The presence of a 557 bp band indicated a WT genotype which would be found in clones that are unedited or are heterozygous for the KI construct, as homozygous clones will not have a band.

For determining CIITA zygosity, PCR for relevant regions was performed using Platinum Taq Supermix (Invitrogen, cat #125320176 and Cat #11495017). The sequences of the PCR primers are presented in Table 28; and the cycling conditions provided in Table 29.

TABLE 28

CIITA Zygosity Primers

| Name | Type | Sequence (5'-3') | SEQ ID NO: |
|---|---|---|---|
| CIITA-OUT-F | forward | GCCCCACCCCTCCTACTTTATGTCTCCAT GGATTTGCCTGTTTTGGTCATTTCA | 62 |
| CIITA-OUT-R | reverse | CTCTAATGCAAACTTGGGTAGGTCGTTTC ACCTCTCTAAACCTCAATTTCCTCATTTG | 63 |

TABLE 29

CIITA Zygosity PCR Cycling Parameters

| Step | Temperature | Time | Cycles |
|---|---|---|---|
| Denaturation | 94° C. | 2 min | 1 |
| Denaturation | 98° C. | 10 sec | 30 |
| Annealing | 65° C. | 30 sec | |
| Extension | 68° C. | 5 min 30 sec | |
| Elongation | 68° C. | 5 min | 1 |
| Hold | 4° C. | hold | |

Figure 14:
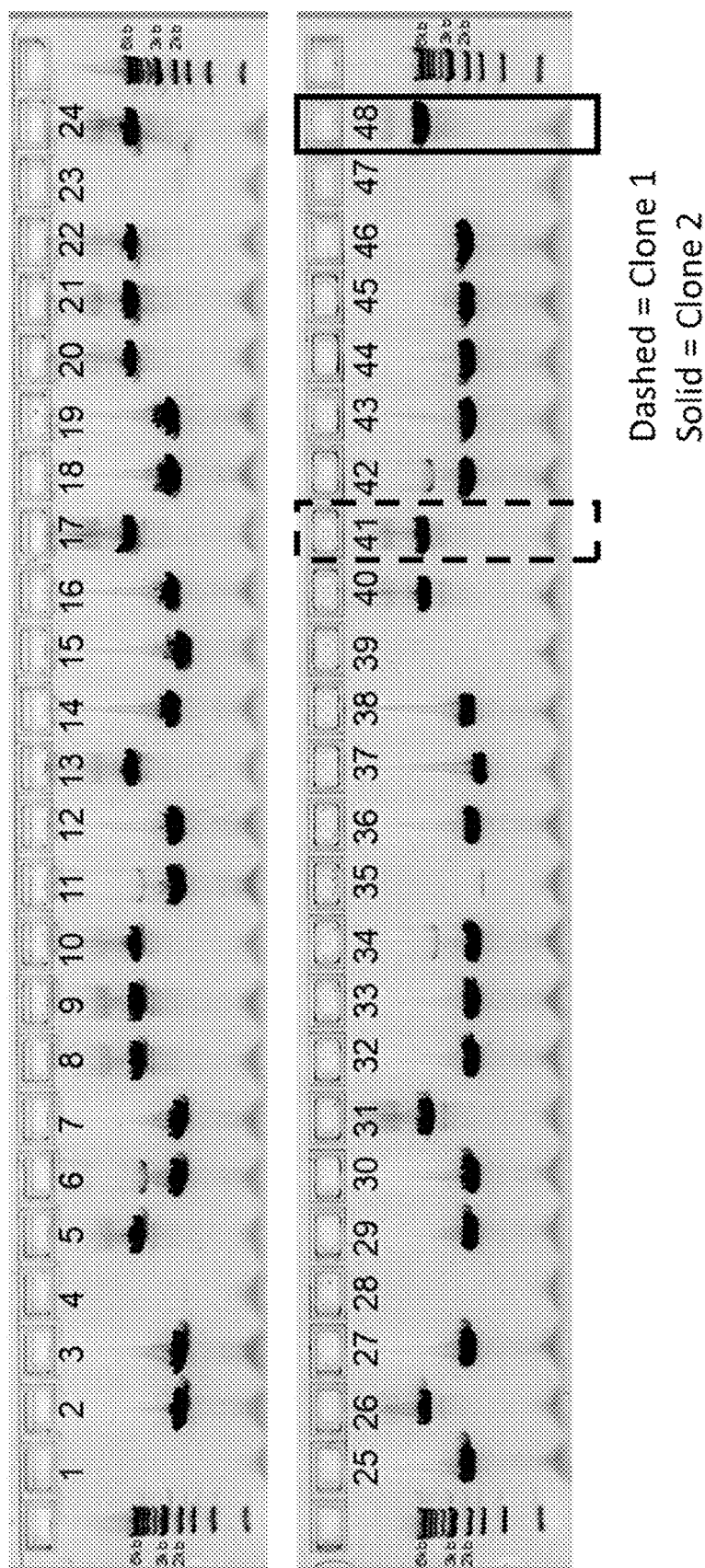
FIG. 14 provides an image of an agarose gel demonstrating CIITA zygosity results. results. A 2.5 kb band indicates a WT unedited clone. A 5.6 kb band indicates successful integration of the BCMA-CAR into the CIITA gene locus.

FIG. 14 shows the CIITA zygosity results for various edited clones. The presence of a ~2.5 kb band indicated a WT genotype while the presence of a 5.6 kb band indicated successful integration of the KI construct into the CIITA gene locus. Unedited clones would only have the WT band, clone heterozygous for the KI would have both bands, and homozygous clones would only have the KI band. The resulting amplicons were submitted for PCR cleanup and Sanger sequencing. Sanger sequencing results were input into Tsunami software along with the guide sequence. The resulting DNA sequences of the target CIITA region were aligned in Snapgene software to determine indel identity and homo- or heterozygosity.

For determining BCMA CAR knock-in genotyping in the target CIITA sequence, PCR for relevant regions was performed using Platinum Taq Supermix (Invitrogen, cat #125320176 and Cat #11495017). The sequences of the PCR primers are presented in Table 30; and the cycling conditions provided in Table 31.

TABLE 30

CIITA KI Primer

| Name | Type | Sequence (5'-3') | SEQ ID NO: |
|---|---|---|---|
| CD3Z-seq-F1 | forward | GAGTGAAGTTTTCCCGAAGCGCAGACGCTC CGGCATATCAGCAAGGACAG | 64 |
| CIITA-OUT-R | reverse | CTCTAATGCAAACTTGGGTAGGTCGTTTCA CCTCTCTAAACCTCAATTTCCTCATTTG | 65 |

TABLE 31

CIITA KI PCR Cycling Parameters

| Step | Temperature | Time | Cycles |
|---|---|---|---|
| Denaturation | 98° C. | 30 sec | 1 |
| Denaturation | 98° C. | 10 sec | 30 |
| Annealing | 65° C. | 30 sec | |
| Extension | 72° C. | 1 min 30 sec | |
| Elongation | 72° C. | 5 min | 1 |
| Hold | 4° C. | hold | |

Figure 15:
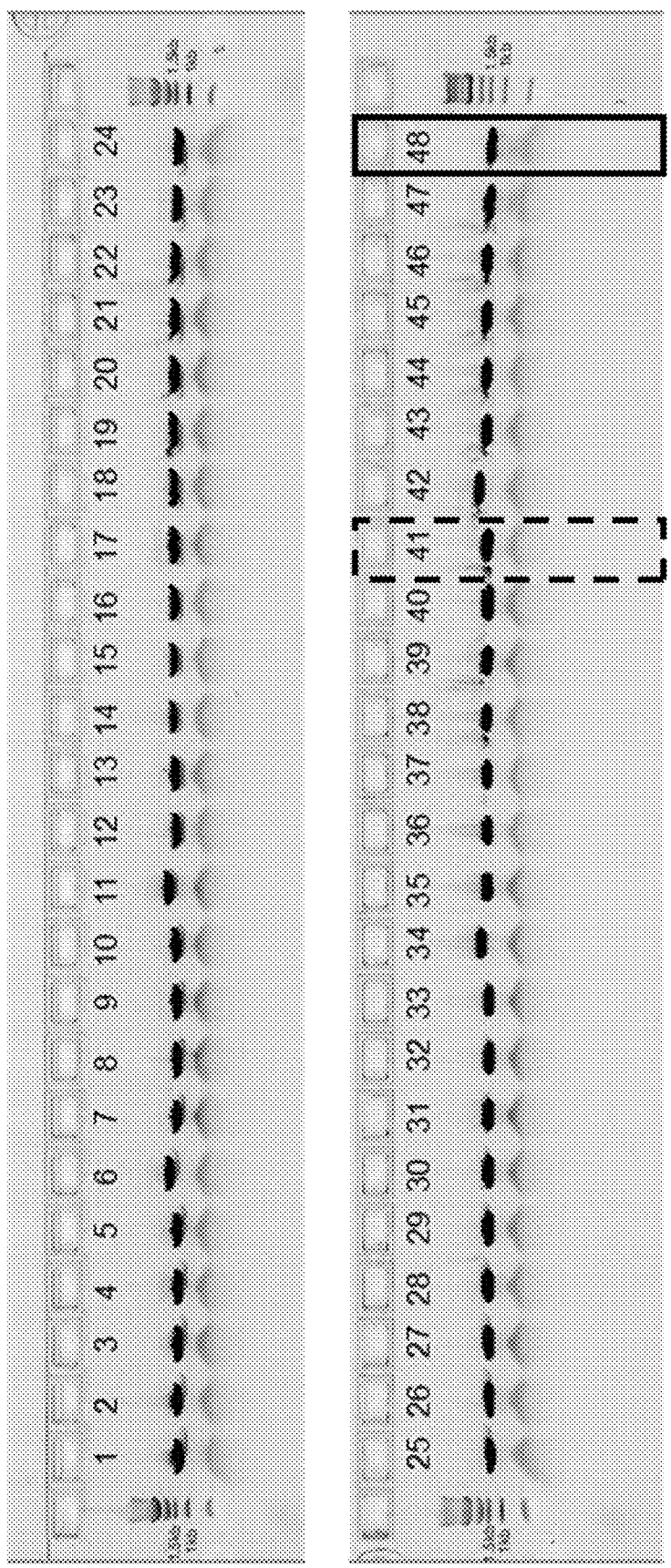
FIG. 15 provides an image of an agarose gel demonstrating CIITA genotyping results. The presence of a 1.5 kb band indicates successful integration of the KI construct into the CIITA gene locus, while the absence of a band indicates a WT genotype.

FIG. 15 shows the CIITA KI genotyping results for various edited clones. The presence of a 1.5 kb band indicated successful integration of the KI construct into the CIITA gene locus, while the absence of a band indicated a WT genotype. For determining indels in the target ADAM17 sequence, PCR for relevant regions was performed using Platinum Taq Supermix (Invitrogen, cat #125320176 and Cat #11495017). The sequence of the PCR primers are presented in Table 13; and the cycling conditions provided in Table 14. The resulting amplicons were submitted for PCR cleanup and Sanger sequencing. Sanger sequencing results were input into Tsunami software along with the guide sequence. The resulting DNA sequences of the target ADAM17 region were aligned in Snapgene software to determine indel identity and homo- or heterozygosity.

Based on the PCR and Sanger sequencing analysis of the edited clones, the clone shown in lane 41 in FIGS. 10-15 was chosen as "clone 1" and the clone shown in lane 48 was chosen as "clone 2," which were shown to have the BCMA CAR KI and the IL15/ILRa-P2A-HLA-E KI, while the sequencing data confirmed that B2M, CIITA, and ADAM17 were completely knocked-out. Clone 1 was heterozygous for the B2M KI and had an indel of +1T in the B2M WT band (Table 32). Clone 1 was homozygous for the CIITA KI and contained a homozygous +1G indel in the ADAM17 WT band (Table 33).

TABLE 32

KI genotypes of IL15/IR15α-P2A-HLA-E trimer knock-in, BCMA CAR knock-in, CIITA Null, B2M Null, ADAM17 Null Human Pluripotent Stem Cells Clones

| Clone | IL-15/IR-15 fusion-P2A-HLA-E into B2M | BCMA CAR into CIITA |
|---|---|---|
| 1 | Heterozygous KI | Homozygous KI |
| 2 | Heterozygous KI | Homozygous KI |

TABLE 33

KO genotypes of IL15/IR15α-P2A-HLA-E trimer knock-in, BCMA CAR knock-in, CIITA Null, B2M Null, ADAM17 Null Human Pluripotent Stem Cells Clones

| Clone | B2M indel | CIITA indel | ADAM17 indel |
|---|---|---|---|
| 1 | KI/+1 T | KI/KI | +1 G/+1 G |
| 2 | KI/+1 T | KI/KI | −20/large insertion |

Confirmation of KI gene expression and KO status at the hiPSC stage. To detect the BCMA CAR, HLA-E, and IL15 surface expression, fluorescent antibodies were used (see Table 21). Undifferentiated clone 1, the hiPSC clone containing all the edits (IL15/IR15α-P2A-HLA-E trimer knock-in, BCMA CAR knock-in, CIITA Null, B2M Null, ADAM17 Null) was assessed by flow cytometry with unedited WT cells as a negative control (Table 34). The gene edited clone 1 showed >99% BCMA CAR expression, >99% HLA-E expression, and >99% IL15 expression. To confirm KO status, fluorescent antibodies for HLA-ABC were used (see Table 21) with unedited WT iNK cells as a negative control (Table 34).

TABLE 34

|  | WT iPSC | Clone 1 iPSC |
|---|---|---|
| CAR$^+$ | 1.06% | 99.7% |
| HLA-E$^+$ | 0.22% | 100% |
| IL-15$^+$ | 0.03% | 99.2% |
| HLA-A, B, C (MHC-I)$^-$ | 97.3% | 0.74% |

Figure 16:
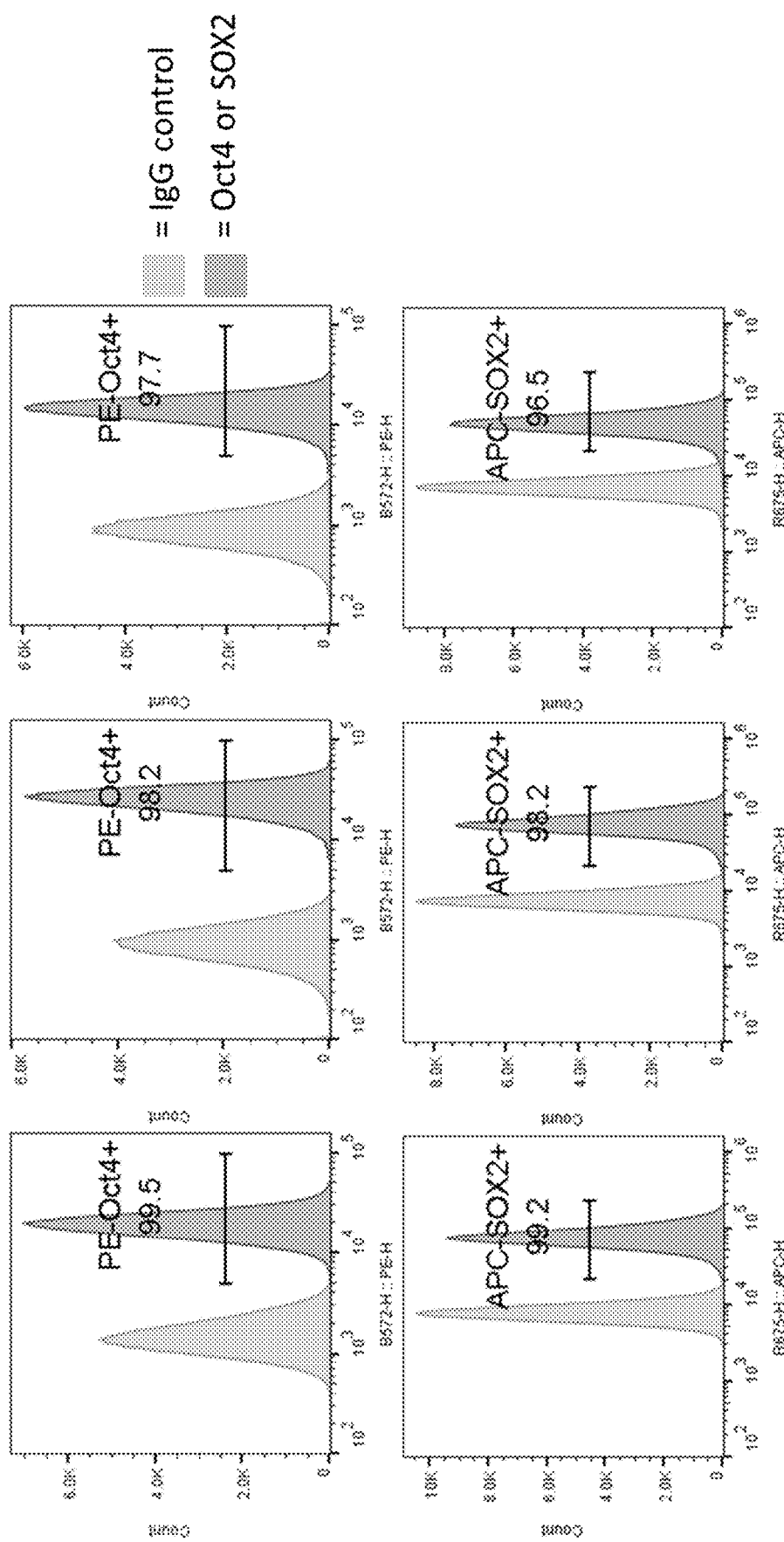
FIG. 16 provides histograms demonstrating pluripotency in hiPSC after genome editing. WT, Clone 1, and Clone 2 were stained for Oct4 and Sox2 and analyzed by flow cytometry.

Confirmation of hiPSC pluripotency after genome editing. To detect the Oct4 and Sox 2 intracellular expression fluorescent antibodies were used. iPS cells: WT and undifferentiated clones 1 and 2, containing all the edits (IL15/IR15α-P2A-HLA-E trimer knock-in, BCMA CAR knock-in, CIITA Null, B2M Null, ADAM17 Null) were assessed by flow cytometry. IgG-labeled cells served as a negative control (FIG. 16). Oct4 expression was 99.5% in WT, 98.2% in the gene edited clone 1 and 97.7% in the gene edited clone 2 (FIG. 16). There were the following percentages of Sox2-positive cells in iPSC populations: WT iPSC had >99%, edited clones 1 and 2 had >98 and >96% positive correspondently (FIG. 16). Edited clones retained high level of pluripotency.

Figure 17:
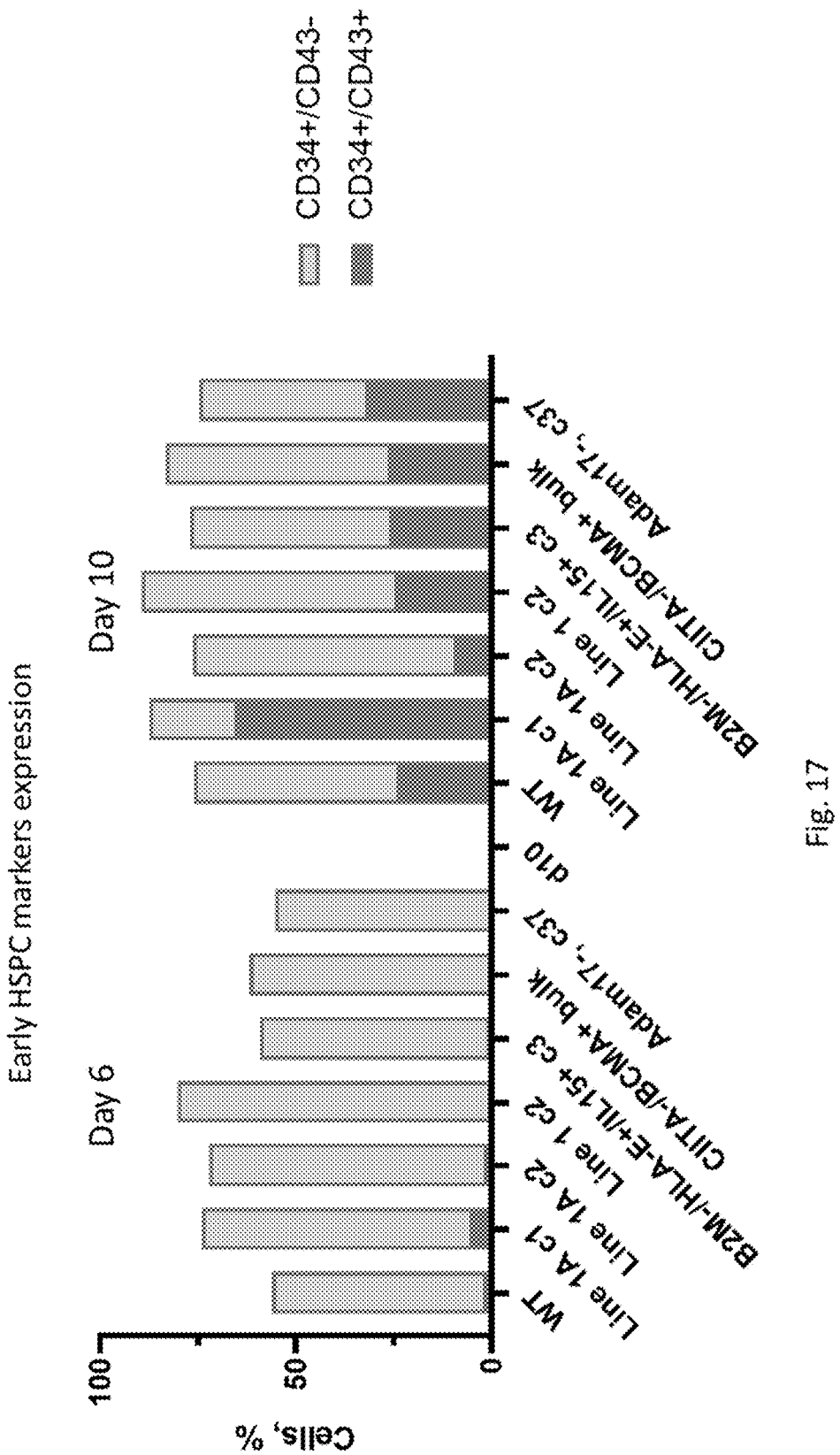
FIG. 17 provides a graph demonstrating CD34/CD43 expression in Clone 1 (Line 1A c1), Clone 2 (Line 1A c2), Clone 3 (B2M$^-$/HLA-E$^+$/IL15$^+$), a Line 1 clone, a CIITA–/BCMA CAR$^+$ bulk population, and a ADAM17 KO clone ("Adam17$^-$", c37") cells compared to WT at Day 6 and Day 10 of differentiation from iPSC to iNK cells. Cells were analyzed by flow cytometry for CD34 and CD43 expression.
Figure 18:
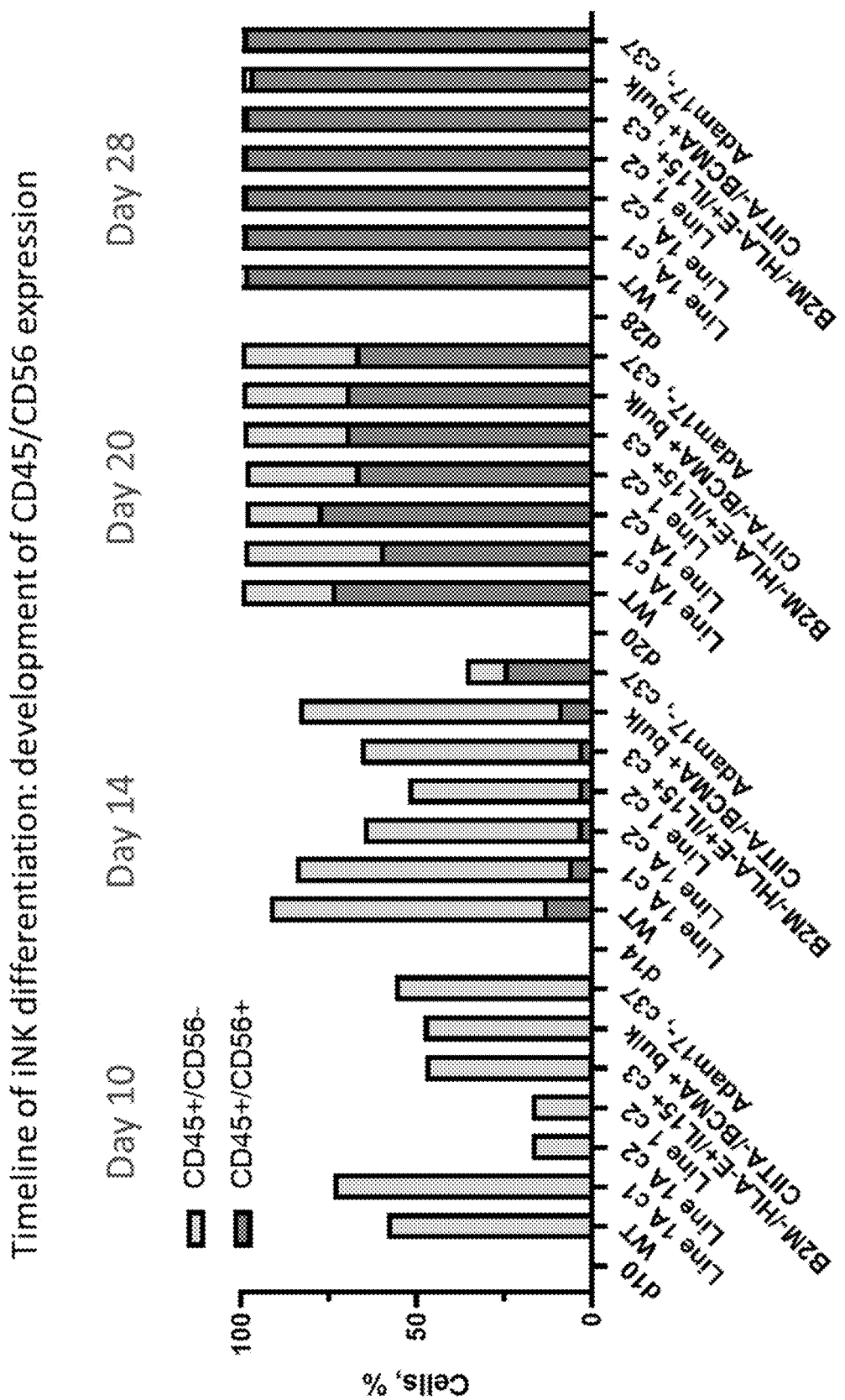
FIG. 18 provides a graph demonstrating CD45/CD56 expression in Clone 1 (Line 1A c1), Clone 2 (Line 1A c2), Clone 3 (B2M$^-$/HLA-E$^+$/IL15$^+$), a Line 1 clone 2, a CIITA–/BCMA CAR$^+$ bulk population, and a ADAM17 KO clone ("Adam17$^-$", c37") cells compared to WT at Day 10 and Day 14, Day 20, and Day 28 of differentiation from iPSC to iNK cells. Cells were analyzed by flow cytometry for CD45 and CD56 expression.

Example 10: Differentiation and Characterization of IL15/IR15α-P2A-HLA-E Trimer Knock-In, BCMA CAR Knock-In, CIITA Null, B2M Null, ADAM17 Null hPSC WT, Clones 1 and 2 ("Line1A c1 and c2"; hiPSC gene edited clones containing the edits IL15/IR15α-P2A-HLA-E trimer knock-in, BCMA CAR knock-in, CIITA Null, B2M Null, ADAM17 Null), Clone 3 ("B2M–/HLA-E$^+$/IL15$^+$ c3"); hiPSC gene edited clone containing the edits IL15/IR15α-P2A-HLA-E trimer knock-in, B2M Null), Line 1 clone 2 ("Line 1 c2"; hiPSC gene edited clone containing the edits IL15/IR15α-P2A-HLA-E trimer knock-in, BCMA CAR knock-in, CIITA Null, B2M Null), a CIITA/BCMA CAR$^+$ bulk population, and a ADAM17 KO clone 37 ("Adam17–, c37") were differentiated to iNK cells using Protocol 1, as described in Example 2. Flow cytometry of differentiated cells at Days 6 and 10 showed that all of the edited clones and bulk populations, including both edited iPSC clones 1 and 2, differentiated efficiently to HPSC (CD34$^+$/CD43$^-$) cell population as compared with WT (FIG. 17). Edited iPSC clone 1 expressed CD43 earlier but that did not influence its overall differentiation into iNK and cytotoxicity. Throughout the differentiation process, cells were analyzed for CD45 and CD56 expression by flow cytometry (FIG. 18), showing efficient differentiation for all of the edited clones which was comparable to WT. By day 28, >99% of cells are CD56$^+$.

Figure 19A:
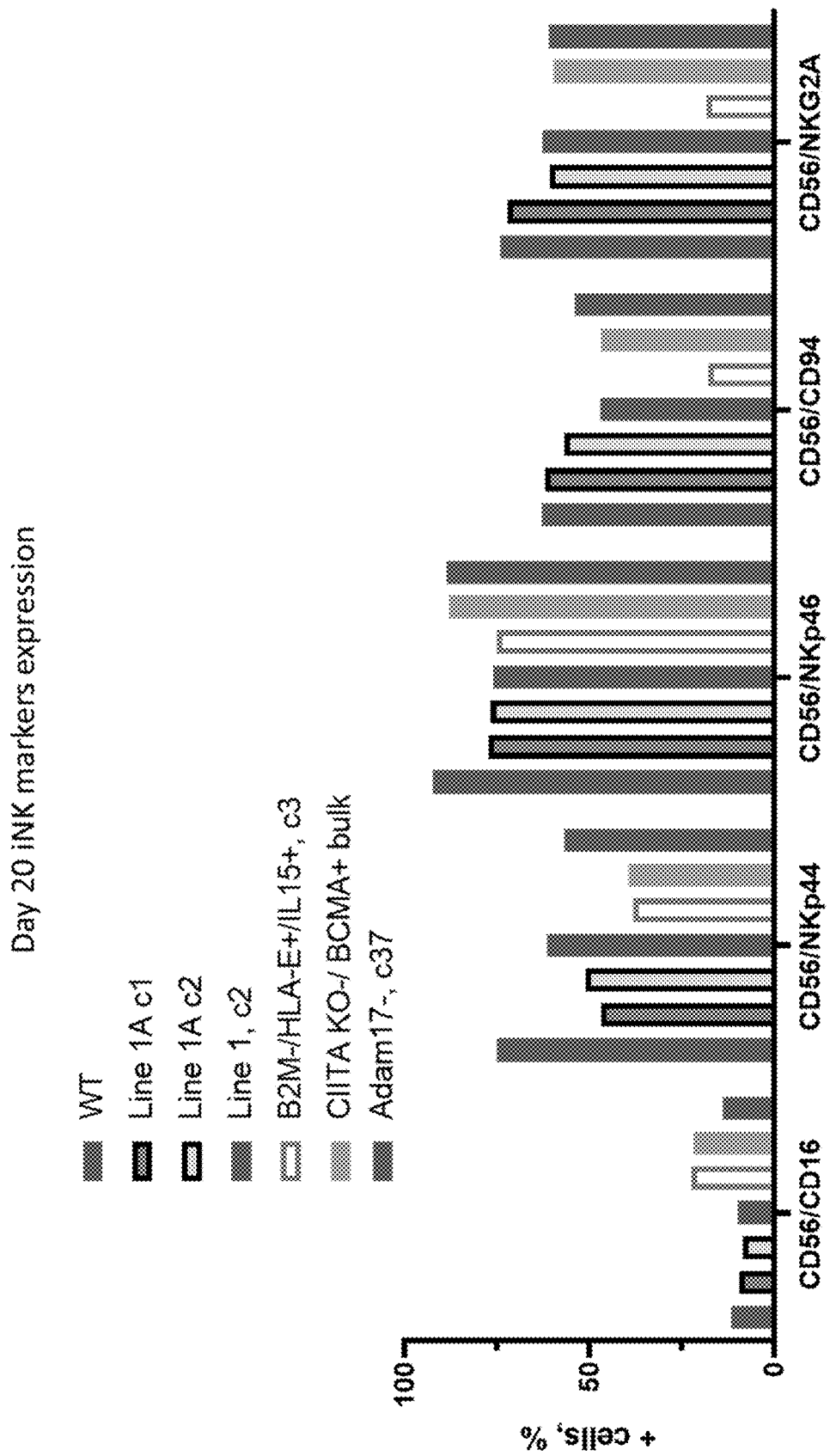
FIG. 19A provides a graph demonstrating expression of differentiation markers in Clone 1 (Line 1A c1), Clone 2 (Line 1A c2), Clone 3 (B2M$^-$/HLA-E$^+$/IL15$^+$), a Line 1 clone 2, a CIITA$^-$/BCMA CAR$^+$ bulk population, and a ADAM17 KO clone ("Adam17$^-$", c37") cells compared to WT at Day 20 of differentiation from iPSC to iNK cells. Cells were analyzed by flow cytometry for CD56$^+$/CD16$^+$, CD56$^+$/NKp44$^+$, CD56$^+$/NKp46$^+$, CD56$^+$/CD94$^+$, and CD56$^+$/NKG2A$^+$ expression.
Figure 19B:
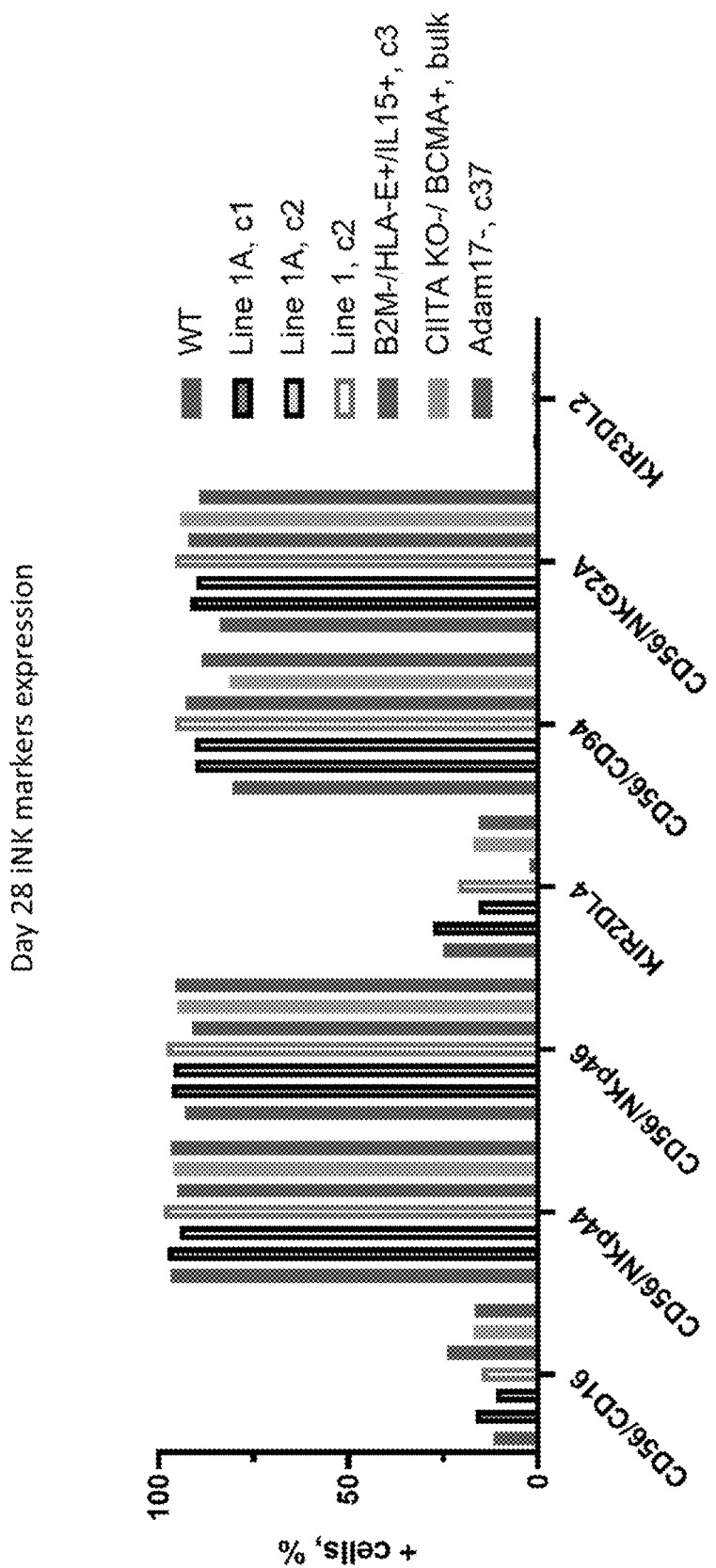
FIGS. 19B and 19C provide graphs demonstrating expression of differentiation markers in Clone 1 (Line 1A c1), Clone 2 (Line 1A c2), Clone 3 (B2M/HLA-E$^+$/IL15$^+$), a Line 1 clone 2, a CIITA-BCMA CAR$^+$ bulk population, and a ADAM17 KO clone ("Adam17$^-$", c37") cells compared to WT at Day 28 (FIG. 19B) and Day 35 (FIG. 19C) of differentiation from iPSC to iNK cells. Cells were analyzed by flow cytometry for CD56$^+$/CD16$^+$, CD56$^+$/NKp44$^+$, CD56$^+$/NKp46$^+$, CD56$^+$/CD94$^+$, CD56$^+$/NKG2A$^+$, KIR2DL4, and KIR3DL2 expression.
Figure 19C:
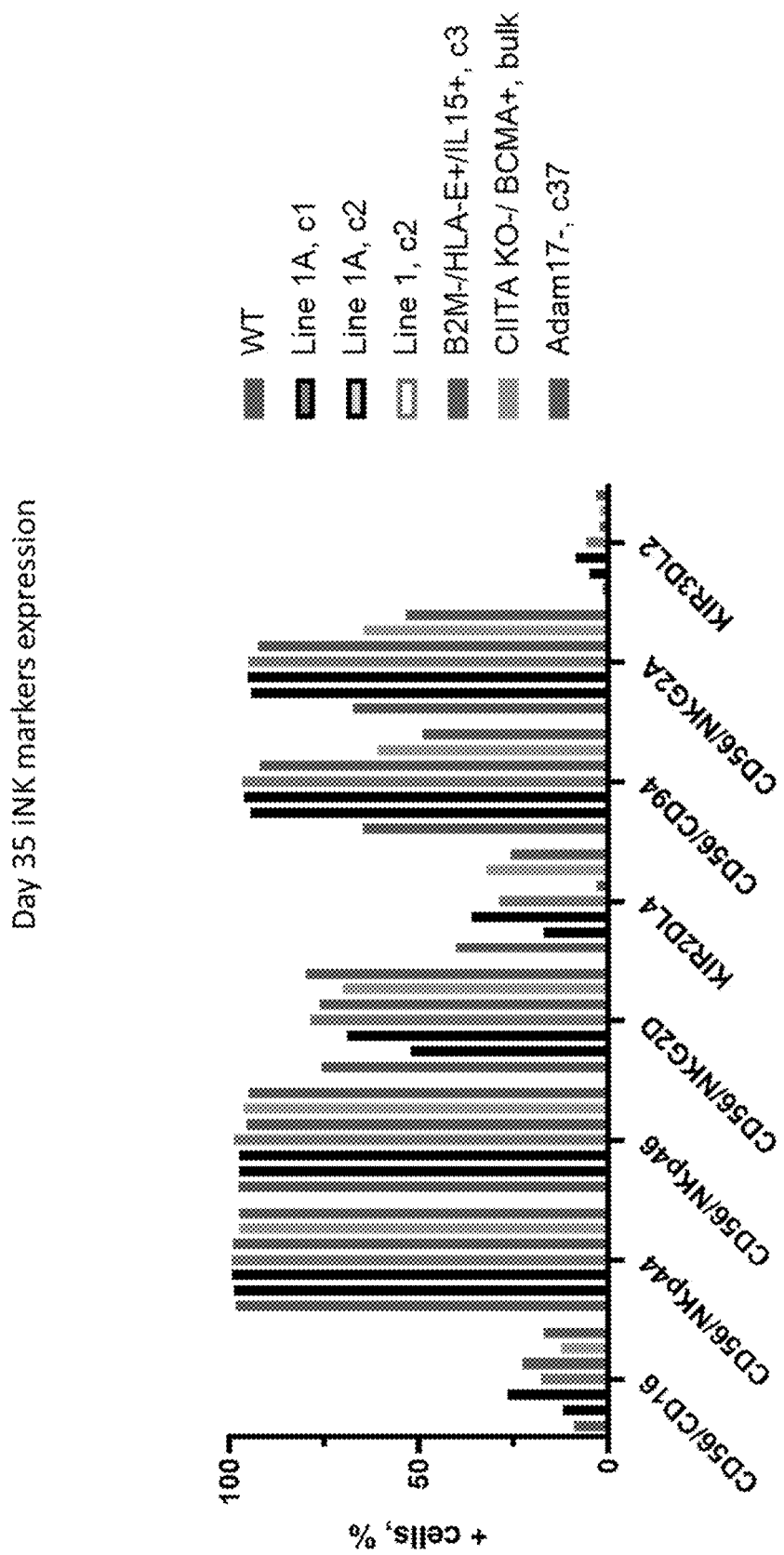
Figure 19D:
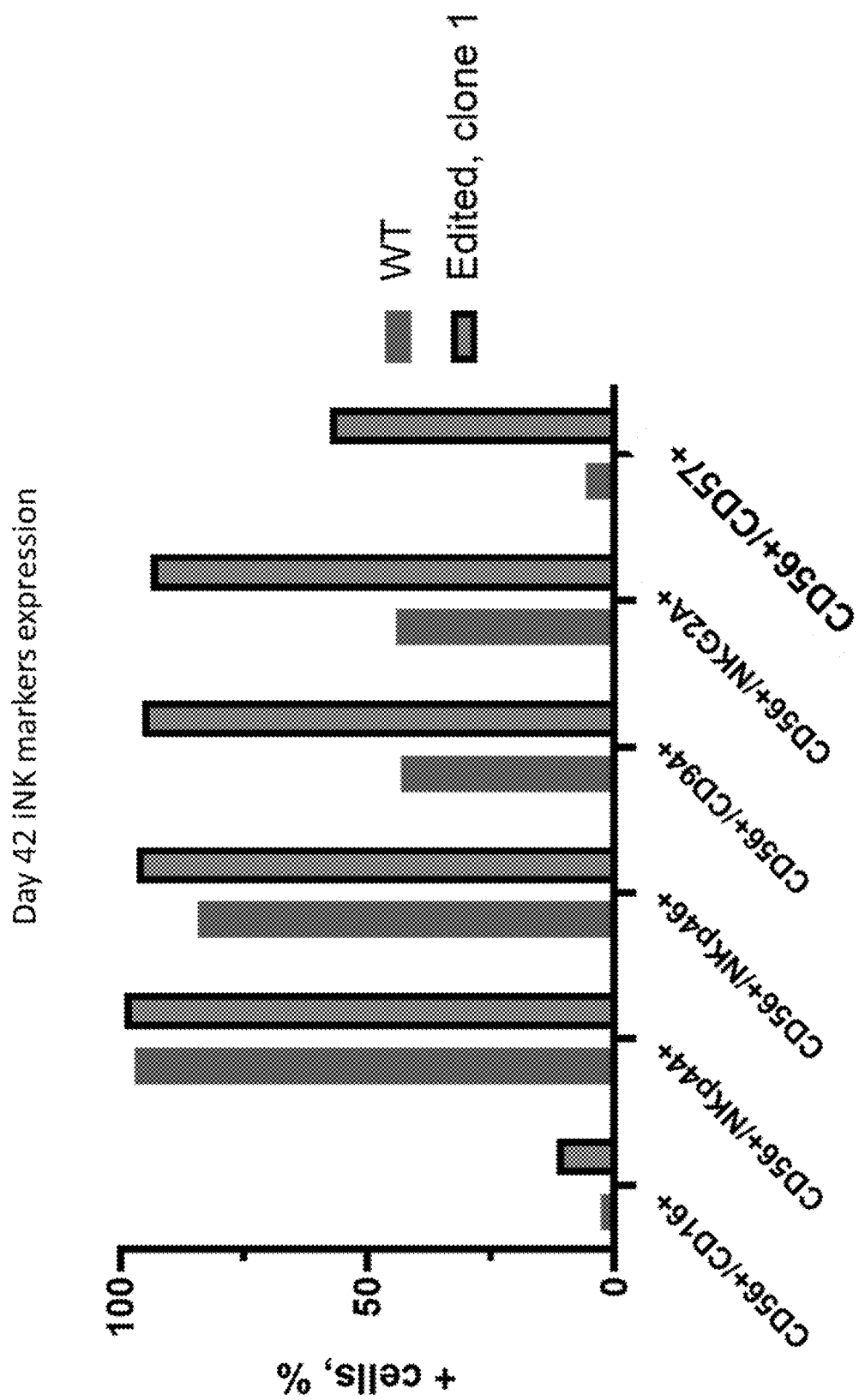
FIG. 19D provides a graph demonstrating expression of differentiation markers in Clone 1 compared to WT at Day 42 of differentiation from iPSC to iNK cells. Cells were analyzed by flow cytometry for CD56$^+$/CD16$^+$, CD56$^+$/NKp44$^+$, CD56$^+$/NKp46$^+$, CD56$^+$/CD94$^+$, CD56$^+$/NKG2A$^+$, and CD56$^+$/CD57$^+$ expression.

Flow cytometry was performed on digested cells aggregates on days 6, 10, and 14; and on single cells on days 20 (FIG. 19A), 28 (FIG. 19B), 35 (FIG. 19C), and 42 (FIG. 19D). Live cells were collected, washed with 1% BSA in PBS, and incubated with appropriate antibody cocktails in 5% BSA in PBS for 30 min on ice. The cells were washed and resuspended in 1% BSA in PBS containing 1:1000 SyTOX Blue cells viability dye followed by loading the plate on the Flow cytometer for analysis (see Table 35 for antibodies used). The differentiated Line 1A, clone 1 and 2, as well as edited IL15/IR15α-P2A-HLA-E trimer knock-in into B2M null, clone 3 iNK cells expressed a majority of maturation markers. On day 20 of differentiation all three edited lines displayed NK markers expression that was somewhat lower than WT. However the same markers were expressed at comparable or even higher than WT levels only a week later (at day 28).

TABLE 35

| antigen | fluorophore | company | catalog # | Dilution |
|---|---|---|---|---|
| CD16 | PE-Cy7 | BioLegend | 360708 | 1:50 |
| CD235a/ Glycophorin A | APC | BioLegend | 349114 | 1:10 |
| CD34 | FITC | Miltenyi | 130-113-178 | 1:25 |
| CD34 | PE | BD | 555822 | 1:10 |
| CD43 | BB515 | BD | 564542 | 1:500 |
| CD45 | PE-Cy7 | BD | 557748 | 1:100 |
| CD45 | BB515 | BD | 564585 | 1:100 |
| CD56 | PE | Miltenyi | 130-113-307 | 1:500 |
| CD56 | BB515 | BD | 564488 | 1:25 |
| CD56/NCAM1 | APC | BD | 555518 | 1:10 |
| CD57 | PE-Cy7 | BioLegend | 359624 | 1:10 |
| CD94/KLRD1 | APC | Miltenyi | 130-098-976 | 1:5 |
| CD95/Fas1 | FITC | BD | 555673 | 1:10 |
| HLA-ABC | FITC | eBioscience | 11-9983-42 | 1:10 |
| HLA-DR, DP, DQ | 647 | BioLegend | 361703 | 1:10 |
| HLA-E | APC | BioLegened | 342605 | 1:10 |
| hTACE/ADAM17 | PE | R&D | FAB9301P | 1:10 |
| IL-15 | APC | Invitrogen | MA5-23627 | 1:10 |
| IL-15 | PE | Invitrogen | MA5-23561 | 1:10 |
| IL-15 | FITC | Invitrogen | MA5-23664 | 1:10 |
| KIR2DL4/CD158d | APC | Miltenyi | 130-112-466 | 1:25 |
| KIR3DL2/CD158e/k | PE-Vio770 | Miltenyi | 130-116-180 | 1:100 |
| NKG2A/CD159a | APC | Miltenyi | 130-113-563 | 1:5 |
| NKG2D | BB515 | BD | 564566 | 1:2.5 |
| NKp44/CD336 | PE | BD | 558563 | 1:5 |
| NKp46/CD335 | PE-Cy7 | BD | 562101 | 1:5 |
| Oct3/4 | PE | BD Bioscience | 560186 | 1:10 |
| PD1/CD279 | APC | BioLegend | 621610 | 1:10 |
| PDL1/CD274 | PE-Cy7 | BD | 558017 | 1:10 |
| SOX2 | Alexa 647 | BD Bioscience | 562139 | 1:10 |
| Perforin, Clone delta G9, | PE | Miltenyi | 130-123-726 | 1:25 |
| Granzyme B Clone REA226, | APC | Miltenyi | 130-120-773 | 1:25 |

Confirmation of KI gene expression and KO status of edited cells differentiated to the iNK stage. Using these differentiated Line 1A clone 1 cells, flow cytometry was repeated to assess KI gene expression and KG status. To detect the BCMA CAR, HLA-E, and IL15 surface expression, fluorescent antibodies were used (see Table 21) with unedited WT iNK cells as a negative control (Table 36). The Line 1A clone 1-derived iNK cells showed >99% BCMA CAR expression, >90% HLA-E expression, and >99% IL15 expression. To confirm KO status, fluorescent antibodies for HLA-ABC were used (see Table 21) with unedited WT iNK cells as a negative control (Table 36).

TABLE 36

|  | WT iNK | Clone 1 iNK |
|---|---|---|
| CAR$^+$ | 0.75% | 99.9% |
| HLA-E$^+$ | 5.65% | 91% |
| IL-15$^+$ | 0.33% | 99.1% |
| HLA-A, B, C (MHC-I)$^-$ | 99.8% | 0.8% |

Figure 20:
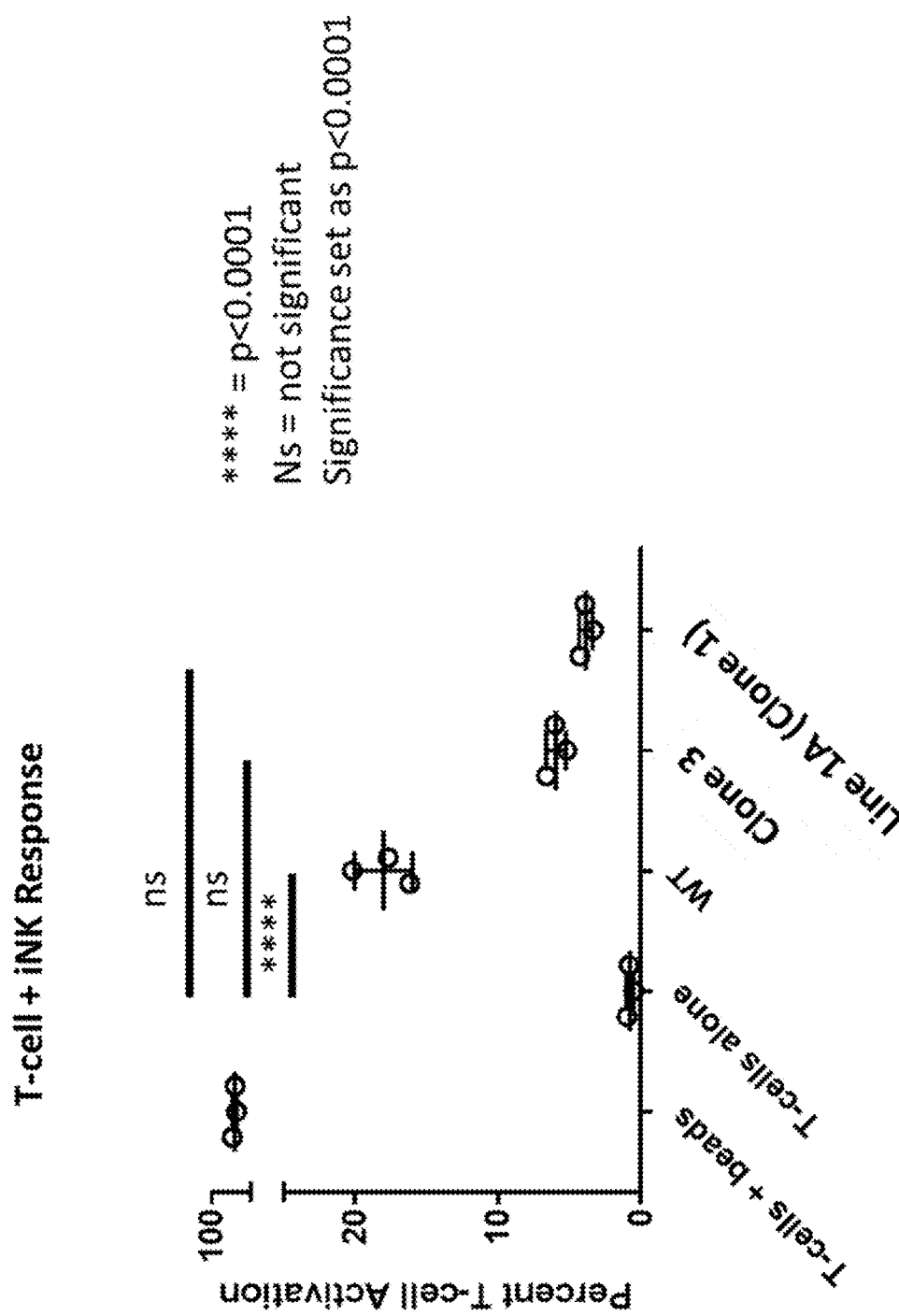
FIG. 20 provides a graph representing T-cell activation by differentiated iNK cells. Line 1A clone 1, Clone 3, and WT cells T cell activation was measured by carboxyfluorescein succinimidyl ester (CFSE) assay.

Immune phenotype of edited iNK cells. At the iNK stage, differentiated cells of clone 1 (an hiPSC gene edited clone containing all the edits (IL15/IR15α-P2A-HLA-E trimer knock-in, BCMA CAR knock-in, CIITA Null, B2M Null, ADAM17 Null) of Example 9 and clone 3 (an hiPSC gene edited clone containing B2M KO (IL15/IR15α-P2A-HLA-E trimer knock-in, B2M Null) of Example 8 and differentiated wild-type iPSC cells were co-cultured with donor derived T-cells that were labeled with CFSE. After 5 days of co-culture, the cells were analyzed for flow cytometry and the degree of CFSE loss was assessed. WT iNK cells induced a loss of CFSE signal in the T-cells, suggesting an allogeneic immune reaction had occurred. iNK cells derived from clone 1 or clone 3 did not produce CFSE loss in the T-cells, suggesting that these cells were immune-evasive (FIG. 20).

Figure 21A:
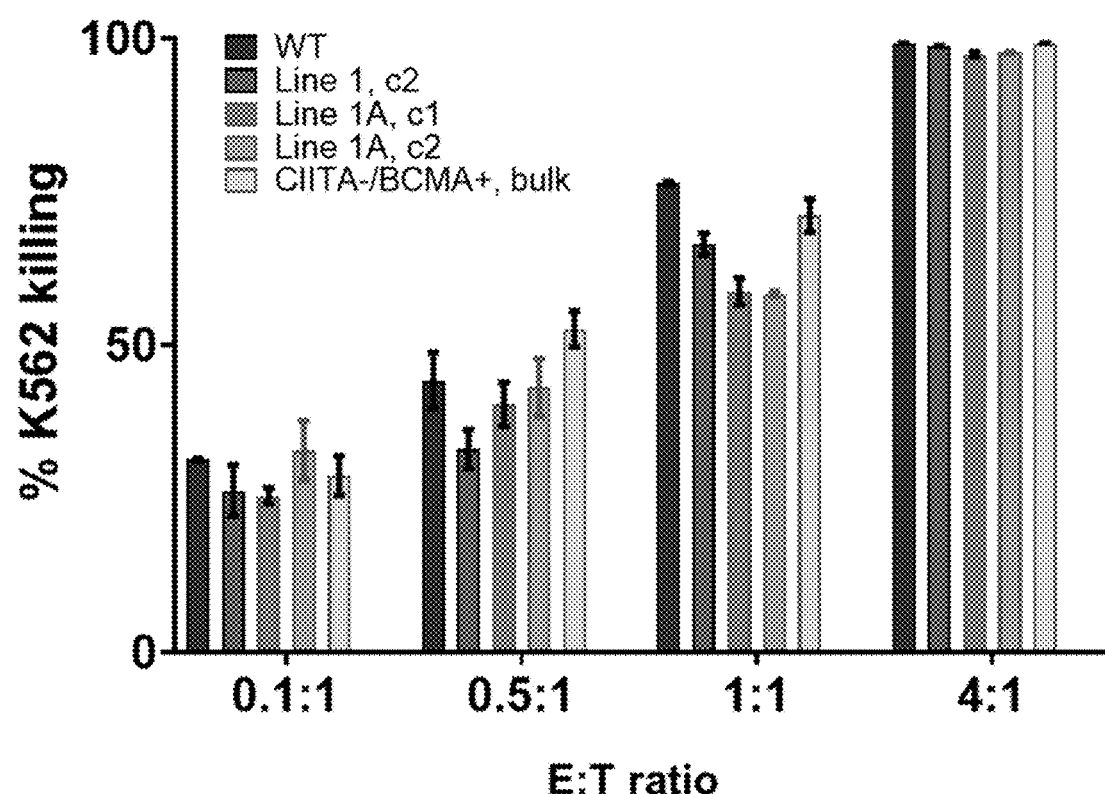
FIGS. 21A and 21B provide graphs measuring K562 (FIG. 21A) and RPMI (FIG. 21B) cell killing by the indicated iNK cell line. WT, Line 1 clone 2, Line 1A Clone 1, Line 1A Clone 2, and CIITA$^-$/BCMA CAR$^+$ ("CIITA$^-$/
Figure 21B:
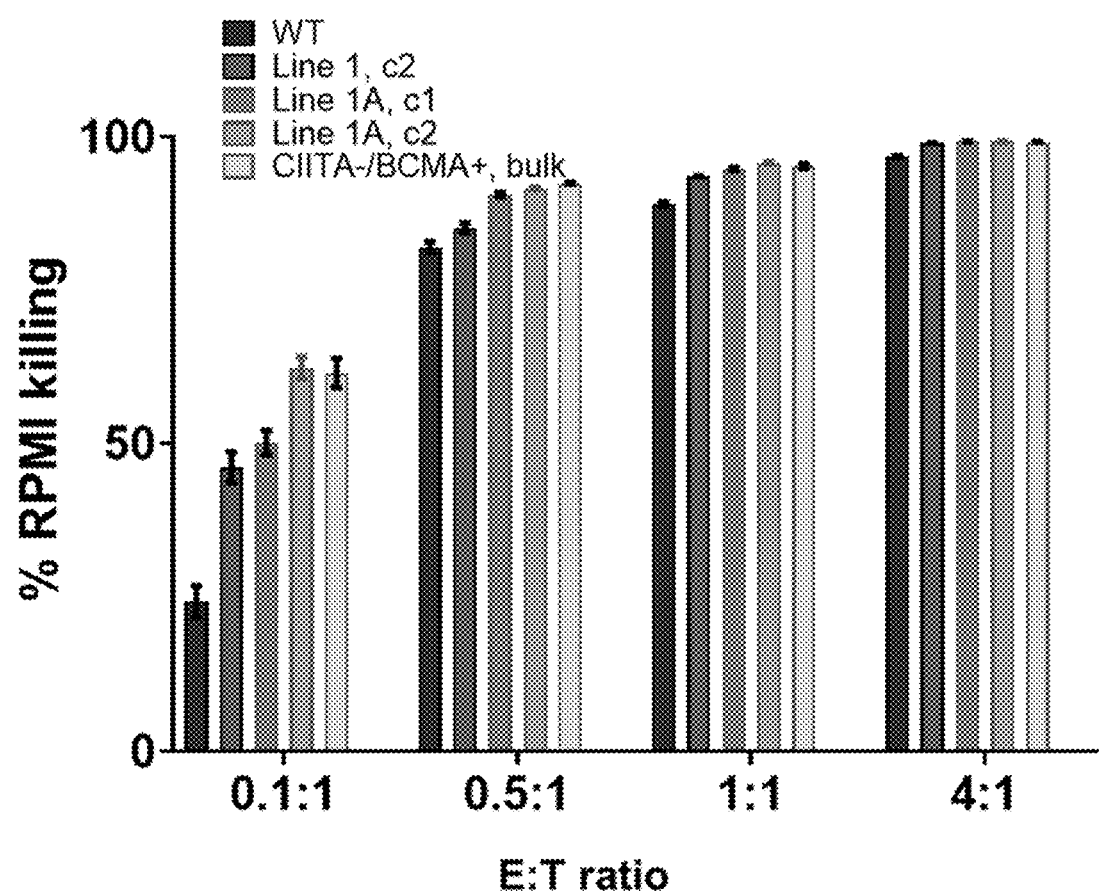

The cytotoxicity of the day 21 Line 1A clones 1 and 2, and Line 1 clone 2 (IL15/IR15α-P2A-HLA-E trimer knock-in, BCMA CAR knock-in, CIITA Null, B2M Null) cells towards K562 and RPMI cells was determined using a 24-hour killing assay, as described in Example 8. The WT and clones 1 and 2 line displayed effective cytotoxicity against K562 (FIG. 21A), while clones 1 and 2 also displayed greater cytotoxicity against BCMA+ expressing RPMI cancer cell line especially at lowest Effector to target cells ratio, 0.1:1 (FIG. 21B).

Cytokines (IFNg, TNFa) were measured using the ProteinSimple Ella system, according to the manufacturer's instructions, with the software version v.3.5.2.20 of the Simple Plex Runner software, and Simple Plex Explorer software. Custom 8-plex Ella cartridges (32×8 Multiplex) were provided by ProteinSimple, along with dilution buffer which was used to dilute each sample (WT and Line 1A clone 1) at a 1:2 ratio prior to loading 40 µL sample per channel. As shown in FIG. 22, the IFNg levels in media correlated with an increased E:T ratio, being higher than WT in low E:T ratios (0.1:1). At higher E:T ratios, IFNg is somewhat lower in edited cells than WT, which might be the result of drastic decrease of target cells due to their efficient lysis over 24 hours. TNFa was higher in WT than in edited clone 1. This effect may be explained by lack of Adam17, a protease that cleaves TNFa.

Perforin and granzyme-B expression in cells were measured by flow cytometry at day 14 and Day 36 of differentiation using commercially available antibodies. FIG. 23 shows that WT cells at day 14 of differentiation had little to no expression of perforin or granzyme-B but had higher expression at day 36. Line 1A clone 1 had similar expression patterns as WT.

Day 20 iNKs differentiated from wild-type (WT), Line 1A clone 1 ("Line 1A, c1"), Line 1A clone 2 ("Line 1A, c2"), and Clone 3 ("B2M−/HLA-E+/IL15IL15Rα"; IL15/IR15α-P2A-HLA-E trimer knock-in, B2M Null hPSC) derived iNK cells were plated at 5×10⁶ cells/well and grown with or without exogenous cytokines. Cells were administered SCF (20 ng/mL), Flt3L (15 ng/mL), IL-7 (20 ng/mL), and IL-15 (15 ng/mL) ("4"), SCF, Flt3L, and IL-7 ("3/-IL15-"), no cytokines ("0"); or only IL-15 ("IL15") on day 0 and day 9 (FIG. 24). The edited clones persisted and expanded in the absence of exogenous IL15 while the WT iNK cell number declined in the absence of exogenous IL5.

Example 11: Generation and Selection of FAS gRNA, CISH gRNA, and REGNASE-1 gRNA Targeting gRNAs were designed for targeting exons 1, 2, and 3 of the FAS coding sequence, exons 1, 2, and 3 of the CISH coding sequence, exons 2 and 4 of the REGNASE-1 coding sequence. The target sequences of the gRNAs are presented in Tables 37, 38, and 39, respectively. Each gRNA comprises an RNA spacer sequence corresponding to the target DNA sequence. These gRNAs had predicted low off-target scores based on sequence homology prediction using gRNA design software.

TABLE 37

FAS Target Sequences

| Name | Target Sequence (5'-3') | SEQ ID NO: | PAM |
|---|---|---|---|
| FAS Ex1 T7 | GGATTGCTCAACAACCATGC | 35 | TGG |
| FAS Ex1 T9 | GATTGCTCAACAACCATGCT | 37 | GGG |
| FAS Ex2 T1 | GTGACTGACATCAACTCCAA | 38 | GGG |
| FAS Ex2 T2 | CACTTGGGCATTAACACTTT | 39 | TGG |
| FAS Ex2 T3 | TTGGAAGGCCTGCATCATGA | 53 | TGG |
| FAS Ex2 T7 | ACTCCAAGGGATTGGAATTG | 55 | AGG |
| FAS Ex3 T1 | CTAGGGACTGCACAGTCAAT | 80 | GGG |

TABLE 38

CISH Target Sequences

| Name | Target Sequence (5'-3') | SEQ ID NO: | PAM |
|---|---|---|---|
| CISH Ex1 T2 | TCGCCGCTGCCGCGGGGACA | 81 | TGG |
| CISH Ex1 T18 | GACATGGTCCTCTGCGTTCA | 82 | GGG |
| CISH Ex2 T1 | GTCCGCTCCACAGCCAGCAA | 83 | AGG |
| CISH Ex2 T2 | GTTCCAGGGACGGGGCCCAC | 84 | AGG |
| CISH Ex3 T1 | TCGGGCCTCGCTGGCCGTAA | 85 | TGG |
| CISH Ex3 T2 | CGTACTAAGAACGTGCCTTC | 86 | TGG |
| CISH Ex3 T3 | GGGTTCCATTACGGCCAGCG | 87 | AGG |
| CISH Ex3 T5 | CAGGTGTTGTCGGGCCTCGC | 88 | TGG |
| CISH Ex3 T6 | TACTCAATGCGTACATTGGT | 89 | GGG |
| CISH Ex3 T9 | AAGGCTGACCACATCCGGAA | 90 | AGG |
| CISH Ex3 T11 | TACATTGGTGGGGCCACGAG | 91 | TGG |
| CISH Ex3 T14 | CTGTCAGTGAAAACCACTCG | 92 | TGG |

TABLE 39

REGNASE-1 Target Sequences

| Name | Target Sequence (5'-3') | SEQ ID NO: | PAM |
|---|---|---|---|
| REGNASE-1 Ex2 T1 | GGTCATCGATGGGAGCAACG | 93 | TGG |
| REGNASE-1 Ex2 T2 | CACCACCCCGCGGGACTAGA | 94 | GGG |
| ZC3H12A_Segment 2 T3 | GGTCTGGCGCTCCCGCTCGG | 95 | TGG |
| REGNASE-1 Ex2 T4 | CCACCACCCCGCGGGACTAG | 96 | AGG |
| REGNASE-1 Ex2 T5 | TTAGGGGTGCCACCACCCCG | 97 | CGG |

TABLE 39-continued

REGNASE-1 Target Sequences

| Name | Target Sequence (5'-3') | SEQ ID NO: | PAM |
|---|---|---|---|
| REGNASE-1 Ex4 T1 | TTCACACCATCACGACGCGT | 98 | GGG |
| ZC3H12A_Segment 4 T2 | ACACCATCACGACGCGTGGG | 99 | TGG |
| ZC3H12A_Segment 4 T3 | CTACGAGTCTGACGGGATCG | 100 | TGG |
| ZC3H12A_Segment 4 T7 | ACGACGCGTGGGTGGCAAGC | 101 | GGG |

To assess their cutting efficiency in hPSCs, iPS cells were electroporated using the Neon Electroporator (Neon Transfection Kit ThermoFisher Cat #MPK5000) with a ribonucleoprotein (RNP) mixture of Cas9 protein and guide RNA at a molar ratio of 5:1 (gRNA:Cas9) with absolute values of 125 pmol Cas9 and 625 pmol gRNA. To form the RNP complex, gRNA and Cas9 were combined in one vessel with R-buffer (Neon Transfection Kit) to a total volume of 25 µL and incubated for 15 min at RT. Cells were dissociated using ACCUTASE®, then resuspended in STEMFLEX™ media (Gibco, cat #11320033), counted using an NC-200 (ChemoMetec) and centrifuged. A total of 1×10$^6$ cells were resuspended with the RNP complex and R-buffer was added to a total volume of 125 µL. This mixture was then electroporated with 1 pulse for 20 ms at 1500 V and 1 pulse for 100 ms at 500 V. Following electroporation, the cells were pipetted out into an Eppendorf tube filled with STEMFLEX™ media with REVITACELL™ Supplement (100×). This cell suspension was then plated into tissue culture dishes pre-coated with BIOLAMININ 521 CTG at 1:10 dilution. Cells were cultured in a normoxia incubator (37° C., 8% CO2) for 48 hours. After 48 hours, genomic DNA was harvested from the cells using QuickExtract (Lucigen, Middleton, WI; Cat #QE09050).

PCR for the target sequences was performed and the resulting amplified DNA was assessed for cutting efficiency by TIDE analysis. PCR for relevant regions was performed using Platinum Taq Supermix (Invitrogen, cat #125320176 and Cat #11495017). The resulting amplicons were submitted for PCR cleanup and Sanger sequencing. Sanger sequencing results were input into Tsunami software along with the guide sequence. Indel percentages and identities were calculated by the software. Particular gRNAs were then selected based on their indel frequency in hPSCs. FAS Ex1 T9 (SEQ ID NO; 37), CISH Ex1 T18 (SEQ ID NO: 82), and REGNASE-1 Ex2-T2 (SEQ ID NO: 94) were chosen for further clone generation due to their high on-target activity.

Example 12: Generation of IL15/IR15α-P2A-HLA-E Trimer Knock-In, BCMA CAR Knock-In, CIITA Null, B2M Null, ADAM17 Null, FAS Null, CISH Null, and REGNASE-1 Null hPSCs FAS Ex1 T9 (SEQ ID NO: 37), CISH Ex1 T18 (SEQ ID NO: 82), and REGNASE-1 Ex2 T2 (SEQ ID NO: 94) gRNAs were used to knock-out the FAS, CISH, and REGNASE-1 genes, respectively. IL15/IR15α-P2A-HLA-E trimer KI, BCMA CAR KI, CIITA Null, B2M Null, ADAM17 Null cells as described in Examples 9 and 10 were electroporated using the Neon Electroporator with RNP mixtures of Cas9 protein and guide RNA at a molar ratio of 5:1 (gRNA:Cas9) with absolute values of 125 pmol Cas9 and 625 pmol gRNA per 1 million cells. To form the RNP complexes, gRNA and Cas9 were combined in one vessel with R-buffer (Neon Transfection Kit) to a total volume of 25-50 µL and incubated for 15 min at room temperature (RT). This mixture was then combined with the cells to a total volume of ~115 µL using R-buffer. This mixture was then electroporated with 1 pulse for 20 ms at 1500 V followed by 1 pulse for 100 ms at 500 V. Following electroporation, the cells were pipetted out into a 6 well plate filled with STEMFLEX™ media with REVITACELL™ Supplement (100×) and laminin 511. Cells were cultured in a normoxia incubator (37° C., 8% CO$_2$).

Three to five days post electroporation, the cells were single-cell sorted as described in Example 1. The anti-BCMA CAR antibody (see Table 21) was used for FACS-sorting into 96-well plates. For FACS-sorting, unedited cells served as a negative control. After sorting, the cells were expanded as described in Example 1 and when confluent, samples were split for maintenance and genomic DNA extraction.

For determining indels in the target FAS, CISH, and REGNASE-1 sequences, PCR for relevant regions was performed using Platinum Taq Supermix (Invitrogen, Cat #125320176 and Cat #11495017). The resulting amplicons were submitted for PCR cleanup and Sanger sequencing. Sanger sequencing results were input into Tsunami software along with the guide sequence. The resulting DNA sequences of the target FAS, CISH, and REGNASE-1 regions were aligned in Snapgene software to determine indel identity and homo- or heterozygosity.

Continued expression of BCMA CAR, HLA-E, and IL15 surface proteins was confirmed using fluorescent antibodies as described above in Example 9. Pluripotency of the edited cells was confirmed by detecting OCT4 and SOX2 expression as described above in Example 9. Clone 1 (020 clone 1), homozygous at FAS, CISH, and REGNASE-1 loci, was chosen for further analysis, Example 13: Characterization of NK Cells Differentiated from IL15/IR15α-P2A-HLA-E TrimerKknock-In, BCMA CARKknock-In, CIITA Null, B2M Null, ADAM17 Null, FAS Null, CISH Null, and REGNASE-1 Null hPSCs The "020 clone 1" hPSCs (IL15/IR15α-P2A-HLA-E trimer knock-in, BCMA CAR knock-in, CIITA Null, B2M Null, ADAM17 Null, FAS Null, CISH Null, and REGNASE-1 Null), as well as "012 clone 1" hPSCs (IL15/IR15α-P2A-HLA-E KI, BCMA CAR KI, CIITA Null, B2M Null, ADAM17 Null), "003 clone 3" hPSCS (IL15/IR15α-P2A-HLA-E KI, B2M Null), and wild-type (WT) were differentiated to iNK cells using Protocol 1, as described in Example 2. Flow cytometry of differentiated cells at Days 10 and 14 showed that the "020 clone 1" differentiated cells had similar patterns if CD31, CD34, and CD43 expression as WT and those differentiated from "012 clone 1" and "003 clone 3" (FIGS. 25A-25B). Throughout the differentiation process, cells were analyzed for CD45 and CD56 expression by flow cytometry, showing efficient differentiation for all of the edited clones as compared to WT. By day 20, similar levels of the edited clones were CD56$^+$ (FIG. 26). By day 35, more than 99% of the edited clones were CD45$^+$/CD56$^+$.

The cytotoxicity of day 31 "020 clone 1" (IL15/IR15α-P2A-HLA-E trimer knock-in, BCMA CAR knock-in, CIITA Null, B2M Null, ADAM17 Null, FAS Null, CISH Null, and REGNASE-1 Null), "012 clone 1" (IL15/IR15α-P2A-HLA-E KI, BCMA CAR KI, CIITA Null, B2M Null, ADAM17 Null), "008 clone 2" (IL15/IR15α-P2A-HLA-E KI, BCMA CAR KI, CIITA Null, B2M Null), and WT iNK cells towards K562 and MM1S cancer cells was determined using a GFP-based killing assay. The cancer cells were labeled with GFP and killing was monitored over 4 hours. WT cells displayed more effective cytotoxicity against K562 cells than the edited cells (FIGS. 27A, 27B). The "012 clone 1" cells displayed greater cytotoxicity against the BCMA⁺ expressing MI S cancer cell line than the WT and other edited cells (FIGS. 28A, 28B).

Example 14: Anti-CD30 CAR Development and Selection

Several CD30 CARS were constructed that included variable light and heavy domains from a mouse monoclonal (SEQ ID NOs: 102 and 103, respectively) or a human anti-CD30 antibody (SEQ ID NOs: 104 and 105, respectively), a CD8 transmembrane domain (SEQ ID NO: 122), a CD28 (SEQ ID NO: 123) or 41BB domain (SEQ ID NO: 124), and a CD3Z domain (SEQ ID NO: 125). Table 40 details anti-CD30 CARs.

TABLE 40

Anti-CD30 CARS

| CAR | Name |
|---|---|
| 1 | Brent_vL_vH_CD28 |
| 2 | 5F11_vH_vL-CD28 |
| 3 | Brent_vL_vH_41BB |
| 4 | Brent_vH-vL_CD28 |
| 5 | 5F11_vH_vL_41BB |
| 6 | 5F11_vL_vH-41BB |
| 7 | Brent_vH_vL_41BB |

The anti-CD30 CARS were delivered to WT NK92 cells via lentiviral vectors. After selection, cytotoxicity against L428 cancer cell line was determined using a luciferase killing assay. FIG. 29A shows the NK92 anti-CD30 CAR killing results after 4 hours, wherein CARs 4, 5, and 6 outperformed WT at every ratio, with CARs 5 and 6 exhibiting the best killing. CD30 KO strongly reduced NK92 killing ability. FIG. 29B presents the results after 24 hours. CARs 4, 5, and 6 outperformed WT at 0.5:1, with CARs 5 and 6 showing nearly 100% killing for all ratios. Cytotoxicity was also tested against another cancer cell line, KM-H2. FIG. 30A present results at 4 hours and FIG. 30B shows killing at 24 hours. CARs 4, 5, and 6 showed the best killing. CARs 4, 5, and 6 were chosen for KI into the CIITA gene locus of iPSCs.

Example 15: Generation of Anti-CD30 CAR-P2A-HLA-E Trimer Knock-In, CIITA Null Human Pluripotent Stem Cells Plasmids were designed to insert an anti-CD30 CAR-P2A-HLA-E trimer into the CIITA gene locus essentially as described above in Example 6 (i.e., 86 bp of the CIITA exon 2 would be removed after undergoing HDR). Each donor plasmid contained a CAGGS promoter operably linked to a cDNA of an anti-CD30 CAR-P2A-HLA-E trimer flanked by 800 base pair homology arms with identical sequence to the CIITA gene locus around exon 2. The HLA-E trimer cDNA was composed of a B2M signal peptide fused to an HLA-G presentation peptide fused to the B2M membrane protein fused to the HLA-E protein without its signal peptide. The HLA-E trimer coding sequence (including linkers) is SEQ ID NO: 75 (i.e., SEQ ID NOs: 46, 47, 48, 49, 50, and 51). The P2A peptide sequence (SEQ ID NO: 45) connecting the anti-CD30 CAR and the HLA-E trimer allows for the separate expression of both proteins from the single mRNA. Each donor plasmid also contained a PD-L1 coding sequence (SEQ ID NO: 146) operably linked to an EF-1 alpha promoter (SEQ ID NO: 149) downstream of the right homology arm sequence (SEQ ID NO: 32) such that PD-L1 would be expressed if the plasmid integrated into the genome. Probes spanning the plasmid backbone can be used to detect plasmid integration using ddPCR. FACS with an anti-PD-L1 antibody can be used to remove PD-L1 positive cells.

FIG. 31 presents a schematic of an anti-CD30 CAR 4-P2A-HLA-E encoding plasmid (SEQ ID NO: 110) and Table 41 identifies the elements and locations therein. The anti-CD30 CAR 4 coding sequence is SEQ ID NO: 108 (i.e., SEQ ID NOS: 26, 106, 126, 107, and 128) and the anti-CD30 CAR 4 amino acid sequence is SEQ ID NO: 109. The anti-CD30 CAR 4-P2A-HLA-E coding sequence is SEQ ID NO: 119 (i.e., SEQ ID NOS: 26, 106, 126, 107, 128, and 44-51).

FIG. 32 presents a schematic of an anti-CD30 CAR 5-P2A-HLA-E encoding plasmid (SEQ ID NO: 114) and Table 42 identifies the elements and locations therein. The anti-CD30 CAR 5 coding sequence is SEQ ID NO: 112 (i.e., SEQ ID NOS: 26, 111, 126, 127, and 128) and the anti-CD30 CAR 4 amino acid sequence is SEQ ID NO: 113. The anti-CD30 CAR 5-P2A-HLA-E coding sequence is SEQ ID NO: 120 (i.e., SEQ ID NOS: 26, 111, 126, 127, 128, and 44-51).

FIG. 33 presents a schematic of an anti-CD30 CAR 6-P2A-HLA-E encoding plasmid (SEQ ID NO: 118) and Table 43 identifies the elements and locations therein. The anti-CD30 CAR 6 coding sequence is SEQ ID NO: 116 (i.e., SEQ ID NOS: 26, 115, 126, 127, and 128) and the anti-CD30 CAR 4 amino acid sequence is SEQ ID NO: 117. The anti-CD30 CAR 6-P2A-HLA-E coding sequence is SEQ ID NO: 121 (i.e., SEQ ID NOS: 26, 115, 126, 127, 128, and 44-51).

TABLE 41

Elements of anti-CD30 CAR 4-P2A-HLA-E Donor Plasmid

| Element | Location (size in bp) | SEQ ID NO: |
|---|---|---|
| LHA-CIITA | 11,107-641 (800) | 22 |
| CMV enhancer | 670-1049 (380) | 23 |
| chicken β-actin promoter | 1052-1327 (276) | 24 |
| chimeric intron | 1328-2336 (1009) | 25 |
| CD8a signal peptide | 2381-2443 (63) | 26 |
| Brent_vH_vL | 2444-3172 (729) | 106 |
| CD8TM | 3173-3436 (264) | 126 |
| CD28 domain | 3437-3556 (120) | 107 |
| CD3Z domain | 3557-3892 (336) | 128 |
| GSG tag | 3893-3901 (9) | 44 |
| P2A | 3902-3958 (57) | 45 |
| B2M signal sequence | 3959-4018 (60) | 46 |
| HLA-G peptide | 4019-4045 (27) | 47 |
| GS linker | 4046-4090 (45) | 48 |
| B2M | 4091-4387 (297) | 49 |
| GS linker | 4388-4447 (60) | 50 |
| HLA-E | 4448-5458 (1011) | 51 |
| 3X Stop codons | 5459-5467 (9) | 52 |
| bGH poly(A) signal | 5485-5709 (225) | 31 |
| RHA-CIITA | 5716-6515 (800) | 32 |
| EF-1 alpha promoter | 6535-7712 (1178) | 149 |
| PD-L1 CDS | 7728-8600 (873) | 146 |
| SV40 poly(A) sequence | 8618-8739 (122) | 147 |
| Total plasmid | 11,265 bp | 110 |

TABLE 42

Elements of anti-CD30 CAR 5-P2A-HLA-E Donor Plasmid

| Element | Location (size in bp) | SEQ ID NO: |
|---|---|---|
| LHA-CIITA | 11,205-766 (800) | 22 |
| CMV enhancer | 774-1153 (380) | 23 |
| chicken β-actin promoter | 1156-1431 (276) | 24 |
| chimeric intron | 1432-2440 (1009) | 25 |
| CD8a signal peptide | 2485-2547 (63) | 26 |
| 5F11_vH_vL | 2548-3249 (702) | 111 |
| CD8TM | 3250-3513 (264) | 126 |
| 41BB co-stim domain | 3514-3639 (126) | 127 |
| CD3Z domain | 3640-3975 (336) | 128 |
| GSG tag | 3976-3984 (9) | 44 |
| P2A | 3985-4041 (57) | 45 |
| B2M signal sequence | 4042-4101 (60) | 46 |
| HLA-G peptide | 4102-4128 (27) | 47 |
| GS linker | 4129-4173 (45) | 48 |
| B2M | 4174-4470 (297) | 49 |
| GS linker | 4471-4530 (60) | 50 |
| HLA-E | 4531-5541 (1011) | 51 |
| 3X Stop codons | 5542-5550 (9) | 52 |
| bGH poly(A) signal | 5568-5792 (225) | 31 |
| RHA-CIITA | 5799-6598 (800) | 32 |
| EF-1 alpha promoter | 6618-7795 (1178) | 149 |
| PD-L1 CDS | 7811-8683 (873) | 146 |
| SV40 poly(A) sequence | 8701-8822 (122) | 147 |
| Total plasmid | 12,224 | 114 |

TABLE 43

Elements of anti-CD30 CAR 6-P2A-HLA-E Donor Plasmid

| Element | Location (size in bp) | SEQ ID NO: |
|---|---|---|
| LHA-CIITA | 11,205-766 (800) | 22 |
| CMV enhancer | 795-1174 (380) | 23 |
| chicken β-actin promoter | 1177-1452 (276) | 24 |
| chimeric intron | 1453-2461 (1009) | 25 |
| CD8a signal peptide | 2500-2568 (63) | 26 |
| 5F11_vL_vH | 2569-3270 (700) | 115 |
| CD8TM | 3271-3528 (264) | 126 |
| 41BB co-stim domain | 3529-3654 (126) | 127 |
| CD3Z domain | 3655-3990 (336) | 128 |
| GSG tag | 3991-3999 (9) | 44 |
| P2A | 4000-4056 (57) | 45 |
| B2M signal sequence | 4057-4116 (60) | 46 |
| HLA-G peptide | 4117-4143 (27) | 47 |
| GS linker | 4144-4188 (45) | 48 |
| B2M | 4189-4485 (297) | 49 |
| GS linker | 4486-4545 (60) | 50 |
| HLA-E | 4546-5556 (1011) | 51 |
| 3X Stop codons | 5557-5565 (9) | 52 |
| bGH poly(A) signal | 5583-5807 (225) | 31 |
| RHA-CIITA | 5814-6613 (800) | 32 |
| EF-1 alpha promoter | 6633-7810 (1178) | 149 |
| PD-L1 CDS | 7826-8698 (873) | 146 |
| SV40 poly(A) signal | 8716-8837 (122) | 147 |
| Total plasmid | 11,238 bp | 118 |

The CIITA-T6 gRNA (Table 19) was used to facilitate insertion of the anti-CD30 CAR transgenes at the targeted CIITA gene locus. The target sequence of CIITA-T6 is not present in the donor plasmid and thus the donor plasmid itself would not be targeted by this gRNA. CIITA-T6 induced CRISPR cutting in the human genome at exon 2 of CIITA would lead to a frameshift and loss of CIITA protein. Each CD30 CAR donor plasmid was introduced along with a RNP complex made up of the CIITA targeting gRNA and Cas9 protein. Per 1 million of human embryonic stem cells, 2 μg of plasmid DNA was delivered along with the RNP via electroporation. Electroporation was carried out using the Neon Electroporator with the RNP mixture of Cas9 protein and guide RNA at a molar ratio of 1:5 with absolute values of 125 pmol Cas9 and 625 pmol gRNA per 2 million cells. To form the RNP complex, gRNA and Cas9 were combined in one vessel with R-buffer (Neon Transfection Kit) to a total volume of 25-50 μL and incubated for 15 min at room temperature (RT). Cells were dissociated using ACCUTASE®, then resuspended in STEMFLEX™ media, counted using an NC-200 (ChemoMetec) and centrifuged. A total of 2×10⁶ cells were resuspended with the RNP complex and R-buffer was added to a total volume of 115 μL. This mixture was then electroporated with 3 pulses for 30 ms at 1000 V. Following electroporation, the cells were pipetted out into a well of a 6 well plate filled with STEMFLEX™ media with REVITACELL™ Supplement (100×) and BIO-LAMININ 521 CTG at 1:10 dilution. Cells were cultured in a normoxia incubator (37° C., 8% $CO_2$).

At 2 days post electroporation, the cells were enriched for transfection via fluorescence activated cell sorting (FACS) using an antibody against HLA-E (see Table 21). Plasmid integration analysis revealed that 1/46 cell clones was free of integrated plasmid. However, if PD-L1 positive cells were removed prior to the cell sorting, 24/82 cell clones were plasmid free. Thus, FACS was performed using PD-L1 negative cells. Seven to ten days post electroporation, the cells were again enriched for HLA-E trimer knock in cells using FACS. These enriched cells represent bulk KI population of anti-CD30 CAR-P2A-HLA-E trimer positive cells. PCR for the genotyping of the edited clones was performed and the resulting amplified DNA was assessed for cutting efficiency by TIDE analysis.

Example 16: Differentiating Stem Cells into Natural Killer Cells—Protocol 2

It was discovered that some induced pluripotent stem cells did not differentiate efficiently with Protocol 1 described above in Example 1. Thus, Protocol 2 (also called Aligned Process 2.0 or AP2.0) was developed to differentiate these iPSCs into hematopoietic stem and progenitor cells (HSPCs) and then into natural killer (NK) cells. Prior to differentiation, frozen iPSCs were thawed and re-suspended in NK-MED-001a medium (Table 44). Flasks pre-coated with laminin-521 were used for cell culturing. Medium was changed daily using NK-MED-002a (Table 45) medium until cells were used for differentiation.

NK Cell Differentiation. iPS cells were differentiated using the following steps:
1. Day −1 (afternoon), iPSC aggregation: NK-MED-002a medium was aspirated from flasks containing iPSC and the cells were washed with DPBS (no calcium, no magnesium) (Thermo Fisher Scientific, 14190250). DPBS was aspirated and 2 mL ACCUTASE® (Innovative Cell Technologies, AT-104) was added per T25 flask (or 80 μL of ACCUTASE® per 1 cm²). Cells were incubated at 37° C. for 3-5 min (not more than 7 minutes). Accutase digested cells were diluted with cold NK-MED-002a medium to a ratio of at least 3:1 (NK-MED-002:ACCUTASE®). Cells were gently resuspended and transferred to a conical tube. Optionally, enough NK-MED-002a medium was added to cells to dilute the ACCUTASE® to a ratio of at least 1:1 and up to 4:1 (NK-MED-002a:ACCUTASE®). Cells were pelleted by spinning at 20-300 g for 4 to 5 minutes and re-suspended in 10 mL of NK-MED-003a medium (Table 46). Cells were counted and the cell concentration was diluted to 1×10⁶/mL. 6×10⁶ cells were transferred to another tube and resuspended in a total of 6 mL of NK-MED-003a medium. The cells were transferred to 1 well of ultra-low adhesion 6-well plate (Corning, 3471) and the plate was placed on a platform shaker and rotated at 98 RPM for 18+/−2 hours (overnight).

2. At day 0, morning, at 18+/−2 hours after iPSC aggregation: The plate was rotated in a circular motion to move aggregates towards center of the well and aggregates were collected in a conical tube. Alternatively, all the aggregate solution mix was collected. Aggregates were allowed to settle for 15+/−5 minutes. Cells were resuspended in NK-MED-004 medium (Table 47). The cell number in aggregates was counted. The seeding density was adjusted as needed to resuspend $3\times10^5$ cells in aggregates in 2 mL NK-MED-004 medium and plated in one well of a 6-well low adhesion plate. Alternatively, for scale up, an appropriate number of cells was resuspended and transferred to a PBS spinner vessel (PBS Biotech). Seeding density tested for PBS seeding vessel was approximately $1\times10^5$ cells per mL per final media volume (day 0+8 hrs). The plate was placed on a platform shaker and rotated at 98 RPM for 8 hours or the PBS spinner vessel were placed on a PBS base (PBS-MINI MagDrive Base Unit; PBS Biotech), in $CO_2$ incubator with a rotation speed of RPM 38 to 39.

3. At day 0, afternoon, at 8 hours after NK-MED-004 medium addition: 50 mL or 250 mL per well or spinner vessel, respectively, of NK-MED-005c medium (Table 48) was added. The plate was returned to platform shaker or PBS spinner vessel to its base in the $CO_2$ incubator and left undisturbed until day 2. NK-MED-005c medium components were 2× of their final concentration, therefore it was added to cells in NK-MED-004 at a 1:1 volume ratio.

4. At day 2: NK-MED-005c medium was replaced with NK-MED-006b medium (Table 49).

5. At day 4: NK-MED-006b medium was replaced with NK-MED-007 medium (Table 50).

6. At day 6: NK-MED-007 medium was replaced with NK-MED-008b medium (Table 51), or alternatively: starting at day 6, medium with all aggregates and single cells was transferred into an appropriate volume centrifuge conical tube. Cells were centrifuged and resuspended in NK-MED-008b medium and placed back into original wells and onto platform shaker, or into original vessels and onto base, and returned for continued culture.

7. At day 10: Half or full media change was made with NK-MED-008b medium.

8. At day 14: Full media change was made with NK-MED-009b medium (Table 52).

9. At day 17: One-third media change was made NK-MED-009b medium and then a full media change was made with NK-MED-009b medium.

From day 20 onwards: Starting at day 20, single cell density was estimated from cell culture. A full media change was made with NK-MED-010 medium (Table 53) and cell density adjusted to within 0.8 to $1.5\times10^6$ cells/mL. A full media change with NK-MED-010 medium and adjustment of cell density to $0.8$-$1.5\times10^6$ cells/mL was performed every 2-3 days from day 20 to 30.

In the tables below, the volumes are approximate to get the desired concentrations.

TABLE 44

Medium composition for NK-MED-001a

| Component | Working Conc. | Volume | Stock Conc. |
| --- | --- | --- | --- |
| StemBrew Basal Media | 90% | 980 mL | 100% |
| StemBrew Supplement | 1X | 20 mL | 50X |
| Thiazovivin (Biological Industry, 1226056-71-8) | 2 μM | 200 μL | 10 mM |

TABLE 45

Medium composition for NK-MED-002a

| Component | Working Conc. | Volume | Stock Conc. |
| --- | --- | --- | --- |
| StemBrew Basal Media | 90% | 980 mL | 100% |
| StemBrew Supplement | 1X | 20 mL | 50X |

TABLE 46

Medium composition for NK-MED-003a

| Component | Working Conc. | Volume | Stock Conc. |
| --- | --- | --- | --- |
| StemBrew Basal | 90% | 979 mL | 100% |
| StemBrew Supplement | 1X | 20 mL | 50X |
| Thiazovivin (Biological Industry, 1226056-71-8) | 10 μM | 1000 μL | 10 mM |

TABLE 47

Medium composition for NK-MED-004

| Component | Working Conc. | Volume | Stock Conc. |
| --- | --- | --- | --- |
| STEMdiff APEL 2 Medium (STEMCELL Technologies, 05275) | 100% | 999 mL | 100% |
| rh BMP-4 (Peprotech, 120-05ET) | 30 ng/mL | 300 μL | 100 μg/mL |
| Thiazovivin (Biological Industry, 1226056-71-8) | 10 μM | 1000 μL | 10 mM |

TABLE 48

Medium composition for NK-MED-005c

| Component | Working Conc. | Volume | Stock Conc. |
| --- | --- | --- | --- |
| STEMdiff APEL 2 Medium (STEMCELL Technologies, 05275) | 100% | 998 mL | 100% |
| rh BMP-4 (Peprotech, 120-05ET) | 30 ng/mL | 300 μL | 100 μg/mL |
| rh FGF2 (Peprotech, 100-18C-1MG) | 100 ng/mL | 1000 μL | 100 μg/mL |
| CHIR-99021 (Selleckchem, S1263) | 7 μM | 700 μL | 10 mM |
| Activin-A (R&D Systems, 338-AC-01M/CF) | 5 ng/mL | 100 μL | 50 μg/mL |

TABLE 49

Medium composition for NK-MED-006b

| Component | Working Conc. | Volume | Stock Conc. |
|---|---|---|---|
| STEMdiff APEL 2 Medium (STEMCELL Technologies, 05275) | 100% | 997 mL | 100% |
| rh FGF2 (Peprotech, 100-18C-1MG) | 20 ng/mL | 200 μL | 100 μg/mL |
| rh VEGF165 (Peprotech, 100-20-1MG) | 20 ng/mL | 200 μL | 100 μg/mL |
| rh TPO (Peprotech, 300-18) | 20 ng/mL | 200 μL | 100 μg/mL |
| rh SCF (Peprotech, 300-07) | 100 ng/mL | 1000 μL | 100 μg/mL |
| rh IL-3 (Peprotech, 200-03-100UG) | 40 ng/mL | 400 μL | 100 μg/mL |
| rh Flt3L (Peprotech, 300-19) | 20 ng/mL | 200 μL | 100 μg/mL |
| SB431542 (Selleckchem, S1067) | 5 μM | 500 μL | 10 mM |

TABLE 50

Medium composition for NK-MED-007

| Component | Working Conc. | Volume | Stock Conc. |
|---|---|---|---|
| STEMdiff APEL 2 Medium (STEMCELL Technologies, 05275) | 100% | 998 mL | 100% |
| rh FGF2 (Peprotech, 100-18C-1MG) | 20 ng/mL | 200 μL | 100 μg/mL |
| rh VEGF165 (Peprotech, 100-20-1MG) | 20 ng/mL | 200 μL | 100 μg/mL |
| rh TPO (Peprotech, 300-18) | 20 ng/mL | 200 μL | 100 μg/mL |
| rh SCF (Peprotech, 300-07) | 100 ng/mL | 1000 μL | 100 μg/mL |
| rh IL-3 (Peprotech, 200-03-100UG) | 40 ng/mL | 400 μL | 100 μg/mL |
| rh Flt3L (Peprotech, 300-19) | 20 ng/mL | 200 μL | 100 μg/mL |

TABLE 51

Medium composition for NK-MED-008b

| Component | Working Conc. | Volume | Stock Conc. |
|---|---|---|---|
| DMEM (high glucose, GlutaMAX) (Thermo Fisher, 10566016) | 50.3% | 503 mL | 100% |
| F-12 with GlutaMAX (Thermo Fisher, 31765035) | 28% | 280 mL | 100% |
| GlutaMAX (Thermo Fisher, 35050079) | 1X | 10 mL | 100X |
| Glucose* | 4.66 mM | 4.2 mL | 1110 mM |
| Human AB serum (Valley Biomedical Inc, HP1022) | 20% | 20 mL | 100% |
| Zinc sulfate (Millipore Sigma, Z0251) | 36.2 μM | 978 μL | 37 mM |
| Ethanolamine (Millipore Sigma, E0135) | 50 μM | 3 μL | 16.6M |
| Ascorbic acid (Fisher Scientific, NC0762606) | 15 μg/mL | 15 μL | 10 mg/mL |
| Sodium selenite (Millipore Sigma, S9133-1MG) | 5 ng/mL | 50 μL | 100 μg/mL |
| rh IL-3 (Peprotech, 200-03-100UG) | 5 ng/mL | 50 μL | 100 μg/mL |
| rh IL-7 (Peprotech, 200-07) | 20 ng/mL | 200 μL | 100 μg/mL |
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | 100 μg/mL |

*Total glucose concentration in medium is 20 mM (accounting for glucose in DMEM medium, F12 supplement and added glucose provided here).

TABLE 52

Medium composition for NK-MED-009b

| Component | Working Conc. | Volume | Stock Conc. |
|---|---|---|---|
| DMEM (high glucose, GlutaMAX) (Thermo Fisher, 10566016) | 50.3% | 503 mL | 100% |
| F-12 with GlutaMAX (Thermo Fisher, 31765035) | 28% | 280 mL | 100% |
| GlutaMAX (Thermo Fisher, 35050079) | 1X | 10 mL | 100X |
| Glucose* | 4.66 mM | 4.2 mL | 1110 mM |
| Human AB serum (Valley Biomedical Inc, HP1022) | 20% | 20 mL | 100% |
| Zinc sulfate (Millipore Sigma, Z0251) | 37 μM | 978 μL | 37 mM |
| Ethanolamine (Millipore Sigma, E0135) | 50 μM | 3 μL | 16.6M |
| Ascorbic acid (Fisher Scientific, NC0762606) | 15 μg/mL | 1500 μL | 10 mg/mL |
| Sodium selenite (Millipore Sigma, S9133-1MG) | 5 ng/mL | 50 μL | 100 μg/mL |
| rh IL-7 (Peprotech, 200-07) | 20 ng/mL | 200 μL | 100 μg/mL |
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | 100 μg/mL |

*Total glucose concentration in medium is 20 mM (accounting for glucose in DMEM medium, F12 supplement and added glucose provided here).

TABLE 53

Medium composition for NK-MED-010

| Component | Working Conc. | Volume | Stock Conc. |
|---|---|---|---|
| DMEM (high glucose, GlutaMAX) | 60.5% | 605 mL | 100% |
| F-12 with GlutaMAX | 28% | 280 mL | 100% |
| GlutaMAX | 1X | 10 mL | 100X |
| Glucose* | 2.33 mM | 2.1 mL | 1110 mM |
| Human AB serum | 10% | 100 mL | 100% |
| Zinc sulfate | 37 μM | 978 μL | 37 mM |
| Ethanolamine | 50 μM | 3 μL | 16.6M |
| Ascorbic acid | 15 μg/mL | 1500 μL | 10 mg/mL |
| Sodium selenite | 5 ng/mL | 50 μL | 100 μg/mL |
| Nicotinamide | 6.5 mM | 6.5 mL | 1000 mM |
| rh IL-7 | 10 ng/mL | 100 μL | 100 μg/mL |
| rh Flt3L | 7.5 ng/mL | 75 μL | 100 μg/mL |
| rh IL-15 | 15 ng/mL | 150 μL | 100 μg/mL |
| rh SCF | 20 ng/mL | 200 μL | 100 μg/mL |

*Total glucose concentration in medium is 20 mM (accounting for glucose in DMEM medium, F12 supplement and added glucose provided here).

Example 17. Generation of Human Pluripotent Stem Cells with SERPINB9-P2A-HLA-E Trimer Knock-In and B2M Knock-Out The SERPINB9-P2A-HLA-E trimer sequence was inserted into a human iPSCs cell line. B2M-2 gRNA (SEQ TD NO: 34; Table 19) was used to facilitate the insertion of the SERPINB9-P2A-HLA-E trimer transgene at the targeted B2M gene locus.

A donor plasmid was designed to insert the SERPINB9-P2A-HLA-E trimer transgene into the B2M gene locus such that the starting codon of B2M was removed after undergoing homology directed repair (HDR) to insert the transgene, nullifying any chance of partial B2M expression. The SERPINB9 and HLA-E trimer sequences were linked by P2A peptide sequences to allow for expression of two separate proteins encoded from a single transcript. FIG. 34 presents a schematic of the donor plasmid (SEQ TD NO: 130) and Table 54 identifies the elements and locations therein. The donor plasmid comprises the SERPINB9-P2A-HLA-E trimer transgene (SEQ TD NO: 131) operably linked to a CAGGS promoter (comprising a CMV enhancer, a chicken β-actin promoter, and a chimeric intron) flanked by 800 base pair homology arms with sequence identity to the B2M gene locus around the target site in exon 1. The HLA-E trimer cDNA was composed of a B2M signal peptide fused to an HLA-G presentation peptide fused to the B2M membrane protein fused to the HLA-E protein without its signal peptide. The HLA-E trimer coding sequence (including linkers) is SEQ TD NO: 75 (i.e., SEQ TD NOs: 46, 4, 48, 49, 50, and 51). This HLA-E trimer design has been previously published (Gornalusse et al. (2017) Nat. Biotechnol. 35(8): 765-772).

TABLE 54

Elements of (B2M) SERPINB9-P2A-HLA-E Trimer Donor Plasmid

| Element | Location (size in bp) | SEQ ID NO: |
|---|---|---|
| Left ITR | 1-130 (130) | 21 |
| LHA-B2M | 145-944 (800) | 36 |
| CMV enhancer | 973-1352 (380) | 23 |
| chicken β-actin promoter | 1355-1630 (276) | 24 |
| chimeric intron | 1631-2639 (1009) | 25 |
| SERPINB9 CDS | 2684-3811 (1128) | 129 |
| GSG tag | 3812-3820 (9) | 44 |
| P2A | 3821-3877 (57) | 45 |
| B2M signal sequence | 3878-3937 (60) | 46 |
| HLA-G peptide | 3938-3964 (27) | 47 |
| GS linker 1 | 3965-4009 (45) | 48 |
| B2M membrane protein | 4010-4306 (297) | 49 |
| GS linker 2 | 4307-4366 (60) | 50 |
| HLA-E CDS | 4367-5377 (1011) | 51 |
| 3X Stop codons | 5378-5386 (9) | 52 |
| bGH poly(A) signal | 5404-5628 (225) | 31 |
| RHA-B2M | 5635-6434 (800) | 54 |
| Right ITR | 6476-6616 (141) | 33 |
| Entire plasmid | (8963) | 130 |

The SERPINB9-P2A-HLA-E trimer donor plasmid was introduced along with a ribonucleoprotein (RNP) complex made up of the B2M targeting gRNA and Cas9 protein. Per 1 million of hiPSC cells, 4 μg of plasmid DNA was delivered along with the RNP via electroporation. Electroporation was carried out in hiPSC cells using the Neon Electroporator with the RNP mixture of Cas9 protein (Biomay) and guide RNA (Biospring) at a molar ratio of 5:1 (gRNA:Cas9) with absolute values of 125 pmol Cas9 and 625 pmol gRNA per 1 million cells. To form the RNP complex, gRNA and Cas9 were combined in one vessel with R-buffer (Neon Transfection Kit) to a total volume of 25-50 μL and incubated for 15 min at room temperature (RT). Cells were dissociated using ACCUTASE®, then resuspended in StemFlex media, counted using an NC-200 (Chemometec) and centrifuged. A total of $2\times10^6$ cells were resuspended with the RNP complex and R-buffer was added to a total volume of ~115 μL. This mixture was then electroporated with 3 pulses for 30 ms at 1100 V. Two electroporations was performed. Following electroporation, the cells were pipetted out into a well of a 6 well plate filled with StemFlex media with RevitaCell and laminin 511. The plates were pre-coated with BIOLAMININ 521 CTG at 1:10 dilution. Cells were cultured in a normoxia incubator (37° C., 8% $CO_2$).

Seven to ten days post electroporation, the cells were enriched for HLA-E trimer expressing cells using an antibody against HLA-E (Table 21) via magnetic assisted cell sorting (MACS) using anti-mouse IgG Dynabeads (ThermoFisher, CELLection™ Pan Mouse IgG Kit, 11531D). These enriched cells represent a bulk KI population of SERPINB9-P2A-HLA-E trimer positive cells. This population was assessed for HLA-E expression by flow cytometry, showing >90% HLA-E expression (FIG. 35).

Following MACS-enrichment, the cells were single-cell sorted as described in Example 1. The anti-HLA-E-PE antibody (Table 21) was used for FACS-sorting into 96-well plates. For FACS-sorting, unedited cells served as a negative control. After sorting, the cells were expanded as described in Example 1 and when confluent, samples were split for maintenance and genomic DNA extraction.

PCR for the genotyping of the edited clones (SERPINB9-P2A-HLA-E trimer knock-in, B2M Null Human Pluripotent Stem Cells (hPSCs)) was performed and the resulting amplified DNA was assessed for cutting efficiency by TIDE analysis.

For determining SERPINB9-P2A-HLA-E trimer knock-in genotyping in the target B2M sequence, PCR for relevant regions was performed using a 2-step protocol with Platinum Taq Supermix (Invitrogen, cat #125320176 and Cat #11495017). The sequences of the PCR primers are presented above in Table 26; and the cycling conditions are provided in Table 27.

FIG. 36 shows genotyping results of the transgene KI into B2M gene locus for various edited clones. The presence of a 1.1 kb band indicated successful integration of the KI construct into the B2M gene locus, while the absence of a band indicated a WT genotype.

For determining the presence of any unwanted bacterial plasmid elements from the KI plasmid, two PCRs were performed using Platinum Taq Supermix (Invitrogen, cat #125320176 and Cat #11495017). The sequences of the PCR primers are presented in Tables 55 and 57; and the cycling conditions are provided in Tables 56 and 58.

TABLE 55

Plasmid #1 Primers

| Name | Type | Sequence (5'-3') | SEQ ID NO: |
|---|---|---|---|
| Ori-F2 | forward | CCCTTAACGTGAGTTTTCGTTCCACTGAGC GTCAGACCCCGTAGAAAAGATCAAAGG | 132 |
| Ori-R | reverse | GTCCAACCCGGTAAGACACGACTTATCGC CACTGGCAGCAGCCACTGGTAACAG | 133 |

TABLE 56

Plasmid #1 PCR Cycling Parameters

| Step | Temperature | Time | Cycles |
|---|---|---|---|
| Denaturation | 98° C. | 30 sec | 1 |
| Denaturation | 98° C. | 10 sec | 30 |
| Extension | 72° C. | 10 sec | |
| Elongation | 72° C. | 1 min | 1 |
| Hold | 4° C. | hold | |

TABLE 57

Plasmid #2 Primers

| Name | Type | Sequence (5'-3') | SEQ ID NO: |
|---|---|---|---|
| F1-Ori-F | forward | CACTTGCCAGCGCCCTAGCGCCCGCTCCTTTCGCTTTCTTCCCTTCCTTTCTC | 134 |
| F1-Ori-R2 | reverse | GGGCGCGTCAGCGGGTGTTGGCGGGTGTCGGGG | 135 |

TABLE 58

Plasmid #2 PCR Cycling Parameters

| Step | Temperature | Time | Cycles |
|---|---|---|---|
| Denaturation | 98° C. | 30 sec | 1 |
| Denaturation | 98° C. | 10 sec | 30 |
| Extension | 72° C. | 10 sec | |
| Elongation | 72° C. | 1 min | 1 |
| Hold | 4 | hold | |

FIG. 37 shows the first PCR amplifying the bacterial plasmid elements that are not supposed to integrate into the genome by HDR because they are outside the homology arms. Both the 5' and 3' primers bind outside of the homology arms within the KI plasmid. The presence of a 340 bp band indicates that there is random integration of the plasmid backbone within the genome, clones without bands do not have plasmid insertion.

FIG. 38 shows the second PCR amplifying the bacterial plasmid elements outside of the homology arms. The presence of a 476 bp band indicates that there is random integration of the plasmid backbone within the genome, clones without bands do not have plasmid insertion.

For determining indels in the target B2M sequence, PCR for relevant regions was performed using Platinum Taq Supermix (Invitrogen, cat #125320176 and Cat #11495017). The sequences of the PCR primers are presented above in Table 22; and the cycling conditions are provided in Table 23.

FIG. 39 shows the B2M indel results for various edited clones. The presence of a 573 bp band indicated a WT genotype which would be found in clones that are unedited or are heterozygous for the KI construct, as homozygous clones will not have a band. The B2M KO state of clones was confirmed via PCR and Sanger sequencing. The resulting DNA sequences of the target B2M region were aligned in Snapgene software to determine indel identity and homo- or heterozygosity.

Based on the PCR and Sanger sequencing analysis of the edited clones, the clone shown in lane 25 in FIGS. 36-39 was chosen as "clone 1" and the clone shown in lane 42 was chosen as "clone 2," which were shown to have the SER-PINB9-P2A-HLA-E KI and no bacterial plasmid elements, while the sequencing data confirmed that B2M was completely knocked-out. Clone 1 was homozygous for the KI into B2M while clone 2 was heterozygous for the KI and had an indel of +1T in the B2M WT band. Clones in lanes 2, 19, 23, and 33 were also chosen as "clones 3-6," respectively, and were confirmed homozygous for the SERPINB9-P2A-HLA-E KI into B2M.

Example 18: Differentiation of Stem Cells into Natural Killer Cells

The SERPINB9 KI/HLA-E KI/B2M KO stem cells (clones 1-4) prepared in Example 17, were differentiated into natural killer (NK) cells (iNK cells). FIG. 40 provides a schematic timeline and cell stages of iNK differentiation, as well as the characteristic cell markers at each stage. The iNK differentiation protocol was developed and based on published protocols (see e.g., Ng et al., Nat Protocols 3:768:776 (2008) and U.S. Pat. No. 9,260,696). The iNK cells expressed NK cell markers. FIG. 41 presents an example of $CD45^+/CD56^+$ iNK cells development during IPSC WT and SERPINB9 KI/HLA-E KI/B2M KO lines differentiation to iNK using the iNK differentiation protocol. Listed edits introduced into IPSC did not affect iNK differentiation.

Example 19: SERPINB9 Protects Differentiated Cells from NK Cell Killing

The ability of cells differentiated from the SERPINB9 KI stem cells to survive attack from peripheral blood NK (PB-NK) cells was determined using a luminescent cell viability assay (CellTiter-Glo®, Promega). This assay determines the number of viable cells based on quantitation of the ATP present, which signals the presence of metabolically active cells. After incubation with effector cells, the CellTiter-Glo reagent was added to the target cells and luminescence was measured. The light intensity is linearly related to ATP concentration.

The cytotoxicity of PB-NK cells toward iNK cells differentiated from edited iPSCs was examined. PB-NK effector cells derived from several donors were incubated with day 31 iNK target cells (derived from clones 1 and 2) prepared above in Example 18 at E:T ratios of 1:1 or 2:1 for 18-24 hour. Control target cells included iNK derived from wild-type iPSC cells and B2M KO iPSC cells. FIG. 42A and FIG. 42B present the percent of target cell lysis in the presence of PB-NK cells from two different donors, PBNK donor 4 (FIG. 42A) and PBNK donor 6 (FIG. 42B), respectively. The B2M KO/SERPINB9 KI/HLA-E KI provided protection from NK killing as compared to B2M KO alone. FIGS. 42C-42E show the percent of target cell lysis (i.e., day 35 iNK target cells (derived from clone 4) prepared above in Example 3) in the presence of PB-NK cells from 3 different donors, PBNK-CLL-donor #1 (FIG. 42C), PBNK donor 4 (FIG. 42D), and PB-NK donor 6 (FIG. 42E), respectively, at E:T ratios of 0.5:1, 1:1 or 2:1 for 24 hours.

Example 20: Generation Off Human Pluripotent Stem Cells with SERPINB9-P2A-IL15/IL15Rα Fusion Knock-In and B2M Knock-Out A transgene comprising SERPINB9-P2A-IL15/IL15Rα fusion was inserted in the B2M gene locus of human iPSCs. The B2M-2 gRNA (SEQ ID NO: 34) shown in Table 19 was used. The donor plasmid was designed such that the starting codon of B2M was removed after undergoing homology directed repair to insert the SERPINB9-P2A-IL15/IL15Rα sequence, nullifying any chance of partial B2M expression. FIG. 43 presents a schematic of the plasmid (SEQ ID NO: 148) and Table 59 identifies the elements and locations therein. The donor plasmid contained a CAGGS promoter driven SERPINB9-P2A-IL15/IL15Rα cDNA sequence flanked by 800 base pair homology arms with identical sequence to the B2M gene locus around exon 1. The IL15/IR15α fusion sequence was designed as previously published (Hurton et al. (2016) Proc Natl Acad Sci U S A; 113(48):E7788-E7797. doi: 10.1073/pnas.1610544113). The IL15/IR15α~fusion coding sequence (including linkers) is SEQ TD NO 76 (i.e., SEQ TD NOs: 40, 41, 42, and 43). The SERPINB9-P2A-IL15/IL15Rα coding sequence is SEQ TD NO: 137 (i.e., SEQ ID NOS: 129, 44, 45, and 40-43). The donor plasmid (SEQ TD NO: 148) also contained sequence encoding PD-L1 (SEQ TD NO: 146) driven by an EF-1 alpha promoter (SEQ TD NO: 145) downstream of the right homology arm for screening and removing cell clones in which the donor plasmid erroneously integrated into the genome.

TABLE 59

Elements of (B2M) SERPINB9-P2A-IL15/IL15Rα Donor Plasmid

| Element | Location (size in bp) | SEQ ID NO: |
| --- | --- | --- |
| LHA-B2M | 9791-10590 (800) | 36 |
| CMV enhancer | 10619-353 (380) | 23 |
| chicken β-actin promoter | 356-631 (276) | 24 |
| chimeric intron | 632-1640 (1009) | 25 |
| SERPINB9 CDS | 1685-2812(1128) | 129 |
| GSG tag | 2813-2821(9) | 44 |
| P2A | 2822-2878 (57) | 45 |
| IgE signal peptide | 2879-2932 (54) | 40 |
| IL-15 CDS | 2933-3331 (399) | 41 |
| linker | 3332-3409 (78) | 42 |
| IL15Rα CDS | 3410-4120(711) | 43 |
| bGH poly(A) signal | 4144-4368 (225) | 31 |
| RHA-B2M | 4375-5174 (800) | 54 |
| EF-1α promoter | 5194-6396 (1203) | 145 |
| PD-L1 | 6412-7284 (873) | 146 |
| SV40 poly(A) signal | 7302-7423 (122) | 147 |
| Entire plasmid | 10,645 bp | 148 |

The cells were electroporated with an RNP comprising Cas9 and B2M-2 gRNA and the donor plasmid, cultured, and characterized essentially as described above in Examples 15 and 17. For example, PD-L1 negative cells were cell sorted for IL15 positive cells by FACS on day 2 post electroporation. IL15 positive cells were again cell sorted by FACS post day. 7. FIG. 44 shows that the edited cells were effectively edited and maintained in bulk populations. The bulk population of edited cells were differentiated, essentially as described in Example 16. iNK biomarkers were measured on Day 28 (FIGS. 45A and 45B). In a cell killing assay, day 28 and 35 iNK cells had high level of cytotoxicity against K562 cells (4 hr incubation).

After confirmation of the transgene KI and B2M KO, the cells with the base edits (SERPINB9 KI, IL15/IL15Rα KO, B2M KO) were further edited to have CISH KO (CISH Ex1 T18; SEQ ID NO: 82) and FAS KO (FAS Ex 1 T9; SEQ ID NO: 37) (i.e., prototype edits) and differentiated essentially as described above in Example 18.

Example 21: Generation of Human Pluripotent Stem Cells with SERPINB9-P2A-IL15/IL15Rα Fusion Knock-In and B2M Knock-Out, Anti-CD30 CAR-P2A-HLA-E Trimer Knock-In and CIITA Knock-Out, CISH Knock-Out, and Fas Knock-Out iPSC cells were generated to have SERPINB9-P2A-IL15/IR15α KI and B2M KO, anti-CD30 CAR-P2A-HLA-E KI and CIITA KO, as well as CISH KO and FAS KO, generally as described in Examples 15 and 20, with modifications.

First, SERPINB9-P2A-IL15/IR15α was knocked into the cells using the SERPINB9-P2A-IL15/IR15α plasmid (SEQ ID NO: 148) and the B2M-T2 gRNA. The iPSCs were passaged the day before electroporation and seeded as 10 million cells per T75 flask. On day of electroporation, the cells were split again and electroporated using the Neon Electroporator with the RNP mixture of Cas9 protein (Biomay) and guide RNA (IDT) at a molar ratio of 5:1 (gRNA:Cas9) with absolute values of 625 pmol gRNA and 125 pmol Cas9 per 2 million cells. To form the RNP complex, gRNA and Cas9 were combined in one vessel with R-buffer (Neon Transfection Kit) to a total volume of 25-50 μL and incubated for 15 min at room temperature (RT). This mixture was then combined with the cells to a total volume of ~115 μL using R-buffer. This mixture was then electroporated with 3 pulses for 30 ms at 1000 V. Following electroporation, the cells were pipetted out into a 6 well plate filled with STEMFLEX™ media with REVITACELL™ Supplement (100×) and BIOLAMININ 521 CTG at 1:10 dilution. Cells were cultured in a normoxia incubator (37° C., 8% $CO_2$).

On day 2 post electroporation, the PD-L1 negative cells were FACS-sorted (FACS #1) for IL15 positive cells to enrich for transfected cells. At 7 to 10 days post electroporation, the cells were FACS-sorted (FACS #2) again for IL15' cells to enrich for knock in positive cells (e.g., L5V018B cells). The cells were allowed to expand, and then FAS was knocked out using the FAS Ex1 T9 gRNA (SEQ ID NO: 37). The knockout edits were performed using an RNP of 5:1 (gRNA:Cas9) with absolute values of 625 pmol gRNA and 125 pmol Cas9 per 1 million cells. This mixture was then electroporated with 1 pulse for 20 ms at 1500 V followed by 1 pulse for 100 ms at 500 V. The cells were electroporated with RNP targeting FAS twice 3 days apart to ensure near 100% knockout. Following knockout of FAS, the cells were treated with RNP targeting CISH (CISH Ex1 T18 gRNA (SEQ ID NO: 82)) and were also electroporated twice 3 days apart to ensure near 100% knockout of CISH. After this targeting, the bulk population represents an enriched population of SERPINB9-P2A-IL15/IR15α KI cells with knockouts of B2M, FAS, and CISH (e.g., BL5V019B cells).

This population was expanded and the cells were electroporated with a plasmid encoding anti-CD30 CAR-P2A-HLA-E trimer (e.g., SEQ ID NO: 110, 114, or 118 encoding anti-CD30 CAR 4, 5, or 6, respectively) and RNP targeting CIITA. This electroporation for KI was done the same way as the electroporation for KI of SERPINB9-P2A-IL15/IR15α above. At 2 days post electroporation, the cells were enriched for transfection by performing FACS (FACS #3) for HLA-E. At 7 to 10 days post electroporation, the cells were FACS (FACS #4) sorted again for HLA-E to enrich for HLA-E knock in positive cells. After FACS #4, the cells were bulk sorted to remove residual PD-L1 positive cells. This population represents an enriched bulk of SERPINB9-P2A-IL15/IR15α KI and anti-CD30 CAR-P2A-HLA-E KI double positive cells with a knockout of B2M, FAS, CISH, and CIITA (e.g., termed L5V024B (anti-CD30 CAR4), L5V025B (anti-CD30 CAR5), or L5V026B (anti-CD30 CAR6) cells). The cells were differentiated essentially as described in Example 18 and characterized. Some of the cells from the bulk population cells were single cell sorted for IL15 and HLA-E double positive cells and plated on 96 well plates for the generation of single cell clones.

Example 22: Characterization of iNK Cells Derived from SERPINB9 KI, IL15/IL15Rα KI, Anti-CD30 CAR KI, HLA-E KI, B2M KO, CIITA KO, CISH KO, FAS KO Cells FIG. 46 presents expression patterns of CD45 and CD56 during iNK differentiation of the cells with base edits (e.g., SERPINB9-P2A-IL15/IR15α KI, B2M KO), prototype edits (e.g., SERPINB9-P2A-IL15/IR15α KI, B2M KO, CISH KO, FAS KO), and the CAR inserts (e.g., SERPINB9-P2A-IL15/IR15α KI, anti-CD30 CAR-P2A-HLA-E KI, B2M KO, FAS KO, CISH KO, and CIITA KO). By day 36, more than 99% of all the cell lines were CD45+/CD56+, indicating efficient iNK differentiation.

Co-incubation of day 29 iNK cells with various CD30+ cancer cells revealed that the cells with the anti-CD30 CARS were more effective killers than the cells with base edits or prototype edits (see FIGS. 47A-D). Some of the anti-CD30 CAR cells had more than 90% killing after 4 hrs at the highest effector-target ratio (5:1). In general, CAR5 outperformed CAR4 and CAR6 in the CD30 cancer cell cytotoxicity assay.

Example 23: In Vivo Testing of iNK Cells Derived from SERPINB9 KI, IL15/IL15Rα KI, Anti-CD30 CAR KI, HLA-E KI, B2M KO, CIITA KO, CISH KO, FAS KO Cells Mice were intravenously injected with $5 \times 10^6$ L428 cancer cells labeled with luciferase. Four days later (day 0), $10 \times 10^6$ iNK cells comprising CAR5 (2:1 E:T ratio) were intravenously injected into the mice. Two more intravenous injections of 10 million iNK cells at days 7 and 14 of iNK cells will be given, and the organs will be harvested at day 28 for cancer cell localization. FIG. 48 presents a schematic of the protocol.

Example 24: Alternatives to Differentiating Stem Cells into Natural Killer Cells—Protocol 2.5

The differentiation protocol according to Example 16 was repeated with the following alterations, alone or in combination:
1. During the NK Cell differentiation stage, iPS cells were cultured and aggregated using a "scaled up" approach. Specifically, the NK cell differentiation, Step 1 (Day −1 (afternoon), iPSC aggregation) step was performed as follows. iPSCs were grown in T175, T225, 1-cells stack or 2-cell stack and digested with Accutase as previously described. Accutase digested cells were diluted 1:1 with cold NK-MED-002 medium. Cells were gently resuspended and transferred to a conical tube. Cells were pelleted by spinning at 20-300 g for 4 to 5 minutes and re-suspended in 10 mL of NK-MED-003 medium. Cells were counted and the cell concentration was diluted to $1 \times 10^6$/mL. $60$-$100 \times 10^6$ cells were transferred to PBS100 and resuspended in a total of 60-100 mL of NK-MED-003 medium correspondingly. PBS vessels were placed onto PBS base and rotated overnight at 45 RPM.
2. ROCK Inhibitor: The ROCK inhibitor used in NK-MED-003 in the previous step, was Y-27652 (10 μM) instead of thiazovivin.
3. Nicotinamide: Nicotinamide was omitted from NK-MED-010 (used at day 20 onwards).

Cells were differentiated and characterized as described in previous examples.

INCORPORATION BY REFERENCE

Various references such as patents, patent applications, and publications, are cited herein, the disclosures of which are hereby incorporated by reference herein in their entireties.

What is claimed is:

1. An in vitro method of generating a genetically modified cell, comprising delivering to a cell:
   (a) a first CRISPR associated endonuclease;
   (b) a first guide RNA (gRNA) targeting a target site in the Class II major histocompatibility complex transactivator (CIITA) gene locus; and
   (c) a first vector comprising a nucleic acid, wherein the nucleic acid comprises (i) a nucleotide sequence having sequence homology with a genomic region located left of the target site in the CIITA gene locus, (ii) a polynucleotide sequence encoding HLA class I histocompatibility antigen, alpha chain E (HLA-E), and (iii) a nucleotide sequence having sequence homology with a genomic region located right of the target site in the CIITA gene locus, wherein (ii) is flanked by (i) and (iii), wherein the polynucleotide encoding HLA-E encodes an HLA-E trimer, wherein the HLA-E trimer comprises a beta-2-microglobulin (B2M) signal peptide fused to an HLA-G presentation peptide fused to a B2M membrane protein fused to HLA-E without its signal peptide;

wherein the CIITA gene locus is cleaved at the target site and the nucleic acid is inserted into the CIITA gene locus, thereby disrupting the CIITA gene.

2. The method of claim 1, wherein the genetically modified cell has reduced or eliminated expression of CIITA.

3. The method of claim 1, wherein the polynucleotide encoding HLA-E comprises a coding sequence of a chimeric antigen receptor (CAR).

4. The method of claim 3, wherein the CAR is an anti-CD30 CAR, anti-CD19 CAR, anti-CD70 CAR, anti-CD33 CAR, or anti-BCMA CAR.

5. The method of claim 3, wherein the polynucleotide encoding HLA-E and CAR comprises a nucleotide sequence encoding a self-cleaving peptide between the coding sequence of CAR and the coding sequence of HLA-E.

6. The method of claim 5, wherein the self-cleaving peptide is P2A, E2A, F2A or T2A.

7. The method of claim 1, wherein the nucleotide sequence having sequence homology with a genomic region located left of the target site in the CIITA gene locus comprises SEQ ID NO: 22, the nucleotide sequence having sequence homology with a genomic region located right of the target site in the CIITA gene locus comprises SEQ ID NO: 32, or both.

8. The method of claim 1, wherein the first CRISPR associated endonuclease is a Cas9 nuclease and the first gRNA comprises a spacer sequence corresponding to a target sequence selected from the group consisting of SEQ ID NOs: 13-17.

9. The method of claim 1, comprising delivering to the cell:
  a second CRISPR associated endonuclease;
  a second guide RNA (gRNA) targeting a target site in the B2M gene locus; and
  a second vector comprising a nucleic acid, wherein the nucleic acid comprises (i) a nucleotide sequence having sequence homology with a genomic region located left of the target site in the B2M gene locus, (ii) a polynucleotide sequence encoding SERPINB9, and (iii) a nucleotide sequence having sequence homology with a genomic region located right of the target site in the B2M gene locus, wherein (ii) is flanked by (i) and (iii);
  wherein the B2M gene locus is cleaved at the target site and the nucleic acid is inserted into the B2M gene locus, thereby disrupting the B2M gene to result in reduced or eliminated expression of B2M.

10. The method of claim 9, wherein the polynucleotide sequence encoding SERPINB9 comprises a coding sequence of a fusion protein of interleukin 15 (IL15) and interleukin 15 receptor subunit alpha (IL15Rα).

11. The method of claim 10, wherein the polynucleotide sequence encoding SERPINB9 and the fusion protein of IL15 and IL15Rα comprises a self-cleaving peptide between the coding sequence of the SERPINB9 protein and the coding sequence of the fusion protein.

12. The method of claim 11, wherein the polynucleotide sequence encoding SERPINB9 and the fusion protein of IL15 and IL15Rα comprises a nucleotide sequence of SEQ ID NO: 137.

13. The method of claim 10, wherein the polynucleotide sequence encoding SERPINB9 and the fusion protein of IL15 and IL15Rα is operably linked to an exogenous promoter.

14. The method of claim 9, wherein the second-RNA guided CRISPR associated endonuclease is a Cas9 nuclease.

15. The method of claim 9, wherein the nucleotide sequence having sequence homology with a genomic region located left of the target site in the B2M gene locus comprises SEQ ID NO: 36, the nucleotide sequence having sequence homology with a genomic region located right of the target site in the B2M gene locus comprises SEQ ID NO: 54, or both.

16. The method of claim 1, comprising delivering to the cell
  a third CRISPR associated endonuclease;
  a third guide RNA (gRNA) targeting a target site in the cytokine-inducible SH2-containing protein (CISH) gene locus;
  wherein the CISH gene locus is cleaved at the target site and at least one insertion or deletion mutation is introduced into the CISH gene, thereby disrupting the CISH gene.

17. The method of claim 1, comprising delivering to the cell
  a fourth CRISPR associated endonuclease;
  a fourth guide RNA (gRNA) targeting a target site in the Fas cell surface death receptor (FAS) gene locus;
  wherein the FAS gene locus is cleaved at the target site and at least one insertion or deletion mutation is introduced into the FAS gene, thereby disrupting the FAS gene.

18. The method of claim 1, wherein the cell is a stem cell.

19. The method of claim 18, wherein the stem cell is an embryonic stem cell, an adult stem cell, an induced pluripotent stem cell, a pluripotent stem cell, or a hematopoietic stem and progenitor cell.

* * * * *

SEQUENCE LISTING

```
Sequence total quantity: 149
SEQ ID NO: 1            moltype = DNA  length = 20
FEATURE                 Location/Qualifiers
source                  1..20
                        mol_type = genomic DNA
                        organism = Homo sapiens
SEQUENCE: 1
ggtcgcggcg ccagcacgaa                                                  20

SEQ ID NO: 2            moltype = DNA  length = 20
FEATURE                 Location/Qualifiers
source                  1..20
                        mol_type = genomic DNA
                        organism = Homo sapiens
SEQUENCE: 2
ccgaagcccg ggtcatccgg                                                  20

SEQ ID NO: 3            moltype = DNA  length = 20
FEATURE                 Location/Qualifiers
source                  1..20
                        mol_type = genomic DNA
                        organism = Homo sapiens
SEQUENCE: 3
ccgcgacctc cggatgaccc                                                  20

SEQ ID NO: 4            moltype = DNA  length = 20
```

```
FEATURE                Location/Qualifiers
source                 1..20
                       mol_type = genomic DNA
                       organism = Homo sapiens
SEQUENCE: 4
cgtgctggcg ccgcgacctc                                              20

SEQ ID NO: 5           moltype = DNA  length = 20
FEATURE                Location/Qualifiers
source                 1..20
                       mol_type = genomic DNA
                       organism = Homo sapiens
SEQUENCE: 5
cgaaaggaac cacgctggtc                                              20

SEQ ID NO: 6           moltype = DNA  length = 20
FEATURE                Location/Qualifiers
source                 1..20
                       mol_type = genomic DNA
                       organism = Homo sapiens
SEQUENCE: 6
cagcgtggtt cctttcgtgc                                              20

SEQ ID NO: 7           moltype = DNA  length = 20
FEATURE                Location/Qualifiers
source                 1..20
                       mol_type = genomic DNA
                       organism = Homo sapiens
SEQUENCE: 7
gccgcgacct ccggatgacc                                              20

SEQ ID NO: 8           moltype = DNA  length = 20
FEATURE                Location/Qualifiers
source                 1..20
                       mol_type = genomic DNA
                       organism = Homo sapiens
SEQUENCE: 8
gaaccacgct ggtcaggaat                                              20

SEQ ID NO: 9           moltype = DNA  length = 20
FEATURE                Location/Qualifiers
source                 1..20
                       mol_type = genomic DNA
                       organism = Homo sapiens
SEQUENCE: 9
cagcacgaaa ggaaccacgc                                              20

SEQ ID NO: 10          moltype = DNA  length = 20
FEATURE                Location/Qualifiers
source                 1..20
                       mol_type = genomic DNA
                       organism = Homo sapiens
SEQUENCE: 10
gtagcggggc cgggaacatg                                              20

SEQ ID NO: 11          moltype = DNA  length = 20
FEATURE                Location/Qualifiers
source                 1..20
                       mol_type = genomic DNA
                       organism = Homo sapiens
SEQUENCE: 11
agaatcttcc cagtaggcgg                                              20

SEQ ID NO: 12          moltype = DNA  length = 20
FEATURE                Location/Qualifiers
source                 1..20
                       mol_type = genomic DNA
                       organism = Homo sapiens
SEQUENCE: 12
ctcaggcgct cagtcactac                                              20

SEQ ID NO: 13          moltype = DNA  length = 20
FEATURE                Location/Qualifiers
source                 1..20
                       mol_type = genomic DNA
                       organism = Homo sapiens
SEQUENCE: 13
ggtccatctg gtcatagaag                                              20
```

```
SEQ ID NO: 14            moltype = DNA   length = 20
FEATURE                  Location/Qualifiers
source                   1..20
                         mol_type = genomic DNA
                         organism = Homo sapiens
SEQUENCE: 14
gctccaggta gccaccttct                                                   20

SEQ ID NO: 15            moltype = DNA   length = 20
FEATURE                  Location/Qualifiers
source                   1..20
                         mol_type = genomic DNA
                         organism = Homo sapiens
SEQUENCE: 15
tagggggcccc aactccatgg                                                  20

SEQ ID NO: 16            moltype = DNA   length = 20
FEATURE                  Location/Qualifiers
source                   1..20
                         mol_type = genomic DNA
                         organism = Homo sapiens
SEQUENCE: 16
ggcttatgcc aatatcggtg                                                   20

SEQ ID NO: 17            moltype = DNA   length = 20
FEATURE                  Location/Qualifiers
source                   1..20
                         mol_type = genomic DNA
                         organism = Homo sapiens
SEQUENCE: 17
aggtgatgaa gagaccaggg                                                   20

SEQ ID NO: 18            moltype = DNA   length = 22
FEATURE                  Location/Qualifiers
source                   1..22
                         mol_type = genomic DNA
                         organism = Homo sapiens
SEQUENCE: 18
tcctgactct ctggtgtgag at                                                22

SEQ ID NO: 19            moltype = DNA   length = 19
FEATURE                  Location/Qualifiers
source                   1..19
                         mol_type = genomic DNA
                         organism = Homo sapiens
SEQUENCE: 19
cagagagcgt cccacagac                                                    19

SEQ ID NO: 20            moltype = DNA   length = 86
FEATURE                  Location/Qualifiers
source                   1..86
                         mol_type = genomic DNA
                         organism = Homo sapiens
SEQUENCE: 20
gccaccatgg agttggggcc cctagaaggt ggctacctgg agcttcttaa cagcgatgct        60
gaccccctgt gcctctacca cttcta                                            86

SEQ ID NO: 21            moltype = DNA   length = 130
FEATURE                  Location/Qualifiers
misc_feature             1..130
                         note = Synthetic
source                   1..130
                         mol_type = other DNA
                         organism = synthetic construct
SEQUENCE: 21
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct                                                              130

SEQ ID NO: 22            moltype = DNA   length = 800
FEATURE                  Location/Qualifiers
source                   1..800
                         mol_type = genomic DNA
                         organism = Homo sapiens
SEQUENCE: 22
catatttatg gggtatatgt gaatatttat tacatgcata gaaggtataa tgatcatgtc        60
aggatatttg aggtatccac atttgggatt gtttaaagat taaatgaaat agtgttaaaa       120
gtatttaata tgcccttcaa caaatgatga ggaaatctta gaatctgctc agactccttc       180
agtttacata ttaggaaact gaggcacaga aaggagcaga gacttgctca agtccaccca       240
```

```
aagcagtaga gcattgtggt taaatgcagg acttcagtca gactgtctgg gttcaaatcc    300
tggttccact tggacatggg tttccttaca taaatcactt cacctctctg agcctcagtt    360
ttctcatatg caaagtgagg ataataataa taccttcctt acatggttac tgatatgagt    420
attaaatgtg ccagctcatg tgcctggcgt ataggaggtg ctttataaac cttagctgtt    480
accactcatg gcattgccaa atgtgggacg ggtctcctga ctctctggtg tgagattgat    540
ggaatccaca ctttccagtt ccctttttcta cctcctgggt atcttctcat atggttgtaa    600
gttccttgga ggaagggaat gtggcttgct ctctccacca cgctgagcat ataagaggtg    660
ctgaatgagc gcttttattc actcctctca tccccagccc tcaccagctg ggagttgttg    720
taggtgtcaa ttttctgcct cttttccaaca ccctgtgagg tgactgagca ttgtcttccc    780
tcccaggcag ctcacagtgt                                                 800

SEQ ID NO: 23           moltype = DNA   length = 380
FEATURE                 Location/Qualifiers
misc_feature            1..380
                        note = Synthetic - Cytomegalovirus
source                  1..380
                        mol_type = other DNA
                        organism = synthetic construct
SEQUENCE: 23
gacattgatt attgactagt tattaatagt aatcaattac ggggtcatta gttcatagcc    60
catatatgga gttccgcgtt acataactta cggtaaatgg cccgcctggc tgaccgccca    120
acgaccccg cccattgacg tcaataatga cgtatgttcc catagtaacg ccaatgggga    180
ctttccattg acgtcaatgg gtggactatt tacggtaaac tgcccacttg gcagtacatc    240
aagtgtatca tatgccaagt acgccccta ttgacgtcaa tgacggtaaa tggcccgcct    300
ggcattatgc ccagtacatg acctttatggg actttcctac ttggcagtac atctacgtat    360
tagtcatcgc tattaccatg                                                 380

SEQ ID NO: 24           moltype = DNA   length = 276
FEATURE                 Location/Qualifiers
source                  1..276
                        mol_type = genomic DNA
                        organism = Gallus gallus
SEQUENCE: 24
tcgaggtgag ccccacgttc tgcttcactc tccccatctc cccccctcc ccacccccaa    60
ttttgtattt atttattttt taattatttt gtgcagcgat gggggcgggg ggggggggg    120
cgcgcgccag gcggggcggg gcggggcgag gggcggggcg gggcgaggcg gagaggtgcg    180
gcggcagcca atcagagcgg cgcgctccga aagtttcctt ttatggcgag gcggcggcgg    240
cggcggccct ataaaaagcg aagcgcgcgg cgggcg                                276

SEQ ID NO: 25           moltype = DNA   length = 1009
FEATURE                 Location/Qualifiers
misc_feature            1..1009
                        note = Synthetic
source                  1..1009
                        mol_type = other DNA
                        organism = synthetic construct
SEQUENCE: 25
ggagtcgctg cgttgccttc gccccgtgcc ccgctccgcg ccgcctcgcg ccgcccgccc    60
cggctctgac tgaccgcgtt actcccacag gtgagcgggc gggacggccc ttctcctccg    120
ggctgtaatt agcgcttggt ttaatgacgg ctcgtttctt ttctgtggct gcgtgaaagc    180
cttaaagggc tccgggaggg cccttttgtgc gggggggagc ggctcggggg gtgcgtgcgt    240
gtgtgtgtgc gtggggagcg ccgcgtgcgg cccgcgctgc ccggcggctg tgagcgctgc    300
gggcgcggcg cggggctttg tgcgctccgc gtgtgcgcga gggagcgcg gccggggcg    360
gtgccccgcg gtgcgggggg gctgcgaggg gaacaaaggc tgcgtgcggg gtgtgtgcgt    420
ggggggtga gcagggggtg tgggcgcggc ggtcggggctg taaccccccc ctgcaccccc    480
ctccccgagt tgctgagcac ggcccggctt cgggtgcggg gctccgtgcg gggcgtggcg    540
cggggctcgc cgtgccgggc gggggggtggc ggcaggtggg ggtgccgggc ggggcgggc    600
cgcctcgggc cgggagggc tcgggggagg ggcgcggcgg ccccggagcg ccggcggctg    660
tcgaggcgcg gcgagccgca gccattgcct tttatgctaa tcgtgcgaga gggcgcaggg    720
acttcctttg tcccaaatct ggcggagccg aaatctggaa ggcgccgccg cacccctcc    780
agcgggcgcg ggcgaagcgg tgcggcgccg gcaggaagga aatgggcggg gagggccttc    840
gtgcgtcgcc gcgccgccgt cccccttctcc atctccagcc tcggggctgc cgcagggga    900
cggctgcctt cggggggggac ggggcagggc ggggttcggg ttctggcgtg tgaccggcgg    960
ctctagagcc tctgctaacc atgttcatgc cttcttcttt ttcctacag                 1009

SEQ ID NO: 26           moltype = DNA   length = 63
FEATURE                 Location/Qualifiers
source                  1..63
                        mol_type = genomic DNA
                        organism = Homo sapiens
SEQUENCE: 26
atggcgcttc cggtgacagc actgctcctc cccttggcgc tgttgctcca cgcagcaagg    60
ccg                                                                    63

SEQ ID NO: 27           moltype = DNA   length = 735
FEATURE                 Location/Qualifiers
misc_feature            1..735
                        note = Synthetic
source                  1..735
```

```
                       mol_type = other DNA
                       organism = synthetic construct
SEQUENCE: 27
caggtgcagc tggtgcagag cggagccgag ctcaagaagc ccggagcctc cgtgaaggtg    60
agctgcaagg ccagcggcaa caccctgacc aactacgtga tccactggtt gagacaagcc   120
cccggccaaa ggctggagtg gatgggctac atcctgccct acaacgacct gaccaagtac   180
agccagaagt tccagggcag ggtgaccatc accagggata gagcgcctc caccgcctat    240
atggagctga gcagcctgag gagcgaggac accgctgtgt actactgtac aaggtggac    300
tgggacggct tctttgaccc ctggggccag ggcacaacag tgaccgtcag cagcggcggc   360
ggaggcagcg gcggcggcgg cagcggcgga ggcggcaagcg aaatcgtgat gacccagagc   420
cccgccacac tgagcgtgag ccctggcgag agggccagca tctcctgcag ggctagccaa   480
agcctggtgc acagcaacgg caacacccac ctgcactggt accagcagag acccggacag   540
gctcccaggc tgctgatcta cagcgtgagc aacaggttct ccgaggtgcc tgccaggttt   600
agcggcagcg gaagcggcac cgactttacc ctgaccatca gcagcctgga gtccgaggac   660
ttcgccgtgt attactgcag ccagaccagc cacatccctt acaccttcgg cggcggcacc   720
aagctggaga tcaaa                                                    735

SEQ ID NO: 28          moltype = DNA    length = 264
FEATURE                Location/Qualifiers
source                 1..264
                       mol_type = genomic DNA
                       organism = Homo sapiens
SEQUENCE: 28
agtgctgctg cctttgtccc ggtatttctc ccagccaaac cgaccacgac tcccgccccg    60
cgccctccga caccgctcc caccatcgcc tctcaacctc ttagtcttcg ccccgaggca    120
tgccgacccg ccgccggggg tgctgttcat acgagggggct tggacttcgc ttgtgatatt   180
tacatttggg ctccgttggc gggtacgtgc ggcgtccttt tgttgtcact cgttattact   240
ttgtattgta atcacaggaa tcgc                                          264

SEQ ID NO: 29          moltype = DNA    length = 126
FEATURE                Location/Qualifiers
source                 1..126
                       mol_type = genomic DNA
                       organism = Homo sapiens
SEQUENCE: 29
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

SEQ ID NO: 30          moltype = DNA    length = 336
FEATURE                Location/Qualifiers
source                 1..336
                       mol_type = genomic DNA
                       organism = Homo sapiens
SEQUENCE: 30
cgagtgaagt tttcccgaag cgcagacgct ccggcatatc agcaaggaca gaatcagctg    60
tataacgaac tgaatttggg acgccgcgag gagtatgacg tgcttgataa acgccggggg   120
agagacccgg aaatgggggg taaaccccga agaaagaatc cccaagaagg actctacaat   180
gaactccaga aggataagat ggcggaggcc tactcagaaa taggtatgaa gggcgaacga   240
cgacggggaa aaggtcacga tggcctctac caagggttga gtacggcaac caaagatacg   300
tacgatgcac tgcatatgca ggccctgcct cccaga                             336

SEQ ID NO: 31          moltype = DNA    length = 225
FEATURE                Location/Qualifiers
source                 1..225
                       mol_type = genomic DNA
                       organism = Bos taurus
SEQUENCE: 31
ctgtgccttc tagttgccag ccatctgttg tttgcccctc cccgtgcct tccttgaccc     60
tggaaggtgc cactcccact gtcctttcct aataaaatga ggaaattgca tcgcattgtc   120
tgagtaggtg tcattctatt ctgggggtg gggtggggca ggacagcaag ggggaggatt   180
gggaagacaa tagcaggcat gctggggatg cggtgggctc tatgg                   225

SEQ ID NO: 32          moltype = DNA    length = 795
FEATURE                Location/Qualifiers
source                 1..795
                       mol_type = genomic DNA
                       organism = Homo sapiens
SEQUENCE: 32
tgaccagatg gacctggctg gagaagaaga gattgagctc tactcaggtg ggccctcctc    60
cctctggtct cttccggtat ccccacccc tcagcttgct gtagagacgg caatcagggg   120
aaattctggt ccctgccctc ccgtcagcac acgacgacagc tcccacgtct gtgggacgct   180
ctctgcagat ggggatgatc tcccagccct gccccgcctc tccctcgttc cccaccagcc   240
ctcttccag aaatttcctt cttcatccaa gggacttttc ctccagaac ccgacacaga    300
caccatcaac tgcgaccagt tcagcaggct gttgtgtgac atggaaggtg atgaagagac   360
cagggaggct tatgccaata tcggtgagga agcacctgag cccagaaaag acaatcaag    420
ggcaagagtt ctttgctgcc acttgtcaat atcacccatt catcatgagc cacgtcagtc   480
ccctcccaca gaaatcattg caggggggat gcggagcaat ggctgaggga acggagactc   540
cagggaagag aggggagatg gaggccagtg ggggaaatag gccccttcac taatgaccac   600
```

```
caagaaaaca aaatctcatg tttacatcct ccacctccat ttctatacgc atttctgctt    660
cttgctcttc tgtccatcct ttctacaaag cccataccat acaccccttt cccttttcct    720
cccagctcct tagccaagct actctagtat ttgtaataac tagcatttac tggatactca    780
tagtatgctc attgc                                                     795

SEQ ID NO: 33          moltype = DNA   length = 141
FEATURE                Location/Qualifiers
misc_feature           1..141
                       note = Synthetic
source                 1..141
                       mol_type = other DNA
                       organism = synthetic construct
SEQUENCE: 33
aggaacccct agtgatggag ttggccactc cctctctgcg cgctcgctcg ctcactgagg     60
ccgggcgacc aaaggtcgcc cgacgcccgg gctttgcccg gcggcctca gtgagcgagc     120
gagcgcgcag ctgcctgcag g                                              141

SEQ ID NO: 34          moltype = DNA   length = 20
FEATURE                Location/Qualifiers
source                 1..20
                       mol_type = genomic DNA
                       organism = Homo sapiens
SEQUENCE: 34
ggccgagatg tctcgctccg                                                20

SEQ ID NO: 35          moltype = DNA   length = 20
FEATURE                Location/Qualifiers
source                 1..20
                       mol_type = genomic DNA
                       organism = Homo sapiens
SEQUENCE: 35
ggattgctca acaaccatgc                                                20

SEQ ID NO: 36          moltype = DNA   length = 800
FEATURE                Location/Qualifiers
source                 1..800
                       mol_type = genomic DNA
                       organism = Homo sapiens
SEQUENCE: 36
gttctagggt ggaaactaag agaatgatgt acctagaggg cgctggaagc tctaaagccc     60
tagcagttac tgcttttact attagtggtc gttttttttct ccccccgcc ccccgacaaa    120
tcaacagaac aaagaaaatt acctaaacag caaggcacata gggaggaact tcttggcaca   180
gaactttcca aacacttttt cctgaaggga tacaagaagc aagaaaggta ctctttcact    240
aggaccttct ctgagctgtc ctcaggatgc ttttgggact attttttctta cccagagaat   300
ggagaaaccc tgcagggaat tcccaagctg tagttataaa cagaagttct ccttctgcta    360
ggtagcattc aaagatctta atcttctggg tttccgtttt ctcgaatgaa aaatgcaggt    420
ccgagcagtt aactggctgg ggcaccatta gcaagtcact tagcatctct ggggccagtc    480
tgcaaagcga gggggcagcc ttaatgtgcc tccagcctga agtcctagaa tgagcgcccg    540
gtgtcccaag ctggggcgcg caccccagat cggaggcgc cgatgtacag acagcaaact    600
cacccagtct agtgcatgcc ttcttaaaca tcacagagact ctaagaaaag gaaactgaaa   660
acgggaaagt ccctctctct aacctggcac tgcgtcgctg gcttggagac aggtgacggt    720
ccctgcgggc cttgtcctga ttggctgggc acgcgtttaa tataagtgga ggcgtcgcgc    780
tggcgggcat tcctgaagct                                                800

SEQ ID NO: 37          moltype = DNA   length = 20
FEATURE                Location/Qualifiers
source                 1..20
                       mol_type = genomic DNA
                       organism = Homo sapiens
SEQUENCE: 37
gattgctcaa caaccatgct                                                20

SEQ ID NO: 38          moltype = DNA   length = 20
FEATURE                Location/Qualifiers
source                 1..20
                       mol_type = genomic DNA
                       organism = Homo sapiens
SEQUENCE: 38
gtgactgaca tcaactccaa                                                20

SEQ ID NO: 39          moltype = DNA   length = 20
FEATURE                Location/Qualifiers
source                 1..20
                       mol_type = genomic DNA
                       organism = Homo sapiens
SEQUENCE: 39
cacttgggca ttaacacttt                                                20

SEQ ID NO: 40          moltype = DNA   length = 54
```

```
FEATURE                 Location/Qualifiers
misc_feature            1..54
                        note = Synthetic
source                  1..54
                        mol_type = other DNA
                        organism = synthetic construct
SEQUENCE: 40
atggactgga cctggatcct gttcctggtg gccgccgcca ccagggtgca cagc          54

SEQ ID NO: 41           moltype = DNA  length = 399
FEATURE                 Location/Qualifiers
source                  1..399
                        mol_type = genomic DNA
                        organism = Homo sapiens
SEQUENCE: 41
ggcattcatg tcttcatttt gggctgtttc agtgcagggc ttcctaaaac agaagccaac    60
tgggtgaatg taataagtga tttgaaaaaa attgaagatc ttattcaatc tatgcatatt   120
gatgctactt tatatacgga aagtgatgtt caccccagtt gcaaagtaac agcaatgaag   180
tgctttctct tggagttaca agttatttca cttgagtccg gagatgcaag tattcatgat   240
acagtagaaa atctgatcat cctagcaaac aacagtttgt cttctaatgg gaatcatgaca   300
gaatctggat gcaaagaatg tgaggaactg gaggaaaaaa atattaaaga atttttgcag   360
agttttgtac atattgtcca aatgttcatc aacacttct                          399

SEQ ID NO: 42           moltype = DNA  length = 78
FEATURE                 Location/Qualifiers
misc_feature            1..78
                        note = Synthetic
source                  1..78
                        mol_type = other DNA
                        organism = synthetic construct
SEQUENCE: 42
agcggcggcg gcagcggcgg cggcggcagc ggcggcggcg gcagcggcgg cggcggcagc    60
ggcggcggca gcctgcag                                                  78

SEQ ID NO: 43           moltype = DNA  length = 711
FEATURE                 Location/Qualifiers
source                  1..711
                        mol_type = genomic DNA
                        organism = Homo sapiens
SEQUENCE: 43
atcacgtgcc ctccccccat gtccgtggaa cacgcagaca tctgggtcaa gagctacagc    60
ttgtactcca gggagcggta catttgtaac tctggtttca agcgtaaagc cggcacgtcc   120
agcctgacgg agtgcgtgtt gaacaaggcc acgaatggtcg cccactggac aacccccagt   180
ctcaaatgca ttagagaccc tgccctggtt caccaaaggc cagcgccacc ctccacagta   240
acgacggcag gggtgacccc acagccagag agcctctccc cttctggaaa agagcccgca   300
gcttcatctc cagctcaaa caacacagcg ccacaacag cagctattgt cccgggctcc     360
cagctgatgc cttcaaaatc accttccaca ggaaccacag agataagcag tcatgagtcc   420
tcccacggca ccccctctca gacaacagcc aagaactggg aactcacagc atccgcctcc   480
caccagccgc caggtgtgta tccacagggc cacagcgaca ccactgtggc tatctccacg   540
tccactgtcc tgctgtgtgg gctgagcgct gtgtctctcc tggcatgcta cctcaagtca   600
aggcaaaactc ccccgctggc cagcgttgaa atggaagcca tggaggctct gccggtgact   660
tgggggacca gcagcagaga tgaagacttg gaaaactgct ctcaccacct a             711

SEQ ID NO: 44           moltype =    length =
SEQUENCE: 44
000

SEQ ID NO: 45           moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 45
gctactaact tcagcctgct gaagcaggct ggagacgtgg aggagaaccc tggacct        57

SEQ ID NO: 46           moltype = DNA  length = 60
FEATURE                 Location/Qualifiers
misc_feature            1..60
                        note = Synthetic
source                  1..60
                        mol_type = other DNA
                        organism = synthetic construct
SEQUENCE: 46
atgtctcgct ccgttgcctt agctgtgctc gcgctactct ctctttctgg attagaggct    60

SEQ ID NO: 47           moltype = DNA  length = 27
FEATURE                 Location/Qualifiers
```

```
source                   1..27
                         mol_type = genomic DNA
                         organism = Homo sapiens
SEQUENCE: 47
gtcatggcgc cccgaacccct cttcctg                                         27

SEQ ID NO: 48            moltype = DNA  length = 45
FEATURE                  Location/Qualifiers
misc_feature             1..45
                         note = Synthetic
source                   1..45
                         mol_type = other DNA
                         organism = synthetic construct
SEQUENCE: 48
ggtggaggcg gttcaggcgg aggtggctct ggcggtggcg gatcg                      45

SEQ ID NO: 49            moltype = DNA  length = 297
FEATURE                  Location/Qualifiers
source                   1..297
                         mol_type = genomic DNA
                         organism = Homo sapiens
SEQUENCE: 49
atccagcgta ctccaaagat tcaggtttac tcacgtcatc cagcagagaa tggaaagtca      60
aatttcctga attgctatgt gtctgggttt catccatccg acattgaagt tgacttactg     120
aagaatggag agagaattga aaaagtggag cattcagact tgtctttcag caaggactgg    180
tcttttctatc tcttgtacta cactgaattc accccactg aaaaagatga gtatgcctgc     240
cgtgtgaacc atgtgacttt gtcacagccc aagatagtta gtgggatcg agacatg        297

SEQ ID NO: 50            moltype = DNA  length = 60
FEATURE                  Location/Qualifiers
misc_feature             1..60
                         note = Synthetic
source                   1..60
                         mol_type = other DNA
                         organism = synthetic construct
SEQUENCE: 50
ggtggtggtg gttctggtgg tggtggttct ggcggcggcg gctccggtgg tggtggatcc      60

SEQ ID NO: 51            moltype = DNA  length = 1011
FEATURE                  Location/Qualifiers
source                   1..1011
                         mol_type = genomic DNA
                         organism = Homo sapiens
SEQUENCE: 51
ggctccccact ccttgaagta tttccacact tccgtgtccc ggcccggccg cggggagccc     60
cgcttcatct ctgtgggcta cgtggacgac acccagttcg tgcgcttcga caacgacgcc    120
gcgagtccga ggatggtgcc gcgggcgccg tggatggagc aggaggggtc agagtattgg    180
gaccgggaga cacgagcgc cagggacacc gcacagattt tccgagtgaa tctgcgcacg     240
ctgcgcggct actacaatca gagcgaggcc ggtctcaca ccctgcagtg gatgcatggc    300
tgcgagctgg ggcccgacgg gcgcttcctc cgcgggtatg aacagttcgc ctacgacggc    360
aaggattatc tcaccctgaa tgaggacctg cgctcctgga ccgcggtgga cacggcggct    420
cagatctccg agcaaaagtc aaatgatgcc tctgaggcgg agcaccagag agcctacctg    480
gaagacacat gcgtggagtg gctccacaaa tacctggaga aggggaagga gacgctgctt    540
cacctggagc cccaaagac acacgtgact caccaccca tctctgacca tgaggccacc     600
ctgaggtgct gggccctggg cttctaccct gcggagatca cactgacctg gcagcaggat    660
ggggagggcc ataccccagga cacggagctc gtggagacca ggcctgcagg ggatggaacc    720
ttccagaagt gggcagctgt ggtggtgcct tctggagagg agcagagata cacgtgccat    780
gtgcagcatg agggggctacc cgagcccgtc accctgagat ggaagccggc ttcccagccc    840
accatcccca tcgtgggcat cattgctggc ctggttctcc ttggatcgt ggtctctgga    900
gctgtggttg ctgctgtgat atggaggaag aagagctcag tgaaaaagg agggagctac    960
tctaaggctg agtggagcga cagtgcccag ggtctgagt ctcacagctt g             1011

SEQ ID NO: 52            moltype =   length =
SEQUENCE: 52
000

SEQ ID NO: 53            moltype = DNA  length = 20
FEATURE                  Location/Qualifiers
source                   1..20
                         mol_type = genomic DNA
                         organism = Homo sapiens
SEQUENCE: 53
ttggaaggcc tgcatcatga                                                  20

SEQ ID NO: 54            moltype = DNA  length = 800
FEATURE                  Location/Qualifiers
source                   1..800
                         mol_type = genomic DNA
                         organism = Homo sapiens
```

```
SEQUENCE: 54
ccagcgtgag tctctcctac cctcccgctc tggtccttcc tctcccgctc tgcaccctct    60
gtggccctcg ctgtgctctc tcgctccgtg acttcccttc tccaagttct ccttggtggc   120
ccgccgtggg gctagtccag ggctggatct cggggaagcg gcggggtggc ctgggagtgg   180
ggaaggggt gcgcacccgg gacgcgcgct acttgcccct ttcggcgggg agcaggggag    240
acctttggcc tacggcgacg ggagggtcgg gacaaagttt agggcgtcga taagcgtcag   300
agcgccgagg ttggggggagg gtttctcttc cgctctttcg cggggcctct ggctccccca  360
gcgcagctgg agtgggggac gggtaggctc gtcccaaagg cgcggcgctg aggtttgtga   420
acgcgtggag gggcgcttgg ggtctggggg aggcgtcgcc cgggtaagcc tgtctgctgc   480
ggctctgctt cccttagact ggagagctgt ggacttcgtc taggcgcccg ctaagttcgc   540
atgtcctagc acctctgggt ctatgtgggg ccacaccgtg ggaggaaac agcacgcgac    600
gtttgtagaa tgcttggctg tgatacaaag cggtttcgaa taattaactt atttgttccc   660
atcacatgtc acttttaaaa aattataaga actaccgtt attgacatct ttctgtgtgc    720
caaggacttt atgtgctttg cgtcatttaa ttttgaaaac agttatcttc cgccatagat   780
aactactatg gttatcttct                                               800

SEQ ID NO: 55            moltype = DNA  length = 20
FEATURE                  Location/Qualifiers
source                   1..20
                         mol_type = genomic DNA
                         organism = Homo sapiens
SEQUENCE: 55
actccaaggg attggaattg                                                20

SEQ ID NO: 56            moltype = DNA  length = 20
FEATURE                  Location/Qualifiers
source                   1..20
                         mol_type = genomic DNA
                         organism = Homo sapiens
SEQUENCE: 56
cagacagcaa actcacccag                                                20

SEQ ID NO: 57            moltype = DNA  length = 20
FEATURE                  Location/Qualifiers
source                   1..20
                         mol_type = genomic DNA
                         organism = Homo sapiens
SEQUENCE: 57
aaactttgtc ccgaccctcc                                                20

SEQ ID NO: 58            moltype = DNA  length = 52
FEATURE                  Location/Qualifiers
source                   1..52
                         mol_type = genomic DNA
                         organism = Homo sapiens
SEQUENCE: 58
aaaagatctg tggactccac caccacgaaa tggcggcacc ttatttatgg tc             52

SEQ ID NO: 59            moltype = DNA  length = 59
FEATURE                  Location/Qualifiers
source                   1..59
                         mol_type = genomic DNA
                         organism = Homo sapiens
SEQUENCE: 59
gctctggaga atctcacgca gaaggcaggc gttttcttta aaaaaaatg cacgaatta       59

SEQ ID NO: 60            moltype = DNA  length = 42
FEATURE                  Location/Qualifiers
source                   1..42
                         mol_type = genomic DNA
                         organism = Homo sapiens
SEQUENCE: 60
aggattggga agacaatagc aggcatgctg gggatgcggt gg                       42

SEQ ID NO: 61            moltype = DNA  length = 59
FEATURE                  Location/Qualifiers
source                   1..59
                         mol_type = genomic DNA
                         organism = Homo sapiens
SEQUENCE: 61
gctctggaga atctcacgca gaaggcaggc gttttcttta aaaaaaatg cacgaatta       59

SEQ ID NO: 62            moltype = DNA  length = 54
FEATURE                  Location/Qualifiers
source                   1..54
                         mol_type = genomic DNA
                         organism = Homo sapiens
SEQUENCE: 62
gccccacccc tcctactttta tgtctccatg gatttgcctg ttttggtcat ttca          54
```

```
SEQ ID NO: 63           moltype = DNA  length = 58
FEATURE                 Location/Qualifiers
source                  1..58
                        mol_type = genomic DNA
                        organism = Homo sapiens
SEQUENCE: 63
ctctaatgca aacttgggta ggtcgtttca cctctctaaa cctcaatttc ctcatttg      58

SEQ ID NO: 64           moltype = DNA  length = 50
FEATURE                 Location/Qualifiers
source                  1..50
                        mol_type = genomic DNA
                        organism = Homo sapiens
SEQUENCE: 64
gagtgaagtt ttcccgaagc gcagacgctc cggcatatca gcaaggacag               50

SEQ ID NO: 65           moltype = DNA  length = 58
FEATURE                 Location/Qualifiers
source                  1..58
                        mol_type = genomic DNA
                        organism = Homo sapiens
SEQUENCE: 65
ctctaatgca aacttgggta ggtcgtttca cctctctaaa cctcaatttc ctcatttg      58

SEQ ID NO: 66           moltype = DNA  length = 7788
FEATURE                 Location/Qualifiers
misc_feature            1..7788
                        note = Synthetic
source                  1..7788
                        mol_type = other DNA
                        organism = synthetic construct
SEQUENCE: 66
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcgccgcac gcgtcatatt tatgggtat atgtgaatat ttattacatg     180
catagaaggt ataatgatca tgtcaggata tttgaggtat ccacatttgg gattgtttaa   240
agattaaatg aaatagtgtt aaaagtattt aatatgccct tcaacaaatg atgaggaaat   300
cttagaatct gctcagactc cttcagttta catattagga aactgaggca cagaaaggag   360
cagagacttg ctcaagtcca cccaaagcag tagagcattg tggttaaatg caggacttca   420
gtcagactgt ctgggttcaa atccggttc cacttggaca tgggtttcct tacataaatc    480
acttcacctc tctgagcctc agttttctca tatgcaaagt gaggataata ataatacctt   540
cctracatgg ttactgatat gagtattaaa tgtgccagct catgtgcctg gcgtatagga   600
ggtgctttat aaaccttagc tgttaccact catggcattg ccaaatgtgg gacgggtctc   660
ctgactctct ggtgtgagat tgatggaatc cacactttcc agttccctt tctacctcct    720
gggtatcttc tcatatggtt gtaagttcct tggaggaagg gaatgtggct tgctctctc    780
accacgctga gcatataaga ggtgctgaat gagcgcttt attcactcct ctcatcccca    840
gccctcacca gctgggagtt gttgtaggtg tcaatttct gcctctttcc aacacccgt     900
gaggtgactg agcattgtct tccctcccag gcagctcaca gtgtaagctt gtggacgata   960
tcgaattcgc acgacattga ttattgacta gttattaata gtaatcaatt acgggtcat   1020
tagttcatag cccatatatg gagttccgcg ttacataact tacggtaaat ggcccgcctg  1080
gctgaccgcc caacgacccc cgcccattga cgtcaataat gacgtatgtt cccatagtaa  1140
cgccaatagg gactttccat tgacgtcaat gggtggacta tttacggtaa actgcccact  1200
tggcagtaca tcaagtgtat catatgccaa gtacgccccc tattgacgtc aatgacggta  1260
aatggcccgc ctggcattat gcccagtaca tgaccttatg gactttcct acttggcagt   1320
acatctacgt attagtcatc gctattacca tgggtcgagg tgagcccac gttctgcttc   1380
actctcccca tctcccccc ctccccaccc caattttgt atttatttat tttttaatta   1440
ttttgtgcag cgatggggc ggggggggg gggcgcgcg ccaggcgggg cggggcgggg   1500
cgagggggcgg ggcgggggcga ggcggagagg tgcggcggca gccaatcaga gcgcgcgct  1560
ccgaaagttt cctttatgg cgaggcggcg gcggcggccg ccctataaaa agcgaagcgc   1620
gcggcgggcg ggagtcgctg cgttgccttc gcccgtgcc ccgctccgcg ccgcctcgcg   1680
ccgcccgccc cggctctgac tgaccgcgtt actcccacag gtgagcgggc gggacggccc  1740
ttctcctccg ggctgtaatt agcgcttggt ttaatgacgg ctcgtttctt ttctgtggct  1800
gcgtgaaagc cttaaagggc tccgggaggg ccctttgtgc gggggggagc ggctcggggg  1860
gtgcgtgcgt gtgtgtgtgc gtgggggagcg ccgcgtgcgg cccgcgctgc ccggcggctg  1920
tgagcgctgc gggcgcggcg cggggctttg tgcgctccgc gtgtgcgcga gggagcgcg   1980
gccggggcg gtgccccgcg gtgcgggggg gctgcgaggg gaacaaaggc tgcgtgcggg  2040
gtgtgtgcgt ggggggtga gcaggggtg tgggcgcggc ggtcgggctg taacccccc    2100
ctgcaccccc ctccccgagt tgctgagcac ggcccggctt cgggtgcggg gctccgtgcg  2160
gggcttggcg cggggctcgc cgtgccgggc gggggtggc ggcaggtggg ggtgccggc    2220
ggggcgggc cgcctcggc cgggggaggc tcgggtgagg ggcggcggcg cccggagcg    2280
ccggcggctg tcgaggcgcg gcgagccgca gccattgcct tttatggtaa tcgtgcgaga  2340
gggcgcaggg acttccttg tcccaaatct ggcggagccg aaatctggga ggcgccgccg   2400
cacccctct agcgggcgcg gggcgaagcg tgcggcgcg gcggaaagaa atggcccccc   2460
gagggccttc gtgcgtcgcc gcgccgccgt cccttctcc atctccagcc tcggggctgc   2520
cgcagggga cggctgcctt cgggggggac gggcagggc ggggttcggc ttctggcgtg    2580
tgaccggcgg ctctagagcc tctgctaacc atgttcatgc cttcttcttt ttcctacagg  2640
ggggatccgt ttatctgcag aattcgccct tgacgtcgcc accatggcgc ttccggtgac  2700
agcactgctc ctccccttgg cgctgttgct ccacgcagca aggccgcagg tgcagctggt  2760
```

```
gcagagcgga gccgagctca agaagcccgg agcctccgtg aaggtgagct gcaaggccag    2820
cggcaacacc ctgaccaact acgtgatcca ctgggtgaga caagcccccg gccaaaggct    2880
ggagtggatg ggctacatcc tgccctacaa cgacctgacc aagtacagcc agaagttcca    2940
gggcagggtg accatcacca gggataagag cgcctccacc gcctatatgg agctgagcag    3000
cctgaggagc gaggacaccg ctgtgtacta ctgtacaagg tgggactggg acggcttctt    3060
tgacccctgg ggccagggca caacagtgac cgtcagcagc ggcggcggag gcagcggcgg    3120
cggcggcagc ggcggaggcg gaagcgaaat cgtgatgacc cagagccccg ccacactgag    3180
cgtgagccct ggcgagaggg ccagcatctc ctgcagggct agccaaagcc tggtgcacag    3240
caacggcaac acccacctgc actggtacca gcagagacca ggacaggctc ccaggctgct    3300
gatctacagc gtgagcaaca ggttctccga ggtgcctgcc aggtttagcg gcagcggaag    3360
cggcaccgac tttaccctga ccatcagcag cgtggagtcc gaggacttcg ccgtgtatta    3420
ctgcagccag accagccaca tcccttacac cttcggcggc ggcaccaagc tggagatcaa    3480
aagtgctgct gcctttgtcc cggtatttct cccagccaaa ccgaccacga ctccgcccc    3540
gcgccctccg cacaccgctc ccaccatcgc ctctcaacct cttagtcttc gccccgaggc    3600
atgccgaccc gccgccgggg gtgctgttca tacgagggc ttggacttcg cttgtgtatat    3660
ttacatttgg gctccgttgg cgggtacgtg cggcgtcctt ttgttgtcac tcgttattac    3720
tttgtattgt aatcacagga atcgcaaacg gggcagaaag aaactcctgt atatattcaa    3780
acaaccattt atgagaccag tacaaactac tcaagaggaa gatggctgta gctgccgatt    3840
tccagaagaa gaagaaggag gatgtgaact gcgagtgaag ttttcccgaa gcgcagacgc    3900
tccggcatat cagcaaggac agaatcagct gtataacgaa ctgaatttgg gacgccgcga    3960
ggagtatgac gtgcttgata acgccgggga gagacccg gaaatggggg gtaaaccccg    4020
aagaaagaat ccccaagaag gactctacaa tgaactccaa aaggataaga tggcggaggc    4080
ctactcagaa ataggtatga agggcgaacg acgacgggga aaaggtcacg atggcctcta    4140
ccaagggttg agtacggcaa ccaaagatac gtacgatgca ctgcatatgc aggccctgcc    4200
tcccagataa tccgctgatc agcctcgact gtgccttcta gttgccagcc atctgttgtt    4260
tgcccctccc ccgtgccttc cttgaccctg gaaggtgcca ctcccactgt cctttcctaa    4320
taaatgaggg aaattgcatc gcattgtctg agtaggtgtc attctattct gggggtggg    4380
gtggggcagg acagcaaggg ggaggattgg gaagacaata gcaggcatgc tggggatgcg    4440
gtgggctcta tgggtcgact gaccagatgg acctggctgg agaagaagag attgagctct    4500
actcaggtgg gccctcctcc ctctggtctc ttccggtatc ccccaccct cagcttgctg    4560
tagagacggc aatcagggga aattctggtc cctgccctcc cgtcagcacc acggacagct    4620
cccacgtctg tgggacgctc tctgcagatg gggatgatct cccagccctg cccgcctct    4680
ccctcgttcc ccaccagccc tcttcccaga aatttccttc ttcatccaag ggacttttcc    4740
tcccagaacc cgacacagac accatcaact gcgaccagtt cagcaggctg ttgtgtgaca    4800
tggaaggtga tgaagagacc agggaggctt atgccaatat cggtgaggaa gcacctgagc    4860
ccagaaaagg acaatcaagg gcaagagttc tttgctgcca cttgtcaata tcacccattc    4920
atcatgagcc acgtcagtcc cctcccacag aaatcattgc aagggggatg cggagcaatg    4980
gctggaggaa cggagactcc agggaagaga ggggagatgg aggccagtgg gggaaatagg    5040
cccctttcact aatgaccacc aagaaaacaa aatctcatgt ttacatccctc cacctccatt    5100
tctatacgca tttctgcttc ttgctcttct gtccatcctt tctacaaagc ccataccata    5160
caccccttc cctttccctc ccagctcctt agccaagcta ctctagtatt tgtaataact    5220
agcatttact ggatactcat agtatgctca ttgctgtccg gtaaccacgt gcggaccgag    5280
gctgcagcgt cgtcctccct aggaacccct agtgatggag ttggccactc cctctctgcg    5340
cgctcgctcg ctcactgagg ccgggcgacc aaaggtcgcc cgacgcccgg gctttgcccg    5400
ggcggcctca gtgagcgagc gagcgcgcag ctgcctgcag gggcgcctga tgcggtattt    5460
tctccttacg catctgtgcg gtatttcaca ccgcatacgt caaagcaacc atagtacgcg    5520
ccctgtagcg gcgcattaag cgcggcgggt gtggtggtta cgcgcagcgt gaccgctaca    5580
cttgccagcg ccctagcgcc cgctcctttc gctttcttcc cttcctttct cgccacgttc    5640
gccggctttc cccgtcaagc tctaaatcgg gggctccctt tagggttccg atttagtgct    5700
ttacggcacc tcgaccccaa aaaacttgat ttgggtgatg gttcacgtag tgggccatcg    5760
ccctgataga cggtttttcg ccctttgacg ttggagtcca cgttctttaa tagtggactc    5820
ttgttccaaa ctggaacaac actcaaccct atctcgggct attctttga tttataaggg    5880
attttgccga tttcggccta ttggttaaaa aatgagctga tttaacaaaa atttaacgcg    5940
aattttaaca aaatattaac gtttacaatt ttatggtgca ctctcagtac aatctgctct    6000
gatgccgcat agttaagcca gccccgacac ccgccaacac ccgctgacgc gccctgacgg    6060
gcttgtctgc tcccggcatc cgcttacaga caagctgtga ccgtctccgg gagctgcatg    6120
tgtcagaggt tttcaccgtc atcaccgaaa cgcgcgagac gaaagggcct cgtgatacgc    6180
ctatttttat aggttaatgt catgaacaat aaaactgtct gcttacataa acagtaatac    6240
aagggtgtt atgagccata ttcaacggga aacgtcgagg ccgcgattaa attccaacat    6300
ggatgctgat ttatatgggt ataaatgggc tcgcgataat gtcgggcaat caggtgcgac    6360
aatctatcgc ttgtatggga agcccgatgc gccagagttg tttctgaaac atggcaaagg    6420
tagcgttgcc aatgatgtta cagatgagat ggtcagacta aactggctga cggaatttat    6480
gcctcttccg accatcaagc atttatccg tactcctgat gatgcatggt tactcaccac    6540
tgcgatcccc ggaaaaacag cattccaggt attagaagaa tatcctgatt caggtgaaaa    6600
tattgttgat gcgctggcag tgttcctgcg ccggttgcat tcgattcctg tttgtaattg    6660
tccttttaac agcgatcgcg tatttcgtct cgctcaggcg caatcacgaa tgaataacgg    6720
tttggttgat gcgagtgatt ttgatgacga gcgtaatggc tggcctgttg aacaagtctg    6780
gaaagaaatg cataaacttt tgccattctc accggattca gtcgtcactc atggtgattt    6840
ctcacttgat aaccttattt ttgacgaggg gaaattaata ggttgtattg atgttggacg    6900
agtcggaatc gcagaccgat accaggatct tgccatccta tggaactgcc tcggtgagtt    6960
ttctccttca ttacagaaac ggcttttca aaaatatggt attgataatc ctgatatgaa    7020
taaattgcag tttcatttga tgctcgatga gttttctaa tctcatgacc aaaatcccctt    7080
aacgtgagtt ttcgttccac tgagcgtcag acccgtaga aagatcaaa ggatcttctt    7140
gagatccttt ttttctgcgc gtaatctgct gcttgcaaac aaaaaaacca ccgctaccag    7200
cggtggtttg tttgccggat caagagctac caactctttt tccgaaggta actggcttca    7260
gcagagcgca gataccaaat actgtccttc tagtgtagcc gtagttaggc caccacttca    7320
agaactctgt agcaccgcct acatacccg ctctgctaat cctgttacca gtggctgctg    7380
ccagtggcga taagtcgtgt cttaccgggt tggactcaag acgatagtta ccggataagg    7440
cgcagcggtc gggctgaacg gggggttcgt gcacacagcc cagcttggag cgaacgacct    7500
```

```
acaccgaact gagatacctacagcgtgagc tatgagaaag cgccacgctt cccgaaggga     7560
gaaaggcgga caggtatccg gtaagcggca gggtcggaac aggagagcgc acgagggagc    7620
ttccagggggg aaacgcctgg tatctttata gtcctgtcgg gtttcgccac ctctgacttg   7680
agcgtcgatt tttgtgatgc tcgtcagggg ggcggagcct atggaaaaac gccagcaacg   7740
cggcctttttt acggttcctg gccttttgct ggccttttgc tcacatgt               7788

SEQ ID NO: 67           moltype = DNA   length = 9077
FEATURE                 Location/Qualifiers
misc_feature            1..9077
                        note = Synthetic
source                  1..9077
                        mol_type = other DNA
                        organism = synthetic construct
SEQUENCE: 67
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcac gcgtgttcta gggtggaaac taagagaatg atgtacctag   180
agggcgctgg aagctctaaa gccctagcag ttactgcttt tactattagt ggtcgttttt   240
ttctcccccc cgccccccga caaatcaaca gaacaaagaa aattacctaa acagcaagga   300
catagggagg aacttcttgg cacagaactt ccaaacact ttttcctgaa gggatacaag    360
aagcaagaaa ggtactcttt cactaggacc ttctctgagc tgtcctcagg atgctttttgg  420
gactattttt cttacccaga gaatggagaa accctgcagg gaatttcccaa gctgtagtta  480
taaacagaag ttctccttct gctaggtagc attcaaagat cttaatcttc tgggtttccg   540
ttttctcgaa tgaaaaatgc aggtccgagc agttaactgg ctgggcacc attagcaagt    600
cacttagcat ctctggggcc agtctgcaaa gcgaggggc agccttaatg tgcctccagc    660
ctgaagtcct agaatgagcg cccggtgtcc caagctgcag cgcaccccc agatccgagg   720
gcgccgatgt acagacagca aactcaccca gtctagtgca tgccttctta aacatcacga   780
gactctaaga aaaggaaact gaaaacggga aagtccctct ctctaacctg gcactgcgtc   840
gctggcttgg agacaggtga cggtccctgc gggccttgtc ctgattggct gggcacgcgt   900
ttaatataag tggaggcgtc gcgctggcgg gcattcctga agctaagctt gtggacgata   960
tcgaattcgc acgacattga ttattgacta gttattaata gtaatcaatt acggggtcat  1020
tagttcatag cccatatatg gagttccgcg ttacataact tacggtaaat ggcccgcctg  1080
gctgaccgcc caacgacccc cgcccattga cgtcaataat gacgtatgtt cccatagtaa  1140
cgccaatagg gactttccat tgacgtcaat gggtggacta tttacggtaa actgcccact  1200
tggcagtaca tcaagtgtat catatgccaa gtacgcccc tattgacgtc aatgacggta   1260
aatggcccgc ctggcattat gcccagtaca tgaccttatg gactttcct acttggcagt  1320
acatctacgt attagtcatc gctattacca tgggtcgagg tgagcccac gttctgcttc   1380
actctcccca tctcccccc ctccccaccc caatttttgt atttatttat tttttaatta   1440
ttttgtgcag cgatggggc ggggggggg gggcgcggc ccaggcggg cggggcgggg     1500
cgagggggcgg ggcggggcga ggcggagagg tgcggcggca gccaatcaga gcggcgcgct  1560
ccgaaagttt ccttttatgg cgaggcggcg cggcggcgg ccctataaaa agcgaagcgc   1620
gcggcgggcg ggagtcgctg cgttgccttc gccccgtgcc ccgctccgcg ccgcctcgcg   1680
ccgcccgccc cggctctgac tgaccgcgtt actcccacag gtgagcgggc gggacggccc  1740
ttctcctccg ggctgtaatt agcgcttggt ttaatgacgg ctcgtttctt ttctgtggct   1800
gcgtgaaagc cttaaagggc tccggggaggg ccctttgtgc gggggggagc ggctcggggg  1860
gtgcgtgcgt gtgtgtgtgc gtggggagcg ccgcgtgcgg cccgcgctgc ccggcggctg  1920
tgagcgctgc gggcgcggc cggggcttttg tgcgctccgc gtgtgcgcga ggggagcgcg   1980
gccgggggcg gtgccccgcg gtgcgggggg gctgcgaggg gaacaaaggc tgcgtgcggg  2040
gtgtgtgcgt gggggggtga gcaggggggtg tgggcgcggc ggtcgggctg taacccccc   2100
ctgcacccc ctccccgagt tgctgagcac ggcccggctt cgggtgcggg gctccgtgcg   2160
gggcgtggcg cggggctcgc cgtgccgggc ggggggtggc ggcaggtggg ggtgccgggc  2220
ggggcgggc cgcctcgggc cggggaggc tcgggggagg ggcgcggcgg ccccggagcc   2280
ccggcggctg tcgaggcgcg gcgagccgca gccattgcct tttatggtaa tcgtgcgaga  2340
gggcgcaggg acttccttttg tcccaaatct ggcggagccg aaatctggga ggcgccgccg   2400
cacccctct agcgggcgcg ggcgaagcgg tgcggcgcga gcaggaagga aatgggcggg  2460
gagggccttc gtgcgtcgcc gcgccgcgt ccccttctcc atctccagcc tcggggctgc   2520
cgcaggggga cggctgcctt cgggggggac ggggcagggc ggggtcggc ttctggcgtg   2580
tgaccggcgg ctctagagcc tctgctaacc atgttcatgc cttcttcttt ttcctacagg  2640
ggggatccgt ttatctgcag aattcgcct tgacgtcgcc accatggact ggacctggat  2700
cctgttcctg gtggccgccg ccaccagggt gcacagcggc attctgtct tcatttttggg  2760
ctgtttcagt gcagggcttc ctaaaacaga agccaactgg gtgaatgtaa taagtgattt   2820
gaaaaaaatt gaagatctta ttcaatctat gcatattgat gctactttat atacggaaag  2880
tgatgttcac cccagttgca aagtaacagc aatgaagtgc tttctcttgg agttacaagt  2940
tatttcactt gagtccggag atgcaagtat tcatgataca gtagaaaatc tgatcatcct  3000
agcaaacaac agtttgtctt ctaatggaa tgtaacagaa tctggatgca aagaatgtga  3060
ggaactggag gaaaaaaata ttaaagaatt tttgcagagt tttgtacata ttgtccaaat  3120
gttcatcaac acttctagcg gcggcggcag cggcggcggc ggcagcggcg gcggcggcag  3180
cggcggcggc ggcagcggcg gcggcagcct gcagatcacg tgccctccc ccatgtccgt  3240
ggaacacgca gacatctggg tcaagagcta cagcctgtac tccaggggag cggtacatttg  3300
taactctggt ttcaagcgta aagcggcac gtccagcctg acggagtgcg tgttgaacaa   3360
ggccacgaat gtcgcccact ggacaacccc cagtctcaaa tgcattagag accctgccct   3420
ggttcaccaa aggccagcgc caccctccac agtaacgacg gcagggtga ccccacagcc   3480
agagagcctc tccccttctg gaaaagagcc cgcagcttca tctcccagct caaacaacac  3540
agcgggcaca acagcagcta ttgtcccggg cgggtcagcc atgccttcaa aatcaccttc   3600
cacaggaacc acagagataa gcagtcatga gtcctccac ggcacccct ctcagacaac    3660
agccaagaac tgggaactca cagcatccgc ctcccaccag ccgccaggtg tgtatcccaca  3720
gggccacagc gacaccactg tggctatctc cacgtccact gtcctgctgt gtgggctgag  3780
cgctgtgtct ctcctggcat gctacctcaa gtcaaggcaa actccccgc tggccagcgt  3840
tgaaatggaa gccatggagg ctctgccggt gacttggggg accagcagca gagatgaaga  3900
```

```
cttggaaaac tgctctcacc acctaggaag cggagctact aacttcagcc tgctgaagca 3960
ggctggagac gtggaggaga accctggacc tatgtctcgc tccgttgcct tagctgtgct 4020
cgcgctactc tctctttctg gattagaggc tgtcatggcg ccccgaaccc tcttcctggg 4080
tggaggcggt tcaggcggag gtggctctgg cggtggcgga tcgatccagc gtactccaaa 4140
gattcaggtt tactcacgtc atccagcaga gaatggaaag tcaaatttcc tgaattgcta 4200
tgtgtctggg tttcatccat ccgacattga agttgactta ctgaagaatg gagagagaat 4260
tgaaaaagtg gagcattcag acttgtcttt cagcaaggac tggtctttct atctcttgta 4320
ctacactgaa ttcaccccca ctgaaaaaga tgagtatgcc tgccgtgtga accatgtgac 4380
tttgtcacag cccaagatag ttaagtggga tcgagacatg ggtggtggtg gttctggtgg 4440
tggtggttct ggcggcggcg gctccggtgg tggtggatcc ggctcccact ccttgaagta 4500
tttccacact tccgtgtccc ggcccggccg cggggagccc cgcttcatct ctgtgggcta 4560
cgtggacgac acccagttcg tgcgcttcga caacgacgcc gcgagtccga ggatggtgcc 4620
gcgggcgccg tggatggagc aggaggggtc agagtattgg gacgggagac cacggagcgc 4680
cagggacacc gcacagattt tccgagtgaa tctgcggacg ctgcgcggct actacaatca 4740
gagcgaggcc gggtctcaca ccctgcagtg gatgcatggc tgcgagctgg ggcccgacgg 4800
gcgcttcctc cgcgggtatg aacagttcgc ctacgacggc aaggattatc tcaccctgaa 4860
tgaggacctg cgctcctgga ccgcggtgga cacggcggct cagatctccg agcaaaagtc 4920
aaatgatgcc tctgaggcgg aagaccagag agcctacctg gaagacacat gcgtggagtg 4980
gctccacaaa tacctggaga aggggaagga gacgctgctt cacctggagc cccaaaagac 5040
acacgtgact caccaccccca tctctgacca tgaggccacc ctgaggtgct gggccctggg 5100
cttctaccct gcggagatca cactgacctg gcagcaggat ggggagggcc atacccagga 5160
cacggagctc gtggagacca ggcctgcagg ggatggaacc ttccagaagt gggcagctgt 5220
ggtggtgcct tctggagagg agcagagata cacgtgccat gtgcagcatg aggggctacc 5280
cgagcccgtc accctgagat ggaagccggc ttcccagccc accatcccca tcgtgggcat 5340
cattgctggc ctggttctcc ttggatctgt ggtctctgga gctgtggttg ctgctgtgat 5400
atggaggaag aagagctcag gtggaaaagg agggagctac tctaaggctg agtggagcga 5460
cagtgcccag gggtctgagt ctcacagctt gtaatgatag ccgctgatca gcctcgactg 5520
tgccttctag ttgccagcca tctgttgttt gcccctcccc cgtgccttcc ttgaccctgg 5580
aaggtgccac tcccactgtc ctttcctaat aaaatgagga aattgcatcg cattgtctga 5640
gtaggtgtca ttctattctg gggggtgggg tggggcagga cagcaagggg gaggattggg 5700
aagacaatag caggcatgct ggggatgcgg tgggctctat gggtcgaccc agcgtgagtc 5760
tctcctaccc tcccgctctg gtccttcctc tcccgctctg cacctctgt ggccctcgct 5820
gtgctctctc gctccgtgac ttcccttctc caagttctcc ttggtggccc gccgtggggc 5880
tagtccaggg ctggatctcg gggaagcggc ggggtggcct gggagtgggg aaggggtgc 5940
gcacccgagg cgcgcgctac ttgcccctt cggcggggag cagggagac ctttggccta 6000
cggcgacggg agggtcggga caaagtttag ggcgtcgata agcgtcagag cgccgaggtt 6060
gggggagggt ttctcttccg ctctttcgcg gggcctctgg ctcccccagc gcagctggag 6120
tggggacggg gtaggctcgt cccaaaggcg cggcgctgag gtttgtgaac gcgtggaggg 6180
gcgcttgggg tctgggggag gcgtcgcccg ggtaagcctg tctgctgcgg ctctgcttcc 6240
cttagactgg agagctgtgg acttcgtcta ggcgcccgct aagttcgcat gtcctagcac 6300
ctctgggtct atgtggggcc acccgtgggg gaggaaacag cacgcgacgt ttgtagaatg 6360
cttggctgtg atacaaagcg gtttcgaata attaacttat ttgttcccat cacatgtcac 6420
tttaaaaaa ttataagaac tacccgttat tgacatcttt ctgtgtgcca aggactttat 6480
gtgctttgcg tcatttaatt ttgaaaacag ttatcttccg ccatagataa ctactatggt 6540
tatcttctgg taaccacgtg cggaccgagg ctgcagcgtc gtcctcccta ggaaccccta 6600
gtgatggagt tggccactcc ctctctgcgc gctcgctcgc tcactgaggc cgggcgacca 6660
aaggtcgccc gacgcccggg cttgcccgg gcggcctcag tgaccgagcg agcgcgcagc 6720
tgcctgcagg ggcgcctgat gcggtatttt ctccttacgc atctgtgcgg tatttcacac 6780
cgcatacgtc aaagcaacca tagtacgcgc cctgtagcgg cgcattaagc gcggcgggtg 6840
tggtggttac gcgcagcgtg accgctacac ttgccagcgc cctagcgccc gctcctttcg 6900
ctttcttccc ttcctttctc gccacgttcg ccggctttcc ccgtcaagct ctaaatcggg 6960
ggctcccttt agggttccga tttagtgctt tacggcacct cgaccccaaa aaacttgatt 7020
tgggtgatgg ttcacgtagt gggccatcgc cctgatagac ggtttttcgc cctttgacgt 7080
tggagtccac gttctttaat agtggactct tgttccaaac tggaacaaca ctcaaccta 7140
tctcggcta ttcttttgat ttataaggga ttttgccgat ttcggcctat tggttaaaaa 7200
atgagctgat ttaacaaaaa tttaacgcga attttaacaa aatattaacg tttacaattt 7260
tatggtgcac tctcagtaca atctgctctg atgccgcata gttaagccag ccccgacacc 7320
cgccaacacc cgctgacgcg ccctgacggg cttgtctgct cccggcatcc gcttacagac 7380
aagctgtgac cgtctccggg agctgcatgt gtcagaggtt ttcaccgtca tcaccgaaac 7440
gcgcgagacg aaagggcctc gtgatacgcc tatttttata ggttaatgtc atgaacaata 7500
aaactgtctg cttacataaa cagtaataca aggggtgtta tgagccatat tcaacgggaa 7560
acgtcgaggc cgcgattaaa ttccaacatg gatgctgatt tatatgggta taatgggct 7620
cgcgataatg tcgggcaatc aggtgcgaca atctatcgct tgtatgggaa gcccgatgcg 7680
ccagagttgt ttctgaaaca tggcaaaggt agcgttgcca atgatgttac agatgagatg 7740
gtcagactaa actggctgac ggaatttatg cctcttccga ccatcaagca ttttatccgt 7800
actcctgatg atgcatggtt actcaccact gcgatcccg gaaaaacagc attccaggta 7860
ttagaagaat atcctgattc aggtgaaaat attgttgatg cgctggcagt gttcctgcgc 7920
cggttgcatt cgattcctgt ttgtaattgt ccttttaaca gcgatcgcgt atttcgtctc 7980
gctcaggcgc aatcacgaat gaataacggt ttggttgatg cgagtgattt tgatgacgag 8040
cgtaatggct ggcctgttga acaagtctgg aaagaaatgc ataaactttt gccattctca 8100
ccggattcag tcgtcactca tggtgatttc tcacttgata accttatttt tgacgagggg 8160
aaattaatag gttgtattga tgttggacga gtcggaatcg cagaccgata ccaggatctt 8220
gccatcctat ggaactgcct cggtgagttt tctccttcat tacagaaacg gctttttcaa 8280
aaatatggta ttgataatcc tgatatgaat aaattgcatc ttcatttgat gctcgatgag 8340
ttttcctaat ctcatgacca aaatccctta acgtgagttt tcgttccact gagcgtcaga 8400
ccccgtagaa aagatcaaag gatcttcttg agatccttt tttctgcgcg taatctgctg 8460
cttgcaaaca aaaaaaccac cgctaccagc ggtggtttgt ttgccggatc aagagctacc 8520
aactcttttt ccgaaggtaa ctggcttcag cagagcgcag ataccaaata ctgtcctct 8580
agtgtagccg tagttaggcc accacttcaa gaactctgta gcaccgccta catacctcgc 8640
```

```
tctgctaatc ctgttaccag tggctgctgc cagtggcgat aagtcgtgtc ttaccgggtt   8700
ggactcaaga cgatagttac cggataaggc gcagcggtcg ggctgaacgg ggggttcgtg   8760
cacacagccc agcttggagc gaacgaccta caccgaactg agatacctac agcgtgagct   8820
atgagaaagc gccacgcttc ccgaaggag aaaggcggac aggtatccgg taagcggcag    8880
ggtcggaaca ggagagcgca cgagggagct tccagggga aacgcctggt atcttttatag   8940
tcctgtcggg tttcgccacc tctgacttga gcgtcgattt ttgtgatgct cgtcaggggg   9000
gcggagccta tggaaaaacg ccagcaacgc ggccttttta cggttcctgg ccttttgctg   9060
gccttttgct cacatgt                                                   9077

SEQ ID NO: 68           moltype = AA   length = 22
FEATURE                 Location/Qualifiers
source                  1..22
                        mol_type = protein
                        organism = Homo sapiens
SEQUENCE: 68
MLLLVTSLLL CELPHPAFLL IP                                              22

SEQ ID NO: 69           moltype = AA   length = 21
FEATURE                 Location/Qualifiers
source                  1..21
                        mol_type = protein
                        organism = Homo sapiens
SEQUENCE: 69
MALPVTALLL PLALLLHAAR P                                               21

SEQ ID NO: 70           moltype = DNA   length = 1524
FEATURE                 Location/Qualifiers
misc_feature            1..1524
                        note = Synthetic
source                  1..1524
                        mol_type = other DNA
                        organism = synthetic construct
SEQUENCE: 70
atggcgcttc cggtgacagc actgctcctc cccttggcgc tgttgctcca cgcagcaagg    60
ccgcaggtgc agctggtgca gagcggagcc gagctcaaga gcccggagc ctccgtgaag    120
gtgagctgca aggccagcgg caacaccctg accaactacg tgatccactg ggtgagacaa   180
gccccccggc aaaggctgga gtggatgggc tacatcctgc cctacaacga cctgaccaag   240
tacagccaga agttccaggg cagggtgacc atcaccaggg ataagagcgc ctccaccgcc   300
tatatggagc tgagcagcct gaggagcgag gacaccgctg tgtactactg tacaaggtgg   360
gactgggacg gcttctttga cccctggggc cagggcacaa cagtgaccgt cagcagcggc   420
ggcggaggca gcggcggcgg cggcagcggc ggaggcggaa gcgaaatcgt gatgacccag   480
agccccgcca cactgagcgt gagccctggc gagagggcca gcatcctg cagggctagc     540
caaagctctgg tgcacagcaa cggcaacacc cacctgcact ggtaccagca gagacccgga   600
caggctccca ggctgctgat ctacagcgtg agcaacaggt tctccgaggt gcctgccagg   660
tttagcggca gcggaagcgg caccgacttt accctgacca tcagcagcgt ggagtccgag   720
gacttcgccg tgtattactg cagccagacc agccacatcc cttacacctt cggcggcggc   780
accaagctgg agatcaaaag tgctgctgcc tttgtcccgg tatttctccc agccaaaccg   840
accacgactc ccgccccgcg ccctccgaca cccgctccca ccatcgcctc tcaacctctt   900
agtcttcgcc ccgaggcatg ccgaccegcc gcggggggtg ctgttcatac gaggggcttg   960
gacttcgctt gtgatattta catttgggct ccgttggcgg gtacgtgcgg cgtcctttg   1020
ttgtcactcg ttattacttt gtattgtaat cacaggaatc gcaaacgggg cagaaagaaa   1080
ctcctgtata tattcaaaca accatttatg agaccagtac aaactactca agaggaagat   1140
ggctgtagct gccgatttcc agaagaagaa gaaggaggat gtgaactgcg agtgaagttt   1200
tcccgaagcg cagacgctcc ggcatatcag caaggacaga atcagctgta taacgaactg   1260
aaattgggac gccgcgagga gtatgacgtg cttgataaac gccgggggag agacccggaa   1320
atggggggta aaccccgaag aaagaatccc caagaaggac tctacaatga actccagaag   1380
gataagatgg cggaggccta ctcagaaata ggtatgaagg gcgaacgacg acggggaaaa   1440
ggtcacgatg gcctctacca agggttgagt acggcaacca aagatacgta cgatgcactg   1500
catatgcagg ccctgcctcc caga                                          1524

SEQ ID NO: 71           moltype = DNA   length = 735
FEATURE                 Location/Qualifiers
misc_feature            1..735
                        note = Synthetic
source                  1..735
                        mol_type = other DNA
                        organism = synthetic construct
SEQUENCE: 71
caggtgcagc tggtgcagag cggagccgag ctcaagaagc ccggagcctc cgtgaaggtg    60
agctgcaagg ccagcggcaa caccctgacc aactacgtga tccactgggt gagacaagcc   120
cccggccaaa ggctggagtg gatgggctac atcctgccct acaacgacct gaccaagtac   180
agccagaagt tccagggcag ggtgaccatc accagggata gagcgcctc accgcctat    240
atggagctga gcagcctgag gagcgaggac accgctgtgt actactgtac aaggtgggac   300
tgggacggct tctttgaccc ctggggccag gcacaacag tgaccgtcag cagcggcggc   360
ggaggcagcg gcggcggcgg cagcggcgga ggcggaagcg aaatcgtgat gacccagagc   420
cccgccacac tgagcgtgag ccctggcgag agggccagca tcctgcag ggctagccaa     480
agcctggtgc acagcaacgg caacacccac ctgcactggt accagcagag acccggacag   540
gctcccaggc tgctgatcta cagcgtgagc aacaggttct ccgaggtgcc tgccaggttt   600
agcggcagcg gaagcggcac cgactttacc ctgaccatca gcagcgtgga gtccgaggac   660
```

```
ttcgccgtgt attactgcag ccagaccagc cacatcccct acaccttcgg cggcggcacc    720
aagctggaga tcaaa                                                     735
```

```
SEQ ID NO: 72           moltype = AA  length = 84
FEATURE                 Location/Qualifiers
source                  1..84
                        mol_type = protein
                        organism = Homo sapiens
SEQUENCE: 72
FVPVFLPAKP TTTPAPRPPT PAPTIASQPL SLRPEACRPA AGGAVHTRGL DFACDIYIWA     60
PLAGTCGVLL LSLVITLYCN HRNR                                           84

SEQ ID NO: 73           moltype = AA  length = 23
FEATURE                 Location/Qualifiers
source                  1..23
                        mol_type = protein
                        organism = Homo sapiens
SEQUENCE: 73
IYIWAPLAGT CGVLLLSLVI TLY                                            23

SEQ ID NO: 74           moltype = AA  length = 508
FEATURE                 Location/Qualifiers
REGION                  1..508
                        note = Synthetic
source                  1..508
                        mol_type = protein
                        organism = synthetic construct
SEQUENCE: 74
MALPVTALLL PLALLLHAAR PQVQLVQSGA ELKKPGASVK VSCKASGNTL TNYVIHWVRQ     60
APGQRLEWMG YILPYNDLTK YSQKFQGRVT ITRDKSASTA YMELSSLRSE DTAVYYCTRW    120
DWDGFFDPWG QGTTVTVSSG GGGSGGGGSG GGGSEIVMTQ SPATLSVSPG ERASISCRAS    180
QSLVHSNGNT HLHWYQQRPG QAPRLLIYSV SNRFSEVPAR FSGSGSGTDF TLTISSVESE    240
DFAVYYCSQT SHIPYTFGGG TKLEIKSAAA FVPVFLPAKP TTTPAPRPPT PAPTIASQPL    300
SLRPEACRPA AGGAVHTRGL DFACDIYIWA PLAGTCGVLL LSLVITLYCN HRNRKRGRKK    360
LLYIFKQPFM RPVQTTQEED GCSCRFPEEE EGGCELRVKF SRSADAPAYQ QGQNQLYNEL    420
NLGRREEYDV LDKRRGRDPE MGGKPRRKNP QEGLYNELQK DKMAEAYSEI GMKGERRRGK    480
GHDGLYQGLS TATKDTYDAL HMQALPPR                                      508

SEQ ID NO: 75           moltype = DNA  length = 1500
FEATURE                 Location/Qualifiers
misc_feature            1..1500
                        note = Synthetic
source                  1..1500
                        mol_type = other DNA
                        organism = synthetic construct
SEQUENCE: 75
atgtctcgct ccgttgcctt agctgtgctc gcgctactct ctctttctgg attagaggct     60
gtcatggcgc cccgaaccct cttcctgggt ggaggcggtt caggcggagg tggctctggc    120
ggtggcggat cgatccagcg tactccaaag attcaggttt actcacgtca tccagcagag    180
aatgaaagt caaatttcct gaattgctat gtgtctgggt tcatccatc cgacattgaa     240
gttgacttac tgaagaatgg agagagaatt gaaaaagtgg agcattcaga cttgtctttc    300
agcaaggact ggtctttcta tctcttgtac tacactgaat tcacccccac tgaaaaagat    360
gagtatgcct gccgtgtgaa ccatgtgact tgtcacagc caagatagt taagtgggat     420
cgagacatgg gtggtggtgg ttctggtggt ggtggtctg cggcggcgg ctccggtggt     480
ggtggatccg gctcccactc cttgaagtat tccacactt ccgtgtcccg gcccggccgg    540
ggggagcccc gcttcatctc tgtgggctac gtggacgaca cccagttcgt gcgcttcgac    600
aacgacgccg cgagtccgag gatggtgccg cgggcgccgt ggatggagca ggagggtca    660
gagtattggg accgggagac acggagcgcc agggacaccg cacagatttt ccgagtgaat    720
ctgcggacgc tgcgcggcta ctacaatcag agcgaggccg ggtctcacac cctgcagtgg    780
atgcatggct gcgagctggg gcccgacgtg cgcttcctcc gcgggtatga cagttcgcc    840
tacgacggca aggattatct cacctgaat gaggacctgc gctcctggac cgcggtgga     900
acggcggctc agatctccga gcaaaagtca aatgatgcct ctgaggcgga gcaccagaga    960
gcctacctgg aagacactg cgtggagtgg ctccacaaat acctgagaa ggggaaggag    1020
acgctgcttc acctggagcc cccaaagaca cacgtgactc accccat ctctgaccat     1080
gaggccaccc tgaggtgctg gccctgggc ttctaccctg cggagatcac actgacctgg    1140
cagcaggat gggagggcca tacccaggac acggagctcg tggagaccag gcctgcaggg    1200
gatgaacct tccagaagtg ggcagctgtg gtggtgcctt ctggagagga gcagagatac    1260
acgtgccatg tgcagcatga ggggctaccc gagcccgtca cctgagatg gaagccggct    1320
tcccagccca ccatcccat cgtgggcatc attgctgctc ttgtttctct tggatcctgg    1380
gtctctggag ctgtggttgc tgctgtgata tggaggaaga agagctcagg tgaaaaggga   1440
gggagctact caaggctga gtggagcgac agtgccagg ggtctgagtc tcacagcttg    1500

SEQ ID NO: 76           moltype = DNA  length = 1251
FEATURE                 Location/Qualifiers
misc_feature            1..1251
                        note = Synthetic
source                  1..1251
                        mol_type = other DNA
                        organism = synthetic construct
```

```
SEQUENCE: 76
atggactgga cctggatcct gttcctggtg gccgccgcca ccagggtgca cagcggcatt    60
catgtcttca tttttgggctg tttcagtgca gggcttccta aaacagaagc caactgggtg   120
aatgtaataa gtgatttgaa aaaaattgaa gatcttattc aatctatgca tattgatgct   180
actttatata cggaaagtga tgttcacccc agttgcaaag taacagcaat gaagtgcttt   240
ctcttggagt tacaagttat ttcacttgag tccggagatg caagtattca tgatacagta   300
gaaaatctga tcatcctagc aaacaacagt ttgtcttcta atgggaatgt aacagaatct   360
ggatgcaaag aatgtgagga actggaggaa aaaatatta aagaattttt gcagagtttt   420
gtacatattg tccaaatgtt catcaacact tctagcggcg gcggcagcgg cggcggcggc   480
agcggcggcg gcggcagcgg cggcggcggc agcggcggcg gcagcctgca gatcacgtgc   540
cctccccca tgtccgtgga acacgcagac atctgggtca agagctacag cttgtactcc   600
agggagcggt acatttgtaa ctctggtttc aagcgtaaag ccggcacgtc cagcctgacg   660
gagtgcgtgt tgaacaaggc cacgaatgtc gcccactgga caaccccag tctcaaatgc   720
attagagacc ctgccctggt tcaccaaagg ccagcgccac cctccacagt aacgacggca   780
ggggtgaccc cacagccaga gagcctctcc ccttctggaa aagagcccgc agcttcatct   840
cccagctcaa acaacacagc ggccacaaca gcagctattg tccgggctc ccagctgatg   900
ccttcaaaat caccttccac aggaaccaca gagataagca gtcatgagtc ctcccacggc   960
acccccctc agacaacagc caagaactgg gaactcacag catccgcctc ccaccagccg  1020
ccaggtgtgt atccacaggg ccacagcgac accactgtgg ctatctccac gtccactgtc  1080
ctgctgtgtg ggctgagcgc tgtgtctctc ctggcatgct acctcaagtc aaggcaaact  1140
cccccgctgg ccagcgttga aatggaagcc atggaggctc tgccggtgac ttgggggacc  1200
agcagcagag atgaagactt ggaaaactgc tctcaccacc taggaagcgg a            1251

SEQ ID NO: 77         moltype = DNA   length = 2808
FEATURE               Location/Qualifiers
misc_feature          1..2808
                      note = Synthetic
source                1..2808
                      mol_type = other DNA
                      organism = synthetic construct
SEQUENCE: 77
atggactgga cctggatcct gttcctggtg gccgccgcca ccagggtgca cagcggcatt    60
catgtcttca tttttgggctg tttcagtgca gggcttccta aaacagaagc caactgggtg   120
aatgtaataa gtgatttgaa aaaaattgaa gatcttattc aatctatgca tattgatgct   180
actttatata cggaaagtga tgttcacccc agttgcaaag taacagcaat gaagtgcttt   240
ctcttggagt tacaagttat ttcacttgag tccggagatg caagtattca tgatacagta   300
gaaaatctga tcatcctagc aaacaacagt ttgtcttcta atgggaatgt aacagaatct   360
ggatgcaaag aatgtgagga actggaggaa aaaatatta aagaattttt gcagagtttt   420
gtacatattg tccaaatgtt catcaacact tctagcggcg gcggcagcgg cggcggcggc   480
agcggcggcg gcggcagcgg cggcggcggc agcggcggcg gcagcctgca gatcacgtgc   540
cctccccca tgtccgtgga acacgcagac atctgggtca agagctacag cttgtactcc   600
agggagcggt acatttgtaa ctctggtttc aagcgtaaag ccggcacgtc cagcctgacg   660
gagtgcgtgt tgaacaaggc cacgaatgtc gcccactgga caaccccag tctcaaatgc   720
attagagacc ctgccctggt tcaccaaagg ccagcgccac cctccacagt aacgacggca   780
ggggtgaccc cacagccaga gagcctctcc ccttctggaa aagagcccgc agcttcatct   840
cccagctcaa acaacacagc ggccacaaca gcagctattg tccgggctc ccagctgatg   900
ccttcaaaat caccttccac aggaaccaca gagataagca gtcatgagtc ctcccacggc   960
acccccctc agacaacagc caagaactgg gaactcacag catccgcctc ccaccagccg  1020
ccaggtgtgt atccacaggg ccacagcgac accactgtgg ctatctccac gtccactgtc  1080
ctgctgtgtg ggctgagcgc tgtgtctctc ctggcatgct acctcaagtc aaggcaaact  1140
cccccgctgg ccagcgttga aatggaagcc atggaggctc tgccggtgac ttgggggacc  1200
agcagcagag atgaagactt ggaaaactgc tctcaccacc taggaagcgg agctactaac  1260
ttcagcctgc tgaagcaggc tggagacgtg gaggagaacc ctggacctat gtctcgctcc  1320
gttgcctag ctgtgctcgc gctactctct ctttctggat tagaggctgt catggcgccc  1380
cgaaccctct tcctgggtgg aggcggttca ggcggaggtg gctctggcgg tggcggatcg  1440
atccagcgta ctccaaagat tcaggtttac tcacgtcatc cagcagagaa tggaaagtca  1500
aatttcctga attgctatgt gtctgggttt catccatccg acattgaagt tgacttactg  1560
aagaatggga gagaattga aaagtggag cattcagact tgtctttcag caaggactgg  1620
tctttctatc tcttgtacta cactgaattc acccccactg aaaaagatga gtatgcctgc  1680
cgtgtgaacc atgtgacttt gtcacagccc aagatagtta agtgggatcg agacatgggt  1740
ggtggtggtt ctggtggtgg tggttctggc ggcggcggct ccgtggtgg tggatccggc  1800
tcccactcct tgaagtattt ccacacttcc gtgtcccggc ccggccgcgg ggagccccgc  1860
ttcatctctg tgggctacgt ggacgacacc cagttcgtgc gcttcgacaa cgacgccgcg  1920
agtccgaggga tggtgccgcg ggcgccgtgg atggagcagg aggttcaga gtattgggac  1980
cgggagacac ggagcgccag ggacaccgca cagatttttcc gagtgaatct gcggacgctg  2040
cgcggctact acaatcagag cgaggccggg tctcacaccc tgcagtggat gcatggctgc  2100
gagctggggc ccgacgggcg cttcctccgc gggtatgaac agttcgccta cgacggcaag  2160
gattatctca ccctgaatga ggacctcgc tcctggaccg cggtggacac ggcggctcag  2220
atctccgagc aaaagtcaaa tgatgcctct gaggcggagc accagagagc ctacctggaa  2280
gacacatgcg tggagtggct ccacaaatac ctggagaagg gaaggagac gctgcttcac  2340
ctggagcccc caaagacaca cgtgactcac caccccatct ctgaccatga ggccaccctg  2400
aggtgctggg ccctggggctt ctaccctgcg agatcacac tgacctggca gcaggatggg  2460
gagggccata cccaggacac ggagctcgtg gagaccaggc ctgcaggga tggaaccttc  2520
cagaagtggg cagctgtggt ggtgccttct ggagaggagc agagatacac gtgccatgtg  2580
cagcatgagg ggctacccga gcccgtcacc ctgagatgga gccggcttc ccagcccacc  2640
atccccatcg tgggcatcat tgctggcctg gttctccttg gatctgtggt ctctggagct  2700
gtggttgctg ctgtgatatg gaggaagaag agctcaggtg gaaaggagg gagctactct  2760
aaggctgagt ggagcgacag tgcccagggg tctgagtctc acagcttg              2808
```

```
SEQ ID NO: 78          moltype = DNA   length = 20
FEATURE                Location/Qualifiers
source                 1..20
                       mol_type = genomic DNA
                       organism = Homo sapiens
SEQUENCE: 78
gctactctct ctttctggcc                                                    20

SEQ ID NO: 79          moltype = DNA   length = 20
FEATURE                Location/Qualifiers
source                 1..20
                       mol_type = genomic DNA
                       organism = Homo sapiens
SEQUENCE: 79
cgcgagcaca gctaaggcca                                                    20

SEQ ID NO: 80          moltype = DNA   length = 20
FEATURE                Location/Qualifiers
source                 1..20
                       mol_type = genomic DNA
                       organism = Homo sapiens
SEQUENCE: 80
ctagggactg cacagtcaat                                                    20

SEQ ID NO: 81          moltype = DNA   length = 20
FEATURE                Location/Qualifiers
source                 1..20
                       mol_type = genomic DNA
                       organism = Homo sapiens
SEQUENCE: 81
tcgccgctgc cgcggggaca                                                    20

SEQ ID NO: 82          moltype = DNA   length = 20
FEATURE                Location/Qualifiers
source                 1..20
                       mol_type = genomic DNA
                       organism = Homo sapiens
SEQUENCE: 82
gtccgctcca cagccagcaa                                                    20

SEQ ID NO: 83          moltype = DNA   length = 20
FEATURE                Location/Qualifiers
source                 1..20
                       mol_type = genomic DNA
                       organism = Homo sapiens
SEQUENCE: 83
gtccgctcca cagccagcaa                                                    20

SEQ ID NO: 84          moltype = DNA   length = 20
FEATURE                Location/Qualifiers
source                 1..20
                       mol_type = genomic DNA
                       organism = Homo sapiens
SEQUENCE: 84
gttccaggga cggggcccac                                                    20

SEQ ID NO: 85          moltype = DNA   length = 20
FEATURE                Location/Qualifiers
source                 1..20
                       mol_type = genomic DNA
                       organism = Homo sapiens
SEQUENCE: 85
tcgggcctcg ctggccgtaa                                                    20

SEQ ID NO: 86          moltype = DNA   length = 20
FEATURE                Location/Qualifiers
source                 1..20
                       mol_type = genomic DNA
                       organism = Homo sapiens
SEQUENCE: 86
cgtactaaga acgtgccttc                                                    20

SEQ ID NO: 87          moltype = DNA   length = 20
FEATURE                Location/Qualifiers
source                 1..20
                       mol_type = genomic DNA
                       organism = Homo sapiens
SEQUENCE: 87
gggttccatt acggccagcg                                                    20
```

```
SEQ ID NO: 88            moltype = DNA  length = 20
FEATURE                  Location/Qualifiers
source                   1..20
                         mol_type = genomic DNA
                         organism = Homo sapiens
SEQUENCE: 88
caggtgttgt cgggcctcgc                                                     20

SEQ ID NO: 89            moltype = DNA  length = 20
FEATURE                  Location/Qualifiers
source                   1..20
                         mol_type = genomic DNA
                         organism = Homo sapiens
SEQUENCE: 89
tactcaatgc gtacattggt                                                     20

SEQ ID NO: 90            moltype = DNA  length = 20
FEATURE                  Location/Qualifiers
source                   1..20
                         mol_type = genomic DNA
                         organism = Homo sapiens
SEQUENCE: 90
aaggctgacc acatccggaa                                                     20

SEQ ID NO: 91            moltype = DNA  length = 20
FEATURE                  Location/Qualifiers
source                   1..20
                         mol_type = genomic DNA
                         organism = Homo sapiens
SEQUENCE: 91
tacattggtg gggccacgag                                                     20

SEQ ID NO: 92            moltype = DNA  length = 20
FEATURE                  Location/Qualifiers
source                   1..20
                         mol_type = genomic DNA
                         organism = Homo sapiens
SEQUENCE: 92
ctgtcagtga aaaccactcg                                                     20

SEQ ID NO: 93            moltype = DNA  length = 20
FEATURE                  Location/Qualifiers
source                   1..20
                         mol_type = genomic DNA
                         organism = Homo sapiens
SEQUENCE: 93
ggtcatcgat gggagcaacg                                                     20

SEQ ID NO: 94            moltype = DNA  length = 20
FEATURE                  Location/Qualifiers
source                   1..20
                         mol_type = genomic DNA
                         organism = Homo sapiens
SEQUENCE: 94
caccaccccg cgggactaga                                                     20

SEQ ID NO: 95            moltype = DNA  length = 20
FEATURE                  Location/Qualifiers
source                   1..20
                         mol_type = genomic DNA
                         organism = Homo sapiens
SEQUENCE: 95
ggtctggcgc tcccgctcgg                                                     20

SEQ ID NO: 96            moltype = DNA  length = 20
FEATURE                  Location/Qualifiers
source                   1..20
                         mol_type = genomic DNA
                         organism = Homo sapiens
SEQUENCE: 96
ccaccacccc gcgggactag                                                     20

SEQ ID NO: 97            moltype = DNA  length = 20
FEATURE                  Location/Qualifiers
source                   1..20
                         mol_type = genomic DNA
                         organism = Homo sapiens
SEQUENCE: 97
```

```
ttaggggtgc caccacccccg                                                    20

SEQ ID NO: 98           moltype = DNA   length = 20
FEATURE                 Location/Qualifiers
source                  1..20
                        mol_type = genomic DNA
                        organism = Homo sapiens
SEQUENCE: 98
ttcacaccat cacgacgcgt                                                     20

SEQ ID NO: 99           moltype = DNA   length = 20
FEATURE                 Location/Qualifiers
source                  1..20
                        mol_type = genomic DNA
                        organism = Homo sapiens
SEQUENCE: 99
acaccatcac gacgcgtggg                                                     20

SEQ ID NO: 100          moltype = DNA   length = 20
FEATURE                 Location/Qualifiers
source                  1..20
                        mol_type = genomic DNA
                        organism = Homo sapiens
SEQUENCE: 100
ctacgagtct gacgggatcg                                                     20

SEQ ID NO: 101          moltype = DNA   length = 20
FEATURE                 Location/Qualifiers
source                  1..20
                        mol_type = genomic DNA
                        organism = Homo sapiens
SEQUENCE: 101
acgacgcgtg ggtggcaagc                                                     20

SEQ ID NO: 102          moltype = AA    length = 111
FEATURE                 Location/Qualifiers
REGION                  1..111
                        note = Synthetic
source                  1..111
                        mol_type = protein
                        organism = synthetic construct
SEQUENCE: 102
DIVLTQSPAS LAVSLGQRAT ISCKASQSVD FDGDSYMNWY QQKPGQPPKV LIYAASNLES          60
GIPARFSGSG SGTDFTLNIH PVEEEDAATY YCQQSNEDPW TFGGGTKLEI K                  111

SEQ ID NO: 103          moltype = AA    length = 117
FEATURE                 Location/Qualifiers
REGION                  1..117
                        note = Synthetic
source                  1..117
                        mol_type = protein
                        organism = synthetic construct
SEQUENCE: 103
QIQLQQSGPE VVKPGASVKI SCKASGYTFT DYYITWVKQK PGQGLEWIGW IYPGSGNTKY          60
NEKFKGKATL TVDTSSSTAF MQLSSLTSED TAVYFCANYG NYWFAYWGQG TQVTVSA            117

SEQ ID NO: 104          moltype = AA    length = 107
FEATURE                 Location/Qualifiers
REGION                  1..107
                        note = Synthetic
source                  1..107
                        mol_type = protein
                        organism = synthetic construct
SEQUENCE: 104
DIQMTQSPTS LSASVGDRVT ITCRASQGIS SWLTWYQQKP EKAPKSLIYA ASSLQSGVPS          60
RFSGSGSGTD FTLTISSLQP EDFATYYCQQ YDSYPITFGQ GTRLEIK                       107

SEQ ID NO: 105          moltype = AA    length = 112
FEATURE                 Location/Qualifiers
REGION                  1..112
                        note = Synthetic
source                  1..112
                        mol_type = protein
                        organism = synthetic construct
SEQUENCE: 105
QVQLQQWGAG LLKPSETLSL TCAVYGGSFS AYYWSWIRQP PGKGLEWIGD INHGGGTNYN          60
PSLKSRVTIS VDTSKNQFSL KLNSVTAADT AVYYCASLTA YWGQGSLVTV SS                 112

SEQ ID NO: 106          moltype = DNA   length = 729
```

```
FEATURE              Location/Qualifiers
misc_feature         1..729
                     note = Synthetic
source               1..729
                     mol_type = other DNA
                     organism = synthetic construct
SEQUENCE: 106
cagatccagc tgcagcagag cggccccgag gtggtgaagc ccggcgccag cgtgaagatc    60
agctgcaagg ccagcggcta caccttcacc gactactaca tcacctgggt gaagcagaag   120
cccggccagg gcctggagtg gatcggctgg atctacccccg gcagcggcaa caccaagtac  180
aacgagaagt tcaagggcaa ggccaccctg accgtggaca ccagcagcag caccgccttc   240
atgcagctga gcagcctgac cagcgaggac accgccgtgt acttctgcgc caactacggc   300
aactactggt tcgcctactg gggccagggc acccaggtga ccgtgagcgc cggcggcggc   360
ggcagcggcg gcggcggcag cggcggcggc ggcagcgaca tcgtgctgac ccagagcccc   420
gccagcctgg ccgtgagcct gggccagaga gccaccatca gctgcaaggc cagccagagc   480
gtggacttcg acggcgacag ctacatgaac tggtaccagc agaagcccgg ccagcccccc   540
aaggtgctga tctacgccgc cagcaacctg gagagcggca tccccgccag attcagcggc   600
agcggcagcg gcaccgactt caccctgaac atccaccccg tggaggagga ggacgccgcc   660
acctactact gccagcagag caacgaggac cctggaccct tcgcgggcgg caccaagctg   720
gagatcaag                                                           729

SEQ ID NO: 107       moltype = DNA  length = 120
FEATURE              Location/Qualifiers
misc_feature         1..120
                     note = Synthetic
source               1..120
                     mol_type = other DNA
                     organism = synthetic construct
SEQUENCE: 107
agcaagagaa gcagactgct gcacagcgac tacatgaaca tgaccccccag aagacccggc    60
cccaccagaa agcactacca gccctacgcc ccccccagag acttcgccgc ctacagaagc   120

SEQ ID NO: 108       moltype = DNA  length = 1512
FEATURE              Location/Qualifiers
misc_feature         1..1512
                     note = Synthetic
source               1..1512
                     mol_type = other DNA
                     organism = synthetic construct
SEQUENCE: 108
atggcgcttc cggtgacagc actgctcctc cccttggcgc tgttgctcca cgcagcaagg    60
ccgcagatcc agctgcagca gagcggcccc gaggtggtga agcccggcgc cagcgtgaag   120
atcagctgca aggccagcgg ctacaccttc accgactact acatcacctg ggtgaagcag   180
aagcccggcc agggcctgga gtggatcggc tggatctacc ccggcagcgg caacaccaag   240
tacaacgaga agttcaaggg caaggccacc ctgaccgtgg acaccagcag cagcaccgcc   300
ttcatgcagc tgagcagcct gaccagcgag gacaccgccg tgtacttctg cgccaactac   360
ggcaactact ggttcgccta ctggggccag ggcacccagg tgaccgtgag cgccggcggc   420
ggcggcagcg gcggcggcgg cagcggcggc ggcggcagcg acatcgtgct gacccagagc   480
cccgccagcc tggccgtgag cctgggccag agagccacca tcagctgcaa ggccagccag   540
agcgtggact tcgacggcga cagctacatg aactggtacc agcagaagcc cggccagccc   600
cccaaggtgc tgatctacgc cgccagcaac ctggagagcg gcatccccgc cagattcagc   660
ggcagcggca gcggcaccga cttcaccctg aacatccacc ccgtggagga ggaggacgcc   720
gccacctact actgccagca gagcaacgag gaccctggac cttcggcggc ggcaccaag   780
ctggagatca gagagcgccgc cgccttcgtg cccgtgttcc tgcccgccaa gcccaccacc   840
acccccgccc ccagaccccc caccccccgcc cccaccaccc cagccagcc cctgagcctg   900
agacccgagg cctgcagacc cgccgccggc ggcgccgtgc acaccagagg cctggacttc   960
gcctgcgaca tctacatctg gcccccccctg gccggcacct cgggcgtgct gctgctgagc  1020
ctggtgatca ccctgtactg caaccacaga aacagaagca agagaagcag actgctgcac  1080
agcgactaca tgaacatgac ccccagaaga cccggcccca gaaagcacta ccagccc     1140
tacgccccccc ccagagactt cgccgcctac agaagcagag tgaagttcag cagaagcgcc  1200
gacgcccccg cctaccagca gggccagaac cagctgtaca acgagctgaa cctgggcaga  1260
agagaggagt acgacgtgct ggacaagaga agaggcagag accccgagat gggcggcaag  1320
ccccagaaga agaaccccca ggagggcctg tacaacgagc tgcagaagga caagatggcc  1380
gaggcctaca gcgagatcgg catgaagggc gagagaagga ggggcaaggg ccacgacggc  1440
ctgtaccagg gcctgagcac cgccaccaag gacacctacg acgccctgca catgcaggcc  1500
ctgccccccca ga                                                     1512

SEQ ID NO: 109       moltype = AA  length = 483
FEATURE              Location/Qualifiers
REGION               1..483
                     note = Synthetic
source               1..483
                     mol_type = protein
                     organism = synthetic construct
SEQUENCE: 109
QIQLQQSGPE VVKPGASVKI SCKASGYTFT DYYITWVKQK PGQGLEWIGW IYPGSGNTKY    60
NEKFKGKATL TVDTSSSTAF MQLSSLTSED TAVYFCANYG NYWFAYWGQG TQVTVSAGGG   120
GSGGGGSGGG GSDIVLTQSP ASLAVSLGQR ATISCKASQS VDFDGDSYMN WYQQKPGQPP   180
KVLIYAASNL ESGIPARFSG SGSGTDFTLN IHPVEEEDAA TYYCQQSNED PWTFGGGTKL   240
```

```
EIKSAAAFVP VFLPAKPTTT PAPRPPTPAP TIASQPLSLR PEACRPAAGG AVHTRGLDFA      300
CDIYIWAPLA GTCGVLLLSL VITLYCNHRN RSKRSRLLHS DYMNMTPRRP GPTRKHYQPY      360
APPRDFAAYR SRVKFSRSAD APAYQQGQNQ LYNELNLGRR EEYDVLDKRR GRDPEMGGKP      420
RRKNPQEGLY NELQKDKMAE AYSEIGMKGE RRRGKGHDGL YQGLSTATKD TYDALHMQAL      480
PPR                                                                   483

SEQ ID NO: 110          moltype = DNA   length = 11265
FEATURE                 Location/Qualifiers
misc_feature            1..11265
                        note = Synthetic
source                  1..11265
                        mol_type = other DNA
                        organism = synthetic construct
SEQUENCE: 110
agaatctgct cagactcctt cagtttacat attaggaaac tgaggcacag aaaggagcag      60
agacttgctc aagtccaccc aaagcagtag agcattgtgg ttaaatgcag gacttcagtc     120
agactgtctg ggttcaaatc ctggttccac ttggacatgg gtttccttac ataaatcact     180
tcacctctct gagcctcagt tttctcatat gcaaagtgag gataataata ataccttcct     240
tacatggtta ctgatatgag tattaaatgt gccagctcat gtgcctggcg tataggaggt     300
gctttataaa cctagctgt taccactcat ggcattgcca aatgtgggac gggtctcctg      360
actctctggt gtgagattga tggaatccac acttttccagt tccctttttct acctcctggg    420
tatcttctca tatgttgta agttccttgg aggaaggaaa tgtggcttgc tctctccacc     480
acgctgagca tataagaggt gctgaatgag cgctttttatt cactcctctc atccccagcc    540
ctcaccagct gggagttgtt gtaggtgtca attttctgcc tctttccaac accctgtgag    600
gtgactgagc attgtcttcc ctcccaggca gctcacagtg taagcttgtg gacgatatcg    660
aattcgcacg acattgatta ttgactagtt attaatgata atcaattacg gggtcattag    720
ttcatagccc atatatggag ttccgcgtta cataacttac ggtaaatggc ccgcctggct    780
gaccgcccaa cgaccccgc ccattgacgt caataatgac gtatgttccc atagtaacgc     840
caatagggac tttccattga cgtcaatggg tggactattt acggtaaact gcccacttgg    900
cagtacatca agtgtatcat atgccaagta cgccccctat tgacgtcaat gacggtaaat    960
ggcccgcctg gcattatgcc cagtacatga cctttatggga ctttcctact tggcagtaca   1020
tctacgtatt agtcatcgct attaccatgg gtcgaggtga gccccacgtt ctgcttcact   1080
ctccccatct ccccccctc cccacccca attttgtatt tatttatttt ttaattattt     1140
tgtgcagcga tggggcggg gggggggggg gcgcgcgcca ggcggggcgg ggcggggcga   1200
gggcggggc gggcgcgagc ggagaggtgc gcggcagcc aatcagagcg gcgcgctccg   1260
aaagtttcct tttatggcga ggcggcggcg gcggcggccc tataaaaagc gaagcgcgcg   1320
gcgggcggga gtcgctgcgt tgccttcgcc ccgtgccccg ctccgcgccg cctcgcgccg   1380
cccgcccgg ctctgactga ccgcgttact cccacaggtg agcgggcggg acggcccttc    1440
tcctcggggc tgtaattagc gcttggttta atgacggctc gtttcttttc tgtggctgcg   1500
tgaaagcctt aaagggctcc gggagggccc tttgtgcggg ggggagcggc tcgggggtg    1560
cgtgcgtgtg tgtgtgcgtg gggagcgccg cgtgcggccc gcgctgcccg gcggctgtga   1620
gcgctgcggg cgcggcgcgg ggctttgtgc gctccgcgtg tgcgcgaggg gagcgcggcc   1680
ggggcggtg ccccgcggtg cagggggct gcgaggggaa caaggctgc gtgcggggtg    1740
tgtgcgtggg ggggtgagca gggggtgtgg gcgcggcggt cgggctgtaa cccccccctg   1800
cacccccctc cccgagttgc tgagcacggc ccggcttcgg gtgcggggct ccgtgcgggg   1860
cgtggcgcgg ggctcgccgt gccggggcgg gggtggcggc aggtggggt gccgggcggg    1920
gcgggggcgc ctcggggcgg ggagggctcg ggggagggc gcggcggcgcc cggagcgcgg   1980
gcggctgtcg aggcgcggcg agccgcagcc attgcctttt atggtaatcg tgcgagaggg   2040
cgcagggact tcctttgtcc caaatctggc ggagccgaaa tctgggaggc gccgccgcac   2100
cccctctagc gggcgcgggc gaagcggtgc ggcgccggca ggaaggaaat gggcgggag    2160
ggcctctgtg cgtcgccgcg ccgccgtccc ctttctccatc tccagcctcg gggctgccgc   2220
agggggacgg ctgccttcgg ggggacggg gcagggcggg gttcggcttc tggcgtgtga   2280
ccggcggctc tagagcctct gctaaccatg ttcatgcctt cttctttttc ctacaggggg   2340
gatccgttta tctgcagaat tcgcccttga cgtcgccacc atggcgcttc cggtgacagc   2400
actgcctcctc cccttggcgc tgttgctcca cgcagcaggc cgcagatcc agctgcagca    2460
gagcggcccc gaggtggtga agccggcgc cagcgtgaag atcagctgca aggccagcgc   2520
ctacaccttc accgactact acatcacctg ggtgaagcag aagcccggcc agggcctgga   2580
gtggatcggc tggatctacc ccggcagcgg caacaccaag tacaacgaga gttcaaggc    2640
caaggccacc ctgaccgtgg acaccagcag cagcaccgcc ttcatgagc tgacagcct    2700
gaccagcgag gacaccgccg tgtacttctg cgccaactac ggcaactact ggttcgccta   2760
ctgggcccag ggcacccagg tgaccgtgag cgccggcggc ggcggcagcg gcggcggcgg   2820
cagcggcggc ggcggcagcg acatcgtgct gacccagagc cccgcagcc tggccgtgag   2880
cctgggccag agagccacca tcagctgcaa ggccagcag agcgtggact cgacggcga   2940
cagctacatg aactggtacc agcagaagcc cggcaagccc aagctggtgc tgatctgcg    3000
cgccagcaac ctggagagcg gcatccccgc cagattcagc ggcagcggca cggcaccga    3060
cttcaccctg aacatccacc ccgtggagga ggaggacgcc gccacctact actgccagca   3120
gagcaacgag gacccctgga ccttcggcgg cggcaccaag ctggagatca agagcgccgc   3180
cgccttcgtg cccgtgttcc tgcccgccaa gcccaccacc cccgccccc ccagacctcc    3240
caccccgcc ccccaccatcg ccagcgcagc cctgagcctg agaccgagg cctgcagacc   3300
cgccgcggc ggcgccgtgc acaccagagg cctggacttc gcctgcgaca tctacatctg   3360
ggccccctg gccggcacct gccgcgtgct gtgctgagc ctggtgatca cctgtactg    3420
caaccacaga aacagaagca gagaagcag actgctgcac agcgactaca tgaacatgac   3480
ccccagaaga cccggcccca cagaaagca ctaccagccc tacgccccc ccagagactt    3540
cgccgcctac agaagcgtga tgaagttcag ccgcagcgcc gatgcctaccaga ggccagaaa   3600
gggcagaac cagctgtaca acgagctgaa cctgggcaga agagaggagt acgacgtgct   3660
ggacaagaga agagcagag accccgagat gggcggcaag cccagaagaa gaaccccca   3720
ggagggcctg tacaacgagc tgcagaagga caagatggcc gaggcctaca gcgagatcgg   3780
catgaagggc gagagaagaa gaggcaaggg ccacgacggc ctgtaccagg gcctgagcac   3840
cgccaccaag gacacctacg acgccctgca catgcaggcc ctgcccccca gaggaagcgg   3900
```

```
agctactaac ttcagcctgc tgaagcaggc tggagacgtg gaggagaacc ctggacctat   3960
gtctcgctcc gttgccttag ctgtgctcgc gctactctct cttctctggat tagaggctgt  4020
catggcgccc cgaaccctct tcctgggtgg aggcggttca ggcggaggtg gctctggcgg   4080
tggcggatcg atccagcgta ctccaaagat tcaggtttac tcacgtcatc cagcagaaa    4140
tggaaagtca aatttcctga attgctatgt gtctgggttt catccatccg acattgaagt   4200
tgacttactg aagaatggag agagaattga aaaagtggag cattcagact tgtctttcag   4260
caaggactgg tctttctatc tcttgtacta cactgaattc accccactg aaaaagatga    4320
gtatgcctgc cgtgtgaacc atgtgacttt gtcacagccc aagatagtta agtgggatcg   4380
agacatgggt ggtggtggtt ctggtggtgg tggttctggc ggcggcggct ccggtggtgg   4440
tggatccggc tcccactcct tgaagtattt ccacacttcc gtgtcccggc ccggccgcgg   4500
ggagccccgc ttcatctctg tgggctacgt ggacgacacc cagttcgtgc gcttcgacaa   4560
cgacgccgcg agtccgagga tggtgccgcg ggcgccgtgg atggagcagg aggggtcaga   4620
gtattgggac cgggagacac ggagcgccag ggacaccgca cagattttcc gagtgaatct   4680
gcggacgctg cgcggctact acaatcagag cgaggccggg tctcacaccc tgcagtggat   4740
gcatggctgc gagctggggc ccgacgggcg cttcctccgc gggtatgaac agttcgccta   4800
cgacggcaag gattatctca ccctgaatga ggacctgcgc tcctgaccg cggtggacac    4860
ggcggctcag atctccgagc aaaagtcaaa tgatgcctct gaggcggagc accagagagc   4920
ctacctggaa gacacatgcg tggagtggct ccacaaatac ctggagaagg ggaaggagac   4980
gctgcttcac ctggagcccc caaagacaca cgtgactcac caccccatct ctgaccatga   5040
ggccaccctg aggtgctggg ccctgggctt ctaccctgcg gagatcacac tgacctggca   5100
gcaggatggg gagggcccata cccaggacac ggagctcgtg gagaccaggc ctgcaggga    5160
tggaaccttc cagaagtggg cagctgtggt ggtgccttct ggagaggagc agagatacac   5220
gtgccatgtg cagcatgagg ggctacccga gcccgtcacc ctgagatgga gccggcttc    5280
ccagcccacc atcccccatcg tgggcatcat tgctggcctg gttctccttg gatctgtggt   5340
ctctggagct gtggttgctg ctgtgatatg gaggaagaag agctcaggtg gaaaaggagg   5400
gagctactct aaggctgagt ggagcgacag tgcccaggsg tctgagtctc acagcttgta   5460
atgatagccg ctgatcagcc tcgactgtgc cttctagttg ccagccatct gttgtttgcc   5520
cctccccgt gccttccttg acccctggaag gtgccactcc cactgtcctt tcctaataaa    5580
atgaggaaat tgcatcgcat tgtctgagta ggtgtcattc tattctgggg ggtggggtgg   5640
ggcaggacag caaggggag gattgggaag acaatagcag cgatgctggg gatgcggtgg    5700
gctctatggg tcgactgacc agatggacct ggctggagaa gaagagattg agctctactc   5760
aggtgggccc tcctccctct ggtctcttcc ggtatcccc accccctcagc ttgctgtaga   5820
gacggcaatc aggggaaatt ctggtccctg ccctcccgtc agcaccacgg acagctccca   5880
cgtctgtggg acgctctctg cagatgggga tgatctccca gccctgcccc gcctctcccc   5940
cgttccccac cagccctctt tccagaaatt tccttcttca tccaagggac ttttcctccc   6000
agaacccgac acagacacca tcaactgcga ccagttcagc aggctgttgt gtgacatgga   6060
aggtgatgaa gagaccaggg aggcttatgc caatatcggt gaggaagcac ctgagcccag   6120
aaaaggacaa tcaagggcca gagttctttg ctgccacttg tcaatatcac ccattcatca   6180
tgagccacgt cagtcccctc ccacagaaat cattgcaagg gggatgcgga gcaatggctg   6240
gaggaacgga gactcaggg aagagagggg agatggaggc cagtggggga aataggcccc    6300
ttcactaatg accaccaaga aaacaaaatc tcatgtttac atcctccacc tccatttcta   6360
tacgcatttc tgcttcttgc tctttctgtcc atcctttcta caaagcccat accatacacc   6420
cctttccctt ttcctcccag ctcctagcc aagctactct agtatttgta ataactagca    6480
tttactggat actcatagta tgctcattgc tgtccggtaa ccacgtgcgg accgggctcc   6540
ggtgcccgtc agtgggcaga gcgcacatcg cccacagtcc ccgagaagtt gggggagtgg   6600
gtcggcaatt gaaccggtgc ctagagaagg tggcgcgggg taaactggga aagtgatgtc   6660
gtgtactggc tccgccttt tcccgagggt gggggagaac cgtatataag tgcagtagtc    6720
gccgtgaacg ttctttttcg caacgggttt gccgccagaa cacaggtaag tgccgtgtgt   6780
ggttcccgcg ggcctggcct cttttacgggt tatggccctt gcgtgccttg aattacttcc   6840
actgctgca gtacgtgatt cttgatcccg agcttcgggt tggaagtggg tgggagagtt   6900
cgaggccttg cgcttaagga gcccccttcgc ctcgtgcttg agttgaggcc tggcctgggc   6960
gctgggccg ccgcgtgcga atctggtggc accttcgcgc ctgtctcgct gctttcgata   7020
agtctctagc catttaaaat ttttgatgac ctgctgcgac gctttttttc tggcaagata   7080
gtcttgtaaa tgcgggccaa gatctgcaca ctggtatttc ggttttttggg gccgcgggcg   7140
gcgacgggca ccgtgcgtcc cagcgcacat gttcggcgag gcggggcctg cgagcgcggc   7200
caccgagaat cggacggggg tagtctcaag ctggccggcc tgctctggtg cctggcctcg   7260
cgccgccgtg tatcgcccg ccctgggcgg caaggctggc ccggtcggca ccagttgcgt    7320
gagcggaaag atggccgctt cccggccctg ctgcagggag ctcaaaatgg aggacgcggc   7380
gctcgggaga gcgggcgggt gagtcaccca cacaaaggaa aagggccttt ccgtcctcag   7440
ccgtcgcttc atgtgactcc acggagtacc gggcgccgtc caggcacctc gattagttct   7500
cgagcttttg gagtacgtcg tctttaggtt gggggagggg gttttatgcg atggagtttc   7560
cccacactga gtgggtggag actgaagtta ggccagcttg gcacttgatg taattctcct   7620
tggaatttgc cctttttgag tttggatctt ggttcattct caagcctcag acagtggttc   7680
aaagttttttt tcttccattt caggtgtcgt gacttgacgt cgccaccatg aggatatttg   7740
ctgtctttat attcatgacc tactggcatt tgctgaacgc atttactgtc acggttccca    7800
aggacctata tgtggtagag tatggtagca atatgacaat tgaatgcaaa ttcccagtag   7860
aaaaacaatt agacctggct gcactaattg tctattggga aatggaggat aagaacatta   7920
ttcaatttgt gcatggagag gaagacctga aggttcagca tagtagctac agacagaggg   7980
cccggctgtt gaaggaccag ctctccctgg gaaatgctgc acttcagatc acagatgtga   8040
aattgcagga tgcaggggtg taccgctgca tgatcagcta tggtggtgcc gactacaagc   8100
gaattactgt gaaagtcaat gccccataca acaaaatcaa ccaagaatt tggttgtgg     8160
atccagtcac ctctgaacat gaactgacat gtcaggctga gggctacccc aaggccgaag   8220
tcatctggac aagcagtgac catcaagtcc tgagtggtaa gaccaccacc accaattcca   8280
agagagaga gaaactttc aatgtgacca gcacactgaga catcaacaca acaactaatg    8340
agattttcta ctgcactttt aggagattag atcctgagga aaaccataca gctgaattgg   8400
tcatcccaga actacctctg gcacatcctc caaatgaaag gactcacttg gtaattctgg   8460
gagccatctt attatgcctt ggtgtagcac tgacattcat cttccgttta agaaaggga    8520
gaatgatgga tgtgaaaaaa tgtggcatcc aagatacaaa ctcaaagaag caagtgata   8580
cacatttgga ggagacgtaa ccgctgatca gcctcgaaac ttgtttattg cagcttataa   8640
```

```
tggttacaaa taaagcaata gcatcacaaa tttcacaaat aaagcatttt tttcactgca   8700
ttctagttgt ggtttgtcca aactcatcaa tgtatcttag gcgcctgatg cggtattttc   8760
tccttacgca tctgtgcggt atttcacacc gcatacagta ctgtcaaagc aaccatagta   8820
cgcgccctgt agcggcgcat taagcgcggc gggtgtggtg gttacgcgca gcgtgaccgc   8880
tacacttgcc agcgccctag cgcccgctcc tttcgctttc ttcccttcct ttctcgccca   8940
gttcgccggc tttccccgtc aagctctaaa tcggggggctc cctttagggt tccgatttag   9000
tgctttacgg cacctcgacc ccaaaaaact tgatttgggt gatggttcac gtagtgggcc   9060
atcgccctga tagacggttt ttcgcccttt gacgttggag tccacgttct ttaatagtgg   9120
actcttgttc caaactggaa caacactcaa ccctatctcg ggctattctt ttgatttata   9180
agggattttg ccgatttcgg cctattggtt aaaaaatgag ctgatttaac aaaaatttaa   9240
cgcgaatttt aacaaaatat taacgtttac aattttatgg tgcactctca gtacaatctg   9300
ctctgatgcc gcatagttaa gccagccccg acacccgcca cacccgctg acgcgccctg    9360
acgggcttgt ctgctcccgg catccgctta cagacaagct gtgaccgtct ccgggagctg   9420
catgtgtcag aggttttcac cgtcatcacc gaaacgcgcg agacgaaagg gcctcgtgat   9480
acgcctattt ttataggtta atgtcatgaa caataaaact gtctgcttac ataaacagta   9540
atacaagggg tgttatgagc catattcaac gggaaacgtc gaggccgcga ttaaattcca   9600
acatggatgc tgatttatat gggtataaat gggctcgcga taatgtcggg caatcaggtg   9660
cgacaatcta tcgcttgtat gggaagcccg atgcgccaga gttgtttctg aaacatggca   9720
aaggtagcgt tgccaatgat gttacagatg atggtcag actaaactgg ctgacggaat     9780
ttatgcctct tccgaccatc aagcatttta tccgtactcc tgatgatgca tggttactca   9840
ccactgcgat ccccggaaaa acagcattcc aggtattaga agaatatcct gattcaggtg   9900
aaaatattgt tgatgcgctg gcagtgttcc tgcgccggtt gcattcgatt cctgtttgta   9960
attgtccttt taacagcgat cgcgtatttc gtctcgctca ggcgcaatca cgaatgaata  10020
acggtttggt tgatgcgagt gattttgatg acgagcgtaa tggctggcct gttgaacaag  10080
tctgaaagaa aatgcataaa cttttgccat tctcaccgga ttcagtcgtc actcatggtg  10140
atttctcact tgataaactt attttttgacg agggaaatt aataggttgt attgatgttg   10200
gacgagtcgg aatcgcagac cgataccagg atcttgccat cctatggaac tgcctcggtg  10260
agttttctcc ttcattacag aaacggcttt ttcaaaaata tggtattgat aatcctgata  10320
tgaataaatt gcagtttcat ttgatgctcg atgagttttt ctaatctcat gaccaaaatc  10380
ccttaacgtg agttttcgtt ccactgagcg tcagaccccg tagaaaagat caaaggatct  10440
tcttgagatc ctttttttct gcgcgtaatc tgctgcttgc aaacaaaaaa accaccgcta  10500
ccagcggtgg tttgtttgcc ggatcaagag ctaccaactc ttttttccgaa ggtaactggc  10560
ttcagcagag cgcagatacc aaatactgtc cttctagtgt agccgtagtt aggccaccac  10620
ttcaagaact ctgtagcacc gcctacatac ctcgctctgc taatcctgtt accagtggct  10680
gctgccagtg gcgataagtc gtgtcttacc gggttggact caagacgata gttaccggat  10740
aaggcgcagc ggtcgggctg aacggggggt tcgtgcacac agcccagctt ggagcgaacg  10800
acctacaccg aactgagata cctacagcgt gagctatgag aaagcgccac gcttcccgaa  10860
gggagaaagg cggacaggta tccggtaagc ggcagggtcg gaacaggaga gcgcacgagg  10920
gagcttccag ggggaaacgc ctggtatctt tatagtcctg tcgggtttcg ccacctctga  10980
cttgagcgtc gatttttgtg atgctcgtca gggggggcgga gcctatggaa aaacgccagc  11040
aacgcggcct ttttacggtt cctggccttt tgctggcctt ttgctcacat gtgcggccgc  11100
acgcgtcata tttatggggt atatgtgaat atttattaca tgcatagaag gtataatgat  11160
catgtcagga tatttgaggt atccacattt gggattgttt aaagattaaa tgaaatagtg  11220
ttaaaagtat ttaatatgcc cttcaacaaa tgatgaggaa atctt                   11265

SEQ ID NO: 111           moltype = DNA  length = 702
FEATURE                  Location/Qualifiers
misc_feature             1..702
                         note = Synthetic
source                   1..702
                         mol_type = other DNA
                         organism = synthetic construct
SEQUENCE: 111
caggtgcagc tgcagcagtg gggcgccggc ctgctgaagc ccagcgagac cctgagcctg    60
acctgcgccg tgtacggcgg cagcttcagc gcctactact ggagctggat cagacagccc   120
cccggcaagg gcctggagtg gatcggcgac atcaaccacg gcggcggcac caactacaac   180
cccagcctga gagcagagt gaccatcagc gtggacacca gcaagaacca gttcagcctg   240
aagctgaaca gcgtgaccgc cgccgacacc gccgtgtact actgcgccag cctgaccgcc   300
tactggggcc agggccagct ggtgaccgtg agcagcggcg gcggcggcag cggcggcggc   360
ggcagcggcg gcggcggcag cgacatccag atgacccaga gccccaccag cctgagcgcc   420
agcgtgggcg acagagtgac catcacctgc agagccagcc agggcatcag cagctggctg   480
acctggtacc agcagaagcc cgagaaggcc cccaagagcc tgatctacgc cgccagcagc   540
ctgcagagcg gcgtgcccag cagattcagc ggcagcggca gcggcaccga cttcacccctg   600
accatcagca gcctgcagcc cgaggacttc gccacctact actgccagca gtacgacagc   660
tacccccatca ccttcggcca gggcaccaga ctggagatca ag                     702

SEQ ID NO: 112           moltype = DNA  length = 1491
FEATURE                  Location/Qualifiers
misc_feature             1..1491
                         note = Synthetic
source                   1..1491
                         mol_type = other DNA
                         organism = synthetic construct
SEQUENCE: 112
atggcgcttc cggtgacagc actgctcctc cccttggcgc tgttgctcca cgcagcaagg    60
ccgcaggtgc agctgcagca gtggggcgcg gcctgctga agcccagcga gaccctgagc    120
ctgacctgcg ccgtgtacgg cggcagcttc agcgcctact actggagctg atcagacag    180
cccccccggca agggcctgga gtggatcggc gacatcaacc acgcggcgg caccaactac   240
aacccccagcc tgaagagcag agtgaccatc agcgtggaca ccagcaagaa ccagttcagc   300
```

```
ctgaagctga acagcgtgac cgccgccgac accgccgtgt actactgcgc cagcctgacc    360
gcctactggg gccagggcag cctggtgacc gtgagcagcg gcggcggcgg cagcggcggc    420
ggcggcagcg gcggcggcgg cagcgacatc cagatgaccc agagcccac cagcctgagc    480
gccagcgtgg gcgacagagt gaccatcacc tgcagagcca gcagggcat cagcagctgg    540
ctgacctggt accagcagaa gcccgagaag gcccccacag gcctgatcta cgccgccagc    600
agcctgcaga gcggcgtgcc cagcagattc agcggcagcg gcagcggcac cgacttcacc    660
ctgaccatca gcagcctgca gcccgaggac ttcgccacct actactgcca gcagtacgac    720
agctacccca tcaccttcgg ccagggcacc agactggaga tcaagagcgc cgccgccttc    780
gtgcccgtgt tcctgcccgc caagcccacc accacccccg cccccagcc ccccaccccc    840
gcccccacca tcgccagcca gcccctgagc ctgagaccca ggcctgcag acccgccgc    900
ggcggcgcc tgcacaccag aggcctggac ttcgcctgcg acatctacat ctgggccccc    960
ctggccggca cctgcggcgt gctgctgctg agcctggtga tcaccctgta ctgcaaccac   1020
agaaacagaa agagaggcag aaagaagctg ctgtacatct tcaagcagcc cttcatgaga   1080
cccgtgcaga ccacccagga ggaggacggc tgcagctgca gattcccga ggaggaggag   1140
ggcggctgcg agctgagagt gaagttcagc agaagcgccg acgcccccgc ctaccagcag   1200
ggccagaacc agctgtacaa cgagctgaac ctgggcagaa gagaggagta cgacgtgctg   1260
gacaagagaa gaggcagaga ccccgagatg ggcggcaagc cagaagaaa gaaccccag   1320
gagggcctgt acaacgagct gcagaaggac aagatggccg aggcctacag cgagatcggc   1380
atgaagggcg agagaagaag aggcaagggc cacgacgcc tgtaccaggg cctgagcacc   1440
gccaccaagg acacctacga cgccctgcac atgcaggccc tgcccccag a             1491

SEQ ID NO: 113         moltype = AA    length = 476
FEATURE                Location/Qualifiers
REGION                 1..476
                       note = Synthetic
source                 1..476
                       mol_type = protein
                       organism = synthetic construct
SEQUENCE: 113
QVQLQQWGAG LLKPSETLSL TCAVYGGSFS AYYWSWIRQP PGKGLEWIGD INHGGGTNYN     60
PSLKSRVTIS VDTSKNQFSL KLNSVTAADT AVYYCASLTA YWGQGSLVTV SSGGGGSGGG    120
GSGGGGSDIQ MTQSPTSLSA SVGDRVTITC RASQGISSWL TWYQQKPEKA PKSLIYAASS    180
LQSGVPSRFS GSGSGTDFTL TISSLQPEDF ATYYCQQYDS YPITFGQGTR LEIKSAAAFV    240
PVFLPAKPTT TPAPRPPTPA PTIASQPLSL RPEACRPAAG GAVHTRGLDF ACDIYIWAPL    300
AGTCGVLLLS LVITLYCNHR NRKRGRKKLL YIFKQPFMRP VQTTQEEDGC SCRFPEEEEG    360
GCELRVKFSR SADAPAYQQG QNQLYNELNL GRREEYDVLD KRRGRDPEMG GKPRRKNPQE    420
GLYNELQKDK MAEAYSEIGM KGERRRGKGH DGLYQGLSTA TKDTYDALHM QALPPR        476

SEQ ID NO: 114         moltype = DNA    length = 11235
FEATURE                Location/Qualifiers
misc_feature           1..11235
                       note = Synthetic
source                 1..11235
                       mol_type = other DNA
                       organism = synthetic construct
SEQUENCE: 114
atgtcaggat atttgaggta tccacatttg ggattgttta aagattaaat gaaatagtgt     60
taaaagtatt taatatgccc ttcaacaaat gatgaggaaa tcttagaatc tgctcagact    120
ccttcagttt acatattagg aaactgaggc acagaaagga gcagagactt gctcaagtcc    180
acccaaagca gtagagcatt gtggttaaat gcaggacttc agtcagactg tctgggttca    240
aatcctggtt ccacttggac atgggttttcc ttacataaat cacttcacct ctctgagcct    300
cagttttctc atatgcaaag tgaggataat aataatacct tccttacatg gttactgata    360
tgagtattaa atgtgccagc tcatgtgcct ggcgtatagg aggtgcttta taaacccttag   420
ctgttaccac tcatgcgatt gccaaatgtg ggacgggtct cctgactctc tggtgtgaga    480
ttgatggaat ccacactttc cagttccctt ttctacctcc tgggtatctt ctcatatggt    540
tgtaagttcc ttggaggaag ggaatgtggc ttgctctctc caccacgctg agcatataag    600
aggtgctgaa tgagcgcttt tattcactcc tctcatcccc agccctcacc agctgggagt    660
tgttgtaggt gtcaatttc tgcctctttc caacaccctg tgaggtgact gagcattgtc     720
ttccctccca ggcagctcac agtgtaagct tgtggacgat atcgaattcg cacgacattg    780
attattgact agttattaat agtaatcaat tacgggtca ttagttcata gcccatatat     840
ggagttccgc gttacataac ttacggtaaa tggcccgcct ggctgaccgc ccaacgaccc    900
ccgcccattg acgtcaataa tgacgtatgt tcccatagta acgccaatag ggactttcca   960
ttgacgtcaa tgggtggact atttacggta aactgcccac ttggcagtac atcaagtgta   1020
tcatatgcca agtacgcccc ctattgacgt caatgacggt aaatggcccg cctggcatta   1080
tgcccagtac atgaccttat gggactttcc tacttggcag tacatctacg tattagtcat    1140
cgctattacc atgggtcgag gtgagcccca cgttctgctt cactctcccc atctcccccc    1200
cctcccacc cccaatttg tatttattta ttttttaatt attttgtgca gcgatggggg      1260
cgggggggg ggggcgcgc gccaggcggg gcggcgcgg gcgaggggcg gggcgggcg         1320
aggcggagag gtgcggcgga ggcaatcag agccgcggc tccgaaagtt tccttttatg     1380
gcgaggcggc ggcggcggcg gccctataaa aagcgaagcg cgcggcgggc gggagtcgct    1440
gcgttgcctt cgccccgtgc cccgctccgc gccgcctcgc gccgcccgcc ccggctctga    1500
ctgaccgcgt tactcccaca ggtgagcggg cgggacggc ctctcctcc gggctgtaat     1560
tagcgcttgg tttaatgacg gctcgtttct tttctgtggc tgcgtgaaag ccttaaaggg    1620
ctccgggagg gccctttgtg cgggggggag cggctgcggg ggtgcgtgcg tgtgtgtgta    1680
cgtggggagc gccgcgtgcg gccgcgcgct cccggcggct gtgagcgctg gggcgcggc    1740
gcggggcttt gtgcgctccg cgtgtgcgcg agggagcgc ggcgggggc ggtgcccgc      1800
ggtgcggggg ggctgcgagg ggaacaaagg ctgcgtgcgg ggtgtgtgcg tgggggggtg   1860
agcagggggt gtgggcgcgg cggtcgggct gtaacccccc cctgcacccc cctccccgag   1920
ttgctgagca cggcccggct tcgggtgcgg ggctccgtgc ggggcgtggc gcgggctcg    1980
```

```
ccgtgccggg cggggggtgg cggcaggtgg gggtgccggg cggggcgggg ccgcctcggg   2040
ccggggaggg ctcggggag gggcgcggcg gccccggagc gccggcggct gtcgaggcgc    2100
ggcgagccgc agccattgcc ttttatggta atcgtgcgag agggcgcagg gacttccttt   2160
gtcccaaatc tggcggagcc gaaatctggg aggcgccgcc gcaccccctc tagcgggcgc   2220
gggcgaagcg gtgcggcgcc ggcaggaagg aaatgggcgg ggagggcctt cgtgcgtgcg   2280
cgcgccgccg tccccttctc catctccagc ctcggggctg ccgcaggggg acggctgcct   2340
tcgggggga cggggcaggg cggggttcgg cttctggcgt gtgaccggcg gctctagagc    2400
ctctgctaac catgttcatg ccttcttctt tttcctacag gggggatccg tttatctgca   2460
gaattcgccc ttgacgtcgc caccatggcg cttccggtga cagcactgct cctccccttg   2520
gcgctgttgc tccacgcagc aaggccgcag gtgcagctgc agcagtgggg cgccggcctg   2580
ctgaagccca gcgagaccct gagcctgacc tgcgccgtgt acggcggcag cttcagcgcc   2640
tactactgga gctggatcag acagcccccc ggcaagggcc tggagtggat cggcgacatc   2700
aaccacggcg gcggcaccaa ctacaacccc agcctgaaga gcagagtgac catcagcgtg   2760
gacaccagca agaaccagtt cagcctgaag ctgaacagcg tgaccgccgc cgacaccgcc   2820
gtgtactact gcgccagcct gaccgcctac tggggccagg gcagcctggt gaccgtgagc   2880
agcggcggcg gcggcagcgg cggcggcggc agcggcggcg gcggcagcga catccagatg   2940
acccagagcc ccaccagcct gagcgccagc gtgggcgaca gagtgaccat cacctgcaga   3000
gccagcagg gcatcagcag ctggctgacc tggtaccagc agaagcccga gaaggcccc    3060
aagagcctga tctacgccgc cagcagcctg cagagcggcg tgcccagcag attcagcggc   3120
agcggcagcg gcaccgactt caccctgacc atcagcagcc tgcagcccga ggacttcgcc   3180
acctactact gccagcagta cgacagctac cccatcacct tcggccaggg caccagactg   3240
gagatcaaga gcgccgccgc cttcgtgccc gtgttcctgc cgccaagcc caccaccacc   3300
cccgccccca gaccccccac ccccgccccc accatcgcca gccagcccct gagcctgaga   3360
cccgaggcct gcagaccgc cgccggcggg gccgtgcaca ccagaggcct ggacttcgcc   3420
tgcgacatct acatctgggc cccctggcc ggcacctgcg gcgtgctgct gctgagcctg    3480
gtgatcaccc tgtactgcaa ccacagaaac agaaagagag acaaagaa gctgctgtac    3540
atcttcaagc agcccttcat gagaccgtg cagaccaccc aggaggagga cggctgcagc   3600
tgcagattcc ccgaggagga ggagggcggc tgcgagctga gagtgaagtt cagcagaagc   3660
gccgacgccc ccgcctacca gcagggccag aaccagctgt acaacgagct gaacctgggc   3720
agaagagagg agtacgacgt gctggacaag agaagaggca gaccccga gatgggcggc    3780
aagcccagaa gaaagaaccc ccaggagggc ctgtacaacg agctgcagaa ggacaagatg   3840
gccgaggcct acagcgagat cggcatgaag ggcgagagaa gaagaggcaa gggccacgac   3900
ggcctgtacc agggcctgag caccgccacc aaggacacct acgacgccct gcacatgcag   3960
gccctgcccc ccagaggaag cggattcagc ctgctgaagc aggctggaga cgtggaggag   4020
aaccctggac ctatgtctcg ctccgttgcc ttagctgtgc tcgcgctact ctctctttct   4080
ggattagagg ctgtcatggc gccccgaacc ctcttcctgg gtgaggcgg ttcaggcgga   4140
ggtggctctg gcgtggcgg atcgatccag cgtactccaa agattcaggt ttactcacgt   4200
catccagcag agaatggaaa gtcaaatttc ctgaattgct atgtgtctgg gttcatcca   4260
tccgacattg aagttgactt actgaagaat ggagagaa ttgaaaagt ggagcattca    4320
gacttgtctt tcagcaagga ctggtctttt tatctcttgt actacactga attcacccc   4380
actgaaaag atgagtatgc ctgccgtgtg aaccatgtga ctttgtcaca gcccaagata    4440
gttaagtggg atcgagacat gggtggtgt ggttctggtg gtgtggttc tggcggcggc    4500
ggctccggtg gtggttgatc cggctcccac tccttgagt attccacac ttccgtgtcc    4560
cggcccggcc gcggggagcc ccgcttcatc tctgtgggct acgtggacga cacccagttc   4620
gtgcgcttcg acaacgacgc cgcgagtccg aggatggtgc cgcgggcgcc gtggatggag   4680
caggaggggt cagagtattg ggaccgggag acacggagcg ccaggacac cgcacagatt   4740
ttccgagtga atctcggac ggctgaggc tactacaatc agagcgaggc gggtctcac    4800
accctgcagt ggatgcatgg ctgcgagctg gggcccgacg ggcgcttcct ccgcgggtat   4860
gaacagttcg cctacgacgg caaggattat ctcaccctga atgaggacct gcgctcctgg   4920
accgcggtgg acacggcggc tcagatctcc gagcaaaagt caaatgatgc ctctgaggcg   4980
gagcaccaga gagcctacct ggaagacaca tgcgtggagg ggctccacaa atacctggag   5040
aaggggaagg agacgctgct tcacctggag cccccaaaga cacacgtgac tcaccacccc   5100
atctctgacc atgaggccac cctgaggtgc tgggccctgg gcttctaccc tgcggagatc   5160
acactgacct ggcagcagga tggggaggc catacccagg acacgagct cgtggagacc   5220
aggcctgcag gggatggaac cttccagaag tgggcagctg tggtggtgcc ttctggagag   5280
gagcagagat acacgtgcca tgtgcagcat gaggggctac ccgagccgt caccctgaga   5340
tggaagccgg cttcccagcc caccatcccc atcgtgggca tcattgctgg cctggttctc   5400
cttggatctg tggtctctgg agctgtggtt gctgctgtga tatggaggaa gaagagctca   5460
ggtggaaaag gagggagcta ctctaaggct gagtggagcg acagtgccca gggtctgga   5520
tctcacagct tgtaatgata gccgctgatc agcctcgact gtgccttcta gttgccagcc   5580
atctgttgtt tgcccctccc ccgtgccttc cttgaccctg gaaggtgcca ctcccactgt   5640
cctttcctaa taaaatgagg aaattgcatc gcattgtctg agtaggtgtc attctattct   5700
ggggggtggg gtgggcagg acagcaaggg ggaggattgg gaagacaata gcaggcatgc    5760
tggggatgcg gtgggctcta tgggtcgact gaccagatgg acctggctgg agaagaagag   5820
attgagctct actcaggtgg gccctcctcc ctctggtctc ttccggtatc ccccacccct   5880
cagcttgctg tagagacggc aatcagggga aattctggtc cctgccctcc cgtcagcacc   5940
acggacagct cccacgtctg tgggacgctc tctcagatg gggatgatct cccagccctg   6000
ccccgcctct ccctcgttcc ccaccagccc tctttccaga aatttccttc ttcatccaag   6060
ggactttcc tcccagaacc cgacacagac accatcaact gcgaccagtt cagcaggctg    6120
ttgtgtgaca tggaaggtga tgaagagacc agggaggctt atgccaatat cggtgaggaa   6180
gcacctgagc ccagaaaagg acaatcaagg gcaagagttc tttgctgcca cttgtcaata   6240
tcacccattc atcatgagcc acgtcagtcc cctcccacag aaatcattgc aaggggatg    6300
cggagcaatg gctggaggaa cggagactcc agggaagaga ggggagatgg aggccagtgg   6360
gggaaataag cccttcact aatgaccacc aagaaaacaa aatctcatgt ttacatcctc    6420
cacctccatt tctatacgca tttctgcttc ttgctcttct gtccatcctt tctacaaagc   6480
ccataccata caccccttc ccttttcctc ccagctcctt agccaagcta ctctagtatt   6540
tgtaataact agcatttact ggatactcat agtatgctca ttgctgtccg gtaaccacgt   6600
gcggaccggg ctccggtgcc cgtcagtggg cagagcgcac atcgcccaca gtccccgaga   6660
agttgggggg aggggtcggc aattgaaccg gtgcctagaa aggtggcgc ggggtaaact     6720
```

```
gggaaagtga tgtcgtgtac tggctccgcc ttttcccga gggtggggga gaaccgtata  6780
taagtgcagt agtcgccgtg aacgttcttt ttcgcaacgg gtttgccgcc agaacacagg  6840
taagtgccgt gtgtggttcc cgcgggcctg gcctctttac gggttatggc ccttgcgtgc  6900
cttgaattac ttccactggc tgcagtacgt gattcttgat cccgagcttc gggttggaag  6960
tgggtgggag agttcgaggc cttgcgctta aggagccccc tcgcctcgtg cttgagttga  7020
ggcctggcct gggcgctggg gccgccgcgt gcgaatctgg tggcaccttc gcgcctgtct  7080
cgctgctttc gataagtctc tagccattta aaattttga tgacctgctg cgacgctttt  7140
tttctggcaa gatagtcttg taaatgcggg ccaagatctg cacactggta tttcggtttt  7200
tggggccgcg ggcggcgacg gggcccgtgc gtcccagcgc acatgttcgg cgagcgcggg  7260
cctgcgagcg cggccaccga gaatcggacg ggggtagtct caagctggcg ggcctgctct  7320
ggtgcctggc ctcgcgccgc cgtgtatcgc cccgccctgg gcggcaaggc tggcccggtc  7380
ggcaccagtt gcgtgagcgg aaagatggcc gcttcccggc cctgctgcag ggagctcaaa  7440
atggaggacg cggcgctcgg gagagcgggc gggtgagtca cccacacaaa ggaaaagggc  7500
ctttccgtcc tcagccgtcg cttcatgtga ctccacggag taccgggccgc cgtccaggca  7560
cctcgattag ttctcgagct tttgagtac gtcgtctta ggtggggggg aggggtttta  7620
tgcgatggag tttccccaca ctgagtgggt ggagactgaa gttaggccag cttggcactt  7680
gatgtaattc tccttggaat ttgcccttt tgagtttgga tcttggttca ttctcaagcc  7740
tcagacagtg gttcaaagtt tttttcttcc atttcaggtg tcgtgacttg acgtcgccac  7800
catgaggata tttgctgtct ttatattcat gacctactgg catttgctga acgcatttac  7860
tgtcacggtt cccaaggacc tatatgtggt agagtatggt agcaatatga caattgaatg  7920
caaattccca gtagaaaaac aattagacct ggctgcacta attgtctatt gggaaatgga  7980
ggataagaac attattcaat ttgtgcatgg agaggaagac ctgaaggttc agcatagtag  8040
ctacagacag agggcccggc tgttgaagga ccagctctcc ctgggaaatg ctgcacttca  8100
gatcacagat gtgaaattgc aggatgcagg ggtgtaccgc tgcatgatca gctatggtgg  8160
tgccgactac aagcgaatta ctgtgaaagt caatgccca tacaacaaaa tcaaccaaag  8220
aattttggtt gtggatccag tcacctctga acatgaactg acatgtcagg ctgagggcta  8280
ccccaaggcc gaagtcatct ggacaagcag tgaccatcaa gtcctgagtg gtaagaccac  8340
caccaccaat tccaagagag aggagaaact tttcaatgtg accagcacac tgagaatcaa  8400
cacaacaact aatgagattt tctactgcac ttttaggaga ttagatcctg aggaaaacca  8460
tacagctgaa ttggtcatcc cagaactacc tctggcacat cctccaaatg aaaggactca  8520
cttggtaatt ctgggagcca tcttattatg ccttggtgta gcactgacat tcatcttccg  8580
tttaagaaaa gggagaatga tggatgtgaa aaaatgtggc atccaagata caaactcaaa  8640
gaagcaaagt gatacacatt tggaggagac gtaaccgctg atcagcctcg aaacttgttt  8700
attgcagctt ataatggtta caaataaagc aatgcatca caaatttcac aaataaagca  8760
ttttttttcac tgcattctag ttgtggtttg tccaaactca tcaatgtatc ttaggcgcct  8820
gatgcggtat tttctcctta cgcatctgtg cggtatttca caccgcatac agtactgtca  8880
aagcaaccat agtacgcgcc ctgtagcggg gcattaagcg cggcgggtgt ggtggttacg  8940
cgcagcgtga ccgctcacct tgccagcgcc ctagcgcccg ctccttcgc ttcttccct  9000
tccttctcg ccacgttcgc cggctttccc cgtcaagctc taaatcgggg gctccctta  9060
gggttccgat ttagtgcttt acggcacctc gaccccaaaa aacttgattt gggtgatggt  9120
tcacgtagtg ggccatcgcc ctgatagacg gtttttcgcc cttgactt ggagtccacg  9180
ttctttaata gtggactctt gttccaaact ggaacaacaa tcaaccctat ctcgggctat  9240
tcttttgatt tataagggat tttgccgatt tcggcctatt ggttaaaaaa tgagctgatt  9300
taacaaaaat ttaacgcgaa ttttaacaaa atattaacgt ttacaatttt atggtgcact  9360
ctcagtacaa tctgctctga tgccgcatag ttaagccagc cccgacaccc gccaacaccc  9420
gctgacgcgc cctgacgggc ttgtctgctc ccggcatccg cttacagaca agctgtgacc  9480
gtctccggga gctgcatgtg tcagaggttt tcaccgtcat caccgaaacg cgcgagacga  9540
aagggcctcg tgatacgcct atttttatag gttaatgtca tgaacaataa aactgtctgc  9600
ttacataaac agtaatacaa gggggtgttat gagccatatt caacgggaaa cgtcgaggcc  9660
gcgattaaat tccaacatgg atgctgattt atatgggtat aaatgggctc gcgataatgt  9720
cgggcaatca ggtgcgacaa tctatcgctt gtatgggaag cccgatgcgc cagagttgtt  9780
tctgaaacat ggcaaaggta gcgttgccaa tgatgttaca gatgagatgg tcagactaaa  9840
ctggctgacg gaatttatgc ctcttccgac catcaagcat tttatccgta ctcctgatga  9900
tgcatggtta ctcaccactg cgatcccgg aaaaacagca ttccaggtat tagaagaata  9960
tcctgattca ggtgaaaata ttgttgatgc gctggcagtg ttcctgcgcc ggttgcattc  10020
gattcctgtt tgtaattgtc cttttaacag cgatcgcgta tttcgtctcg ctcaggcgca  10080
atcacgaatg aataacggtt tggttgatgc gagtgatttt gatgacgagc gtaatggctg  10140
gcctgttgaa caagtctgga agaaatgca taaacttttg ccattctcac cggattcagt  10200
cgtcactcat ggtgatttct cacttgataa ccttatttt gacgagggga aattaataggg  10260
ttgtattgat gttggacgag tcggaatcgc agaccgatac caggatcttg ccatcctatg  10320
gaactgcctc ggtgagtttt ctccttcatt acagaaacgg ctttttcaaa aatatggtat  10380
tgataatcct gatatgaata aattgcagtt tcatttgatg ctcgatgagt ttttctaatc  10440
tcatgaccaa aatcccttaa cgtgagtttt cgttccactg agcgtcagac cccgtagaaa  10500
agatcaaagg atcttcttga gatccttttt ttctgcgcgt aatctgctgc ttgcaaacaa  10560
aaaaaccacc gctaccagcg gtggtttgtt tgccggatca agagctacca actctttttc  10620
cgaaggtaac tggcttcagc agagcgcaga taccaaatac tgtccttcta gtgtagccgt  10680
agttaggcca ccacttcaag aactctgtag caccgcctac atacctcgct ctgctaatcc  10740
tgttaccagt ggctgctgcc agtggcgata agtcgtgtct taccgggttg gactcaagac  10800
gatagttacc ggataaggcg cagcggtcgg gctgaacggg gggttcgtgc acacagccca  10860
gcttggagcg aacgacctac accgaactga gatacctaca gcgtgagcta tgagaaagcg  10920
ccacgcttcc cgaagggaga aagcggaca ggtatccggt aagcggcagg gtcggaacag  10980
gagagcgcac gagggagctt ccaggggaa acgcctggta tctttatagt cctgtcggt  11040
ttcgccacct ctgacttgag cgtcgatttt tgtgatgctc gtcaggggg cggagccat  11100
ggaaaaacgc cagcaacgcg gcctttttac ggttcctggc cttttgctgg ccttttgctc  11160
acatgtgcgg ccgcacgcgt catatttatg gggtatatgt gaatatttat tacatgcata  11220
gaaggtataa tgatc                                                  11235

SEQ ID NO: 115         moltype = DNA  length = 7176
FEATURE                Location/Qualifiers
```

```
misc_feature       1..7176
                   note = Synthetic
source             1..7176
                   mol_type = other DNA
                   organism = synthetic construct
SEQUENCE: 115
atgtcaggat atttgaggta tccacatttg ggattgttta aagattaaat gaaatagtgt    60
taaaagtatt taatatgccc ttcaacaaat gatgaggaaa tcttagaatc tgctcagact   120
ccttcagttt acatattagg aaactgaggc acagaaagga gcagagactt gctcaagtcc   180
acccaaagca gtagagcatt gtggttaaat gcaggacttc agtcagactg tctgggttca   240
aatcctggtt ccacttggac atgggtttcc ttacataaat cacttcacct ctctgagcct   300
cagttttctc atatgcaaag tgaggataat aataatacct tccttacatg gttactgata   360
tgagtattaa atgtgccagc tcatgtgcct ggcgtatagg aggtgcttta taaaccttag   420
ctgttaccac tcatggcatt gccaaatgtg ggacggtctc cctgactctc tggtgtgaga   480
ttgatggaat ccacactttc cagttccctt ttctacctcc tgggtatctt ctcatatggt   540
tgtaagttcc ttggaggaag ggaatgtggc ttgctctctc caccacgctg agcatataag   600
aggtgctgaa tgagcgcttt tattcactcc tctcatcccc agccctcacc agctgggagt   660
tgttgtaggt gtcaattttc tgcctctttc caacacccctg tgaggtgact gagcattgtc   720
ttccctccca gcagctcac agtgtaagct tgtggacgat atcgaattcg cacgacattg    780
attattgact agtyattaat agtaatcaat acgggtgtca ttagttcata gcccatatat    840
ggagttccgc gttacataac ttacggtaaa tggcccgcct ggctgaccgc ccaacgaccc    900
ccgccattg acgtcaataa tgacgtatgt tcccatagta acgccaatag ggactttcca    960
ttgacgtcaa tgggtggact atttacggta aactgcccac ttggcagtac atcaagtgta   1020
tcatatgcca gtacgcccc ctattgacgt caatgacggt aaatggcccg cctggcatta   1080
tgcccagtac atgaccttat gggactttcc tacttggcag tacatctacg tattagtcat   1140
cgctattacc atgggtcgag gtgagcccca cgttctgctt cactctcccc atctccccc   1200
cctcccccacc cccaatttg tatttattta ttttttaatt attttgtgca gcgatggggg   1260
cggggggggg ggggcgcgc gccaggcggg gcggggcggg gcgaggggcg gggcggggcg   1320
aggcggagag gtgcggcggc agccaatcag agcggcgcgc tccgaaagtt tccttttatg   1380
gcgagggcgg ggcggcggcg gccctataaa aagcgaagcg cgcggcgggc gggagtcgct   1440
gcgttgcctt cgccccgtgc cccgctccgc gccgcctcgc gccgcccgcc ccggctctga   1500
ctgaccgcgt tactcccaca ggtgagcggg cgggacggcc cttctcctcc gggctgtaat   1560
tagcgcttgg tttaatgacg gctcgtttct tttctgtggc tgcgtgaaag ccttaaaggg   1620
ctccgggagg gccctttgtg cggggggag cggctccggg ggtgcgtgcg tgtgtgtgtg   1680
cgtgggcaga gccgcgtgcg gcccgcgctg cccggccctg gtgagcgctg cgggcgcggg   1740
gcggggcttt gtgcgctccg cgtgtgcgcg agggagcgc ggccggggc ggtgcccgc   1800
ggtgcggggg ggctgcgagg ggaacaaagg ctgcgtgcgg ggtgtgtgcg tgggggggtg   1860
agcaggggt gtgggcgcgg cggtcgggct gtaaccccc cctgcaccc cctccccgag   1920
ttgctgagca cggcccggct tcgggtgcgg ggctccgtgc gggcgtggc gcgggggctcg   1980
ccgtgccggg cggggggtgg cggcaggtgg gggtgccggg cgggcgggg ccgcctcggg   2040
ccggggaggg ctcgggggag gggcgcggcg gccccggagc gccggcggct gtcgaggcgc   2100
ggcgagccgc agccattgcc ttttatggta atcgtgcgag agggcgcagg gacttccttt   2160
gtcccaaatc tggcggagcc gaaatctggg aggcgccgcc gcacccctc tagcgggcgc   2220
gggcgaagcg gtgcggcgcc ggcaggaagg aaatgggcgg ggagggcctt cgtgcgtcgc   2280
cgcgccgccg tccccttctc catctccagc ctcggggctg ccgcaggggg acggctgcct   2340
tcggggggga cggggcaggg cggggttcgg cttctggcgt gtgaccggcg gctctagagc   2400
ctctgctaac catgttcatg cctttcttctt ttttcctaag ggggggatccg tttatctgca   2460
gaattcgccc ttgacgtcgc caccatggcg cttccggtga cagcactgct cctccccttg   2520
gcgctgttgc tccacgcagc aaggccgcag gtgcagctgc agcagtgggg cgccggcctg   2580
ctgaagccca gcgagaccct gagcctgacc tgcgccgtgt acggcggcag cttcagcgcc   2640
tactactgga gctggatcag acagcccccc ggcaagggcc tggagtggat cggcgacatc   2700
aaccacggcg gcggcaccaa ctacaacccc agcctgaaga gcagagtgac catcagcgtg   2760
gacaccagca gaaccagtt cagcctgaag ctgaacagcg tgaccgccgc cgacaccgcc   2820
gtgtactact gcgccagcct gaccgcctac tgggcccagg gcagcctggt gaccgtgagc   2880
agcggcggcg gcggcagcgg cggcggcggc agcggcggcg gcggcagcga catccagatg   2940
acccagagcc ccaccagcct gagcgccagc gtgggcgaca gagtgaccat cacctgcaga   3000
gccagcagg gcatcagcag ctggctgacc tggtaccagc agaagcccga gaggccccc    3060
aagagcctga tctacgccgc cagcagcctg cagagcggcg tgcccagcag attcagcggc   3120
agcggcagcg gcaccgactt caccctgacc atcagcagcc tgcagcccga ggacttcgcc   3180
acctactact gccagcagta cgacagctac cccatcacct tcggccaggg caccagactg   3240
gagatcaaga gcgccgccgc cttcgtgccc gtgttcctgc ccgccaagcc caccaccacc   3300
cccgccccca ccccccccac ccccgccccc accatcgcca gccagcccct gagcctgaga   3360
cccgaggcct gcagacccgc cgccggcggc gccgtgcaca ccagaggcct ggacttcgcc   3420
tgcgacatct acatctgggc cccctgcc ggcacctgt gcgtgctgct gctgagcctg   3480
gtgatcaccc tgtactgcaa ccacagaaac agaaagagag cagaaagaa gctgctgtac   3540
atcttcaagc agcccttcat gagacccgtg cagaccaccc aggaggagga cggctgcagc   3600
tgcagattcc ccgaggagga ggagggcggc tgcgagctga gagtgaagtt cagcagaagc   3660
gccgacgccc ccgcctacca gcagggccag aaccagctgt acaacgagct gaacctgggc   3720
agaagagagg agtacgacgt gctgaacaag agaagagccgg agaccccga gatgggcggc   3780
aagcccagaa gaaagaaccc caggagggc ctgtacaacg agctgcagaa ggacaagatg   3840
gccgaggcct acagcgagat cggcatgaag ggcgagagaa gaaggcaa gggccacgac   3900
ggcctgtacc agggcctgag caccgccacc aaggacacct acgacgccct gcacatgcag   3960
gccctgcccc cagaggaag cggattcagc tgctgaagc aggctggaga cgtggaggag   4020
aaccctggac ctatgtctcg ctccgttgcc ttagctgtc tcgctact ctctcttct   4080
ggattagagg ctgtcatggc gcccgaacc ctcttcctgg gtgaggcgg ttcaggcgga   4140
ggtggctctg gcggtggcgg atcgatccag cgtactccaa agattcaggt ttactcacgt   4200
catccagcag agaatggaaa gtcaaatttc ctgaattgct atgtgtctgg gtttcatcca   4260
tccgacattg aagttgactt actgaagaat ggagagagaa ttgaaaaagt ggagcattca   4320
gacttgtctt tcagcaagga ctggtctttc tatctccttg actacactga attcaccccc   4380
```

```
actgaaaaag atgagtatgc ctgccgtgtg aaccatgtga cttttgtcaca gcccaagata 4440
gttaagtggg atcgagacat gggtggtggt ggttctggtg gtggtggttc tgcggcggc  4500
ggctccgtg  gtggtggatc cggctcccac tccttgaagt atttccacac ttccgtgtcc  4560
cggcccggcc gcggggagcc ccgcttcatc tctgtgggct acgtggacga cacccagttc 4620
gtgcgcttcg acaacgacgc cgcgagtccg aggatggtgc cgcgggcgcc gtggatggag 4680
caggaggggt cagagtattg ggaccgggag acacggagcg ccagggacac cgcacagatt 4740
ttccgagtga atctgcggac gctgcgcggc tactacaatc agagcgaggc cgggtctcac 4800
accctgcagt ggatgcatgg ctgcgagctg ggccccgacg ggcgcttcct ccgcgggtat 4860
gaacagttcg cctacgacgg caaggattat ctcaccctga atgaggacct gcgctcctgg 4920
accgcggtgg acacggccgg ctcagatctcc gagcaaaagt caaatgatgc ctctgaggcg 4980
gagcaccaga gagcctacct ggaagacaca tgcgtggagt ggctccacaa atacctggag 5040
aaggggaagg agacgctgct tcacctggag cccccaaaga cacacgtgac tcaccacccc 5100
atctctgacc atgaggccac cctgaggtgc tgggccctgg gcttctaccc tgcggagatc 5160
acactgacct ggcagcagga tggggaggc catacccagg acagcgagct cgtggagacc 5220
aggcctgcag gggatggaac cttccagaag tgggcagctg tggtggtgcc ttctggagag 5280
gagcagagat acacgtgcca tgtgcagcat gaggggctac ccgagcccgt caccctgaga 5340
tggaagccgg cttcccagcc caccatcccc atcgtgggca tcattgctgg cctgttctc  5400
cttggatctg tggtctctgg agctgtgtt gctgctgtga tatggaggaa gaagagctca 5460
ggtgaaaag  gagggagcta ctctaaggct gagtggagcg acagtgccca ggggtctgag 5520
tctcacagct tgtaatgata gccgctgatc agcctcgact gtgccttcta gttgccagcc 5580
atctgttgtt tgcccctccc ccgtgccttc cttgaccctg gaaggtgcca ctcccactgt 5640
cctttcctaa taaatgagg  aaattgcatc gcattgtcatc agtaggtgtc attctattct 5700
gggggtggg  gtgggcagg  acagcaaggg ggaggattgg gaagacaata gcaggcatgc 5760
tggggatgcg gtgggctcta tgggtcgact gaccagatgg acctggctgg agaagaagag 5820
attgagctct actcaggtgg gccctcctcc ctctggtctc ttccggtatc ccccaccct  5880
cagcttgctg tagagacggc aatcagggga aattctggtc cctgccctcc cgtcagcacc 5940
acggacagct cccacgtctg tgggacgctc tctgcagatg gggatgatct cccagccctg 6000
cccgcctct  ccctcgttcc ccaccagccc tctttccaga aatttccttc ttcatccaag 6060
ggacttttcc tcccagaacc cgacacagac accatcaact gcgaccagtt cagcaggctg 6120
ttgtgtgaca tggaaggtga tgaagagacc agggaggctt atgccaatat cggtgaggaa 6180
gcacctgagc ccagaaaagg acaatcaagg gcaagagttc tttgctgcca cttgtcaata 6240
tcacccattc atcatgagcc acgtcagtcc cctcccacag aaatcattgc aaggggatg  6300
cggagcaatg gctggaggaa cggagactcc agggaagaga ggggagatgg aggccagtgg 6360
gggaaatagg cccctttcac tattgaccacc aagaaaacaa aatctcatgt ttacatcctc 6420
cacctccatt tctatacgca tttctgcttc ttgctcttct gtccatcctt tctacaaagc 6480
gacatccaga tgacccagag ccccaccagc ctgagcgcca gcgtgggcga cagagtgacc 6540
atcacctgca gagccagcca gggcatcagc agctggctga cctggtacca gcagaagccc 6600
gagaaggccc ccaagagcct gatctacgcc gccagcagcc tgcagagcgg cgtgcccagc 6660
agattcagcg gcagcggcag cggcaccgac ttcaccctga ccatcagcag cctgcagccc 6720
gaggacttcg ccacctacta ctgccagcag tacgacagct accccatcac cttcggccaa 6780
ggcaccagac tggagatcaa gggcggcggc ggcagcggcg gcggcggcag cggcggcggc 6840
ggcagccagg tgcagctgca gcagtggggc ccgcctgc   tgaagcccag cgagaccctg 6900
agcctgacct gcgccgtgta cggcggcagc ttcagcggcc actactggag ctggatcaga 6960
cagcccccg  gcaagggcct ggagtggatc ggcgacatca accacggcgg cggcaccaac 7020
tacaacccca gcctgaagag cagagtgacc atcagcgtgg acaccagcaa gaaccagttc 7080
agcctgaagc tgaacagcgt gaccgccgcc gacaccgccg tgtactactg cgccagcctg 7140
accgcctact gggccagggg cagcctggtg accgtg                             7176
```

SEQ ID NO: 116          moltype = DNA   length = 1485
FEATURE                 Location/Qualifiers
misc_feature            1..1485
                        note = Synthetic
source                  1..1485
                        mol_type = other DNA
                        organism = synthetic construct
SEQUENCE: 116

```
atggcgcttc cggtgacagc actgctcctc cccttggcgc tgttgctcca cgcagcaagg   60
ccggacatcc agatgaccca gagccccacc agcctgagcg ccagcgtggg cgacagagtg  120
accatcacct gcagagccag cagggcatc  agcagctggc tgacctggta ccagcagaag  180
cccgagaagg cccccaagag cctgatctac gccgccagca gcctgcagag cggcgtgccc  240
agcagattca gcggcagcgg cagcggcacc gacttcaccc tgaccatcag cagcctgcag  300
cccgaggact tcgccaccta ctactgccag cagtacgaca gctaccccat caccttcggc  360
cagggcacca gactggagat caagggcggc ggcggcagcg gcggcggcgg cagcggcggc  420
ggcggcagcc aggtgcagct gcagcagtgg ggcgccgcc  tgctgaagcc cagcgagacc  480
ctgagcctga cctgcgccgt gtacggcggc agcttcagcg gccactactg gagctggatc  540
agacagcccc ccggcaaggg cctggagtgg atcggcgaca tcaaccacgg cggcggcacc  600
aactacaacc cagcctgaa  gagcagagtg accatcagcg tggacaccag caagaaccag  660
ttcagcctga agctgaacag cgtgaccgcc gccgacaccg ccgtgtacta ctgcgccagc  720
ctgaccgcct actgggccag gggcagcctg gtgaccgtgc gcgttcgtgc             780
gtgttcctgc cgccaagcc  caccaccacc ccgcccccca cccccca    cccgccccc   840
accatcgcca gccagcccct gagcctgaga cccgaggcct gcagaccgcc cgccggcggc   900
gccgtgcaca ccagaggcct ggacttcgcc tgcgacatct acatctgggc ccccctggcc   960
ggcacctgcg gcgtgctgct gctgagcctg gtgatcaccc tgtactgcaa ccacagaaac 1020
agaaagagag cagaaaagca gcatctttaa gctgctgtac atcttcaagc agcccttcat 1080
cagaccaccc aggaggagga cggctgcagc tgcagattcc cgaggagga  ggagggcggc 1140
tgcgagctga gagtgaagtt cagcagaagc gccgacgccc cgcctaccag caggggccag 1200
aaccagctgt acaacgagct gaacctgggc agaagagagg agtacgacgt gctggacaag 1260
agaagaggca gagaccccga gatgggcggc aagcccagaa gaagaacccc caggagggc  1320
ctgtacaacg agctgcagaa ggacaagatg gccgaggcct acagcgagat cggcatgaag 1380
```

```
ggcgagagaa gaagaggcaa gggccacgac ggcctgtacc agggcctgag caccgccacc 1440
aaggacacct acgacgccct gcacatgcag ggcctgcccc ccaga              1485

SEQ ID NO: 117          moltype = AA  length = 474
FEATURE                 Location/Qualifiers
REGION                  1..474
                        note = Synthetic
source                  1..474
                        mol_type = protein
                        organism = synthetic construct
SEQUENCE: 117
DIQMTQSPTS LSASVGDRVT ITCRASQGIS SWLTWYQQKP EKAPKSLIYA ASSLQSGVPS  60
RFSGSGSGTD FTLTISSLQP EDFATYYCQQ YDSYPITFGQ GTRLEIKGGG GSGGGGSGGG 120
GSGQVQLQQWG AGLLKPSETL SLTCAVYGGS FSAYYWSWIR QPPGKGLEWI GDINHGGGTN 180
YNPSLKSRVT ISVDTSKNQF SLKLNSVTAA DTAVYYCASL TAYWGQGSLV TVSAAAFVPV 240
FLPAKPTTTP APRPPTPAPT IASQPLSLRP EACRPAAGGA VHTRGLDFAC DIYIWAPLAG 300
TCGVLLLSLV ITLYCNHRNR KRGRKKLLYI FKQPFMRPVQ TTQEEDGCSC RFPEEEEGGC 360
ELRVKFSRSA DAPAYQQGQN QLYNELNLGR REEYDVLDKR RGRDPEMGGK PRRKNPQEGL 420
YNELQKDKMA EAYSEIGMKG ERRRGKGHDG LYQGLSTATK DTYDALHMQA LPPR       474

SEQ ID NO: 118          moltype = DNA  length = 11238
FEATURE                 Location/Qualifiers
misc_feature            1..11238
                        note = Synthetic
source                  1..11238
                        mol_type = other DNA
                        organism = synthetic construct
SEQUENCE: 118
tgcatagaag gtataatgat catgtcagga tatttgaggt atccacattt gggattgttt   60
aaagattaaa tgaaatagtg ttaaaagtat ttaatatgcc cttcaacaaa tgatgaggaa  120
atcttagaat ctgctcagac tccttcagtt tacatattag gaaactgagg cacagaaagg  180
agcagagact tgctcaagtc cacccaaagc agtagagcat tgtggttaaa tgcaggactt  240
cagtcagact gtctggggtc aaatcctggt tccacttgga catgggtttc cttacataaa  300
tcacttcacc tctctgagcc tcagttttct catatgcaga gtgaggataa taataatacc  360
ttccttacat ggttactgat atgagtatta aatgtgccag ctcatgtgcc tgcgtatag   420
gaggtgcttt ataaacctta gctgttacca ctcatggcat tgccaaatgt gggacgggtc  480
tcctgactct ctggtgtgag attgatgaa tccacactt ccagttccct tttctacctc    540
ctgggtatct tctcatatgg ttgtaagttc cttggaggaa gggaatgtgg cttgctctct  600
ccaccacgct gagcatataa gaggtgctga atgagcgctt ttattcactc ctctcatccc  660
cagccctcac cagctgggag ttgttgtagg tgtcaatttt ctgcctcttt ccaacacccct 720
gtgaggtgac tgagcattgt cttccctccc aggcagctca cagtgtaagc ttgtggacga  780
tatcgaattc gcacgacatt gattattgac tagttattaa tagtaatcaa ttacggggtc  840
attagttcat agcccatata tggagttccg cgttacataa cttacggtaa atggcccgcc  900
tggctgaccg cccaacgacc cccgcccatt gacgtcaata atgacgtatg ttcccatagt  960
aacgccaata gggactttcc attgacgtca atgggtggac tatttacggt aaactgccca 1020
cttggcagta catcaagtgt atcatatgcc aagtacgccc cctattgacg tcaatgacgg 1080
taaatggccc gcctggcatt atgcccagta catgacctta tgggactttc ctacttggca 1140
gtacatctac gtattagtca tcgctattac catgggtcga ggtgagcccc acgttctgct 1200
tcactctccc catctccccc ccctccccac cccaattttg tatttatttt atttttaat   1260
tattttgtgc agcgatgggg gcgggggggg ggggggcgcg cgccaggcgg ggcggggcgg 1320
ggcgagggc ggggcgggc gaggcggaga ggtgcggcgg cagccaatca gagcggcgcg   1380
ctccgaaagt ttccttttat ggcgaggcgg cggcggcggc ggccctataa aaagcgaagc 1440
gcgcggcggg cgggagtcgc tgcgttgcct tcgccccgtg cccgctccg cgccgcctcg   1500
cgccgcccgc cccggctctg actgaccgcg ttactccac aggtgagcgg gcgggacggc   1560
ccttctcctc cgggctgtaa ttagcgcttg gtttaatgac ggcttgtttc ttttctgtgg 1620
ctgcgtgaaa gccttaaagg gctccggag ggccctttgt gcggggggga gcggctcggg   1680
gggtgcgtgc gtgtgtgtgt gcgtgggag cgccgcgtgc ggcccgcgct gcccggcggc   1740
tgtgagcgct gcgggcgcgg cgcggggctt tgtgcgctcc gcgtgtgcgc gaggggagcg 1800
cggccggggg cggtgccccg cggtgcgggg gggctgcgag gggaacaaag gctgcgtgcg 1860
gggtgtgtgc gtgggggggt gagcagggg tgtgggcgtg tgtaacccgc                1920
ccctgcaccc cctccccga gttgctgagc acgccggc ttcgggtgcg gggctccgtg      1980
cggggcgtgg cgcggggctc gccgtgccgg gcggggggtg gcgcaggtg ggggtgccgg    2040
gcggggcggg gccgcctcgg gccggggagg gctcggggga ggggcgcggc ggccccggag 2100
cgccggccgc tgtcgaggcg cggcgagccg cagccattgc ctttatggt aatcgtgcga   2160
gagggcgcag ggacttcctt tgtcccaaat ctgcgagc gaaatctgg gaggcgccgc     2220
cgcacccct ctagcgggcg cgggcgaagc ggtgcggcgc cggcaggaag gaaatgggcg   2280
gggaggcct tcgtgcgtcg ccgcgccgcc gtcccttct ccatctccag cctcggggct    2340
gccgcagggg gacggctgcc ttcgggggg acggggcagg gcggggttcg gcttctggcg   2400
tgtgaccggc ggctctagag cctctgctaa ccatgtgcat gccttcttct ttttcctaca  2460
gggggatcc gtttatctgc agaattcgcc cttgacgtcg ccaccatggc ggcttccggtt 2520
acagcactgc tcctccccttt ggcgctgttg ctccacgcag caaggccgga catccagatg 2580
acccagagcc ccaccagcct gagcgccagc gtgggcgaca gtgaccat cacctgcaga   2640
gccagccagg gcatcagcag ctggctgacc tggtaccagc agaagcccga aaggccccc   2700
aagagcctga tctacgcgc cagcagcctg cagagcggtg tgcccagcag attcagcggc   2760
agcggcagcg gcaccgactt caccctgacc atcagcagcc tgcagcccga ggacttcgcc  2820
acctactact gccagcagta cgacagctac cccatcacct tcggccaggg caccagactg 2880
gagatcaagg gcggcggcgg cagcggcggc ggcggcagcg gcggcggcgg cagcaggtg   2940
cagctgcagc agtggggcgc cggcctgctg aagcccagcg agaccctgag cctgacctgc 3000
gccgtgtacg gcggcagctt cagcgcctac tactggagct ggatcagaca gcccccggc   3060
```

-continued

```
aagggcctgg agtggatcgg cgacatcaac cacggcggcg gcaccaacta caacccagc    3120
ctgaagagca gagtgaccat cagcgtggac accagcaaga accagttcag cctgaagctg   3180
aacagcgtga ccgccgccga caccgccgtg tactactgcg ccagcctgac cgcctactgg   3240
ggccagggca gcctggtgac cgtgagcgcc gccgccttcg tgcccgtgtt cctgcccgcc   3300
aagcccacca ccaccccgc ccccagaccc ccacccccg ccccccaccat cgccagccag    3360
cccctgagcc tgagacccga ggcctgcaga cccgccgccg cggcgccgt gcacaccaga    3420
ggcctggact cgcctgcga catctacatc tgggccccc tggccggcac ctgcggcgtg    3480
ctgctgctga gcctggtgat caccctgtac tgcaaccaca gaaacagaaa gagaggcaga   3540
aagaagctgc tgtacatctt caagcagccc ttcatgagac ccgtgcagac cacccaggag   3600
gaggacggct gcagctgcag attccccgag gaggaggagg gcggctgcga gctgagagtg   3660
aagttcagca gaagcgccga cgccccccgcc taccagcagg gccagaacca gctgtacaac   3720
gagctgaacc tgggcagaag agaggagtac gacgtgctgg acaagagaag aggcagagac   3780
cccgagatgg gcggcaagcc cagaagaaag aaccccccagg agggcctgta caacgagctg   3840
cagaaggaca agatggccga ggcctacagc gagatcggca tgaagggcga gagaagaaga   3900
ggcaagggcc acgacggcct gtaccagggc ctgagcaccg ccaccaagga cacctacgac   3960
gccctgcaca tgcaggccct gccccccaga ggaagcggag ctactaactt cagcctgctg   4020
aagcaggctg gagacgtgga ggagaaccct ggacctatgt ctcgctccgt tgccttagct   4080
gtgctcgcgc tactctctct ttctggatta gaggctgtca tggcccccg aaccctcttc    4140
ctgggtggag gcggttcagg cggaggtggc tctgcggtg gcggatcgat ccagcgtact    4200
ccaaagattc aggtttactc acgtcatcca gcagagaatg gaaagtcaaa ttcctgaat    4260
tgctatgtgt ctgggtttca tccatccgac attgaagttg acttactgaa gaatggagag   4320
agaattgaaa aagtggagca ttcagacttg tcttcagca aggactggtc tttctatctc    4380
ttgtactaca ctgaattcac ccccactgaa aaagatgagt atgcctgccg tgtgaaccat   4440
gtgactttgt cacagcccaa gatagttaag tgggatcgag acatgggtgg tggtggttct   4500
ggtggtggtg gttctggcgg cggcggctcc ggtggtggtg gatccggctc ccactccttg   4560
aagtatttcc acacttccgt gtcccggccc ggccgcgggc agcccgctt catctctcttg   4620
ggctacgtgg acgacaccca gttcgtgcgc ttcgacaacg acgccgcgg tccggaggatg   4680
gtgccgcggg cgccgtgggat ggagcaggag gggtcagagt attgggaccg ggagacacgg   4740
agcgccaggg acaccgcaca gatttttccga gtgaatctgc ggacgctgcg cggctactac   4800
aatcagacga aggccgggtc tcacaccctg cagtggatgc atggctgcga gctggggccc   4860
gacgggcgct tcctccgcgg gtatgaacag ttcgcctacg acggcaagga ttatctcacc   4920
ctgaatgagg acctgcgctc ctggaccgcg gtggacacgg cggctcagat ctccgagcaa   4980
aagtcaaatg atgcctctga ggcggagcac cagagagcct acctgaaga cacatgcgtg    5040
gagtggctcc acaaatacct ggagaagggg aaggaacgc tgcttcacct ggagccccca    5100
aagacacacg tgactcacca ccccatctct gaccatgaag ccaccctgcg gtgctgggcc   5160
ctgggcttct accctgcgga gatcacactg acctggcagc aggatgggga gggccatacc   5220
caggacacgg agctcgtgga gaccaggcct gcagggggatg gaaccttcca gaagtgggca   5280
gctgtggtgg tgccttctgg agaggagcag agatacacgt gccatgtgca gcatgagggg   5340
ctacccgagc ccgtcaccct gagatggaag ccggcttccc agcccaccat cccatcgtg    5400
ggcatcattg ctggcctggt tctccttgga tctgtggtct ctggagctgt ggttgctgct    5460
gtgatatgga ggaagaagag ctcaggtgga aaggaggga gctactctaa ggctgagtgg   5520
agcgacagtg cccaggggtc tgagtctcac agcttgtaat gatagccgct gatcagcctc   5580
gactgtgcct tctagttgcc agccatctgt tgtttgcccc tcccccgtgc cttccttgac    5640
cctggaaggt gccactccca ctgtcccttc ctaataaat gaggaaattg catcgcattg    5700
tctgagtagg tgtcattcta ttctgggggg tgggtgggg caggacagca agggggagga   5760
ttgggaagac aatagcaggc atgctgggga tgcgtgggc tctatgggtc gactgaccag   5820
atggacctgg ctgagagaa agagattgag tctctactcag gtgggccctc ctccctctgg   5880
tctcttccgg tatcccccac ccctcagctt gctgtagaga cggcaatcag ggaaattct    5940
ggtccctgcc ctcccgtcag caccacggac agctcccacg tctgtgggac gctctctgca   6000
gatgggatg atctcccagc cctgcccgc ctctccctcg ttcccacca gccctctttc     6060
cagaaatttc cttcttcatc caagggactt ttcctcccaa aacccgacac agacaccatc   6120
aactgcgacc agttcagcag gctgttgtgt gacatggaag gtgatgaaga gaccaggag    6180
gcttatgcca atatcggtga ggaagcacct gagcccagaa aaggcaaatc aagggcaaga   6240
gttctttgct gccacttgtc aatatcaccc attcatcatg agccacgtca gtcccctccc    6300
acagaaatca ttgcaagggg gatgcgggagc aatggctgga ggaacggaga ctccagggaa   6360
gagagggaag atggaggcca gtggggaaa taggccccctt cactaatgac caccagaaa    6420
acaaaatctc atgtttacat cctccacctc catttctata cgcatttctg cttcttgctc   6480
ttctgtccat cctttctaca aagcccatac catacacccc tttcccttt cctcccagct    6540
ccttagccaa gctactctag tatttgtaat aactagcatt tactggatac tcatagtatg   6600
ctcattgctg tccggtaacc acgtgcggac cggctccgg tgcccgtcag tgggcagagc    6660
gcacatcgcc cacagtcccc gagaagttgg ggggaggggt cggcaattga accggtgcct   6720
agagaaggtg gcgcggggta aactgggaaa gtgatgtcgt gtactggctc cgccttttc    6780
ccgagggtgg gggagaaccg tatataagtg cagtagtcgc cgtgaacgtt cttttttcgca   6840
acgggtttgc cgcagaaca caggtaagtg ccgtgtgtgg ttcccgcggg cctggcctct    6900
ttacggggtta tggcccttgc gtgccttgaa ttacttccac tggctgcagt acgtgattct    6960
tgatcccgag cttcggggttg gaagtggggtg ggagagttcg aggcccttgcg cttaaggagc   7020
cccttcgcct cgtgcttgag ttgaggcctg gcctgggcgc tgggccgcc gcgtgcgaat    7080
ctggtggcac cttcgcgcct gtctcgctgc ttttcgataag tctctagcca tttaaaattt   7140
ttgatgacct gctgcgacgc tttttttctg gcaagatagt cttgtaaatg cgggccaaga   7200
tctgcacact ggtatttcgg tttttgggc cgcgggcggc gacgggccc gtgcgtccca    7260
gcgcacatgt tcggcgaggc ggggcctgcg agcgcggcca ccgagaatcg gacgggggta   7320
gtctcaagct ggccggcctg ctctggtgcc tggcctcgcg ccgccgtgta tcgcccgcc    7380
ctgggcggca aggctggccc ggtcggcacc agttgcgtga gcggaaagat ggccgcttcc    7440
cggccctgct gcagggagct caaaatggag gacgcgcgtc tcgggagac gggcgggtga    7500
gtcacccaca caaaggaaaa gggccttttcc gtcctcagcc gtcgcttcat gtgactccac    7560
ggagtaccgg gcgccgtcca ggcacctcga ttagttctcg agcttttgga gtacgtcgtc   7620
tttaggttgg ggggagggggt tttatgcgat ggagtttccc cacactgagt gggtggagac    7680
tgaagttagg ccagcttggc acttgatgta attctccttg gaattttgccc ttttttgagtt   7740
tggatcttgg ttcattctca agcctcagac agtggttcaa agttttttc ttccatttca     7800
```

```
ggtgtcgtga cttgacgtcg ccaccatgag gatatttgct gtctttatat tcatgaccta  7860
ctggcatttg ctgaacgcat ttactgtcac ggttcccaag gacctatatg tggtagagta  7920
tggtagcaat atgacaattg aatgcaaatt cccagtagaa aaacaattag acctggctgc  7980
actaattgtc tattgggaaa tggaggataa gaacattatt caatttgtgc atggagagga  8040
agacctgaag gttcagcata gtagctacag acagagggcc cggctgttga aggaccagct  8100
ctccctggga aatgctgcac ttcagatcac agatgtgaaa ttgcaggatg caggggtgta  8160
ccgctgcatg atcagctatg gtggtgccga ctacaagcga attactgtga aagtcaatgc  8220
cccatacaac aaaatcaacc aaagaatttt ggttgtggat ccagtcacct ctgaacatga  8280
actgacatgt caggctgagg gctaccccaa ggccgaagtc atctggacaa gcagtgacca  8340
tcaagtcctg agtggtaaga ccaccaccac caattccaag agagaggaga aacttttcaa  8400
tgtgaccagc acactgagaa tcaacacaac aactaatgag attttctact gcactttag  8460
gagattagat cctgaggaaa accatacagc tgaattggtc atcccagaac tacctctggc  8520
acatcctcca aatgaaagga ctcacttggt aattctggga gccatcttat tatgccttgg  8580
tgtagcactg acattcatct tccgtttaag aaaagggaga atgatggatg tgaaaaatg   8640
tggcatccaa gatacaaact caaagaagca aagtgataca catttggagg agacgtaacc  8700
gctgatcagc ctcgaaactt gtttattgca gcttataatg gttacaaata aagcaatagc  8760
atcacaaatt tcacaaataa agcatttttt tcactgcatt ctagttgtgg tttgtccaaa  8820
ctcatcaatg tatcttaggc gcctgatgcg gtattttctc cttacgcatc tgtgcggtat  8880
ttcacaccgc atacagtact gtcaaagcaa ccatagtacg cgccctgtag cggcgcatta  8940
agcgcggcgg gtgtggtggt tacgcgcagc gtgaccgcta cacttgccag cgccctagcg  9000
cccgctcctt tcgctttctt cccttccttt ctcgccacgt tcgccggctt tccccgtcaa  9060
gctctaaatc ggggggctcc ctttagggtt cgatttagtg cttacggcca cctcgacccc  9120
aaaaaacttg atttgggtga tggttcacgt agtgggccat cgccctgata gacggttttt  9180
cgccctttga cgttggagtc cacgttcttt aatagtggac tcttgttcca aactggaaca  9240
acactcaacc ctatctcggg ctattctttt gatttataag gattttgcc gatttcggcc  9300
tattggttaa aaaatgagct gatttaacaa aaatttaaa caaatattta  9360
acgtttacaa ttttatggtg cactctcagt acaatctgct ctgatgccgc atagttaagc  9420
cagccccgac acccgccaac acccgctgac gcgccctgac gggcttgtct gctcccggca  9480
tccgcttaca gacaagctgt gaccgtctcc gggagctgca tgtgtcagag gttttcaccg  9540
tcatccaccga aacgcgcgag acgaaagggc ctcgtgatac cctatttt ataggttaat  9600
gtcatgaaca ataaaactgt ctgcttacat aaacagtaat acaagggtg ttatgagcca  9660
tattcaacgg gaaacgtcga ggccgcgatt aaattccaac atggatgctg atttatatgg  9720
gtataaatgg gctcgcgata atgtcgggca atcaggtgcg acaatctatc gcttgtatgg  9780
gaagcccgat gcgccagagt tgtttctgaa acatggcaaa ggtagcgttg ccaatgatgt  9840
tacagatgag atggtcagac taaactggct gacggaattt atgcctcttc cgaccatcaa  9900
gcattttatc cgtactcctg atgatgcatg gttactcacc actgcgatcc ccggaaaaac  9960
agcattccag gtattagaag aatatcctga ttcaggtgaa atattgttg atgcgctggc 10020
agtgttcctg cgccggttgc attcgattcc tgtttgtaat tgtccttta acagcgatcg 10080
cgtatttcgt ctcgctcagg cgcaatcacg aatgaataac ggtttggttg atgcgagtga 10140
ttttgatgac gagcgtaatg gctggcctgt tgaacaagtc tggaaagaaa tgcataaact 10200
tttgccattc tcaccggatt cagtcgtcac tcatggtgat ttctcacttg ataaccttat 10260
ttttgacgag gggaaattaa taggttgtat tgatgttgga cgagtcggaa tcgcagaccg 10320
ataccaggat cttgccatcc tatggaactg cctcggtgag ttttctcctt cattacagaa 10380
acggcttttt caaaaatatg gtattgataa tcctgatatg aataaattgc agtttcattt 10440
gatgctcgat gagttttct aatctcatga ccaaatccc ttaacgtgag ttttcgttcc 10500
actgagcgtc agacccgta gaaaagatca aaggatcttc ttgagatcct ttttttctgc 10560
gcgtaatctg ctgcttgcaa acaaaaaaac caccgctacc agcggtggtt tgtttgccgg 10620
atcaagagct accaactctt tttccgaagg taactggctt cagcagagcg cagataccaa 10680
atactgtcct tctagtgtag ccgtagttag gccaccactt caagaactct gtagcaccgc 10740
ctacatacct cgctctgcta atcctgttac cagtggctgc tgccagtggc gataagtcgt 10800
gtcttaccgg gttggactca agacgatagt taccggataa ggcgcagcgg tcgggctgaa 10860
cgggggggttc gtgcacacag cccagcttgg agcgaacgac ctacaccgaa ctgagatacc 10920
tacagcgtga gctatgagaa agcgccacgc ttcccgaagg gagaaaggcg gacaggtatc 10980
cggtaagcgg cagggtcgga acaggagagc gcacgaggga gcttccaggg ggaaacgcct 11040
ggtatcttta tagtcctgtc gggtttcgcc acctctgact tgagcgtcga ttttgtgat  11100
gctcgtcagg ggggcggagc ctatggaaaa acgccagcaa cgcggccttt ttacggttcc 11160
tggccttttg ctggcctttt gctcacatgt gcggccgcac gcgtcatatt tatggggtat 11220
atgtgaatat ttattaca                                              11238
```

SEQ ID NO: 119        moltype = DNA   length = 3015
FEATURE              Location/Qualifiers
misc_feature       1..3015
                      note = Synthetic
source               1..3015
                      mol_type = other DNA
                      organism = synthetic construct
SEQUENCE: 119

```
cagatccagc tgcagcagag cggccccgag gtggtgaagc ccggcgccag cgtgaagatc   60
agctgcaagg ccagcggcta caccttcacc gactactaca tcacctgggt gaagcagaag  120
cccggccagg gcctggagtg gatcggctgg atctacccg gcagcggcaa caccaagtac  180
aacgagaagt tcaagggcaa ggccaccctg accgtggaca ccagcagcag caccgccttc  240
atgcagctga gcagcctgac cagcgaggac accgccgtgt acttctgcgc caactacggc  300
aactactggt tcgcctactg gggccagggc acccaggtga ccgtgagcgc cggcggcggc  360
ggcagcggcg gcggcggcag cggcggcggc ggcagcgaca tcgtgctgac ccagagcccc  420
gccagcctgg ccgtgagcct gggccagaga gccaccatca gctgcaaggc cagcagagc   480
gtggacttcg acggcgacag ctacatgaac tggtaccagc agaagcccgg ccagcccccc  540
aaggtgctga tctacgccgc cagcaacctg gagagcggca tccccgccag attcagcggc  600
agcggcagcg gcaccgactt cacccctgaac atccacccg tggaggagga ggacgccgcc  660
acctactact gccagcagag caacgaggac ccctggacct cggcggcgg caccaagctg  720
```

```
gagatcaaga gcgccgccgc cttcgtgccc gtgttcctgc ccgccaagcc caccaccacc     780
cccgccccca gacccccac ccccgccccc accatcgcca gccagcccct gagcctgaga     840
cccgaggcct gcagacccgc cgccggcggc gccgtgcaca ccagaggcct ggacttcgcc     900
tgcgacatct acatctgggc cccctggcc ggcacctgcg gcgtgctgct gctgagcctg     960
gtgatcaccc tgtactgcaa ccacagaaac agaagcaaga gaagcagact gctgcacagc    1020
gactacatga acatgacccc cagaagacccc ggccccacca gaaagcacta ccagcctac    1080
gccccccca gagacttcgc cgcctacaga agcagagtga agttcagcag aagcgccgac    1140
gcccccgcct accagcaggg ccagaaccag ctgtacaacg agctgaacct gggcagaaga    1200
gaggagtacg acgtgctgga caagagaaga ggcagagacc ccgagatggg cggcaagccc    1260
agaagaaaga accccagga gggcctgtac aacgagctgc agaaggacaa gatggccgag    1320
gcctacagcg agatcggcat gaagggcgag agaagaagag gcaagggcca cgacggcctg    1380
taccagggcc tgagcaccgc caccaaggac acctacgacg ccctgcacat gcaggccctg    1440
ccccccagag gaagcggagc tactaacttc agcctgctga gcaggctgg agacgtggag    1500
gagaaccctg gacctatgtc tcgctccgtt gcctagctg tgctcgcgct actctctctt    1560
tctggattag aggctgtcat ggcgcccga accctcttcc tgggtggagg cggttcaggc    1620
ggaggtggct ctggcggtgg cggatcgatc cagcgtactc caaagattca ggtttactca    1680
cgtcatccag cagagaatgg aaagtcaaat ttcctgaatt gctatgtgtc tgggtttcat    1740
ccatccgaca ttgaagttga cttactgaag aatggagaga gaattgaaaa agtggagcat    1800
tcagacttgt ctttcagcaa ggactggtct ttctatctct tgtactacac tgaattcacc    1860
cccactgaaa aagatgagta tgcctgccgt gtgaaccatg tgactttgtc acagcccaag    1920
atagttaagt gggatcgaga catgggtggt ggtggttctg gtggtggtgg ttctggcggc    1980
ggcggctccg gtggtggtgg atccggctcc cactccttga agtatttcca cactteegtg    2040
tcccggcccg gccgcgggga gccccgcttc atctctgtgg gctacgtgga cgacacccag    2100
ttcgtgcgct tcgacaacga cgccgcgagt ccgaggatgg tgccgcggc gccgtggatg    2160
gagcaggagg ggtcagagta ttgggaccgg agacacgga gcgccaggga caccgcacag    2220
atttccgag tgaatctgcg gacgctgcgc ggctactaca atcagagcga ggccgggtct    2280
cacaccctgc agtggatgca tggctgcgag ctggggcccg acgggcgctt cctccgcggg    2340
tatgaacagt tcgcctacga cggcaaggat tatctcaccc tgaatgagga cctgcgctcc    2400
tggaccgcgt ggacacggc ggctcagatc tccgagcaaa agtcaaatga tgcctctgag    2460
gccgagcacc agagagccta cctggaagac acatgcgtgg agtggctcca caaatacctg    2520
gagaagggga aggagacgct gcttcacctg gagcccccaa agacacacgt gactcaccac    2580
cccatctctg accatgaggc cacccctgagg tgctgggccc tgggcttcta ccctgcggag    2640
atcacactga cctggcagca ggatggggag gccataccc aggacacgga gctcgtggag    2700
accaggcctg caggggatgg aaccttccag aagtgggcag ctgtggtggt gcctctggga    2760
gaggagagga gatacactg ccatgtgcag catgaggggc tacccgagcc cgtcaccctg    2820
agatggaagc cggcttccca gcccaccatc cccatcgtgg gcatcattgc tggcctggtt    2880
ctccttggat ctgtggtctc tggagctgtg gttgctgctg tgatatggag aagaagagc    2940
tcaggtggaa aaggagggag ctactctaag gctgagtgga cgacagtgc ccaggggtct    3000
gagtctcaca gcttg                                                   3015
```

SEQ ID NO: 120      moltype = DNA  length = 2985
FEATURE               Location/Qualifiers
misc_feature      1..2985
                    note = Synthetic
source              1..2985
                    mol_type = other DNA
                    organism = synthetic construct
SEQUENCE: 120

```
caggtgcagc tgcagcagtg gggcgccggc ctgctgaagc ccagcgagac cctgagcctg       60
acctgcgccg tgtacggcgg cagcttcagc gcctactact ggagctggat cagacagccc      120
cccggcaagg gcctggagtg gatcggcgac atcaaccacg gcggcggcac caactacaac      180
cccagcctga agagcagagt gaccatcagc gtggacacca gcaagaacca gttcagcctg      240
aagctgaaca gcgtgaccgc cgccgacacc gccgtgtact actgcgccag cctgaccgcc      300
tactggggcc agggcagcct ggtgaccgtg agcagcggcg gcggcggcag cggcggcggc      360
ggcagcggcg gcggcggcag cgacatccag atgacccagc cccccaccag cctgagcgcc      420
agcgtgggcg acagagtgac catcacctgc agagccagcc agggcatcag cagctgctg       480
acctggtacc agcagaagcc cgagaaggcc ccaagagcc tgatctacgc cgccagcagc       540
ctgcagagcg gcgtgcccag cagattcagc ggcagcggca gcggcaccga cttcaccctg       600
accatcagca gctgcagcc cgaggacttc gccacctact actgccagca gtacgacagc       660
taccccatca ccttcggcca gggcaccaga ctggagatca gagcgccgc cgccttcgtg       720
cccgtgttcc tgcccgccaa gcccaccacc ccccgccc cagacccccc accccccgcc       780
cccaccatcg ccagccagcc cctgagcctg agacccgagg cctgcagacc cgccgccggc       840
ggcgccgtga caccagagg cctggacttc gcctgcgaca tctacatctg gccccccctg       900
gccggcacct gcggggcgtgct gctgctgagc ctggtgatca ccctgtactg caaccacaga       960
aacagaaaga gaggcagaaa gaagctgctg tacatcttca gcagcccctt catgagaccc      1020
gtgcagacca cccaggagga ggacggctgc agctgcagat tccccgagga ggaggaggc      1080
ggctgcgagc tgagagtgaa gttcagcaga agcgccgacg ccccgccta ccagcaggc      1140
cagaaccagc tgtacaacga gctgaacctg ggcagaagag gagtacga cgtgctggac      1200
aagagaagag gcagacccc cagatgggc gcaagccca gaagaaaga cccccagga      1260
ggcctgtaca acgagctgca gaaggacaag atggccgagg cctacagcga gatcggcatg      1320
aagggcgaga agaagaagg caagggccac gacggcctgt accagggcct gagcaccgcc      1380
accaaggaca cctacgacgc cctgcacatg caggccctgc ccccagagg aagcggattc      1440
agcctgctga gcaggctgg agacgtggag gagaaccctg gacctatgtc tcgctccgtt      1500
gccttagctg tgctcgcgct actctctctt tctggattag aggctgtcat ggcgcccga       1560
acctcttcc tgggtggagg cggttcaggc ggaggtggct ctggcggtgg cggatcgatc      1620
cagcgtactc caaagattca ggtttactca cgtcatccag cagagaatgg aaagtcaaat      1680
ttcctgaatt gctatgtgtc tgggtttcat ccatccgaca ttgaagttga cttactgaag      1740
aatggagaga gaattgaaaa agtggagcat tcagacttgt ctttcagcaa ggactggtct      1800
ttctatctct tgtactacac tgaattcacc cccactgaaa aagatgagta tgcctgccgt      1860
```

```
gtgaaccatg tgactttgtc acagcccaag atagttaagt gggatcgaga catgggtggt 1920
ggtggttctg gtggtggtgg ttctggcggc ggcggctccg gtggtggtgg atccggctcc 1980
cactccttga agtatttcca cacttccgtg tcccggcccg gccgcgggga gccccgcttc 2040
atctctgtgg gctacgtgga cgacacccag ttcgtgcgct tcgacaacga cgccgcgagt 2100
ccgaggatgg tgccgcgggc gccgtggatg gagcaggagg ggtcagagta ttgggaccgg 2160
gagacacgga gcgccaggga caccgcacag attttccgag tgaatctgcg gacgctgcgc 2220
ggctactaca atcagagcga ggccgggtct cacaccctgc agtggatgca tggctgcgag 2280
ctggggcccg acgggcgctt cctccgcggg tatgaacagt tcgcctacga cggcaaggat 2340
tatctcaccc tgaatgagga cctgcgctcc tggaccgcgg tggacaccggc ggctcagatc 2400
tccgagcaaa agtcaaatga tgcctctgag gcggagcacc agagagccta cctggaagac 2460
acatgcgtgg agtggctcca caaatacctg gagaagggga aggagacgct gcttcacctg 2520
gagcccccaa agacacacgt gactcaccac cccatctctg accatgaggc caccctgagg 2580
tgctgggccc tgggcttcta ccctgcggag atcacactga cctggcagca ggatggggag 2640
ggcatacccc aggacacgga gctcgtggag accaggcctg caggggatgg aacccttcag 2700
aagtgggcag ctgtggtggt gccttctgga gaggagcaga gatacacgtg ccatgtgcag 2760
catgaggggc tacccgagcc cgtcaccctg agatggaagc cggcttccca gcccaccatc 2820
cccatcgtgg gcatcattgc tggcctggtt ctccttggat ctgtggtctc tggagctgtg 2880
gttgctgctg tgatatggag aagaagagc tcaggtggaa aaggagggag ctactctaag 2940
gctgagtgga gcgacagtgc caggggtct gagtctcaca gcttg 2985

SEQ ID NO: 121       moltype = DNA  length = 2988
FEATURE              Location/Qualifiers
misc_feature         1..2988
                     note = Synthetic
source               1..2988
                     mol_type = other DNA
                     organism = synthetic construct
SEQUENCE: 121
gacatccaga tgacccagag ccccaccagc ctgagcgcca gcgtgggcga cagagtgacc 60
atcacctgca gagccagcca gggcatcagc agctggctga cctggtacca gcagaagccc 120
gagaaggccc ccaagagcct gatctacgcc gccagcagcc tgcagagcgg cgtgcccagc 180
agattcagcg gcagcggcag cggcaccgac ttcaccctga ccatcagcag cctgcagccc 240
gaggacttcg ccacctacta ctgccagcag tacgacagct accccatcac cttcggccag 300
ggcaccagac tggagatcaa gggcggcggc ggcagcggcg gcggcggcag cggcggcggc 360
ggcagccagg tgcagctgca gcagtggggc gccggcctgc tgaagcccag cgagaccctg 420
agcctgacct cgcgcgtgta cggcggcagc ttcagcgcct actactgag ctggatcaga 480
cagcccccg gcaagggcct ggagtggatc ggcgacatca accacggcgg cggcaccaac 540
tacaacccca gcctgaagag cagagtgacc atcagcgtgg acaccagcaa gaaccagttc 600
agcctgaagc tgaacagcgt gaccgccgcc gacaccgccg tgtactactg cgccagcctg 660
accgcctact ggggcagggg cagcctggtg accgtgagcg ccgccgcctt cgtgccgtg 720
ttcctgcccg ccaagcccac caccaccccc gccccagac ccccacccc cgcccccacc 780
atcgccagcc agcccctgag cctgagaccc gaggcctgca gacccgccgc cggcggcgcc 840
gtgcacacca aggcctgga cttcgcctgc gacatctaca tctgggcccc cctggccggc 900
acctgcggcg tgctgctgct gagcctggtg atcaccctgt actgcaacca cagaaacaga 960
aagagaggca gaaagaagct gctgtacatc ttcaagcagc ccttcatgag acccgtgcag 1020
accacccagg aggaggacgg ctgcagctgc agattccccg aggaggagga gggcggctgc 1080
gagctgagag tgaagttcag cagaagcgcc gacgccccg cctaccagca gggccagaac 1140
cagctgtaca cgagctgaa cctgggcaga agagaggagt acgacgtgct ggacaagaga 1200
agaggcagag accccgagat gggcggcaag cccagaagaa agaacccca ggagggcctg 1260
tacaacgagc tgcagaagga caagatggcc gaggcctaca gcgagatcgg catgaagggc 1320
gagagaagaa gaggcaaggg ccacgacggc ctgtaccagg gcctgagcac cgccaccaag 1380
gacacctacg acgccctgca catgcaggcc ctgccccca gaggaagcgg agctactaac 1440
ttcagcctgc tgaagcaggc tggagacgtg gaggagaacc ctggacctat gtctcgctcc 1500
gttgccttag ctgtgctcgc gctactctct ctttctggat tagaggctgt catggcgccc 1560
cgaaccctct tcctgggtgg aggcggttca ggcggaggtg gctctggcgg tggcggatcg 1620
atccagcgta ctccaaagat tcaggtttac tcacgtcatc cagcagagaa tggaaagtca 1680
aatttcctga attgctatgt gtctgggttt catccatccg acattgaagt tgacttactg 1740
aagaatggaa agaagaattga aaagtggag cattcagact tgtctttcag caaggactgg 1800
tctttctatc tcttgtacta cactgaattc accccccactg aaaaaagatga gtatgcctga 1860
cgtgtgaacc atgtgacttt gtcacagccc aagatagtta agtgggatcg agacatggtt 1920
ggtggtggtt ctggtggtgg tggttctggc ggcggcggct ccgtggtggg tggatccggc 1980
tcccactcct tgaagtattt ccacacttcc gtgtcccggc ccggccgcgg ggagccccgc 2040
ttcatctctg tgggctacgt ggacgacacc cagttcgtgc gcttcgacaa cgacgccgcg 2100
agtccgagga tggtgccgcg ggccgtggat ggagcaggag gggtcagata gtattgggaa 2160
cgggagacac ggagcgccag ggacaccgca cagattttcc gagtgaatct gcggacgctg 2220
cgcggctact acaatcagag cgaggccggg tctcacaccc tgcagtggat gcatggctgc 2280
gagctggggc ccgacgggcg cttcctccgc gggtatgaac agttcgccta cgacggcaag 2340
gattatctca ccctgaatga ggacctgcgc tcctggaccg cggtggacac ggcggctcag 2400
atctccgagc aaaagtcaaa tgatgcctct gaggcggagc accagagcgg aacctggaag 2460
gacacatgcg tggagtggct ccacaaatac ctggagaagg gaaggagac gctgcttcac 2520
ctggagcccc aaagacaca cgtgactcac caccccatct gaccatga ggccaccctg 2580
aggtgctggg ccctgggctt ctaccctgcg gagatcacac tgacctggca gcaggatggg 2640
gagggccata cccaggacac ggagctcgtg gagaccaggc ctgcagggga tggaaccttc 2700
cagaagtggg cagctgtgtg gtggtccttct ggagaggaga gagatacac gtgccatgtg 2760
cagcatgagg ggctacccga gcccgtcacc ctgagatgga gccggcttc ccagcccacc 2820
atccccatcg tgggcatcat tgctggcctg gttctccttg gatctgtggt ctctggagct 2880
gtggttgctg ctgtgatatg gaggaagaag agctcaggtg gaaaggagg gagctactct 2940
aaggctgagt ggagcgacag tgcccagggg tctgagtctc acagcttg 2988
```

-continued

```
SEQ ID NO: 122            moltype = AA   length = 88
FEATURE                   Location/Qualifiers
REGION                    1..88
                          note = Synthetic
source                    1..88
                          mol_type = protein
                          organism = synthetic construct
SEQUENCE: 122
SAAAFVPVFL PAKPTTTPAP RPPTPAPTIA SQPLSLRPEA CRPAAGGAVH TRGLDFACDI    60
YIWAPLAGTC GVLLLSLVIT LYCNHRNR                                      88

SEQ ID NO: 123            moltype = AA   length = 40
FEATURE                   Location/Qualifiers
source                    1..40
                          mol_type = protein
                          organism = Homo sapiens
SEQUENCE: 123
SKRSRLLHSD YMNMTPRRPG PTRKHYQPYA PPRDFAAYRS                          40

SEQ ID NO: 124            moltype = AA   length = 42
FEATURE                   Location/Qualifiers
source                    1..42
                          mol_type = protein
                          organism = Homo sapiens
SEQUENCE: 124
KRGRKKLLYI FKQPFMRPVQ TTQEEDGCSC RFPEEEEGGC EL                      42

SEQ ID NO: 125            moltype = AA   length = 112
FEATURE                   Location/Qualifiers
source                    1..112
                          mol_type = protein
                          organism = Homo sapiens
SEQUENCE: 125
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 126            moltype = DNA  length = 264
FEATURE                   Location/Qualifiers
misc_feature              1..264
                          note = Synthetic
source                    1..264
                          mol_type = other DNA
                          organism = synthetic construct
SEQUENCE: 126
agcgccgccg ccttcgtgcc cgtgttcctg cccgccaagc ccaccaccac ccccgccccc    60
agaccccca ccccgccccc caccatcgcc agccagcccc tgagcctgag acccgaggcc   120
tgcagacccg ccgcggcgg cgccgtgcac accagagctg tggactttgc ctgcgacatc   180
tacatctggg cccccctggc cggcacctgc ggcgtgctgc tgctgagcct ggtgatcacc   240
ctgtactgca accacagaaa caga                                         264

SEQ ID NO: 127            moltype = DNA  length = 126
FEATURE                   Location/Qualifiers
misc_feature              1..126
                          note = Synthetic
source                    1..126
                          mol_type = other DNA
                          organism = synthetic construct
SEQUENCE: 127
aagagaggca gaaagaagct gctgtacatc ttcaagcagc ccttcatgag acccgtgcag    60
accacccagg aggaggacgg ctgcagctgc agattccccg aggaggagga gggcggctgc   120
gagctg                                                             126

SEQ ID NO: 128            moltype = DNA  length = 336
FEATURE                   Location/Qualifiers
misc_feature              1..336
                          note = Synthetic
source                    1..336
                          mol_type = other DNA
                          organism = synthetic construct
SEQUENCE: 128
agagtgaagt tcagcagaag cgccgacgcc cccgcctacc agcagggcca gaaccagctg    60
tacaacgagc tgaacctggg cagaagagag gagtacgacg tgctggacaa gagaagaggc   120
agagaccccg agatgggcgg caagcccaga agaaagaacc cccaggaggg cctgtacaac   180
gagctgcaga aggacaagat ggccgaggcc tacagcgaga tcggcatgaa gggcgagaga   240
agaagaggca agggccacga cggcctgtac cagggcctga gcaccgccac caaggacacc   300
tacgacgccc tgcacatgca ggcccctgccc cccaga                           336

SEQ ID NO: 129            moltype = DNA  length = 1128
FEATURE                   Location/Qualifiers
```

| source | 1..1128 |
| --- | --- |
| | mol_type = genomic DNA |
| | organism = Homo sapiens |

SEQUENCE: 129

| atggaaactc | tttctaatgc | aagtggtact | tttgccatac | gccttttaaa | gatactgtgt | 60 |
|---|---|---|---|---|---|---|
| caagataacc | cttcgcacaa | cgtgttctgt | tctcctgtga | gcatctcctc | tgccctggcc | 120 |
| atggttctcc | taggggcaaa | gggaaacacc | gcaacccaga | tggcccaggc | actgtcttta | 180 |
| aacacagagg | aagacattca | tcgggctttc | cagtcgcttc | tcactgaagt | gaacaaggct | 240 |
| ggcacacagt | acctgctgag | aacggccaac | aggctctttg | gagagaaaac | ttgtcagttc | 300 |
| ctctcaacgt | ttaaggaatc | ctgtcttcaa | ttctaccatg | ctgagctgaa | ggagctttcc | 360 |
| tttatcagag | ctgcagaaga | gtccaggaaa | cacatcaaca | cctgggtctc | aaaaaagacc | 420 |
| gaaggtaaaa | ttgaagagtt | gttgccgggt | agctcaattg | atgcagaaac | caggctggtt | 480 |
| cttgtcaatg | ccatctactt | caaaggaaag | tggaatgaac | cgtttgacga | aacatacaca | 540 |
| agggaaatgc | cctttaaaat | aaaccaggag | gagcaaaggc | cagtgcagat | gatgtatcag | 600 |
| gaggccacgt | ttaagctcgc | ccacgtgggc | gaggtgcgcg | cgcagctgct | ggagctgccc | 660 |
| tacgccagga | aggagctgag | cctgctggtg | ctgctgcctg | acgacggcgt | ggagctcagc | 720 |
| acggtggaaa | aagtctcac | ttttgagaaa | ctcacagcct | ggaccaagcc | agactgtatg | 780 |
| aagagtactg | aggttgaagt | tctccttcca | aaatttaaac | tacaagagga | ttatgacatg | 840 |
| gaatctgtgc | ttcggcattt | gggaattgtt | gatgccttcc | aacagggcaa | ggctgacttg | 900 |
| tcggcaatgt | cagcggagag | agaccgtgt | ctgtccaagt | tcgtgcacaa | gagttttgtg | 960 |
| gaggtgaatg | aagaaggcac | cgaggcagcg | gcagcgtcga | gctgctttgt | agttgcgagg | 1020 |
| tgctgcatgg | aatctggccc | caggttctgt | gctgaccacc | cttccttttt | cttcatcagg | 1080 |
| cacaacagag | ccaacagcat | tctgttctgt | ggcaggttct | catcgcca | | 1128 |

| SEQ ID NO: 130 | moltype = DNA  length = 8963 |
| --- | --- |
| FEATURE | Location/Qualifiers |
| misc_feature | 1..8963 |
| | note = Synthetic |
| source | 1..8963 |
| | mol_type = other DNA |
| | organism = synthetic construct |

SEQUENCE: 130

| cctgcaggca | gctgcgcgct | cgctcgctca | ctgaggccgc | ccgggcgtcg | ggcgaccttt | 60 |
|---|---|---|---|---|---|---|
| ggtcgcccgg | cctcagtgag | cgagcgagcg | cgcagagagg | gagtggccaa | ctccatcact | 120 |
| aggggttcct | gcggccgcac | gcgtgttcta | gggtgagaac | taagagaatg | atgtacctag | 180 |
| agggcgctgg | aagctctaaa | gccctagcag | ttactgcttt | tactattagt | ggtcgttttt | 240 |
| ttctccccc | cgcccccga | caaatcaaca | gaacaaagaa | aattacctaa | acagcaagga | 300 |
| catagggagg | aacttcttgg | cacagaactt | tccaaacact | ttttcctgaa | gggatacaag | 360 |
| aagcaagaaa | ggtactcttt | cactaggacc | ttctctgagc | tgtcctcagg | atgcttttga | 420 |
| gactattttt | cttacccaga | gaatggagaaa | accctgcagg | gaattcccaa | gctgtagtta | 480 |
| taaacagaag | ttctccttct | gctaggtagc | attcaaagat | cttaatcttc | tgggtttccg | 540 |
| ttttctcgaa | tgaaaaatgc | aggtccgagc | agttaactgg | ctggggcacc | attagcaagt | 600 |
| cacttagcat | ctctgggggcc | agtctgcaaa | gcgaggggc | agccttaatg | tgcctccagc | 660 |
| ctgaagtcct | agaatgagcg | cccggtgtcc | caagctgggg | cgcgcacccc | agatcggagg | 720 |
| gcgccgatgt | acagacagca | aactcaccca | gtcagtgca | tgccttctta | aacatcacga | 780 |
| gactctaaga | aaaggaaact | gaaacgggaa | aagtccctct | ctcaacctg | gcactgcgtc | 840 |
| gctggcttgg | agacaggtga | cggtccctgc | gggccttgtc | ctgattggct | gggcacgcgt | 900 |
| ttaatataag | tggaggcgtc | gcgctgcgg | gcattcctga | agctaagctt | gtggacgata | 960 |
| tcgaattcgc | acgacattga | ttattgacta | gttattaata | gtaatcaatt | acggggtcat | 1020 |
| tagttcatag | cccatatatg | gagttccgcg | ttacataact | tacggtaaat | ggcccgcctg | 1080 |
| gctgaccgcc | caacgacccc | cgcccattga | cgtcaataat | gacgtatgtt | cccatagtaa | 1140 |
| cgccaatagg | gactttccat | tgacgtcaat | gggtggacta | tttacggtaa | actgcccact | 1200 |
| tggcagtaca | tcaagtgtat | catatgccaa | gtacgccccc | tattgacgtc | aatgacggta | 1260 |
| aatggcccgc | ctggcattat | gcccagtaca | tgaccttatg | ggactttcct | acttggcagt | 1320 |
| acatctacgt | attagtcatc | gctattacca | tgggtcgagg | tgagccccac | gttctgcttc | 1380 |
| actctcccca | tctcccccc | ctccccaccc | ccaattttgt | atttatttat | ttttttaatta | 1440 |
| ttttgtgcag | cgatggggc | ggggggggg | gggcgcgcg | ccaggcgggg | cggggcgggg | 1500 |
| cgaggggcgg | ggcggggcga | ggcggagagg | tgcggcggca | gccaatcaga | gcggcgcgct | 1560 |
| ccgaaagttt | ccttttatgg | cgaggcggcg | cggcggcgg | ccctataaaa | agcgaagcgc | 1620 |
| gcggcgggcg | ggagtcgctg | cgttgccttc | gccccgtgcc | ccgctccgcg | ccgcctcgcg | 1680 |
| ccgcccgccc | cggctctgac | tgaccgcgtt | actccacag | gtgagcgggc | gggacggccc | 1740 |
| ttctcctccg | ggctgtaatt | agcgcttggt | ttaatgacgg | ctcgtttctt | ttctgtggct | 1800 |
| gcgtgaaagc | cttaaagggc | tccggagggc | ccctttgtgc | gggggggagc | ggctcggggg | 1860 |
| gtgcgtgcgt | gtgtgtgtgc | gtggggagcg | ccgcgtgcgg | cccgcgctgc | ccggcgggcg | 1920 |
| tgagcgctgc | gggcgcggcg | cggggctttg | tgcgctccgc | gtgtgcgcga | ggggagcgcg | 1980 |
| gccggggcg | gtgccccgcg | gtgcgggggg | gctgcgaggg | gaacaaaggc | tgcgtgcggg | 2040 |
| gtgtgtgcgt | ggggggtga | gcaggggtg | tgggcgcggc | ggtcgggctg | taaccccccc | 2100 |
| ctgcaccccc | ctccccgagt | tgctgagcac | ggcccggctt | cgggtgcggg | gctccgtgcg | 2160 |
| gggcggttcgc | cgggctcgc | cgtgccgggc | gggggatggc | ggcaggtggg | ggtgccggc | 2220 |
| ggggcgggc | cgcctcgggc | cggggagggc | tcggggagg | ggcgcggcgg | cccggagcg | 2280 |
| ccggcggctg | tcgaggcgcg | gcgagccgca | gccattgcct | tttatggtaa | tcgtgcgaga | 2340 |
| gggcgcaggg | acttcctttg | tcccaaatct | ggcggagccg | aaatctggga | ggcgccgccg | 2400 |
| caccccctct | agcgggcgcg | ggcgaagcgg | tgcggcgccg | caggaagga | aatgggcggg | 2460 |
| gagggccttc | gtgcgtcgcc | gcgccgccgt | cccttctcc | atctccagcc | tcggggctg | 2520 |
| cgcaggggga | cggctgcctt | cggggggac | ggggcaggc | ggggttcggc | ttctggcgtg | 2580 |
| tgaccggcgg | ctctagagcc | tctgctaacc | atgttcatgc | cttcttcttt | ttcctacagg | 2640 |
| ggatccgg | ttatctgcag | aattcgccct | tgacgtcgcc | accatggaaa | ctctttctaa | 2700 |
| tgcaagtggt | acttttgcca | tacgcctttt | aaagatactg | tgtcaagata | acccttcgca | 2760 |
| caacgtgttc | tgttctcctg | tgagcatctc | tctgccctg | gccatggttc | tctagggc | 2820 |

```
aaagggaaac accgcaaccc agatggccca ggcactgtct ttaaacacag aggaagacat  2880
tcatcgggct ttccagtcgc ttctcactga agtgaacaag gctggcacac agtacctgct  2940
gagaacggcc aacaggctct ttggagagaa aacttgtcag ttcctctcaa cgtttaagga  3000
atcctgtctt caattctacc atgctgagct gaaggagctt tcctttatca gagctgcaga  3060
agagtccagg aaacacatca acacctgggt ctcaaaaaag accgaaggta aaattgaaga  3120
gttgttgccg ggtagctcaa ttgatgcaga aaccaggctg gttcttgtca atgccatcta  3180
cttcaaagga aagtggaatg aaccgtttga cgaaacatac acaagggaaa tgcccttaa   3240
aataaaccag gaggagcaaa ggccagtgca gatgatgtat caggaggcca cgtttaagct  3300
cgcccacgtg ggcgaggtgc gcgcgcagct gctggagctg ccctacgccg ggaaggagct  3360
gagcctgctg gtgctgctgc ctgacgacgg cgtggagctc agcacggtgg aaaaaagtct  3420
cacttttgag aaactcacag cctgaccaa gccagactgt atgaagagta ctgaggttga   3480
agttctcctt ccaaaattta aactacaaga ggattatgac atggaatctg tgcttcggca  3540
tttgggaatt gttgatgcct tccaacaggg caaggctgac ttgcggcaa tgtcagcgga   3600
gagagacctg tgtctgtcca agttcgtgca caagagtttt gtggaggtga atgaagaagg  3660
caccgaggca gcggcagcgt cgagctgctt tgtagttgca gagtgctgca tggaatctgg  3720
ccccaggttc tgtgctgacc acccttttcct tttcttcatc aggcacaaca gagccaacag  3780
cattctgttc tgtggcaggt tctcatcgcc aggaagcgga gctactaact tcagcctgct  3840
gaagcaggct ggagacgtgg aggagaaccc tggacctatg tctcgctccg ttgccttagc  3900
tgtgctcgcg ctactctctc tttctggatt agaggctgtc atggcgcccc gaaccctctt  3960
cctgggtgga ggcggttcag gcggaggtgg ctctggcggt ggcggatcga tccagcgtac  4020
tccaaagatt caggtttact cacgtcatcc agcagagaat ggaaagtcaa atttcctgaa  4080
ttgctatgtg tctgggtttc atccatccga cattgaagtt gacttactga agaatggaaa  4140
gagaattgaa aaagtggagc attcagactt gtctttcagc aaggactggt cttctatct   4200
cttgtactac actgaattca cccccactga aaagatgag tatgcctgcc gtgtgaacca   4260
tgtgactttg tcacagccca agatagttaa gtgggatcga cacatgggtg gtggtggttc  4320
tggtggtggt ggttctggcg gcggcggctc cggtggtggt ggatccggct cccactcctt  4380
gaagtatttc cacacttccg tgtcccggcc cggccgcggg gagccccgct tcatctctgt  4440
gggctacgtg gacgacaccc agttcgtgcg cttcgacaac gacgccgcga gtccgaggat  4500
ggtgccgcgg gcgccgtgga tggagcagga ggggtcagag tattgggacc gggagacacg  4560
gagcgccagg gacaccgcac agatttttccg agtgaatctg cggacgctgc gcggctacta  4620
caatcagagc gaggccgggt ctcacaccct gcagtggatg catggctgcg agctggggcc  4680
cgacgggcgc ttcctccgcg gtatgaacaa gttcgcctac gacggcaagg attatctcac  4740
cctgaatgag gacctgcgct cctggaccgc ggtggacacg cggctcaga tctccgagca   4800
aaagtcaaat gatgcctctg aggcggagca ccagagagcc tacctggaag acacatgcgt  4860
ggagtggctc cacaaatacc tggagaaggg gaaggagacg ctgcttcacc tggagccccc  4920
aaagacacac gtgactcacc accccatctc tgaccatgag gccaccctga ggtgctgggc  4980
cctgggcttc taccctgcgg agatcacact gacctgcag caggatgggg agggccatac   5040
ccaggacacg gagctcgtgg agaccaggcc tgcagggat ggaaccttcc agaagtgggc   5100
agctgtggtg gtgccttctg gagaggagca gagatacacg tgccatgtgc agcatgaggg  5160
gctacccgag cccgtcaccc tgagatgaa gccggcttcc cagcccacca tcccatcgt   5220
gggcatcatt gctggcctgg ttctccttgg atctgtggtc tctggagctg tggttctgc   5280
tgtgatatgg aggaagaaga gctcaggtgg aaaaggaggg agctactcta aggctgagtg  5340
gagcgacagt gcccagggt ctgagtctca cagcttgtaa tgatagccgc tgatcagcct   5400
cgactgtgcc ttctagttgc cagccatctg ttgtttgccc ctccccgtg ccttccttga   5460
ccctggaagg tgccactccc actgtccttt cctaataaaa tgaggaaatt gcatcgcatt  5520
gtctgagtag gtgtcattct attctggggg gtggggtggg gcaggacagc aagggggagg  5580
attgggaaga caatagcagg catgctgggg atgcggtggg ctctatgggt cgacccagcg  5640
tgagtctctc ctaccctccc gctctggtcc ttcctctccc gctctgcacc ctctgtggcc  5700
ctcgctgtgc tctctcgctc cgtgacttcc cttctccaag ttctccttgg tggcccgccg  5760
tggggctagt ccagggctgg atctcgggga agcggcgggg tggcctggga gtggggaagg  5820
gggtgccac ccgggacgcg cgctacttgc ccctttcggc ggggagcagg ggagaccttt   5880
ggcctacggc gacgggaggg tcgggacaaa gtttagggcg tcgataagcg tcagagcgcc  5940
gaggttgggg gagggtttct cttccgctct ttcgcggggc ctctggctcc cccagcgcag  6000
ctggagtggg ggacgggtag gctcgtccca aggcgcggc gctgaggttt gtgaacgcgt   6060
ggagggccgc ttggggtctg ggggaggcgt cgcccgggta agcctgtctg ctgcggctct  6120
gcttccctta gactggagag ctgtggactt cgtctaggcg cccgctaagt tcgcatgtcc  6180
tagcacctct gggtctatgt ggggccacac cgtggggagg aaacagcacg cgacgtttgt  6240
agaatgcttg gctgtgatac aaagcggttt cgaataatta acttatttgt tcccatcaca  6300
tgtcacttt aaaaaattat aagaactacc cgttattgac atctttctgt gtgccaagga   6360
ctttatgtgc tttgcgtcat ttaattttga aaacagttat cttccgccat agataactac  6420
tatggttatc ttctcggtaac cacgtgcgga ccgaggctgc agcgtcgtcc tccctaggaa  6480
cccctagtga tggagttggc cactccctct ctgcgcgctc gctcgctcac tgaggccggg  6540
cgaccaaagg tcgcccgacg cccgggcttt gcccgggcgg cctcagtgag cgagcgagcg  6600
cgcagctgcc tcaggggcg cctgatgcgg tattttctcc ttcactcatct gtgcggtatt   6660
tcacaccgca tacgtcaaag caaccatagt acgcgccctg tagcggcgca ttaagcgcgg  6720
cgggtgtggt ggttacgcgc agcgtgaccg ctacacttgc cagcgcccta gcgcccgctc  6780
ctttcgcttt cttcccttcc tttctcgcca cgttcgccgg cttcccccgt caagctctaa  6840
atcgggggct ccctttaggg ttccgattta gtgctttacg cacctgtgac cccaaaaaac  6900
ttgatttggg tgatggttca cgtagtgggc catcgccctg ataacgcctt tttcgccctt  6960
tgacgttgga gtccacgttc tttaatagtg gactcttgtt ccaaactgga acaacactca  7020
accctatctc gggctattct tttgatttat aagggatttt gccgatttcg gcctattggt  7080
taaaaaatga gctgatttaa caaaaattta acgcgaattt aacaaaata ttaacgttta   7140
caattttatg gtgcactctc agtacaatct gctctgatgc cgcatagtta agcagcccc   7200
gacaccgca aacacccgct gacgcgccct gacgggcttg tctgctcccg gcatccgctt  7260
acagacaagc tgtgaccgtc tccgggagct gcatgtgtca gaggttttca ccgtcatcac  7320
cgaaacgcgc gagacgaaag gcctcgtga tacgcctatt tttataggtt aatgtcatga  7380
acaataaaac tgtctgctta cataaacagt aatacaaggg gtgttatgag ccatattcaa  7440
cgggaaacgt cgaggccgcg attaaattcc aacatgatga ctgattata tgggtataaa   7500
tgggctcgcg ataatgtcgg gcaatcaggt gcgacaatct atcgcttgta tgggaagccc  7560
```

```
gatgcgccag agttgtttct gaaacatggc aaaggtagcg ttgccaatga tgttacagat   7620
gagatggtca gactaaactg gctgacggaa tttatgcctc ttccgaccat caagcatttt   7680
atccgtactc ctgatgatgc atggttactc accactgcga tccccggaaa acagcattc    7740
caggtattag aagaatatcc tgattcaggt gaaaatattg ttgatgcgct ggcagtgttc   7800
ctgcgccggt tgcattcgat tcctgttttgt aattgtcctt ttaacagcga tcgcgtattt   7860
cgtctcgctc aggcgcaatc acgaatgaat aacggtttgg ttgatgcgag tgattttgat   7920
gacgagcgta atggctggcc tgttgaacaa gtctggaaag aaatgcataa acttttgcca   7980
ttctcaccgg attcagtcgt cactcatggt gatttctcac ttgataacct tatttttgac   8040
gagggaaat taataggttg tattgatgtt ggacgagtcg gaatcgcaga ccgataccag    8100
gatcttgcca tcctatggaa ctgcctcggt gagttttctc cttcattaca gaaacggctt   8160
tttcaaaaat atggtattga taatcctgat atgaataaat tgcagtttca tttgatgctc   8220
gatgagtttt tctaatctca tgaccaaaat cccttaacgt gagttttcgt tccactgagc   8280
gtcagacccc gtagaaaaga tcaaaggatc ttcttgagat ccttttttc tgcgcgtaat    8340
ctgctgcttg caaacaaaaa aaccaccgct accagcggtg gtttgtttgc cggatcaaga   8400
gctaccaact cttttttccga aggtaactgg cttcagcaga gcgcagatac caaatactgt   8460
ccttctagtg tagccgtagt taggccacca cttcaagaac tctgtagcac cgcctacata   8520
cctcgctctg ctaatcctgt taccagtggc tgctgccagt ggcgataagt cgtgtcttac   8580
cgggttggac tcaagacgat agttaccgga taaggcgcag cggtcgggct gaacggggg    8640
ttcgtgcaca cagcccagct tggagcgaac gacctacacc gaactgagat acctacagcg   8700
tgagctatga gaaagcgcca cgcttcccga agggagaaag gcggacaggt atccggtaag   8760
cggcagggtc ggaacaggag agcgcacgag ggagcttcca gggggaaacg cctggtatct   8820
ttatagtcct gtcgggtttc gccacctctg acttgagcgt cgatttttgt gatgctcgtc   8880
agggggggcgg agcctatgga aaaacgccag caacgcggcc ttttttacggt tcctggcctt   8940
ttgctggcct tttgctcaca tgt                                           8963

SEQ ID NO: 131         moltype = DNA   length = 2944
FEATURE                Location/Qualifiers
misc_feature           1..2944
                       note = Synthetic
source                 1..2944
                       mol_type = other DNA
                       organism = synthetic construct
SEQUENCE: 131
atggaaactc tttctaatgc aagtggtact tttgccatac gccttttaaa gatactgtgt   60
caagataacc cttcgcacaa cgtgttctgt tctcctgtga gcatctcctc tgccctggcc   120
atggttctcc taggggcaaa gggaaacacc gcaacccaga tggcccaggc actgtcttta   180
aacacagagg aagacattca tcgggctttc cagtcgcttc tcactgaagt gaacaaggct   240
ggcacacagt acctgctgag aacggccaac aggctctttg gagagaaaac ttgtcagttc   300
ctctcaacgt ttaaggaatc ctgtcttcaa ttctaccatg ctgagctgaa ggagctttcc   360
tttatcagag ctgcagaaga gtccaggaaa cacatcaaca cctgggtctc aaaaagacc    420
gaaggtaaaa ttgaagagtt gttgccgggt agctcaattg atgcagaaac caggctggtt   480
cttgtcaatg ccatctactt caaaggaaag tggaatgaac cgtttgacga acatacaca    540
agggaaatgc cctttaaaat aaaccaggag gagcaaagtc cagtcagat gatgtatcag   600
gaggccacgt ttaagctcgc ccacgtgggc gaggtgcgcg cgcagctgct ggagctgccc   660
tacgccagga aggagctgag cctgctggtg ctgctgcctg acgacggcgt ggagctcagc   720
acggtggaaa aaagtctcac ttttgagaaa ctcacagcct ggaccaagcc agactgtatg   780
aagagtactg aggttgaagt tctccttcca aaatttaaac tacaagagga ttatgacatg   840
gaatctgtgc ttcggcattt gggaattgtt gatgccttcc aacagggcaa ggctgacttg   900
tcggcaatgt cagcggagag agacctgtgt gtgtccaagt tcgtgcacaa gagttttgtg   960
gaggtgaatg aagaaggcac cgaggcagcg gcagcgtcga gctgctttgt agttgcagag   1020
tgctgatga aatctggccc caggttctgt gctgaccacc cttttcctttt cttcatcagg   1080
cacaacagag ccaacagcat tctgttctgt ggcaggttct catcgccagg aagcggagct   1140
actaacttca gcctgctgaa gcaggctgga gacgttgagg agaaccctgg acctatgtct   1200
cgctccgttg ccttagctgt gctcgcgcta ctctctcttt ctggattaga ggctgtcatg   1260
gcgccccgaa ccctcttcct gggtggaggc ggttcaggcg gaggtggctc tggcggtggc   1320
ggatccgatc cagcgtactc caaagattcag gtttactcac gtcatccagc agagaatgga   1380
aagtcaaatt tcctgaattg ctatgtgtct gggtttcatc catccgacat tgaagttgac   1440
ttactgaaga atggagagag aattgaaaaa gtggagcatt cagacttgtc tttcagcaag   1500
gactggtctt tctatctctt gtactacact gaattcacc ccactgaaaa agatgagtat   1560
gcctgccgtg tgaaccatgt gactttgtca cagcccaaga tagttaagtg ggatcgagac   1620
atgggtggtg tggttctggg tggtggtggt ctggcggcg gcggctccgg tggtggtgga   1680
tccggctccc actccttgaa gtatttccac acttccgtgt cccggccggg ccgcggggag   1740
ccccgcttca tctctgtggg ctacgtggac acccccagt cgtgcgctt cgacaacgac   1800
gccgcgagtc cgaggatggt gccgcgggcg ccgtggcgcg agcaggaggg gtcagagtat   1860
tgggaccggg agacacgcag cgccaggcac accgcacaga ttttccgagt gaatctgcgg   1920
acgctgcgcg gctactacaa tcagagcgag gccgggtctc acaccctgca gtggatgcat   1980
ggctgcgagc tggggcccga cggcgcttc tccgcgggt atgaacagtt cgcctacgac   2040
ggcaaggatt atctcaccct gaatgaggac ctgcgctctg gaccgcggt ggacacgggc   2100
gtcgatctcc ccagcaaaa gtcaaatgat gcctctgagg tgcagacca gagagcctac   2160
ctggaagaca catgcgtgga gtggctccac aaatacctgg agaagggaa ggagacgctg   2220
cttcacctgg agccccaaaa gacacacgtg actcaccacc catctctga ccatgaggcc   2280
accctgaggt gctgggccct gggcttctac cctgcggaga tcactgacctggcagcag   2340
gatgggggagg ccatacccca ggacacgagc tcgtggaga ccaggcctgc aggggatgga   2400
accttccaga agtgggcagc tgtggtggtg ccttctgagg aggagataca acgtgt       2460
catgtgcagc atgaggggct acccgagccc gtcaccctga gatggaagcc ggcttcccag   2520
cccaccatcc ccatcgtggg catcattgct ggcctggttc ccttggate tgtggtctct   2580
ggagctgtgt tgctgctgt gatatggagg aagaagagct caggtggaaa aggagggagc   2640
tactctaagg ctgagtggag cgacagtgcc aggggtctg agtctcacag cttgtaatga   2700
tagccgctga tcagcctcga ctgtgccttc tagttgccag ccatcgttg tttgcccctc   2760
```

```
cccgtgcct tccttgaccc tggaaggtgc cactcccact gtcctttcct aataaaatga  2820
ggaaattgca tcgcattgtc gagtaggtgt cattctattc tggggggtgg ggtggggcag  2880
gacagcaagg gggaggattg ggaagacaat agcaggcatg ctggggatgc ggtgggctct  2940
atgg                                                               2944

SEQ ID NO: 132          moltype = DNA   length = 57
FEATURE                 Location/Qualifiers
misc_feature            1..57
                        note = Synthetic
source                  1..57
                        mol_type = other DNA
                        organism = synthetic construct
SEQUENCE: 132
cccttaacgt gagttttcgt tccactgagc gtcagacccc gtagaaaaga tcaaagg      57

SEQ ID NO: 133          moltype = DNA   length = 54
FEATURE                 Location/Qualifiers
misc_feature            1..54
                        note = Synthetic
source                  1..54
                        mol_type = other DNA
                        organism = synthetic construct
SEQUENCE: 133
gtccaacccg gtaagacacg acttatcgcc actggcagca gccactggta acag          54

SEQ ID NO: 134          moltype = DNA   length = 53
FEATURE                 Location/Qualifiers
misc_feature            1..53
                        note = Synthetic
source                  1..53
                        mol_type = other DNA
                        organism = synthetic construct
SEQUENCE: 134
cacttgccag cgccctagcg cccgctcctt tcgctttctt cccttccttt ctc           53

SEQ ID NO: 135          moltype = DNA   length = 33
FEATURE                 Location/Qualifiers
misc_feature            1..33
                        note = Synthetic
source                  1..33
                        mol_type = other DNA
                        organism = synthetic construct
SEQUENCE: 135
gggcgcgtca gcgggtgttg gcgggtgtcg ggg                                 33

SEQ ID NO: 136          moltype = DNA   length = 8702
FEATURE                 Location/Qualifiers
misc_feature            1..8702
                        note = Synthetic
source                  1..8702
                        mol_type = other DNA
                        organism = synthetic construct
SEQUENCE: 136
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact  120
aggggttcct gcggccgcac gcgtgttcta gggtggaaac taagagaatg atgtacctag  180
agggcgctgg aagctctaaa gccctagcag ttactgcttt tactattagt ggtcgttttt  240
ttctccccc cgcccccga caaatcaaca gaacaaagaa aattacctaa acagcaagga    300
catagggagg aacttcttgg cacagaactt tccaaacatt ttttcctgaa gggatacaag  360
aagcaagaaa ggtactcttt cactaggacc ttctctgagc tgtcctcagg atgctttgat  420
gactattttt cttacccaga gaatggagaa accctgcagg gaattcccaa gctgtagtta  480
taaacagaag ttctccttct gctaggtagc attcaaagat cttaatcttc tgggtttccg  540
ttttctcgaa tgaaaaatgc aggtccgagc agttaactgg ctgggcacc attagcaagt   600
cacttagcat ctctggggcc agtctgcaaa gcgaggggc agccttaatg tgcctccagc   660
ctgaagtcct agaatgagcg cccggtgtcc caagctgggg gcgcgcaccc agatcggagg  720
gcgccgatgt acagacagca aactcaccca gtctagtgca tgccttctta acatcacga   780
gactctaaga aaaggaaact gaaaacggga agtccctct ctctaacctg gcactgcgtc   840
gctggcttgg agacaggtga cggtccctgc gggccttgtc ctgattggct gggcacgcgt   900
ttaatataag tggaggcgtc gcgctggcgg gcattcctga agctaagctt gtggacgata   960
tcgaattcgc acgacattga ttattgacta gttattaata gtaatcaatt acggggtcat  1020
tagttcatag cccatatatg gagttccgcg ttacataact tacggtaaat ggcccgcctg  1080
gctgaccgcc caacgacccc cgcccattga cgtcaataat gacgtatgtt cccatagtaa  1140
cgccaatagg gactttccat tgacgtcaat gggtggacta tttacggtaa actgcccact  1200
tggcagtaca tcaagtgtat catatgccaa tacgccccta tattgacgtc aatgacggta  1260
aatggcccgc ctggcattat gcccagtaca tgaccttatg ggactttcct acttggcagt  1320
acatctacgt attagtcatc gctattacca tgggtcgagg tgagcccac gttctgcttc   1380
actccccca tctcccccc ctccccaccc ccaattttgt atttatttat ttttaatta     1440
ttttgtgcag cgatggggc ggggggggg gggcgcgcg ccaggcgggg cggggcgggg    1500
cgaggggcgg ggcgggggcga ggcggagagg tgcggcggca gccaatcaga gcggcgcgct  1560
```

```
ccgaaagttt cctttatgg cgaggcggcg gcggcggcgg ccctataaaa agcgaagcgc   1620
gcggcgggcg ggagtcgctg cgttgccttc gccccgtgcc ccgctccgcg ccgcctcgcg   1680
ccgcccgccc cggctctgac tgaccgcgtt actccacag gtgagcgggc gggacggccc    1740
ttctcctccg ggctgtaatt agcgcttggt ttaatgacgg ctcgtttctt ttctgtggct   1800
gcgtgaaagc cttaaagggc tccgggaggg ccctttgtgc ggggggagc ggctcggggg    1860
gtgcgtgcgt gtgtgtgtgc gtggggagcg ccgcgtgcgg cccgcgctgc ccggcggctg   1920
tgagcgctgc gggcgcggcg cggggctttg tgcgctccgc gtgtgcgcga ggggagcgcg   1980
gccggggggcg gtgccccgcg gtgcggggg gctgcgaggg gaacaaaggc tgcgtgcggg    2040
gtgtgtgcgt gggggggtga gcaggggtg tgggcgcggc ggtcgggctg taaccccccc    2100
ctgcaccccc ctccccgagt tgctgagcac ggcccggctt cgggtgcggg gctccgtgcc   2160
gggcttggcg cggggctcgc cgtgccgggc gggggtggc ggcaggtggg ggtgccgggc    2220
ggggcgggc cgcctcggc cggggaggc tcggggagg ggcgcggcgg ccccggagcg       2280
ccggcggctg tcgaggcgcg gcgagccgca gccattgcct tttatggtaa tcgtgcgaga   2340
gggcgcaggg acttccttg tcccaaatct ggcggagccg aaatctggga ggcgccgcgc   2400
caccccctct agcgggcgcg ggcgaagcgg tgcggcgccg gcaggaagga aatgggcggg   2460
gagggccttc gtgcgtcgcc gcgccgccgt cccctctcc atctccagcc tcggggctgc   2520
cgcaggggga cggctgcctt cgggggggac ggggcaggc ggggttcggc ttctggcgtg    2580
tgaccggcgg ctctagagcc tctgctaacc atgttcatgc cttcttcttt ttcctacagg   2640
ggggatccgt ttatctgcag aattcgcccc tgacgtcgcc accatggaaa ctctttctaa   2700
tgcaagtggt acttttgcca tacgcctttt aaagatactg tgtcaagata cccttcgca    2760
caacgtgttc tgttctcctg tgagcatctc ctctgccctg gccatggttc tcctaggggc   2820
aaagggaaac accgcaaccc agatggccca ggcactgtct ttaaacacag aggaagacat   2880
tcatcgggct ttccagtcgc ttctcactga agtgaacaag gctggcacac agtacctgct   2940
gagaacggcc aacaggctct ttggagagaa aactgtcag ttcctctcaa cgtttaagga    3000
atcctgtctt caattctacc atgctgagct gaaggagctt tcctttatca gagctgcaga   3060
agagtccagg aaacacatca acacctgggt ctcaaaaaag accgaaggta aaattgaaga   3120
gttgttgccg ggtagctcaa ttgatgcaga aaccaggctg gttcttgtca atgccatcta   3180
cttcaaagga aagtggaatg aaccgtttga cgaaacatac acaagggaaa tgccctttaa   3240
aataaaccag gaggagcaaa ggccagtgca gatgatgtat caggaggcca cgtttaagct   3300
cgcccacagt ggcgaggtgc gcgcgacgct gctggagctg ccggaaggagct             3360
gagcctgctg gtgctgctgc ctgacgacgg cgtggagctc agcacggtgg aaaaaagtct   3420
cacttttgag aaactcacag cctggaccaa gccagactgt atgaagagta ctgaggttga   3480
agttctcctt ccaaaattta aactacaaga ggattatgac atggaatctg tgcttcggca   3540
tttgggaatt gttgatgcct tccaacaggg caaggctgac ttgtcggcaa tgtcagcgga   3600
gagagacctg tgtctgtcca agttcgtgca caagagtttt gtggaggtga atgaagagga   3660
caccgaggca gcggcagcgt cgagctgctg tgtagttgca gagtgctgca tggaatctgg   3720
ccccaggttc tgtgctgacc accctttcct tttcttcatc aggcacaaca gagccaacag   3780
cattctgttc tgtggcaggt tctcatcgcc aggaagcgga gctactaact tcagcctgct   3840
gaagcaggct ggagactgg aggagaaccc tggacctatg gactggacct ggatcctgtt   3900
cctggtggcc gccgccacca gggtgcacag cggcattcat gtcttcattt tgggctgttt   3960
cagtgcaggg cttcctaaaa cagaagccaa ctgggtgaat gtaataagtg atttgaaaaa   4020
aattgaagat cttattcaat ctatgcatat tgatgctact ttatatacgg aaagtgatgt   4080
tcaccccagt tgcaaagtaa cagcaatgaa gtgctttctc ttggagttac aagttattc    4140
acttgagtcc ggagatgcaa gtattcatga tacagtagaa aatctgatca tcctagcaaa   4200
caacagtttg tcttctaatg ggaatgtaac agaatctgga tgcaaagaat gtgaggaact   4260
ggaggaaaaa aatattaaag aatttttgca gagttttgta catattgtcc aaatgttcat   4320
caacacttct agcggcggcg gcagcggcgg cggcggcgcg gcggcggcgg cagcggccgg   4380
cggcggcagc ggcggcggca gcctgcagat cacgtgccct ccccccatgt ccgtgaaca    4440
cgcagacatc tgggtcaaga gctacagctt gtactccagg gagcggtaca tttgtaactc   4500
tggtttcaag cgtaaagccg gcacgtccag cctgacggag tgcgtgttga acaaggccac   4560
gaatgtcgcc cactgacaa cccccagtct caaatgcatt agagaccctg ccctggttca   4620
ccaaaggcca gcgccaccct ccacagtaac gacggcaggg gtgaccccac agccagagag   4680
cctctccccct tctggaaaag agccgcagc ttcatctccc agtcaaaaca acacagcggc   4740
cacaacagca gctattgtcc cgggctccca gctgatgcct tcaaaatcac cttccacagg   4800
aaccacagag ataagcagtc atgagtcctc ccacggcctc ccctctcaga caacagccaa   4860
gaactgggaa ctcacagcat ccgcctccca ccagccgcca ggtgtgtatc cacagggcca   4920
cagcgacacc actgtggcta tctccacgtc cactgtcctg ctgtgtgggc tgagcgctgt   4980
gtctctcctg gcatgctacc tcaagtcaag gcaaactccc ccgctggcca gcgttgaaat   5040
ggaagccatg gaggctctgc cggtgacttg ggggaccagc agcagagatg aagacttgga   5100
aaactgctct caccacctat gataaccgct gatcagcctc gactgtgcct tctagttgca   5160
agccatctgt tgtttgcccc tccccgtgc cttccttgac cctggaaggt gccactccca    5220
ctgtcctttc ctaataaaat gaggaaattg catcgcattg tctgagtagg tgtcattcta   5280
ttctgggggg tggggtgggg caggacagca aggggagga ttgggaagac aatagcaggc   5340
atgctgggga tgcggtgggc tctatgggtc gacccagcg aggtctctcc taccctcccg   5400
ctctggtcct tcctctcccg ctctgcaccc tctgtggccc tcgctgtgct ctctcgctcc   5460
gtgacttccg ttctccaagt tctccttggt ggcccgccgt gggctagtc cagggctgga   5520
tctcggggaa gcgggggt ggcctgggag tggggagg ggtgcgcacc cgggacgcgc       5580
gctacttgcc cctttcggcg gggagcaggg gagacctttg gcctacgcg acgggagggt    5640
cgggacaaag tttagggcgt cgataagcgt cagagccgta aggttgggg aggttctc      5700
ttccgctctt tcgcggggcc tctggctccc ccagcgcagc tggagtgggg gacgggtagg   5760
ctcgtcccaa aggcgcggcg ctgaggtttg tgaacgcgtg gaggggcgct ggggtctgg    5820
gggaggcgtc gcccggtaa gcctgtctgc tgcggctctg cttcccttag actggagagc   5880
tgtggacttc gtctaggcgc ccgctaagtt cgcatgtcct agcacctctg ggtctatgtg   5940
gggccacacc gtgggagga aacagcacg gacgcttggg tgtgataca                 6000
aagcggtttc gaataattaa ctatttgtt cccatcacat gtcactttta aaaaattata    6060
agaactaccc gttattgaca tctttctgtg tgccaaggac tttatgtgct ttgcgtcatt   6120
taatttgaa aacagttatc ttccgccata gataactact atggttatct tctggtaacc   6180
acgtgcggac cgaggctgca gcgtcgtcct ccctaggaac ccctagtgat ggagttggcc   6240
actccctctc tgcgcgctcg ctcgctcact gaggccgggc gaccaaggt cgcccgacgc    6300
```

```
ccgggctttg cccgggcggc ctcagtgagc gagcgagcgc gcagctgcct gcagggcgc    6360
ctgatgcggt attttctcct tacgcatctg tgcggtattt cacaccgcat acgtcaaagc    6420
aaccatagta cgcgccctgt agcggcgcat taagcgcggc gggtgtggtg gttacgcgca    6480
gcgtgaccgc tacacttgcc agcgccctag cgcccgctcc tttcgctttc ttcccttcct    6540
ttctcgccac gttcgccggc tttccccgtc aagctctaaa tcgggggctc cctttagggt    6600
tccgatttag tgctttacgg cacctcgacc ccaaaaaact tgatttgggt gatggttcac    6660
gtagtgggcc atcgccctga tagacggttt ttcgcccttt gacgttggag tccacgttct    6720
ttaatagtgg actcttgttc caaactggaa caacactcaa ccctatctcg ggctattctt    6780
ttgatttata agggattttg ccgatttcgg cctattggtt aaaaaatgag ctgatttaac    6840
aaaaatttaa cgcgaatttt aacaaaatat taacgtttac aattttatgg tgcactctca    6900
gtacaatctg ctctgatgcc gcatagttaa gccagccccg acacccgcca cacccgctg    6960
acgcgccctg acgggcttgt ctgctcccgg catccgctta cagacaagct gtgaccgtct    7020
ccgggagctg catgtgtcag aggttttcac cgtcatcacc gaaacgcgcg agacgaaagg    7080
gcctcgtgat acgcctattt ttataggtta atgtcatgaa caataaaact gtctgcttac    7140
ataaacagta atacaagggg tgttatgagc catattcaac gggaaacgtc gaggccgcga    7200
ttaaattcca acatggatgc tgatttatat gggtataaat gggctcgcga taatgtcggg    7260
caatcaggtg cgacaatcta tcgcttgtat gggaagcccg atgcgccaga gttgtttctg    7320
aaacatgtgca aagtagcgt tgccaatgat gttacagatg agatggtcag actaaactgg    7380
ctgacggaat ttatgcctct tccgaccatc aagcatttta tccgtactcc tgatgatgca    7440
tggttactca ccactgcgat cccgggaaaa acagcattcc aggtattaga agaatatcct    7500
gattcaggtg aaaatattgt tgatgcgctg gcagtgttcc tgcgccggtt gcattcgatt    7560
cctgtttgta attgtccttt taacagcgat cgcgtattcg gtctcgctca ggcgcaatca    7620
cgaatgaata acggtttggt tgatgcgagt gattttgatg acgagcgtaa tggctggcct    7680
gttgaacaag tctggaaaga aatgcataaa cttttgccat tctcaccgga ttcagtcgtc    7740
actcatggtg atttctcact tgataacctt atttttgacg aggggaaatt aataggttgt    7800
attgatgttg gacgagtcgg aatcgcagac cgataccagg atcttgccat cctatggaac    7860
tgcctcggtg agttttctcc ttcattacag aaacggcttt ttcaaaaata tggtattgat    7920
aatcctgata tgaataaatt gcagtttcat ttgatgctcg atgagttttt ctaatctcat    7980
gaccaaaatc ccttaacgtg agttttcgtt ccactgagcg tcagacccg tagaaaagat    8040
caaaggatct tcttgagatc cttttttct gcgcgtaatc tgctgcttgc aaacaaaaaa    8100
accaccgcta ccagcggtgg tttgtttgcc ggatcaagag ctaccaactc ttttccgaa    8160
ggtaactggc ttcagcagag cgcagatacc aaatactgtc cttctagtgt agccgtagtt    8220
aggccaccac ttcaagaact ctgtagcacc gcctacatac ctcgctctgc taatcctgtt    8280
accagtggct gctgccagtg gcgataagtc gtgtcttacc gggttggact caagacgata    8340
gttaccggat aaggcgcagc ggtcgggctg aacggggggt tcgtgcacac agcccagctt    8400
ggagcgaacg acctacaccg aactgagata cctacagcgt gagctatgag aaagcgccac    8460
gcttcccgaa gggagaaagg cggacaggta tccggtaagc ggcagggtcg gaacaggaga    8520
gcgcacgagg gagcttccag ggggaaacgc ctggtatctt tatagtcctg tcgggtttcg    8580
ccacctctga cttgagcgtc gatttttgtg atgctcgtca ggggggcgga gcctatgaa    8640
aaacgccagc aacgcggcct ttttacggtt cctggccttt tgctggcctt ttgctcacat    8700
gt                                                                   8702
```

SEQ ID NO: 137          moltype = DNA   length = 2684
FEATURE                 Location/Qualifiers
misc_feature            1..2684
                        note = Synthetic
source                  1..2684
                        mol_type = other DNA
                        organism = synthetic construct
SEQUENCE: 137

```
atggaaactc tttctaatgc aagtggtact tttgccatac gccttttaaa gatactgtgt    60
caagataacc cttcgcacaa cgtgttctgt tctcctgtga gcatctcctc tgccctggcc    120
atggttctcc taggggcaaa gggaaacacc gcaacccaga tggcccaggc actgtcttta    180
aacacagagg aagacattca tcgggctttc cagtcgcttc tcactgaagt gaacaaggct    240
ggcacacagt acctgctgag aacggccaac aggctctttg gagagaaaac ttgtcagttc    300
ctctcaacgt ttaaggaatc ctgtcttcaa ttctaccatg ctgagctgaa ggagcttttcc    360
tttatcagag ctgcagaaga gtccaggaaa cacatcaaca cctgggtctc aaaaaagacc    420
gaaggtaaaa ttgaagagtt gttgccgggt agctcaattg atgcagaaac caggctggtt    480
cttgtcaatg ccatctactt caaaggaaag tggaatgaac cgtttgacga aacatacaca    540
agggaaatgc cctttaaaat aaaccaggag gagcaaaggc cagtgcagat gatgtatcag    600
gaggccacgt ttaagctcgc ccacgtgggc gaggtgcgcg cgcagctgct ggagctgccc    660
tacgccagga aggagctgag cctgctggtg ctgctgcctg acgacggcgt ggagctcagc    720
acggtggaaa aagtctcac ttttgagaaa ctcacagcct ggaccaagcc agactgtatg    780
aagagtactg aggttgaagt tctccttcca aaatttaaac tacaagagga ttatgacatg    840
gaatctgtgc ttcggcattt gggaattgtt gatgccttcc aacagggcaa gctgactga    900
tcggcaatgt cagcggagag agacctgtgt ctgtccaagt cgtgcacaa gagttttgtg    960
gaggtgaatg aagaaggcac cgaggcagcg gcagcgtcga gctgctttgt agttgcagag    1020
tgctgcatgg aatctggccc caggttctgt gctgaccacc ctttccttt cttcatcagg    1080
cacaacagag ccaacagcat tctgttctgt ggcaggttct catccgccagg aagcggagct    1140
actaacttca gcctgctgaa gcaggctgga gacgttgagg agaaccctgg acctatggac    1200
tggacctgga tcctgttcct ggtggccgcc gccaccaggg tgcacagcgg cattcatgtc    1260
ttcattttgg gctgtttcag tgcagggctt cctaaaacag aagccaactg gtgaatgta    1320
ataagtgatt tgaaaaaaat tgaagatctt attcaatcta tgcatattga tgctacttta    1380
tatcaggaaa gtgatgttca cccagttgc aaagtaacaa caatgaagtg cttctcttg    1440
gagttacaag ttattcact tgagtccgga gatgcaagta ttcatgatac agtagaaaat    1500
ctgatcatcc tagcaaacaa cagtttgtct ctaatgggga atgtaacaga atctggatgc    1560
aaagaatgtg aggaactgga ggaaaaaaat attaagaat ttttgcagag ttttgtacat    1620
attgtccaaa tgttcatcaa cacttctagc ggcggcggca gcggcggcgg cggcagcggc    1680
ggcggcggca gcggcggcgg cggcagcggc ggcggcagcc tgcagatcac gtgccctccc    1740
```

```
cccatgtccg tggaacacgc agacatctgg gtcaagagct acagcttgta ctccagggag   1800
cggtacattt gtaactctgg tttcaagcgt aaagccggca cgtccagcct gacggagtgc   1860
gtgttgaaca aggccacgaa tgtcgcccac tggacaaccc ccagtctcaa atgcattaga   1920
gaccctgccc tggttcacca aaggccagcg ccaccctcca cagtaacgac ggcaggggtg   1980
accccacagc cagagagcct ctcccttct ggaaaagagc ccgcagcttc atctcccagc    2040
tcaaacaaca cagcggccac aacagcagct attgtcccgg gctcccagct gatgccttca   2100
aaatcacctt ccacaggaac cacagagata agcagtcatg agtcctccca cggcaccccc   2160
tctcagacaa cagccaagaa ctgggaactc acagcatccg cctcccacca gccgccaggt   2220
gtgtatccac agggccacag cgacaccact gtggctatct ccacgtccac tgtcctgctg   2280
tgtgggctga gcgctgtgtc tctcctggca tgctacctca agtcaaggca aactcccccg   2340
ctggccagcg ttgaaatgga agccatgag gctctgccgg tgacttgggg gaccagcagc    2400
agagatgaag acttggaaaa ctgctctcac cacctatgat aaccgctgat cagcctcgac   2460
tgtgccttct agttgccagc catctgttgt ttgcccctcc ccgtgcctt ccttgaccct    2520
ggaaggtgcc actcccactg tcctttccta ataaaatgca gaaattgcat cgcattgtct   2580
gagtaggtgt cattctattc tgggggtgg ggtgggcag acagcaagg gggaggattg      2640
ggaagacaat agcaggcatg ctggggatgc ggtgggctct atgg                   2684

SEQ ID NO: 138        moltype = DNA   length = 4395
FEATURE               Location/Qualifiers
misc_feature          1..4395
                      note = Synthetic
source                1..4395
                      mol_type = other DNA
                      organism = synthetic construct
SEQUENCE: 138
gacattgatt attgactagt tattaatagt aatcaattac gggtcatta gttcatagcc    60
catatatgga gttccgcgtt acataactta cggtaaatgg cccgcctggc tgaccgccca   120
acgacccccg cccattgacg tcaataatga cgtatgttcc catagtaacg ccaatagga    180
ctttccattg acgtcaatgg gtggactatt tacggtaaac tgcccacttg gcagtacatc   240
aagtgtatca tatgccaagt acgccccta ttgacgtcaa tgacggtaaa tggcccgcct    300
ggcattatgc ccagtacatg accttatggg actttcctac ttggcagtac atctacgtat   360
tagtcatcgc tattaccatg gtcgaggtg agccccacgt tctgcttcac tctcccatc     420
tccccccct ccccaccccc aattttgtat ttatttattt tttaattatt ttgtgcagcg    480
atgggggcgg gggggggggg ggcgcgcgcc aggcggggcg gggcggggcg aggggcgggg   540
cggggcgagg cggagaggtg cggcggcagc caatcagagc ggcgcgctcc gaaagtttcc   600
ttttatggcg aggcggcggc ggcggcggcc ctataaaaag cgaagcgcgc ggcgggcggg   660
agtcgctgcg ttgccttcgc cccgtgcccc gctccgcgcc gcctcgcgcc gcccgccccg   720
gctctgactg accgcgttac tcccacaggt gagcgggcgg gacggccctt ctcctccggg   780
ctgtaattag cgcttggttt aatgacggct cgtttctttt ctgtggctgc gtgaaagcct   840
taaagggctc cggagggcc ctttgtgcgg ggggagcgg ctcgggggt gcgtgcgtgt     900
gtgtgtgcgt ggggagcggcc gcgtgcgcc cgcgctgccc ggcggctgtg agcgctgcgg   960
gcgcggcgcg gggcttgtg cgctccgcgt gtgcgcgagg ggagcgcggc cggggcggt    1020
gccccgcggt gcggggggc tgcgaggga acaaaggcgg gtgtgcgtgg                1080
ggggtgagc agggggtgtg ggcgcggcgg tcgggctgta accccccct gcaccccct     1140
ccccgagttg ctgagcacgg cccggcttcg ggtgcgggc tccgtgcggg gcgtggcgcg   1200
gggctcgccg tgccgggcgg ggggtggcgg caggtggggg tgccgggcgg ggcggggccg   1260
cctcgggcg gggagggctc ggggaggg cgcggggcgg ccggagcgcc gcggggctgc     1320
gaggcgcggc gagccgcagc cattgccttt tatggtaatc gtgcgagagg gcgcaggac    1380
ttcctttgtc ccaaatctgg cggagccgaa atctgggagg cgccgccgca ccccctctag   1440
cgggcgcggg cgaagcggtg cggcgccggc aggaaggaaa tgggcgggga gggccttcgt   1500
gcgtcgccgc gccgccgtcc cctttctccat ctccagcctc gggcgctgccg caggggacg   1560
gctgccttcg gggggacgg ggcagggcgg ggttcggctt ctggcgtgtg accggcggct   1620
ctagagcctc tgctaaccat gttcatgcct tcttctttt cctacagggg ggatccgttt   1680
atctgcagaa ttcgccctttg acgtcgccac catggaaact ctttctaatg caagtggtac   1740
ttttgccata cgccttttaa agatactgtg tcaagataac ccttcgcaca acgtgttctg   1800
ttctcctgtg agcatctcct ctgccctgcc catggttctc ctagggggcaa agggaaacac   1860
cgcaacccag atgcccagg cactgtcttt aaacacagag gaagcattc atcgggcttt    1920
ccagtcgctt ctcactgaag tgaacaaggc tggcacacag tacctgctga aacggccaa    1980
caggtctttt ggagagaaaa cttgtcagtt cctctcaacg tttaaggaat cctgtcttca    2040
attctaccat gctgagctga aggagctttc ctttatcaga gctgcagaag agtccaggaa    2100
acacatcaac acctgggtct caaaaaagac cgaaggtaaa attgaagagt tgttgccggg   2160
tagctcaatt gatgcagaaa ccaggctggt tcttgtcaat gccatctact tcaaaggaaa   2220
gtggaatgaa ccgtttgacg aaacatacac aaggggaaatg cccttttaaaa taaccagga   2280
ggagcaaagg ccagtgcaga tgatgtatca ggaggccacg tttaagctcg cccacgtgga   2340
cgaggtgcgc gcgcagctgc tggagctgcc ctacgcgaag aaggagctga gcctgctggt   2400
gctgctgcct gacgacggcg tggagctcag cacggtggaa aaaagtctca cttttgagaa   2460
actcacagcc tggaccaagc cagactgtat gaagagtact gaggttgaag ttctccttcc   2520
aaaatttaaa ctacaagagg attatgacat ggaatctgtg cttcggcatt tggaattgt    2580
tgatgccttc caacagggca aggctgactt gtcgcaatg tcagcggaga gagacctgtg   2640
tctgtccaag ttcgtgcaca agagtttgt ggaggtgaat gaagaaggca ccgaggcagc    2700
ggcagcgtcg agctgctttg tagttgcaga gtgctgcatg gaatctggcc ccaggttctg   2760
tgctgaccac ccttttcctt tcttcatcag gcacaacaga gccaacagca ttctgttctg   2820
tggcaggttc tcatcgccag gaagcggagc tactaacttc agcctgctga agcaggctgg   2880
agacgtggag gagaaccctg gacctatgga ctggacatcc tgttcc tggtgccgcc        2940
cgccaccagg gtgcacagcg gcattcatgt cttcattttg gctgtttca gtgcagggct    3000
tcctaaaaca gaagccaact gggtgaatgt aataagtgat ttgaaaaaaa ttgaagatct   3060
tattcaatct atgcatattg atgctacttt atatacggaa agtgatgttc accccagttg   3120
caaagtaaca gcaatgaagt gctttctctt ggagttacaa gttatttcac ttgagtccgg   3180
agatgcaagt attcatgata cagtagaaaa tctgatcatc ctagcaaaca acagttgtc    3240
```

-continued

```
ttctaatggg aatgtaacag aatctggatg caaagaatgt gaggaactgg aggaaaaaaa    3300
tattaaagaa tttttgcaga gttttgtaca tattgtccaa atgttcatca acacttctag    3360
cggcggcggc agcggcggcg gcggcagcgg cggcggcggc agcggcggcg gcggcagcgg    3420
cggcggcagc ctgcagatca cgtgccctcc cccatgtcc gtggaacacg cagacatctg    3480
ggtcaagagc tacagcttgt actccaggga gcggtacatt tgtaactctg gtttcaagcg    3540
taaagccggc acgtccagcc tgacggagtg cgtgttgaac aaggccacga atgtcgccca    3600
ctggacaacc cccagtctca aatgcattag agaccctgcc ctggttcacc aaaggccagc    3660
gccaccctcc acagtaacga cggcaggggt gaccccacag ccagagagcc tctccccttc    3720
tggaaaagag cccgcagctt catctcccag ctcaaacaac acagcggcca caacagcagc    3780
tattgtcccg ggctcccagc tgatgccttc aaaatcacct tccacaggaa ccacagagat    3840
aagcagtcat gagtcctccc acggcacccc ctctcagaca acagccaaga actgggaact    3900
cacagcatcc gcctcccacc agccgccagg tgtgtatcca cagggccaca gcgacaccac    3960
tgtggctatc tccacgtcca ctgtcctgct gtgtgggctg agcgctgtgt ctctcctggc    4020
atgctacctc aagtcaaggc aaactccccc gctggccagc gttgaaatgg aagccatgga    4080
ggctctgccg gtgacttggg ggaccagcag cagagatgaa gacttggaaa actgctctca    4140
ccacctatga taaccgctga tcagcctcga ctgtgccttc tagttgccag ccatctgttg    4200
tttgcccctc ccccgtgcct tccttgaccc tggaaggtgc cactcccact gtcctttcct    4260
aataaaatga ggaaattgca tcgcattgtc tgagtaggtg tcattctatt ctgggggtg    4320
gggtggggca ggacagcaag ggggaggatt gggaagacaa tagcaggcat gctggggatg    4380
cggtgggctc tatgg                                                     4395
```

SEQ ID NO: 139    moltype = DNA   length = 4789
FEATURE          Location/Qualifiers
misc_feature     1..4789
                 note = Synthetic
source           1..4789
                 mol_type = other DNA
                 organism = synthetic construct
SEQUENCE: 139

```
gacattgatt attgactagt tattaatagt aatcaattac ggggtcatta gttcatagcc      60
catatatgga gttccgcgtt acataactta cggtaaatgg cccgcctggc tgaccgccca     120
acgacccccg cccattgacg tcaataatga cgtatgttcc catagtaacg ccaataggga     180
ctttccattg acgtcaatgg gtggactatt tacggtaaac tgcccacttg gcagtacatc     240
aagtgtatca tatgccaagt acgccccta ttgacgtcaa tggtcccgcct     300
ggcattatgc ccagtacatg accttatggg actttcctac ttggcagtac atctacgtat     360
tagtcatcgc tattaccatg gtcgaggtg agccccacgt tctgcttcac tctccccatc     420
tccccccct ccccacccc aattttgtat ttatttattt tttaattatt ttgtgcagcg     480
atgggggcg ggggggggg ggcgcgcgcc aggcggggcg gggcggggcg aggggcgggg     540
cggggcgagg cggagaggtg cggcggcagc caatcagagc ggcgcgctcc gaaagtttcc     600
ttttatggcg aggcggcggc ggcggcggcc ctataaaaag cgaagcgcgc ggcgggcggg     660
agtcgctgcg ttgccttcgc cccgtgcccc gctccgcgcc gctcgcgcc gcccgcccg     720
gctctgactg accgcgttac tcccacaggt gagcgggcgg gacggccctt ctcctccggg     780
ctgtaattag cgcttggttt aatgacggct cgtttctttt ctgtgctgc gtgaaagcct     840
taaagggctc cggagggcc ctttgtgcgg ggggagcgg ctcggggggt gcgtgcgtgt     900
gtgtgtgcgt ggggagcgcc gcgtgcggcc cgcgctgccc ggcggctgtg agcgctgcgg     960
gcgcggcgcg gggctttgtg cgctccgcgt gtgcgcgagg gagcgcggc cggggcggt    1020
gccccgcggt gcggggggc tgcgaggga acaaaggctg cgtgcgggt gtgtgcgtgg    1080
gggggtgagc aggggggtgtg ggcgcggcgg tcgggctgta accccccct gcaccccct    1140
cccgagttg ctgagcacgg cccggcttcg ggtgcgggc tccgtgcggg gcgtggcgcg    1200
gggctcgccg tgccgggcgg ggggtggcgg caggtggggg tgccgggcgg ggcggggccg    1260
cctccgggcg gggagggctc gggagggg cgcggccgcc ccggagcgcc gcggctgtc    1320
gaggcgcggc gagccgcagc cattgccttt tatggtaatc gtgcgagagg gcgcagggac    1380
ttcctttgtc ccaaatctgg cggagccgaa atctgggagg cgccgccgca ccccctctag    1440
cgggcgcggg cgaagcggtg cggcgccggc aggaaggaaa tgggcgggga gggccttcgt    1500
gcgtcgccgc gccgccgtcc cctttctccat ctccagcctc ggggctgccg caggggacg    1560
gctgccttcg gggggacgg ggcagggcgg ggttcggctt ctggcgtgtg accggcggct    1620
ctagagcctc tgctaaccat gttcatgcct tcttctttt cctacagggg ggatccgttt    1680
atctgcagaa ttcgcccttg acgtcgccac catggcgctt ccggtgacag cactgctcct    1740
cccctggcg ctgttgctcc acgcagcaag gccgcagatc cagctgcag agagcggccc    1800
cgaggtggtg aagccggcg ccagcgtgaa gatcagctgc aaggccagcg gctcaccctt    1860
caccgactac tacatcacct gggtgaagca gaagcccggc cagggcctgg agtggatcgg    1920
ctggatctac cccggcagcg gcaacaccaa gtacaacgag aagttcaagg gcaaggccac    1980
cctgaccgtg gacaccagca gcagcaccgc cttcatgcag ctgagcagcc tgaccagcga    2040
ggacaccgcc gtgtacttct gcgccaacta cggcaactac tggttcgcct actggggcca    2100
gggcacccag gtgaccgtga gcgcggcg cggcggcagc ggcggcggcg gcagcggcgg    2160
cggcggcagc gacatcgtgc tgacccagag ccccgccagc ctggccgtga gcctgggcca    2220
gagagccacc atcagctgca aggccagcca gagcgtggac ttcgacgcg acagctacat    2280
gaactggtac cagcagaagc ccggcagcc ccccaaggtg ctgatctacg ccgccagcaa    2340
cctggagagc ggcatccccg ccagattcag cggcagcggc agcggcaccg acttcacct    2400
gaacatccac cccgtggagg aggaggacgc cgccacctac tactgccagc agagcaacga    2460
ggaccccctgg accttcggcg gcggcaccaa gctggagatc aagagcgccg ccgccttcgt    2520
gcccgtgttc ctgccgccca agcccaccac cacccccgcc ccagacccc caccccgc    2580
ccccaccatc gccagccagc ccctgagcct gagacccgag gcctgcagac cgcgcgg    2640
cggcgccgtg cacaccagga gcttggactt cgcctgcgac atctactcct gggcccctc    2700
ggccggcacc tgcggcgtgc tgctgctgag cctggtgatc accctgtact gcaaccacag    2760
aaacagaagc aagagaagca gactgctgca cagcgactac atgaacatga ccccagaag    2820
acccggcccc accagaaagc actaccagcc ctacgccccc cagagact cgccgccta    2880
cagaagcaga gtgaagttca gcagaagcgc cgacgccccc gcctaccagc agggccagaa    2940
ccagctgtac aacgagctga acctgggcag aagagaggag tacgacgtgc tggacaagag    3000
```

```
aagaggcaga gaccccgaga tgggcggcaa gcccagaaga aagaaccccc aggagggcct  3060
gtacaacgag ctgcagaagg acaagatggc cgaggcctac agcgagatcg catgaaggg   3120
cgagagaaga agaggcaagg gccacgacgg cctgtaccag ggcctgagca ccgccaccaa  3180
ggacacctac gacgccctgc acatgcaggc cctgcccccc agaggaagcg gagctactaa  3240
cttcagcctg ctgaagcagc ctggagacgt ggaggagaac cctggaccta tgtctcgctc  3300
cgttgcctta gctgtgctcg cgctactctc tctttctgga ttagaggctg tcatggcgcc  3360
ccgaaccctc ttcctgggtg gaggcggttc aggcggaggt ggctctggcg gtggcggatc  3420
gatccagcgt actccaaaga ttcaggttta ctcacgtcat ccagcagaga atggaaagtc  3480
aaatttcctg aattgctatg tgtctgggtt tcatccatcc gacattgaag ttgacttact  3540
gaagaatgga gagagaattg aaaaagtgga gcattcagac ttgtctttca gcaaggactg  3600
gtctttctat ctcttgtact acactgaatt caccccact gaaaaagatg agtatgcctg   3660
ccgtgtgaac catgtgactt tgtcacagcc caagatagtt aagtgggatc gagacatggg  3720
tggtggtggt tctggtggtg gtggttctgg cggcggcggc tccggtggtg gtggatccgg  3780
ctcccactcc ttgaagtatt tccacacttc cgtgtcccgg ccccggccgg gggagccccg  3840
cttcatctct gtgggctacg tggacgacac ccagttcgtg cgcttcgaca acgacgccgc  3900
gagtccgagg atggtgccgc gggcgccgtg gatggagcag gaggggtcag agtattggga  3960
ccgggagaca cggagcgcca gggacaccgc acagattttc cgagtgaatc tgcggacgct  4020
gcgcggctac tacaatcaga gcgaggccgg gtctcacacc ctgcagtgga tgcatggctg  4080
cgagctgggg cccgacgggc gcttcctccg cgggtatgaa cagttcgcct acgacgcaa   4140
ggattatctc accctgaatg aggacctgcg ctcctggacc gcgtggacca cggcggctca  4200
gatctccgag caaaagtcaa atgatgcctc tgaggcggag caccagagag cctacctgga  4260
agacacatgc gtggagtggc tccacaaata cctggagaag gcgctgcttca            4320
cctggagccc caaagacac acgtgactca ccacccatc tctgaccatg aggccaccct    4380
gaggtgctgg gccctgggct tctaccctgc ggagatcaca ctgacctggc agcaggatgg  4440
ggagggccat acccaggaca cggagctcgt ggagaccagg cctgcagggg atggaacctt  4500
ccagaagtgg cagctgtgg tggtgccttc tggagaggag cagagataca gtgccatgt    4560
gcagcatgag gggctacccg agcccgtcac cctgagatgg aagccggctt cccagcccac  4620
catccccatc gtgggcatca ttgctggcct ggttctcctt ggatctgtgg tctctggagc  4680
tgtggttgct gctgtgatat ggaggaagaa gagctcaggt ggaaaaggag ggagctactc  4740
taaggctgag tggagcgaca gtgcccaggg gtctgagtct cacagcttg              4789

SEQ ID NO: 140          moltype = DNA   length = 4759
FEATURE                 Location/Qualifiers
misc_feature            1..4759
                        note = Synthetic
source                  1..4759
                        mol_type = other DNA
                        organism = synthetic construct
SEQUENCE: 140
gacattgatt attgactagt tattaatagt aatcaattac ggggtcatta gttcatagcc    60
catatatgga gttccgcgtt acataactta cggtaaatgg cccgcctggc tgaccgccca   120
acgaccccg cccattacg tcaataatga cgtatgttcc catagtaacg ccaatagga     180
ctttccattg acgtcaatgg gtggactatt tacggtaaac tgcccacttg gcagtacatc   240
aagtgtatca tatgccaagt acgccccta ttgacgtcaa tgacggtaaa tggcccgcct    300
ggcattatgc ccagtacatg accttatggg actttcctac ttggcagtac atctacgtat   360
tagtcatcgc tattaccatg gtcgaggtg agccccacgt tctgcttcac tctccccatc   420
tccccccct cccacccc aatttgtat ttatttattt tttaattatt ttgtgcagcg      480
atgggggcgg ggggggggg ggcgcgcgcc aggcggggcg gggctgggcg agggcgggg   540
cgggggcgagg cggagaggtg cggcggcagc caatcagagc ggcgcgctcc gaaagttttcc  600
ttttatggcg aggcggcggc ggcggcggcc ctataaaaag cgaagcgcgc ggcgggcggg   660
agtcgctgcg ttgccttcgc cccgtgcccc gctccgccgc cgcctcgcgc cgcccgcccg   720
gctctgactg accgcgttac tcccacaggt gagcgggcgg gacggccctt ctcctccggg   780
ctgtaattag cgcttggttt aatgacggct cgtttctttt ctgtggctgc gtgaaagcct   840
taaagggctc cgggagggcc ctttgtgcgg gggggagcgg ctcgggggt gcgtgcgtgt    900
gtgtgtgcgt gggggagcgc gcgtgcggcc cgcgctgccc ggcggctgtg agcgctgcgg   960
gcgcggcgcg gggctttgtg cgctccgcgt gtgcgcgagg ggagcgcggc cgggggcggt  1020
gccccgcgt gcgggggggc tgcgagggga acaaaggctg cgtgcgggt gtgtgcgtgg    1080
gggggtgagc aggggggtgtg ggcgcggcgg tcgggctgta accccccct gcacccccct   1140
ccccgagttg ctgagcacgg cccggcttcg ggtgcgggc tccgtgcggg gcgtggccgcg  1200
gggctgccgg tgccgggcgg ggggtgcgg caggtggggg tgccgggcgg gcgggggccg   1260
cctcgggccg ggggaggctc gggggagggg cgcggcggcc ccgagcgcc ggcggctgtc    1320
gaggcgcggc gagccgcagc cattgccttt tatggtaatc gtgcgagagg gcgcagggac   1380
ttcctttgtc ccaaatctgg cggagccgaa atctgggagg cgccgccgca cccccctctag  1440
cgggcgggcg cgaagcggtg cggcgccggc aggaaggaaa tgggcgggga gggccttcgt   1500
gcgtcgccgc gccgccgtcc ccttctccat ctccagcctc gggctgccg cagggggacg    1560
gctgccttcg gggggacggg gcagggcgg ggttcggctt ctggcgtgtg accggcggct    1620
ctagagcctc tgctaaccat gttcatgcct tcttctttttt cctacagggg ggatccgttt    1680
atctgcagaa ttcgcccttg acgtcgccac catggcgctt ccggtgacag cactgctcct    1740
cccctgggcg ctgttgctcc acgcagcaag gccgcaggc cagctgcacc agtggggcgc     1800
cggcctgctg aagcccagcg agaccctgag cctgacctgc gccgtgtacg gcggcagctt    1860
cagcgcctac tactggagct ggatcagaca gccccccggc aagggcctgg agtggatcgg    1920
cgacatcaac cacggcgcg caccaactaa caaccccagc ctgaagagca gagtgaccat    1980
cagcgtggac accagcaaga accagttcag cctgaagctg aacagcgtga ccgccgcga    2040
caccgcgtga tactactgcg tcgtcgtgac cgtcgtcgac caggggcc gctgcgtgac    2100
cgtgagcagc ggcgggccgg cagcggcggc cggcggcagc ggcggcggcg cagcgcgat    2160
ccagatgacc cagagcccca ccagcctgag cgccagcgtg ggcgacagag tgaccatcac    2220
ctgcagagcc agcagggca tcagcagctg gctgacctgg taccagcaga agcccggaaa    2280
ggccccccaag agcctgatct acgccgccag cagcctgcag agcggcgtgc ccagcagatt    2340
cagcggcagc ggcagcggca ccgacttcac cctgaccatc agcagcctgc agcccgagga    2400
```

-continued

```
cttcgccacc tactactgcc agcagtacga cagctacccc atccacttcg gccagggcac    2460
cagactggag atcaagagcg ccgccgcctt cgtgcccgtg ttcctgcccg ccaagcccac    2520
caccacccccc gccccccagac cccccaccccc cgccccaccc atcgccagcc agccccctgag 2580
cctgagaccc gaggcctgca gacccgccgc cggcggcgcc gtgcacacca gaggcctgga    2640
cttcgcctgc gacatctaca tctgggcccc cctggccggc acctgcggcg tgctgctgct    2700
gagcctggtg atcaccctgt actgcaacca cagaaacaga aagagaggca gaaagaagct    2760
gctgtacatc ttcaagcagc ccttcatgag acccgtgcag accacccagg aggaggacgg    2820
ctgcagctgc agattccccg aggaggagga gggcggctgc gagctgagag tgaagttcag    2880
cagaagcgcc gacgccccccg cctaccagca gggccagaac cagctgtaca acgagctgaa    2940
cctgggcaga agagaggagt acgacgtgct ggacaagaga agaggcagag accccgagat    3000
gggcggcaag cccagaagaa agaaccccca ggagggcctg tacaacgagc tgcagaagga    3060
caagatggcc gaggcctaca gcgagatcgg catgaagggc gagagaagaa gaggcaaggg    3120
ccacgacggc ctgtaccagg gcctgagcac cgccaccaag gacacctacg acgccctgca    3180
catgcaggcc ctgcccccca gaggaagcgg attcagcctg ctgaagcagg ctggagacgt    3240
ggaggagaac cctggaccta tgtctcgctc cgttgcctta gctgtgctcg cgctactctc    3300
tctttctgga ttagaggctg tcatggcgcc ccgaaccctc ttcctgggtg gaggcggttc    3360
aggcggaggt ggctctggcg gtggcggatc gatccagcgt actccaaaga ttcaggttta    3420
ctcacgtcat ccagcagaga atgaaagtc aatttcctg aattgctatg tgtctgggtt    3480
tcatccatcc gacattgaag ttgacttact gaagaatgga gagagaattg aaaaagtgga    3540
gcattcagac ttgtcttca gcaaggactg gtctttctat ctcttgtact acactgaatt    3600
caccccccact gaaaaagatg agtatgcctg ccgtgtgaac catgtgactt tgtcacagcc    3660
caagatagtt aagtgggatc gagacatggg tggtggtggt tctggtggtg gtggttctgg    3720
cggcggcggc tccggtggtg gtggatccgg ctcccactcc ttgaagtatt tccacacttc    3780
cgtgtcccgg cccggccgcg gggagcccg cttcatctct gtgggctacg tggacgacac    3840
ccagttcgtg cgcttcgaca cgacgccgc gagtccgagg atggtgccgc gggcgccgtg    3900
gatggagcag gagggtcag agtattggga ccgggagca cggagcgca gggacaccgc    3960
acagattttc cgagtgaatc tgcggacgct cgcggctac tacaatcaga gcgaggccgg    4020
gtctcacacc ctgcagtgga tgcatggctg cgagctgggg cccgacgggc gcttcctccg    4080
cgggtatgaa cagttcgcct acgacggcaa ggattatctc accctgaatg aggacctgcg    4140
ctcctggacc gcggtggaca cggccggctca gatctccgag caaaagtcaa atgatgcctc    4200
tgaggcggaa caccagagag cctacctgga agacacatgc gtggagtggc tccacaaata    4260
cctggagaag gggaaggaga cgctgcttca cctggagccc ccaaagacac acgtgactca    4320
ccaccccatc tctgaccatg aggccaccct gaggtgctgg gccctgggct ctaccctgc    4380
ggagatcaca ctgacctggc agcaggatgg ggagggccat ccccaggaca cggagctcgt    4440
ggagaccagg cctcagggg atggaacctt ccagaagtgg tgagctgtgg tggtgcctc     4500
tggagaggag cagagataca cgtgccatgt gcagcatgag gggctacccg agcccgtcac    4560
cctgagatgg aagccggctt cccagcccac catcccatc gtgggcatca ttgctggcct    4620
ggttctcctt ggatctgtgg tctctggagc tgtggttgct gctgtgatat ggaggaagaa    4680
gagctcaggt ggaaaaggag ggagctactc taaggctgag tggagcgaca gtgcccaggg    4740
gtctgagtct cacagcttg                                                4759

SEQ ID NO: 141        moltype = DNA  length = 4762
FEATURE               Location/Qualifiers
misc_feature          1..4762
                      note = Synthetic
source                1..4762
                      mol_type = other DNA
                      organism = synthetic construct
SEQUENCE: 141
gacattgatt attgactagt tattaatagt aatcaattac ggggtcatta gttcatagcc    60
catatatgga gttccgcgtt acataactta cggtaaatgg cccgcctggc tgaccgccca    120
acgacccccg cccattgacg tcaataatga cgtatgttcc catagtaacg ccaatagggga    180
ctttccattg acgtcaatgg gtggactatt tacggtaaac tgcccacttg gcagtacatc    240
aagtgtatca tatgccaagt acgccccccta ttgacgtcaa tgacggtaaa tggcccgcct    300
ggcattatgc ccagtacatg accttatggg actttcctac ttggcagtac atctacgtat    360
tagtcatcgc tattaccatg gtcgaggtg agccccacgt tctgcttcac tctccccatc    420
tccccccct cccaccccc aattttgtat ttatttattt tttaattatt ttgtgcagcg    480
atggggggcgg ggggggggg gggcgcgcgcc aggcggggcg gggcgggcg agggggcgggg    540
cggggcgagg cggagaggtg cggcggcagc caatcagagc ggcgcgctcc gaaagtttcc    600
ttttatgcga aggcggcggc ggcggcggcc ctataaaaag cgaagcggcg gcggcgggg    660
agtcgctgcg ttgccttcgc cccgtgcccc gctccgcgcc gcctcgcgcc gcccgccccg    720
gctctgactg accgcgttac tcccacaggt gagcgggcgg gacggccctt ctcctccggg    780
ctgtaattag cgcttggttt aatgacggct cgtttctttt ctgtggctgc gtgaaagcct    840
taaagggctc cgggagggcc ctttgtgcgg gggggagccg cgtgtgcggg gctgtccgtt    900
gtgtgtgcgt gggggagcgcc gcgtgcggcc cgcgctgccc ggcggctgtg agcgctgcgg    960
gcgcggcgcg gggctttgtg cgctccgcgt gtgcgcgagg gagcgcggcc ggggggcggt    1020
gccccgcggt gcggggggc tgcgagggga acaaaggctg cgtgcggggt gtgtgcgtgg    1080
gggggtgagc aggggggtgtg ggcgcggcgg tcgggctgta accccccct gcaccccct    1140
ccccgagttg ctgagcacgg cccggcttcg ggtgcggggc tcctgcggg gtggccggg    1200
gggctcgccg tgccgggcgg ggggtggcgg caggtggggg tgccgccgg ggcggggccg    1260
cctcgggccg ggagggctc ggggaggggg cgcggcggcc ccgagcgcc ggcggctgtc    1320
gaggcgcggc gagccgcagc cattgccttt tatggtaatc gtgcgagagg gcgcagggac    1380
ttcctttgtc ccaaatctgg cggagccgaa atctgggagg cgccgccgca ccccctctag    1440
cgggcgggg cgaagcggtg cggcgccggc aggaaggaaa tgggcgggga gggccttcgt    1500
gcgtcgccgc gccgccgtcc ccttctccat ctccagcctc ggggctgccg caggggacg    1560
gctgccttcg ggggggacgg ggcagggcgg ggttcggctt ctggcgtgtg accggcggct    1620
ctagagcctc tgctaaccat gttcatgcct tcttcttttt cctacagggg ggatccgttt    1680
atctgcagaa ttcgcccttg acgtcgccac catggcgctt ccggtgacag cactgctcct    1740
ccccttggcg ctgttgctcc acgcagcaag gccggacatc cagatgaccc agagcccac    1800
```

-continued

```
cagcctgagc gccagcgtgg gcgacagagt gaccatcacc tgcagagcca gccaggcat  1860
cagcagctgg ctgacctggt accagcagaa gcccgagaag gcccccaaga gcctgatcta  1920
cgccgccagc agcctgcaga gcggcgtgcc cagcagattc agcggcagcg gcagcggcac  1980
cgacttcacc ctgaccatca gcagcctgca gcccgaggac ttcgccacct actactgcca  2040
gcagtacgac agctacccca tcaccttcgg ccagggcacc agactggaga tcaagggcgg  2100
cggcggcagc ggcggcggcg gcagcggcgg cggcggcagc caggtgcagc tgcagcagtg  2160
gggcgccggc ctgctgaagc ccagcgagac cctgagcctg acctgcgccg tgtacgcggg  2220
cagcttcagc gcctactact ggagctggat cagacagccc cccggcaagg gcctggagtg  2280
gatcggcgac atcaaccacg gcggcggcac caactacaac cccagcctga agagcagagt  2340
gaccatcagc gtggacacca gcaagaacca gttcagcctg aagctgaaca gcgtgaccgc  2400
cgccgacacc gccgtgtact actgcgccag cctgaccgcc tactgggccc agggcagcct  2460
ggtgaccgtg agcgccgccg ccttcgtgcc cgtgttcctg cccgcaagc ccaccaccac  2520
ccccgccccc agacccccca cccccgcccc caccatcgcc agccagcccc tgagcctgag  2580
acccgaggcc tgcagaccg cggcggcggc gccgtgcac accagaggcc tggacttcgc  2640
ctgcgacatc tacatctggg cccccctggc cggcaccgc ggcgtgctgc tgctgagcct  2700
ggtgatcacc ctgtactgca accacagaaa cagaaagaga ggcagaaaga agctgctgta  2760
catcttcaag cagcccttca tgagacccgt gcagaccacc caggaggagg acggctgcag  2820
ctgcagattc cccgaggagg aggagggcgg ctgcgagctg agagtgaagt tcagcagaag  2880
cgccgacgcc cccgcctacc agcagggcca gaaccagctg tacaacgagc tgaacctggg  2940
cagaagagag gagtacgacg tgctggacaa gagaagaggc agagaccccg agatgggcgg  3000
caagcccaga gaaagaaacc cccaggaggg cctgtacaac gagctgcaga aggacaagat  3060
ggccgaggcc tacagcgaga tcggcatgaa gggcgagaga agaagaggca agggccaggg  3120
cggcctgtac cagggcctga gcaccgccca caaggacacc tacgacgccc tgcacatgca  3180
ggccctgccc cccagaggaa gcggagctac taacttcagc ctgctgaagc aggctggaga  3240
cgtggaggag aaccctggac ctatgtccg ctccgttgcc ttagctgtgc tcgcgctact  3300
ctctctttct ggattagagg ctgtcatggc gccccgaacc tcttcctgg tgtggaggcgg  3360
ttcaggcgga ggtggctctg gcggtggcgg atcgatccag cgtactccaa agattcaggt  3420
ttactcacgt catccagcag agaatggaaa gtcaaatttc ctgaattgct atgtgtctgg  3480
gtttcatcca tccgacattg aagttgactt actgaagaat ggagagagaa ttgaaaaagt  3540
ggagcattca gacttgtctt tcagcaagga ctggtctttc tatctcttgt actacactga  3600
attcacccccc actgaaaaag atgagtatgc ctgccgtgtg aaccatgtga ctttgtcaca  3660
gcccaagata gttaagtggg atcgagacat gggtggtggt ggttctggtg gtggtggttc  3720
tggcggcggc ggctccggtg gtggtggatc cggctcccac tccttgaagt atttccacac  3780
ttccgtgtcc cggcccggcc gcggggagcc ccgcttcatc tctgtgggct acgtggacga  3840
cacccagttc gtgcgcttcg acaacgacgc cgcgagtccg aggatggtgc cgcgggcgcc  3900
gtggatggag caggagggt cagagtattg gaccgggag acacggagcg ccagggacac  3960
cgcacagatt ttccgagtga atctgcggac gctgcgcggc tactacaatc agagcgaggc  4020
cgggtctcac accctgcagt ggatgcatgg ctgcgagctg gggcccgacg gcgcttcct  4080
ccgcggggta gaacagttcg cctacgacgg caaggattat ctcacccta atgaggacct  4140
gcgctcctgg accgcggtgg acacggcggc tcagatctcc gagcaaaagt caaatgatgc  4200
ctctgaggcg gagcaccaga gagcctacct ggaagacaca tgcgtggagt ggctccacaa  4260
atacctggag aagggggaag gacgctgct caacctggag cccccaaaga cacacgtgac  4320
tcaccacccc atctctgacc atgaggccac cctgagtgc tgggccctgg gcttctaccc  4380
tgcggagatc acactgacct ggcagcagga tgggggagg cataccagg acacggagct  4440
cgtggagacc aggcctgcag gggatggaac cttccagaag tgggcagctg tggtggtgcc  4500
ttctggagag gagcagagat acacgtgcca tgtgcagcat gaggggctac ccgagcccgt  4560
cacccctgaga tggaagccgg cttcccagcc caccatcccc atgtgggcta tcattgctgg  4620
cctggttctc cttggatctg tggtctctgg agctgtggtt gctgctgtga tatgcaggaa  4680
gaagagctca ggtggaaaag gagggagcta ctctaaggct gagtggagcg acagtgccca  4740
ggggtctgag tctcacagct tg                                           4762
```

```
SEQ ID NO: 142          moltype = AA   length = 500
FEATURE                 Location/Qualifiers
REGION                  1..500
                        note = Synthetic
source                  1..500
                        mol_type = protein
                        organism = synthetic construct
SEQUENCE: 142
MSRSVALAVL ALLSLSGLEA VMAPRTLFLG GGGSGGGSG GGGSIQRTPK IQVYSRHPAE    60
NGKSNFLNCY VSGFHPSDIE VDLLKNGERI EKVEHSDLSF SKDWSFYLLY YTEFTPTEKD  120
EYACRVNHVT LSQPKIVKWD RDMGGGGSGG GGSGGGGSGG GGSGSHSLKY FHTSVSRPGR  180
GEPRFISVGY VDDTQFVRFD NDAASPRMVP RAPWMEQEGS EYWDRETRSA RDTAQIFRVN  240
LRTLRGYYNQ SEAGSHTLQW MHGCELGPDG RFLRGYEQFA YDGKDYLTLN EDLRSWTAVD  300
TAAQISEQKS NDASEAEHQR AYLEDTCVEW LHKYLEKGKE TLLHLEPPKT HVTHHPISDH  360
EATLRCWALG FYPAEITLTW QQDGEGHTQD TELVETRPAG DGTFQKWAAV VVPSGEEQRY  420
TCHVQHEGLP EPVTLRWKPA SQPTIPIVGI IAGLVLLGSV VSGAVVAAVI WRKKSSGGKG  480
GSYSKAEWSD SAQGSESHSL                                              500

SEQ ID NO: 143          moltype = AA   length = 417
FEATURE                 Location/Qualifiers
REGION                  1..417
                        note = Synthetic
source                  1..417
                        mol_type = protein
                        organism = synthetic construct
SEQUENCE: 143
MDWTWILFLV AAATRVHSGI HVFILGCFSA GLPKTEANWV NVISDLKKIE DLIQSMHIDA   60
TLYTESDVHP SCKVTAMKCF LLELQVISLE SGDASIHDTV ENLIILANNS LSSNGNVTES  120
```

```
GCKECEELEE  KNIKEFLQSF  VHIVQMFINT  SSGGGGSGGGG  SGGGGSGGGG  SGGGSLQITC   180
PPPMSVEHAD  IWVKSYSLYS  RERYICNSGF  KRKAGTSSLT  ECVLNKATNV  AHWTTPSLKC   240
IRDPALVHQR  PAPPSTVTTA  GVTPQPESLS  PSGKEPAASS  PSSNNTAATT  AAIVPGSQLM   300
PSKSPSTGTT  EISSHESSHG  TPSQTTAKNW  ELTASASHQP  PGVYPQGHSD  TTVAISTSTV   360
LLCGLSAVSL  LACYLKSRQT  PPLASVEMEA  MEALPVTWGT  SSRDEDLENC  SHHLGSG      417

SEQ ID NO: 144          moltype = AA   length = 376
FEATURE                 Location/Qualifiers
source                  1..376
                        mol_type = protein
                        organism = Homo sapiens
SEQUENCE: 144
METLSNASGT  FAIRLLKILC  QDNPSHNVFC  SPVSISSALA  MVLLGAKGNT  ATQMAQALSL    60
NTEEDIHRAF  QSLLTEVNKA  GTQYLLRTAN  RLFGEKTCQF  LSTFKESCLQ  FYHAELKELS   120
FIRAAEESRK  HINTWVSKKT  EGKIEELLPG  SSIDAETRLV  LVNAIYFKGK  WNEPFDETYT   180
REMPFKINQE  EQRPVQMMYQ  EATFKLAHVG  EVRAQLLELP  YARKELSLLV  LLPDDGVELS   240
TVEKSLTFEK  LTAWTKPDCM  KSTEVEVLLP  KFKLQEDYDM  ESVLRHLGIV  DAFQQGKADL   300
SAMSAERDLC  LSKFVHKSFV  EVNEEGTEAA  AASSCFVVAE  CCMESGPRFC  ADHPFLFFIR   360
HNRANSILFC  GRFSSP                                                      376

SEQ ID NO: 145          moltype = DNA   length = 1203
FEATURE                 Location/Qualifiers
misc_feature            1..1203
                        note = Synthetic
source                  1..1203
                        mol_type = other DNA
                        organism = synthetic construct
SEQUENCE: 145
ggctccggtg  cccgtgtgcg  gaccgggctc  cggtgcccgt  cagtgggcag  agcgcacatc    60
gcccacagtc  cccgagaagt  tggggggagg  ggtcggcaat  tgaaccggtg  cctagagaag   120
gtggcgcggg  gtaaactggg  aaagtgatgt  cgtgtactgg  ctccgccttt  ttcccgaggg   180
tgggggagaa  ccgtatataa  gtgcagtagt  cgccgtgaac  gttctttttc  gcaacgggtt   240
tgccgccaga  acacaggtaa  gtgccgtgtg  tggttcccgc  gggcctggcc  tctttacggg   300
ttatggccct  tgcgtgcctt  gaattacttc  cactggctgc  agtacgtgat  tcttgatccc   360
gagcttcggg  ttggaagtgg  gtgggagagt  tcgaggcctt  gcgcttaagg  agcccctccg   420
cctcgtgctt  gagttgaggc  ctggcctggg  cgctggggcc  gccgcgtgcg  aatctggtgg   480
caccttcgcg  cctgtctcgc  tgctttcgat  aagtctctag  ccatttaaaa  tttttgatga   540
cctgctgcga  cgctttttttt  ctggcaagat  agtcttgtaa  atgcgggcca  agatctgcac   600
actggtattt  cggttttttgg  ggccgcgggc  ggcgacgggg  cccgtgcgtc  ccagcgcaca   660
tgttcggcga  ggcggggcct  gcgagcgcgg  ccaccgagaa  tcggacgggg  gtagtctcaa   720
gctggccggc  ctgctctggt  gcctggcctc  gcgccgccgt  gtatcgcccc  gccctggggcg   780
gcaaggctgg  cccggtcggc  accagttgcg  tgagcggaaa  gatggccgct  tcccggccct   840
gctgcaggga  gctcaaaatg  gaggacgcgg  cgctcgggag  agcgggcggg  tgagtgctac   900
acacaaagga  aaagggcctt  tccgtcctca  gccgtcgctt  catgtgactc  cacgagtac   960
cgggcgccgt  ccaggcacct  cgattagttc  tcgagctttt  ggagtacgtc  gtctttaggt  1020
tgggggagg  ggttttatgc  gatggagttt  ccccacactg  agtgggtgga  gactgaagtt  1080
aggccagctt  ggcacttgat  gtaattctcc  ttggaatttg  ccctttttga  gtttggatct  1140
tggttcattc  tcaagcctca  gacagtggtt  caaagttttt  ttcttccatt  tcaggtgtcg  1200
tga                                                                    1203

SEQ ID NO: 146          moltype = DNA   length = 873
FEATURE                 Location/Qualifiers
source                  1..873
                        mol_type = genomic DNA
                        organism = Homo sapiens
SEQUENCE: 146
atgaggatat  ttgctgtctt  tatattcatg  acctactggc  atttgctgaa  cgcatttact    60
gtcacggttc  ccaaggacct  atatgtggta  gagtatggta  gcaatatgac  aattgaatgc   120
aaattcccag  tagaaaaaca  attagacctg  gctgcactaa  ttgtctattg  ggaaatggag   180
gataagaaca  ttattcaatt  tgtgcatgga  gaggaagacc  tgaaggttca  gcatagtagc   240
tacagacaga  gggcccggct  gttgaaggac  cagctctccc  tgggaaatgc  tgcacttcag   300
atcacagatg  tgaaattgca  ggatgcaggg  gtgtaccgct  gcatgatcag  ctatggtggt   360
gccgactaca  agcgaattac  tgtgaaagtc  aatgccccat  acaacaaaat  caaccaaaga   420
attttggttg  tggatccagt  cacctctgaa  catgaactga  catgtcaggc  tgagggctac   480
cccaaggccg  aagtcatctg  gacaagcagt  gaccatcaag  tcctgagtgg  taagaccacc   540
accaccaatt  ccaagagaga  ggagaaactt  tcaatgtga  ccagcacact  gagaatcaac   600
acaacaacta  atgagatttt  ctactgcact  tttaggagat  tagatcctga  ggaaaaccat   660
acagctgaat  tggtcatccc  agaactacct  ctggcacatc  ctccaaatga  aaggactcac   720
ttggtaattc  tgggagccat  cttattatgc  cttggtgtag  cactgacatt  catcttccgt   780
ttaagaaaag  ggagaatgat  cttatgtgaa  aaatgtggca  tccaagatac  aaactcaaag   840
aagcaaagtg  atacacattt  ggaggagacg  taa                                  873

SEQ ID NO: 147          moltype = DNA   length = 122
FEATURE                 Location/Qualifiers
misc_feature            1..122
                        note = Synthetic
source                  1..122
                        mol_type = other DNA
                        organism = synthetic construct
```

```
SEQUENCE: 147
aacttgttta ttgcagctta taatggttac aaataaagca atagcatcac aaatttcaca   60
aataaagcat ttttttcact gcattctagt tgtggtttgt ccaaactcat caatgtatct  120
ta                                                                 122

SEQ ID NO: 148           moltype = DNA  length = 10645
FEATURE                  Location/Qualifiers
misc_feature             1..10645
                         note = Synthetic
source                   1..10645
                         mol_type = other DNA
                         organism = synthetic construct
SEQUENCE: 148
agtaatcaat tacggggtca ttagttcata gcccatatat ggagttccgc gttacataac   60
ttacggtaaa tggcccgcct ggctgaccgc ccaacgaccc ccgcccattg acgtcaataa  120
tgacgtatgt tcccatagta acgccaatag ggactttcca ttgacgtcaa tgggtggact  180
atttacggta aactgcccac ttggcagtac atcaagtgta tcatatgcca agtacgcccc  240
ctattgacgt caatgacggt aaatggcccg cctggcatta tgcccagtac atgaccttat  300
gggactttcc tacttggcag tacatctacg tattagtcat cgctattacc atgggtcgag  360
gtgagcccca cgttctgctt cactctcccc atctcccccc cctccccacc cccaattttg  420
tatttatttta ttttttaatt attttgtgca gcgatggggg cggggggggg ggggcgcgc  480
gccaggcggg gcggggcggg gcgaggggcg gggcggggcg aggcggagag gtgcggcggc  540
agccaatcag agcggcgcgc tccgaaagtt tccttttatg gcgaggcggc ggcggcggcg  600
gccctataaa aagcgaagcg cgcggcgggc gggagtcgct gcgttgcctt cgccccgtgc  660
cccgctccgc gccgcctcgc gccgcccgcc ccggctctga ctgaccgcgt tactcccaca  720
ggtgagcggg cgggacggcc cttctcctcc gggctgtaat tagcgcttgg tttaatgacg  780
gctcgtttct tttctgtggc tgcgtgaaag ccttaaaggg ctccgggagg gccctttgtg  840
cggggggag cggctcgggg ggtgcgtgcg tgtgtgtgtg cgtggggagc gccgcgtgcg  900
gcccgcgctg cccggcggct gtgagcgctg cgggcgcggc gcgggctttt gtgcgctccg  960
cgtgtgcgcg agggagcgc ggccgggggc ggtgccccgc ggtggggggg ggctgcgagg  1020
ggaacaaagg ctgcgtgcgg ggtgtgtgcg tgggggggtg agcagggggt gtgggcgcgg 1080
cggtcgggct gtaacccccc cctgcacccc cctccccgag ttgctgagca ggcccggct  1140
tcgggtgcgg ggctccgtgc ggggcgtggc gcggggctcg ccgtgccggg cggggggtgg 1200
cggcaggtgg gggtgccggg cggggcgggg ccgcctcggg ccggggaggg ctcggggag  1260
ggggcgggga gcccccggag gccggcgggct gtcgaggcgg ggcgagcggc agccattgcc 1320
ttttatggta atcgtgcgag agggcgcagg gacttccttt gtcccaaatc tggcggagcc 1380
gaaatctggg aggcgccgcc gcacccccctc tagcgggcgc gggcgaagcg gtgcggcgcc 1440
ggcaggaagg aaatgggcgg ggagggcctt cgtgcgtcgc cgcgccgccg tccccttctc 1500
catctccagc ctcggggctg ccgcaggggg acggctgcct tcgggggga cggggcaggg 1560
cggggggtcgg cttctggcgt gtgaccggcg gctctagagc ctctgctaac catgttcatg 1620
ccttcttctt tttcctacag ggggggatccg tttatctgca gaattcgccc ttgacgtcgc 1680
caccatgaa actctttcta atgcaagtgg tacttttgcc atacgccttt taaagatact  1740
gtgtcaagat aaccctccgc acaacgtgtt ctgttctcgt gtgagcatct cctctgccct  1800
ggccatggtt ctcctagggg caaagggaaa caccgcaacc cagatggccc aggcactgtc  1860
tttaaacaca gaggaagaca ttcatcgggc tttccagtcg cttctcactg aagtgaacaa  1920
ggctggcaca cagtacctgc tgagaacggc caacaggctc tttggagaga aacttgtca  1980
gttcctctca acgtttaagg aatcctgtct tcaattctac catgctgagc tgaaggagct  2040
ttcctttatc agagctgcag aagagtccga gaaacacatc aacacctggg tctcaaaaaa  2100
gaccgaaggt aaaattgaag agttgttgcc gggtagctca attgatgcag aaaccaggct  2160
ggttcttgtc aatgccatct acttcaaagg aaagtggaat gaaccgtttg acgaaacata  2220
cacaagggaa atgcccttta aaataaacca ggaggagcaa gagccagtgc agatgatgta  2280
tcaggaggcc acgtttaagc tcgcccacgt gggcgaggtg cgcgcgcagc tgctggagct  2340
gccctacgcc aggaaggagc tgagcctgct ggtgctgctg cctgacgacg gcgtggagct  2400
cagcacggtg gaaaaaagtc tcactttga gaaactcaca gcctggacca gccagactg  2460
tatgaagagt actgaggttg aagttctcct tccaaaattt aaactacaag aggattatga  2520
catggaatct gtgcttcggc atttgggaat tgttgatgcc ttccaacagg caaggctga  2580
cttgtcggca atgtcagcgg agagagacct gtgtctgtcc aagttcgtgc acaagagttt  2640
tgtggaggta aatgaagaag caccgaggc agcggcagcg tcgagctgct tgtagttgc  2700
agagtgctgc atgaaatctg gccccaggtt ctgtgctgag cacccttttcc ttttcttcat  2760
caggcacaac agagccaaca gcattctgtt ctgtggcagg ttctcatcgc caggaagcgg  2820
agctactaac ttcagcctgc tgaagcaggc tggagacgtg gaggagaacc ctggacctat  2880
ggactggacc tggatcctgt tcctggtggc cgccgccacc agggtgcaca gcggcattca  2940
tgtcttcatt ttgggctgtt tcagtgcagg cttcctaaa acagaagcca actgggtgaa  3000
tgtaataagt gatttgaaaa aaattgaaga tcttattcaa tctatgcata ttgatgctaa  3060
tttatatacg gaaagtgatg ttcacccag ttgcaaagta acagcaatga agtgctttct  3120
cttggagtta caagttattt cacttgagtc cggagatgca agtattcatg atacagtaga  3180
aaatctgatc atcctagcaa caacagtttt gtcttctaat gggaatgtaa cagaatctgg  3240
atgcaaagaa tgtgaggaac tggaggaaaa aaattattaa gaattttgt agagtttttgt  3300
acatattgtc caaatgttca tcaacacttc tagcggcggc ggcagcggcg gcggcggcag  3360
cggcggcggc agcctgcaga tcacgtgccc tccccccatg tccgtggaac acgcagacat  3420
ctggtcaag agctacagct tgtactccag ggagcggtac atttgtaact ctggtttcaa  3480
gcgtaaagcc ggcacgtcca gcctgacgga gtgcgtgttg aacaaggcca cgaatgtcgc  3540
cactgcaca accccccagtc tcaaatgcat tagagacct gccggttc accaaaagcc  3600
agcgccgctc ttctggaaaa gagcccgcag cttcatctcc ggtgaccccca cagccagaga  3660
cagctcaaac aacacagcgg ccacaacagc agctattgtc ccgggctccc agctgatgcc  3720
ttcaaaatca ccttccacag gaaccacaga gataagcagt catgagtcct ccacggcac  3780
cccctctcag acaacagcca agaactggga actcacagca tccgcctccc accagccgcc  3840
aggtgtgtat ccacagggcc acagcgacac cactgtggct atctccacgt ccactgtcct  3900
                                                                 3960
```

```
gctgtgtggg ctgagcgctg tgtctctcct ggcatgctac ctcaagtcaa ggcaaactcc   4020
cccgctggcc agcgttgaaa tggaagccat ggaggctctg ccggtgactt ggggggaccag   4080
cagcagagat gaagacttgg aaaactgctc tcaccaccta tgataaccgc tgatcagcct   4140
cgactgtgcc ttctagttgc cagccatctg ttgtttgccc ctccccgtg ccttccttga    4200
ccctggaagg tgccactccc actgtccttt cctaataaaa ggcaggaaatt gcatcgcatt  4260
gtctgagtag gtgtcattct attctggggg gtgggggtggg gcaggacagc aaggggagg   4320
attgggaaga caatagcagg catgctgggg atgcggtggg ctctatgggt cgacccagcg   4380
tgagtctctc ctaccctccc gctctggtcc ttcctctccc gctctgcacc ctctgtggcc   4440
ctcgctgtgc tctctcgctc cgtgacttcc ctttctccaag ttctccttgg tggcccgcta  4500
tggggctagt ccagggctgg atctcgggga agcggcgggg tggcctggga gtggggaagg   4560
gggtgcgcac ccgggacgcg cgctacttgc ccctttcggc ggggagcagg ggagaccttt   4620
ggcctacggc gacgggaggg tcgggacaaa gtttagggcg tcgataagcg tcagagcgcc   4680
gaggttgggg gagggtttct cttccgctct ttcgcggggc ctctggctcc cccagcgcag   4740
ctggagtggg ggacgggtag gctcgtccca aaggcgcggc gctgaggttt gtgaacgcgt   4800
ggaggggcgc ttgggggtctg ggggaggcgt cgcccgggta agcctgtctg ctgcggctct  4860
gcttccctta gactggagag ctgtggactt cgtctaggcg cccgctaagt tcgcatgtcc   4920
tagcacctct gggtctatgt ggggccacac cgtgggggagg aaacagcacg cgacgtttgt  4980
agaatgcttg gctgtgatac aaagcggttt cgaataatta acttatttgt tcccatcaca   5040
tgtcactttt aaaaaattat aagaactacc cgttattgac atctttctgt gtgccaagga   5100
ctttatgtgc tttgcgtcat ttaatttttga aaacagttat cttccgccat agataactac  5160
tatgttatc ttctggtaac cacgtgcgga ccgggctccg gtgcccgtgt gcggaccggg    5220
ctccggtgcc cgtcagtggg cagagcgcac atcgcccaca gtccccgaga agttgggggg   5280
aggggtcggc aattgaaccg gtgcctagag aaggtggcgc ggggtaaact gggaaagtga   5340
tgtcgtgtac tggctccgcc ttttttcccga gggtggggga gaaccgtata taagtgcagt  5400
agtcgccgtg aacgttcttt ttcgcaacgg gtttgccgcc agaacacagg taagtgccgt   5460
gtgtggttcc cgcggggcctg gcctctttac gggttatggc ccttgcgtgc cttgaattac  5520
ttccactggc tgcagtacgt gattcttgat cccgagcttc gggttggaag tgggtgggag   5580
agttcgaggc cttgcgctta aggagccccct tcgcctcgtg cttgagttga ggcctggcct  5640
gggcgctggg gccgccgcgt gcgaatctgg tggcaccttc gcgcctgtct cgctgctttc   5700
gataagtctc tagccattta aaatttttga tgacctgccg cacgcgtttt tttctggcaa   5760
gatagtcttg taaatgcggg ccaagatctg cacactggta tttcggtttt tggggccgcg   5820
ggcggcgacg gggcccgtgc gtcccagcgc acatgttcgg cgaggcgggg cctgcgagcg   5880
cggccaccga gaatcggacg ggggtagtct caagctggcc ggcctgctct ggtgcctggc   5940
ctcgcgccgc cgtgtatcgc cccgcccctgg gcggcaaggc tggcccggtc ggcaccagtt   6000
gcgtgagcgg aaagatggcc gcttcccggc cctgctgcag ggagctcaaa atggaggacg   6060
cggcgctcgg gagagcgggc gggtgagtca cccacacaaa ggaaaagggc ctttccgtcc   6120
tcagccgtcg cttcatgtga ctccacggag taccgggcgc cgtccaggca cctcgattag   6180
ttctcgagct tttggagtac gtcgtctttta ggttgggggg aggggtttta tgcgatggag   6240
tttccccaca ctgagtgggt ggagactgaa gttaggccag ccttggcactt gatgtaattc  6300
tccttggaat ttgccctttt tgagtttgga tcttggttca ttctcaagcc tcagacagtg   6360
gttcaaagtt tttttcttcc atttcaggtg tcgtgacttg acgtcgccac catgaggata   6420
tttgctgtct ttatattcat gacctactgg catttgctga acgcatttac tgtcacggtt   6480
cccaaggacc tatatgtggt agagtatggt agcaatatga caattgaatg caaattccca   6540
gtagaaaaac aattagacct ggctgcacta attgtctatt gggaaatgga ggataagaac   6600
attattcaat ttgtgcatgg agaggaagac ctgaaggttc agcatagtag ctacagacag   6660
agggcccggc tgttgaagga ccagctctcc ctgggaaatg ctgcacttca gatcacagat   6720
gtgaaattgc aggatgcagg ggtgtaccgc tgcatgatca gctatgctgg tgccgactac   6780
aagcgaatta ctgtgaaagt caatgcccca tacaacaaaa tcaaccaaag aattttggtt   6840
gtggatccag tcacctctga acatgaactg acatgtcagg ctgagggcta ccccaaggcc   6900
gaagtcatct ggacaagcag tgaccatcaa gtcctgagtg gtaagaccac caccaccaat   6960
tccaagagag aggagaaact tttcaatgtg accagcacac tgagaatcaa cacaacaact   7020
aatgagattt tctactgcac ttttaggaga ttagatcctg aggaaaacca tacagctgaa   7080
ttggtcatcc cagaactacc tctgcacat cctccaaatg aaaggactca cttggtaatt    7140
ctgggagcca tcttattatg ccttggtgta gcactgacat tcatcttccg tttaagaaaa   7200
gggagaatga tggatgtgaa aaaatgtggc atccaagata caaactcaaa gaagcaaagt   7260
gatacacatt tggaggagac gtaaccgctg atcagcctcg aaacttgttt attgcagctt   7320
ataatggtta caaataaagc aatagcatca caaatttcac aaataaagca tttttttcac   7380
tgcattctag ttgtggtttg tccaaactca tcaatgtatc ttaggcgcct gatgcggtat   7440
tttctcctta cgcatctgtg cggtatttca caccgcatac agtactgtca aagcaaccat   7500
agtacgcgcc ctgtagcggc gcattaagcc cggcgggtgt ggtggttacg cgcagcgtga   7560
ccgctacact tgccagcgcc ctagcgcccg ctccttttcgc tttcttccct tccttttctcg   7620
ccacgttcgc cggctttccc cgtcaagctc taaatcgggg gctcccttta gggttccgat   7680
ttagtgcttt acggcacctc gacccaaaa aacttgattt gggtgatggt tcacgtagtg    7740
ggccatcgcc ctgatagacg gttttttcgcc cttttgactt ggagtccacg ttctttaata   7800
gtggactctt gttccaaact ggaacaacac tcaaccctat ctcggctat tcttttgatt    7860
tataagggat tttgccgatt tcggcctatt ggttaaaaaa tgagctgatt taacaaaaat   7920
ttaacgcgaa ttttaacaaa atattaacgt ttacaatttt atggtgcact ctcagtacaa   7980
tctgtctga tgccgcatag ttaagccagc cccgacacca gccaacaccc gctgacgcgc    8040
cctgacggc ttgtctgctc ccggcatccg cttacagaca agctgtgacc gtctccggga    8100
gctgcatgtg tcagaggttt tcaccgtcat caccgaaacg cgcgagacga aagggcctcg   8160
tgatacgcct attttatag gttaatgtca tgaacaataa aactgtctgc ttacataaac   8220
agtaatacaa ggggtgttat gagccatatt caacgggaaa cgtcgaggcc gcgattaaat   8280
tccaacatgg atgctgattt atatgggtat aaatgggctc gcgataatgt cggcaatca    8340
gcaa tctatcgtt gtatgggaag cccgatgcgc cagagttgtt tctgaaacat            8400
ggcaaaggta gcgttgccaa tgatgttaca gatgagatgg tcagactaaa ctggctgacg   8460
gaatttatgc ctcttccgac catcaagcat tttatccgta ctcctgatga tgcatggtta   8520
ctcaccactg cgatccccgg aaaaacagca ttccaggtat tagaagaata tcctgattca   8580
ggtgaaaata ttgttgatgc gctggcagtg ttcctgcgcc ggttgcattc gattcctgtt   8640
tgtaattgtc cttttaacag cgatcgcgta tttcgtctcg ctcaggcgca atcacgaatg   8700
```

-continued

```
aataacggtt tggttgatgc gagtgatttt gatgacgagc gtaatggctg gcctgttgaa    8760
caagtctgga aagaaatgca taaacttttg ccattctcac cggattcagt cgtcactcat    8820
ggtgatttct cacttgataa ccttattttt gacgagggga aattaatagg ttgtattgat    8880
gttggacgag tcggaatcgc agaccgatac caggatcttg ccatcctatg gaactgcctc    8940
ggtgagtttt ctccttcatt acagaaacgg cttttcaaa aatatggtat tgataatcct    9000
gatatgaata aattgcagtt tcatttgatg ctcgatgagt ttttctaatc tcatgaccaa    9060
aatcccttaa cgtgagtttt cgttccactg agcgtcagac cccgtagaaa agatcaaagg    9120
atcttcttga gatccttttt ttctgcgcgt aatctgctgc ttgcaaacaa aaaaaccacc    9180
gctaccagcg gtggtttgtt tgccggatca agagctacca actcttttc cgaaggtaac    9240
tggcttcagc agagcgcaga taccaaatac tgtccttcta gtgtagccgt agttaggcca    9300
ccacttcaag aactctgtag caccgcctac ataccctgct ctgctaatcc tgttaccagt    9360
ggctgctgcc agtggcgata agtcgtgtct taccggttg gactcaagac gatagttacc    9420
ggataaggcg cagcggtcgg gctgaacggg gggttcgtgc acacagccca gcttggagcg    9480
aacgacctac accgaactga gatacctaca gcgtgagcta tgagaaagcg ccacgcttcc    9540
cgaagggaga aaggcggaca ggtatccggt aagcggcagg gtcggaacag gagagcgcac    9600
gagggagctt ccaggggaa acgcctggta tctttatagt cctgtcgggt ttcgccacct    9660
ctgacttgag cgtcgatttt tgtgatgctc gtcagggggg cggagcctat ggaaaaacgc    9720
cagcaacgcg gccttttac ggttcctggc cttttgctgg cctttgctc acatgtgcgg    9780
ccgcacgcgt gttctagggt ggaaactaag agaatgatgt acctagaggg cgctggaagc    9840
tctaaagccc tagcagttac tgcttttact attagtggtc gtttttttct cccccccgcc    9900
ccccgacaaa tcaacagaac aaagaaaatt acctaaacag caaggacata gggaggaact    9960
tcttggcaca gaactttcca aacactttt cctgaaggga tacaagaagc aagaaaggta   10020
ctctttcact aggaccttct ctgagctgtc ctcaggatgc ttttgggact attttttctta  10080
cccagagaat ggagaaaccc tgcagggaat tcccaagctg tagttataaa cagaagttct   10140
ccttctgcta ggtagcattc aaagatctta atcttctggg tttccgtttt ctcgaatgaa   10200
aaatgcaggt ccgagcagtt aactggctgg ggcaccatta gcaagtcact tagcatctct   10260
ggggccagtc tgcaaagcga gggggcagcc ttaatgtgcc tccagcctga agtcctagaa   10320
tgagcgcccg gtgtcccaag ctggggcgcg caccccagat cggagggcgc cgatgtacag   10380
acagcaaact cacccagtct agtgcatgcc ttcttaaaca tcacgagact ctaagaaaag   10440
gaaactgaaa acgggaaagt ccctctctct aacctggcac tgcgtcgctg gcttggagac   10500
aggtgacggt ccctgcggc cttgtcctga ttggctgggc acgcgtttaa tataagtgga   10560
ggcgtcgcgc tggcgggcat tcctgaagct aagcttgtgg acgatatcga attcgcacga   10620
cattgattat tgactagtta ttaat                                          10645

SEQ ID NO: 149          moltype = DNA    length = 1178
FEATURE                 Location/Qualifiers
misc_feature            1..1178
                        note = Synthetic
source                  1..1178
                        mol_type = other DNA
                        organism = synthetic construct
SEQUENCE: 149
ggctccggtg cccgtcagtg ggcagagcgc acatcgccca cagtcccga gaagttgggg      60
ggaggggtcg gcaattgaac cggtgcctag agaaggtggc gcggggtaaa ctgggaaagt    120
gatgtcgtgt actggctccg cctttttccc gagggtgggg gagaaccgta tataagtgca    180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccactg gctgcagtac gtgattcttg atcccgagct tcgggttgga agtgggtggg    360
agagttcgag gccttgcgct taaggagccc cttcgcctcg tgcttgagtt gaggcctggc    420
ctgggcgctg gggccgccgc gtgcgaatct ggtggcacct tcgcgcctgt ctcgctgctt    480
tcgataagtc tctagccatt taaaattttt gatgacctgc tgcgacgctt tttttctggc    540
aagatagtct tgtaaatgcg ggccaagatc tgcacactgg tatttcggtt tttgggccg    600
cgggcggcga cggggcccgt gcgtcccagc gcacatgttc ggcgaggcgg ggcctgcgag    660
cgcggccacc gagaatcgga cggggtagt ctcaagctgg ccggcctgct ctggtgcctg    720
gcctcgccgc gccgtgtatc gccccgccct gggcggcaag gctggcccgg tcggcaccag    780
ttgcgtgagc ggaaagatgg ccgcttcccg gccctgctgc agggagctca aaatggagga    840
cgcggcgctc gggagagcgg gcgggtgagt cacccacaca aaggaaaagg gcctttccgt    900
cctcagccgt cgcttcatgt gactccacgg agtaccgggc gccgtccagg cacctcgatt    960
agttctcgag cttttggagt acgtcgtctt taggttgggg ggaggggttt tatgcgatgg   1020
agtttcccca cactgagtgg gtgggagactg aagttaggcc agcttggcac ttgatgtaat   1080
tctccttgga atttgccctt tttgagtttg gatcttggtt cattctcaag cctcagacag   1140
tggttcaaag tttttttctt ccatttcagg tgtcgtga                             1178
```